United States Patent
Qi et al.

(10) Patent No.: US 11,802,132 B2
(45) Date of Patent: Oct. 31, 2023

(54) SMALL MOLECULES FOR INDUCING SELECTIVE PROTEIN DEGRADATION AND USES THEREOF

(71) Applicant: DANA-FARBER CANCER INSTITUTE, INC., Boston, MA (US)

(72) Inventors: Jun Qi, Sharon, MA (US); Lei Wu, Shanghai (CN); Kenneth C. Anderson, Wellesley, MA (US); Yan Song, Brookline, MA (US); Paul Park, Waltham, MA (US); Dharminder Chauhan, Natick, MA (US)

(73) Assignee: DANA-FARBER CANCER INSTITUTE, INC., Boston, MA (US)

( * ) Notice: Subject to any disclaimer, the term of this patent is extended or adjusted under 35 U.S.C. 154(b) by 239 days.

(21) Appl. No.: 16/969,772

(22) PCT Filed: Feb. 22, 2019

(86) PCT No.: PCT/US2019/019180
§ 371 (c)(1),
(2) Date: Aug. 13, 2020

(87) PCT Pub. No.: WO2019/165229
PCT Pub. Date: Aug. 29, 2019

(65) Prior Publication Data
US 2020/0407371 A1    Dec. 31, 2020

Related U.S. Application Data

(60) Provisional application No. 62/634,679, filed on Feb. 23, 2018.

(51) Int. Cl.
C07D 495/14     (2006.01)
C07D 211/60     (2006.01)
A61P 35/00      (2006.01)

(52) U.S. Cl.
CPC ............ *C07D 495/14* (2013.01); *A61P 35/00* (2018.01); *C07D 211/60* (2013.01)

(58) Field of Classification Search
CPC ........................... C07D 495/14; C07D 211/60
See application file for complete search history.

(56) References Cited

U.S. PATENT DOCUMENTS

| | | |
|---|---|---|
| 2009/0053245 A1 | 2/2009 | Mutz et al. |
| 2016/0106725 A1 | 4/2016 | Roden et al. |
| 2016/0176916 A1 | 6/2016 | Bradner et al. |

FOREIGN PATENT DOCUMENTS

| | | |
|---|---|---|
| JP | 2018-502097 A | 1/2018 |
| WO | 2014182744 A1 | 11/2014 |
| WO | 2016105518 A1 | 6/2016 |
| WO | 2016169989 A1 | 10/2016 |
| WO | 2017024317 A2 | 2/2017 |

OTHER PUBLICATIONS

Caligluri, M., et al., "MASPIT: Three-Hybrid Trap for Quantitative Proteome Fingerprinting of Small Molecule-Protein Interactions in Mammalian Cells," Chemistry & Biology, 2006, vol. 13, No. 7, pp. 711-722.

*Primary Examiner* — Laura L Stockton
(74) *Attorney, Agent, or Firm* — BURNS & LEVINSON, LLP; Daniel W. Clarke; Shawn P. Foley

(57) ABSTRACT

Provided herein are bifunctional compounds that bind a target protein (e.g., a selected protein) and/or induce ubiquitination for degradation of the target protein. In particular, provided are compounds that bind a bromodomain or bromodomain-containing protein (e.g., BET proteins) or histone methyltransferases (HMTs, e.g., enhancer of zeste homolog 1 (EZH1), or FKBP12) and can promote its degradation by recruiting it to the ubiquitin receptor RPN13 (e.g., RA190), for proteasomal degradation. Also provided are pharmaceutical compositions comprising the bifunctional compounds, methods of treating and/or preventing diseases (e.g., proliferative diseases, cancers, benign neoplasms, pathological angiogenesis, inflammatory diseases, and autoimmune diseases) and musculoskeletal diseases, and methods of inducing the degradation of a target (e.g., a target protein) by recruiting it to the ubiquitin receptor RPN13 of the proteasome in a subject by administering a compound or composition described herein.

14 Claims, 47 Drawing Sheets

IC50>400nM

Different RA190 connecting point

RAJQ14

SMALL MOLECULES FOR INDUCING SELECTIVE PROTEIN DEGRADATION AND USES THEREOF

RELATED APPLICATIONS

This application is a national stage application, filed under 35 U.S.C. § 371, of International Application No. PCT/US2019/019180, filed Feb. 22, 2019, which claims priority under 35 U.S.C. § 119(e) to U.S. Provisional Application, U.S. Ser. No. 62/634,679, filed Feb. 23, 2018, the entire contents of each of which are incorporated herein by reference.

BACKGROUND OF THE INVENTION

Recently, a new therapeutic strategy to reduce and/or eliminate proteins associated with certain pathological states, PROTAC (proteolysis targeting chimeras; e.g., see U.S. Patent application U.S. Ser. No. 14/792,414, filed Jul. 6, 2015; U.S. Ser. No. 14/707,930, filed May 8, 2015, which is incorporated herein by reference), was developed by creating bifunctional compounds that recruit E3 ubiquitin ligase to a target protein, which subsequently induce ubiquitination and proteasome-mediated degradation of the target protein. E3 ubiquitin ligases are proteins that, in combination with an E2 ubiquitin-conjugating enzyme, promote the attachment of ubiquitin to a lysine of a target protein via an isopeptide bond (e.g., an amide bond that is not present on the main chain of a protein). The ubiquitination of the protein results in degradation of the target protein by the proteasome.

RA190 covalently binds to the ubiquitin receptor RPN13 (ADRM1), changing the function of RPN13 to interact with poly ubiquinylated proteins that cannot enter the particle 19S proteasome, which in turn inhibits proteasome function. See US Appl. Pub. No. 2016/0106725. The subsequent accumulation of polyubiquitinated proteins induces apoptosis in cells (e.g., cancer cells). The ubiquitinylation of targeted proteins is not needed, and the E3 ligases are not involved in this process. The bi-functional compound directly brings the targeted proteins to the proteasome.

There remains a need to identify compounds that effectively promote the degradation of target proteins (e.g., a bromodomain, a bromodomain-containing protein, or FKBP12) found to be associated with certain pathological states, including proliferative diseases, cancers, benign neoplasms, pathological angiogenesis, inflammatory diseases, autoimmune diseases, and musculoskeletal diseases. In particular, compounds that can take advantage of cellular machinery involved in protein homeostasis (e.g., ubiquitination and proteasome degradation) to target the degradation of certain proteins may find use as therapeutic agents. There is a need for compounds that both target a target protein, and also bind the ubiquitin receptor RPN13, which brings the selected target protein to the proteasome, thereby inducing proteasome degradation of the target protein.

SUMMARY OF THE INVENTION

The present disclosure stems from the recognition that selected target proteins (e.g., a bromodomain, a bromodomain-containing protein, or FKBP12) are related to certain diseases (e.g., proliferative diseases, cancers, benign neoplasms, pathological angiogenesis, inflammatory diseases, autoimmune diseases, and musculoskeletal diseases), and that by targeting both a selected protein, and the use of a binder of the ubiquitin receptor RPN13, which brings the selected target protein to the proteasome, thereby inducing proteasome degradation of the target protein. This discovery provides a new mode of inhibiting proteasome function. The disclosure therefore provides new compounds, compostions, and methods for the treatment of various diseases (e.g., cancers, benign neoplasms, pathological angiogenesis, inflammatory diseases, and autoimmune diseases) based on this discovery. Described herein are compounds of Formulae (I), (IA), and (IB). The compounds described herein include a component that binds to the ubiquitin receptor RPN13 and a component that binds a target (e.g., a protein) and therefore may be useful in promoting the degradation of the target (e.g., a protein). The compounds may be useful in treating and/or preventing a disease or condition associated with a target protein, e.g., in treating and/or preventing a proliferative disease (e.g., cancers, benign neoplasms, pathological angiogenesis, inflammatory diseases, and autoimmune diseases) in a subject in need thereof. Also provided are pharmaceutical compositions and kits including a compound described herein.

In one aspect, the present disclosure provides compounds of Formula (I):

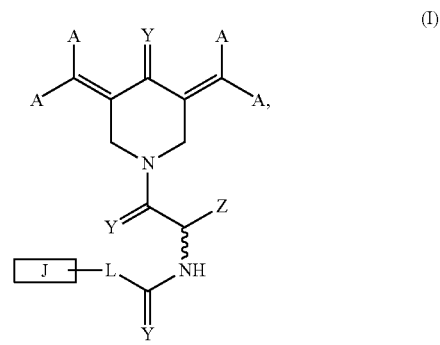

and pharmaceutically acceptable salts, solvates, hydrates, polymorphs, co-crystals, tautomers, stereoisomers, isotopically labeled derivatives, and prodrugs thereof, wherein A, Y, Z, L, and J are as defined herein. The moieties

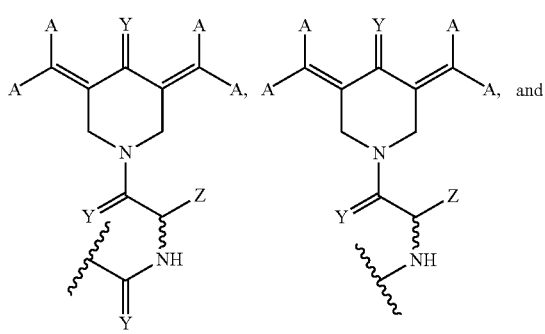

-continued

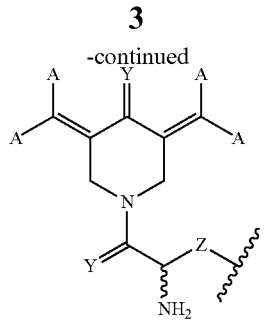

are derived from RA 190, a binder of the ubiquitin receptor RPN13.

In one aspect, the present disclosure provides compounds of Formula (IA):

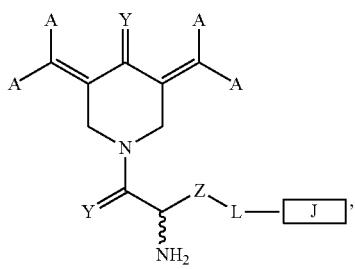

(IA)

and pharmaceutically acceptable salts, solvates, hydrates, polymorphs, co-crystals, tautomers, stereoisomers, isotopically labeled derivatives, and prodrugs thereof, wherein A, Y, Z, L, and J are as defined herein.

In one aspect, the present disclosure provides compounds of Formula (IB):

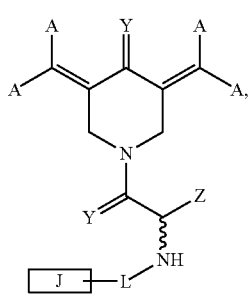

(IB)

and pharmaceutically acceptable salts, solvates, hydrates, polymorphs, co-crystals, tautomers, stereoisomers, isotopically labeled derivatives, and prodrugs thereof, wherein A, Y, Z, L, and J are as defined herein.

In Formulae (I), (IA), and (IB), J is a binder of a target including a bromodomain, a bromodomain-containing protein (e.g., BRD1, BRD4, BRD5, BRD6, BRD7, BRD8, BRD9, BRD10, and/or BRDT), or FKBP12, wherein J is a moiety of Formula (II), (III), (IV), (V), or (IX).

In certain embodiments, J is a binder of a bromodomain and/or a bromodomain-containing protein (e.g., BRD1, BRD4, BRD5, BRD6, BRD7, BRD8, BRD9, BRD10, and/or BRDT).

In certain embodiments, J is of Formula (II):

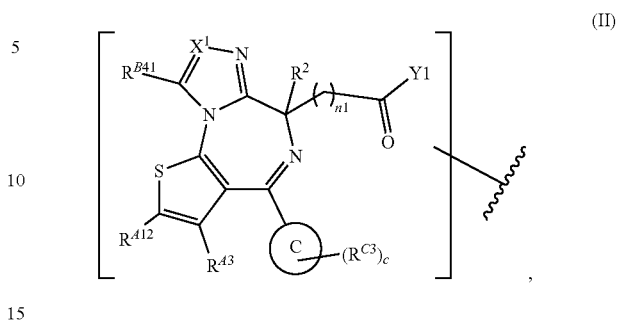

(II)

wherein $R^{A12}$, $R^{B41}$, $X^1$, $R^{A3}$, $R^2$, $R^{C3}$, Ring C, c, n1, and Y1 are as defined herein. In some embodiments, the linker L is attached to any position on the compound of Formula (II). In some embodiments, the linker L is attached to Y1, $R^{A12}$, $R^{C3}$, or Ring C on the compound of Formula (II).

In certain embodiments, J is of Formula (III):

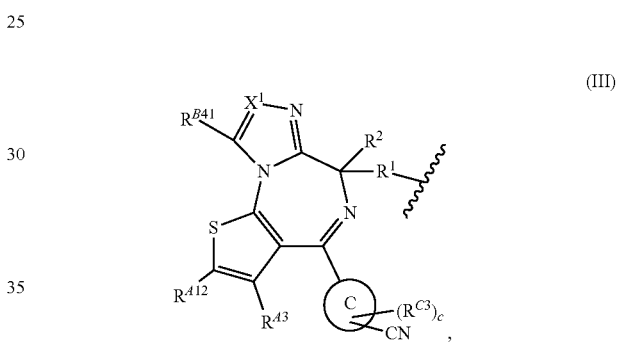

(III)

wherein $R^{A12}$, $R^{B41}$, $X^1$, $R^{A3}$, $R^1$, $R^2$, $R^{C3}$, Ring C, and c are as defined herein. In some embodiments, the linker L is attached to any position on the compound of Formula (III).

In certain embodiments, J is of Formula (IV):

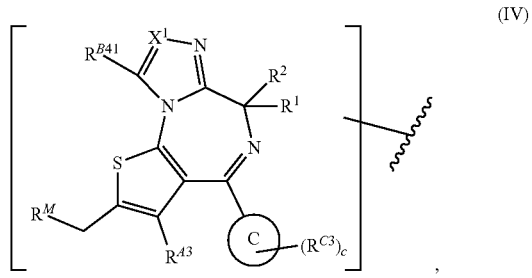

(IV)

wherein $R^M$, $R^{B41}$, $X^1$, $R^{A3}$, $R^1$, $R^2$, $R^{C3}$, Ring C, and c are as defined herein. In some embodiments, the linker L is attached to any position on the compound of Formula (IV). In some embodiments, the linker L is attached to $R^1$ or $R^M$ on the compound of Formula (IV).

In certain embodiments, J is of Formula (V):

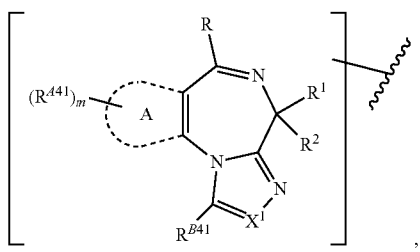

wherein $R^{A41}$, Ring A, $R^{B41}$, $X^1$, $R^2$, $R^1$, $R^{2A}$, R, and m are as defined herein. In some embodiments, the linker L is attached to any position on the compound of Formula (V). In some embodiments, the linker L is attached to $R^{A41}$ or $R^1$ on the compound of Formula (V).

In certain embodiments, J is a moiety of Formula (IX), which is a binder of FKBP. In certain embodiments, J is a moiety of Formula (IX), which is a binder of FKBP12. In certain embodiments, J is of Formula (IX):

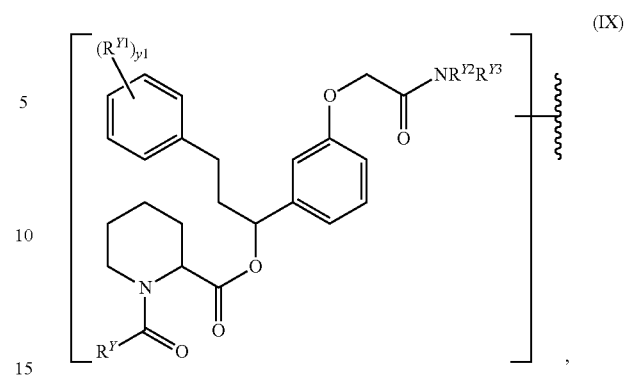

wherein $R^{Y1}$, $R^{Y2}$, $R^{Y3}$, $R^Y$, and y1 are defined herein. In some embodiments, the linker L is attached to any position on the compound of Formula (IX).

Exemplary compounds of Formulae (I) and (IA) include, but are not limited to:

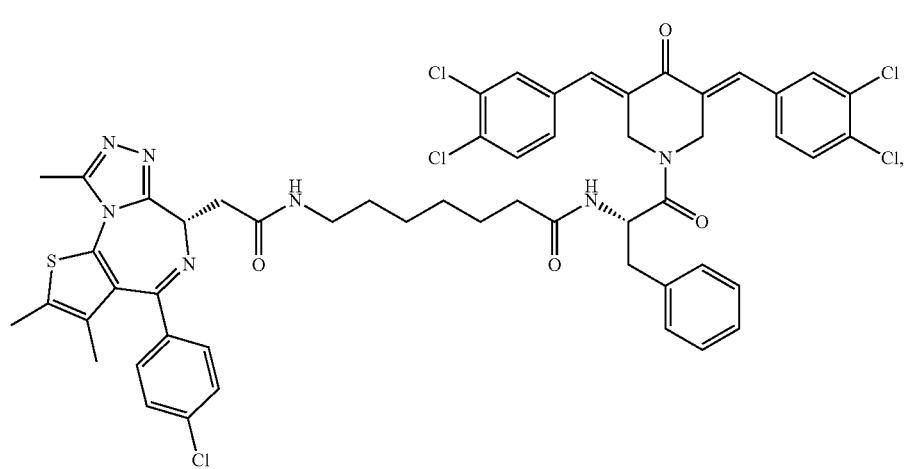

(RA-JQ1; LW-RPN13-3)

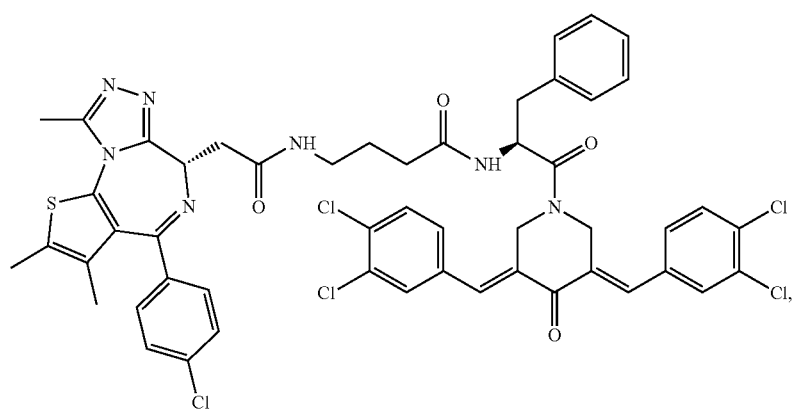

(RA-JQ2; LW-RPN13-5)

(RA-JQ3; LW-RPN13-6)
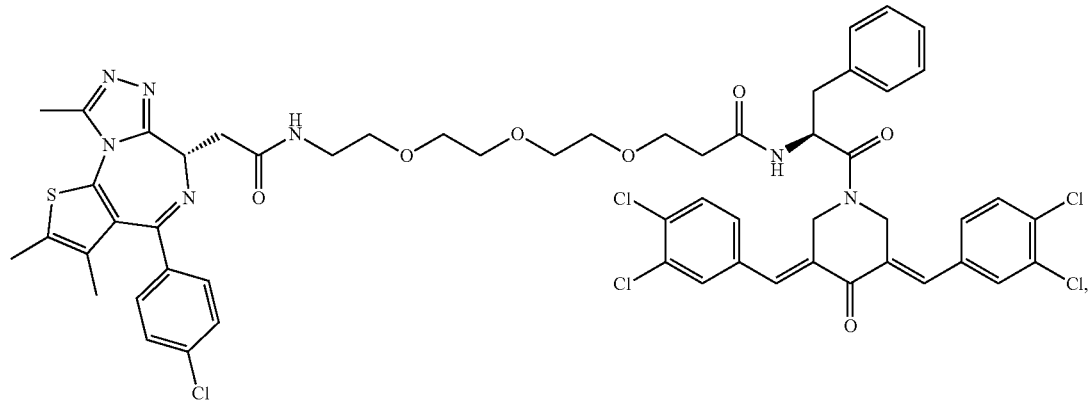
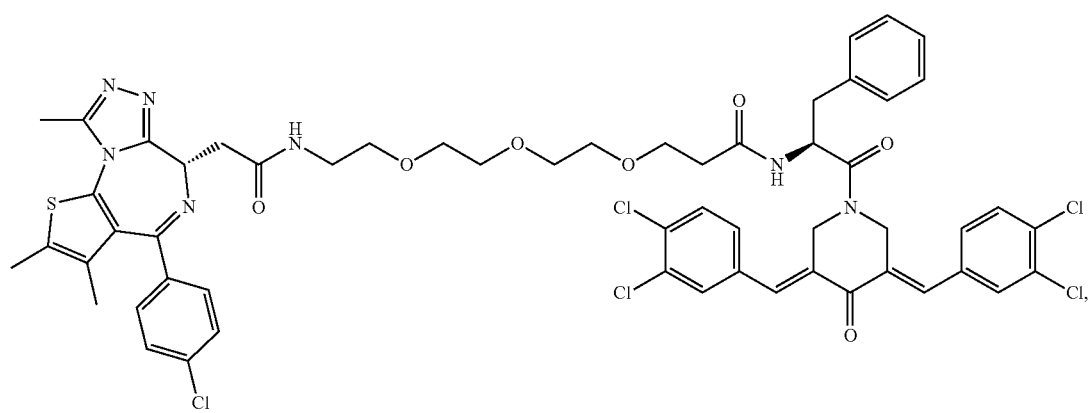
(LW-RPN13-7)
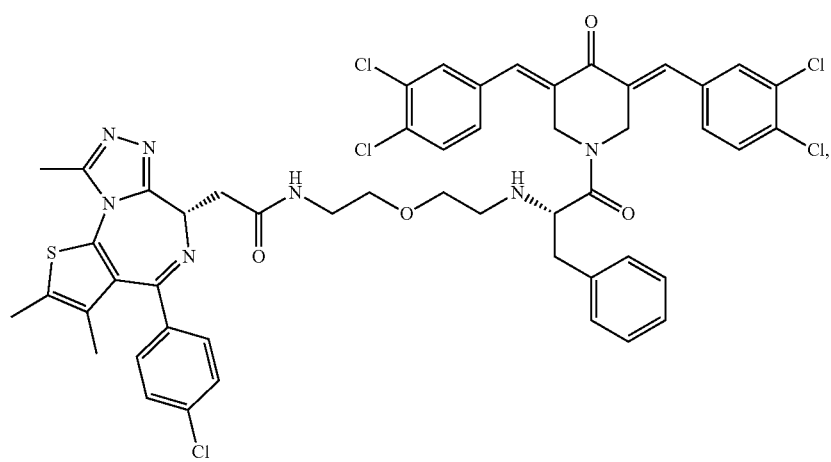

-continued
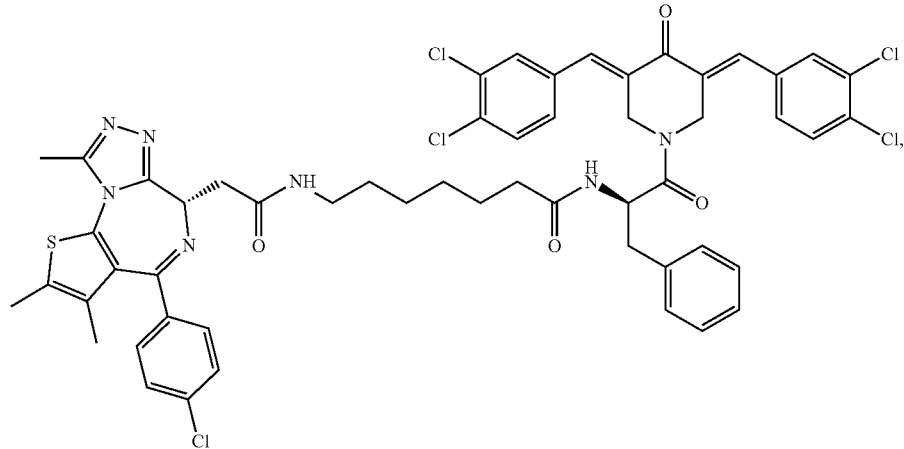
D-RAJQ1
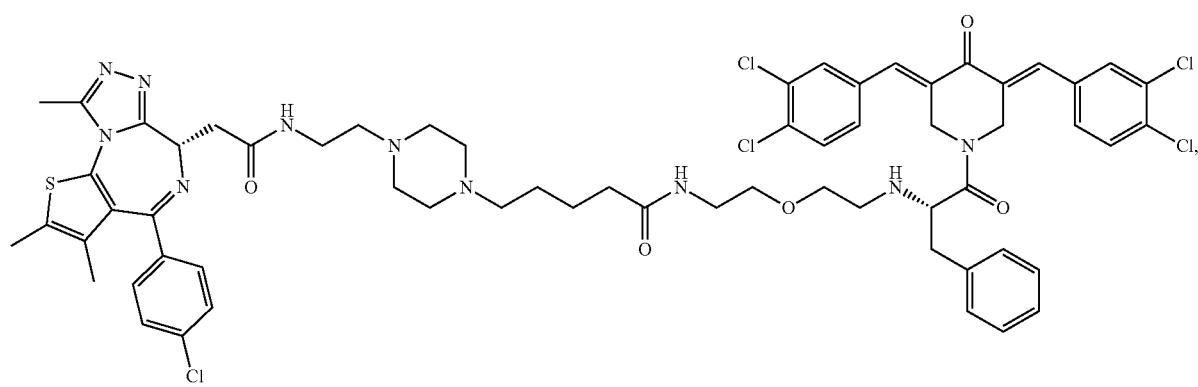
RAJQ8
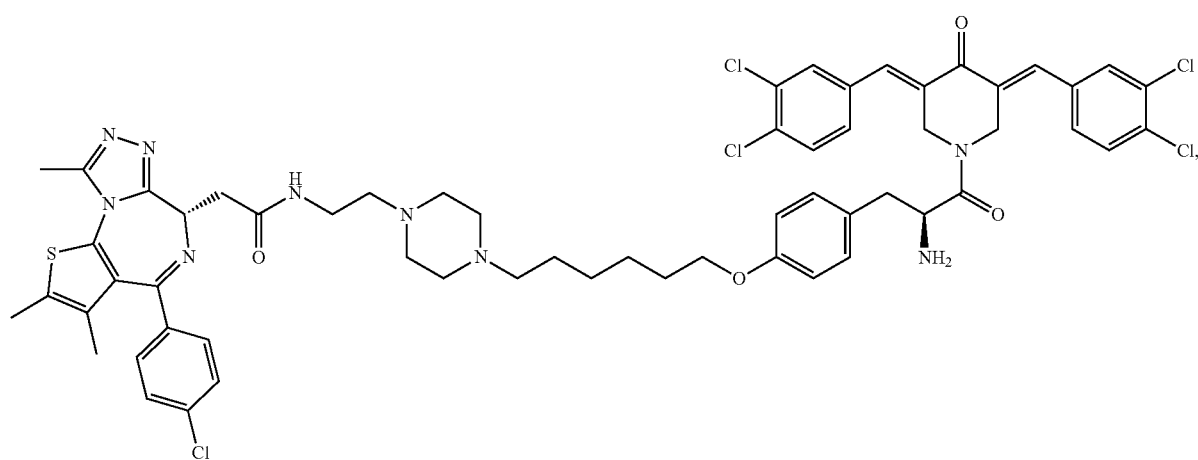
RA-JQ-9

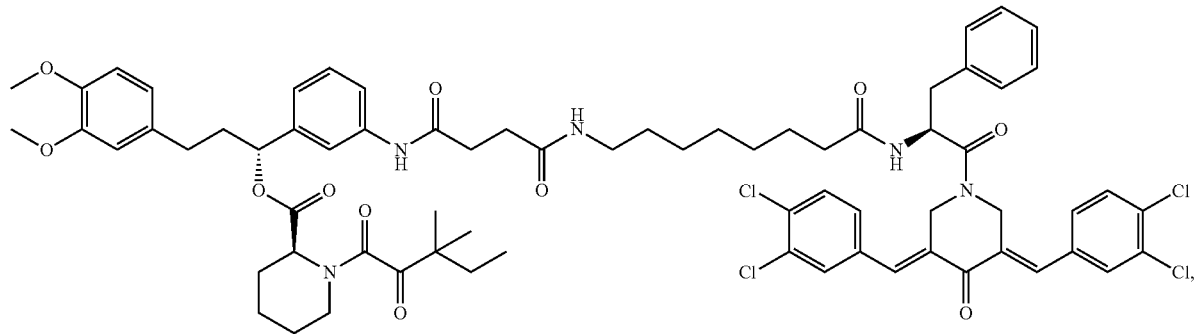
RAFKBP-1
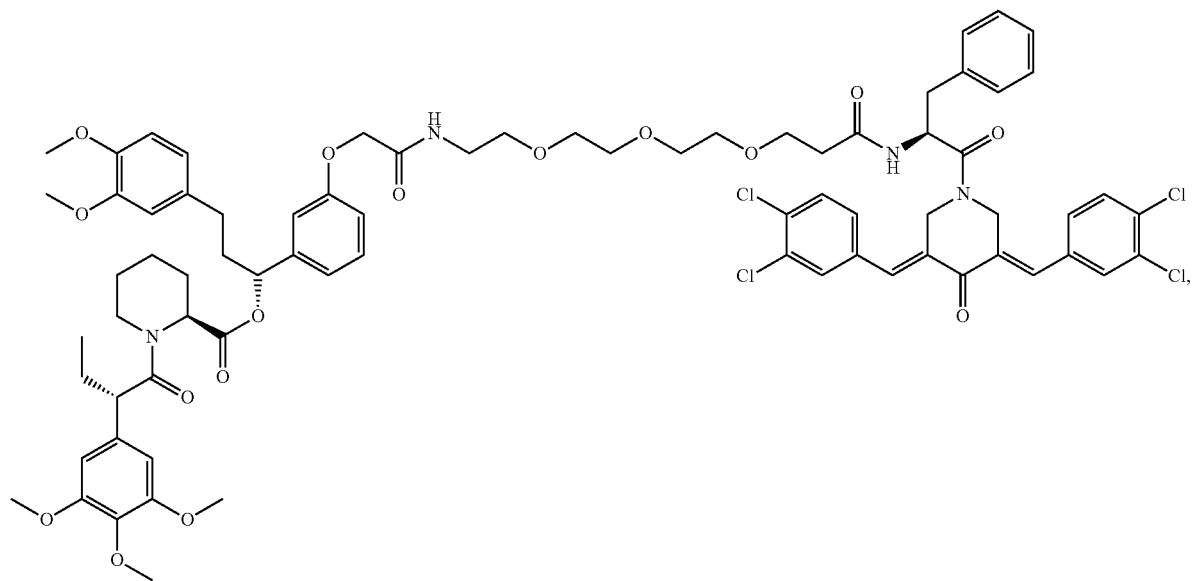
RAFKBP-2
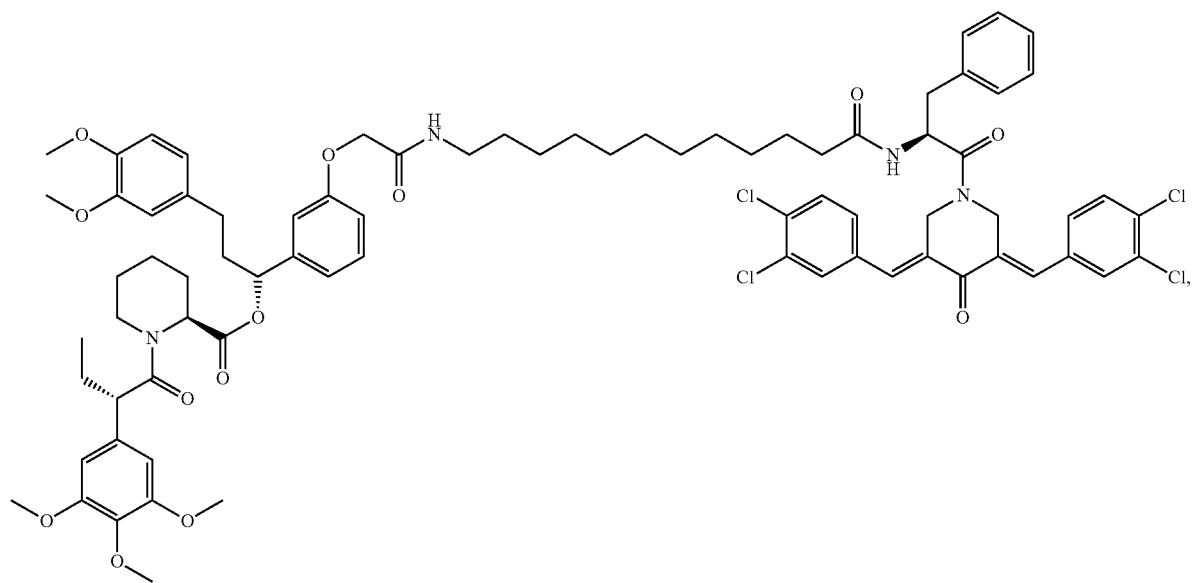
RAFKBP-3

-continued
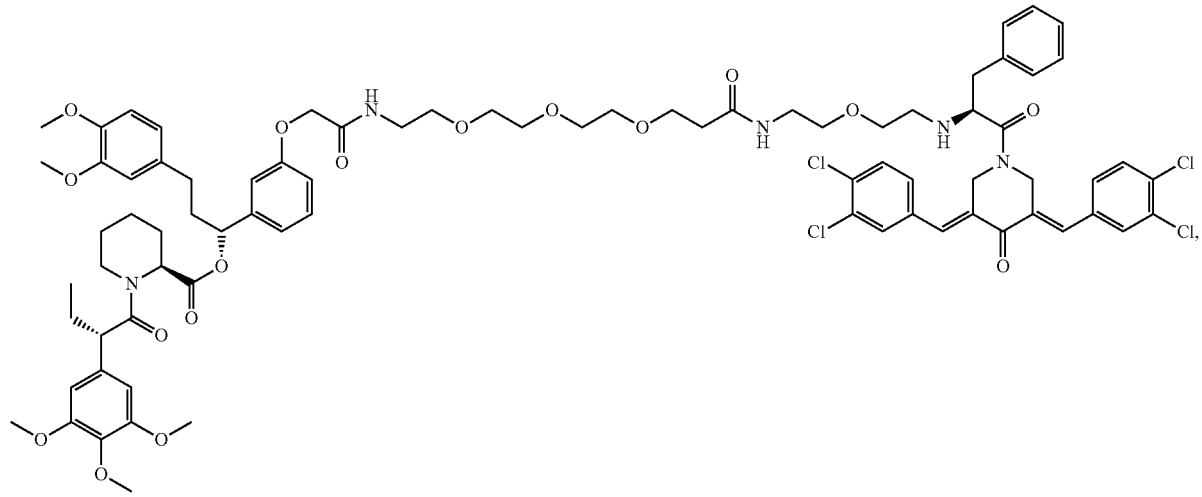
RAFKBP-4
and pharmaceutically acceptable salts, solvates, hydrates, polymorphs, co-crystals, tautomers, stereoisomers, isotopically labeled derivatives, and prodrugs thereof.
Exemplary compounds of Formulae (I), (IA), and (IB) include, but are not limited to:
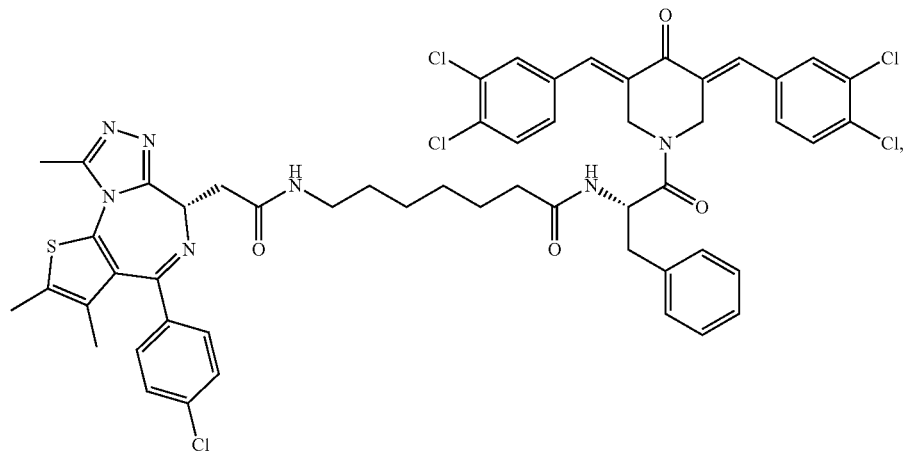
(RA-JQ1; LW-RPN13-3)
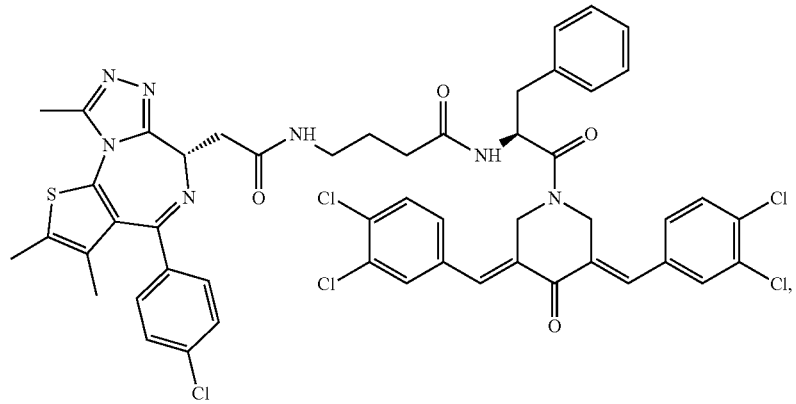
(RA-JQ2; LW-RPN13-5)

(RA-JQ3; LW-RPN13-6)
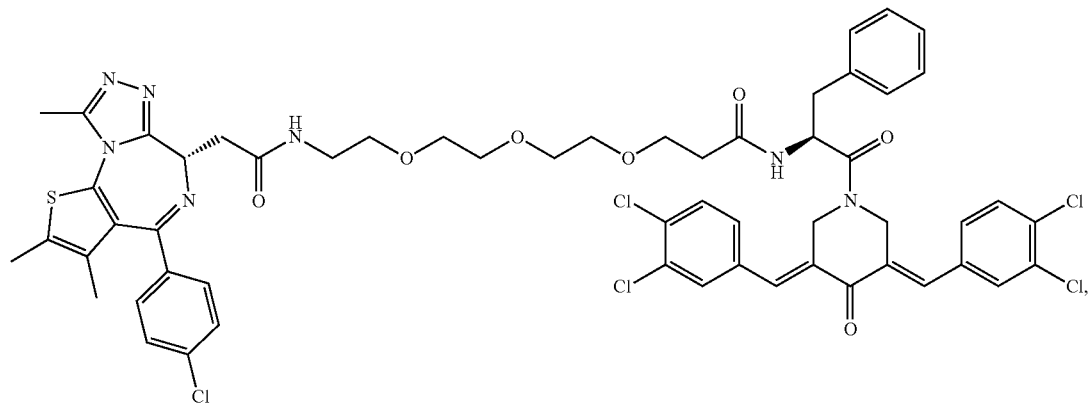
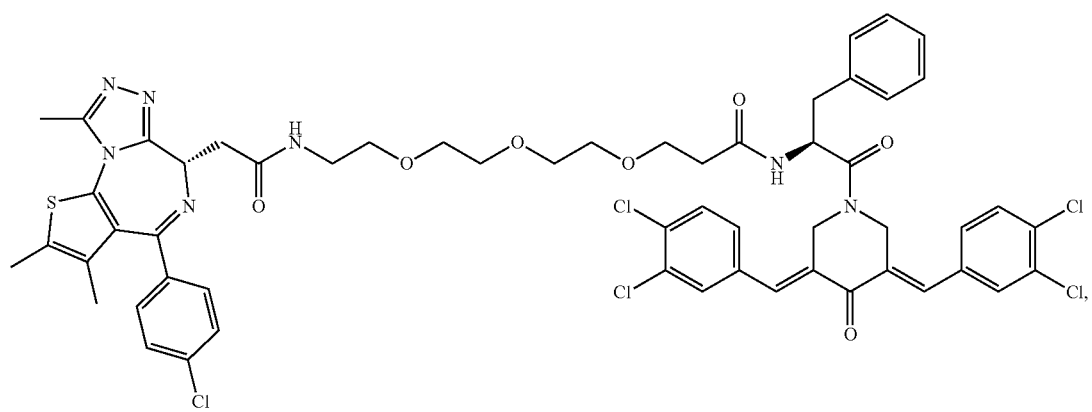
(LW-RPN13-7)
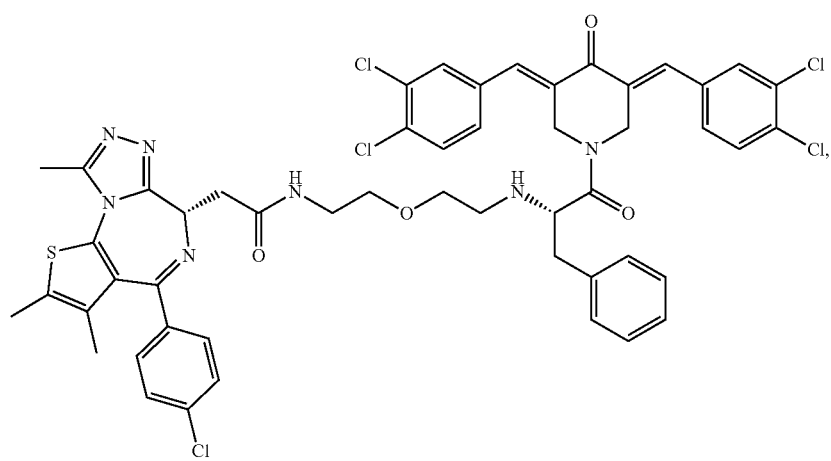

-continued
D-RAJQ1
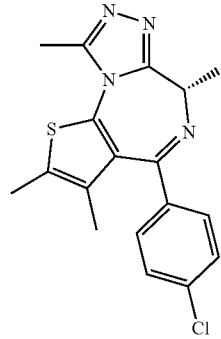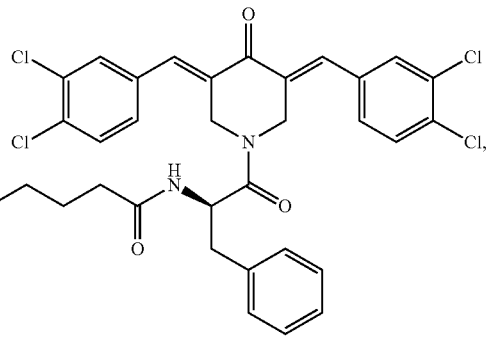
RAJQ8
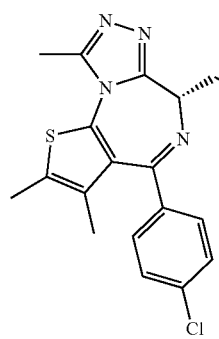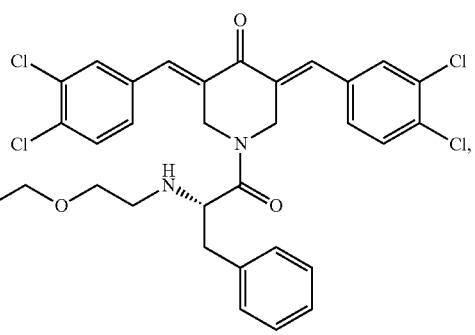
RA-JQ-9
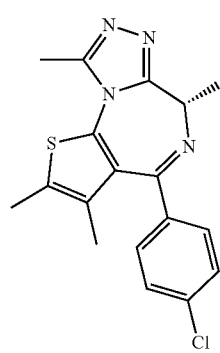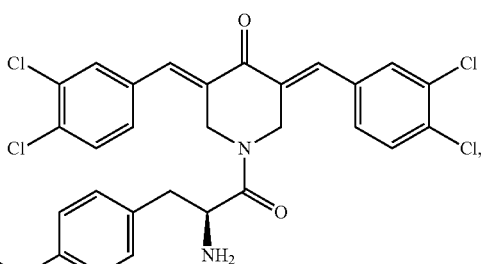
(RA-JQ10; RAJQ10)
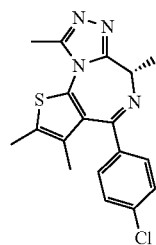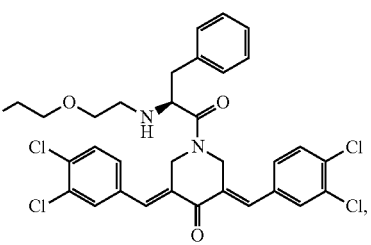

-continued
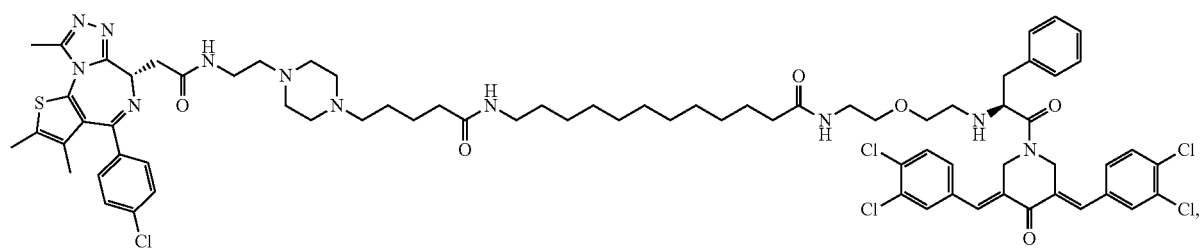
(RA-JQ11; RAJQ11)
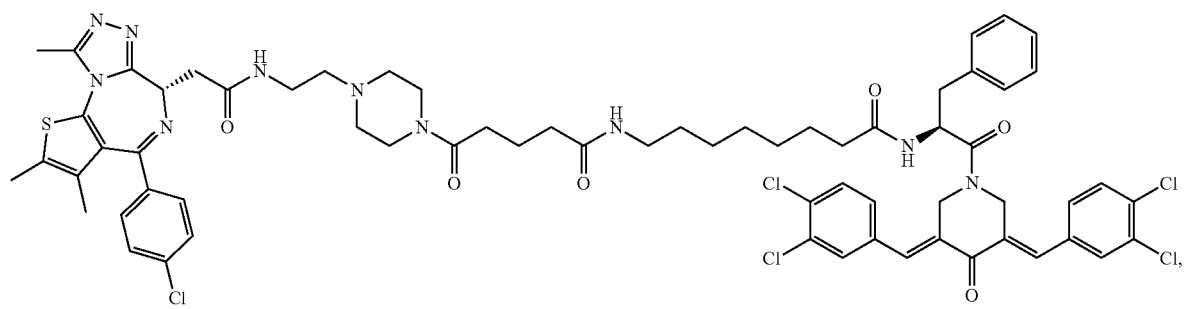
(LW-9296-205)
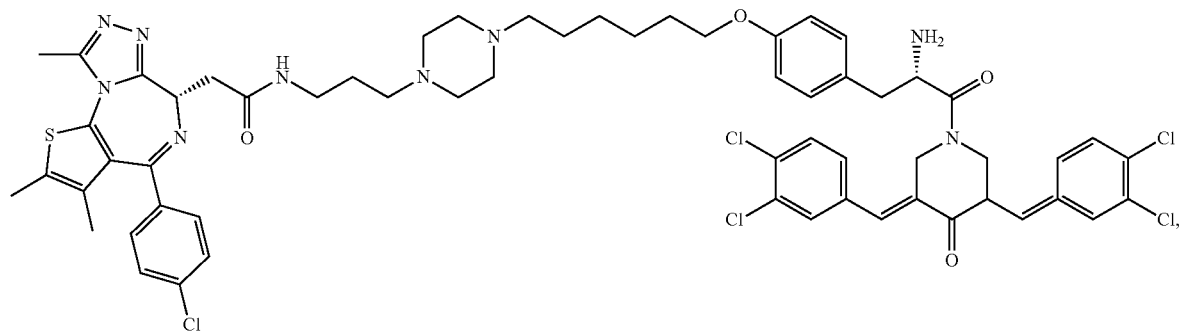
(RA-JQ14)
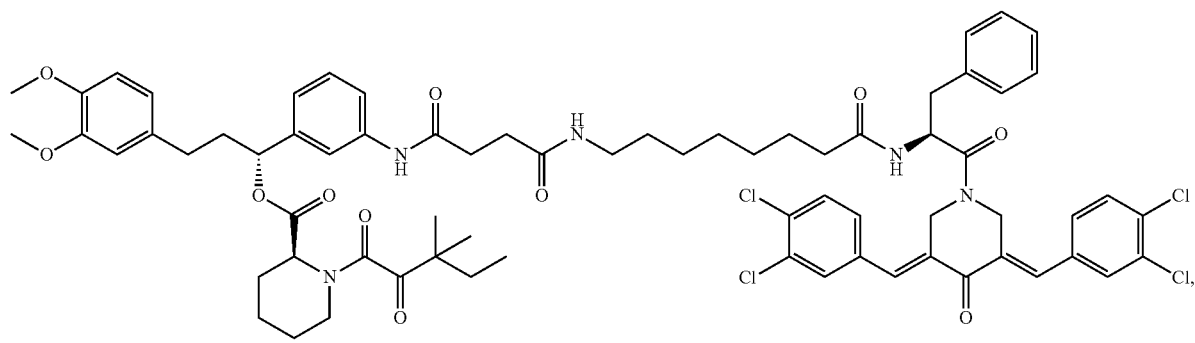
RAFKBP-1

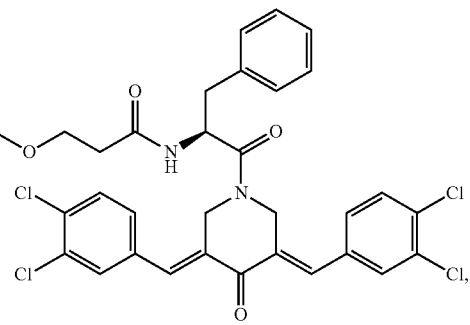
RAFKBP-2
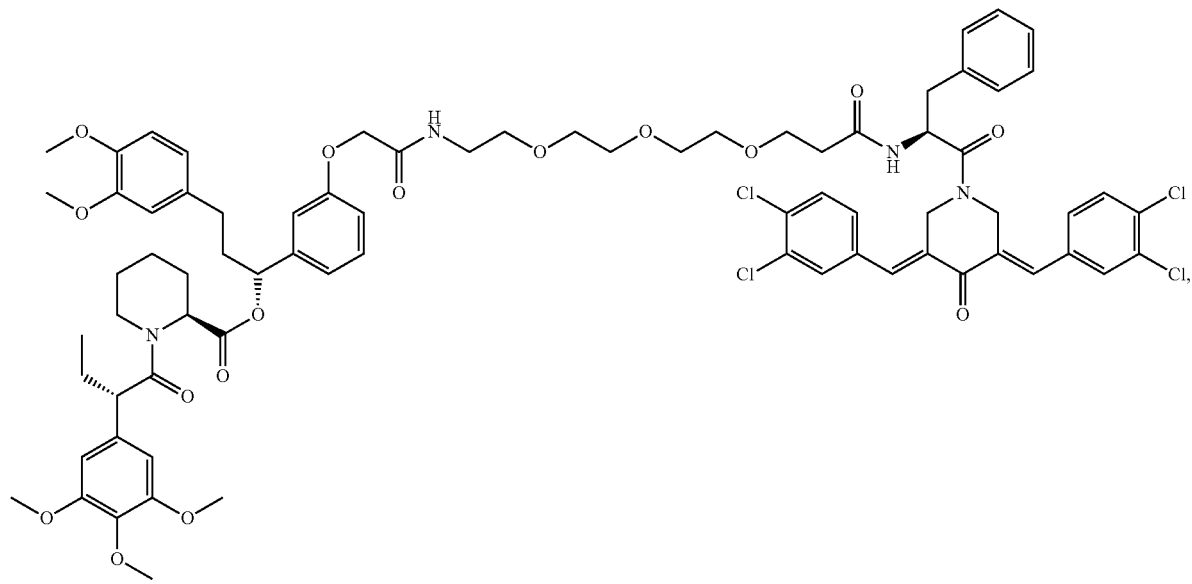
RAFKBP-3
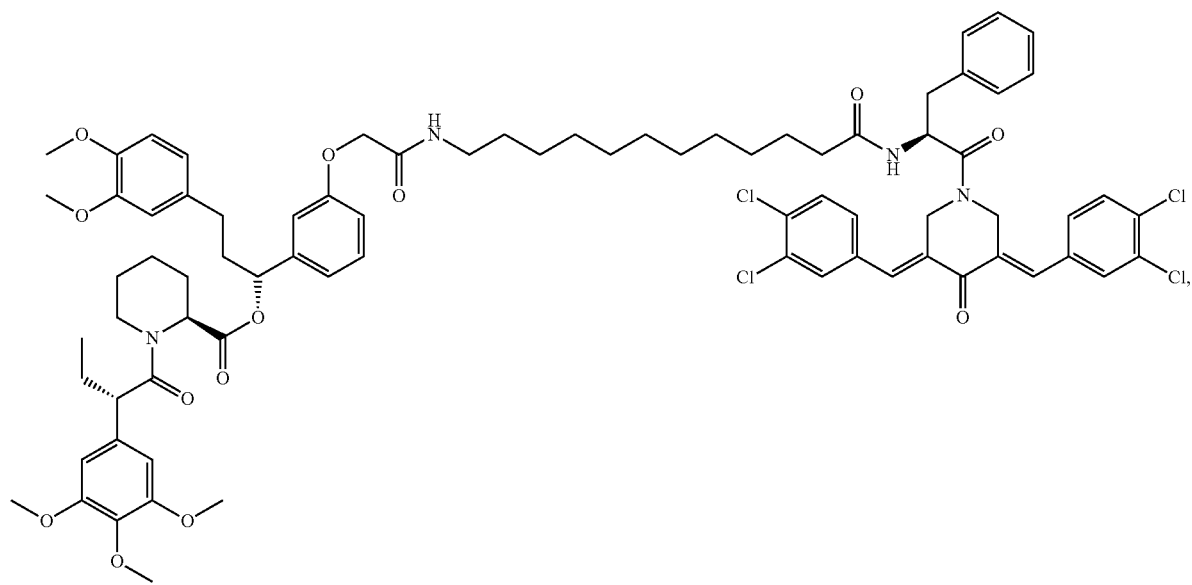

RAFKBP-4

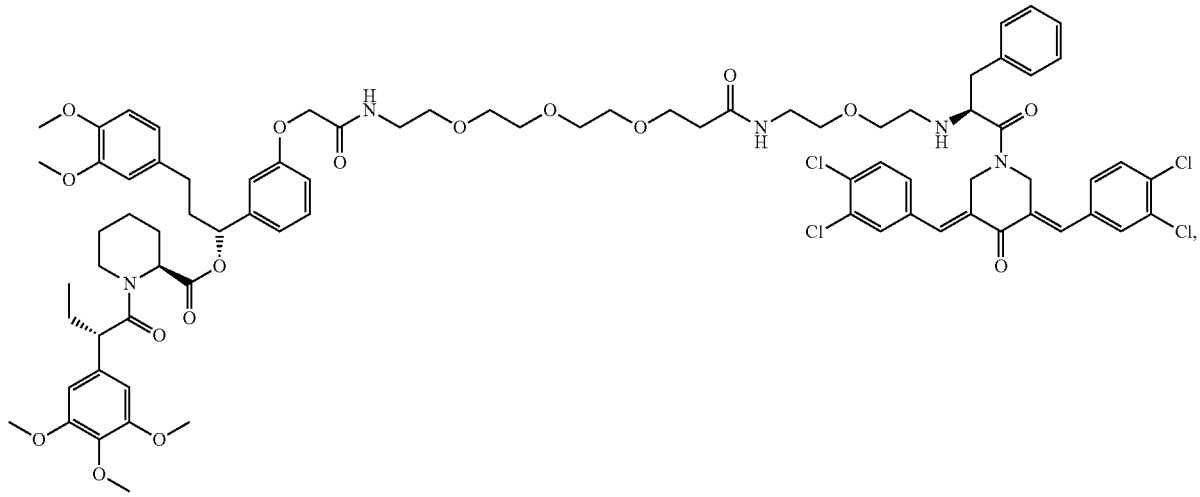

and pharmaceutically acceptable salts, solvates, hydrates, polymorphs, co-crystals, tautomers, stereoisomers, isotopically labeled derivatives, and prodrugs thereof.

In certain embodiments, a compound of Formulae (I), (IA), or (IB) is not of the formula:

(LW-9296-205)

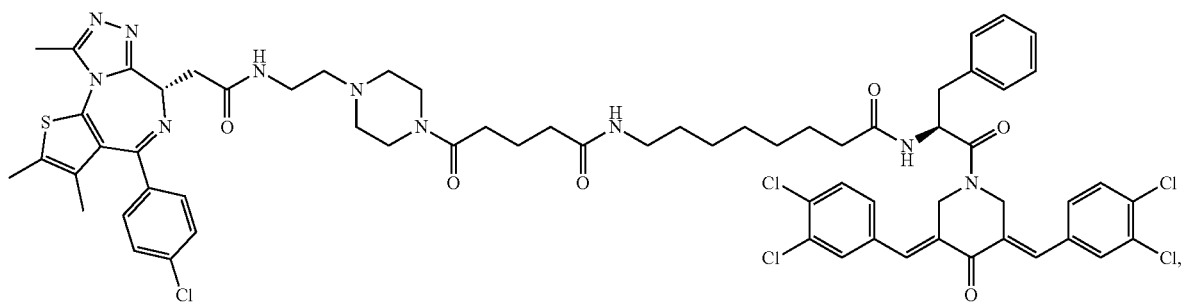

and pharmaceutically acceptable salts, solvates, hydrates, polymorphs, co-crystals, tautomers, stereoisomers, isotopically labeled derivatives, and prodrugs thereof.

In another aspect, described herein are pharmaceutical compositions including a compound described herein, and optionally a pharmaceutically acceptable excipient. In certain embodiments, a pharmaceutical composition described herein includes a therapeutically or prophylactically effective amount of a compound described herein. The pharmaceutical compositions may be useful in inducing degradation of the target (e.g., a target protein) in a subject or cell, in treating a disease (e.g., a proliferative disease) in a subject in need thereof, or in preventing a disease in a subject in need thereof. In certain embodiments, the compound being administered or used induces the degradation of a bromodomain or bromodomain-containing protein (e.g., BET proteins). In certain embodiments, the compound induces the degradation of histone methyltransferases (HMTs, e.g., enhancer of zeste homolog 1 (EZH1)). In certain embodiments, the compound induces the degradation of EZH1. In certain embodiments, the compound induces the degradation of FKBP. In certain embodiments, the compound induces the degradation of FKBP12. In certain embodiments, the compound induces the selective degradation of the target protein.

In still another aspect, described herein are kits including a container with a compound or pharmaceutical composition described herein. A kit described herein may include a single dose or multiple doses of the compound or pharmaceutical composition. The described kits may be useful in inducing the degradation of a bromodomain or bromodomain-containing protein (e.g., BET proteins) or an HMT (e.g., EZH1) in a subject, biological sample, tissue, or cell, in treating a disease associated with aberrant activity of a bromodomain or bromodomain-containing protein (e.g., BET proteins) or an HMT (e.g., EZH1) in a subject in need thereof, in preventing a disease associated with aberrant activity of a bromodomain or bromodomain-containing protein (e.g., BET proteins) or an HMT (e.g., EZH1) in a subject in need thereof, in treating a disease (e.g., a proliferative disease, inflammatory disease, autoimmune disease, genetic disease, hematological disease, neurological disease, painful condition, psychiatric disorder, or metabolic disorder) in a subject in need thereof, and/or in preventing a disease (e.g., proliferative disease, inflammatory disease, autoimmune disease, genetic disease, hematological disease, neurological disease, painful condition, psychiatric disorder, or metabolic disorder) in a subject in need thereof. In certain embodiments, a kit described herein further includes instructions for using the compound or pharmaceutical composition included in the kit.

In another aspect, the present disclosure provides methods of inducing degradation of a bromodomain or bromodomain-containing protein (e.g., BET proteins) or an HMT (e.g., EZH1) in a subject in need thereof, the methods comprising administering to the subject a therapeutically effective amount of a compound or pharmaceutical composition described herein.

In another aspect, the present disclosure provides methods of inducing the degradation of a bromodomain or bromodomain-containing protein (e.g., BET proteins) or an HMT (e.g., EZH1) in a biological sample, tissue, or cell, the methods comprising contacting the biological sample, tissue, or cell with an effective amount of a compound or pharmaceutical composition described herein.

In certain embodiments, the compound being administered or used selectively induces the degradation of a target (e.g., a target protein) (e.g., a bromodomain or bromodomain-containing protein (e.g., BET proteins), a particular HMT (e.g., EZH1), or a cytosolic signaling protein (e.g., FKBP12)). When a compound, pharmaceutical composition, method, use, or kit is referred to as "selectively," "specifically," or "competitively" inducing degradation of a target (e.g., a protein), the compound, pharmaceutical composition, method, use, or kit induces the degradation of a particular target (e.g., a target protein) to a greater extent (e.g., not less than 2-fold, not less than 5-fold, not less than 10-fold, not less than 30-fold, not less than 100-fold, not less than 1,000-fold, or not less than 10,000-fold; and/or: not more than 2-fold, not more than 5-fold, not more than 10-fold, not more than 30-fold, not more than 100-fold, not more than 1,000-fold, or not more than 10,000-fold) than another protein.

In another aspect, the present disclosure provides methods of killing cells (e.g. killing a cancer cell or tumor cell), the methods comprising contacting the cell with an effective amount of a compound or pharmaceutical composition described herein.

Another aspect of the present disclosure relates to methods of treating a disease in a subject in need thereof, the methods comprising administering to the subject a therapeutically effective amount of a compound or pharmaceutical composition described herein. In another aspect, the present disclosure provides methods of preventing a disease in a subject in need thereof, the methods comprises administering to the subject a prophylactically effective amount of a compound or pharmaceutical composition described herein.

In yet another aspect, the present disclosure provides compounds and pharmaceutical compositions described herein for use in a method of the disclosure (e.g., a method of inducing the degradation of a target (e.g., a target protein), a method of killing cells (e.g. cancer cells or tumor cells), a method of treating a disease (e.g., a proliferative disease), or a method of preventing a disease (e.g., a proliferative disease)).

DEFINITIONS

Definitions of specific functional groups and chemical terms are described in more detail below. The chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in Thomas Sorrell, *Organic Chemistry*, University Science Books, Sausalito, 1999; Smith and March, *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987. The disclosure is not intended to be limited in any manner by the exemplary listing of substituents described herein.

Compounds described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw-Hill, N Y, 1962); and Wilen, *Tables of Resolving Agents and Optical Resolutions* p. 268 (E. L. Eliel, Ed., Univ. of Notre Dame Press, Notre Dame, IN 1972). The disclosure additionally encompasses compounds described herein as individual isomers substantially free of other isomers, and alternatively, as mixtures of various isomers.

When a range of values is listed, it is intended to encompass each value and sub-range within the range. For example "$C_{1-6}$" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$.

The term "aliphatic" includes both saturated and unsaturated, straight chain (i.e., unbranched), branched, acyclic, cyclic, or polycyclic aliphatic hydrocarbons, which are optionally substituted with one or more functional groups. As will be appreciated by one of ordinary skill in the art, "aliphatic" is intended herein to include, but is not limited to, alkyl, alkenyl, alkynyl, cycloalkyl, cycloalkenyl, and cycloalkynyl moieties. Thus, the term "alkyl" includes straight, branched and cyclic alkyl groups. An analogous convention applies to other generic terms such as "alkenyl", "alkynyl", and the like. Furthermore, the terms "alkyl", "alkenyl", "alkynyl", and the like encompass both substituted and unsubstituted groups. In certain embodiments, "lower alkyl" is used to indicate those alkyl groups (cyclic, acyclic, substituted, unsubstituted, branched or unbranched) having 1-6 carbon atoms.

In certain embodiments, the alkyl, alkenyl, and alkynyl groups employed in the disclosure contain 1-20 aliphatic carbon atoms. In certain other embodiments, the alkyl, alkenyl, and alkynyl groups employed in the disclosure contain 1-10 aliphatic carbon atoms. In yet other embodiments, the alkyl, alkenyl, and alkynyl groups employed in the disclosure contain 1-8 aliphatic carbon atoms. In still other embodiments, the alkyl, alkenyl, and alkynyl groups employed in the disclosure contain 1-6 aliphatic carbon atoms. In yet other embodiments, the alkyl, alkenyl, and alkynyl groups employed in the disclosure contain 1-4 carbon atoms. Illustrative aliphatic groups thus include, but are not limited to, for example, methyl, ethyl, n-propyl, isopropyl, cyclopropyl, —CH$_2$-cyclopropyl, vinyl, allyl, n-butyl, sec-butyl, isobutyl, tert-butyl, cyclobutyl, —CH$_2$-cyclobutyl, n-pentyl, sec-pentyl, isopentyl, tert-pentyl, cyclopentyl, —CH$_2$-cyclopentyl, n-hexyl, sec-hexyl, cyclohexyl, —CH$_2$-cyclohexyl moieties and the like, which again, may bear one or more substituents. Alkenyl groups include, but are not limited to, for example, ethenyl, propenyl, butenyl, 1-methyl-2-buten-1-yl, and the like. Representative alkynyl groups include, but are not limited to, ethynyl, 2-propynyl (propargyl), 1-propynyl, and the like.

The term "alkyl" refers to a radical of a straight-chain or branched saturated hydrocarbon group having from 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$alkyl"). Examples of $C_{1-6}$ alkyl groups include methyl ($C_1$), ethyl ($C_2$), propyl ($C_3$) (e.g., n-propyl, isopropyl), butyl ($C_4$) (e.g., n-butyl, tert-butyl, sec-butyl, isobutyl), pentyl ($C_5$) (e.g., n-pentyl, 3-pentanyl, amyl, neopentyl, 3-methyl-2-butanyl, tertiary amyl), and hexyl ($C_6$) (e.g., n-hexyl). Additional examples of alkyl groups include n-heptyl ($C_7$), n-octyl (C), and the like. Unless otherwise specified, each instance of an alkyl group is independently unsubstituted (an "unsubstituted alkyl") or substituted (a "substituted alkyl") with one or more substituents (e.g., halogen, such as F). In certain embodiments, the alkyl group is an unsubstituted $C_{1-10}$ alkyl (such as unsubstituted $C_{1-6}$ alkyl, e.g., —CH$_3$ (Me), unsubstituted ethyl (Et), unsubstituted propyl (Pr, e.g., unsubstituted n-propyl (n-Pr), unsubstituted isopropyl (i-Pr)), unsubstituted butyl (Bu, e.g., unsubstituted n-butyl (n-Bu), unsubstituted tert-butyl (tert-Bu or t-Bu), unsubstituted sec-butyl (sec-Bu), unsubstituted isobutyl (i-Bu)). In certain embodiments, the alkyl group is a substituted $C_{1-10}$ alkyl (such as substituted $C_{1-6}$ alkyl, e.g., —CF$_3$, Bn).

"Alkenyl" refers to a radical of a straight-chain or branched hydrocarbon group having from 2 to 20 carbon atoms, one or more carbon-carbon double bonds, and no triple bonds ("$C_{2-20}$ alkenyl"). In some embodiments, an alkenyl group has 2 to 10 carbon atoms ("$C_{2-10}$ alkenyl"). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like.

Examples of $C_{2-6}$alkenyl groups include the aforementioned $C_{2-4}$alkenyl groups as well as pentenyl ($C_5$), pentadienyl (C), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently optionally substituted, i.e., unsubstituted (an "unsubstituted alkenyl") or substituted (a "substituted alkenyl") with one or more substituents. In certain embodiments, the alkenyl group is unsubstituted $C_{2-10}$ alkenyl. In certain embodiments, the alkenyl group is substituted $C_{2-10}$ alkenyl. In an alkenyl group, a C=C double bond for which the stereochemistry is not specified (e.g., —CH=CHCH$_3$ or

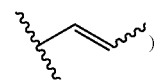
)

may be an (E)- or (Z)-double bond.

"Alkynyl" refers to a radical of a straight-chain or branched hydrocarbon group having from 2 to 20 carbon atoms, one or more carbon-carbon triple bonds, and optionally one or more double bonds ("$C_{2-20}$ alkynyl"). In some embodiments, an alkynyl group has 2 to 10 carbon atoms ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like. Unless otherwise specified, each instance of an alkynyl group is independently optionally substituted, i.e., unsubstituted (an "unsubstituted alkynyl") or substituted (a "substituted alkynyl") with one or more substituents. In certain embodiments, the alkynyl group is unsubstituted $C_{2-10}$ alkynyl. In certain embodiments, the alkynyl group is substituted $C_{2-10}$ alkynyl.

"Carbocyclyl" or "carbocyclic" refers to a radical of a non-aromatic cyclic hydrocarbon group having from 3 to 10 ring carbon atoms ("$C_{3-10}$ carbocyclyl") and zero heteroatoms in the non-aromatic ring system. In some embodiments, a carbocyclyl group has 3 to 8 ring carbon atoms ("$C_{3-8}$ carbocyclyl"). In some embodiments, a carbocyclyl group has 3 to 6 ring carbon atoms ("$C_{3-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include, without limitation, the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl (C), and the like. Exemplary $C_{3-10}$ carbocyclyl groups include, without limitation, the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or contain a fused, bridged or spiro ring system such as a bicyclic system ("bicyclic carbocyclyl") and can be saturated or can be partially unsaturated. "Carbocyclyl" also includes ring systems wherein the carbocyclic ring, as defined above, is fused with one or more aryl or heteroaryl groups wherein the point of attachment is on the carbocyclic ring, and in such instances, the number of carbons continue to designate the number of carbons in the carbocyclic ring system. Unless otherwise specified, each instance of a carbocyclyl group is independently optionally substituted, i.e., unsubstituted (an "unsubstituted carbocyclyl") or substituted (a "substituted carbocyclyl") with one or more substituents. In certain embodiments, the carbocyclyl group is unsubstituted $C_{3-10}$ carbocyclyl. In certain embodiments, the carbocyclyl group is substituted $C_{3-10}$ carbocyclyl.

In some embodiments, "carbocyclyl" is a monocyclic, saturated carbocyclyl group having from 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_5$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl (C). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is unsubstituted $C_{3-10}$ cycloalkyl. In certain embodiments, the cycloalkyl group is substituted $C_{3-10}$ cycloalkyl.

"Heterocyclyl" or "heterocyclic" refers to a radical of a 3- to 10-membered non-aromatic ring system having ring carbon atoms and 1 to 4 ring heteroatoms, wherein each heteroatom is independently selected from nitrogen, oxygen, sulfur, boron, phosphorus, and silicon ("3-10 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged, or spiro ring system, such as a bicyclic system ("bicyclic heterocyclyl"), and can be saturated or can be partially unsaturated. Heterocyclyl bicyclic ring systems can include one or more heteroatoms in one or both rings. "Heterocyclyl" also includes ring systems wherein the heterocyclic ring, as defined above, is fused with one or more carbocyclyl groups wherein the point of attachment is either on the carbocyclyl or heterocyclic ring, or ring systems wherein the heterocyclic ring, as defined above, is fused with one or more aryl or heteroaryl groups, wherein the point of attachment is on the heterocyclic ring, and in such instances, the number of ring members continue to designate the number of ring members in the heterocyclic ring system. Unless otherwise specified, each instance of heterocyclyl is independently optionally substituted, i.e., unsubstituted (an "unsubstituted heterocyclyl") or substituted (a "substituted heterocyclyl") with one or more substituents. In certain embodiments, the heterocyclyl group is unsubstituted 3-10 membered heterocyclyl. In certain embodiments, the heterocyclyl group is substituted 3-10 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, sulfur, boron, phosphorus, and silicon ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has one ring heteroatom selected from nitrogen, oxygen, and sulfur.

Exemplary 3-membered heterocyclyl groups containing one heteroatom include, without limitation, azirdinyl, oxiranyl, and thiiranyl. Exemplary 4-membered heterocyclyl groups containing one heteroatom include, without limitation, azetidinyl, oxetanyl, and thietanyl. Exemplary 5-membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl groups containing two heteroatoms include, without limitation, dioxolanyl, oxasulfuranyl, disulfuranyl, and oxazolidin-2-one. Exemplary 5-membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl, tetrahydropyranyl, dihydropyridinyl, and thianyl. Exemplary 6-membered heterocyclyl groups containing two heteroatoms include, without limitation, piperazinyl, morpholinyl, dithianyl, and dioxanyl. Exemplary 6-membered heterocyclyl groups containing two heteroatoms include, without limitation, triazinanyl. Exemplary 7-membered heterocyclyl groups containing one heteroatom include, without limitation, azepanyl, oxepanyl and thiepanyl. Exemplary 8-membered heterocyclyl groups containing one heteroatom include, without limitation, azocanyl, oxecanyl and thiocanyl. Exemplary 5-membered heterocyclyl groups fused to a $C_6$ aryl ring (also referred to herein as a 5,6-bicyclic heterocyclic ring) include, without limitation, indolinyl, isoindolinyl, dihydrobenzofuranyl, dihydrobenzothienyl, benzoxazolinonyl, and the like. Exemplary 6-membered heterocyclyl groups fused to an aryl ring (also referred to herein as a 6,6-bicyclic heterocyclic ring) include, without limitation, tetrahydroquinolinyl, tetrahydroisoquinolinyl, and the like.

"Aryl" refers to a radical of a monocyclic or polycyclic (e.g., bicyclic or tricyclic) 4n+2 aromatic ring system (e.g., having 6, 10, or 14 pi electrons shared in a cyclic array) having 6-14 ring carbon atoms and zero heteroatoms provided in the aromatic ring system ("$C_{6-14}$ aryl"). In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl). In some embodiments, an aryl group has fourteen ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently optionally substituted, i.e., unsubstituted (an "unsubstituted aryl") or substituted (a "substituted aryl") with one or more substituents. In certain embodiments, the aryl group is unsubstituted $C_{6-14}$ aryl. In certain embodiments, the aryl group is substituted $C_{6-14}$ aryl.

"Aralkyl" is a subset of alkyl and aryl and refers to an optionally substituted alkyl group substituted by an optionally substituted aryl group. In certain embodiments, the aralkyl is optionally substituted benzyl. In certain embodiments, the aralkyl is benzyl. In certain embodiments, the aralkyl is optionally substituted phenethyl. In certain embodiments, the aralkyl is phenethyl.

"Heteroaryl" refers to a radical of a 5-10 membered monocyclic or bicyclic 4n+2 aromatic ring system (e.g., having 6 or 10 pi electrons shared in a cyclic array) having ring carbon atoms and 1-4 ring heteroatoms provided in the aromatic ring system, wherein each heteroatom is independently selected from nitrogen, oxygen and sulfur ("5-10 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently optionally substituted, i.e., unsubstituted (an "unsubstituted heteroaryl") or substituted (a "substituted heteroaryl") with one or more substituents. In certain embodiments, the heteroaryl group is unsubstituted 5-14 membered heteroaryl. In certain embodiments, the heteroaryl group is substituted 5-14 membered heteroaryl.

Exemplary 5-membered heteroaryl groups containing one heteroatom include, without limitation, pyrrolyl, furanyl, and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl.

"Heteroaralkyl" is a subset of alkyl and heteroaryl and refers to an optionally substituted alkyl group substituted by an optionally substituted heteroaryl group.

"Unsaturated" or "partially unsaturated" refers to a group that includes at least one double or triple bond. A "partially unsaturated" ring system is further intended to encompass rings having multiple sites of unsaturation, but is not intended to include aromatic groups (e.g., aryl or heteroaryl groups). Likewise, "saturated" refers to a group that does not contain a double or triple bond, i.e., contains all single bonds.

Alkyl, alkenyl, alkynyl, carbocyclyl, heterocyclyl, aryl, and heteroaryl groups, which are divalent bridging groups, are further referred to using the suffix -ene, e.g., alkylene, alkenylene, alkynylene, carbocyclylene, heterocyclylene, arylene, and heteroarylene.

An atom, moiety, or group described herein may be unsubstituted or substituted, as valency permits, unless otherwise provided expressly. The term "optionally substituted" refers to substituted or unsubstituted.

A group is optionally substituted unless expressly provided otherwise. The term "optionally substituted" refers to being substituted or unsubstituted. In certain embodiments, alkyl, alkenyl, alkynyl, carbocyclyl, heterocyclyl, aryl, and heteroaryl groups are optionally substituted (e.g., "substituted" or "unsubstituted" alkyl, "substituted" or "unsubstituted" alkenyl, "substituted" or "unsubstituted" alkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present disclosure contemplates any and all such combinations in order to arrive at a stable compound. For purposes of this disclosure, heteroatoms such as nitrogen may have hydrogen substituents and/or any suitable substituent as described herein which satisfy the valencies of the heteroatoms and results in the formation of a stable moiety. In certain embodiments, the substituent is a carbon atom substituent. In certain embodiments, the substituent is a nitrogen atom substituent. In certain embodiments, the substituent is an oxygen atom substituent. In certain embodiments, the substituent is a sulfur atom substituent.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$—C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)(R$^{aa}$)$_2$, —P(=O)(OR$^{cc}$)$_2$, —OP(=O)(R$^{aa}$)$_2$, —OP(=O)(OR$^{cc}$)$_2$, —P(=O)(N(R$^{bb}$)$_2$)$_2$, —OP(=O)(N(R$^{bb}$)$_2$)$_2$, —NR$^{bb}$P(=O)(R$^{aa}$)$_2$, —NR$^{bb}$P(=O)(OR$^{cc}$)$_2$, —NR$^{bb}$P(=O)(N(R$^{bb}$)$_2$)$_2$, —P(R$^{cc}$)$_2$, —P(OR$^{cc}$)$_2$, —P(R$^{cc}$)$_3^+$X$^-$, —P(OR$^{cc}$)$_3^+$X$^-$, —P(R$^{cc}$)$_4$, —P(OR$^{cc}$)$_4$, —OP(R$^{cc}$)$_2$, —OP(R$^{cc}$)$_3^+$X$^-$, —OP(OR$^{cc}$)$_2$, —OP(OR$^{cc}$)$_3^+$X$^-$, —OP(R$^{cc}$)$_4$, —OP(OR$^{cc}$)$_4$, —B(R$^{aa}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups; wherein X$^-$ is a counterion;

or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$; each instance of R$^{aa}$ is, independently, selected from C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)(R$^{aa}$)$_2$, —P(=O)(OR$^{cc}$)$_2$, —P(=O)(N(R$^{cc}$)$_2$)$_2$, C$_{1-10}$ alkyl, C$_{1-10}$ perhaloalkyl, C$_{2-10}$ alkenyl, C$_{2-10}$ alkynyl, heteroC$_{1-10}$alkyl, heteroC$_{2-10}$alkenyl, heteroC$_{2-10}$alkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups; wherein X$^-$ is a counterion;

each instance of R$^{cc}$ is, independently, selected from hydrogen, C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)(OR$^{ee}$)$_2$, —P(=O)(R$^{ee}$)$_2$, —OP(=O)(R$^{ee}$)$_2$, —OP(=O)(OR$^{ee}$)$_2$, C$_{1-6}$ alkyl, C$_{1-6}$ perhaloalkyl, C$_{2-6}$ alkenyl, C$_{2-6}$ alkynyl, heteroC$_{1-6}$alkyl, heteroC$_{2-6}$alkenyl, heteroC$_{2-6}$alkynyl, C$_{3-10}$ carbocyclyl, 3-10 membered heterocyclyl, C$_{6-10}$ aryl, 5-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups, or two geminal R$^{dd}$ substituents can be joined to form =O or =S; wherein X$^-$ is a counterion;

each instance of R$^{ee}$ is, independently, selected from C$_{1-6}$ alkyl, C$_{1-6}$ perhaloalkyl, C$_{2-6}$ alkenyl, C$_{2-6}$ alkynyl, heteroC$_{1-6}$ alkyl, heteroC$_{2-6}$alkenyl, heteroC$_{2-6}$ alkynyl, C$_{3-10}$ carbocyclyl, C$_{6-10}$ aryl, 3-10 membered heterocyclyl, and 3-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups;

each instance of $R^{ff}$ is, independently, selected from hydrogen, $C_{1-6}$ alkyl, $C_{1-6}$ perhaloalkyl, $C_{2-6}$ alkenyl, $C_{2-6}$ alkynyl, heteroC$_{1-6}$alkyl, heteroC$_{2-6}$alkenyl, heteroC$_{2-6}$ alkynyl, $C_{3-10}$ carbocyclyl, 3-10 membered heterocyclyl, $C_{6-10}$ aryl and 5-10 membered heteroaryl, or two $R^{ff}$ groups are joined to form a 3-10 membered heterocyclyl or 5-10 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups; and each instance of $R^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3$$^+$X$^-$, —NH(C$_{1-6}$ alkyl)$_2$$^+$X$^-$, —NH$_2$(C$_{1-6}$ alkyl)$^+$X$^-$, —NH$_3$$^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —CO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$—C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)(OC$_{1-6}$ alkyl)$_2$, —P(=O)(C$_{1-6}$ alkyl)$_2$, —OP(=O)(C$_{1-6}$ alkyl)$_2$, —OP(=O)(OC$_{1-6}$ alkyl)$_2$, C$_{1-6}$ alkyl, C$_{1-6}$ perhaloalkyl, C$_{2-6}$ alkenyl, C$_{2-6}$ alkynyl, heteroC$_{1-6}$alkyl, heteroC$_{2-6}$alkenyl, heteroC$_{2-6}$alkynyl, C$_{3-10}$ carbocyclyl, C$_{6-10}$ aryl, 3-10 membered heterocyclyl, 5-10 membered heteroaryl; or two geminal $R^{gg}$ substituents can be joined to form =O or =S; wherein X$^-$ is a counterion.

A "counterion" or "anionic counterion" is a negatively charged group associated with a positively charged group in order to maintain electronic neutrality. An anionic counterion may be monovalent (i.e., including one formal negative charge). An anionic counterion may also be multivalent (i.e., including more than one formal negative charge), such as divalent or trivalent. Exemplary counterions include halide ions (e.g., F$^-$, Cl$^-$, Br$^-$, I$^-$), NO$_3$$^-$, ClO$_4$$^-$, OH$^-$, H$_2$PO$_4$$^-$, HCO$_3$$^-$, HSO$_4$$^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), carboxylate ions (e.g., acetate, propanoate, benzoate, glycerate, lactate, tartrate, glycolate, gluconate, and the like), BF$_4$$^-$, PF$_4$$^-$, PF$_6$$^-$, AsF$_6$$^-$, SbF$_6$$^-$, B[3,5-(CF$_3$)$_2$C$_6$H$_3$]$_4$$^-$, B(C$_6$F$_5$)$_4$$^-$, BPh$_4$$^-$, Al(OC(CF$_3$)$_3$)$_4$$^-$, and carborane anions (e.g., CB$_{11}$H$_{12}$$^-$ or (HCB$_{11}$Me$_5$Br$_6$)$^-$). Exemplary counterions which may be multivalent include CO$_3$$^{2-}$, HPO$_4$$^{2-}$, PO$_4$$^{3-}$, B$_4$O$_7$$^{2-}$, SO$_4$$^{2-}$, S$_2$O$_3$$^{2-}$, carboxylate anions (e.g., tartrate, citrate, fumarate, maleate, malate, malonate, gluconate, succinate, glutarate, adipate, pimelate, suberate, azelate, sebacate, salicylate, phthalates, aspartate, glutamate, and the like), and carboranes.

"Halo" or "halogen" refers to fluorine (fluoro, —F), chlorine (chloro, —Cl), bromine (bromo, —Br), or iodine (iodo, —I).

"Acyl" refers to a moiety selected from the group consisting of —C(=O)R$^{aa}$, —CHO, —CO$_2$R$^{aa}$, —C(=O)N(R$^{bb}$)$_2$, —C(=NR$^{bb}$)R$^{aa}$, —C(=NR$^{bb}$)OR$^{aa}$, —C(=NR$^{bb}$)N(R$^{bb}$)$_2$, —C(=O)NR$^{bb}$SO$_2$R$^{aa}$, —C(=S)N(R$^{bb}$)$_2$, —C(=O)SR$^{aa}$, or —C(=S)SR$^{aa}$, wherein R$^{aa}$ and R$^{bb}$ are as defined herein.

Nitrogen atoms can be substituted or unsubstituted as valency permits, and include primary, secondary, tertiary, and quaternary nitrogen atoms. Exemplary nitrogen atom substituents include, but are not limited to, hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{bb}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)(OR$^{cc}$)$_2$, —P(=O)(R$^{aa}$)$_2$, —P(=O)(N(R$^{cc}$)$_2$)$_2$, C$_{1-10}$ alkyl, C$_{1-10}$ perhaloalkyl, C$_{2-10}$ alkenyl, C$_{2-10}$ alkynyl, heteroC$_{1-10}$alkyl, heteroC$_{2-10}$alkenyl, heteroC$_{2-10}$alkynyl, C$_{3-10}$ carbocyclyl, 3-14 membered heterocyclyl, C$_{6-14}$ aryl, and 5-14 membered heteroaryl, or two R$^{cc}$ groups attached to an N atom are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined above.

In certain embodiments, the substituent present on the nitrogen atom is an nitrogen protecting group (also referred to herein as an "amino protecting group"). Nitrogen protecting groups include, but are not limited to, —OH, —OR$^{aa}$, —N(R$^{cc}$)$_2$, —C(=O)R$^{aa}$, —C(=O)N(R$^{cc}$)$_2$, —CO$_2$R$^{aa}$, —SO$_2$R$^{aa}$, —C(=NR$^{cc}$)R$^{aa}$, —C(=NR$^{cc}$)OR$^{aa}$, —C(=NR)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, C$_{1-10}$ alkyl (e.g., aralkyl, heteroaralkyl), C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl groups, wherein each alkyl, alkenyl, alkynyl, heteroalkyl, heteroalkenyl, heteroalkynyl, carbocyclyl, heterocyclyl, aralkyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined herein. Nitrogen protecting groups are well known in the art and include those described in detail in Protecting Groups in Organic Synthesis, T. W. Greene and P. G. M. Wuts, 3$^{rd}$ edition, John Wiley & Sons, 1999, incorporated herein by reference.

For example, nitrogen protecting groups such as amide groups (e.g., —C(=O)R$^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide and o-(benzoyloxymethyl)benzamide.

Nitrogen protecting groups such as carbamate groups (e.g., —C(=O)OR$^{aa}$) include, but are not limited to, methyl carbamate, ethyl carbamate, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC or Boc), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitrobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium)benzyl carbamate, and 2,4,6-trimethylbenzyl carbamate.

Nitrogen protecting groups such as sulfonamide groups (e.g., —S(=O)$_2$R$^{aa}$) include, but are not limited to, p-toluenesulfonamide (Ts), benzenesulfonamide, 2,3,6-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), 3-trimethylsilylethanesulfonamide (SES), 9-anthracenesulfonamide, 4-(4',8'-dimethoxynaphthylmethyl)benzenesulfonamide (DN/IBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

In certain embodiments, the substituent present on an oxygen atom is an oxygen protecting group (also referred to herein as an "hydroxyl protecting group"). Oxygen protecting groups include, but are not limited to, —R$^{aa}$, —N(R$^{bb}$)$_2$, —C(=O)SR$^{aa}$, —C(=O)R$^{aa}$, —CO$_2$R$^{aa}$, —C(=O)N(R$^{bb}$)$_2$, —C(=NR$^{bb}$)R$^{aa}$, —C(=NR$^{bb}$)OR$^{aa}$, —C(=NR$^{bb}$)N(R$^{bb}$)$_2$, —S(=O)R$^{aa}$, —SO$_2$R$^{aa}$, —Si(R$^{aa}$)$_3$, —P(R$^{cc}$)$_2$, —P(R$^{cc}$)$_3$$^+$X$^-$, —P(OR$^{cc}$)$_2$, —P(OR$^{cc}$)$_3$$^+$X$^-$, —P(=O)(R$^{aa}$)$_2$, —P(=O)(OR$^{cc}$)$_2$, and —P(=O)(N(R$^{bb}$)$_2$)$_2$, wherein X$^-$, R$^{aa}$, R$^{bb}$, and R$^{cc}$ are as defined herein. Oxygen protecting groups are well known in the art and include those described in detail in Protecting Groups in Organic Synthesis, T. W. Greene and P. G. M. Wuts, 3$^{rd}$ edition, John Wiley & Sons, 1999, incorporated herein by reference.

Exemplary oxygen protecting groups include, but are not limited to, methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4''-tris(4,5-dichlorophthalimidophenyl)methyl, 4,4',4''-tris(levulinoyloxyphenyl)methyl, 4,4',4''-tris(benzoyloxyphenyl)methyl, 3-(imidazol-1-yl)bis(4',4''-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), methyl carbonate, 9-fluorenylmethyl carbonate (Fmoc), ethyl carbonate, 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), isobutyl carbonate, vinyl carbonate, allyl carbonate, t-butyl carbonate (BOC or Boc), p-nitrophenyl carbonate, benzyl carbonate, p-methoxybenzyl carbonate, 3,4-dimethoxybenzyl carbonate, o-nitrobenzyl carbonate, p-nitrobenzyl carbonate, S-benzyl thiocarbonate, 4-ethoxy-1-napthtyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

In certain embodiments, the substituent present on a sulfur atom is a sulfur protecting group (also referred to as a "thiol protecting group"). Sulfur protecting groups include, but are not limited to, —$R^{aa}$, —$N(R^{bb})_2$, —$C(=O)SR^{aa}$, —$C(=O)R^{aa}$, —$CO_2R^{aa}$, —$C(=O)N(R^{bb})_2$, —$C(=NR^{bb})$ $R^{aa}$, —$C(=NR^{bb})OR^{aa}$, —$C(=NR^{bb})N(R^{bb})_2$, —$S(=O)$ $R^{aa}$, —$SO_2R^{aa}$, —$Si(R^{aa})_3$, —$P(R^{cc})_2$, —$P(R^{cc})_3^+X^-$, —$P(OR^{cc})_2$, —$P(OR^{cc})_3^+X^-$, —$P(=O)(R^{aa})_2$, —$P(=O)$ $(OR^{cc})_2$, and —$P(=O)(N(R^{bb})_2)_2$, wherein $R^{aa}$, $R^{bb}$, and $R^{cc}$ are as defined herein. Sulfur protecting groups are well known in the art and include those described in detail in Protecting Groups in Organic Synthesis, T. W. Greene and P. G. M. Wuts, 3$^{rd}$ edition, John Wiley & Sons, 1999, incorporated herein by reference.

As used herein, a "leaving group" (LG) is an art-understood term referring to a molecular fragment that departs with a pair of electrons in heterolytic bond cleavage, wherein the molecular fragment is an anion or neutral molecule. As used herein, a leaving group can be an atom or a group capable of being displaced by a nucleophile. See, for example, Smith, March Advanced Organic Chemistry 6th ed. (501-502). Exemplary leaving groups include, but are not limited to, halo (e.g., chloro, bromo, iodo) and activated substituted hydroxyl groups (e.g., —$OC(=O)SR^{aa}$, —$OC(=O)R^{aa}$, —$OCO_2R^{aa}$, —$OC(=O)N(R^{bb})_2$, —$OC(=NR^{bb})R^{aa}$, —$OC(=NR^{bb})OR^{aa}$, —$OC(=NR^{bb})N(R^{bb})_2$, —$OS(=O)R^{aa}$, —$OSO_2R^{aa}$, —$OP(R^{cc})_2$, —$OP(R^{cc})_3$, —$OP(=O)_2R^{aa}$, —$OP(=O)(R^{aa})_2$, —$OP(=O)(OR^{cc})_2$, —$OP(=O)_2N(R^{bb})_2$, and —$OP(=O)(NR^{bb})_2$, wherein $R^{aa}$, $R^{bb}$, and $R^{cc}$ are as defined herein).

A "hydrocarbon chain" refers to a substituted or unsubstituted divalent alkyl, alkenyl, or alkynyl group. A hydrocarbon chain includes (1) one or more chains of carbon atoms immediately between the two radicals of the hydrocarbon chain; (2) optionally one or more hydrogen atoms on the chain(s) of carbon atoms; and (3) optionally one or more substituents ("non-chain substituents," which are not hydrogen) on the chain(s) of carbon atoms. A chain of carbon atoms consists of consecutively connected carbon atoms ("chain atoms") and does not include hydrogen atoms or heteroatoms. However, a non-chain substituent of a hydrocarbon chain may include any atoms, including hydrogen atoms, carbon atoms, and heteroatoms. For example, hydrocarbon chain —$C^AH(C^BH_2C^CH_3)$— includes one chain atom $C^A$, one hydrogen atom on $C^A$, and non-chain substituent —$(C^BH_2C^CH_3)$. The term "$C_X$ hydrocarbon chain," wherein x is a positive integer, refers to a hydrocarbon chain that includes x number of chain atom(s) between the two radicals of the hydrocarbon chain. If there is more than one possible value of x, the smallest possible value of x is used for the definition of the hydrocarbon chain. For example, —$CH(C_2H_5)$— is a $C_1$ hydrocarbon chain, and

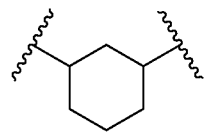 [SMILES: *C1CCCC(*)C1]

is a $C_3$ hydrocarbon chain. When a range of values is used, the meaning of the range is as described herein. For example, a $C_{3-10}$ hydrocarbon chain refers to a hydrocarbon chain where the number of chain atoms of the shortest chain of carbon atoms immediately between the two radicals of the hydrocarbon chain is 3, 4, 5, 6, 7, 8, 9, or 10. A hydrocarbon chain may be saturated (e.g., —$(CH_2)_4$—). A hydrocarbon chain may also be unsaturated and include one or more C=C and/or C≡C bonds anywhere in the hydrocarbon chain. For instance, —CH=CH—$(CH_2)_2$—, —$CH_2$—C=C—$CH_2$—, and —C≡C—CH=CH— are all examples of a unsubstituted and unsaturated hydrocarbon chain. In certain embodiments, the hydrocarbon chain is unsubstituted (e.g., —C≡C— or —$(CH_2)_4$—). In certain embodiments, the hydrocarbon chain is substituted (e.g., —CH(C$_2$H$_5$)— and —CF$_2$—). Any two substituents on the hydrocarbon chain may be joined to form an optionally substituted carbocyclyl, optionally substituted heterocyclyl, optionally substituted aryl, or optionally substituted heteroaryl ring. For instance,

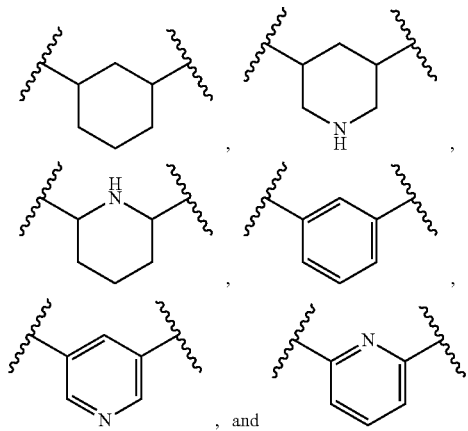

are all examples of a hydrocarbon chain. In contrast, in certain embodiments,

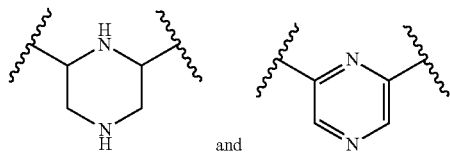 [SMILES: *C1CNCC(*)N1 ; *c1cncc(*)n1]

are not within the scope of the hydrocarbon chains described herein. When a chain atom of a C$_x$ hydrocarbon chain is replaced with a heteroatom, the resulting group is referred to as a C$_x$ hydrocarbon chain wherein a chain atom is replaced with a heteroatom, as opposed to a C$_{x-1}$ hydrocarbon chain. For example,

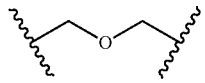 [SMILES: *COC*]

is a C$_3$ hydrocarbon chain wherein one chain atom is replaced with an oxygen atom.

The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well known in the art. For example, Berge et al., describe pharmaceutically acceptable salts in detail in J. Pharmaceutical Sciences, 1977, 66, 1-19, incorporated herein by reference. Pharmaceutically acceptable salts of the compounds described herein include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid, and perchloric acid or with organic acids such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and N$^+$(C$_{1-4}$ alkyl)$_4^-$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

As used herein, use of the phrase "at least one instance" refers to 1, 2, 3, 4, or more instances, but also encompasses a range, e.g., for example, from 1 to 4, from 1 to 3, from 1 to 2, from 2 to 4, from 2 to 3, or from 3 to 4 instances, inclusive.

A "non-hydrogen group" refers to any group that is defined for a particular variable that is not hydrogen.

These and other exemplary substituents are described in more detail in the Detailed Description, Examples, and claims. The invention is not intended to be limited in any manner by the above exemplary listing of substituents.

Other Definitions

The following definitions are more general terms used throughout the present application.

As used herein, the term "salt" refers to any and all salts, and encompasses pharmaceutically acceptable salts.

The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well known in the art. For example, Berge et al. describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids, such as hydrochloric acid, hydrobromic acid, phosphoric acid, sulfuric acid, and perchloric acid or with organic acids, such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium, and $N^+(C_{1-4}\text{ alkyl})_4^-$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

The term "solvate" refers to forms of the compound, or a salt thereof, that are associated with a solvent, usually by a solvolysis reaction. This physical association may include hydrogen bonding. Conventional solvents include water, methanol, ethanol, acetic acid, DMSO, THF, diethyl ether, and the like. The compounds described herein may be prepared, e.g., in crystalline form, and may be solvated. Suitable solvates include pharmaceutically acceptable solvates and further include both stoichiometric solvates and non-stoichiometric solvates. In certain instances, the solvate will be capable of isolation, for example, when one or more solvent molecules are incorporated in the crystal lattice of a crystalline solid. "Solvate" encompasses both solution-phase and isolatable solvates. Representative solvates include hydrates, ethanolates, and methanolates.

The term "hydrate" refers to a compound that is associated with water. Typically, the number of the water molecules contained in a hydrate of a compound is in a definite ratio to the number of the compound molecules in the hydrate. Therefore, a hydrate of a compound may be represented, for example, by the general formula $R \cdot x\ H_2O$, wherein R is the compound, and x is a number greater than 0. A given compound may form more than one type of hydrate, including, e.g., monohydrates (x is 1), lower hydrates (x is a number greater than 0 and smaller than 1, e.g., hemihydrates ($R \cdot 0.5\ H_2O$)), and polyhydrates (x is a number greater than 1, e.g., dihydrates ($R \cdot 2\ H_2O$) and hexahydrates ($R \cdot 6\ H_2O$)).

The term "tautomers" or "tautomeric" refers to two or more interconvertible compounds resulting from at least one formal migration of a hydrogen atom and at least one change in valency (e.g., a single bond to a double bond, a triple bond to a single bond, or vice versa). The exact ratio of the tautomers depends on several factors, including temperature, solvent, and pH. Tautomerizations (i.e., the reaction providing a tautomeric pair) may catalyzed by acid or base. Exemplary tautomerizations include keto-to-enol, amide-to-imide, lactam-to-lactim, enamine-to-imine, and enamine-to-(a different enamine) tautomerizations.

It is also to be understood that compounds that have the same molecular formula but differ in the nature or sequence of bonding of their atoms or the arrangement of their atoms in space are termed "isomers". Isomers that differ in the arrangement of their atoms in space are termed "stereoisomers".

Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The term "polymorphs" refers to a crystalline form of a compound (or a salt, hydrate, or solvate thereof). All polymorphs have the same elemental composition. Different crystalline forms usually have different X-ray diffraction patterns, infrared spectra, melting points, density, hardness, crystal shape, optical and electrical properties, stability, and solubility. Recrystallization solvent, rate of crystallization, storage temperature, and other factors may cause one crystal form to dominate. Various polymorphs of a compound can be prepared by crystallization under different conditions.

The term "prodrugs" refers to compounds that have cleavable groups and become by solvolysis or under physiological conditions the compounds described herein, which are pharmaceutically active in vivo. Such examples include, but are not limited to, choline ester derivatives and the like, N-alkylmorpholine esters and the like. Other derivatives of the compounds described herein have activity in both their acid and acid derivative forms, but in the acid sensitive form often offer advantages of solubility, tissue compatibility, or delayed release in the mammalian organism (see, Bundgard, H., *Design of Prodrugs*, pp. 7-9, 21-24, Elsevier, Amsterdam 1985). Prodrugs include acid derivatives well known to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides, and anhydrides derived from acidic groups pendant on the compounds described herein are particular prodrugs. In some cases it is desirable to prepare double ester type prodrugs such as (acyloxy)alkyl esters or ((alkoxycarbonyl)oxy)alkylesters. $C_1$-$C_8$ alkyl, $C_2$-$C_8$ alkenyl, $C_2$-$C_8$ alkynyl, aryl, $C_7$-$C_{12}$ substituted aryl, and $C_7$-$C_{12}$ arylalkyl esters of the compounds described herein may be preferred.

As used herein the term "inhibit" or "inhibition" in the context of enzymes, for example, in the context of an enzyme, refers to a reduction in the level of protein by promoting degradation of the protein. The reduction in the level of protein thus reduces the level of the activity of the protein. In some embodiments, the term refers to a reduction of the level of enzyme activity, e.g., histone methyltransferase activity, to a level that is statistically significantly lower than an initial level, which may, for example, be a baseline level of enzyme activity. In some embodiments, the term refers to a reduction of the level of enzyme activity, e.g., histone methyltransferase activity, to a level that is less than 75%, less than 50%, less than 40%, less than 30%, less than 25%, less than 20%, less than 10%, less than 9%, less than 8%, less than 7%, less than 6%, less than 5%, less than 4%, less than 3%, less than 2%, less than 1%, less than 0.5%, less than 0.1%, less than 0.01%, less than 0.001%, or less than 0.0001% of an initial level, which may, for example, be a baseline level of enzyme activity.

When a compound, pharmaceutical composition, method, use, or kit is referred to as "selectively," "specifically," or "competitively" inhibiting a target enzyme (e.g., a HMT), the compound, pharmaceutical composition, method, use, or kit inhibits the target enzyme (e.g., a HMT), to a greater extent (e.g., not less than 2-fold, not less than 5-fold, not less than 10-fold, not less than 30-fold, not less than 100-fold, not less than 1,000-fold, or not less than 10,000-fold; and/or: not more than 2-fold, not more than 5-fold, not more than 10-fold, not more than 30-fold, not more than 100-fold, not more than 1,000-fold, or not more than 10,000-fold) than inhibiting a different target enzyme.

The term "aberrant activity" refers to activity deviating from normal activity. In certain embodiments, the aberrant activity is increased activity. In certain embodiments, the aberrant activity is decreased activity. The term "increased activity" refers to activity higher than normal activity. The term "decreased activity" refers to activity lower than normal activity.

The terms "composition" and "formulation" are used interchangeably.

A "subject" to which administration is contemplated refers to a human (i.e., male or female of any age group, e.g., pediatric subject (e.g., infant, child, or adolescent) or adult subject (e.g., young adult, middle-aged adult, or senior adult)) or non-human animal. In certain embodiments, the non-human animal is a mammal (e.g., primate (e.g., cynomolgus monkey or rhesus monkey), commercially relevant mammal (e.g., cattle, pig, horse, sheep, goat, cat, or dog), or bird (e.g., commercially relevant bird, such as chicken, duck, goose, or turkey)). In certain embodiments, the non-human animal is a fish, reptile, or amphibian. The non-human animal may be a male or female at any stage of development. The non-human animal may be a transgenic animal or genetically engineered animal. A "patient" refers to a human subject in need of treatment of a disease. The subject may also be a plant. In certain embodiments, the plant is a land plant. In certain embodiments, the plant is a non-vascular land plant. In certain embodiments, the plant is a vascular land plant. In certain embodiments, the plant is a seed plant. In certain embodiments, the plant is a cultivated plant. In certain embodiments, the plant is a dicot. In certain embodiments, the plant is a monocot. In certain embodiments, the plant is a flowering plant. In some embodiments, the plant is a cereal plant, e.g., maize, corn, wheat, rice, oat, barley, rye, or millet. In some embodiments, the plant is a legume, e.g., a bean plant, e.g., soybean plant. In some embodiments, the plant is a tree or shrub.

The term "biological sample" refers to any sample including tissue samples (such as tissue sections and needle biopsies of a tissue); cell samples (e.g., cytological smears (such as Pap or blood smears) or samples of cells obtained by microdissection); samples of whole organisms (such as samples of yeasts or bacteria); or cell fractions, fragments or organelles (such as obtained by lysing cells and separating the components thereof by centrifugation or otherwise). Other examples of biological samples include blood, serum, urine, semen, fecal matter, cerebrospinal fluid, interstitial fluid, mucous, tears, sweat, pus, biopsied tissue (e.g., obtained by a surgical biopsy or needle biopsy), nipple aspirates, milk, vaginal fluid, saliva, swabs (such as buccal swabs), or any material containing biomolecules that is derived from a first biological sample.

The term "tissue" refers to any biological tissue of a subject (including a group of cells, a body part, or an organ) or a part thereof, including blood and/or lymph vessels, which is the object to which a compound, particle, and/or composition of the invention is delivered. A tissue may be an abnormal or unhealthy tissue, which may need to be treated. A tissue may also be a normal or healthy tissue that is under a higher than normal risk of becoming abnormal or unhealthy, which may need to be prevented. In certain embodiments, the tissue is the central nervous system. In certain embodiments, the tissue is the brain.

The term "administer," "administering," or "administration" refers to implanting, absorbing, ingesting, injecting, inhaling, or otherwise introducing a compound described herein, or a composition thereof, in or on a subject.

The terms "treatment," "treat," and "treating" refer to reversing, alleviating, delaying the onset of, or inhibiting the progress of a disease described herein. In some embodiments, treatment may be administered after one or more signs or symptoms of the disease have developed or have been observed. In other embodiments, treatment may be administered in the absence of signs or symptoms of the disease. For example, treatment may be administered to a susceptible subject prior to the onset of symptoms (e.g., in light of a history of symptoms). Treatment may also be continued after symptoms have resolved, for example, to delay or prevent recurrence.

The terms "condition," "disease," and "disorder" are used interchangeably.

An "effective amount" of a compound described herein refers to an amount sufficient to elicit the desired biological response. An effective amount of a compound described herein may vary depending on such factors as the desired biological endpoint, the pharmacokinetics of the compound, the condition being treated, the mode of administration, and the age and health of the subject. In certain embodiments, an effective amount is a therapeutically effective amount. In certain embodiments, an effective amount is a prophylactic treatment. In certain embodiments, an effective amount is the amount of a compound described herein in a single dose. In certain embodiments, an effective amount is the combined amounts of a compound described herein in multiple doses.

A "therapeutically effective amount" of a compound described herein is an amount sufficient to provide a therapeutic benefit in the treatment of a condition or to delay or minimize one or more symptoms associated with the condition. A therapeutically effective amount of a compound means an amount of therapeutic agent, alone or in combination with other therapies, which provides a therapeutic benefit in the treatment of the condition. The term "therapeutically effective amount" can encompass an amount that improves overall therapy, reduces, or avoids symptoms, signs, or causes of the condition, and/or enhances the therapeutic efficacy of another therapeutic agent. In certain embodiments, a therapeutically effective amount is an amount sufficient for binding a target (e.g., a protein (e.g., a bromodomain or bromodomain-containing protein (e.g., BET proteins) or an HMT (e.g., EZH1) and/or inducing the degradation of the target (e.g., a protein (e.g., a bromodomain or bromodomain-containing protein (e.g., BET proteins) or an HMT (e.g., EZH1). In certain embodiments, a therapeutically effective amount is an amount sufficient for treating a proliferative disease (e.g., cancer). In certain embodiments, a therapeutically effective amount is an amount sufficient for binding a target protein (e.g., a bromodomain or bromodomain-containing protein (e.g., BET proteins) or an HMT (e.g., EZH1) and/or inducing the degradation of the target (e.g., a protein (e.g., a bromodomain or bromodomain-containing protein (e.g., BET proteins), an HMT (e.g., EZH1), or a cytosolic signaling protein (e.g., FKBP12).

A "prophylactically effective amount" of a compound described herein is an amount sufficient to prevent a condition, or one or more signs or symptoms associated with the condition, or prevent its recurrence. A prophylactically effective amount of a compound means an amount of a therapeutic agent, alone or in combination with other agents, which provides a prophylactic benefit in the prevention of the condition. The term "prophylactically effective amount" can encompass an amount that improves overall prophylaxis or enhances the prophylactic efficacy of another prophylactic agent. In certain embodiments, a prophylactically effective amount is an amount sufficient for binding a target protein (e.g., a bromodomain or bromodomain-containing protein (e.g., BET proteins), an HMT (e.g., EZH1), or a cytosolic signaling protein (e.g., FKBP12), and/or inducing the degradation of the target protein (e.g., a bromodomain or bromodomain-containing protein (e.g., BET proteins), an HMT (e.g., EZH1), or a cytosolic signaling protein (e.g., FKBP12). In certain embodiments, a prophylactically effective amount is an amount sufficient for treating a proliferative disease (e.g., cancer). In certain embodiments, a prophylactically effective amount is an amount sufficient for binding a target (e.g., a protein (e.g., a bromodomain or bromodomain-containing protein (e.g., BET proteins), an HMT (e.g., EZH1), or a cytosolic signaling protein (e.g., FKBP12) and/or inducing the degradation of the target (e.g., a protein (e.g., a bromodomain or bromodomain-containing protein (e.g., BET proteins), an HMT (e.g., EZH1), or a cytosolic signaling protein (e.g., FKBP12) and treating a proliferative disease (e.g., cancer).

A "proliferative disease" refers to a disease that occurs due to abnormal growth or extension by the multiplication of cells (Walker, *Cambridge Dictionary of Biology*; Cambridge University Press: Cambridge, UK, 1990). A proliferative disease may be associated with: 1) the pathological proliferation of normally quiescent cells; 2) the pathological migration of cells from their normal location (e.g., metastasis of neoplastic cells); 3) the pathological expression of proteolytic enzymes such as the matrix metalloproteinases (e.g., collagenases, gelatinases, and elastases); or 4) the pathological angiogenesis as in proliferative retinopathy and tumor metastasis. Exemplary proliferative diseases include cancers (i.e., "malignant neoplasms"), benign neoplasms, angiogenesis, inflammatory diseases, and autoimmune diseases.

The term "angiogenesis" refers to the physiological process through which new blood vessels form from pre-existing vessels. Angiogenesis is distinct from vasculogenesis, which is the de novo formation of endothelial cells from mesoderm cell precursors. The first vessels in a developing embryo form through vasculogenesis, after which angiogenesis is responsible for most blood vessel growth during normal or abnormal development. Angiogenesis is a vital process in growth and development, as well as in wound healing and in the formation of granulation tissue. However, angiogenesis is also a fundamental step in the transition of tumors from a benign state to a malignant one, leading to the use of angiogenesis inhibitors in the treatment of cancer. Angiogenesis may be chemically stimulated by angiogenic proteins, such as growth factors (e.g., VEGF). "Pathological angiogenesis" refers to abnormal (e.g., excessive or insufficient) angiogenesis that amounts to and/or is associated with a disease.

The terms "neoplasm" and "tumor" are used herein interchangeably and refer to an abnormal mass of tissue wherein the growth of the mass surpasses and is not coordinated with the growth of a normal tissue. A neoplasm or tumor may be "benign" or "malignant," depending on the following characteristics: degree of cellular differentiation (including morphology and functionality), rate of growth, local invasion, and metastasis. A "benign neoplasm" is generally well differentiated, has characteristically slower growth than a malignant neoplasm, and remains localized to the site of origin. In addition, a benign neoplasm does not have the capacity to infiltrate, invade, or metastasize to distant sites. Exemplary benign neoplasms include, but are not limited to, lipoma, chondroma, adenomas, acrochordon, senile angiomas, seborrheic keratoses, lentigos, and sebaceous hyperplasias. In some cases, certain "benign" tumors may later give rise to malignant neoplasms, which may result from additional genetic changes in a subpopulation of the tumor's neoplastic cells, and these tumors are referred to as "pre-malignant neoplasms." An exemplary pre-malignant neoplasm is a teratoma. In contrast, a "malignant neoplasm" is generally poorly differentiated (anaplasia) and has characteristically rapid growth accompanied by progressive infiltration, invasion, and destruction of the surrounding tissue. Furthermore, a malignant neoplasm generally has the capacity to metastasize to distant sites. The term "metastasis," "metastatic," or "metastasize" refers to the spread or migration of cancerous cells from a primary or original tumor to another organ or tissue and is typically identifiable by the presence of a "secondary tumor" or "secondary cell mass" of the tissue type of the primary or original tumor and not of that of the organ or tissue in which the secondary (metastatic) tumor is located. For example, a prostate cancer that has migrated to bone is said to be metastasized prostate cancer and includes cancerous prostate cancer cells growing in bone tissue.

The term "cancer" refers to a class of diseases characterized by the development of abnormal cells that proliferate uncontrollably and have the ability to infiltrate and destroy normal body tissues. See, e.g., *Stedman's Medical Dictionary*, 25th ed.; Hensyl ed.; Williams & Wilkins: Philadelphia, 1990. Exemplary cancers include, but are not limited to, hematological malignancies. Additional exemplary cancers include, but are not limited to, lung cancer (e.g., bronchogenic carcinoma, small cell lung cancer (SCLC), non-small cell lung cancer (NSCLC), adenocarcinoma of the lung); kidney cancer (e.g., nephroblastoma, a.k.a. Wilms' tumor, renal cell carcinoma); acoustic neuroma; adenocarcinoma; adrenal gland cancer; anal cancer; angiosarcoma (e.g., lymphangiosarcoma, lymphangioendotheliosarcoma, hemangiosarcoma); appendix cancer; benign monoclonal gammopathy; biliary cancer (e.g., cholangiocarcinoma); bladder cancer; breast cancer (e.g., adenocarcinoma of the breast, papillary carcinoma of the breast, mammary cancer, medullary carcinoma of the breast); brain cancer (e.g., meningioma, glioblastomas, glioma (e.g., astrocytoma, oligodendroglioma), medulloblastoma); bronchus cancer; carcinoid tumor; cervical cancer (e.g., cervical adenocarcinoma); choriocarcinoma; chordoma; craniopharyngioma; colorectal cancer (e.g., colon cancer, rectal cancer, colorectal adenocarcinoma); connective tissue cancer; epithelial carcinoma; ependymoma; endotheliosarcoma (e.g., Kaposi's sarcoma, multiple idiopathic hemorrhagic sarcoma); endometrial cancer (e.g., uterine cancer, uterine sarcoma); esophageal cancer (e.g., adenocarcinoma of the esophagus, Barrett's adenocarcinoma); Ewing's sarcoma; ocular cancer (e.g., intraocular melanoma, retinoblastoma); familiar hypereosinophilia; gall bladder cancer; gastric cancer (e.g., stomach adenocarcinoma); gastrointestinal stromal tumor (GIST); germ cell cancer; head and neck cancer (e.g., head and neck squamous cell carcinoma, oral cancer (e.g., oral squamous cell carcinoma), throat cancer (e.g., laryngeal cancer, pharyngeal cancer, nasopharyngeal cancer, oropharyngeal cancer)); heavy chain disease (e.g., alpha chain disease, gamma chain disease, mu chain disease; hemangioblastoma; hypopharynx cancer; inflammatory myofibroblastic tumors; immunocytic amyloidosis; liver cancer (e.g., hepatocellular cancer (HCC), malignant hepatoma); leiomyosarcoma (LMS); mastocytosis (e.g., systemic mastocytosis); muscle cancer; myelodysplastic syndrome (MDS); mesothelioma; myeloproliferative disorder (MPD) (e.g., polycythemia vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)); neuroblastoma; neurofibroma (e.g., neurofibromatosis (NF) type 1 or type 2, schwannomatosis); neuroendocrine cancer (e.g., gastroenteropancreatic neuroendoctrine tumor (GEP-NET), carcinoid tumor); osteosarcoma (e.g., bone cancer); ovarian cancer (e.g., cystadenocarcinoma, ovarian embryonal carcinoma, ovarian adenocarcinoma); papillary adenocarcinoma; pancreatic cancer (e.g., pancreatic andenocarcinoma, intraductal papillary mucinous neoplasm (IPMN), Islet cell tumors); penile cancer (e.g., Paget's disease of the penis and scrotum); pinealoma; primitive neuroectodermal tumor (PNT); plasma cell neoplasia; paraneoplastic syndromes; intraepithelial neoplasms; prostate cancer (e.g., prostate adenocarcinoma); rectal cancer; rhabdomyosarcoma; salivary gland cancer; skin cancer (e.g., squamous cell carcinoma (SCC), keratoacanthoma (KA), melanoma, basal cell carcinoma (BCC)); small bowel cancer (e.g., appendix cancer); soft tissue sarcoma (e.g., malignant fibrous histiocytoma (MFH), liposarcoma, malignant peripheral nerve sheath tumor (MPNST), chondrosarcoma, fibrosarcoma, myxosarcoma); sebaceous gland carcinoma; small intestine cancer; sweat gland carcinoma; synovioma; testicular cancer (e.g., seminoma, testicular embryonal carcinoma); thyroid cancer (e.g., papillary carcinoma of the thyroid, papillary thyroid carcinoma (PTC), medullary thyroid cancer); urethral cancer; vaginal cancer; and vulvar cancer (e.g., Paget's disease of the vulva).

A "hematological disease" includes a disease which affects a hematopoietic cell or tissue. Hematological diseases include diseases associated with aberrant hematological content and/or function. Examples of hematological diseases include diseases resulting from bone marrow irradiation or chemotherapy treatments for cancer, diseases such as pernicious anemia, hemorrhagic anemia, hemolytic anemia, aplastic anemia, sickle cell anemia, sideroblastic anemia, anemia associated with chronic infections such as malaria, trypanosomiasis, HTV, hepatitis virus or other viruses, myelophthisic anemias caused by marrow deficiencies, renal failure resulting from anemia, anemia, polycythemia, infectious mononucleosis (EVI), acute non-lymphocytic leukemia (ANLL), acute myeloid leukemia (AML), acute promyelocytic leukemia (APL), acute myelomonocytic leukemia (AMMoL), polycythemia vera, lymphoma, acute lymphocytic leukemia (ALL), chronic lymphocytic leukemia, Wilm's tumor, Ewing's sarcoma, retinoblastoma, hemophilia, disorders associated with an increased risk of thrombosis, herpes, thalassemia, antibody-mediated disorders such as transfusion reactions and erythroblastosis, mechanical trauma to red blood cells such as micro-angiopathic hemolytic anemias, thrombotic thrombocytopenic purpura and disseminated intravascular coagulation, infections by parasites such as Plasmodium, chemical injuries from, e.g., lead poisoning, and hypersplenism. In certain embodiments, a hematological disease is a hematological malignancy. The term "hematological malignancy" refers to tumors that affect blood, bone marrow, and/or lymph nodes. Exemplary hematological malignancies include, but are not limited to, leukemia, such as acute lymphocytic leukemia (ALL) (e.g., B-cell ALL, T-cell ALL), acute myelocytic leukemia (AML) (e.g., B-cell AML, T-cell AML), chronic myelocytic leukemia (CML) (e.g., B-cell CML, T-cell CML), and chronic lymphocytic leukemia (CLL) (e.g., B-cell CLL, T-cell CLL)); lymphoma, such as Hodgkin lymphoma (HL) (e.g., B-cell HL, T-cell HL) and non-Hodgkin lymphoma (NHL) (e.g., B-cell NHL, such as diffuse large cell lymphoma (DLCL) (e.g., diffuse large B-cell lymphoma (DLBCL, e.g., activated B-cell (ABC) DLBCL (ABC-DLBCL))), follicular lymphoma, chronic lymphocytic leukemia/small lymphocytic lymphoma (CLL/SLL), mantle cell lymphoma (MCL), marginal zone B-cell lymphoma (e.g., mucosa-associated lymphoid tissue (MALT) lymphoma, nodal marginal zone B-cell lymphoma, splenic marginal zone B-cell lymphoma), primary mediastinal B-cell lymphoma, Burkitt lymphoma, Waldenström's macroglobulinemia (WM, lymphoplasmacytic lymphoma), hairy cell leukemia (HCL), immunoblastic large cell lymphoma, precursor B-lymphoblastic lymphoma, central nervous system (CNS) lymphoma (e.g., primary CNS lymphoma and secondary CNS lymphoma); and T-cell NHL, such as precursor T-lymphoblastic lymphoma/leukemia, peripheral T-cell lymphoma (PTCL) (e.g., cutaneous T-cell lymphoma (CTCL) (e.g., mycosis fungoides, Sezary syndrome), angioimmunoblastic T-cell lymphoma, extranodal natural killer T-cell lymphoma, enteropathy type T-cell lymphoma, subcutaneous panniculitis-like T-cell lymphoma, and anaplastic large cell lymphoma); lymphoma of an immune privileged site (e.g., cerebral lymphoma, ocular lymphoma, lymphoma of the placenta, lymphoma of the fetus, testicular lymphoma); a mixture of one or more leukemia/lymphoma as described above; myelodysplasia; and multiple myeloma (MM).

The term "inflammatory disease" refers to a disease caused by, resulting from, or resulting in inflammation. The term "inflammatory disease" may also refer to a dysregulated inflammatory reaction that causes an exaggerated response by macrophages, granulocytes, and/or T-lymphocytes leading to abnormal tissue damage and/or cell death. An inflammatory disease can be either an acute or chronic inflammatory condition and can result from infections or non-infectious causes. Inflammatory diseases include, without limitation, atherosclerosis, arteriosclerosis, autoimmune disorders, multiple sclerosis, systemic lupus erythematosus, polymyalgia rheumatica (PMR), gouty arthritis, degenerative arthritis, tendonitis, bursitis, psoriasis, cystic fibrosis, arthrosteitis, rheumatoid arthritis, inflammatory arthritis, Sjogren's syndrome, giant cell arteritis, progressive systemic sclerosis (scleroderma), ankylosing spondylitis, polymyositis, dermatomyositis, pemphigus, pemphigoid, diabetes (e.g., Type I), myasthenia gravis, Hashimoto's thyroiditis, Graves' disease, Goodpasture's disease, mixed connective tissue disease, sclerosing cholangitis, inflammatory bowel disease, Crohn's disease, ulcerative colitis, pernicious anemia, inflammatory dermatoses, usual interstitial pneumonitis (UIP), asbestosis, silicosis, bronchiectasis, berylliosis, talcosis, pneumoconiosis, sarcoidosis, desquamative interstitial pneumonia, lymphoid interstitial pneumonia, giant cell interstitial pneumonia, cellular interstitial pneumonia, extrinsic allergic alveolitis, Wegener's granulomatosis and related forms of angiitis (temporal arteritis and polyarteritis nodosa), inflammatory dermatoses, hepatitis, delayed-type hypersensitivity reactions (e.g., poison ivy dermatitis), pneumonia, respiratory tract inflammation, Adult Respiratory Distress Syndrome (ARDS), encephalitis, immediate hypersensitivity reactions, asthma, hayfever, allergies, acute anaphylaxis, rheumatic fever, glomerulonephritis, pyelonephritis, cellulitis, cystitis, chronic cholecystitis, ischemia (ischemic injury), reperfusion injury, appendicitis, arteritis, blepharitis, bronchiolitis, bronchitis, cervicitis, cholangitis, chorioamnionitis, conjunctivitis, dacryoadenitis, dermatomyositis, endocarditis, endometritis, enteritis, enterocolitis, epicondylitis, epididymitis, fasciitis, fibrositis, gastritis, gastroenteritis, gingivitis, ileitis, iritis, laryngitis, myelitis, myocarditis, nephritis, omphalitis, oophoritis, orchitis, osteitis, otitis, pancreatitis, parotitis, pericarditis, pharyngitis, pleuritis, phlebitis, pneumonitis, proctitis, prostatitis, rhinitis, salpingitis, sinusitis, stomatitis, synovitis, testitis, tonsillitis, urethritis, urocystitis, uveitis, vaginitis, vasculitis, vulvitis, vulvovaginitis, angitis, chronic bronchitis, osteomyelitis, optic neuritis, temporal arteritis, transverse myelitis, necrotizing fasciitis, and necrotizing enterocolitis. An ocular inflammatory disease includes, but is not limited to, post-surgical inflammation.

An "autoimmune disease" refers to a disease arising from an inappropriate immune response of the body of a subject against substances and tissues normally present in the body. In other words, the immune system mistakes some part of the body as a pathogen and attacks its own cells. This may be restricted to certain organs (e.g., in autoimmune thyroiditis) or involve a particular tissue in different places (e.g., Goodpasture's disease which may affect the basement membrane in both the lung and kidney). The treatment of autoimmune diseases is typically with immunosuppression, e.g., medications which decrease the immune response. Exemplary autoimmune diseases include, but are not limited to, glomerulonephritis, Goodpasture's syndrome, necrotizing vasculitis, lymphadenitis, peri-arteritis nodosa, systemic lupus erythematosis, rheumatoid arthritis, psoriatic arthritis, systemic lupus erythematosis, psoriasis, ulcerative colitis, systemic sclerosis, dermatomyositis/polymyositis, anti-phospholipid antibody syndrome, scleroderma, pemphigus vulgaris, ANCA-associated vasculitis (e.g., Wegener's granulomatosis, microscopic polyangiitis), uveitis, Sjogren's syndrome, Crohn's disease, Reiter's syndrome, ankylosing spondylitis, Lyme disease, Guillain-Barré syndrome, Hashimoto's thyroiditis, and cardiomyopathy.

The term "neurological disease" refers to any disease of the nervous system, including diseases that involve the central nervous system (brain, brainstem and cerebellum), the peripheral nervous system (including cranial nerves), and the autonomic nervous system (parts of which are located in both central and peripheral nervous system). Neurodegenerative diseases refer to a type of neurological disease marked by the loss of nerve cells, including, but not limited to, Alzheimer's disease, Parkinson's disease, amyotrophic lateral sclerosis, tauopathies (including frontotemporal dementia), and Huntington's disease. Examples of neurological diseases include, but are not limited to, headache, stupor and coma, dementia, seizure, sleep disorders, trauma, infections, neoplasms, neuro-ophthalmology, movement disorders, demyelinating diseases, spinal cord disorders, and disorders of peripheral nerves, muscle and neuromuscular junctions. Addiction and mental illness, include, but are not limited to, bipolar disorder and schizophrenia, are also included in the definition of neurological diseases. Further examples of neurological diseases include acquired epileptiform aphasia; acute disseminated encephalomyelitis; adrenoleukodystrophy; agenesis of the corpus callosum; agnosia; Aicardi syndrome; Alexander disease; Alpers' disease; alternating hemiplegia; Alzheimer's disease; amyotrophic lateral sclerosis; anencephaly; Angelman syndrome; angiomatosis; anoxia; aphasia; apraxia; arachnoid cysts; arachnoiditis; Arnold-Chiari malformation; arteriovenous malformation; Asperger syndrome; ataxia telangiectasia; attention deficit hyperactivity disorder; autism; autonomic dysfunction; back pain; Batten disease; Behcet's disease; Bell's palsy; benign essential blepharospasm; benign focal; amyotrophy; benign intracranial hypertension; Binswanger's disease; blepharospasm; Bloch Sulzberger syndrome; brachial plexus injury; brain abscess; bbrain injury; brain tumors (including glioblastoma multiforme); spinal tumor; Brown-Sequard syndrome; Canavan disease; carpal tunnel syndrome (CTS); causalgia; central pain syndrome; central pontine myelinolysis; cephalic disorder; cerebral aneurysm; cerebral arteriosclerosis; cerebral atrophy; cerebral gigantism; cerebral palsy; Charcot-Marie-Tooth disease; chemotherapy-induced neuropathy and neuropathic pain; Chiari malformation; chorea; chronic inflammatory demyelinating polyneuropathy (CIDP); chronic pain; chronic regional pain syndrome; Coffin Lowry syndrome; coma, including persistent vegetative state; congenital facial diplegia; corticobasal degeneration; cranial arteritis; craniosynostosis; Creutzfeldt-Jakob disease; cumulative trauma disorders; Cushing's syndrome; cytomegalic inclusion body disease (CIBD); cytomegalovirus infection; dancing eyes-dancing feet syndrome; Dandy-Walker syndrome; Dawson disease; De Morsier's syndrome; Dejerine-Klumpke palsy; dementia; dermatomyositis; diabetic neuropathy; diffuse sclerosis; dysautonomia; dysgraphia; dyslexia; dystonias; early infantile epileptic encephalopathy; empty sella syndrome; encephalitis; encephaloceles; encephalotrigeminal angiomatosis; epilepsy; Erb's palsy; essential tremor; Fabry's disease; Fahr's syndrome; fainting; familial spastic paralysis; febrile seizures; Fisher syndrome; Friedreich's ataxia; frontotemporal dementia and other "tauopathies"; Gaucher's disease; Gerstmann's syndrome; giant cell arteritis; giant cell inclusion disease; globoid cell leukodystrophy; Guillain-Barre syndrome; HTLV-1 associated myelopathy; Hallervorden-Spatz disease; head injury; headache; hemifacial spasm; hereditary spastic paraplegia; heredopathia atactica polyneuritiformis; herpes zoster oticus; herpes zoster; Hirayama syndrome; HIV-associated dementia and neuropathy (see also neurological manifestations of AIDS); holoprosencephaly; Huntington's disease and other polyglutamine repeat diseases; hydranencephaly; hydrocephalus; hypercortisolism; hypoxia; immune-mediated encephalomyelitis; inclusion body myositis; incontinentia pigmenti; infantile; phytanic acid storage disease; Infantile Refsum disease; infantile spasms; inflammatory myopathy; intracranial cyst; intracranial hypertension; Joubert syndrome; Kearns-Sayre syndrome; Kennedy disease; Kinsbourne syndrome; Klippel Feil syndrome; Krabbe disease; Kugelberg-Welander disease; kuru; Lafora disease; Lambert-Eaton myasthenic syndrome; Landau-Kleffner syndrome; lateral medullary (Wallenberg) syndrome; learning disabilities; Leigh's disease; Lennox-Gastaut syndrome; Lesch-Nyhan syndrome; leukodystrophy; Lewy body dementia; lissencephaly; locked-in syndrome; Lou Gehrig's disease (aka motor neuron disease or amyotrophic lateral sclerosis); lumbar disc disease; lyme disease-neurological sequelae; Machado-Joseph disease; macrencephaly; megalencephaly; Melkersson-Rosenthal syndrome; Menieres disease; meningitis; Menkes disease; metachromatic leukodystrophy; microcephaly; migraine; Miller Fisher syndrome; mini-strokes; mitochondrial myopathies; Mobius syndrome; monomelic amyotrophy; motor neurone disease; moyamoya disease; mucopolysaccharidoses; multi-infarct dementia; multifocal motor neuropathy; multiple sclerosis and other demyelinating disorders; multiple system atrophy with postural hypotension; muscular dystrophy; myasthenia gravis;

myelinoclastic diffuse sclerosis; myoclonic encephalopathy of infants; myoclonus; myopathy; myotonia congenital; narcolepsy; neurofibromatosis; neuroleptic malignant syndrome; neurological manifestations of AIDS; neurological sequelae of lupus; neuromyotonia; neuronal ceroid lipofuscinosis; neuronal migration disorders; Niemann-Pick disease; O'Sullivan-McLeod syndrome; occipital neuralgia; occult spinal dysraphism sequence; Ohtahara syndrome; olivopontocerebellar atrophy; opsoclonus myoclonus; optic neuritis; orthostatic hypotension; overuse syndrome; paresthesia; Parkinson's disease; paramyotonia congenita; paraneoplastic diseases; paroxysmal attacks; Parry Romberg syndrome; Pelizaeus-Merzbacher disease; periodic paralyses; peripheral neuropathy; painful neuropathy and neuropathic pain; persistent vegetative state; pervasive developmental disorders; photic sneeze reflex; phytanic acid storage disease; Pick's disease; pinched nerve; pituitary tumors; polymyositis; porencephaly; Post-Polio syndrome; postherpetic neuralgia (PHN); postinfectious encephalomyelitis; postural hypotension; Prader-Willi syndrome; primary lateral sclerosis; prion diseases; progressive; hemifacial atrophy; progressive multifocal leukoencephalopathy; progressive sclerosing poliodystrophy; progressive supranuclear palsy; pseudotumor cerebri; Ramsay-Hunt syndrome (Type I and Type II); Rasmussen's Encephalitis; reflex sympathetic dystrophy syndrome; Refsum disease; repetitive motion disorders; repetitive stress injuries; restless legs syndrome; retrovirus-associated myelopathy; Rett syndrome; Reye's syndrome; Saint Vitus Dance; Sandhoff disease; Schilder's disease; schizencephaly; septo-optic dysplasia; shaken baby syndrome; shingles; Shy-Drager syndrome; Sjogren's syndrome; sleep apnea; Soto's syndrome; spasticity; spina bifida; spinal cord injury; spinal cord tumors; spinal muscular atrophy; stiff-person syndrome; stroke; Sturge-Weber syndrome; subacute sclerosing panencephalitis; subarachnoid hemorrhage; subcortical arteriosclerotic encephalopathy; sydenham chorea; syncope; syringomyelia; tardive dyskinesia; Tay-Sachs disease; temporal arteritis; tethered spinal cord syndrome; Thomsen disease; thoracic outlet syndrome; tic douloureux; Todd's paralysis; Tourette syndrome; transient ischemic attack; transmissible spongiform encephalopathies; transverse myelitis; traumatic brain injury; tremor; trigeminal neuralgia; tropical spastic paraparesis; tuberous sclerosis; vascular dementia (multi-infarct dementia); vasculitis including temporal arteritis; Von Hippel-Lindau Disease (VHL); Wallenberg's syndrome; Werdnig-Hoffman disease; West syndrome; whiplash; Williams syndrome; Wilson's disease; and Zellweger syndrome.

The term "metabolic disorder" refers to any disorder that involves an alteration in the normal metabolism of carbohydrates, lipids, proteins, nucleic acids, or a combination thereof. A metabolic disorder is associated with either a deficiency or excess in a metabolic pathway resulting in an imbalance in metabolism of nucleic acids, proteins, lipids, and/or carbohydrates. Factors affecting metabolism include, and are not limited to, the endocrine (hormonal) control system (e.g., the insulin pathway, the enteroendocrine hormones including GLP-1, PYY or the like), the neural control system (e.g., GLP-1 in the brain), or the like. Examples of metabolic disorders include, but are not limited to, diabetes (e.g., Type I diabetes, Type II diabetes, gestational diabetes), hyperglycemia, hyperinsulinemia, insulin resistance, and obesity.

The terms "biologic," "biologic drug," and "biological product" refer to a wide range of products such as vaccines, blood and blood components, allergenics, somatic cells, gene therapy, tissues, nucleic acids, and proteins. Biologics may include sugars, proteins, or nucleic acids, or complex combinations of these substances, or may be living entities, such as cells and tissues. Biologics may be isolated from a variety of natural sources (e.g., human, animal, microorganism) and may be produced by biotechnological methods and other technologies.

The term "small molecule" refers to molecules, whether naturally-occurring or artificially created (e.g., via chemical synthesis) that have a relatively low molecular weight. Typically, a small molecule is an organic compound (i.e., it contains carbon). The small molecule may contain multiple carbon-carbon bonds, stereocenters, and other functional groups (e.g., amines, hydroxyl, carbonyls, and heterocyclic rings, etc.). In certain embodiments, the molecular weight of a small molecule is not more than about 1,000 g/mol, not more than about 900 g/mol, not more than about 800 g/mol, not more than about 700 g/mol, not more than about 600 g/mol, not more than about 500 g/mol, not more than about 400 g/mol, not more than about 300 g/mol, not more than about 200 g/mol, or not more than about 100 g/mol. In certain embodiments, the molecular weight of a small molecule is at least about 100 g/mol, at least about 200 g/mol, at least about 300 g/mol, at least about 400 g/mol, at least about 500 g/mol, at least about 600 g/mol, at least about 700 g/mol, at least about 800 g/mol, or at least about 900 g/mol, or at least about 1,000 g/mol. Combinations of the above ranges (e.g., at least about 200 g/mol and not more than about 500 g/mol) are also possible. In certain embodiments, the small molecule is a therapeutically active agent such as a drug (e.g., a molecule approved by the U.S. Food and Drug Administration as provided in the Code of Federal Regulations (C.F.R.)). The small molecule may also be complexed with one or more metal atoms and/or metal ions. In this instance, the small molecule is also referred to as a "small organometallic molecule." Preferred small molecules are biologically active in that they produce a biological effect in animals, preferably mammals, more preferably humans. Small molecules include, but are not limited to, radionuclides and imaging agents. In certain embodiments, the small molecule is a drug. Preferably, though not necessarily, the drug is one that has already been deemed safe and effective for use in humans or animals by the appropriate governmental agency or regulatory body. For example, drugs approved for human use are listed by the FDA under 21 C.F.R. §§ 330.5, 331 through 361, and 440 through 460, incorporated herein by reference; drugs for veterinary use are listed by the FDA under 21 C.F.R. §§ 500 through 589, incorporated herein by reference.

A "protein," "peptide," or "polypeptide" comprises a polymer of amino acid residues linked together by peptide bonds. The term refers to proteins, polypeptides, and peptides of any size, structure, or function. Typically, a protein will be at least three amino acids long. A protein may refer to an individual protein or a collection of proteins. Inventive proteins preferably contain only natural amino acids, although non-natural amino acids (i.e., compounds that do not occur in nature but that can be incorporated into a polypeptide chain) and/or amino acid analogs as are known in the art may alternatively be employed. Also, one or more of the amino acids in a protein may be modified, for example, by the addition of a chemical entity such as a carbohydrate group, a hydroxyl group, a phosphate group, a farnesyl group, an isofarnesyl group, a fatty acid group, a linker for conjugation or functionalization, or other modification. A protein may also be a single molecule or may be a multi-molecular complex. A protein may be a fragment of a naturally occurring protein or peptide. A protein may be naturally occurring, recombinant, synthetic, or any combination of these.

The term "therapeutic agent" refers to any substance having therapeutic properties that produce a desired, usually beneficial, effect. For example, therapeutic agents may treat, ameliorate, and/or prevent disease. Therapeutic agents, as disclosed herein, may be biologics or small molecule therapeutics.

The term "E3 ubiquitin ligase" or "E3 ligase" refers to any protein that recruits an E2 ubiquitin-conjugating enzyme that has been loaded with ubiquitin, recognizes a protein substrate, and assists or directly catalyzes the transfer of ubiquitin from the E2 protein to the protein substrate.

The term "ubiquitin RPN13 receptor," "26S Proteasome regulatory subunit Rpn13," or "Proteasomal ubiquitin receptor ADRM1" refers to a protein encoded by the ADRM1 gene. The ubiquitin RPN13 receptor is a subunit of the 19S proteasome complex.

The term "bromodomain" refers to a protein domain that recognizes acetylated lysine residues such as those on the N-terminal tails of histones. In certain embodiments, a bromodomain of a BET protein comprises about 110 amino acids and shares a conserved fold comprising a left-handed bundle of four alpha helices linked by diverse loop regions that interact with chromatin. In certain embodiments, the bromodomain is ASH1L (GenBank ID: gi|8922081), ATAD2 (GenBank ID: gi|24497618), BAZ2B (GenBank ID: gi|7304923), BRD1 (GenBank ID: gi|11321642), BRD2(1) (GenBank ID: gi|4826806), BRD2(2) (GenBank ID: gi|4826806), BRD3(1) (GenBank ID: gi|11067749), BRD3(2) (GenBank ID: gi|11067749), BRD4(1) (GenBank ID: gi|19718731), BRD4(2) (GenBank ID: gi|19718731), BRD9 (GenBank ID: gi|57770383), BRDT(1) (GenBank ID: gi|46399198), BRPF1 (GenBank ID: gi|51173720), CECR2 (GenBank ID: gi|148612882), CREBBP (GenBank ID: gi|4758056), EP300 (GenBank ID: gi|50345997), FALZ (GenBank ID: gi|38788274), GCN5L2 (GenBank ID: gi|10835101), KIAA1240 (GenBank ID: gi|51460532), LOC93349 (GenBank ID: gi|134133279), PB1(1) (GenBank ID: gi|30794372), PB1(2) (GenBank ID: gi|30794372), PB1(3) (GenBank ID: gi|30794372), PB1(5) (GenBank ID: gi|30794372), PB1(6) (GenBank ID: gi|30794372), PCAF (GenBank ID: gi|40805843), PHIP(2) (GenBank ID: gi|34996489), SMARCA2 (GenBank ID: gi|48255900), SMARCA4 (GenBank ID: gi|21071056), SP140 (GenBank ID: gi|52487219), TAF1(1) (GenBank ID: gi|20357585), TAF1(2) (GenBank ID: gi|20357585), TAF1L(1) (GenBank ID: gi|24429572), TAF1L(2) (GenBank ID: gi|24429572), TIF1 (GenBank ID: gi|14971415), TRIM28 (GenBank ID: gi|5032179), or WDR9(2) (GenBank ID: gi|16445436).

The term "bromodomain-containing protein," "bromodomain protein," or "BET protein" refers to a protein, whether wild-type or mutant, natural or synthetic, truncated or complete, or a variant thereof, that possesses the minimum amino acid sequence sufficient for a functional bromodomain capable of mediating molecular recognition of acetyl-lysine of acetylated lysine residues on a second protein (e.g., a histone), such as on the tails of histones. Bromodomain-containing proteins include, for example, fusion proteins comprising a bromodomain and an additional portion having a desired functionality (e.g., a reporter portion).

The term "BRD4" or "Brd4" refers to Bromodomain-containing protein 4 that in humans is encoded by the BRD4 gene. BDR4 is a member of the BET (bromodomain and extra terminal domain) family, along with BRD2, BRD3, and BRDT. BRD4, similar to its BET family members, contains two bromodomains that recognize acetylated lysine residues. An increase in Brd4 expression leads to increased P-TEFb-dependent phosphorylation of RNA polymerase II (RNAPII) CTD and stimulation of transcription in vivo. Conversely, a reduction in Brd4 expression by siRNA reduced CTD phosphorylation and transcription, revealing that Brd4 is a positive regulatory component of P-TEFb. In chromatin immunoprecipitation (ChP) assays, the recruitment of P-TEFb to a promoter was dependent on Brd4 and was enhanced by an increase in chromatin acetylation. Together, P-TEFb alternately interacts with Brd4 and the inhibitory subunit to maintain functional equilibrium in the cell.

The term "FKBP" refers to an FK506-binding protein, that is part of the immunophilin family which are cis-trans peptidyl-prolyl isomerases. In certain embodiments, the FKBP is FKBP12. In certain embodiments, the FKBP is FKBP12.6. In certain embodiments, the FKBP is FKBP12, FKBP12.6, FKBP13, FKBP25, or FKBP51. In certain embodiments, FKBP12 has GenBank ID: gi| 51702264, GenBank ID: gi|4503725, GenBank ID: gi|182649, or GenBank ID: gi|127796335.

The term "histone" refers to highly alkaline proteins found in eukaryotic cell nuclei that package and order DNA into structural units called nucleosomes. They are the chief protein components of chromatin, acting as spools around which DNA winds, and play a role in gene regulation. In certain embodiments, the histone is histone H1 (e.g., histone H1F, histone HIH). In certain embodiments, the histone is histone H2A (e.g., histone H2AF, histone H2A1, histone H2A2). In certain embodiments, the histone is histone H2B (e.g., histone H2BF, histone H2B1, histone H2B2). In certain embodiments, the histone is histone H3 (e.g., histone H3A1, histone H3A2, histone H3A3). In certain embodiments, the histone is histone H4 (e.g., histone H41, histone H44).

"Histone methyltransferases" or "HMTs" are histone-modifying enzymes that catalyze the transfer of one, two, or three methyl groups to lysine and/or arginine residues of histone proteins. HMTs modify histones at certain sites through methylation. Methylation of histones is of biological significance because such methylation is a principal epigenetic modification of chromatin that determines gene expression, genomic stability, stem cell maturation, cell lineage development, genetic imprinting, DNA methylation, and/or cell mitosis. In certain embodiments, an HMT described herein is a histone-lysine N-methyltransferase. In certain embodiments, an HMT described herein is a histone-arginine N-methyltransferase. In certain embodiments, an HMT described herein is EZH1. In certain embodiments, an HMT described herein is G9a, GLP, MLL1, MLL2, MLL3, MLL4, NSD2, PRMT1, PRMT3, PRMT4, PRMT5, PRMT6, SET1b, SET7/9, SET8, SETMAR, SMYD2, SUV39H1, or SUV39H2.

The term "enhancer of zeste homolog 1," "enhancer of zeste 2 polycomb repressive complex 1 subunit," "EZH1," "EZH1 enzyme," "histone-lysine N-methyltransferase EZH1" refers to an enzyme that is encoded by the EZH gene. ENSEMBL of human EZH gene: ENSG00000108799.

The term "binder" refers to a compound that binds to a protein.

BRIEF DESCRIPTION OF THE DRAWINGS

FIG. 1 illustrates that RPN13 binds to the proteasome, and that the BET inhibitor JQ1-(S) does not dislocate the protein from proteasome. Therefore, a molecule was designed using RPN13 to locate the targeted protein to the proteasome and initiate degradation of the protein.

In FIG. 3, the blots show that RAJQ1 degrades Brd4, not Brd2 and Brd3 in the MM. 1S cell line. In the top gel, bromodomain degradation was observed at 8 hours as indicated in the boxed region.

FIG. 4 RAJQ1 decreased c-myc, Rpn13, Brd2, and Brd3 in CRBN KO MM cell line (left blot). RAJQ2 decreased c-myc in CRBN KO MM cell line (middle blot). RAJQ3 did not decrease c-myc, Rpn13, Brd2, and Brd3 in CRBN KO MM cell line (right blot). With longer treatment, BRD2 and BRD3 are all degraded. More importantly, the c-Myc is down-regulated indicated that it is BRD associated.

FIG. 5 shows blots in both MM. 1 S and CRBN cell lines. The blots indicate that RAJQ1, 2, 3 does not degrade Brd2 and Brd3 at longer time points.

FIG. 7A-FIG. 7C show that compounds RAJQ1 and RAJQ2; and RAJQ3 decrease MM cell viability, and the percentage of viable cells at selected time points (24 hours, 48 hours) after administration with the selected compounds.

FIG. 8 shows that RAJQ1 decreases MM. 1S-CRBN KO cell viability. C— is the MM1S CRBN knockout cell line. FIG. 8 indicates that the function of the molecule does not require CRBN or E3 ligase.

FIG. 9 shows a graph indicating the percent viable cells for RAJQ4 at 24 hours.

FIG. 11 blots show the degradation of RAJQ4 in both MM. 1 S and MM. 1 S-CKO cell lines. The slower degradation might be due to the covalent binding of these compounds with RPN13. FIG. 11 shows that RAJQ4 degrades Brd2, 3, and 4 in MM. 1S cell line (top blot), but not in CRBN KO cell line (bottom blot). This data indicates that the mechanism of protein degradation induced here is not associated with CRNB and additional ligases will be tested.

FIG. 26 also shows the exemplary synthesis of RAJQ9.

FIG. 28 shows that RAJQ1 decreases BRD2 and BRD3 protein level in cell (MM1S) with the compound treatment. C— is the CRBN knockout MM1S cell line, which indicated that this degradation is not CRBN dependent. The antiproliferation effect of RAJQ1 was measured in MM1 S, CRBN knockout MM1 S and lenadimide resistance cell lines. The result indicated that the degradation is not CRBN dependent.

FIG. 31 also shows the structures of RAJQ8 (left) and RAJQ9 (left).

FIG. 32 also shows the structures of RAJQ8 (left) and RAJQ9 (left).

FIG. 38 shows HEK 293T WT cells were treated with exemplary compounds RAFKBP2, RAFKBP3, RAFKBP4, and dTAG48 at the indicated concentrations and times. Cell lysates were loaded on SDS-PAGE, transferred to PVDF membrane, then immunoblotted with anti-FKBP12 and actin antibodies.

FIG. 39 shows HEK 293T CRBN–/– cells were treated with exemplary compounds RAFKBP2, RAFKBP3, RAFKBP4, and dTAG48 at the indicated concentrations and times. Cell lysates were loaded on SDS-PAGE, transferred to PVDF membrane, then immunoblotted with anti-FKBP12 and actin antibodies.

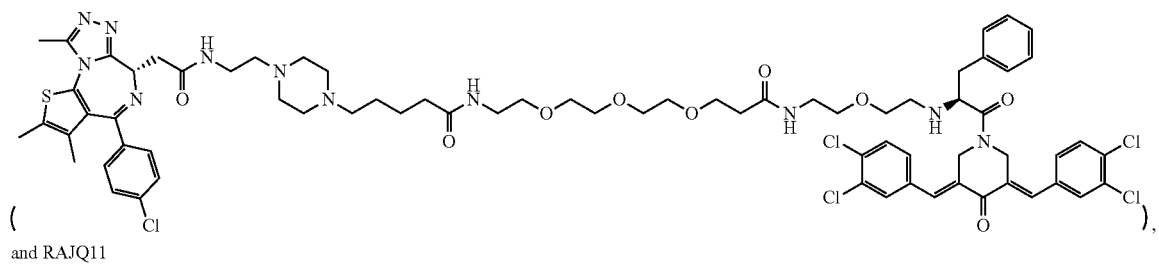

and RAJQ11

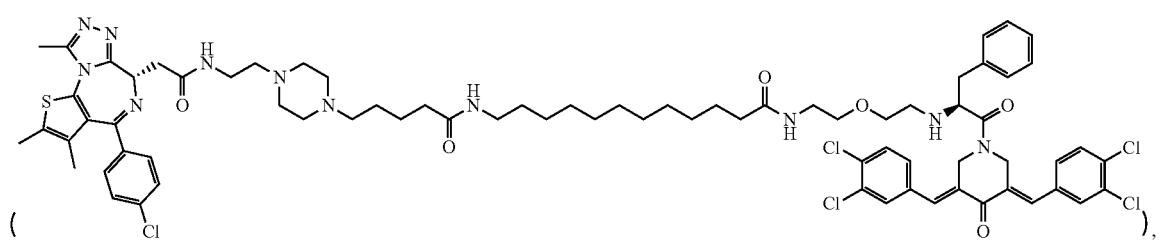

control RA190 at the indicated concentrations and indicated time periods. The dimerization of the exemplary bromodomain (BRD3) and RPN13 was reconfirmed.

Figure 42:
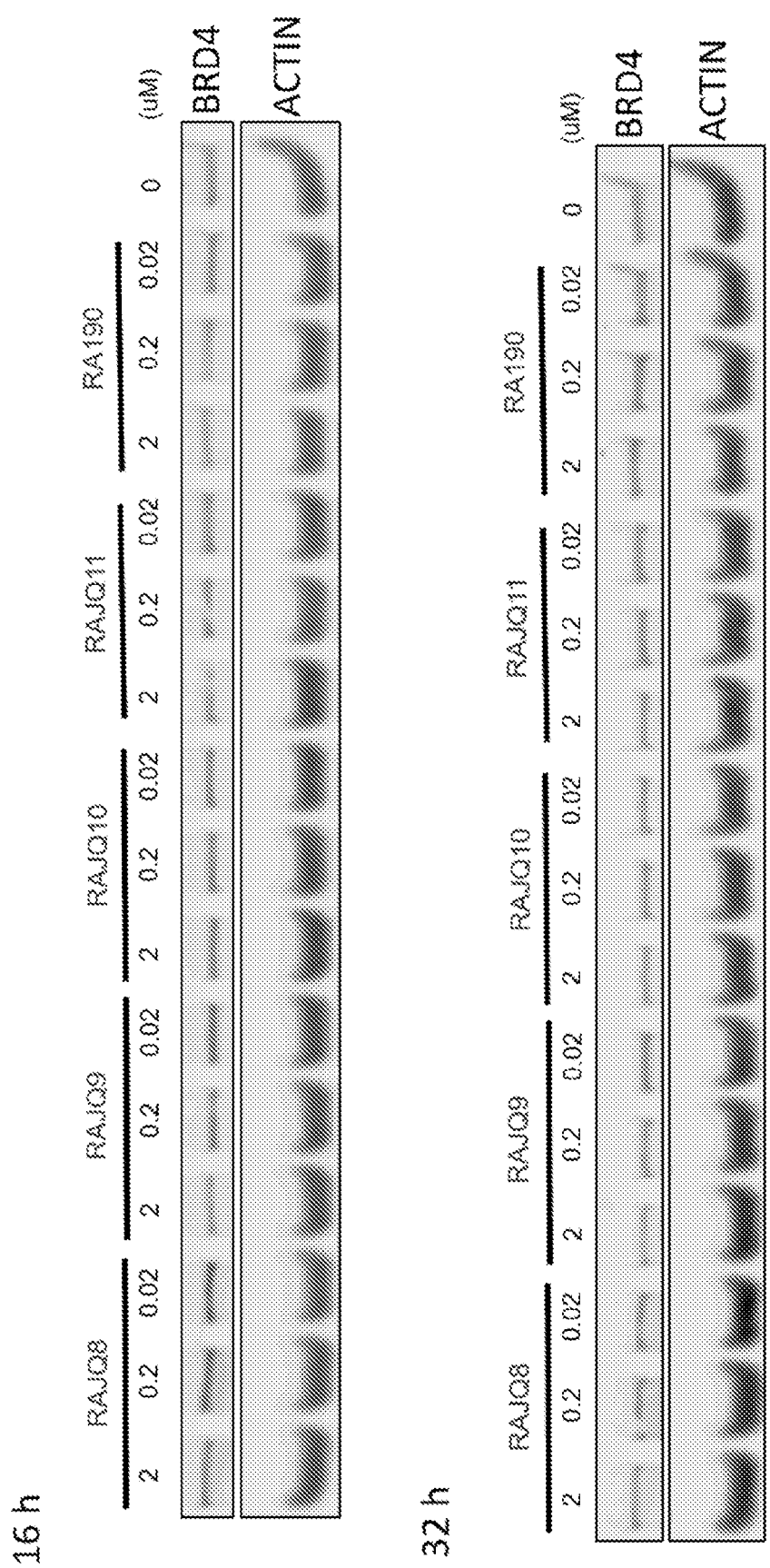

FIG. 42 shows an assay of bromodomain (BRD4) degradation in 293T cells upon treatment of exemplary bromodomain degraders RAJQ8, RAJQ9, RAJQ10, and RAJQ11, and control RA190 at the indicated concentrations and indicated time periods.

Figure 1:
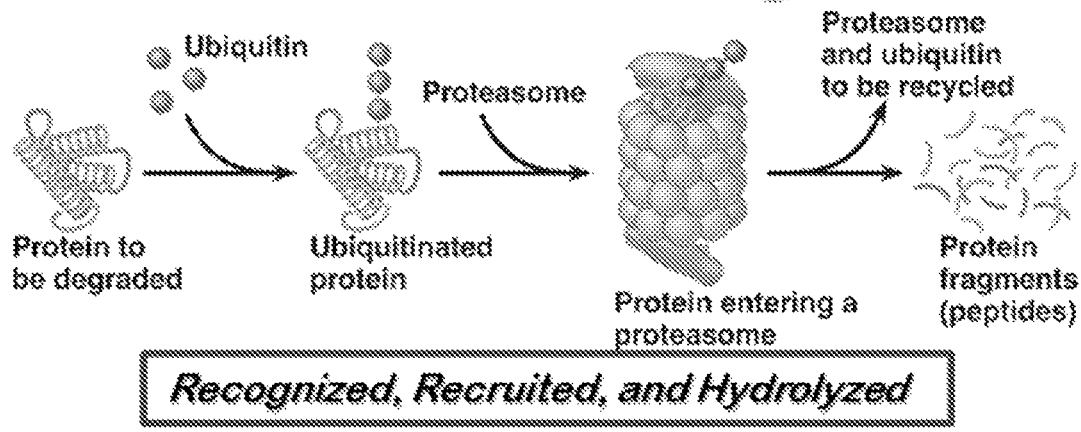
FIG. 1 shows RPN13-based protein degradation.
Figure 1:
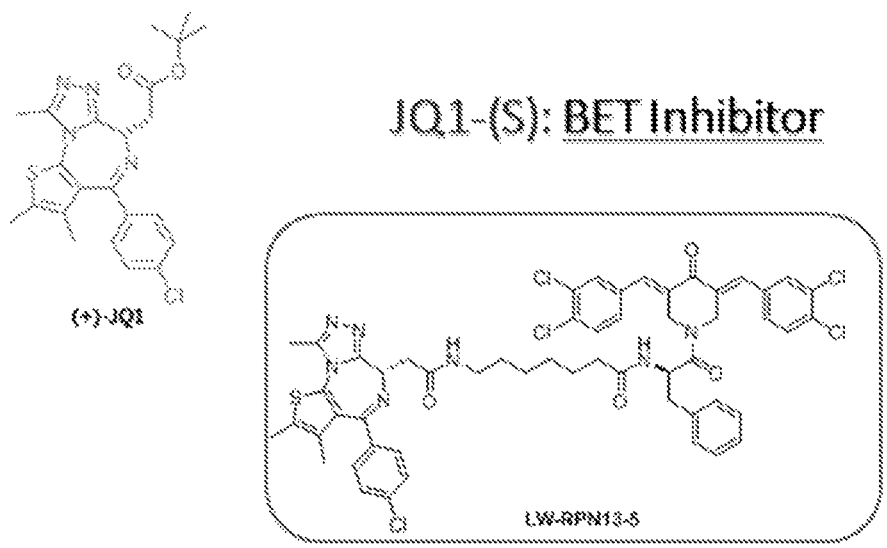
Figure 2:
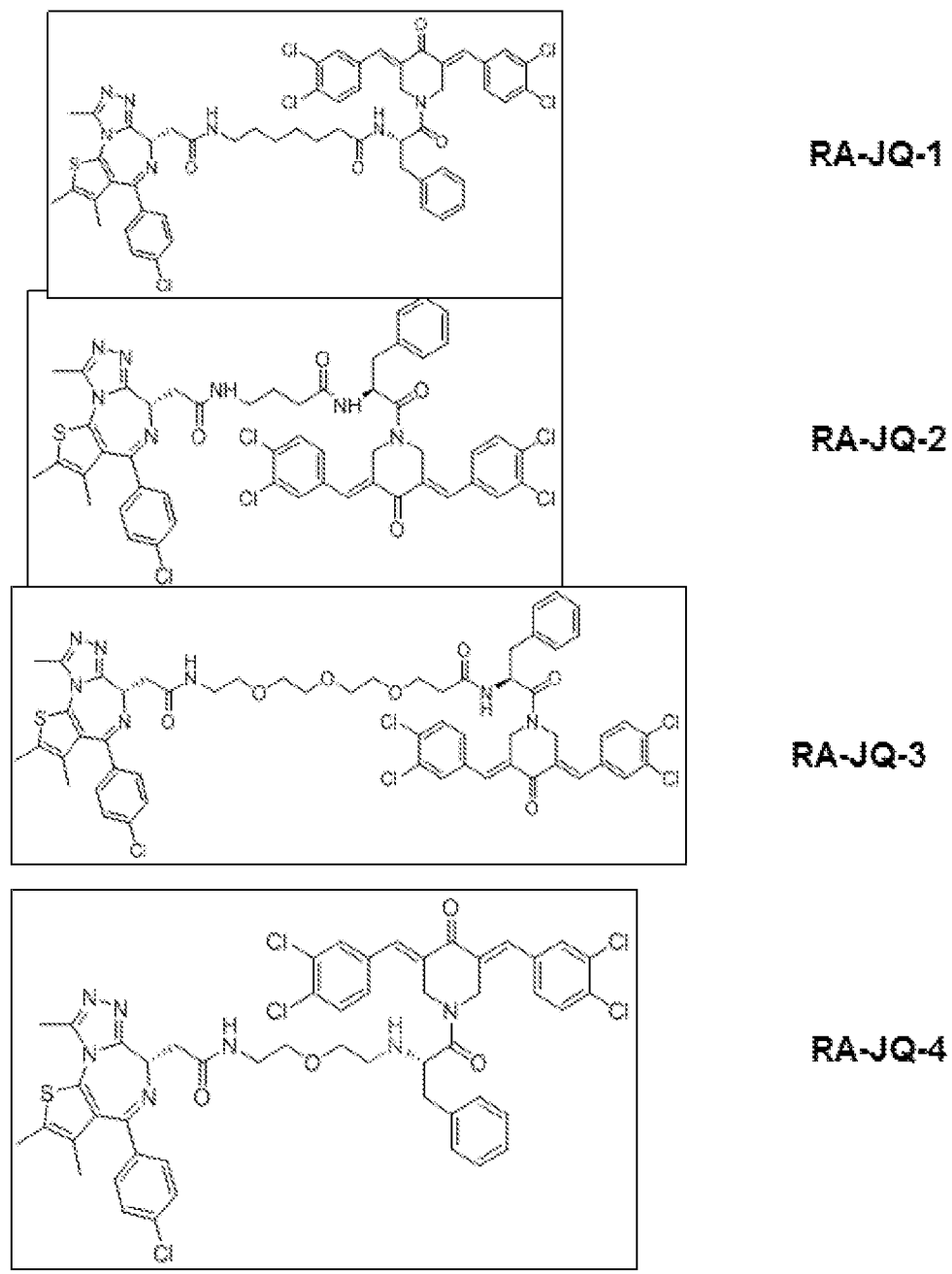
FIG. 2 shows examplary compounds using JQ1 and bromodomain as binders in the model system.
Figure 3:
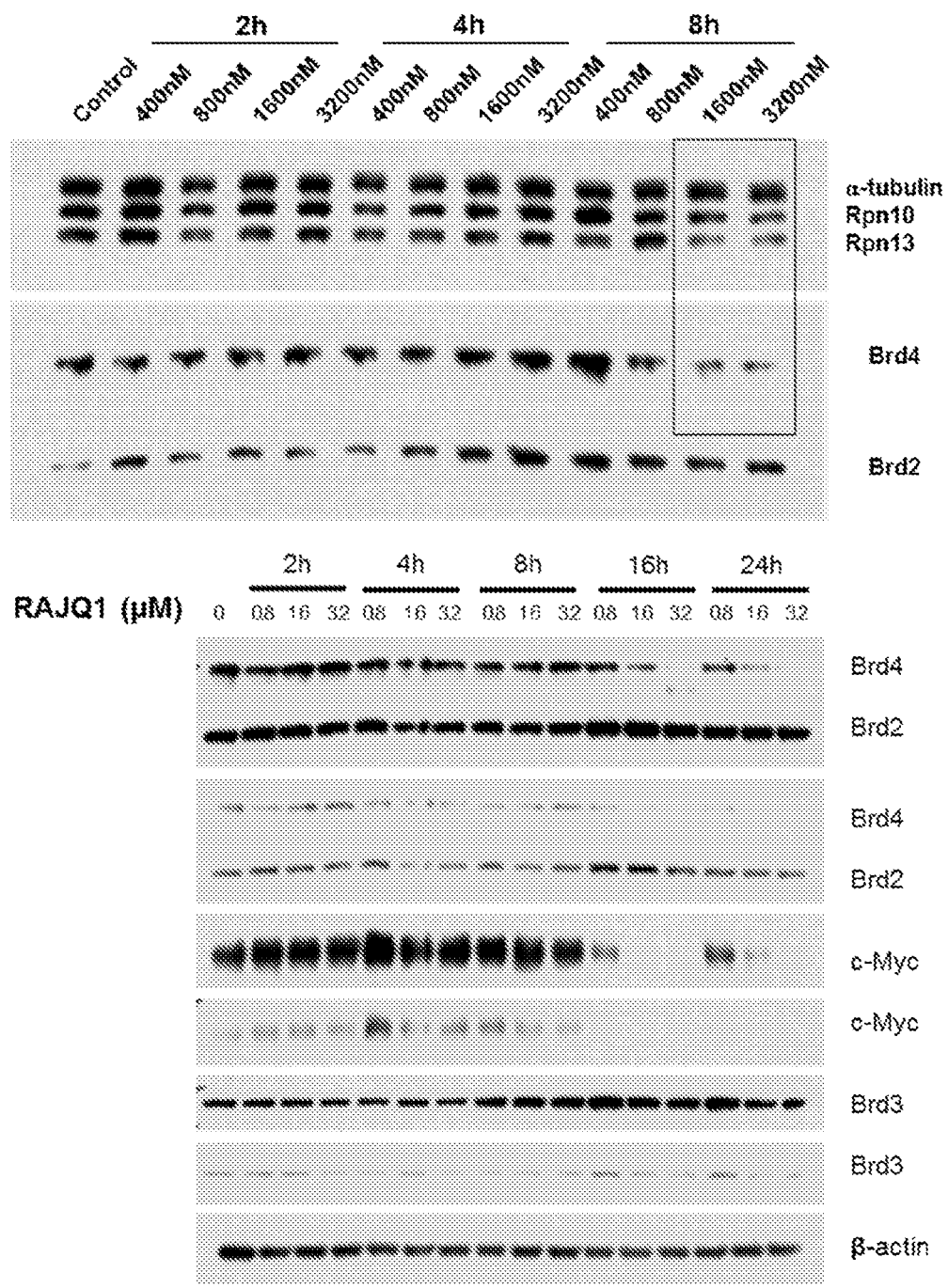
FIG. 3 shows MM. 1S cells were treated with RAJQ1 at indicated concentration and time. Cell lysates were loaded on SDS-PAGE, transferred to PVDF membrane, then immunoblotted with anti-alpha tubulin, Rpn10, Rpn13, Brd4, c-Myc, Brd3, beta-actin and Brd2 antibodies.
Figure 4:
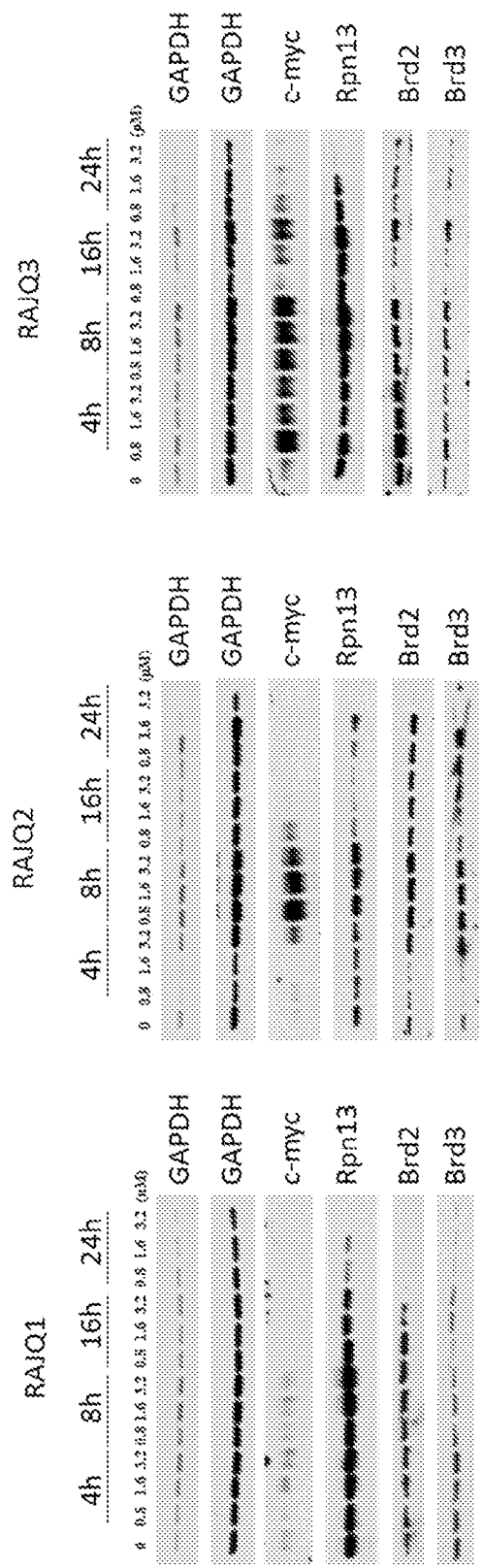
FIG. 4 shows MM. 1S CRBN KO cells treated with RAJQ1, RAJQ2, and RAJQ3, respectively, at 0 µM, 0.8 µM, 1.6 µM, and 3.2 µM, for 4 hours; at 0.8 µM, 1.6 µM, and 3.2 µM, for 8 hours; at 0.8 µM, 1.6 µM, and 3.2 µM, for 16 hours; and at 0.8 µM, 1.6 µM, and 3.2 µM, for 24 hours. Cell lysates were loaded on SDS-PAGE, transferred to PVDF membrane, then immunoblotted with anti-Brd2, c-Myc, Brd3, Rpn13, and GAPDH antibodies.
Figure 5:
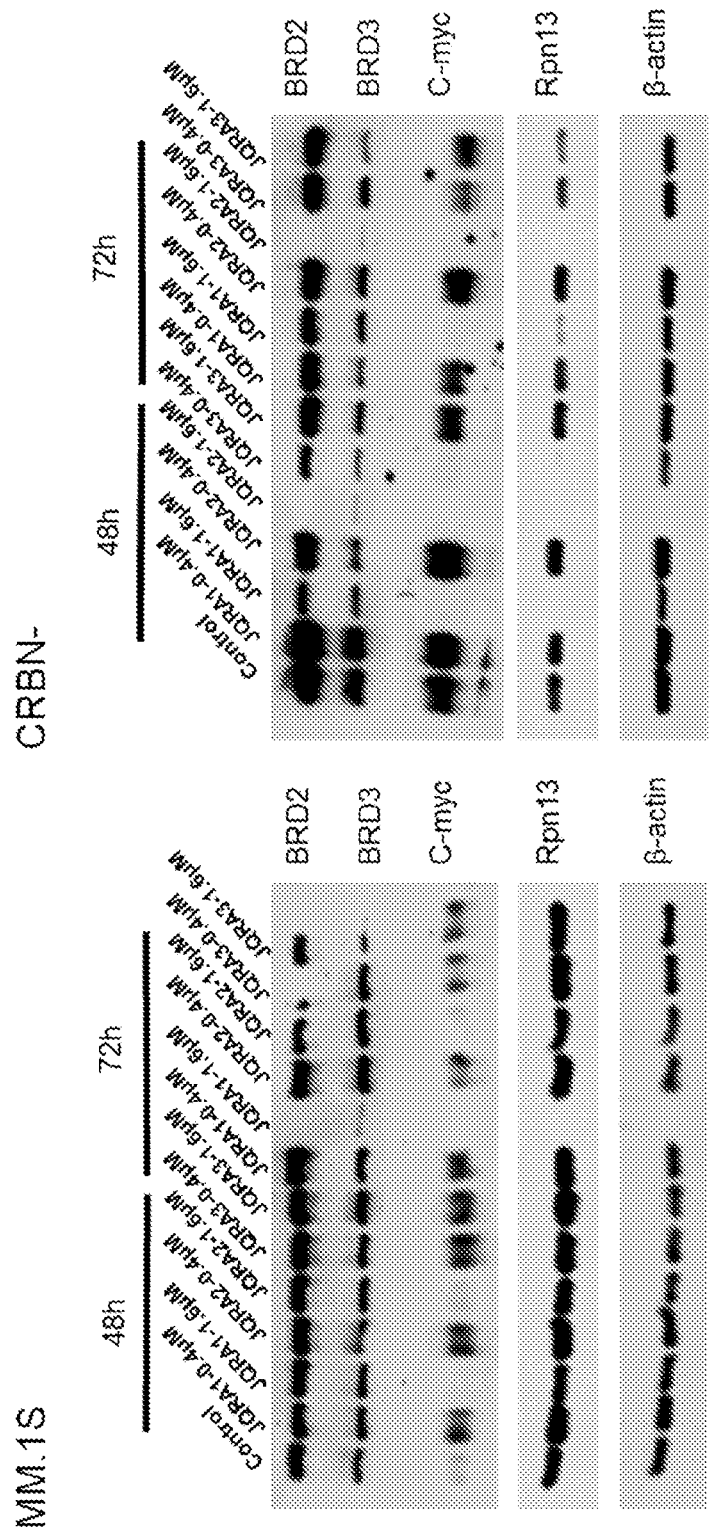
FIG. 5 shows MM. 1S and MM. 1S-CRBN KO (multiple myeloma 1S-cereblon knockout) cells treated with RAJQ1, RAJQ2, and RAJQ3 at 0.4 µM and 1.6 µM for 48 hours and 72 hours, respectively. Cell lysates were loaded on SDS-PAGE, transferred to PVDF membrane, then immunoblotted with anti-Brd2, c-Myc, Brd3, Rpn13, and beta-actin antibodies.
Figure 6:
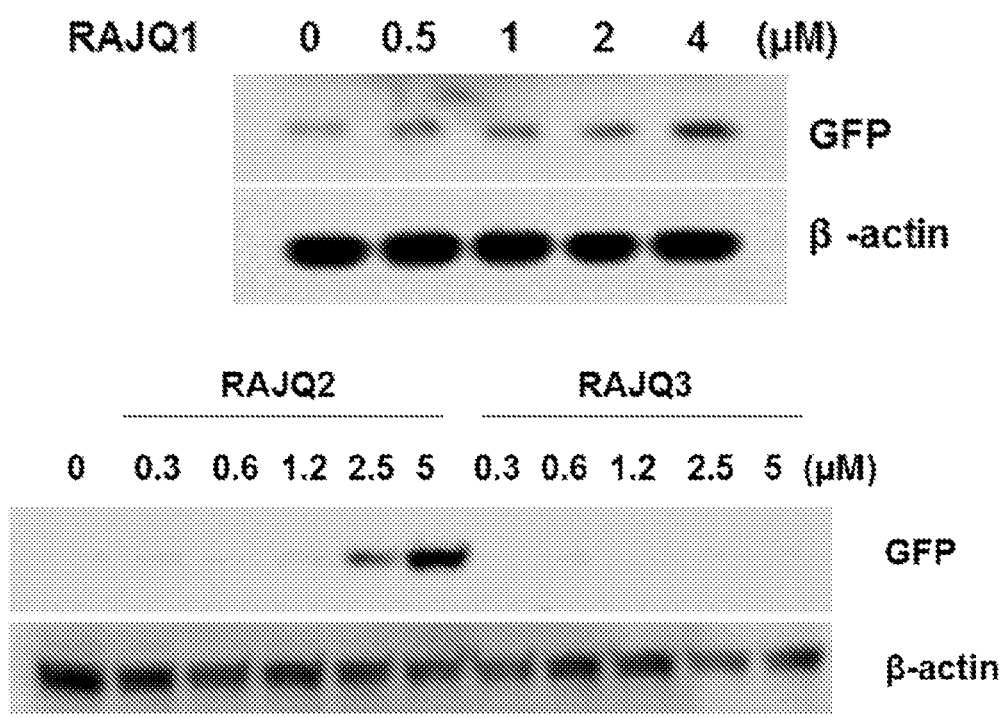
FIG. 6 shows a reporter cell line expressing Ub-tagged GFP that is constitutively targeted for proteasomal degradation that was treated with FAJQ1, RAJQ2, and RAJQ3 at 0 µM, 0.3 µM, 0.6 µM, 1.2 µM, 2.5 µM, and 5.0 µM for 16 hours. Equal amounts of cell lysates were loaded on SDS-PAGE, transferred to PVDF membrane, then immunoblotted with anti-GFP, and anti beta-actin antibodies. The western blots in FIG. 6 show that RAJQ1 and RAJQ2 can block proteasome function, but not RAJQ3. The top gel indicates that the compounds bind to RPN13 in the cell. The proteasome function is blocked by the compound as it binds to RPN13. Thus, the small molecule inhibitor blocked the function of proteasome, and results in only degraded targeted protein, which is much more specific.
Figure 7A:
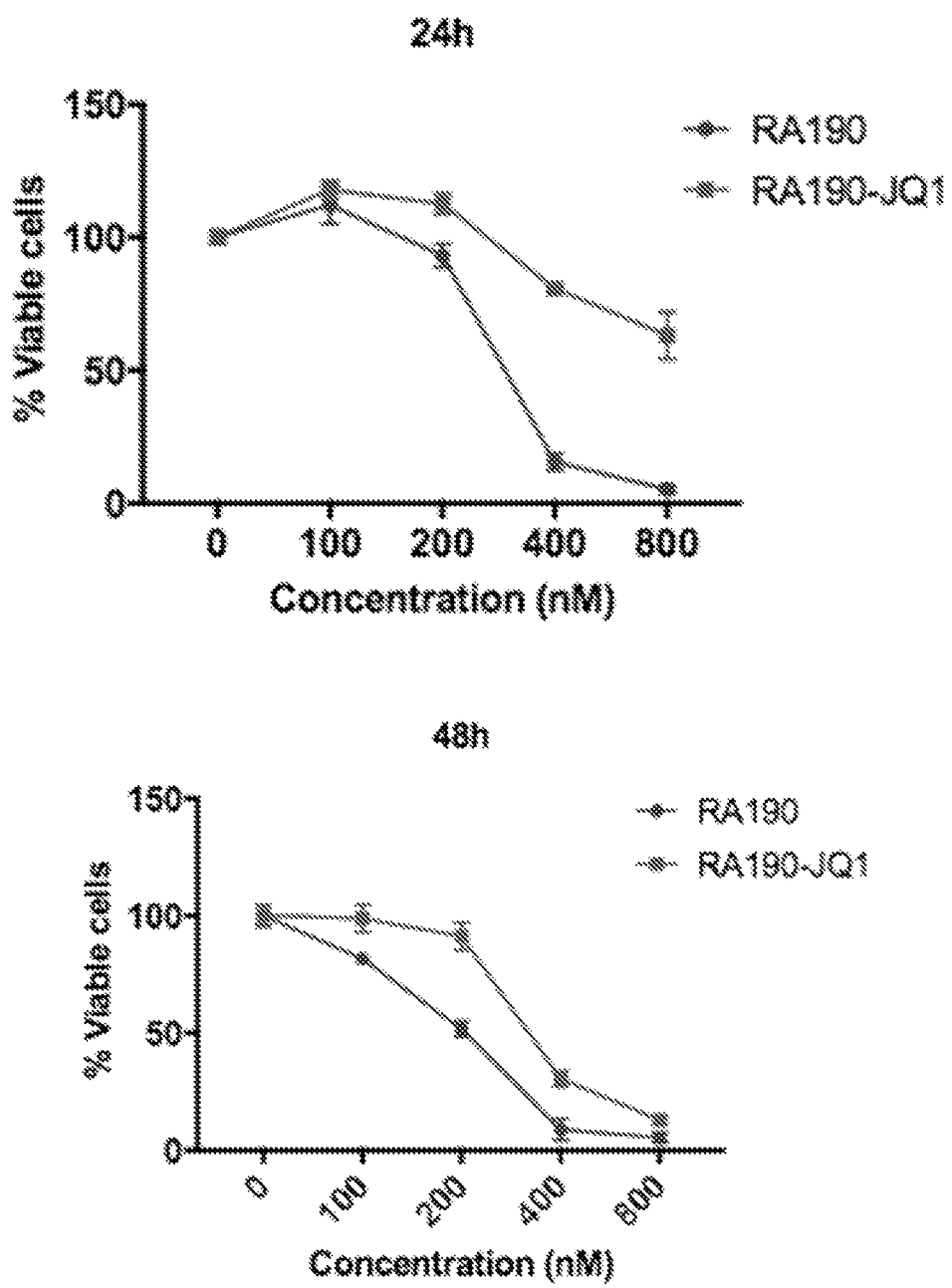
FIG. 7A shows MM. 1S cells were treated with RA190 or RA190-JQ1 at for 24 hours and 48 hours, at the indicated concentration between 0 nM and 800 nM. At 24 hours or 48 hours, wst-1 assay was used to test cell viability.
Figure 7B:
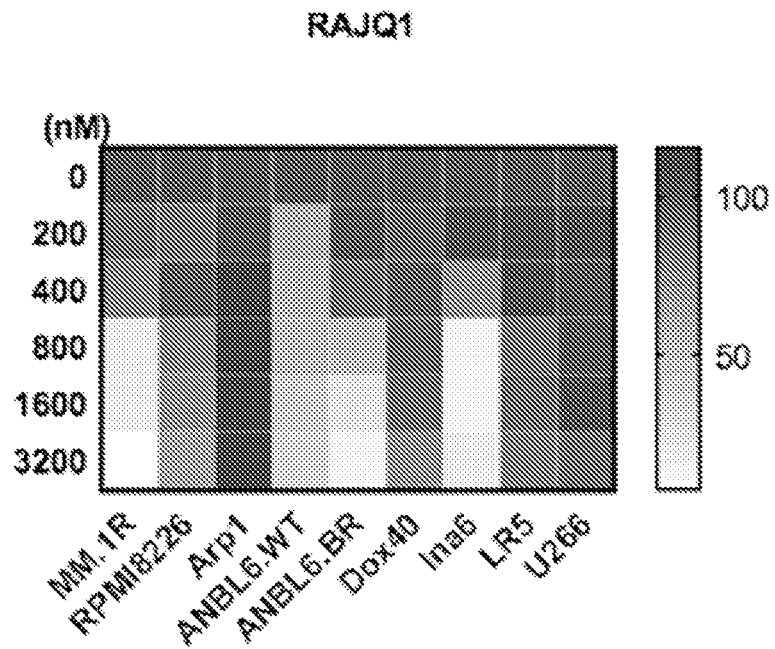
FIG. 7B shows different cells were treated with RAJQ1 at the indicated concentration between 0 nM and 3200 nM.
Figure 7C:
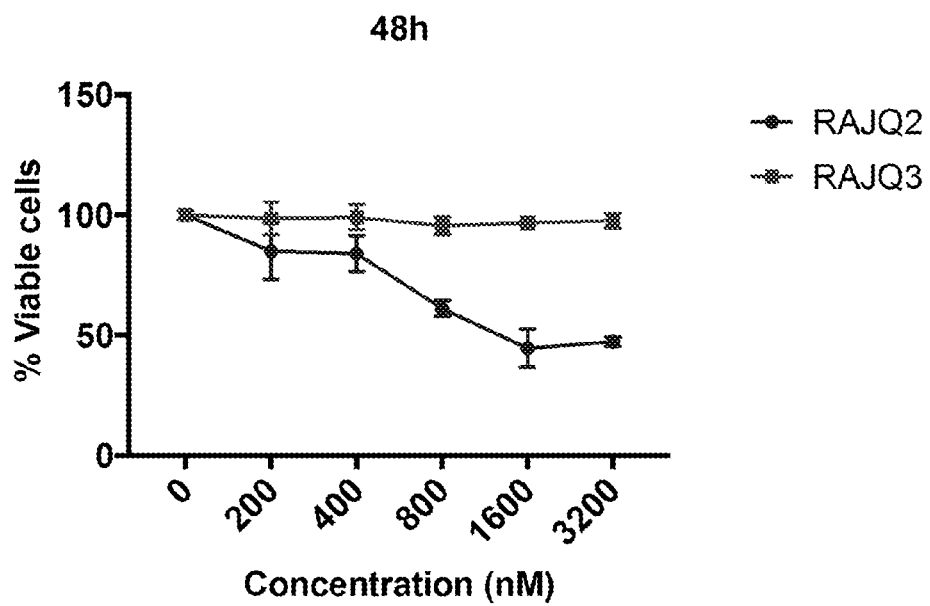
FIG. 7C show that MM. 1 S cells were treated with RA1JQ2 or RAJQ3 at the indicated concentration between 0 nM and 3200 nM. At 48 hours, wst-1 assay was used to test cell viability.
Figure 8:
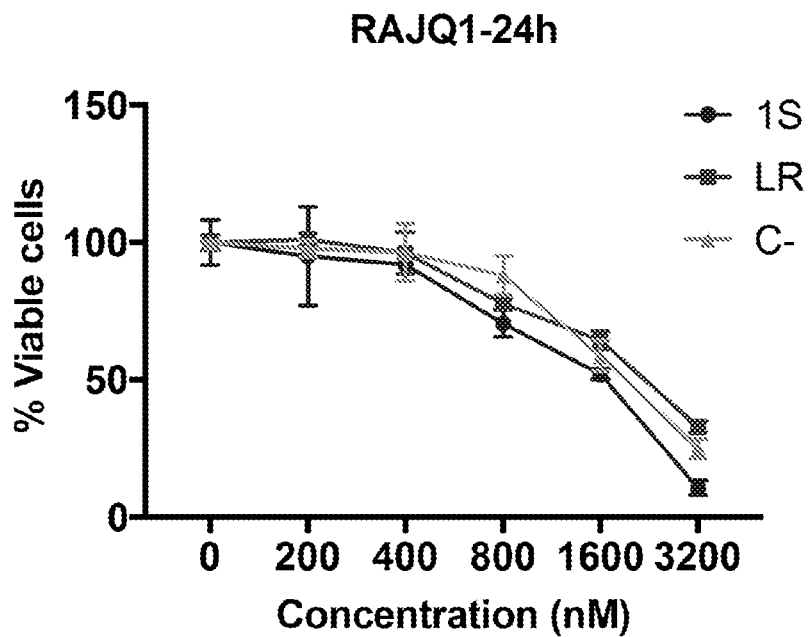
FIG. 8 shows MM. 1 S, MM. 1 S-Len resistant, and MM. 1 S-CRBN KO cells were treated with RA1JQ1 at the indicated concentration between 0 nM and 3200 nM. At 24 hours, wst-1 assay was used to test cell viability.
Figure 9:
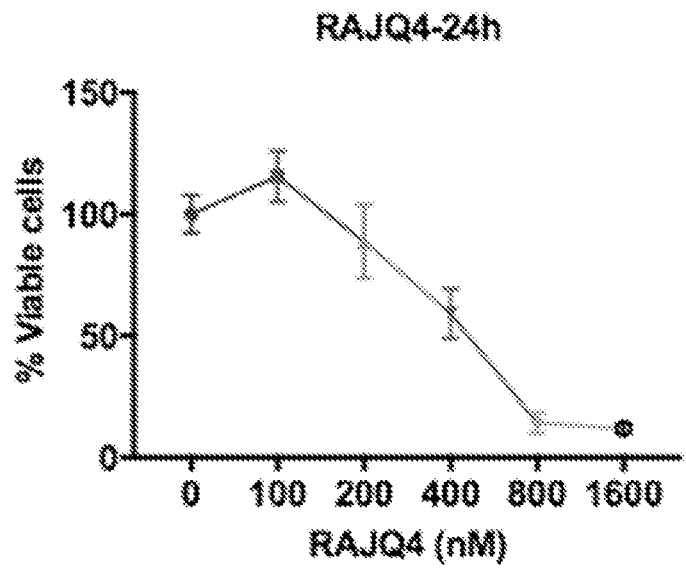
FIG. 9 shows MM. 1 S cells treated with RA1JQ4 at the indicated concentration between 0 nM and 1600 nM. At 24 hours, wst-1 assay was used to test cell viability.
Figure 10:
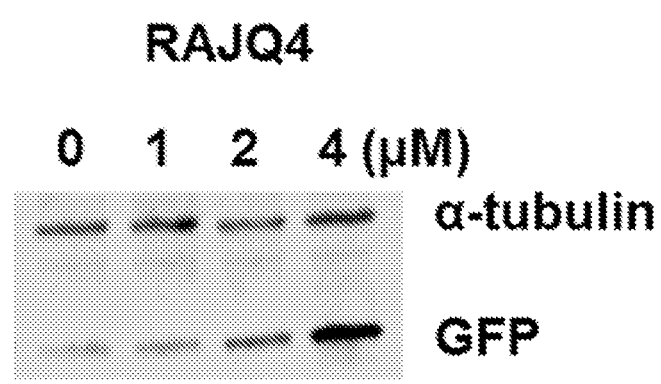
FIG. 10 shows a reporter cell line expressing Ub-tagged GFP that is constitutively targeted for proteasomal degradation, where the reporter cell line was treated with FAJQ4 at indicated concentration of 0 µM, 1.0 µM, 2.0 µM, and 4.0 µM for 16 hours. Equal amounts of cell lysates were loaded on SDS-PAGE, transferred to PVDF membrane, then immunoblotted with anti-GFP, and anti alpha-tubulin antibodies. The blots in FIG. 10 show that RAJQ4 blocks proteasome function.
Figure 11:
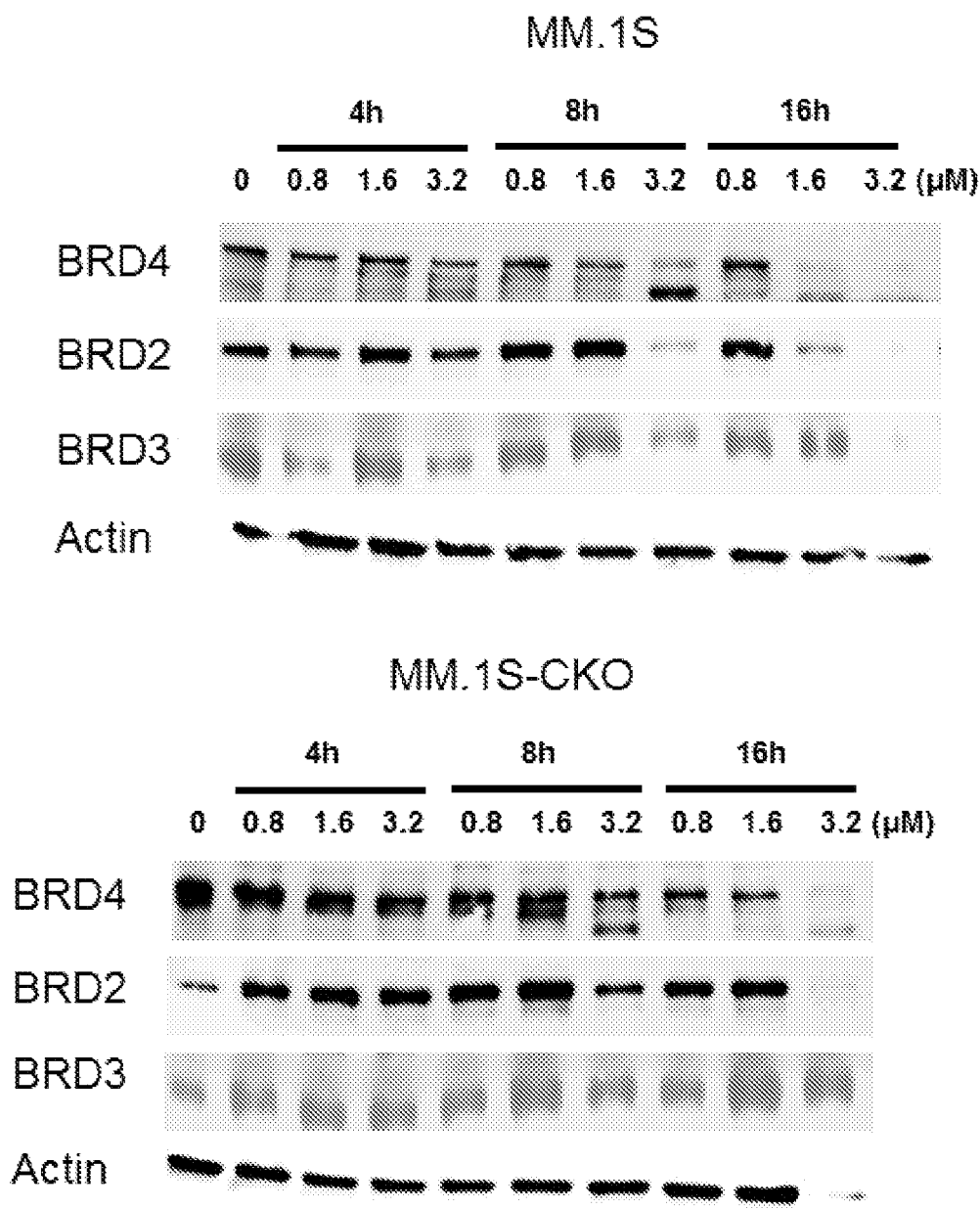
FIG. 11 shows MM. 1 S and MM. 1 S CRBN KO cells treated with RAJQ4 at indicated concentration (0 µM, 0.8 µM, 1.6 µM, and 3.2 µM) for the indicated times (4 hours, 8 hours, and 16 hours). Cell lysates were loaded on SDS-PAGE, transferred to PVDF membrane, then immunoblotted with anti-Brd2, Brd3, Brd4, and beta-actin antibodies.
Figure 12A:
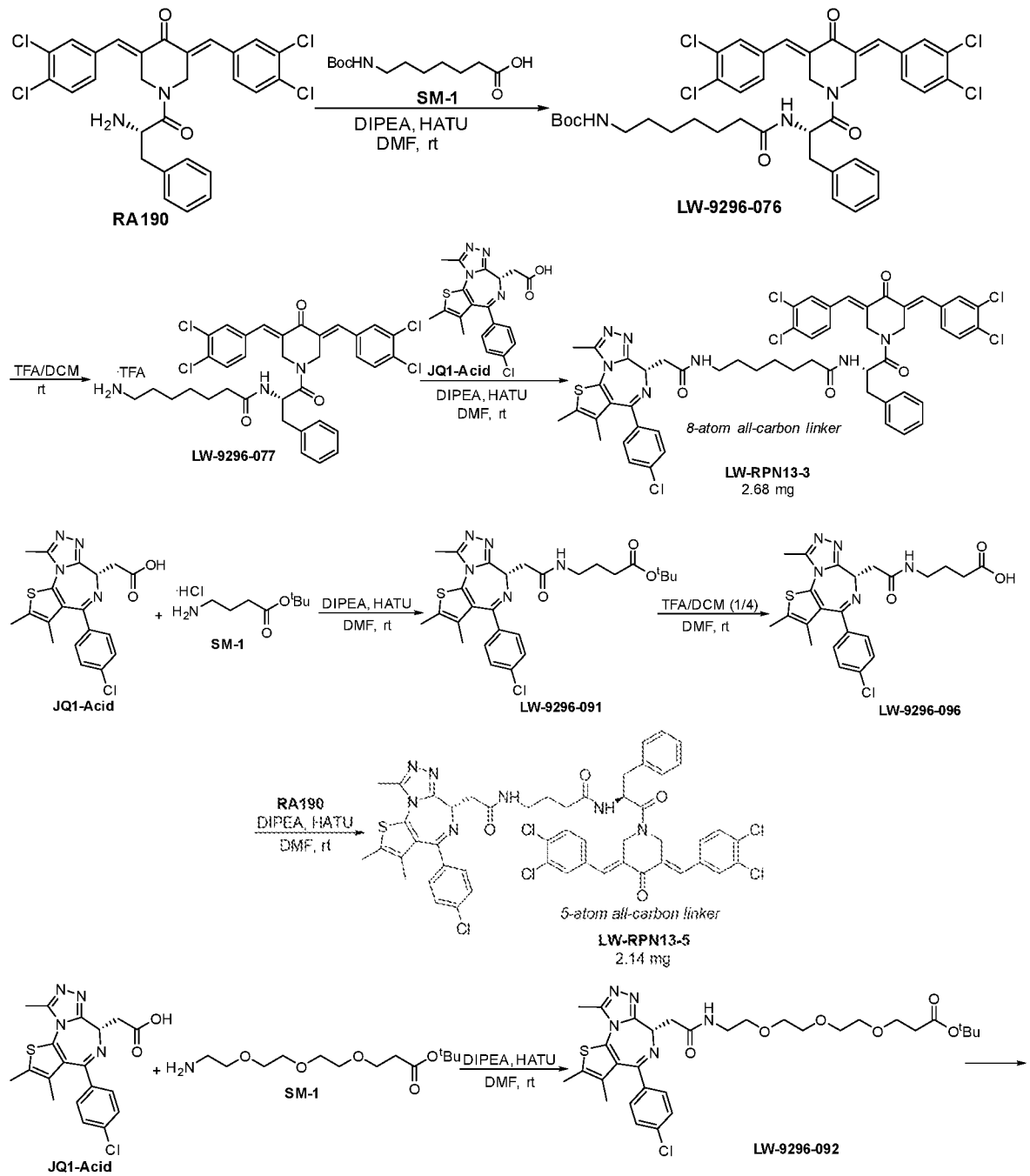
FIG. 12 shows the synthesis of exemplary moieties for the degradation of bromodomains.
Figure 12B:
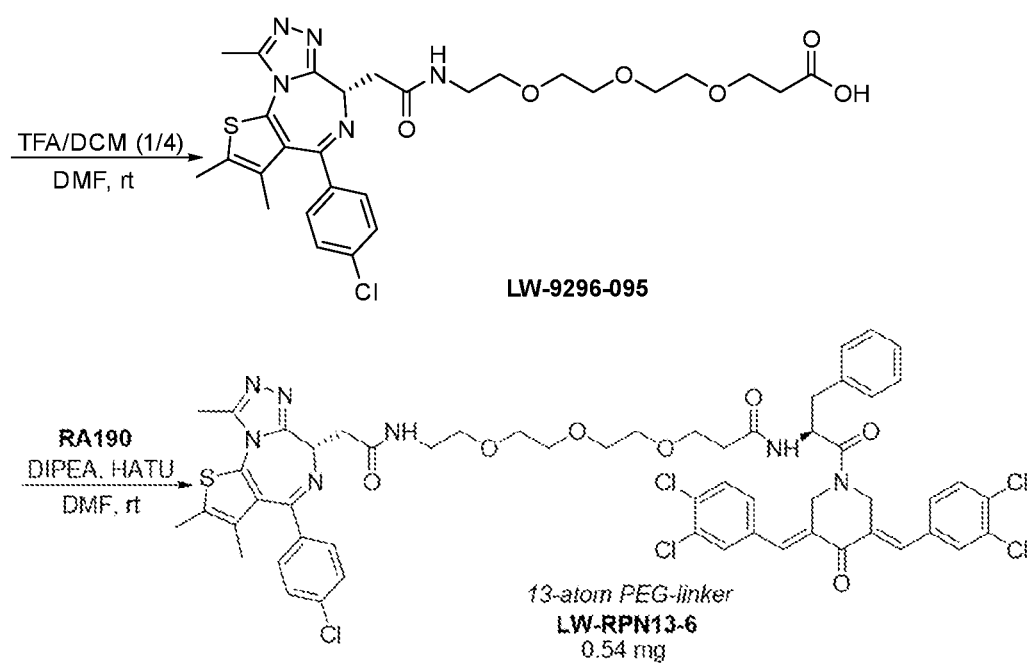
Figure 13:
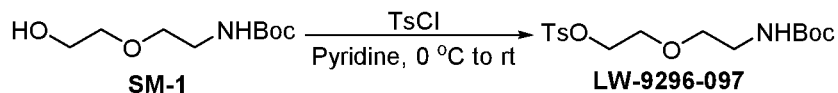
FIG. 13 shows the synthesis of exemplary moieties for the degradation of bromodomains.
Figure 13:
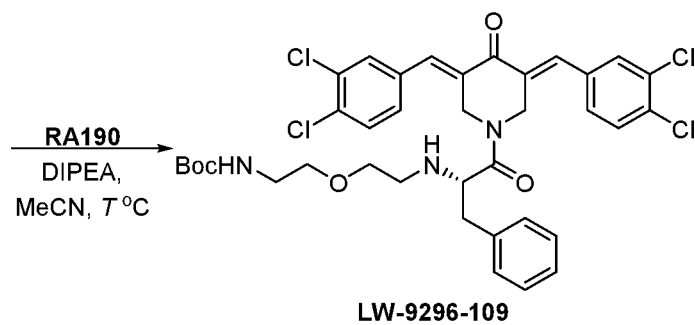
Figure 13:
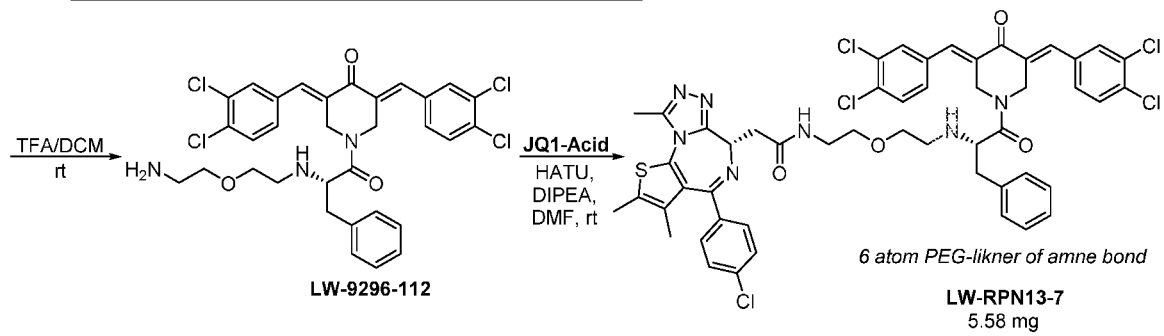
Figure 14:
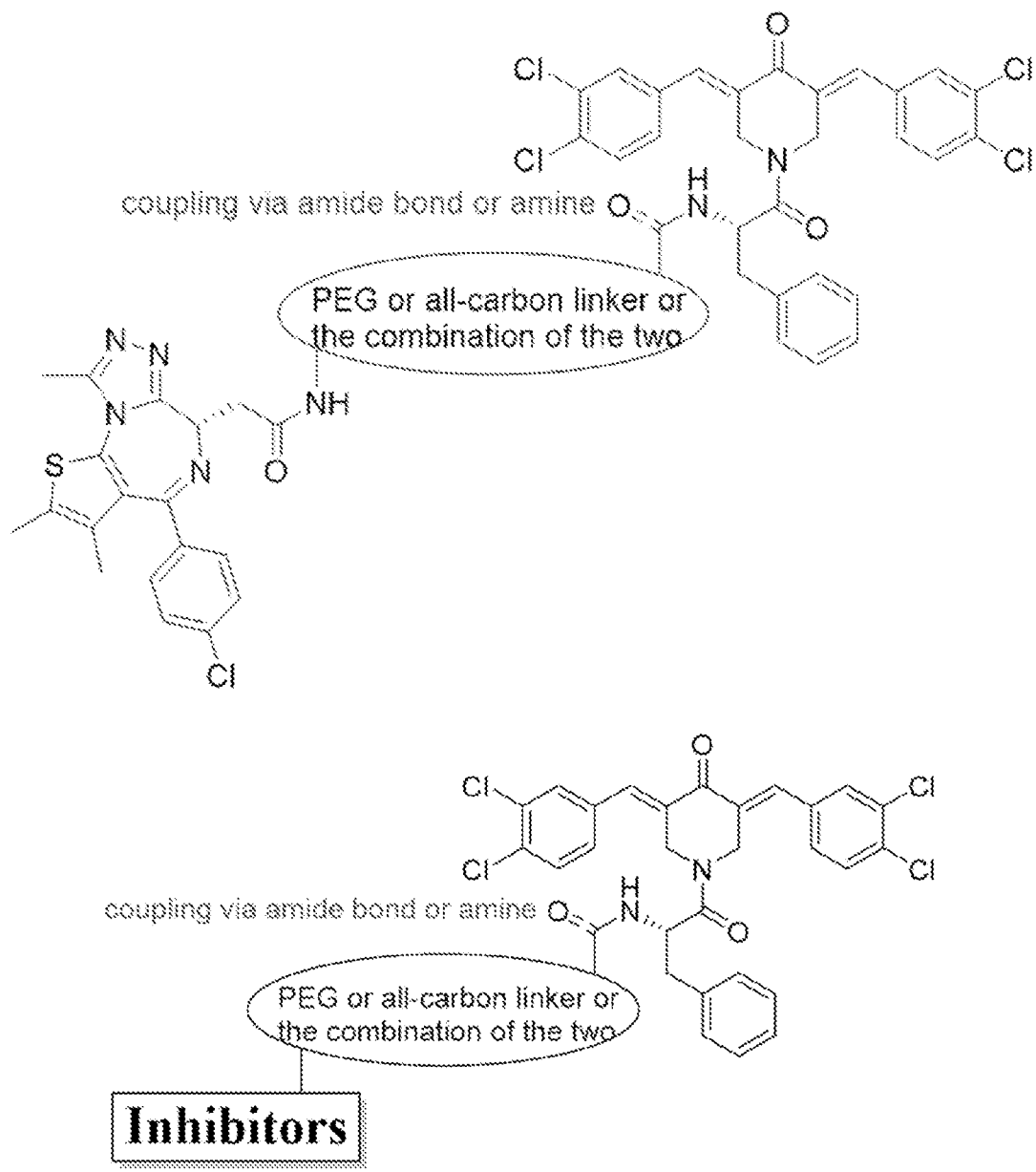
FIG. 14 shows the future plans for developing RPN13 related degrading compounds. Additional bromodomain degraders and new degraders of other proteins that are potent will be developed.
Figure 15:
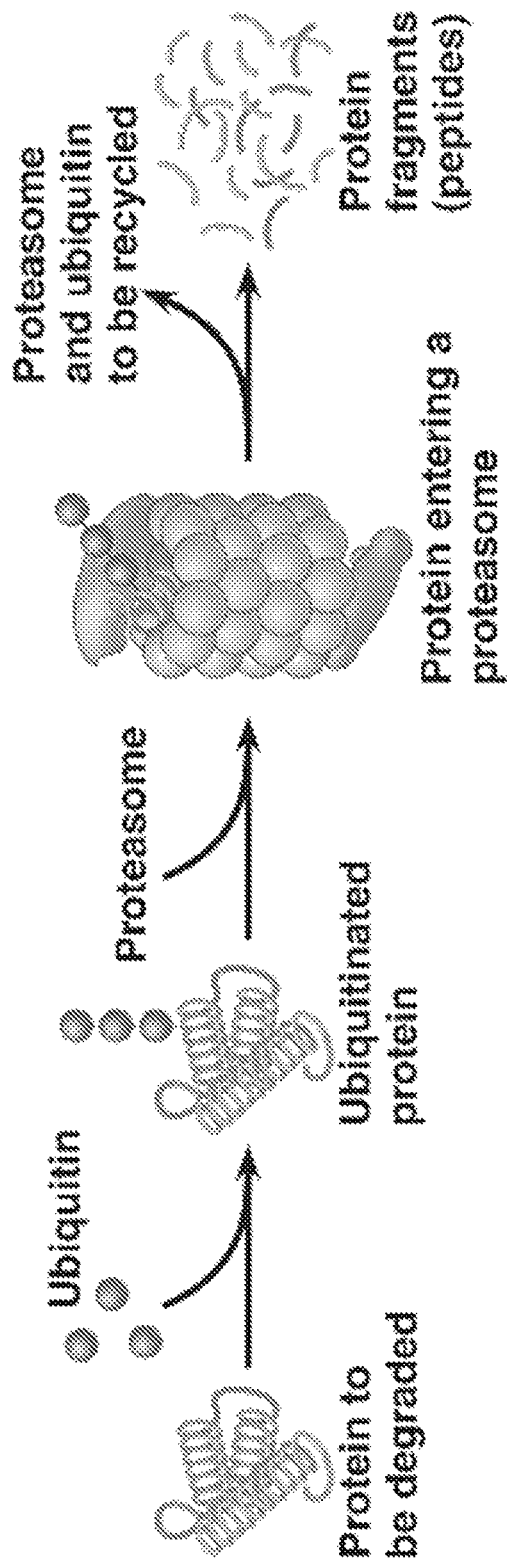
FIG. 15 shows a schematic of RPN13-based protein degradation, in which the protein is recognized and recruited by a proteasome. The protein enters the proteasome and then is hydrolyzed.
Figure 16:
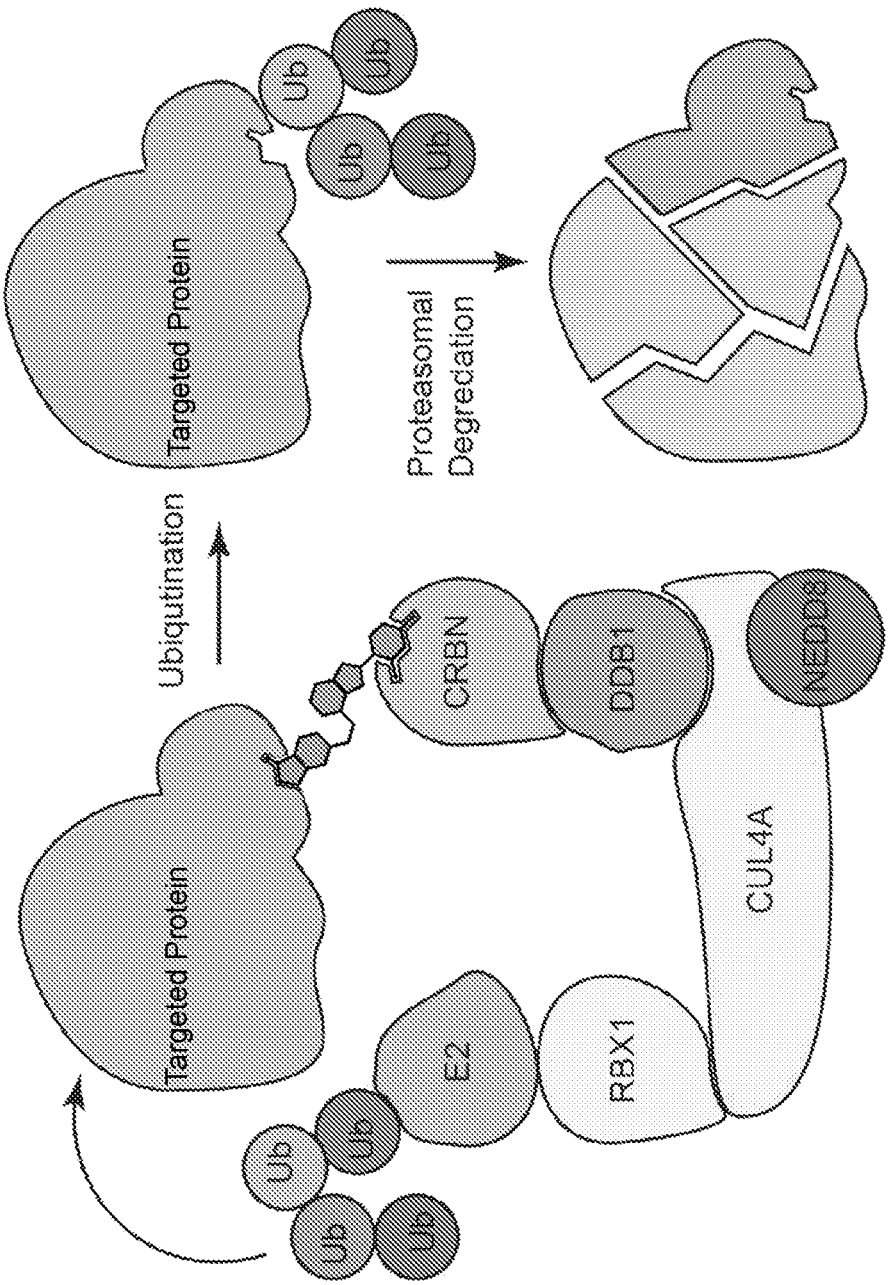
FIG. 16 shows CRBN-induced degradation of a targeted protein, in which ubiquitination occurs, followed by proteasomal degradation.
Figure 17:
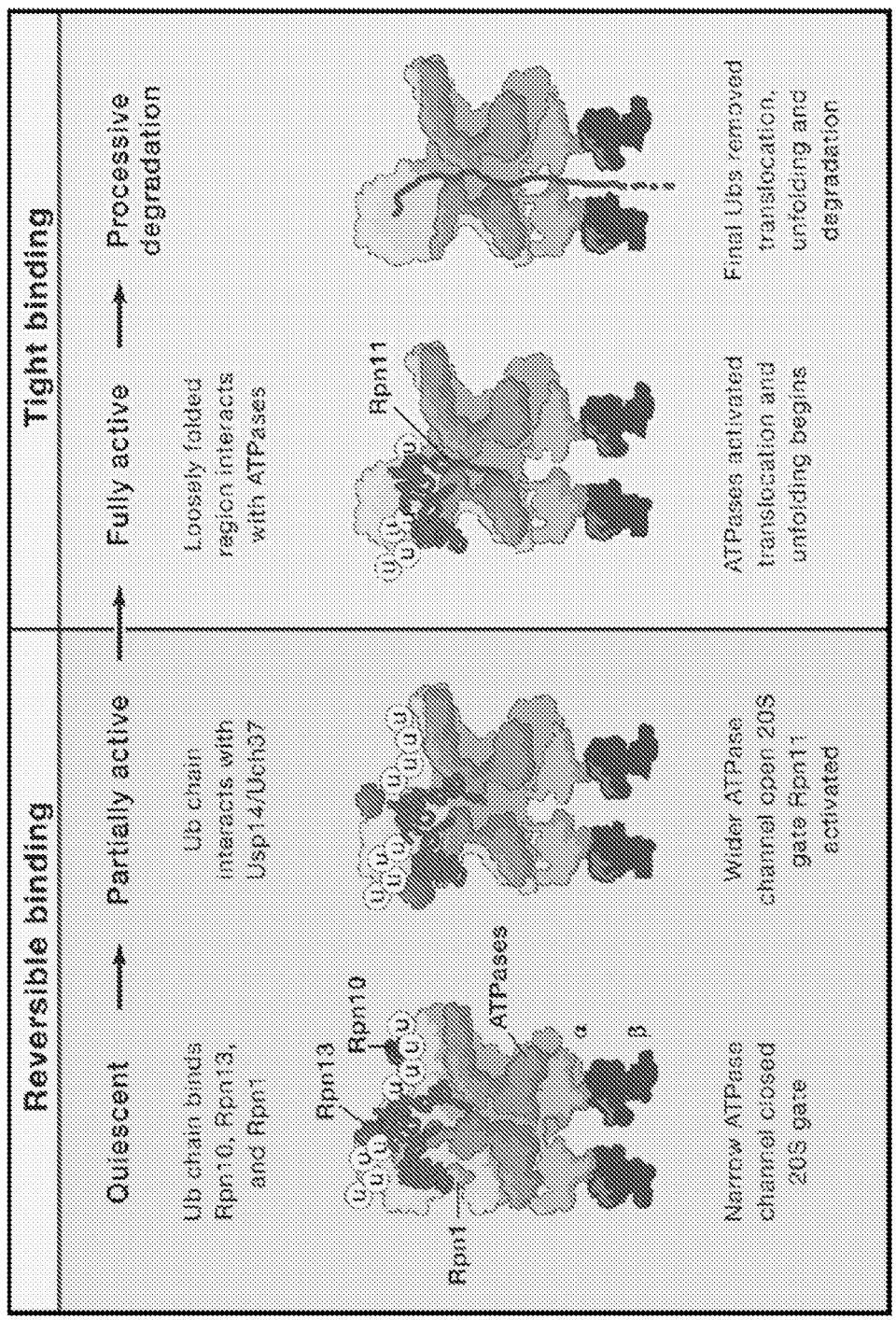
FIG. 17 shows a schematic of the RPN13 function, which is located on the proteasome S19, and function as recognition machinery to put the protein into proteasome.
Figure 18:
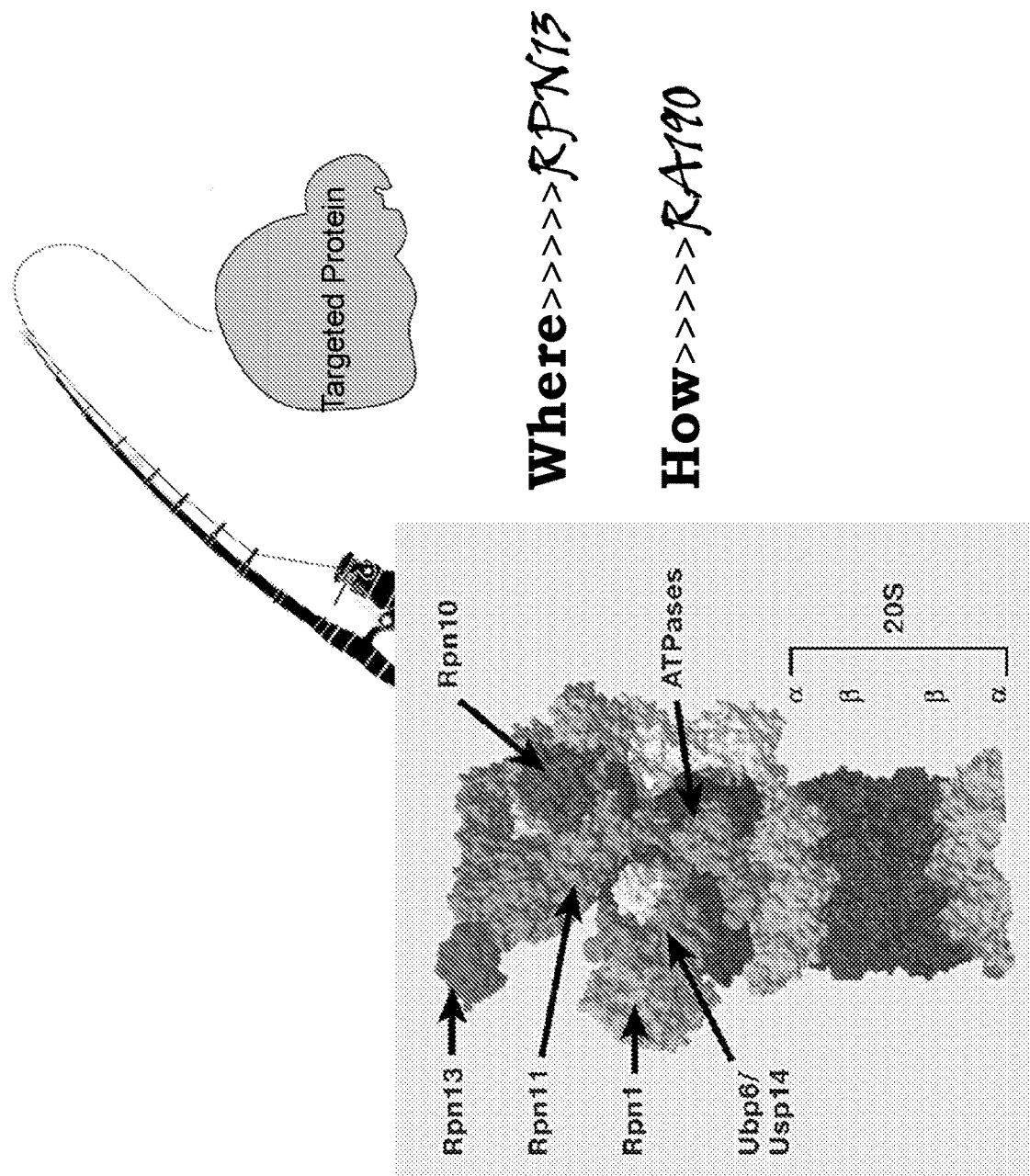
FIG. 18 shows an exemplary compound in which the binder of the ubiquitin receptor RPN13 is RA190, and the compound promotes the degradation of a target protein.
Figure 19:
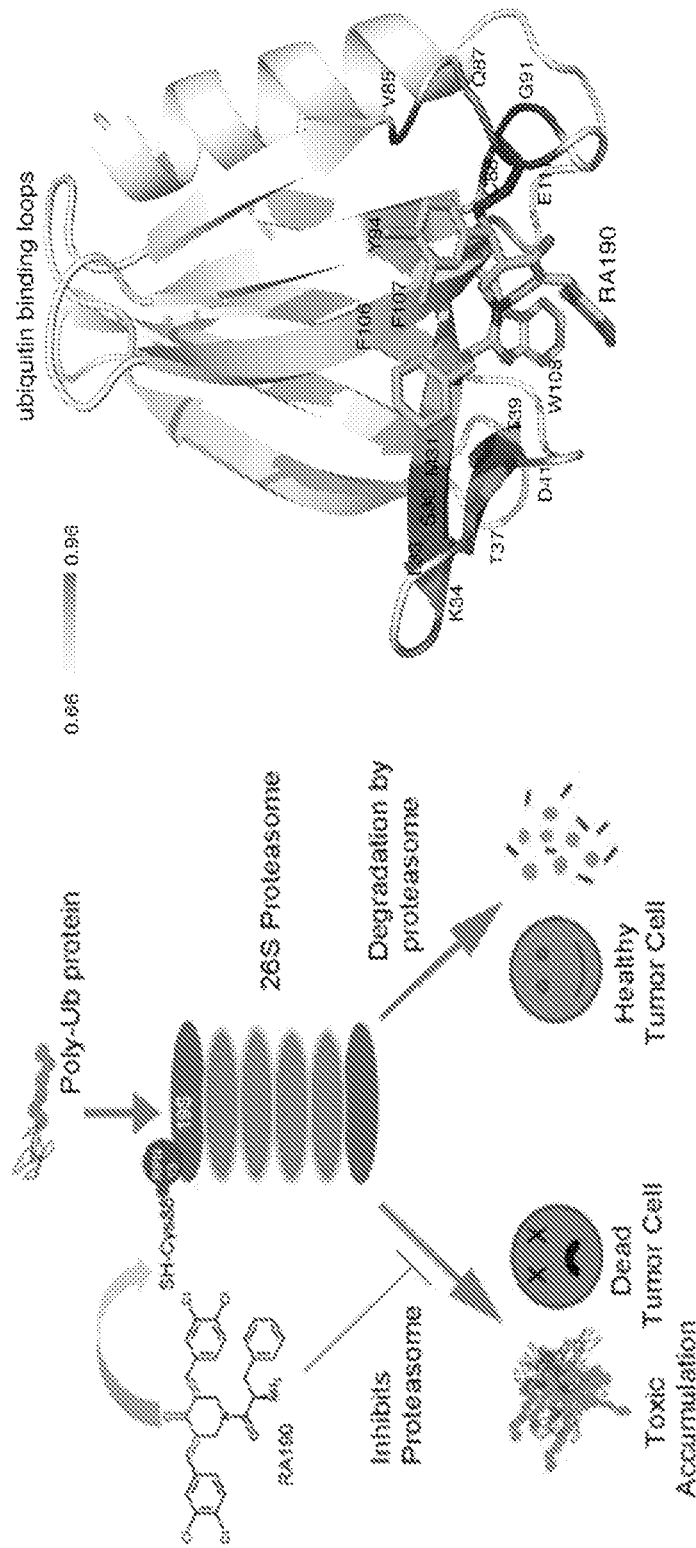
FIG. 19 shows a schematic depicting two different pathways of a polyubiquinated protein wherein degradation of the protein by a proteasome leads to a healthy tumor cell, and conversely, inhibition of the proteasome using an exemplary compound which includes RA190 leads to a dead tumor cell.
Figure 20:
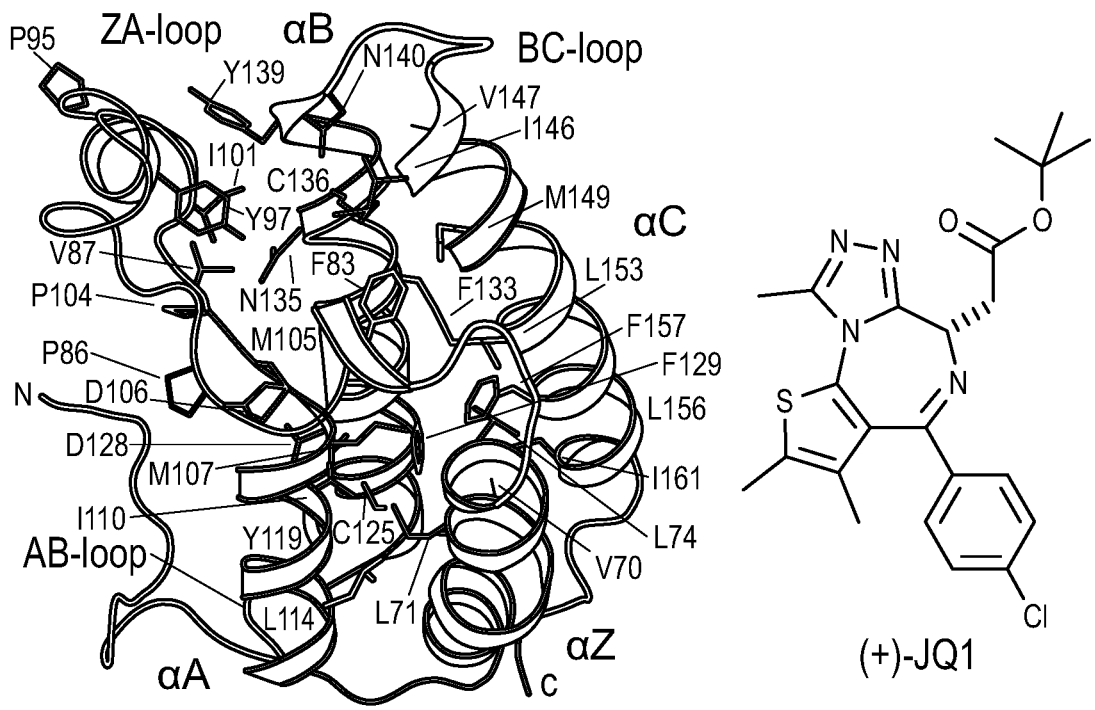
FIG. 20 shows a bromodomain target protein and a BET inhibitor JQ1-(S). The BET inhibitor JQ1-(S) is connected to RA190 via a linker as design principle to move the targeted proteins to proteasome directly.
Figure 20:
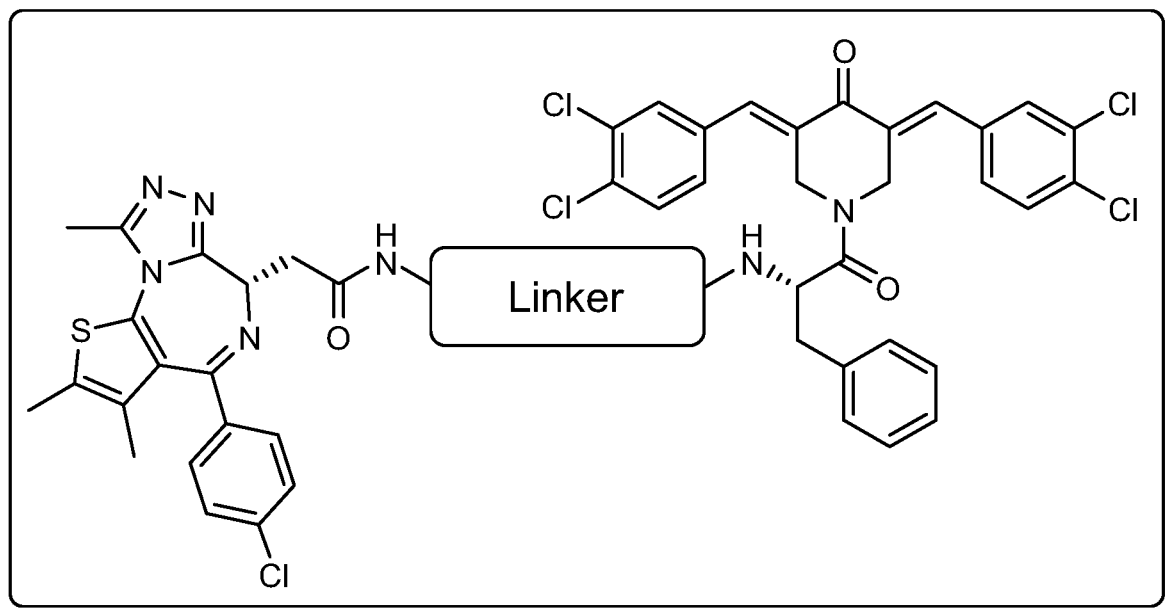
Figure 21:
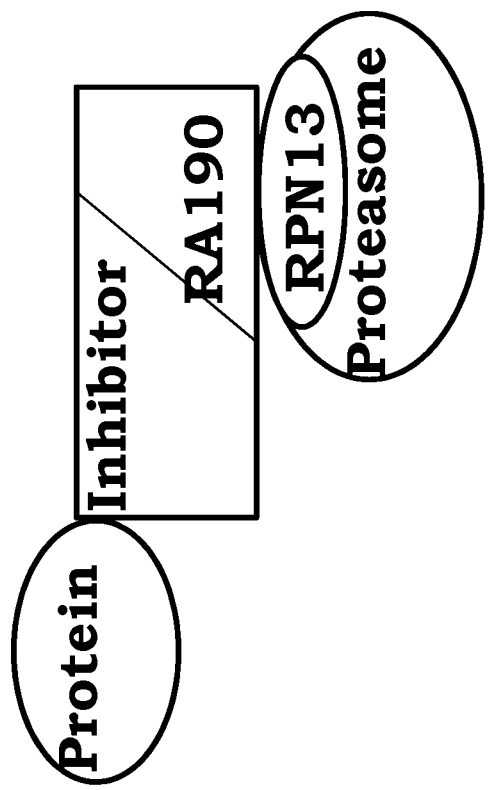
FIG. 21 shows a schematic depicting an exemplary compound which includes a binder of the ubiquitin receptor RPN13 that is RA190, and the compound promotes the degradation of a target protein by proteasomal degradation.
Figure 22:
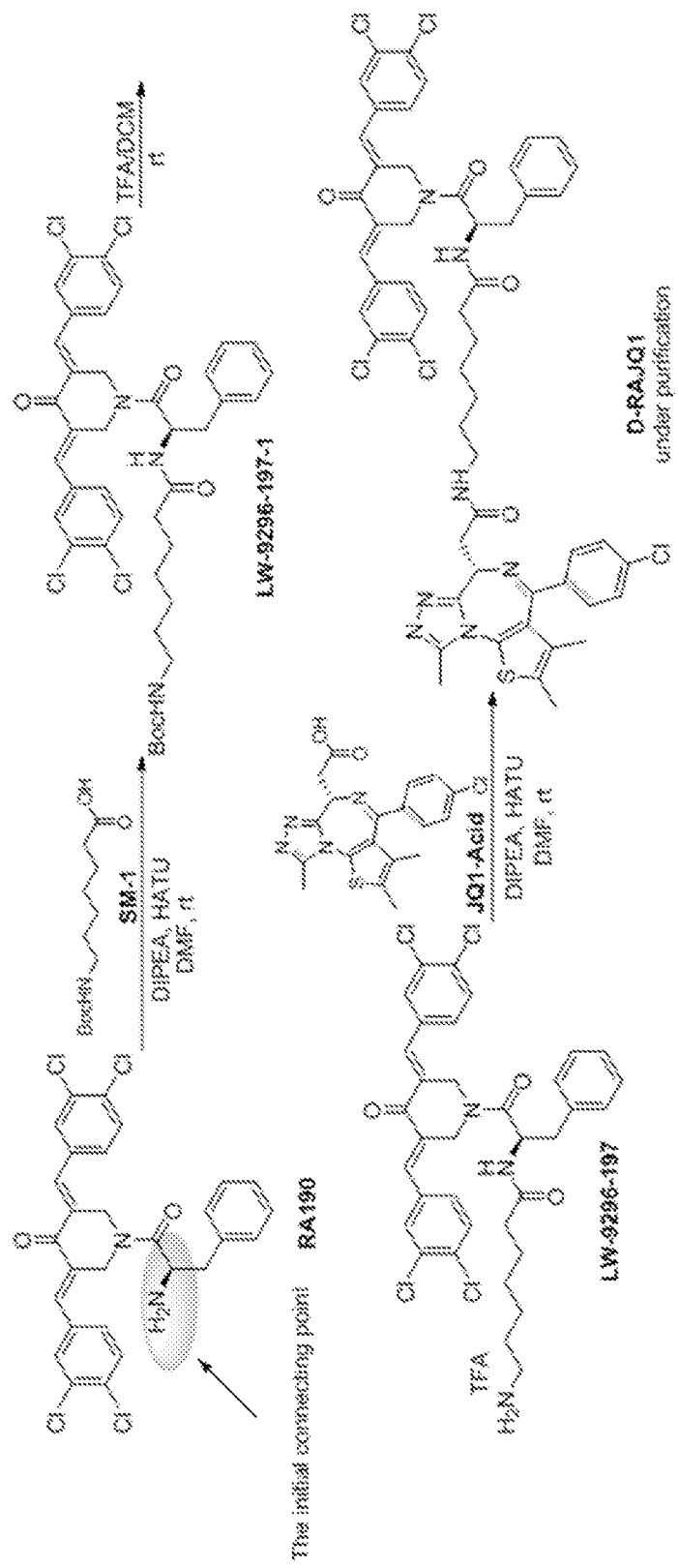
FIG. 22 shows an exemplary synthetic scheme for synthesizing an exemplary compound (D-RAJQ1) which includes a bromodomain inhibitor linked to RA190 via a linker.
Figure 23:
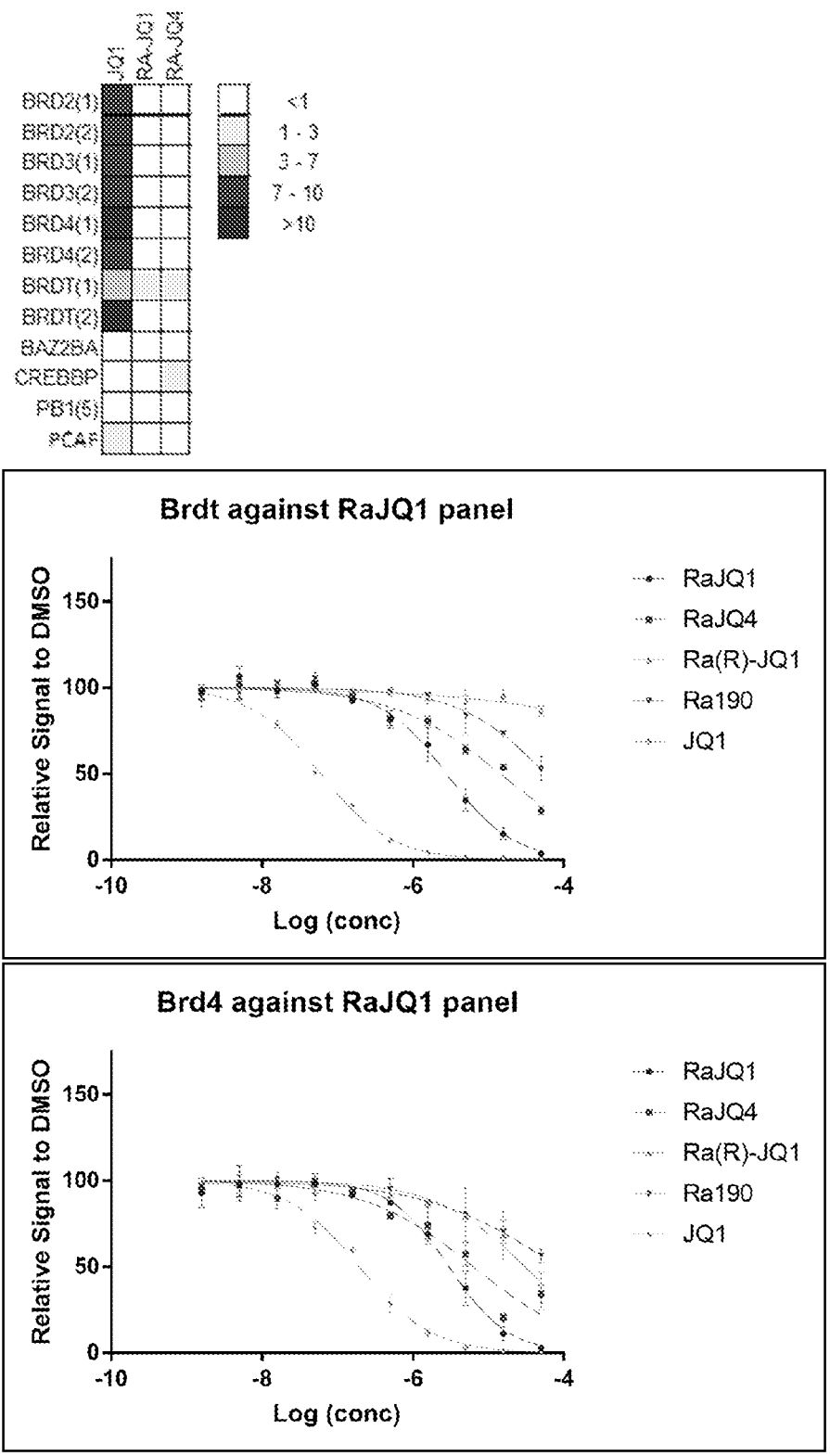
FIG. 23 shows proteins Brd4 and Brdt each interacting with RAJQ1, RAJQ4, RA(R)-JQ, RA190, and JQ1, and the signal relative to DMSO resulting using differentiation scanning fluorometry (DSF) to determine the binding of compounds with BRD4 or BRDT. The AlphaScreen biochemical assay also has been used to measure the binding affinity of compound with BRD4.
Figure 24:
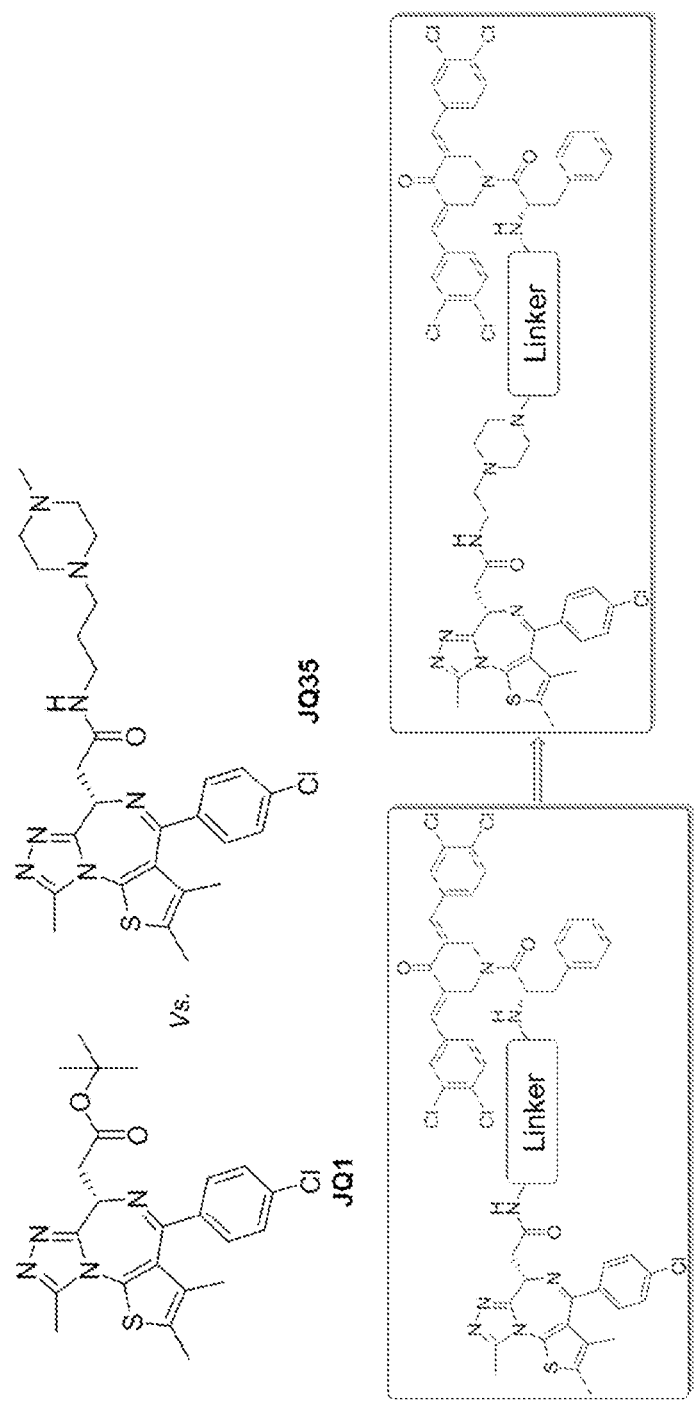
FIG. 24 shows using more potent bromodomain inhibitor compounds (e.g., JQ35) and their respective linker attachments to RA190 to improve the binding of bifunctional molecules against BRD4.
Figure 25:
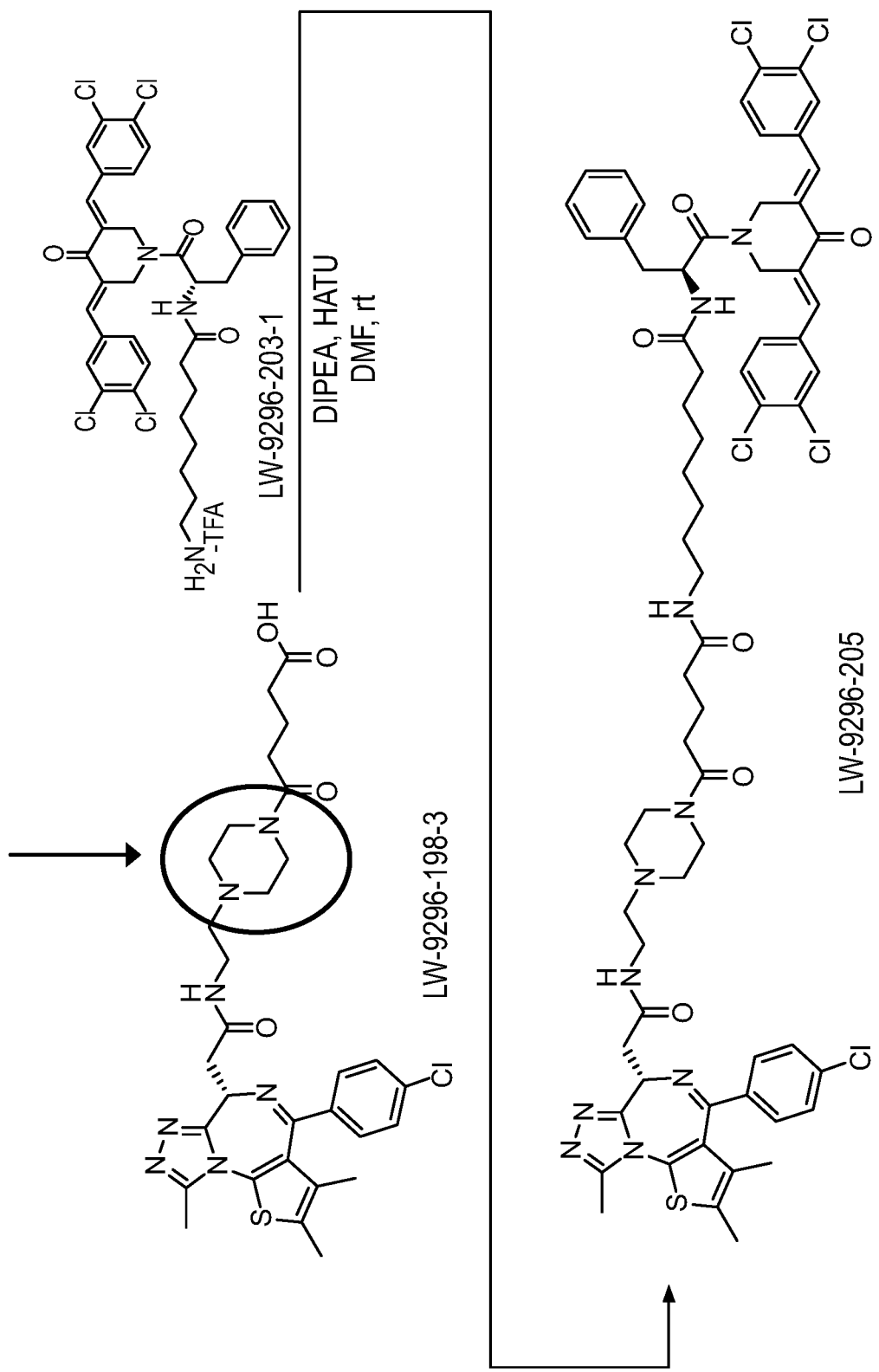
FIG. 25 shows exemplary synthesis of exemplary compound LW-9296-205, which exhibits poor solubility; and was lost in the purification via HPLC (0.1% TFA).
Figure 26:
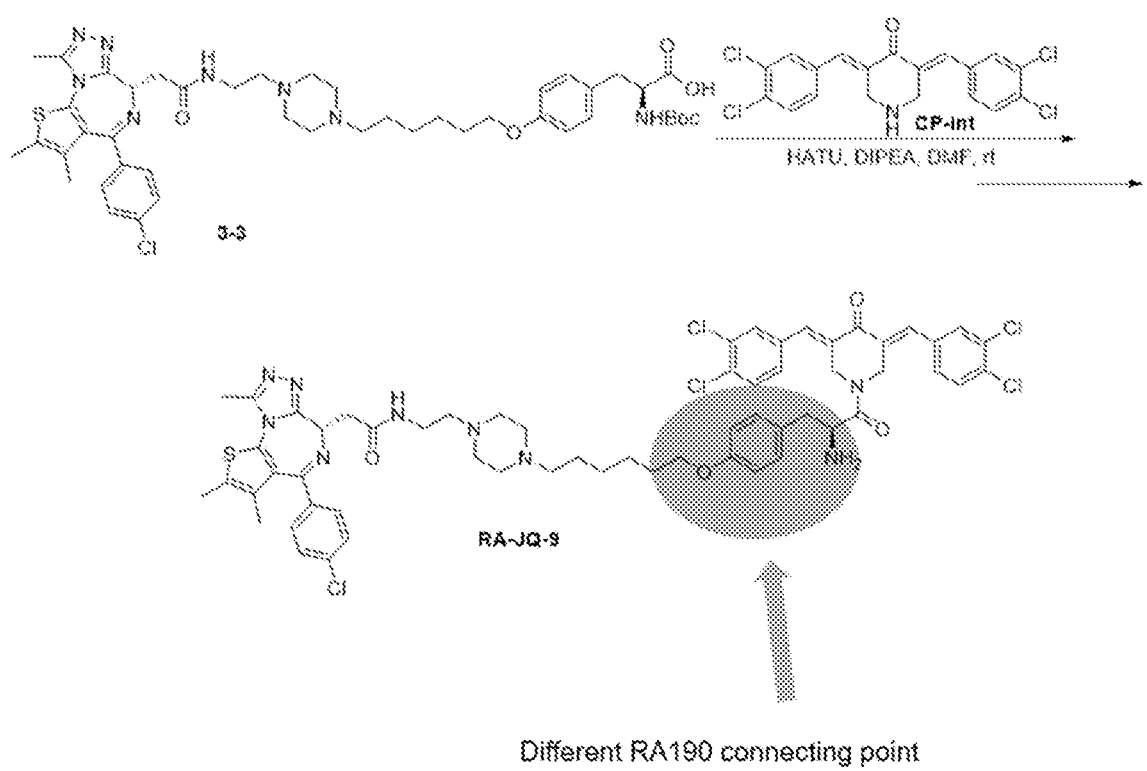
FIG. 26 shows an exemplary compound RA-JQ-9 (RAJQ9), which has a different point of connection of the linker to RA190.
Figure 27:
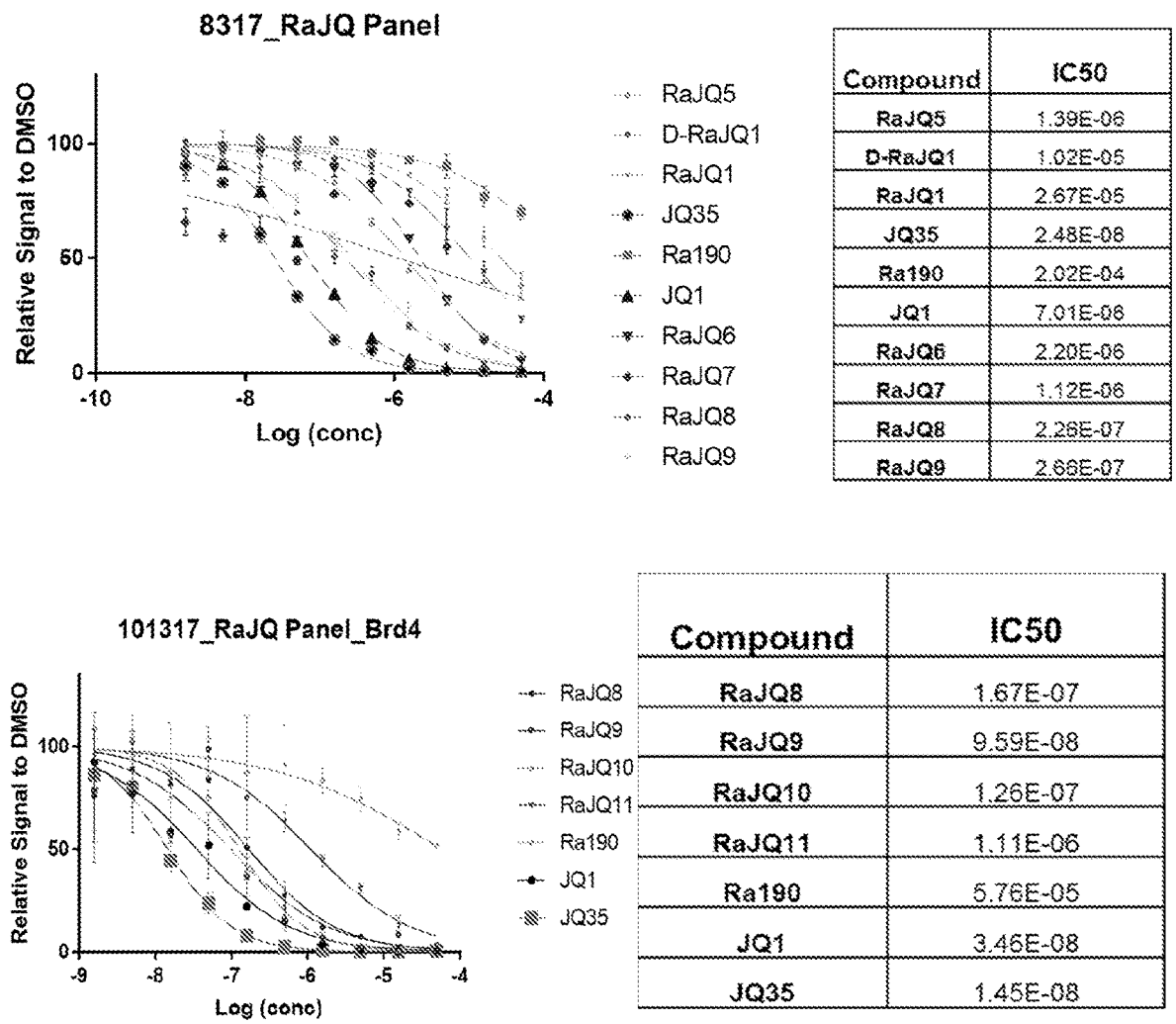
FIG. 27 shows biochemical assays binding of RaJQ exemplary compounds with BRD4 proteins, which shows the relative signal to DMSO resulting when the proteins interact with each of the inhibitor compounds listed. The half maximal inhibitory concentrations ($IC_{50}$) are listed for each compound.
Figure 28:
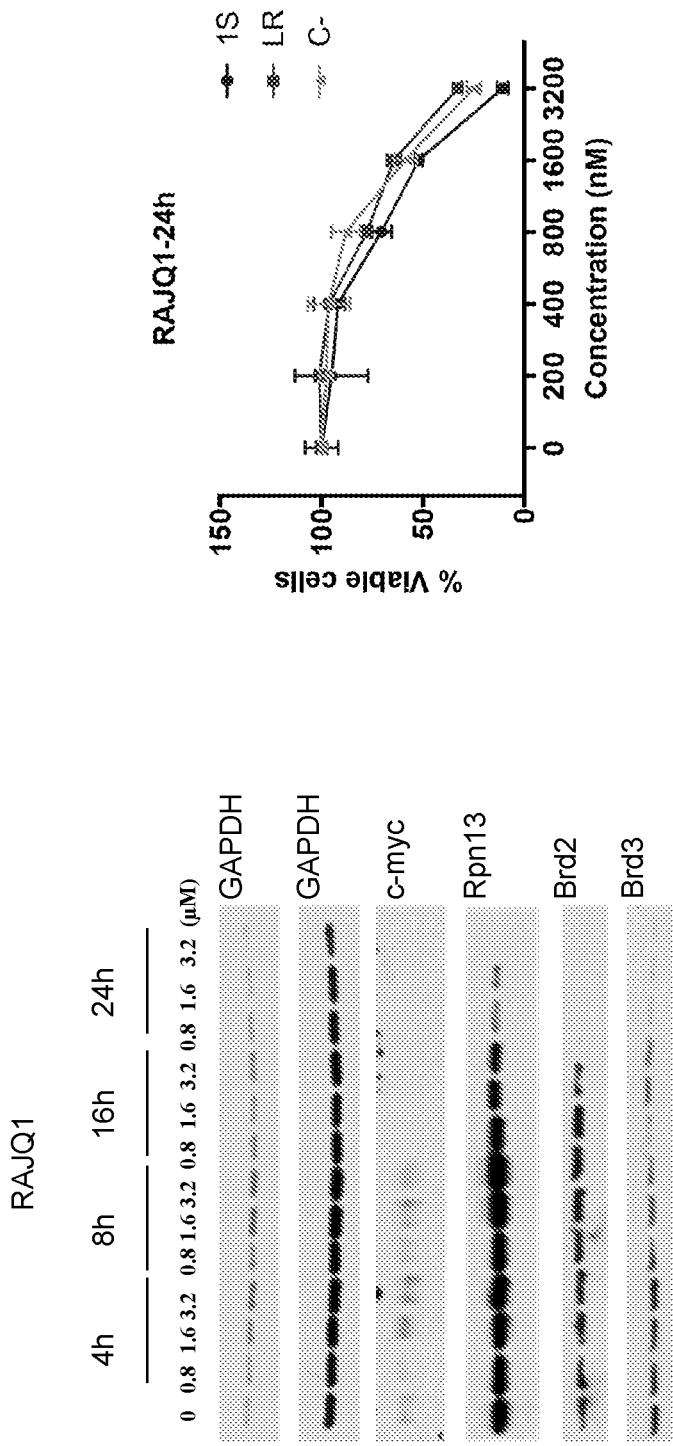
FIG. 28 shows blots of cells that were treated with RAJQ1 at the indicated concentrations and times. Cell lysates were loaded on SDS-PAGE, transferred to PVDF membrane, then immunoblotted with anti-GAPDH, Rpn13, Brd3, Brd2, and c-Myc antibodies.
Figure 29:
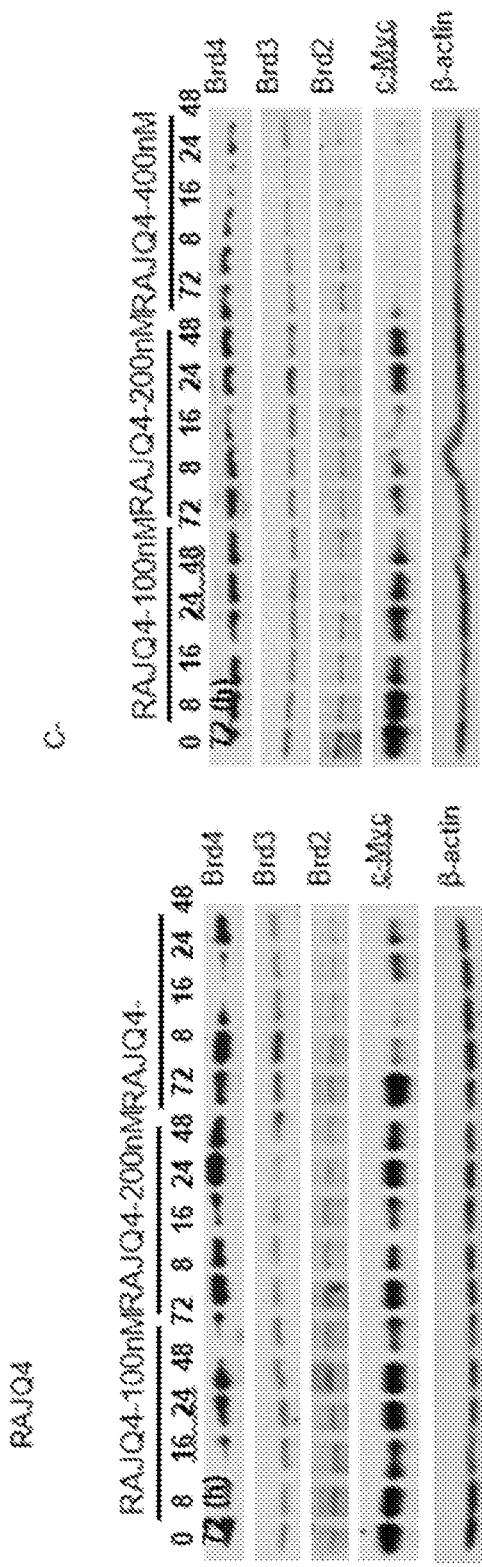
FIG. 29 shows cells that were treated with RAJQ4 at the indicated concentrations and times. Cell lysates were loaded on SDS-PAGE, transferred to PVDF membrane, then immunoblotted with anti-Brd4, Brd3, Brd2, c-Myc, and 3-actin antibodies. C— is the knockout cell line.
Figure 30:
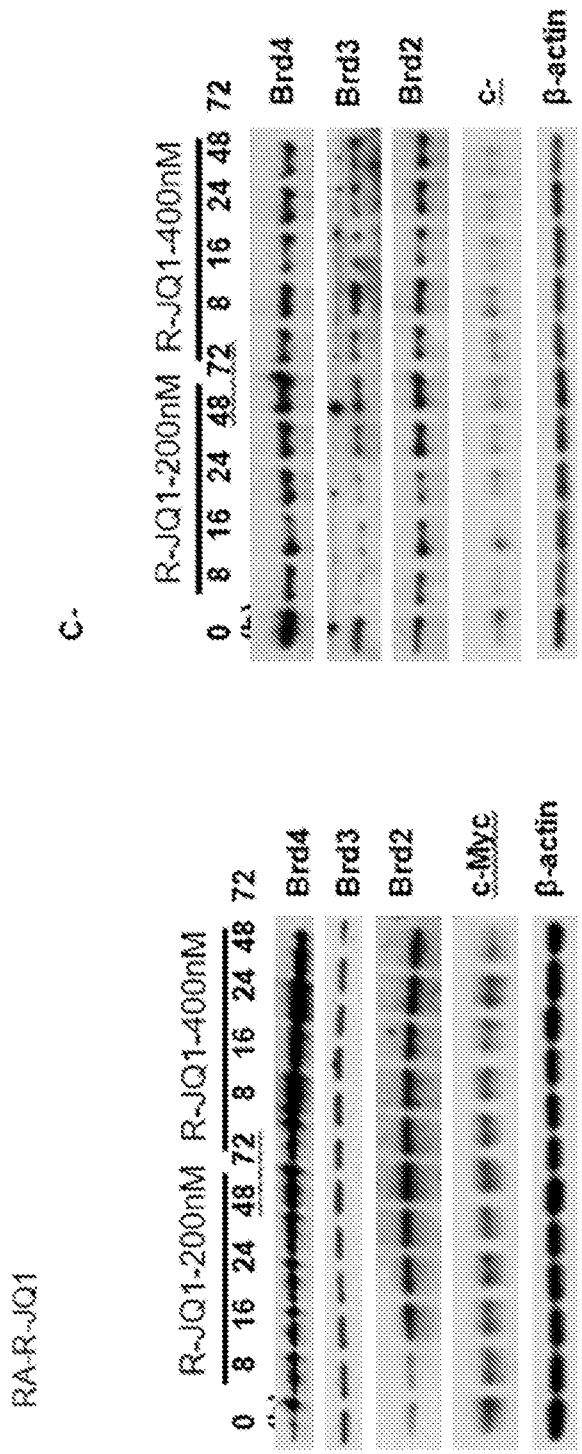
FIG. 30 shows cells that were treated with RA-R-JQ1 at the indicated concentrations and times in MM1S. Cell lysates were loaded on SDS-PAGE, transferred to PVDF membrane, then immunoblotted with anti-Brd4, Brd3, Brd2, c-Myc, and 3-actin antibodies. C— is the CRBN knockout MM1 S cell line.
Figure 31:
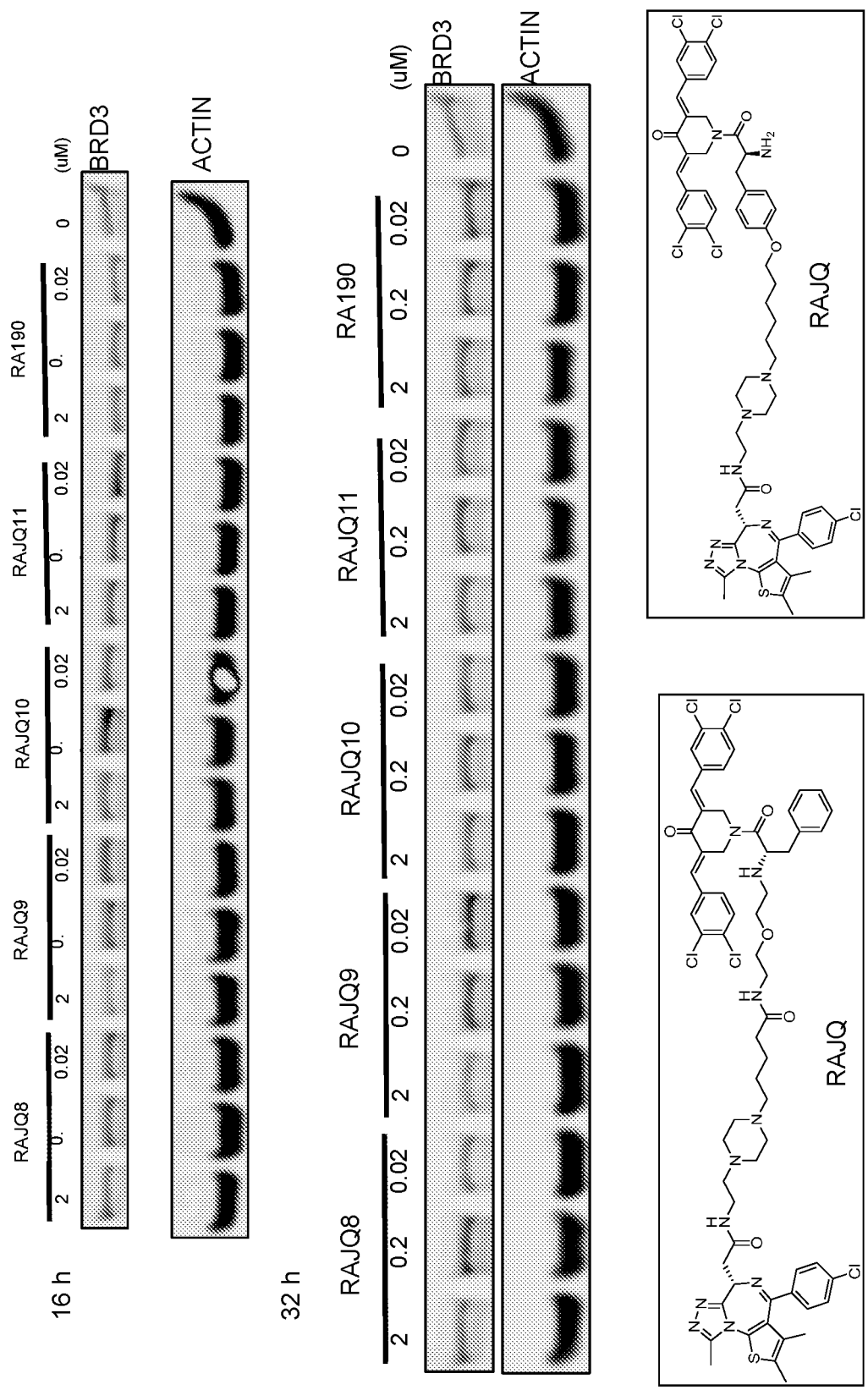
FIG. 31 shows blots showing bromodomain degradation in 293T cells. Cells were treated with RAJQ8, RAJQ9, RAJQ10, RAJQ11, and RA190 at the indicated concentrations and times. Cell lysates were loaded on SDS-PAGE, transferred to PVDF membrane, then immunoblotted with anti-BRD3 and actin antibodies to check the BRD3 degradation.
Figure 32:
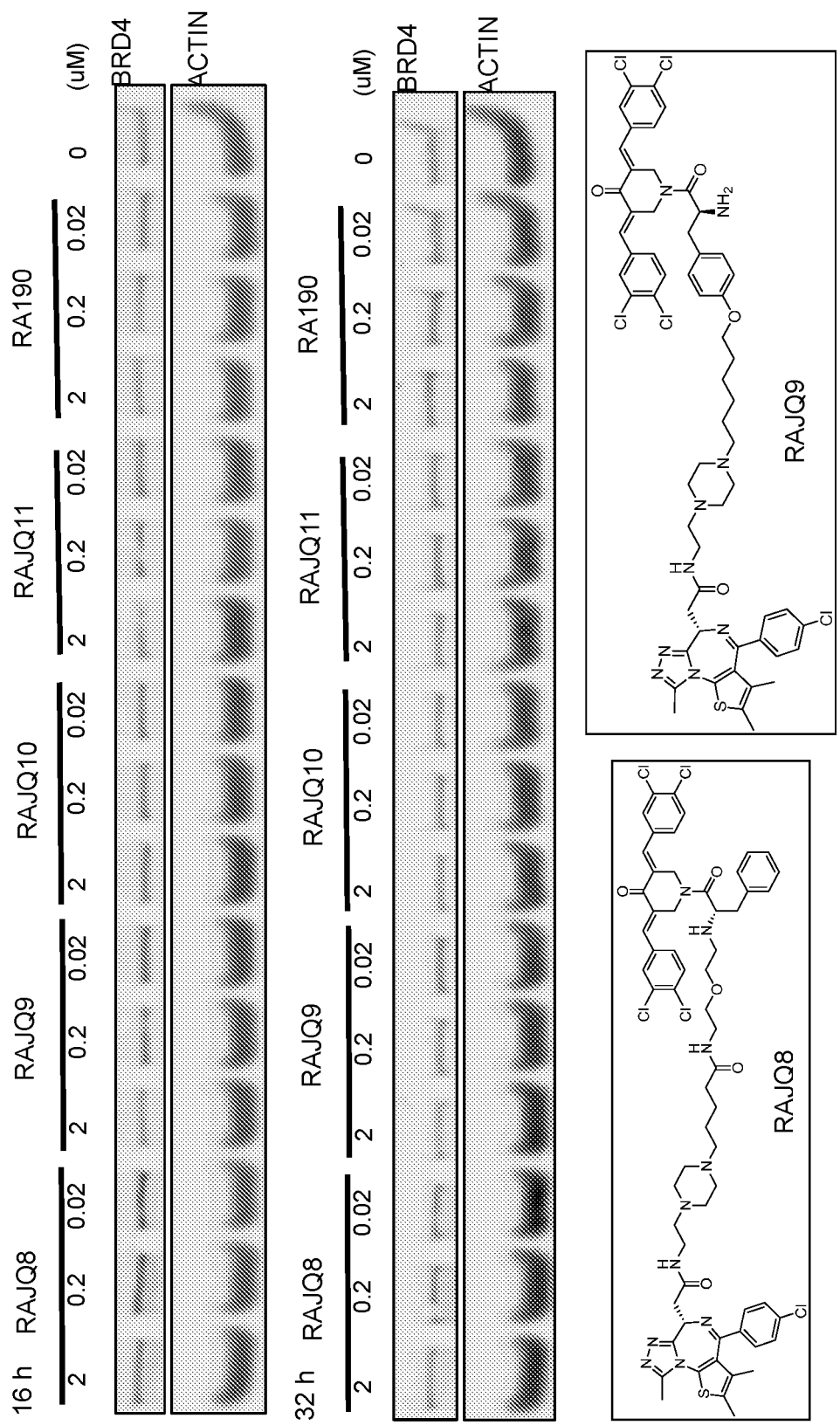
FIG. 32 shows bromodomain degradation in 293T cells. Cells were treated with RAJQ8, RAJQ9, RAJQ10, RAJQ11, and RA190 at the indicated concentrations and times. Cell lysates were loaded on SDS-PAGE, transferred to PVDF membrane, then immunoblotted with anti-BRD4 and actin antibodies.
Figure 33:
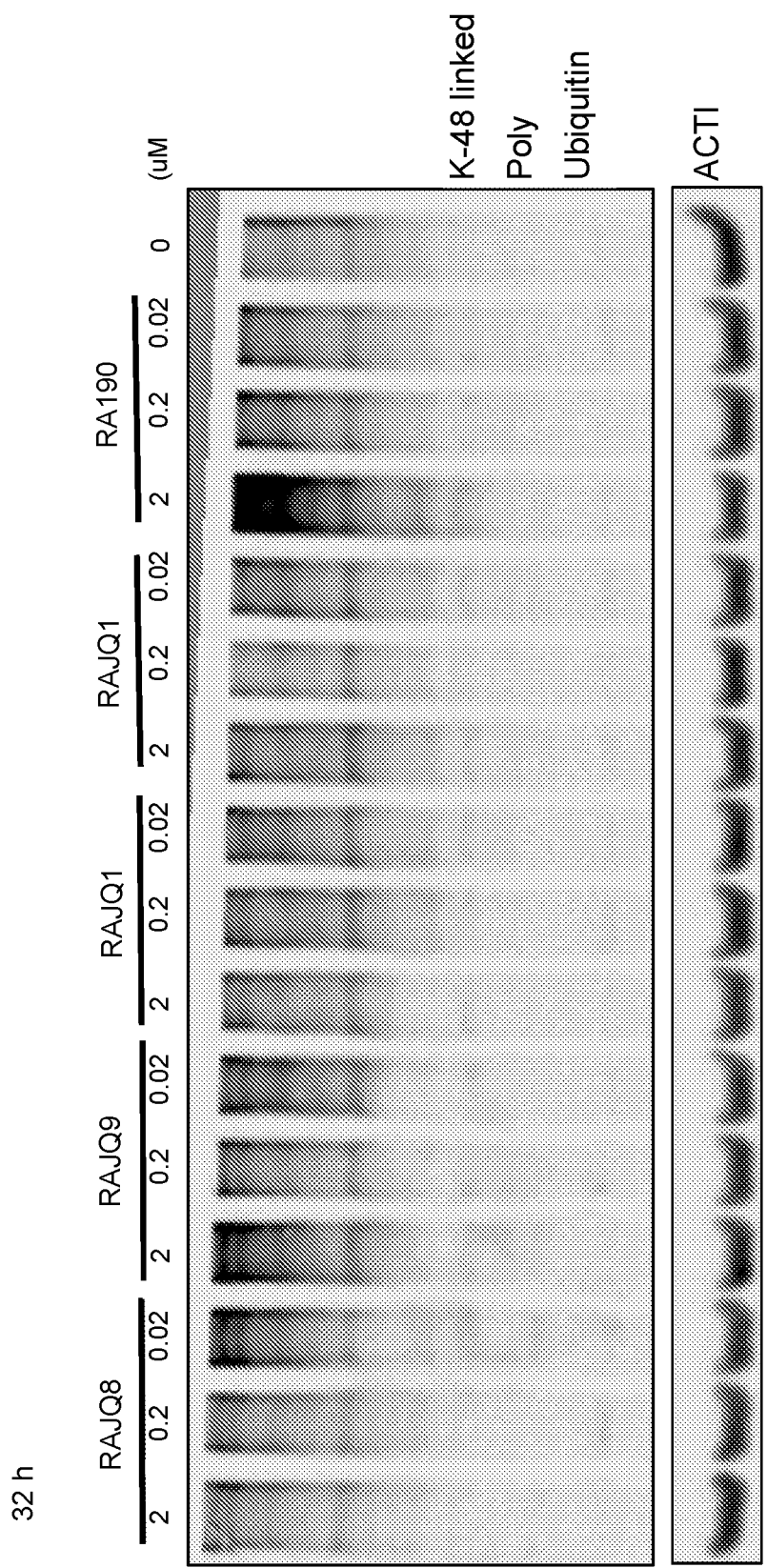
FIG. 33 shows bromodomain degradation in 293T cells. Cells were treated with RAJQ8, RAJQ9, RAJQ10, RAJQ11, and RA190 at the indicated concentrations and times. Cell lysates were loaded on SDS-PAGE, transferred to PVDF membrane, then immunoblotted with K-48 linked Poly Ubiquitin and actin antibodies.
Figure 34:
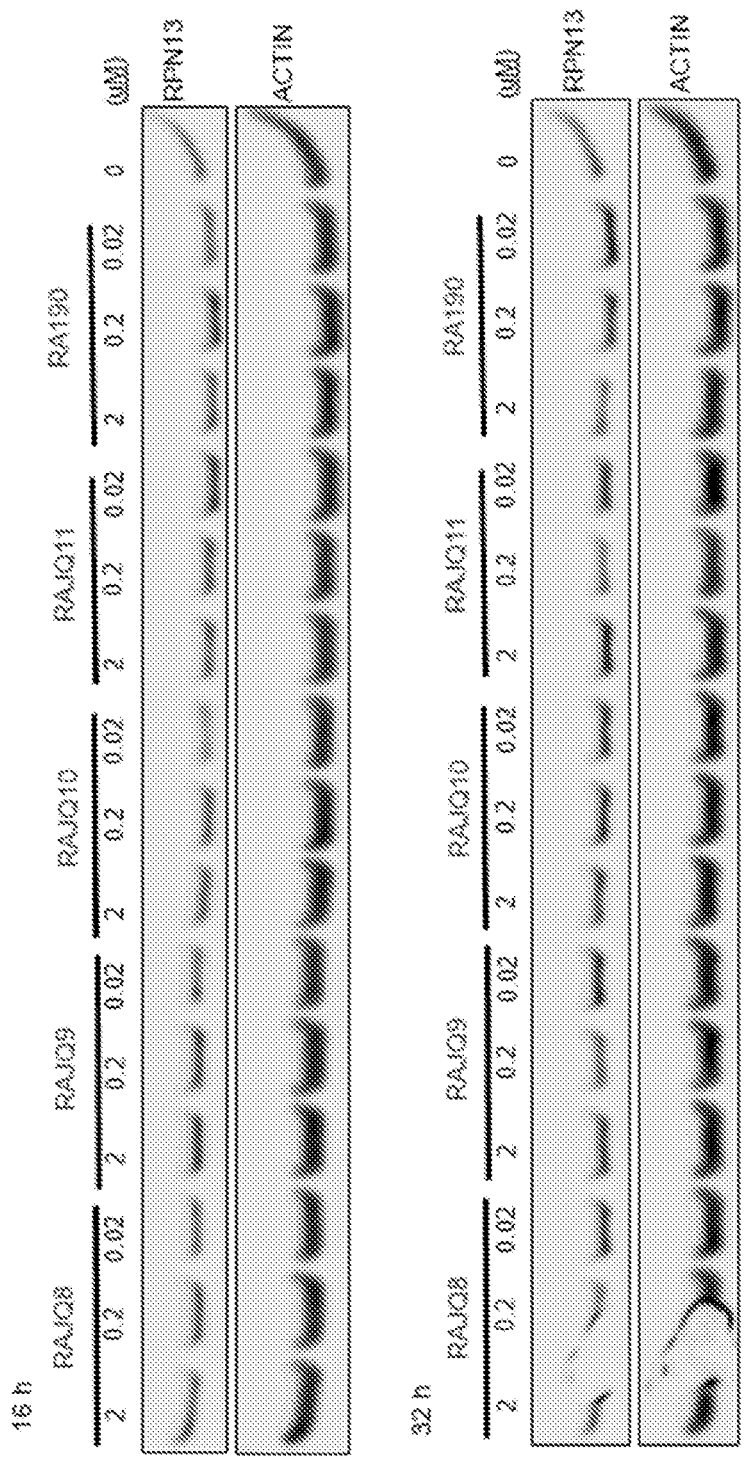
FIG. 34 shows bromodomain degradation in 293T cells. Cells were treated with RAJQ8, RAJQ9, RAJQ10, RAJQ11, and RA190 at the indicated concentrations and times. Cell lysates were loaded on SDS-PAGE, transferred to PVDF membrane, then immunoblotted with anti-RPN13 and actin antibodies.
Figure 35:
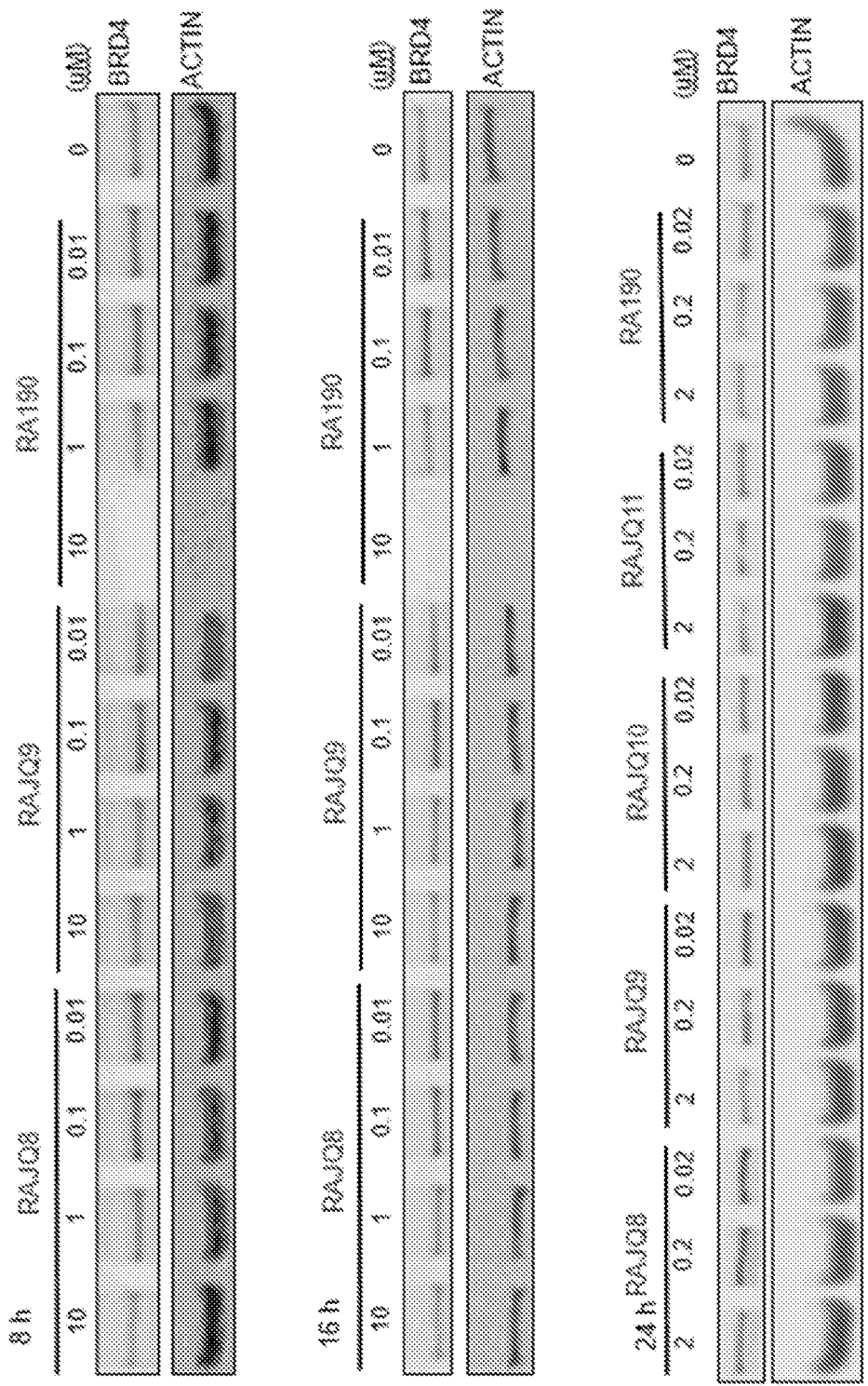
FIG. 35 shows 293T cells that were treated with RAJQ8, RAJQ9, and RA190 at the indicated concentrations and times. Cell lysates were loaded on SDS-PAGE, transferred to PVDF membrane, then immunoblotted with anti-BRD4 and actin antibodies.
Figure 36:
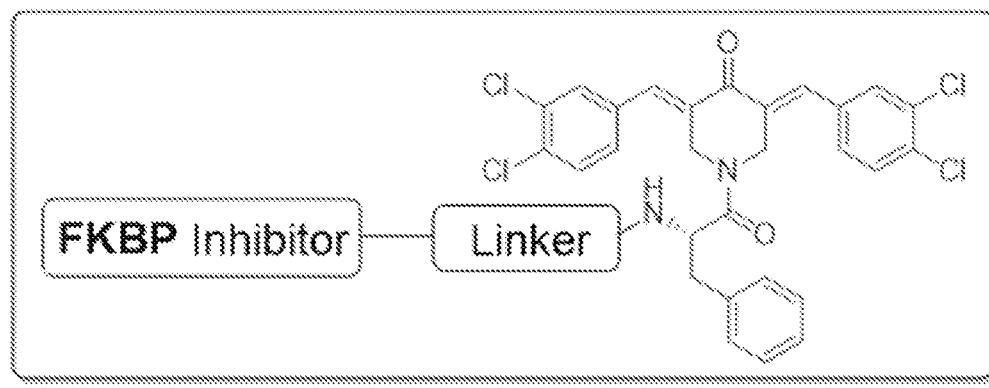
FIG. 36 show exemplary compounds of Formula (I) wherein a linker connects an FKBP inhibitor and RA190. Depicted are the structures of RAFKBP-1 and RAFKBP-4.
Figure 36:
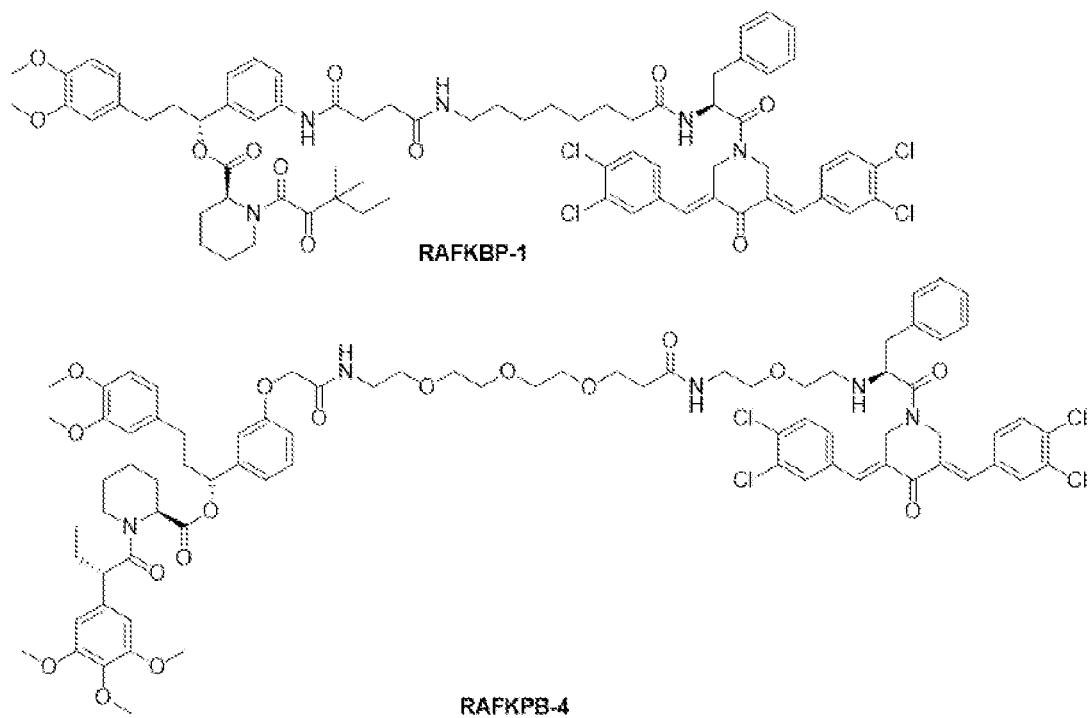
Figure 37:
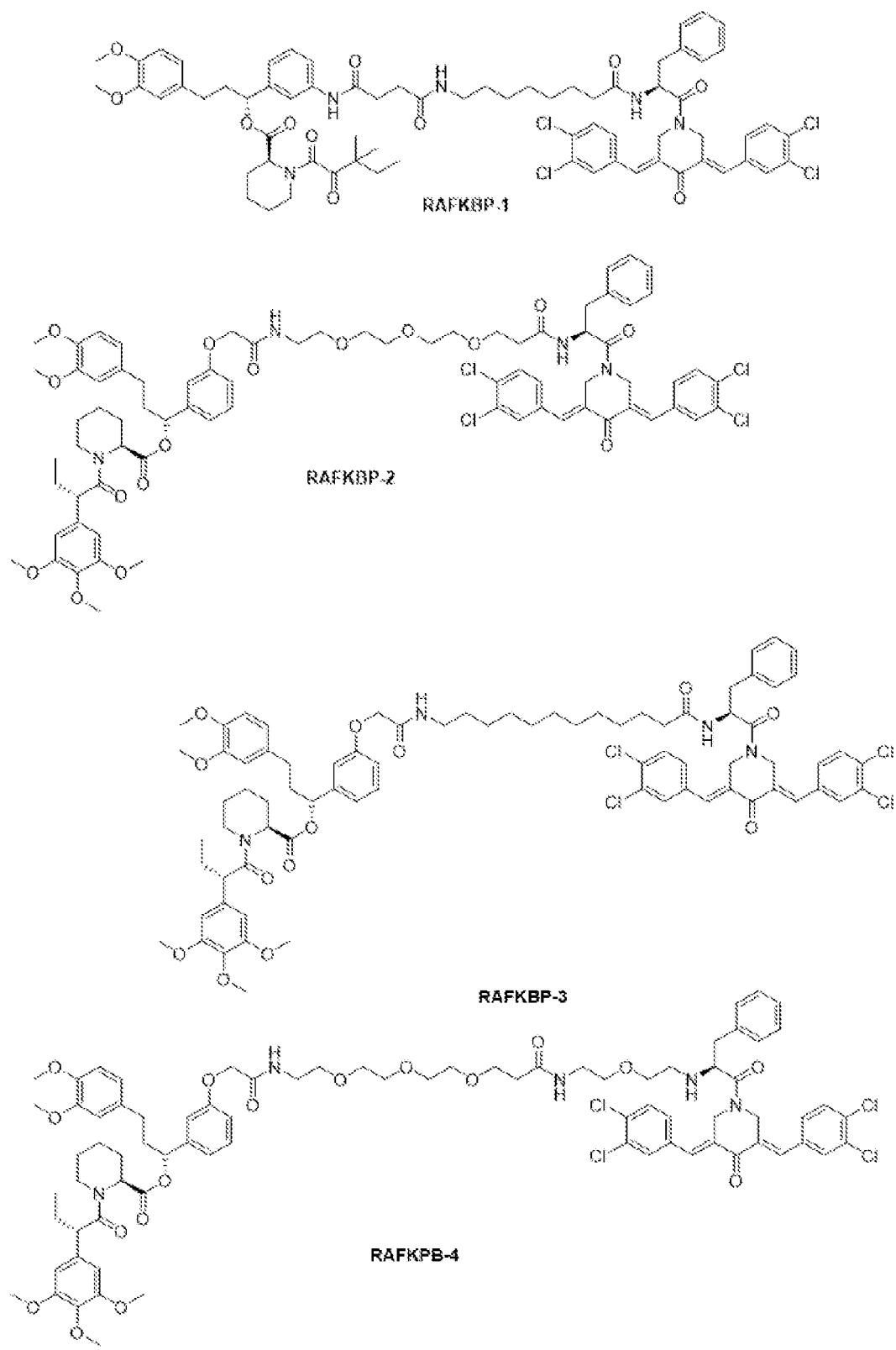
FIG. 37 shows exemplary compounds for the RPN13-based degradation of FKBP. Depicted are the structures of RAFKBP-1, RAFKBP-2, RAFKBP-3, and RAFKBP-4.
Figure 38:
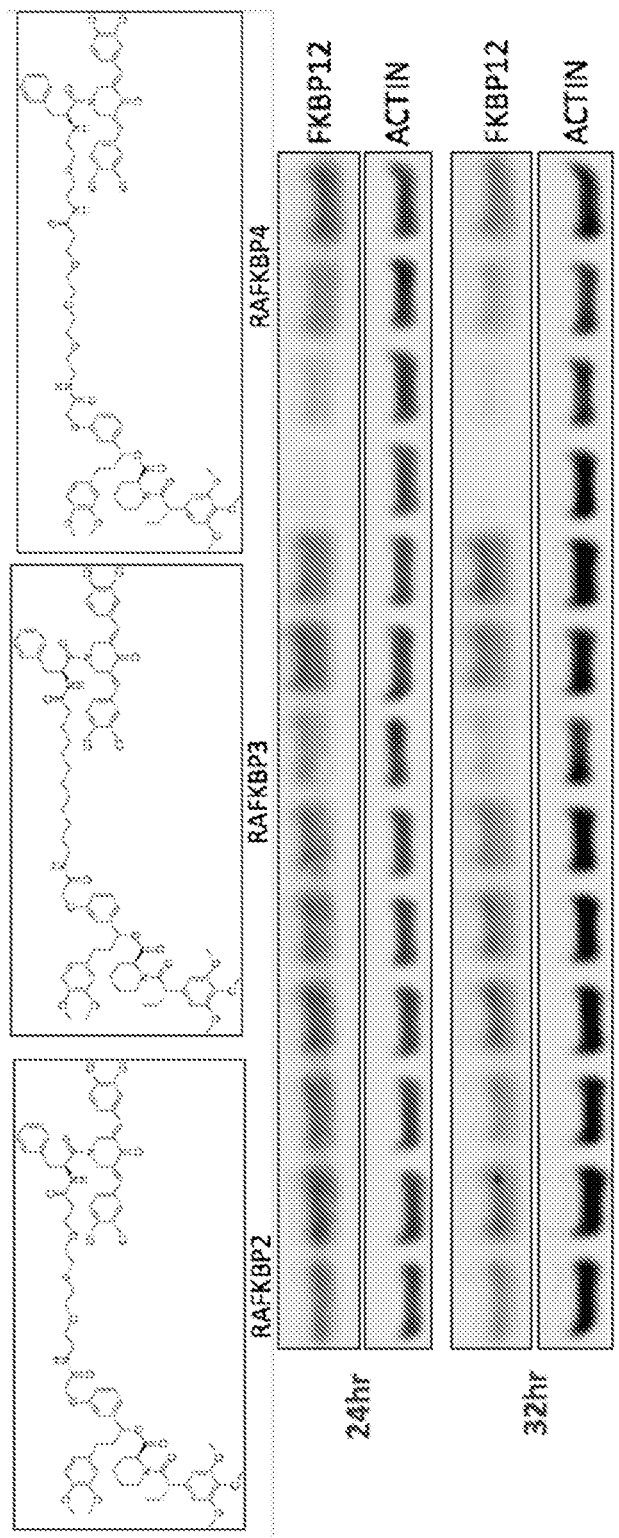
FIG. 38 shows FKBP12 degradation by treatment with exemplary compounds in 293T cells.
Figure 39:
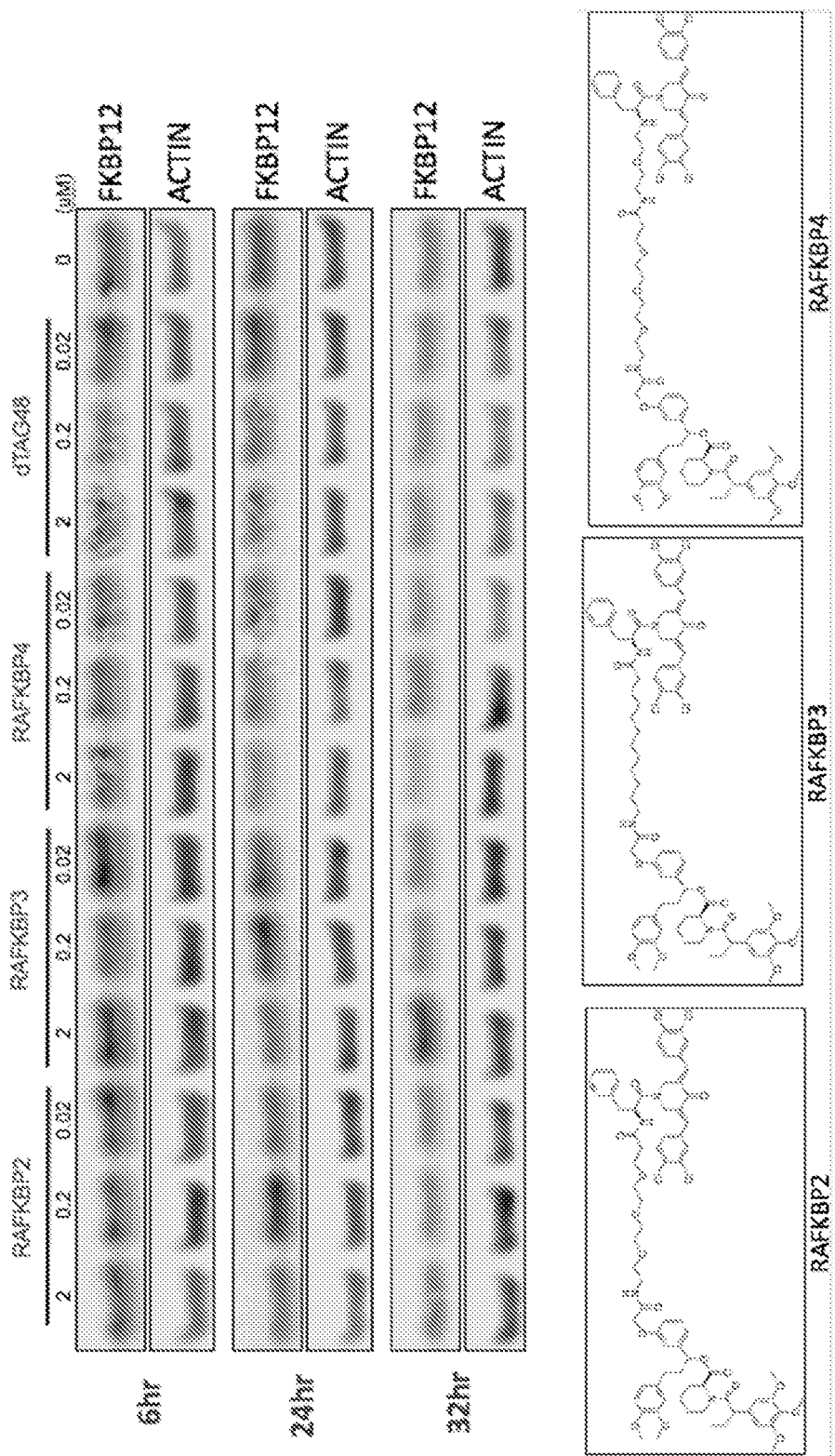
FIG. 39 shows FKBP12 degradation by treatment with exemplary compounds in 293T cells.
Figure 43:
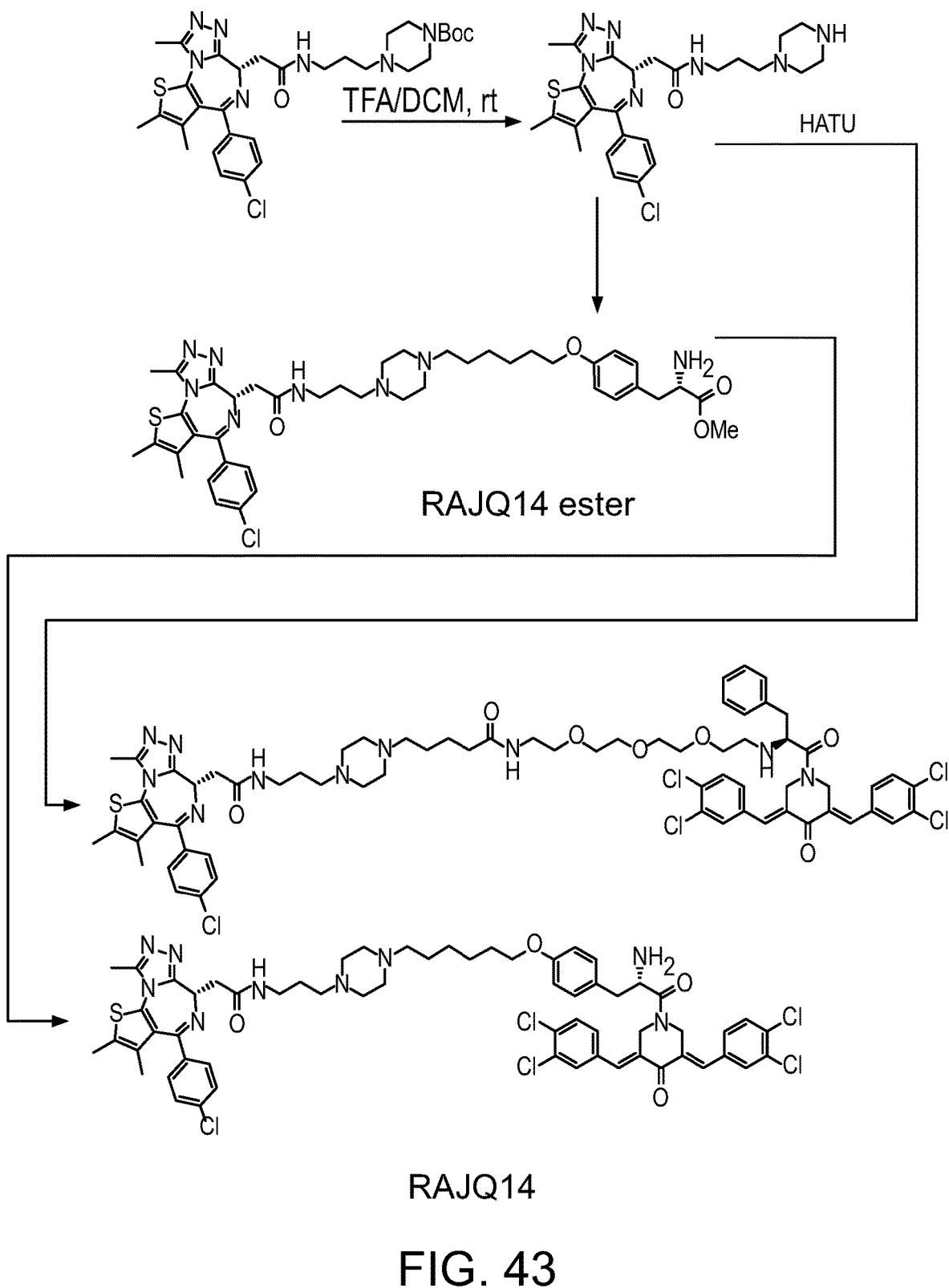

FIG. 43 shows an exemplary synthetic scheme for preparing exemplary BRD4 inhibitor RAJQ14. The same conditions used for preparing RAJQ9 (see FIG. 26) were used for preparing RAJQ14.

Figure 44:
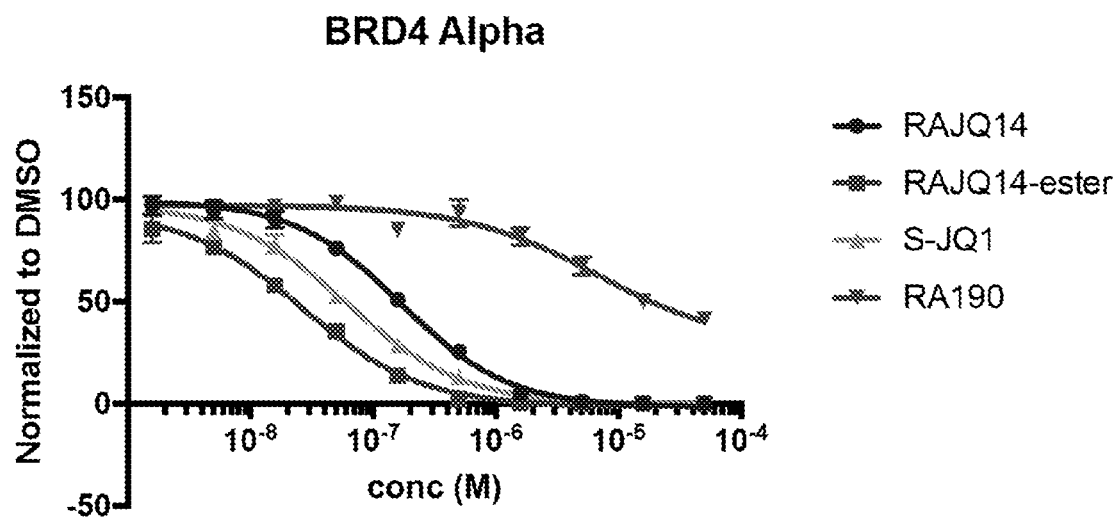

FIG. 44 shows a BRD4 Alpha assay showing the binding of exemplary BRD4 degrader compounds (RAJQ14, RAJQ14-ester) to BRD4.

Figure 45:
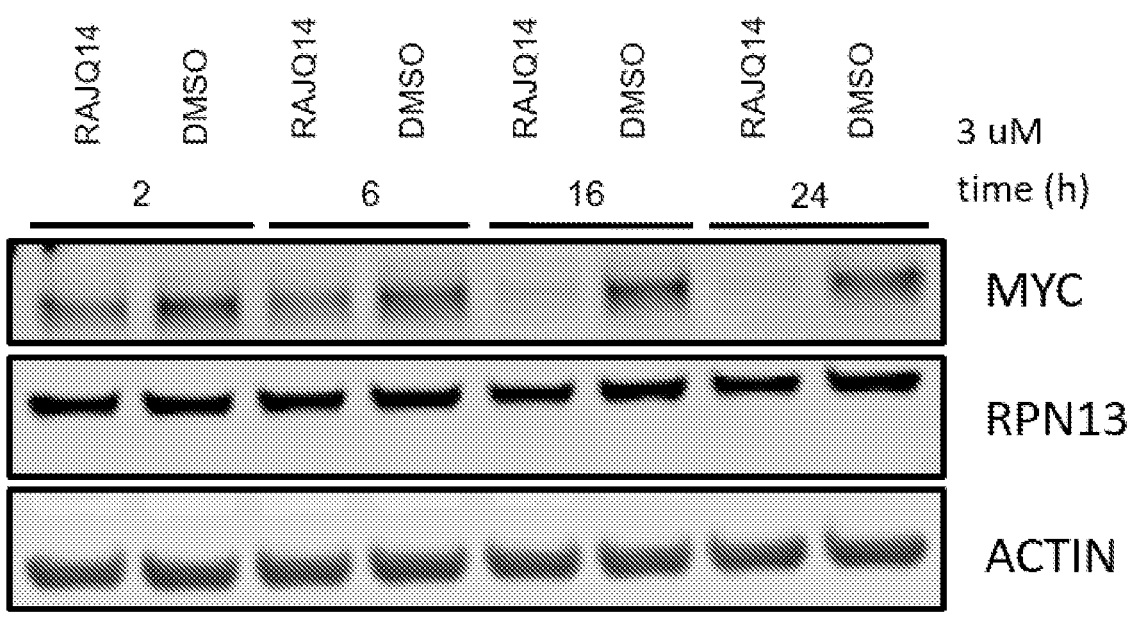

FIG. 45 shows an assay of the treatment of a MCF7 cell line (breast cancer) with exemplary BRD4 degrader RAJQ14 at the indicated concentration (3 μM) and indicated time points (2 hours, 6 hours, 16 hours, and 24 hours).

Figure 46:
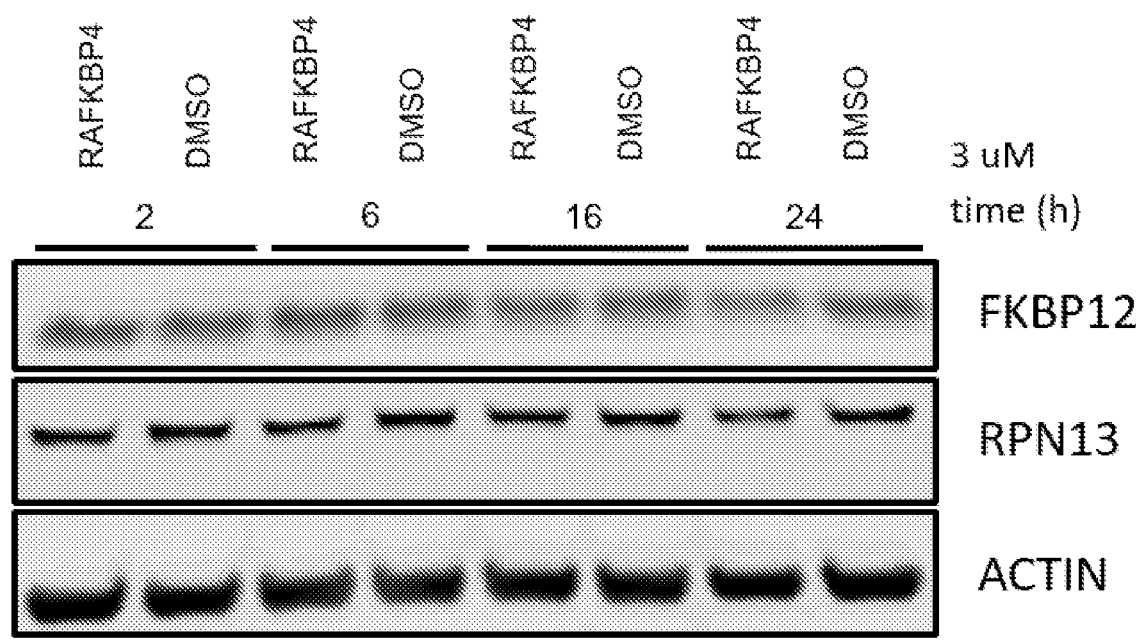

FIG. 46 shows an assay of the treatment of a MCF7 cell line (breast cancer) with exemplary FKBP12 degrader at the indicated concentration (3 μM) and indicated time points (2 hours, 6 hours, 16 hours, and 24 hours).

DETAILED DESCRIPTION OF CERTAIN EMBODIMENTS OF THE INVENTION

The bifunctional compounds described herein interact with a target (e.g., a protein) and an ubiquitin receptor RPN13 (ADRM1) (e.g., RA190). As described herein, without wishing to be bound by any particular theory, the therapeutic effect may be the result of degradation, modulation, or binding of a target (e.g., a target protein) by a compound described herein. The therapeutic effect may be a result of the bifunctional compound, which includes a binder of a ubiquitin receptor RPN13, bringing the target protein to the proteasome, thereby inducing degradation of the target protein.

A compound may be provided for use in any composition, kit, or method described herein as a pharmaceutically acceptable salt, co-crystal, tautomer, stereoisomer, solvate, hydrate, polymorph, isotopically enriched derivative, or prodrug thereof. In certain embodiments, bifunctional compounds of Formulae (I), (IA), and (IB) are bifunctional compounds derived from the bifunctional compounds described in U.S. patent application U.S. Ser. No. 14/889,768, filed May 6, 2014, U.S. Ser. No. 15/148,253, filed May 6, 2016, U.S. Ser. No. 14/707,930, filed May 8, 2015, U.S. Ser. No. 62/096,318, filed Dec. 23, 2014, U.S. Ser. No. 62/128,457, filed Mar. 4, 2015, U.S. Ser. No. 62/149,170, filed Apr. 17, 2015, each of which is incorporated herein by reference.

In certain embodiments, the compounds that bind to RPN13 are compounds derived from the compounds described in U.S. patent application U.S. Ser. No. 14/889,768, filed May 6, 2014.

In one aspect, disclosed are compounds of Formulae (I), (IA), and (IB):

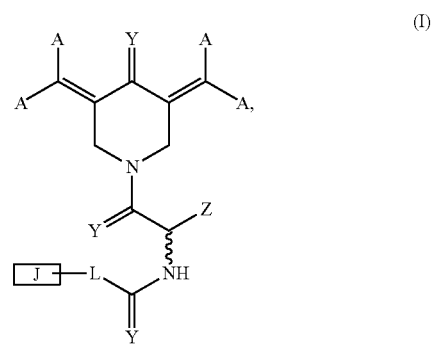

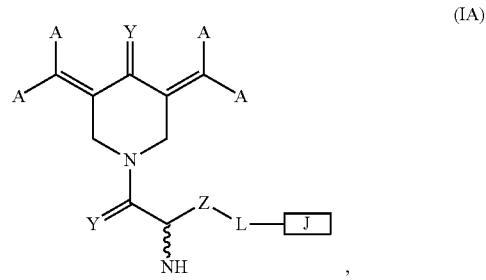

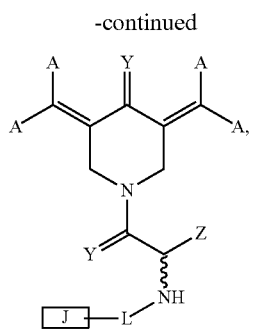

(IB)

or a pharmaceutically acceptable salt, solvate, hydrate, tautomer, or stereoisomer thereof, wherein:

in each pair of A's, one A is hydrogen, and the other A is one of:
  (i) phenyl, optionally substituted with 1-5 substituents selected from the group consisting of $R^1$, $OR^1$, $NR^1R^2$, $S(O)_qR^1$, $SO_2R^1R^2$, $NR^1SO_2R^2$, $C(O)R^1$, $C(O)OR^1$, $C(O)NR^1R^2$, $NR^1C(O)R^2$, $NR^1C(O)OR^2$, $CF_3$, and $OCF_3$;
  (ii) naphthyl, optionally substituted with 1-5 substituents selected from the group consisting of $R^1$, $OR^1$, $NR^1R^2$, $S(O)_qR^1$, $SO_2R^1R^2$, $NR^1SO_2R^2$, $C(O)R^1$, $C(O)OR^1$, $C(O)NR^1R^2$, $NR^1C(O)R^2$, $NR^1C(O)OR^2$, $CF_3$, and $OCF_3$;
  (iii) a 5 or 6 membered monocyclic heteroaryl group, having 1-3 heteroatoms selected from the group consisting of O, N, and S, optionally substituted with 1-3 substituents selected from the group consisting of $R^1$, $OR^1$, $NR^1R^2$, $S(O)_qR^1$, $SO_2R^1R^2$, $NR^1SO_2R^2$, $C(O)R^1$, $C(O)OR^1$, $C(O)NR^1R^2$, $NR^1C(O)R^2$, $NR^1C(O)OR^2$, $CF_3$, and $OCF_3$; and
  (iv) an 8 to 10 membered bicyclic heteroallyl group containing 1-3 heteroatoms selected from the group consisting of 0, N, and S; and the second ring is fused to the first ring using 3 to 4 carbon atoms, and the bicyclic hetero aryl group is optionally substituted with 1-3 substituents selected from the group consisting of $R^1$, $OR^1$, $NR^1R^2$, $S(O)_qR^1$, $SO_2R^1R^2$, $NR^1SO_2R^2$, $C(O)R^1$, $C(O)OR^1$, $C(O)NR^1R^2$, $NR^1C(O)R^2$, $NR^1C(O)OR^2$, $CF_3$, and $OCF_3$;

wherein Y is selected from the group consisting of O, S, $NR^1$ and $CR^1R^2$, and wherein $R^1$ and $R^2$ are selected from the group consisting of hydrogen, nitro, hydroxyl, carboxy, amino, halogen, cyano and $C_1$-$C_{14}$ linear or branched alkyl groups, that are optionally substituted with 1-3 substituents selected from the group consisting of $C_1$-$C_{14}$ linear or branched alkyl, up to perhalo substituted $C_1$-$C_{14}$ linear or branched alkyl, $C_1$-$C_{14}$ alkoxy, hydrogen, nitro, hydroxyl, carboxy, amino, $C_1$-$C_{14}$ alkylamino, $C_1$-$C_{14}$ dialkylamino, halogen, and cyano; and wherein Z is selected from the group consisting of hydrogen; $C_1$ to $C_{14}$ linear, branched, or cyclic alkyls; phenyl; benzyl, 1-5 substituted benzyl, $C_1$ to $C_3$ alkyl-phenyl, wherein the alkyl moiety is optionally substituted with halogen up to perhalo; up to perhalo substituted $C_1$ to $C_{14}$ linear or branched alkyls; —$(CH_2)_q$—K, where K is a 5 or 6 membered monocyclic heterocyclic ring, containing 1 to 4 atoms selected from oxygen, nitrogen and sulfur, which is saturated, partially saturated, or aromatic, or an 8 to 10 membered bicyclic heteroaryl having 1-4 heteroatoms selected from the group consisting of O, N, and S, wherein said alkyl moiety is optionally substituted with halogen up to perhalo, and wherein the variable q is an integer ranging from 0 to 4;

L is a linker; and

J is a binder of a target selected from the group consisting of a bromodomain, a bromodomain-containing protein, and FKBP12.

In one aspect, disclosed are compounds of Formulae (I) and (IA):

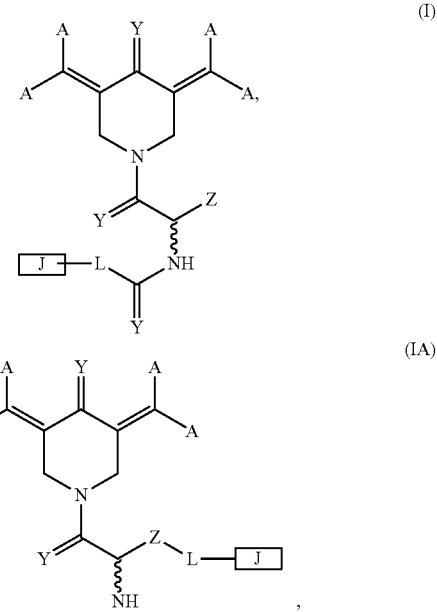

or a pharmaceutically acceptable salt, solvate, hydrate, tautomer, or stereoisomer thereof, wherein:

in each pair of A's, one A is hydrogen, and the other A is one of:
  (i) phenyl, optionally substituted with 1-5 substituents selected from the group consisting of $R^1$, $OR^1$, $NR^1R^2$, $S(O)_qR^1$, $SO_2R^1R^2$, $NR^1SO_2R^2$, $C(O)R^1$, $C(O)OR^1$, $C(O)NR^1R^2$, $NR^1C(O)R^2$, $NR^1C(O)OR^2$, $CF_3$, and $OCF_3$;
  (ii) naphthyl, optionally substituted with 1-5 substituents selected from the group consisting of $R^1$, $OR^1$, $NR^1R^2$, $S(O)_qR^1$, $SO_2R^1R^2$, $NR^1SO_2R^2$, $C(O)R^1$, $C(O)OR^1$, $C(O)NR^1R^2$, $NR^1C(O)R^2$, $NR^1C(O)OR^2$, $CF_3$, and $OCF_3$;
  (iii) a 5 or 6 membered monocyclic heteroaryl group, having 1-3 heteroatoms selected from the group consisting of O, N, and S, optionally substituted with 1-3 substituents selected from the group consisting of $R^1$, $OR^1$, $NR^1R^2$, $S(O)_qR^1$, $SO_2R^1R^2$, $NR^1SO_2R^2$, $C(O)R^1$, $C(O)OR^1$, $C(O)NR^1R^2$, $NR^1C(O)R^2$, $NR^1C(O)OR^2$, $CF_3$, and $OCF_3$; and
  (iv) an 8 to 10 membered bicyclic heteroallyl group containing 1-3 heteroatoms selected from the group consisting of O, N, and S; and the second ring is fused to the first ring using 3 to 4 carbon atoms, and the bicyclic hetero aryl group is optionally substituted with 1-3 substituents selected from the group consisting of $R^1$, $OR^1$, $NR^1R^2$, $S(O)_qR^1$, $SO_2R^1R^2$, $NR^1SO_2R^2$, $C(O)R^1$, $C(O)OR^1$, $C(O)NR^1R^2$, $NR^1C(O)R^2$, $NR^1C(O)OR^2$, $CF_3$, and $OCF_3$;

wherein Y is selected from the group consisting of O, S, $NR^1$ and $CR^1R^2$, and wherein $R^1$ and $R^2$ are selected from the group consisting of hydrogen, nitro, hydroxyl, carboxy, amino, halogen, cyano and $C_1$-$C_{14}$ linear or branched alkyl groups, that are optionally substituted with 1-3 substituents selected from the group consisting of $C_1$-$C_{14}$ linear or branched alkyl, up to perhalo substituted $C_1$-$C_{14}$ linear or branched alkyl, $C_1$-$C_{14}$ alkoxy, hydrogen, nitro, hydroxyl, carboxy, amino, $C_1$-$C_{14}$ alkylamino, $C_1$-$C_{14}$ dialkylamino, halogen, and cyano; and wherein Z is selected from the group consisting of hydrogen; $C_1$ to $C_{14}$ linear, branched, or cyclic alkyls; phenyl; benzyl, 1-5 substituted benzyl, $C_1$ to $C_3$ alkyl-phenyl, wherein the alkyl moiety is optionally substituted with halogen up to perhalo; up to perhalo substituted $C_1$ to $C_{14}$ linear or branched alkyls; —$(CH_2)_q$—K, where K is a 5 or 6 membered monocyclic heterocyclic ring, containing 1 to 4 atoms selected from oxygen, nitrogen and sulfur, which is saturated, partially saturated, or aromatic, or an 8 to 10 membered bicyclic heteroaryl having 1-4 heteroatoms selected from the group consisting of O, N, and S, wherein said alkyl moiety is optionally substituted with halogen up to perhalo, and wherein the variable q is an integer ranging from 0 to 4;

L is a linker; and

J is a binder of a target selected from the group consisting of a bromodomain, a bromodomain-containing protein, and FKBP12.

Group J

In certain embodiments, J is a binder of a target (e.g., a target protein).

In certain embodiments, J is a binder of a bromodomain or a bromodomain-containing protein, or FKBP12. In certain embodiments, J is a binder of a bromodomain. In certain embodiments, J is a binder of a bromodomain-containing protein. In certain embodiments, J is a binder of a bromodomain-containing protein (e.g., BRD1, BRD4, BRD5, BRD6, BRD7, BRD8, BRD9, BRD10, and/or BRDT). In certain embodiments, J is a binder of BRD1, BRD4, BRD5, BRD6, BRD7, BRD8, BRD9, BRD10, and/or BRDT. In certain embodiments, J is a binder of a histone methyltransferase. In certain embodiments, J is a binder of a kinase, a BET bromodomain-containing protein, a cytosolic signaling protein (e.g., FKBP (e.g., FKBP12)), a nuclear protein, a histone deacetylase, a lysine methyltransferase, a protein regulating angiogenesis, a protein regulating immune response, an aryl hydrocarbon receptor (AHR), an estrogen receptor, an androgen receptor, a glucocorticoid receptor, or a transcription factor (e.g., SMARCA4, SMARCA2, TRIM24). In certain embodiments, J is a binder of FKBP, which is a compound of Formula (IX). In certain embodiments, J is a binder of FKBP12, which is a compound of Formula (IX).

In certain embodiments, J is a binder of a tyrosine kinase (e.g., AATK, ABL, ABL2, ALK, AXL, BLK, BMX, BTK, CSF1R, CSK, DDR1, DDR2, EGFR, EPHA1, EPHA2, EPHA3, EPHA4, EPHA5, EPHA6, EPHA7, EPHA8, EPHA10, EPHB1, EPHB2, EPHB3, EPHB4, EPHB6, ERBB2, ERBB3, ERBB4, FER, FES, FGFR1, FGFR2, FGFR3, FGFR4, FGR, FLT1, FLT3, FLT4, FRK, FYN, GSG2, HCK, IGF1R, ILK, INSR, INSRR, IRAK4, ITK, JAK1, JAK2, JAK3, KDR, KIT, KSR1, LCK, LMTK2, LMTK3, LTK, LYN, MATK, MERTK, MET, MLTK, MST1R, MUSK, NPR1, NTRK1, NTRK2, NTRK3, PDG-FRA, PDGFRB, PLK4, PTK2, PTK2B, PTK6, PTK7, RET, ROR1, ROR2, ROS1, RYK, SGK493, SRC, SRMS, STYK1, SYK, TEC, TEK, TEX14, TIE1, TNK1, TNK2, TNNI3K, TXK, TYK2, TYRO3, YES1, or ZAP70), a serine/threonine kinase (e.g., casein kinase 2, protein kinase A, protein kinase B, protein kinase C, Raf kinases, CaM kinases, AKT1, AKT2, AKT3, ALK1, ALK2, ALK3, ALK4, Aurora A, Aurora B, Aurora C, CHK1, CHK2, CLK1, CLK2, CLK3, DAPK1, DAPK2, DAPK3, DMPK, ERK1, ERK2, ERK5, GCK, GSK3, HIPK, KHS1, LKB1, LOK, MAPKAPK2, MAPKAPK, MNK1, MSSK1, MST1, MST2, MST4, NDR, NEK2, NEK3, NEK6, NEK7, NEK9, NEK11, PAK1, PAK2, PAK3, PAK4, PAK5, PAK6, PITM1, PIM2, PLK1, RIP2, RIP5, RSK1, RSK2, SGK2, SGK3, SIK1, STK33, TAO1, TAO2, TGF-beta, TLK2, TSSK1, TSSK2, ULK1, or ULK2), a cyclin dependent kinase (e.g., Cdk1-Cdk11), and a leucine-rich repeat kinase (e.g., LRRK2). Moieties of group J are attached to linker L at any position on compound J.

Substituents A, Y, Z, $R^1$, and $R^2$

Compounds of Formulae (I), (IA), and (IB) are bifunctional compounds that bind to ubiquitin receptor RPN13 on one end and bind to a target protein on the other end. Compounds of Formulae (I), (IA), and (IB) include substituents A, Y, Z, $R^1$, and $R^2$.

In each pair of A's, one A is hydrogen, and the other A is one of:

(i) phenyl, optionally substituted with 1-5 substituents selected from the group consisting of $R^1$, $OR^1$, $NR^1R^2$, $S(O)_qR^1$, $SO_2R^1R^2$, $NR^1SO_2R^2$, $C(O)R^1$, $C(O)OR^1$, $C(O)NR^1R^2$, $NR^1C(O)R^2$, $NR^1C(O)OR^2$, $CF_3$, and $OCF_3$;

(ii) naphthyl, optionally substituted with 1-5 substituents selected from the group consisting of $R^1$, $OR^1$, $NR^1R^2$, $S(O)_qR^1$, $SO_2R^1R^2$, $NR^1SO_2R^2$, $C(O)R^1$, $C(O)OR^1$, $C(O)NR^1R^2$, $NR^1C(O)R^2$, $NR^1C(O)OR^2$, $CF_3$, and $OCF_3$;

(iii) a 5 or 6 membered monocyclic heteroaryl group, having 1-3 heteroatoms selected from the group consisting of 0, N, and S, optionally substituted with 1-3 substituents selected from the group consisting of $R^1$, $OR^1$, $NR^1R^2$, $S(O)_qR^1$, $SO_2R^1R^2$, $NR^1SO_2R^2$, $C(O)R^1$, $C(O)OR^1$, $C(O)NR^1R^2$, $NR^1C(O)R^2$, $NR^1C(O)OR^2$, $CF_3$, and $OCF_3$; and (iv) an 8 to 10 membered bicyclic heteroallyl group containing 1-3 heteroatoms selected from the group consisting of O, N, and S; and the second ring is fused to the first ring using 3 to 4 carbon atoms, and the bicyclic hetero aryl group is optionally substituted with 1-3 substituents selected from the group consisting of $R^1$, $OR^1$, $NR^1R^2$, $S(O)_qR^1$, $SO_2R^1R^2$, $NR^1SO_2R^2$, $C(O)R^1$, $C(O)OR^1$, $C(O)NR^1R^2$, $NR^1C(O)R^2$, $NR^1C(O)OR^2$, $CF_3$, and $OCF_3$.

In each pair of A's, in some embodiments, one A is phenyl, optionally substituted with 1-5 substituents including $R^1$, $OR^1$, $NR^1R^2$, $S(O)_qR^1$, $SO_2R^1R^2$, $NR^1SO_2R^2$, $C(O)R^1$, $C(O)OR^1$, $C(O)NR^1R^2$, $NR^1C(O)R^2$, $NR^1C(O)OR^2$, $CF_3$, or $OCF_3$. In some embodiments, one A is phenyl. In some embodiments, one A is phenyl substituted with halogen.

In each pair of A's, in some embodiments, one A is naphthyl, optionally substituted with 1-5 substituents including $R^1$, $OR^1$, $NR^1R^2$, $S(O)_qR^1$, $SO_2R^1R^2$, $NR^1SO_2R^2$, $C(O)R^1$, $C(O)OR^1$, $C(O)NR^1R^2$, $NR^1C(O)R^2$, $NR^1C(O)OR^2$, $CF_3$, or $OCF_3$.

In some embodiments, Y is selected from the group consisting of O, S, $NR^1$ and $CR^1R^2$. In some embodiments, at least one instance of Y is O. In certain embodiments, both Y are O. In certain embodiments, at least two instances of Y are O. In some embodiments, one instance of Y is O and the other instance of Y is —CH$_2$. In some embodiments, both instances of Y are —CH$_2$. In certain embodiments, at least three instances of Y are O. In certain embodiments, at least one instance of Y is O and the other instance of the moiety

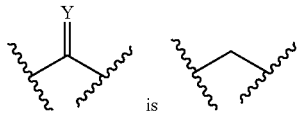

is

In certain embodiments, at least two instances of the moiety

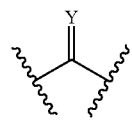

are each

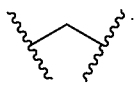

In some embodiments, R$^1$ and R$^2$ are selected from the group consisting of hydrogen, nitro, hydroxyl, carboxy, amino, halogen, cyano and C$_1$-C$_{14}$ linear or branched alkyl groups, that are optionally substituted with 1-3 substituents selected from the group consisting of C$_1$-C$_{14}$ linear or branched alkyl, up to perhalo substituted C$_1$-C$_{14}$ linear or branched alkyl, C$_1$-C$_{14}$ alkoxy, hydrogen, nitro, hydroxyl, carboxy, amino, C$_1$-C$_{14}$ alkylamino, C$_1$-C$_{14}$ dialkylamino, halogen, and cyano. In some embodiments, R$^1$ is substituted or unsubstituted alkyl (e.g., substituted or unsubstituted C$_{1-6}$ alkyl). In some embodiments, R$^1$ is halogen (e.g., F, Br, Cl). In some embodiments, R$^2$ is substituted or unsubstituted alkyl (e.g., substituted or unsubstituted C$_{1-6}$ alkyl). In some embodiments, all the instances of R$^1$ are the same.

In some embodiments, Z is selected from the group consisting of hydrogen; C$_1$ to C$_{14}$ linear, branched, or cyclic alkyls; phenyl; benzyl, 1-5 substituted benzyl, C$_1$ to C$_3$ alkyl-phenyl, wherein the alkyl moiety is optionally substituted with halogen up to perhalo; up to perhalo substituted C$_1$ to C$_{14}$ linear or branched alkyls; and —(CH$_2$)$_q$—K. In some embodiments, K is a 5 or 6 membered monocyclic heterocyclic ring, containing 1 to 4 atoms selected from oxygen, nitrogen and sulfur, which is saturated, partially saturated, or aromatic, or an 8 to 10 membered bicyclic heteroaryl having 1-4 heteroatoms selected from the group consisting of O, N, and S, wherein said alkyl moiety is optionally substituted with halogen up to perhalo, and wherein the variable q is an integer ranging from 0 to 4. In certain embodiments, q is 0. In certain embodiments, q is 1. In certain embodiments, q is 2. In certain embodiments, q is 3. In certain embodiments, q is 4.

In some embodiments, Z is phenyl. In some embodiments, Z is benzyl. In some embodiments, Z is unsubstituted benzyl. In some embodiments, in each pair of A's, one A is hydrogen and the other A is phenyl optionally substituted with R$_1$. In some embodiments, in each pair of A's, one A is hydrogen and the other A is phenyl substituted with halogen.

In certain embodiments, a compound of Formula (I) is of formula:

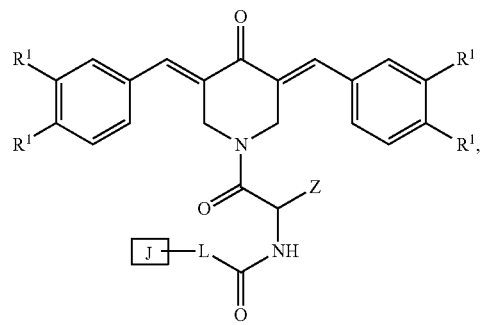

or a pharmaceutically acceptable salt thereof.

In certain embodiments, a compound of Formula (I) is of formula:

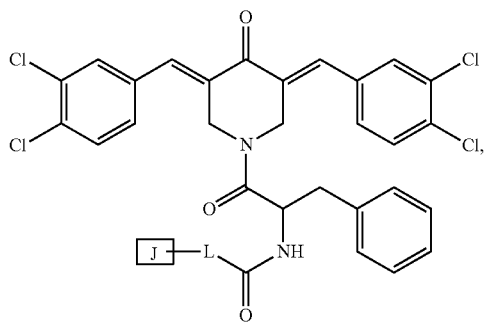

or a pharmaceutically acceptable salt thereof.

In certain embodiments, a compound of Formula (IA) is of formula:

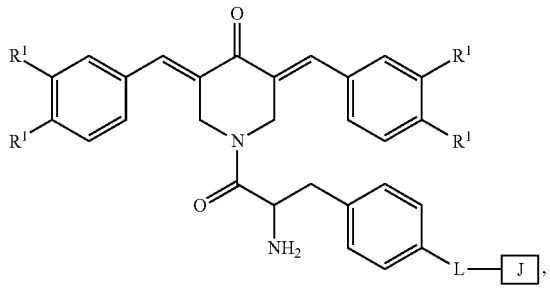

or a pharmaceutically acceptable salt thereof.

In certain embodiments, a compound of Formula (IB) is of formula:

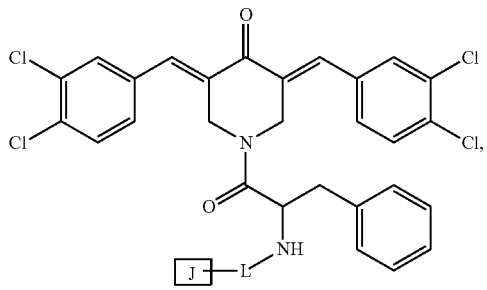

or a pharmaceutically acceptable salt thereof. In certain embodiments, a compound described herein is of formula:

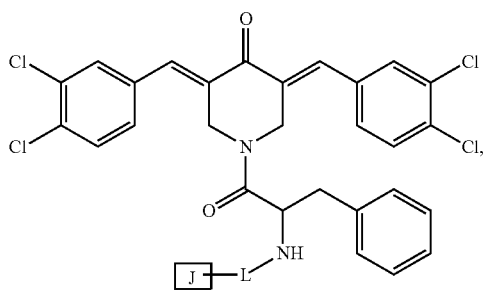

or a pharmaceutically acceptable salt thereof.

Linker L

In Formula (I), L is a divalent moiety linking the group J to the

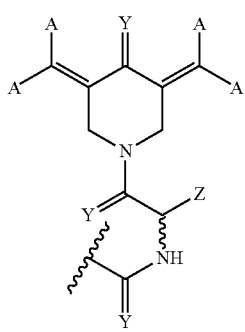

moiety (the RPN13 binding moiety).

In Formula (IA), L is a divalent moiety linking the group J to the

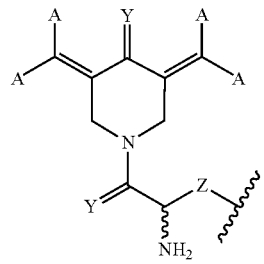

moiety (the RPN13 binding moiety).

In Formula (IB), L is a divalent moiety linking the group J to the

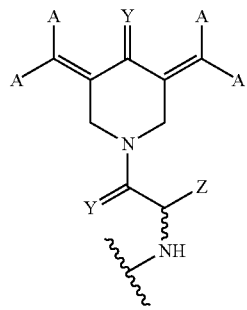

moiety (the RPN13 binding moiety).

In Formulae (I), (IA), and (IB), L is a divalent moiety. In certain embodiments, L is a bond, a substituted or unsubstituted $C_{1-12}$ hydrocarbon chain, optionally wherein one or more chain atoms of the hydrocarbon chain are independently replaced with —C(=O)—, —O—, —S—, —NR$^b$—, —N=, or =N—, substituted or unsubstituted carbocyclylene, substituted or unsubstituted heterocyclylene, substituted or unsubstituted arylene, substituted or unsubstituted heteroarylene, or substituted or unsubstituted heteroalkylene. In certain embodiments, L is any "L0" group recited in U.S. patent application U.S. Ser. No. 14/707,930, filed May 8, 2015, which is incorporated herein by reference.

In certain embodiments, the chain of linker L comprises of up to 50 atoms, as the shortest path between J and the

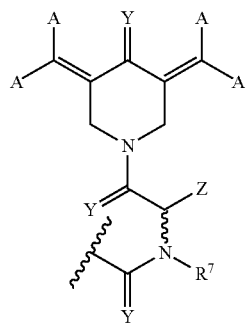

moiety, excluding hydrogen atoms. In certain embodiments, the chain of linker L comprises up to 50 atoms as the shortest path between J and the

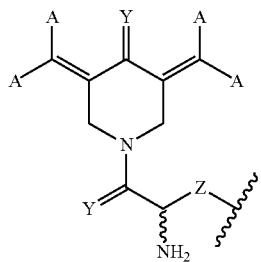

moiety, excluding hydrogen atoms.

In certain embodiments, the chain of linker L comprises up to 50 atoms as the shortest path between J and the

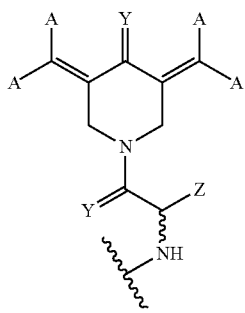

moiety, excluding hydrogen atoms.

In certain embodiments, L comprises of up to 40 atoms, excluding hydrogen atoms. In certain embodiments, L comprises of up to 30 atoms, excluding hydrogen atoms. In certain embodiments, L comprises of up to 20 atoms, excluding hydrogen atoms. In certain embodiments, L comprises of up to 15 atoms, excluding hydrogen atoms. In certain embodiments, L comprises of up to 12 atoms, excluding hydrogen atoms. In certain embodiments, L comprises of up to 10 atoms, excluding hydrogen atoms. In certain embodiments, L comprises of up to 9 atoms excluding hydrogen atoms. In certain embodiments, L comprises of up to 6 atoms excluding hydrogen atoms. In certain embodiments, L comprises of up to 5 atoms excluding hydrogen atoms. In certain embodiments, L comprises of up to 3 atoms excluding hydrogen atoms. In certain embodiments, any of the carbon atoms in L can be substituted.

In certain embodiments, L is a group that covalently binds to the group J and the

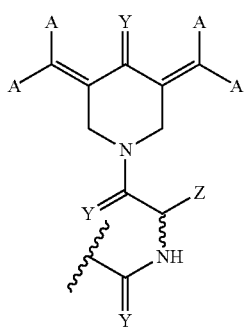

moiety (the RPN13 binding moiety). In certain embodiments, L is a group that covalently binds to the group J and the

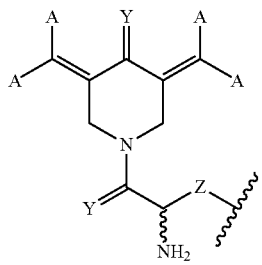

moiety (the RPN13 binding moiety). In certain embodiments, L is a group that covalently binds to the group J and the

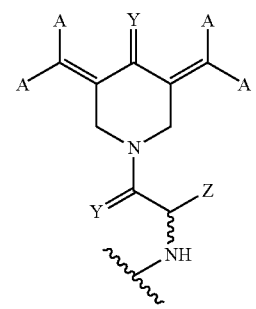

moiety (the RPN13 binding moiety).

In certain embodiments, L is a group that covalently binds to the group J and the moiety of formula

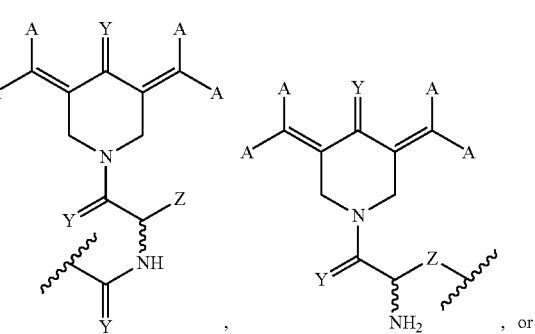

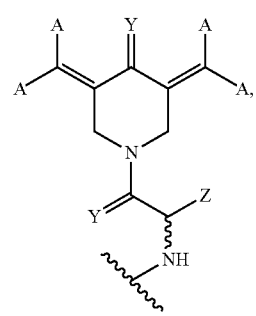

wherein in L, $l^A$ indicates the point of attachment to J, and $l^R$ indicates the point of attachment to the moiety of formula

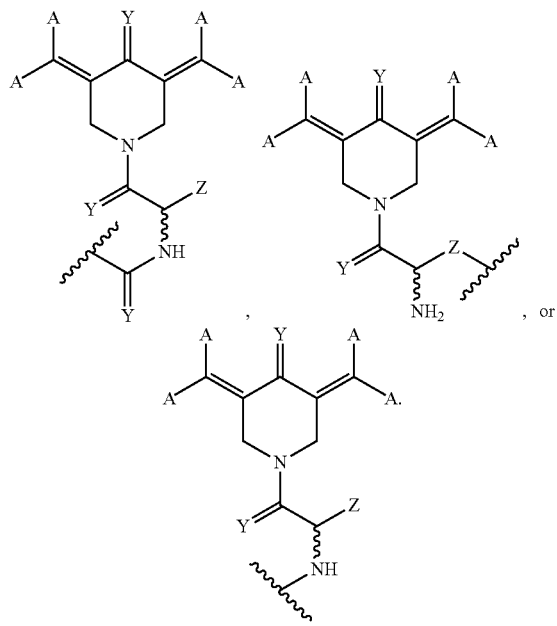

,

In certain embodiments, L is substituted or unsubstituted carbocyclylene, substituted or unsubstituted heterocyclylene, substituted or unsubstituted arylene, substituted or unsubstituted heteroarylene, or substituted or unsubstituted heteroalkylene. In certain embodiments, each instance of $R^b$ is independently hydrogen, substituted or unsubstituted $C_{1-6}$ alkyl, or a nitrogen protecting group, or optionally two instances of $R^b$ are taken together with their intervening atoms to form a substituted or unsubstituted heterocyclic or substituted or unsubstituted heteroaryl ring.

In certain embodiments, L is a substituted or unsubstituted $C_{1-12}$ hydrocarbon chain. In certain embodiments, one or more chain atoms of the hydrocarbon chain of L are independently replaced with —C(=O)—, —O—, —S—, —$NR^b$—, —N=, or =N—. In certain embodiments, L is an unsubstituted $C_{1-3}$ hydrocarbon chain.

In certain embodiments, L is of the formula:

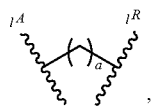

, wherein a is 0, 1, 2, 3, 4, 5, or 6. In certain embodiments, a is 0. In certain embodiments, L is a bond. In certain embodiments, a is 1. In certain embodiments, a is 2. In certain embodiments, a is 3. In certain embodiments, a is 4. In certain embodiments, a is 5. In certain embodiments, a is 6. In certain embodiments, L is of the formula:

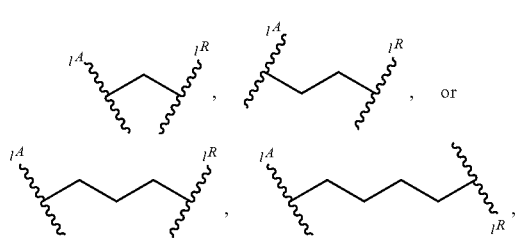

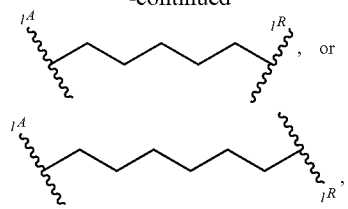

wherein $1^A$ indicates the point of attachment to J, and P indicates the point of attachment to the moiety of formula

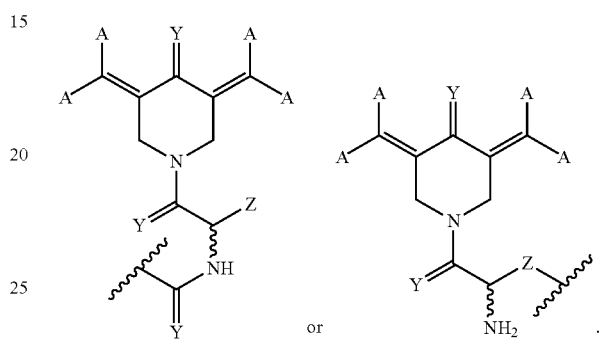

In certain embodiments, L is of the formula:

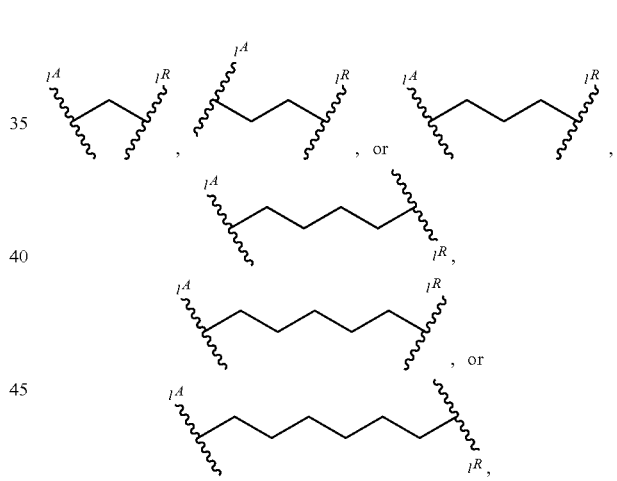

wherein $1^A$ indicates the point of attachment to J, and $1^R$ indicates the point of attachment to the moiety of formula

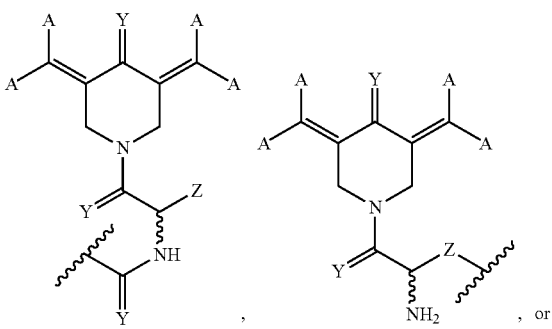

-continued

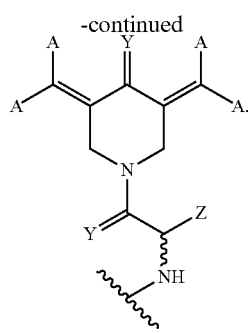

In certain embodiments, L is a substituted or unsubstituted $C_{1-12}$ hydrocarbon chain, optionally wherein one or more chain atoms of the hydrocarbon chain are independently replaced with —C(=O)—, —O—, —S—, —NR$^b$—, —N=, or =N—. In certain embodiments, L is an unsubstituted $C_{1-12}$ hydrocarbon chain, wherein one or more chain atoms of the hydrocarbon chain are independently replaced with —O— or —NR—. In certain embodiments, L is an unsubstituted $C_{1-2}$ hydrocarbon chain, wherein one chain atom of the hydrocarbon chain is replaced with —O—. In certain embodiments, L is of the formula:

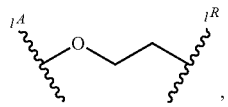

wherein 1$^A$ indicates the point of attachment to J, and 1$^R$ indicates the point of attachment to the

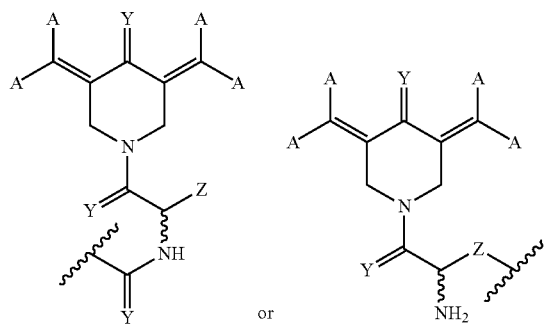

moiety. In certain embodiments, L is of the formula:

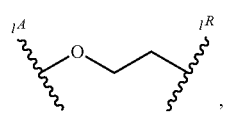

wherein 1$^A$ indicates the point of attachment to J, and 1$^R$ indicates the point of attachment to the

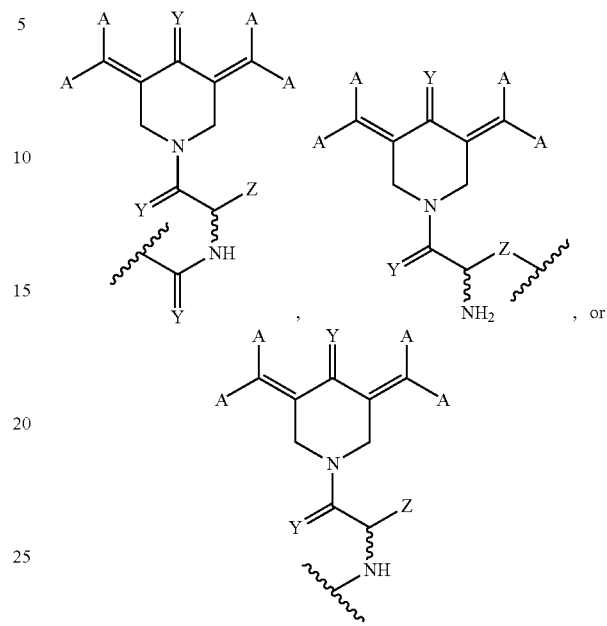

moiety. In certain embodiments, L is of the formula:

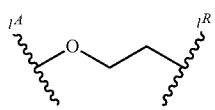

In certain embodiments, L is a substituted $C_{1-6}$ hydrocarbon chain, wherein one chain atom of the hydrocarbon chain is replaced with —N—. In certain embodiments, L is of the formula:

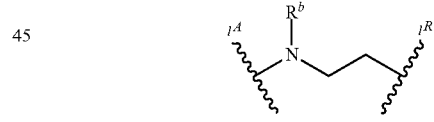

In certain embodiments, L is of the formula:

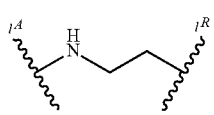

In certain embodiments, L is of the formula:

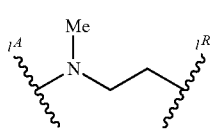

In certain embodiments, L is of the formula:

[Structure: —N(Et)— linker with 1A and 1R attachment points]

In certain embodiments, L is an unsubstituted $C_{1-3}$ hydrocarbon chain, wherein one chain atom of the hydrocarbon chain is replaced with —C(=O)—. In certain embodiments, L is an unsubstituted $C_{1-3}$ hydrocarbon chain, wherein one chain atom of the hydrocarbon chain is replaced with —S—. In certain embodiments, L is an unsubstituted $C_{1-3}$ hydrocarbon chain, wherein one chain atom of the hydrocarbon chain is replaced with —$NR^b$—. In certain embodiments, L is an unsubstituted $C_{1-3}$ hydrocarbon chain, wherein one chain atom of the hydrocarbon chain is replaced with —N=. In certain embodiments, L is an unsubstituted $C_{1-3}$ hydrocarbon chain, wherein one chain atom of the hydrocarbon chain is replaced with =N—.

In certain embodiments, L is of the formula:

[Structure: 1A-NH-CH2CH2-O-CH2CH2-O-CH2CH2-O-CH2CH2-C(=O)-NH-1R]

[Structure: 1A-C(=O)-NH-(CH2)5-C(=O)-NH-1R]

[Structure: 1A-C(=O)-NH-(CH2)3-C(=O)-NH-1R], or

[Structure: 1A-C(=O)-NH-CH2CH2-O-CH2CH2-O-CH2CH2-O-CH2CH2-C(=O)-NH-1R].

In certain embodiments, L is

[Structure: 1A-(CH2CH2-O)g-CH2CH2-1R] or

[Structure: 1A-(CH2)p-NH-(CH2)s-1R];

g is 1-5; p is 2-5; and s is 1-5. In certain embodiments, g is 1. In certain embodiments, g is 2. In certain embodiments, g is 3. In certain embodiments, g is 4. In certain embodiments, g is 5. In certain embodiments, p is 2. In certain embodiments, p is 3. In certain embodiments, p is 4. In certain embodiments, p is 5. In certain embodiments, s is 1. In certain embodiments, s is 2. In certain embodiments, s is 3. In certain embodiments, s is 4. In certain embodiments, s is 5. In certain embodiments, L is of the formula:

[Structure: 1A-(CH2CH2-O)3-CH2CH2-1R] or

[Structure: 1A-(CH2)-NH-(CH2)3-1R].

In certain embodiments, L is an all-carbon, substituted or unsubstituted $C_{1-12}$ hydrocarbon chain. In certain embodiments, L is an all-carbon, substituted $C_{1-12}$ hydrocarbon chain. In certain embodiments, L is an all-carbon, unsubstituted $C_{1-12}$ hydrocarbon chain. In certain embodiments, L is an all-carbon, unsubstituted $C_{11}$ hydrocarbon chain. In certain embodiments, L is an all-carbon, substituted or unsubstituted $C_{6-12}$ hydrocarbon chain. In certain embodiments, L is an all-carbon, substituted or unsubstituted $C_{6-10}$ hydrocarbon chain. In certain embodiments, L is an all-carbon, unsubstituted $C_5$ hydrocarbon chain; an all-carbon, unsubstituted $C_6$ hydrocarbon chain; an all-carbon, unsubstituted $C_7$ hydrocarbon chain; an all-carbon, unsubstituted $C_8$ hydrocarbon chain; an all-carbon, unsubstituted $C_9$ hydrocarbon chain; an all-carbon, unsubstituted $C_9$ hydrocarbon chain; an all-carbon, unsubstituted $C_{10}$ hydrocarbon chain; an all-carbon, unsubstituted $C_{11}$ hydrocarbon chain; or an all-carbon, unsubstituted $C_{12}$ hydrocarbon chain. In certain embodiments, L is an all-carbon, unsubstituted $C_6$ hydrocarbon chain. In certain embodiments, L is of the formula:

[Structure: 1A-(CH2)x1-piperazine-N-CH2-(CH2)x2-C(=O)-NH-CH2CH2-(O-CH2CH2)x3-C(=O)-NH-CH2CH2-(O-CH2CH2)x4-1R], wherein: x1 is 1-6; x2 is 1-6; x3 is 1-8; and x4 is 1-3. In certain embodiments, L is of the formula:

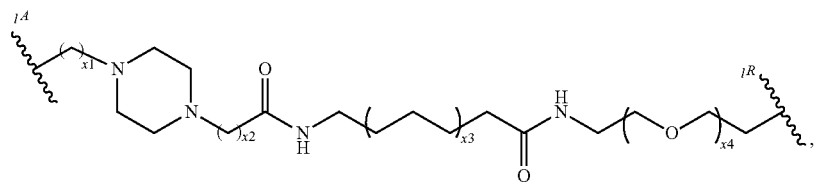

wherein: x1 is 1-6; x2 is 1-6; x3 is 1-8; and x4 is 1-3. In certain embodiments, x1 is 2-5. In certain embodiments, x1 is 2-4. In certain embodiments, x1 is 1. In certain embodiments, x1 is 2. In certain embodiments, x1 is 3. In certain embodiments, x1 is 4. In certain embodiments, x1 is 5. In certain embodiments, x1 is 6. In certain embodiments, x2 is 3-6. In certain embodiments, x2 is 3-5. In certain embodiments, x2 is 3-4. In certain embodiments, x2 is 2-4. In certain embodiments, x2 is 1. In certain embodiments, x2 is 2. In certain embodiments, x2 is 3. In certain embodiments, x2 is 4. In certain embodiments, x2 is 5. In certain embodiments, x2 is 6. In certain embodiments, x3 is 3-6. In certain embodiments, x3 is 3-5. In certain embodiments, x3 is 3-4. In certain embodiments, x3 is 2-4. In certain embodiments, x3 is 1. In certain embodiments, x3 is 2. In certain embodiments, x3 is 3. In certain embodiments, x3 is 4. In certain embodiments, x3 is 5. In certain embodiments, x4 is 1-3. In certain embodiments, x4 is 1-2. In certain embodiments, x4 is 1. In certain embodiments, x4 is 2. In certain embodiments, x4 is 3. In certain embodiments, x1 is 2-4; x2 is 3-6; x3 is 3-6; and x4 is 1-2. In certain embodiments, x1 is 2-3; x2 is 2-4; x3 is 3-4; and x4 is 1-2. In certain embodiments, L is of the formula:

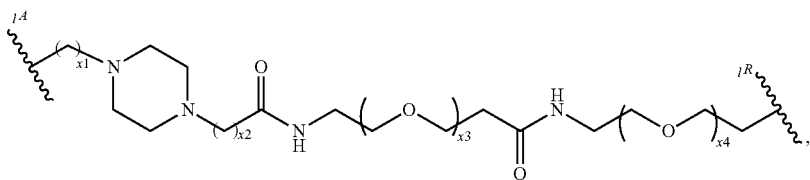

wherein: x1 is 2-4; x2 is 3-6; x3 is 3-6; and x4 is 1-2. In certain embodiments, L is of the formula:

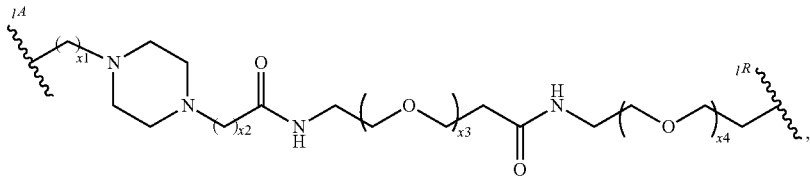

wherein: x1 is 2-3; x2 is 2-4; x3 is 3-4; and x4 is 1-2. In certain embodiments, L is of the formula:

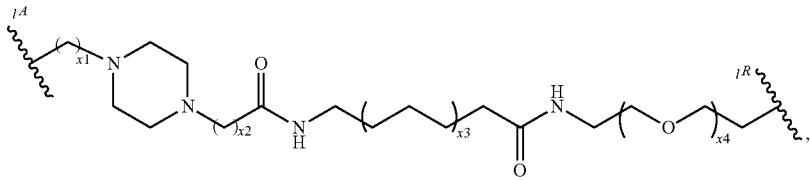

wherein: x1 is 2-4; x2 is 3-6; x3 is 3-6; and x4 is 1-2. In certain embodiments, L is of the formula:

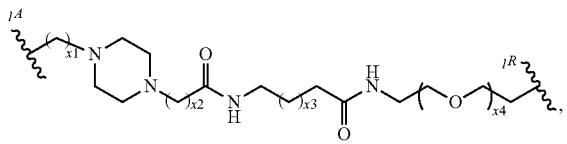

wherein: x1 is 2-3; x2 is 2-4; x3 is 3-4; and x4 is 1-2. In certain embodiments, L is of the formula:

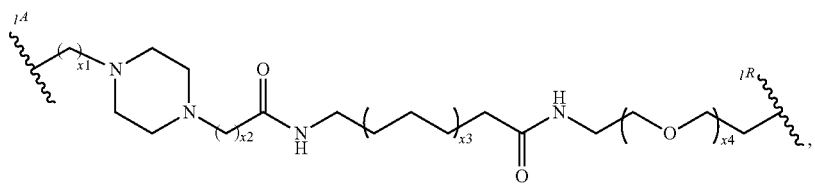

wherein: x1 is 2-3; x2 is 2-4; x3 is 3-4; and x4 is 1-2. In certain embodiments, L is of the formula:

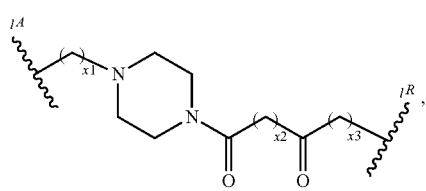

wherein: x1 is 1-6; x2 is 1-6; and x3 is 1-8. In certain embodiments, L is of the formula:

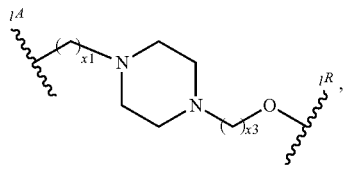

wherein: x1 is 1-6; and x3 is 1-8. In certain embodiments, L is of the formula:

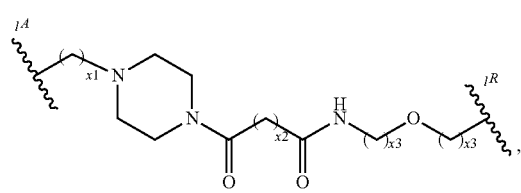

x1 is 1-6; x2 is 1-6; and each instance of x3 is independently 1-8. In certain embodiments, L is of the formula:

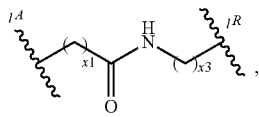

x1 is 1-6; and x3 is 1-8. In certain embodiments, x1 is 2-3 and x3 is 7-8. In certain embodiments, x1 is 1. In certain embodiments, x1 is 2. In certain embodiments, x1 is 3. In certain embodiments, x1 is 4. In certain embodiments, x1 is 5. In certain embodiments, x1 is 6. In certain embodiments, x2 is 1. In certain embodiments, x2 is 2. In certain embodiments, x2 is 3. In certain embodiments, x2 is 4. In certain embodiments, x2 is 5. In certain embodiments, x2 is 6. In certain embodiments, at least one instance of x3 is 1. In certain embodiments, at least one instance of x3 is 2. In certain embodiments, at least one instance of x3 is 3. In certain embodiments, at least one instance of x3 is 4. In certain embodiments, at least one instance of x3 is 5. In certain embodiments, at least one instance of x3 is 6. In certain embodiments, at least one instance of x3 is 7. In certain embodiments, at least one instance of x3 is 8. In certain embodiments, x is 2-3; x2 is 2-4; and x3 is 6-8. In certain embodiments, x1 is 2 or 3; x2 is 2, 3, or 4; and at least one instance of x3 is 6, 7, or 8. In certain embodiments, x1 is 2-3; and x3 is 6-8. In certain embodiments, x is 2 or 3; and x3 is 6, 7, or 8. In certain embodiments, x is 2-3; x2 is 2-4; and x3 is 2-3. In certain embodiments, x is 2 or 3; x2 is 2, 3, or 4; and at least one instance of x3 is 2, 3, or 4. In certain embodiments, x1 is 2 or 3; x2 is 2, 3, or 4; and each instance of x3 is x3 is 2, 3, or 4.

In certain embodiments, L is of the formula:
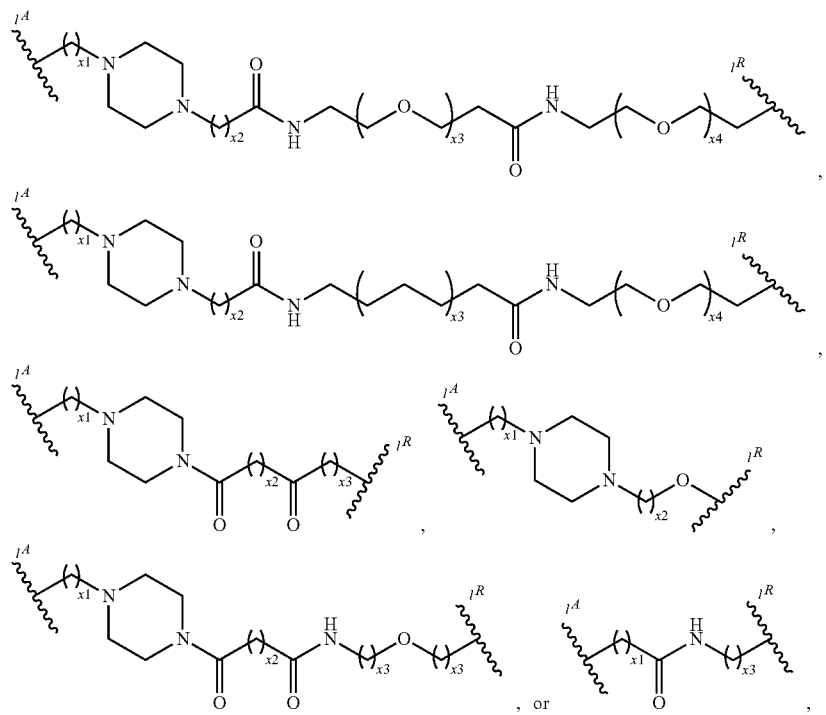
wherein x1 is 2. In certain embodiments, L is of the formula:
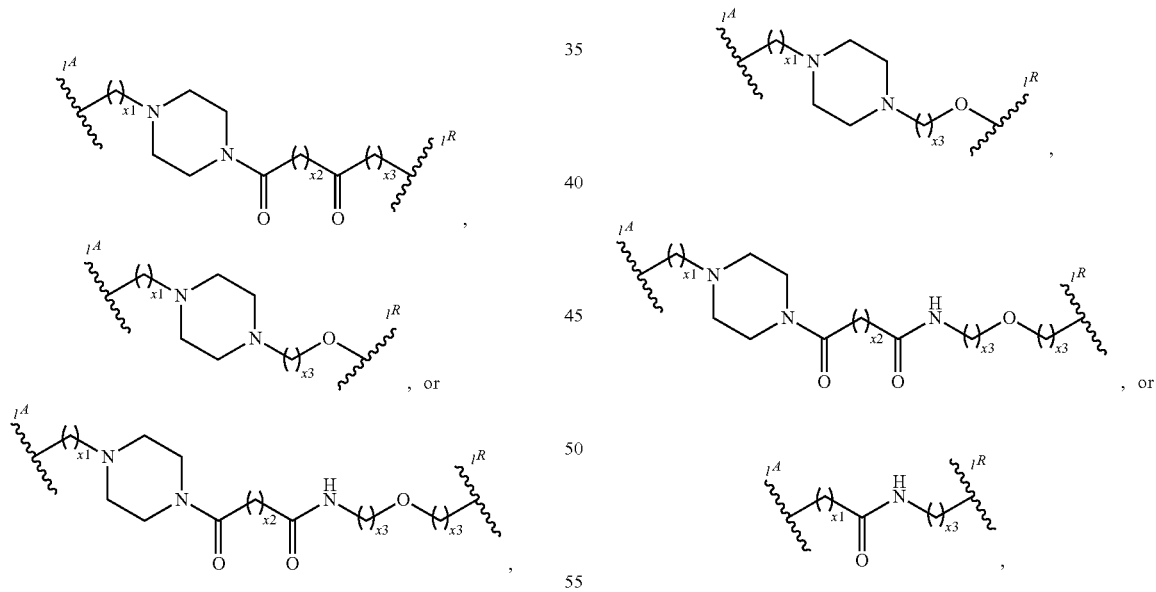
wherein x1 is 2. In certain embodiments, L is of the formula:
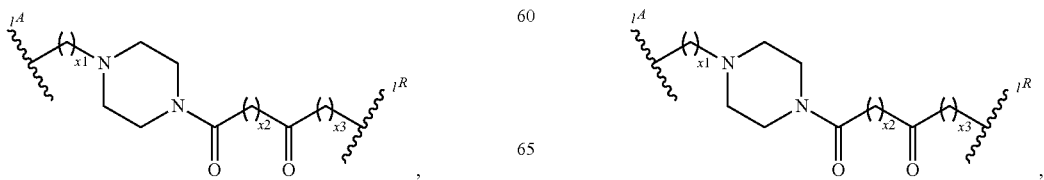
wherein x1 is 3. In certain embodiments, L is of the formula:

-continued
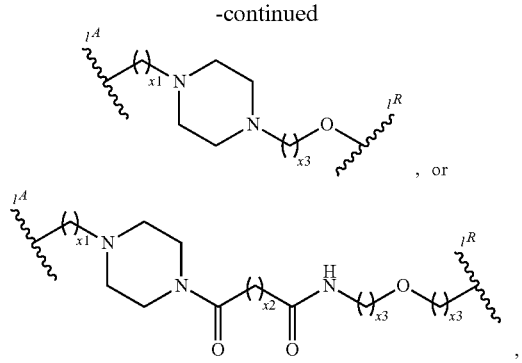
, or
wherein x1 is 3.
In certain embodiments, L is of the formula:
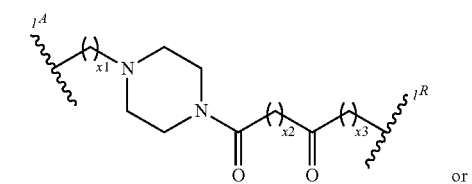
or
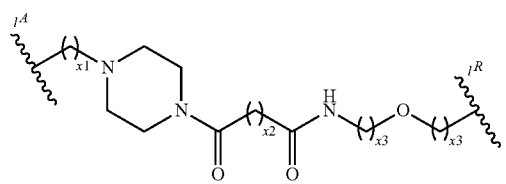
wherein x1 is 2 or 3; and x2 is 3 or 4. In certain embodiments, L is of the formula:
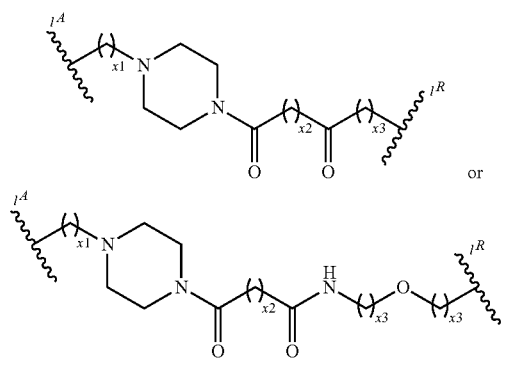
wherein x1 is 2 or 3; and x2 is 3. In certain embodiments, L is of the formula:
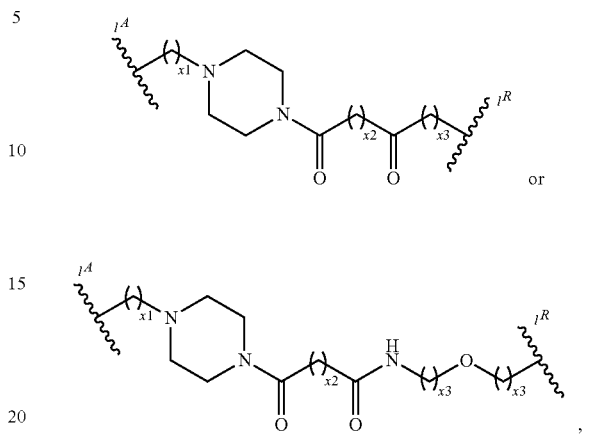
wherein x1 is 2 or 3; and x2 is 4.
In certain embodiments, L is of the formula:
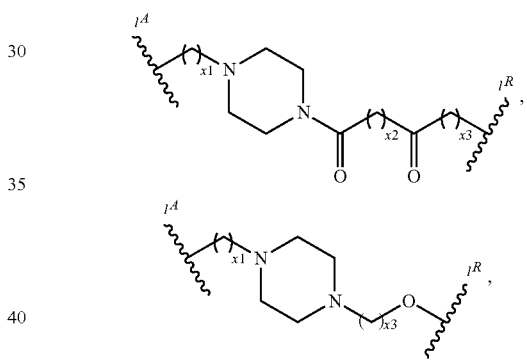
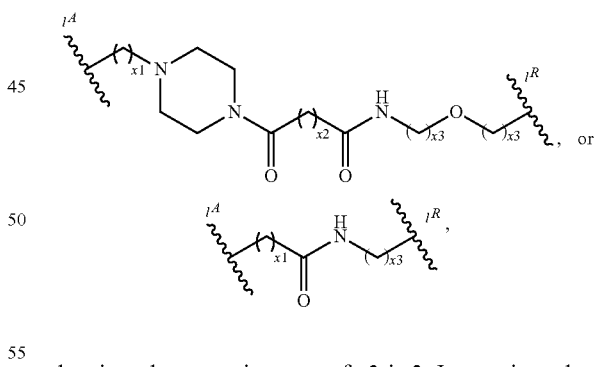
wherein at least one instance of x3 is 2. In certain embodiments, L is of the formula:
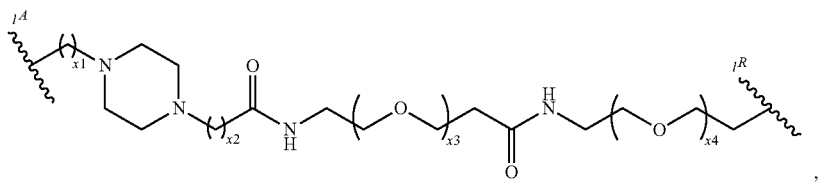

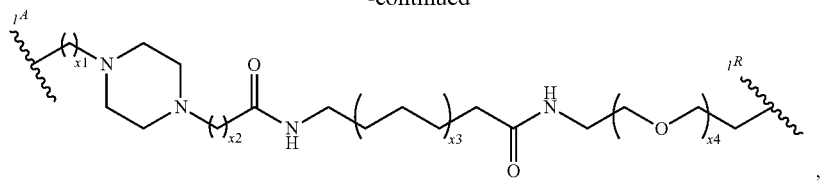
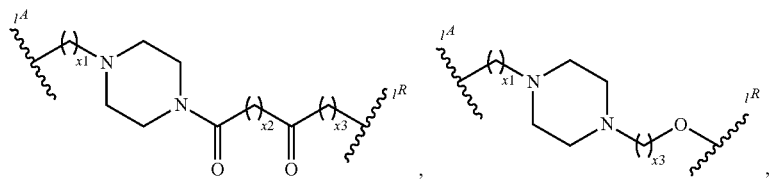
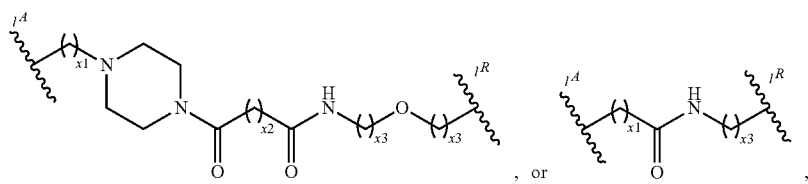
wherein at least one instance of x3 is 2 or 3. In certain embodiments, L is of the formula:
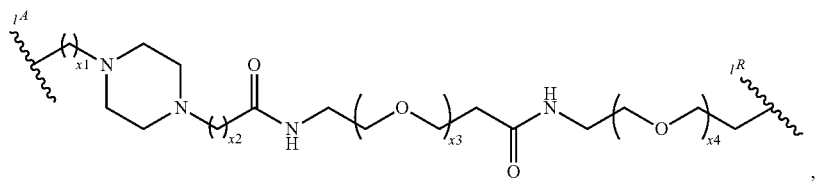
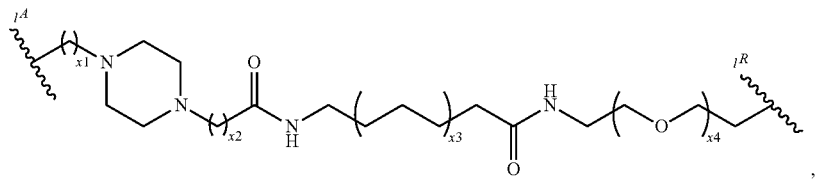
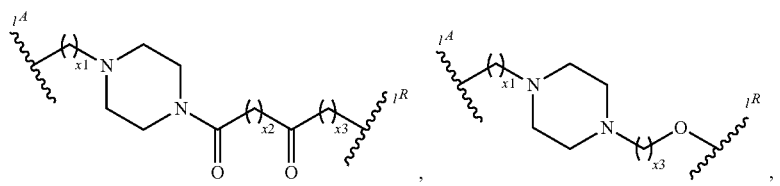
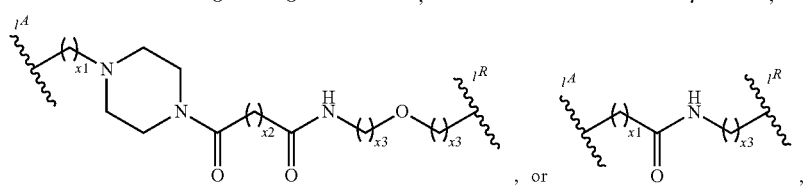

wherein at least one instance of x3 is 3. In certain embodiments, L is of the formula:

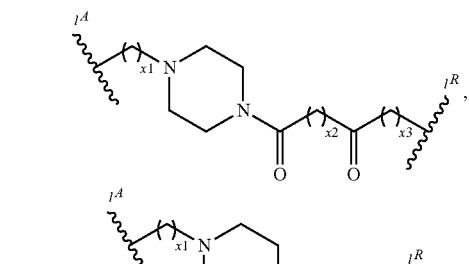

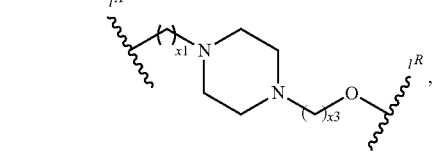

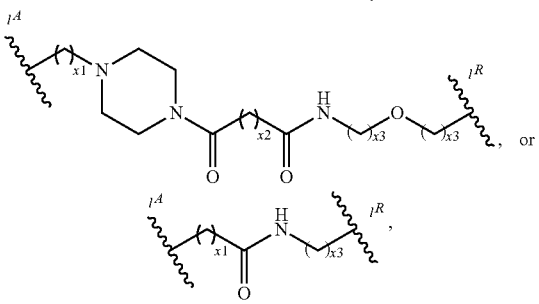, or wherein at least one instance of x3 is 6. In certain embodiments, L is of the formula:

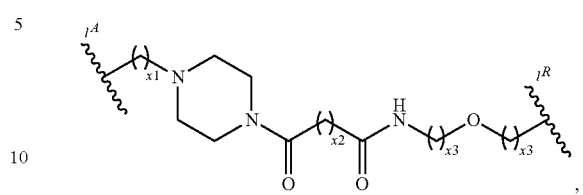

wherein both instances of x3 are 2. In certain embodiments, L is of the formula:

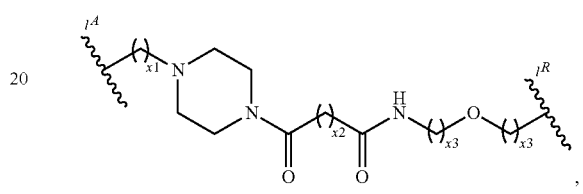

wherein x1 is 2, 3, or 4; x2 is 3, 4, or 5; and both instances of x3 are 2, 3, or 4. In certain embodiments, L is of the formula:

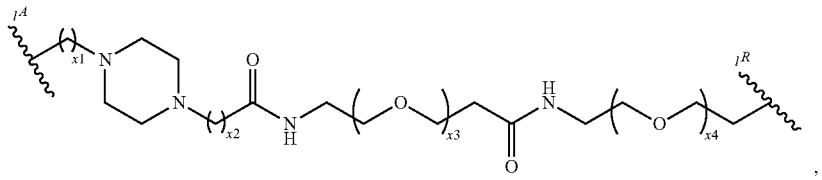

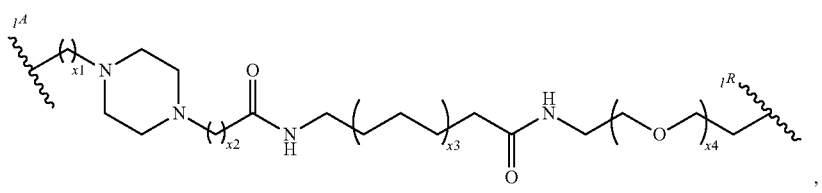

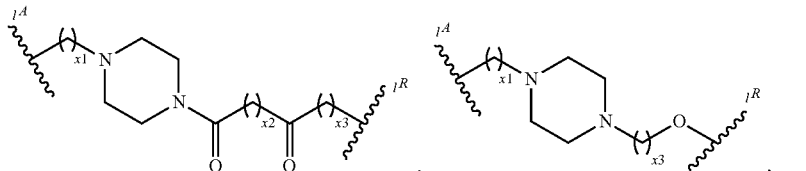

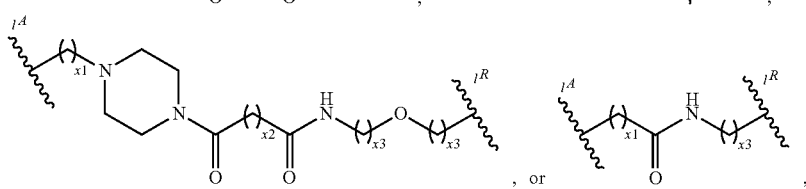

wherein x1 is 2 or 3; x2 is 3 or 4; and at least one instance of x3 is 2, 3, 4, 5, or 6.

In certain embodiments, L is of the formula:
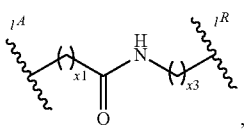
wherein x1 is 2 or 3; and x3 is 6, 7, or 8.
In certain embodiments, L is of the formula:
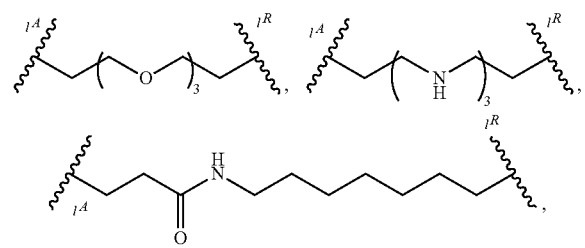
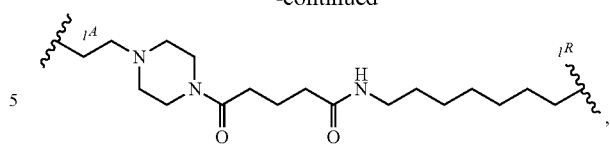
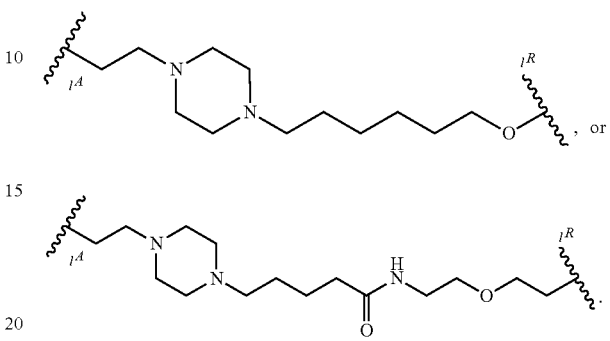
In certain embodiments, L is of the formula:
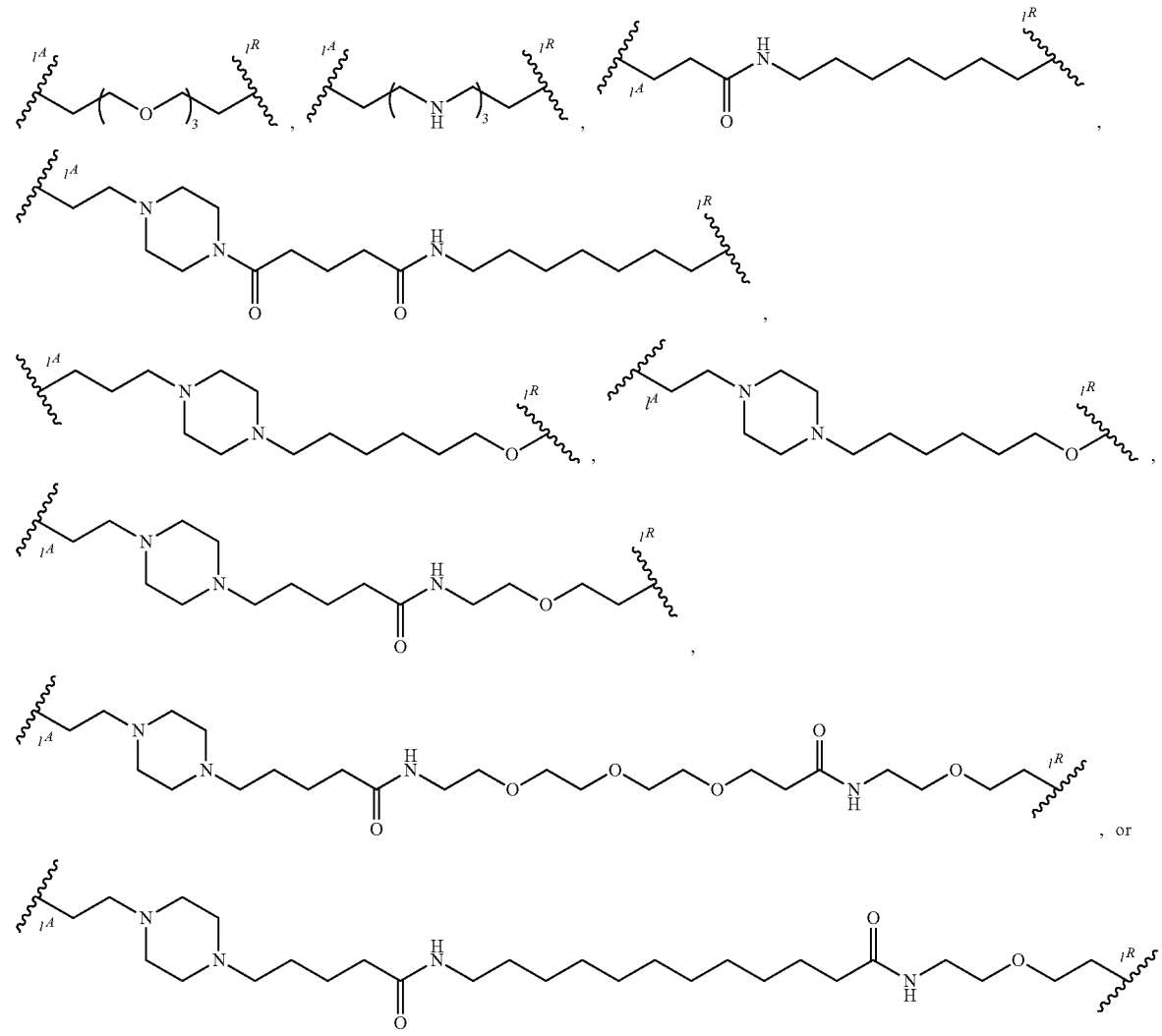

Binder of a Bromodomain or a Bromodomain-Containing Protein

In certain embodiments, J is a binder of a bromodomain or a bromodomain-containing protein. In certain embodiments, J is a binder of a bromodomain or a bromodomain-containing protein, which is a compound of Formula (II), (III), (IV), or (V). In certain embodiments, a BET bromodomain-containing protein to which J is binds includes, but is not limited to, BRD1, BRD2, BRD3, BRD4, BRD5, BRD6, BRD7, BRD8, BRD9, BRD10, and BRDT. In certain embodiments, the BET bromodomain-containing protein is BRD2. In certain embodiments, the BET bromodomain-containing protein is not BRD2. In certain embodiments, the BET bromodomain-containing protein is BRD3. In certain embodiments, the BET bromodomain-containing protein is not BRD3. In certain embodiments, the BET bromodomain-containing protein is not BRD2 or BRD3. In certain embodiments, the BET bromodomain-containing protein is BRD4. In certain embodiments, the BET bromodomain-containing protein is BRD1, BRD4, BRD5, BRD6, BRD7, BRD8, BRD9, BRD10, and/or BRDT. In some embodiments, the linker L is attached to any position on the compound of Formulae (II), (III), (IV), or (V).

In certain embodiments, J is a moiety of Formula (II):

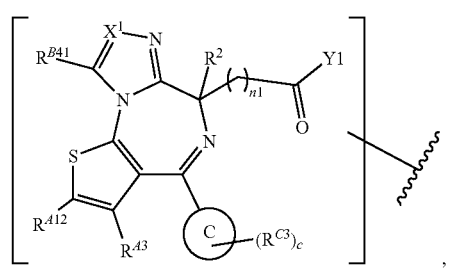
(II)

wherein:

Y1 is of formula:

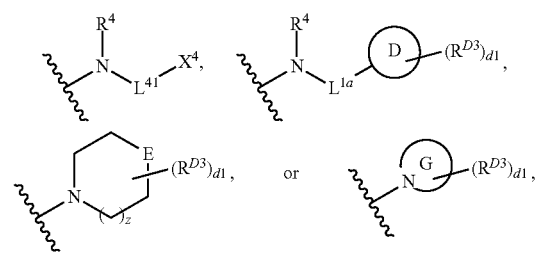

wherein:
$R^4$ is hydrogen, optionally substituted alkyl, optionally substituted acyl, or a nitrogen protecting group;
$L^{1a}$ is optionally substituted alkylene;
$L^{41}$ is unsubstituted branched alkylene or substituted alkylene;
$X^4$ is halogen, $-OR^f$, $-SR^f$, or $-N(R^f)_2$;
Ring D is a carbocyclic or a heterocyclic ring, wherein the heterocyclic ring contains one heteroatom, and the heteroatom is N;
Ring G is a bicyclic heterocyclic or bicyclic heteroaryl ring, wherein the rings share exactly two atoms;
E is O, S, $NR^{E11}$, or $CHR^{E11}$, wherein $R^{E11}$ is optionally substituted carbocyclyl, optionally substituted heterocyclyl, optionally substituted aryl, or optionally substituted heteroaryl;

each occurrence of $R^{D3}$ is independently hydrogen, halogen, optionally substituted alkyl, optionally substituted heteroalkyl, optionally substituted alkenyl, optionally substituted alkynyl, optionally substituted carbocyclyl, optionally substituted heterocyclyl, optionally substituted aryl, optionally substituted heteroaryl, optionally substituted acyl, $-OR^f$, $-SR^f$, $-N(R^f)_2$, $-NO_2$, or $-CN$, or two $R^{D3}$ attached to adjacent atoms are joined to form an optionally substituted carbocyclyl, optionally substituted heterocyclyl, optionally substituted aryl, or optionally substituted heteroaryl ring;

z is 0, 1, or 2; and d1 is 0, 1, 2, 3, or 4;

$R^{A12}$ is hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, $-OR^f$, $-SR^f$, $-N(R^f)_2$, $-NO_2$, or $-CN$;

$R^{A3}$ is hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, $-OR^f$, $-SR^f$, $-N(R^f)_2$, $-NO_2$, or $-CN$;

$X^1$ is N or $CR^5$, wherein $R^5$ is hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, $-OR^f$, $-SR^f$, $-N(R^f)_2$, $-NO_2$, or $-CN$;

$R^{B41}$ is hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, $-OR^f$, $-SR^f$, $-N(R^f)_2$, $-NO_2$, or $-CN$;

Ring C is aryl or heteroaryl;

each occurrence of $R^{C3}$ is independently halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, optionally substituted sulfonyl, $-OR^f$, $-SR^f$, $-N(R^f)_2$, $-NO_2$, or $-CN$;

c is 0, 1, 2, 3, or 4;

n1 is 0, 1, 2, 3, or 4;

$R^2$ is hydrogen, halogen, or optionally substituted alkyl; and each occurrence of $R^f$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, optionally substituted sulfonyl, an oxygen protecting group, or a nitrogen protecting group, or two $R^f$ are joined to form an optionally substituted heterocyclic or optionally substituted heteroaryl ring.

In certain embodiments, J is a moiety of Formula (III):

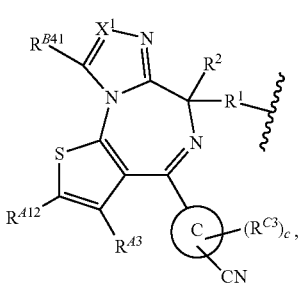

(III)

wherein:
R$^{A12}$ is hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, —OR$^f$, —SR$^f$, —N(R$^f$)$_2$, —NO$_2$, or —CN;

R$^{A3}$ is hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, —OR$^f$, —SR$^f$, —N(R$^f$)$_2$, —NO$_2$, or —CN;

X$^1$ is N or CR$^5$, wherein R$^5$ is hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, —OR$^f$, —SR$^f$, —N(R$^f$)$_2$, —NO$_2$, or —CN;

R$^{B41}$ is hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, —OR$^f$, —SR$^f$, —N(R$^f$)$_2$, —NO$_2$, or —CN;

Ring C is aryl or heteroaryl;
each occurrence of R$^{C3}$ is independently halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, optionally substituted sulfonyl, —OR$^f$, —SR$^f$, —N(R$^f$)$_2$, —NO$_2$, or —CN;

c is 0, 1, 2, 3, or 4;
R$^1$ is hydrogen, halogen, optionally substituted alkyl, or —(CH$_2$)$_n$L$_2$, wherein n is 0, 1, 2, 3 or 4, and L$_2$ is —C(=O)R$^3$, —C(=O)OR$^3$, —C(=O)NR$^3$R$^4$, —S(=O)$_2$R$^3$, —S(=O)$_2$OR$^3$, —S(=O)$_2$NR$^3$R$^4$, —OR$^3$, —NR$^3$R$^4$, —N(R$^4$)C(=O)R$^3$, optionally substituted carbocyclyl, optionally substituted heterocyclyl, optionally substituted aryl, or optionally substituted heteroaryl;

R$^2$ is hydrogen, halogen, or optionally substituted alkyl;
each of R$^3$ and R$^4$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or optionally substituted acyl, an oxygen protecting group, or a nitrogen protecting group, or R$^3$ and R$^4$ are joined to form an optionally substituted heterocyclic or optionally substituted heteroaryl ring; and each occurrence of R$^f$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, optionally substituted sulfonyl, an oxygen protecting group, or a nitrogen protecting group, or two R$^f$ are joined to form an optionally substituted heterocyclic or optionally substituted heteroaryl ring.

In certain embodiments, J is a moiety of Formula (IV):

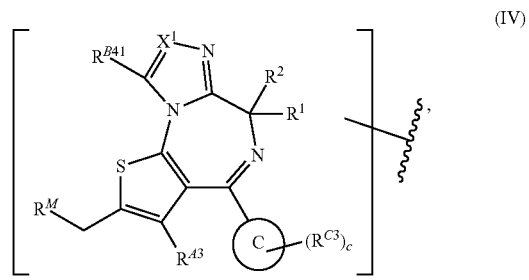

(IV)

wherein:
R$^M$ is —CN, —N(R$^f$)$_2$, or —CH$_2$N(R$^f$)$_2$;
R$^{A3}$ is hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, —OR$^f$, —SR$^f$, —N(R$^f$)$_2$, —NO$_2$, or —CN;

X$^1$ is N or CR$^5$, wherein R$^5$ is hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, —OR$^f$, —SR$^f$, —N(R$^f$)$_2$, —NO$_2$, or —CN;

R$^{B41}$ is hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, —OR$^f$, —SR$^f$, —N(R$^f$)$_2$, —NO$_2$, or —CN;

Ring C is aryl or heteroaryl;
each occurrence of R$^{C3}$ is independently halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, optionally substituted sulfonyl, —OR$^f$, —SR$^f$, —N(R$^f$)$_2$, —NO$_2$, or —CN;

c is 0, 1, 2, 3, or 4;
R$^1$ is hydrogen, halogen, optionally substituted alkyl, or —(CH$_2$)$_n$L$_2$, wherein n is 0, 1, 2, 3, or 4, and L$_2$ is —C(=O)R$^3$, —C(=O)OR$^3$, —C(=O)NR$^3$R$^4$, —S(=O)$_2$R$^3$, —S(=O)$_2$OR$^3$, —S(=O)$_2$NR$^3$R$^4$, —OR$^3$, —NR$^3$R$^4$, —N(R$^4$)C(=O)R$^3$, optionally substituted carbocyclyl, optionally substituted heterocyclyl, optionally substituted aryl, or optionally substituted heteroaryl;

$R^2$ is hydrogen, halogen, or optionally substituted alkyl;

each $R^3$ and $R^4$ is independently hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl, or optionally substituted acyl, an oxygen protecting group, or a nitrogen protecting group, or $R^3$ and $R^4$ are joined to form an optionally substituted heterocyclic or optionally substituted heteroaryl ring; and each occurrence of $R^f$ is independently, hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, optionally substituted sulfonyl, an oxygen protecting group, or a nitrogen protecting group, or two $R^f$ are joined to form an optionally substituted heterocyclic or optionally substituted heteroaryl ring.

In certain embodiments, J is a moiety of Formula (V):

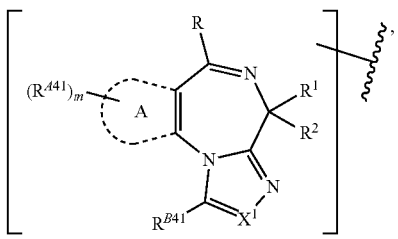

(V)

wherein:

$X^1$ is N or $CR^5$;

$R^5$ is hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, —$OR^f$, —$SR^f$, —$N(R^f)_2$, —$NO_2$, or —CN;

$R^{B41}$ is H, alkyl, hydroxylalkyl, aminoalkyl, alkoxyalkyl, haloalkyl, hydroxy, alkoxy, or —COO—$R_3$, each of which is optionally substituted;

ring A is aryl or heteroaryl;

each $R^{A41}$ is independently alkyl, cycloalkyl, heterocycloalkyl, aryl, or heteroaryl, each of which is optionally substituted; or any two $R^{A41}$ together with the atoms to which each is attached, can form a fused aryl or heteroaryl group;

R is alkyl, cycloalkyl, heterocycloalkyl, aryl, or heteroaryl; each of which is optionally substituted;

$R^1$ is —$(CH_2)_n$-$L_2$, in which n is 0, 1, 2, or 3 and $L_2$ is H, —C(=O)$R^3$, —C(=O)O$R^3$, —C(=O)N$R^3R^4$, —S(=O)$_2R^3$, —S(=O)$_2$N$R^3R^4$, —N$R^3R^4$, —N($R^4$)C(=O)$R^3$, optionally substituted aryl, or optionally substituted heteroaryl; $R^2$ is H, D (deuterium), halogen, or optionally substituted alkyl;

each $R^3$ is independently selected from the group consisting of:

(i) H, aryl, substituted aryl, heteroaryl, or substituted heteroaryl;

(ii) heterocycloalkyl or substituted heterocycloalkyl;

(iii) —$C_1$-$C_8$ alkyl, —$C_2$-$C_8$ alkenyl or —$C_2$-$C_8$ alkynyl, each containing 0, 1, 2, or 3 heteroatoms selected from O, S, or N; —$C_3$-$C_{12}$ cycloalkyl, substituted —$C_3$-$C_{12}$ cycloalkyl, —$C_3$-$C_{12}$cycloalkenyl, or substituted —$C_3$-$C_{12}$ cycloalkenyl, each of which may be optionally substituted;

(iv) N=$CR^4R^6$;

each $R^4$ is independently hydrogen, alkyl, cycloalkyl, heterocycloalkyl, aryl, or heteroaryl, each of which is optionally substituted;

or $R^3$ and $R^4$ are taken together with the nitrogen atom to which they are attached to form a 4-10-membered ring;

$R^6$ is alkyl, alkenyl, cycloalkyl, cycloalkenyl, heterocycloalkyl, aryl, or heteroaryl, each of which is optionally substituted; or $R^4$ and $R^6$ are taken together with the carbon atom to which they are attached to form a 4-10-membered ring; and m is 0, 1, 2, or 3.

Group Y1

Formula (II) includes substituent Y1. In certain embodiments, Y1 is of formula:

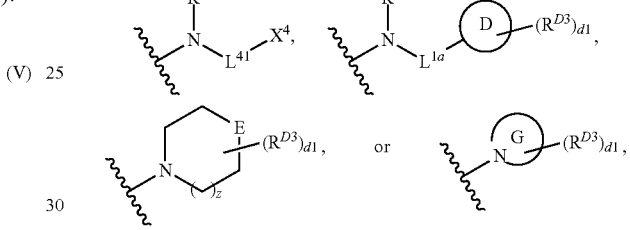

As generally defined herein, n1 is 0, 1, 2, 3, or 4. In certain embodiments, n1 is 0. In certain embodiments, n1 is 1. In certain embodiments, n1 is 2. In certain embodiments, n1 is 3. In certain embodiments, n1 is 4. In certain embodiments, n1 is 0, 1, 2, or 3. In certain embodiments, n1 is 0, 1, or 2. In certain embodiments, n1 is 0 or 1. In certain embodiments, n1 is 1, 2, 3, or 4. In certain embodiments, n1 is 2, 3, or 4. In certain embodiments, n1 is 3 or 4. In certain embodiments, n1 is 0, 2, 3, or 4.

As generally defined herein $R^4$ is hydrogen, optionally substituted alkyl, optionally substituted acyl, or a nitrogen protecting group. In certain embodiments, $R^4$ is hydrogen.

In certain embodiments, $R^4$ is optionally substituted alkyl, e.g., optionally substituted $C_{1-6}$ alkyl, optionally substituted $C_{1-2}$ alkyl, optionally substituted $C_{2-3}$ alkyl, optionally substituted $C_{3-4}$ alkyl, optionally substituted $C_{4-5}$ alkyl, or optionally substituted $C_{5-6}$ alkyl. In certain embodiments, $R^4$ is unsubstituted alkyl, e.g., unsubstituted $C_{1-6}$ alkyl, unsubstituted $C_{1-2}$ alkyl, unsubstituted $C_{2-3}$ alkyl, unsubstituted $C_{3-4}$ alkyl, unsubstituted $C_{4-5}$ alkyl, or unsubstituted $C_{5-6}$ alkyl. In certain embodiments, $R^4$ is methyl. In certain embodiments, $R^4$ is ethyl, propyl, or butyl. In certain embodiments, $R^4$ is haloalkyl, e.g., —$CHF_2$, —$CHCl_2$, —$CH_2CHF_2$, —$CH_2CHCl_2$. In certain embodiments, $R^4$ is perhaloalkyl, e.g., —$CF_3$, —$CF_2CF_3$, —$CCl_3$. In certain embodiments, $R^4$ is hydroxyalkyl, e.g., —$CH_2OH$, —$CH_2CH_2OH$, —$CH_2OR^f$, —$CH_2CH_2OR^f$. In certain embodiments, $R^4$ is aminoalkyl, e.g., —$CH_2NH_2$, —$CH_2CH_2NH_2$, —$CH_2NMe_2$, —$CH_2CH_2NMe_2$, —$CH_2N(R^f)_2$, —$CH_2CH_2N(R^f)_2$.

In certain embodiments, $R^4$ is optionally substituted acyl, e.g., —CHO, —$CO_2H$, or —C(=O)$NH_2$. In certain embodiments, $R^4$ is —C(=O)$R^f$, —C(=O)O$R^f$, —C(=O)NH($R^f$), or —C(=O)N($R^f)_2$. In certain embodiments, $R^4$ is —C(=O)$R^f$, and $R^f$ is optionally substituted alkyl, e.g., —C(=O)Me. In certain embodiments, $R^4$ is —C(=O)$R^f$, and $R^f$ is optionally substituted alkenyl. In certain embodiments, $R^4$ is —C(=O)$R^f$, and $R^f$ is optionally substituted carbocyclyl, heterocyclyl, aryl, or heteroaryl. In certain embodiments, $R^4$ is —C(=O)O$R^f$, and $R^f$ is optionally substituted alkyl. In certain embodiments, $R^4$ is —C(=O)O$R^f$, and $R^f$ is optionally substituted alkenyl. In certain embodiments, $R^4$ is —C(=O)O$R^f$, and $R^f$ is optionally substituted carbocyclyl, heterocyclyl, aryl, or heteroaryl. In certain embodiments, $R^4$ is —C(=O)N($R^f$)$_2$, and at least one $R^f$ is optionally substituted alkyl. In certain embodiments, $R^4$ is —C(=O)NH$R^f$, and $R^f$ is optionally substituted alkyl. In certain embodiments, $R^4$ is —C(=O)NH$R^f$, and $R^f$ is optionally substituted alkenyl. In certain embodiments, $R^4$ is —C(=O)NH$R^f$, and $R^f$ is optionally substituted carbocyclyl, heterocyclyl, aryl, or heteroaryl. In certain embodiments, $R^4$ is a nitrogen protecting group. In some embodiments, $R^4$ is Bn, Boc, Cbz, Fmoc, trifluoroacetyl, triphenylmethyl, acetyl, or Ts.

In certain embodiments, Y1 is of formula:

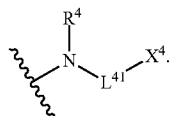

In certain embodiments, Y1 is of formula:

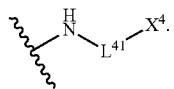

In certain embodiments, Y1 is of formula:

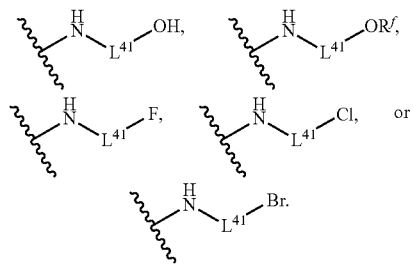

In certain embodiments, Y1 is of formula:

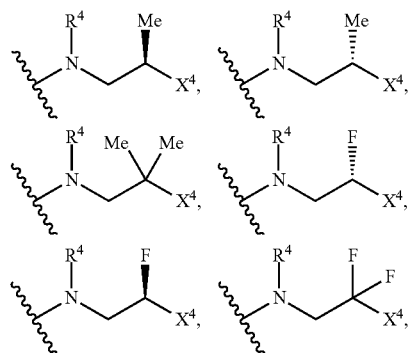

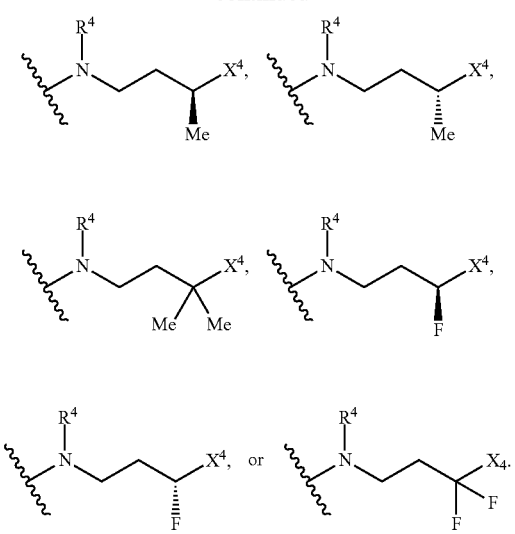

In certain embodiments, Y1 is of formula:

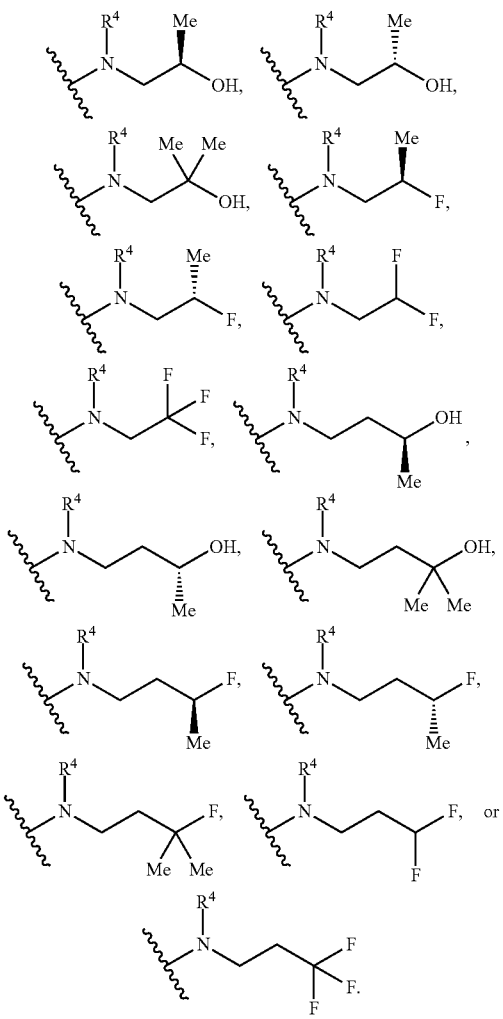

In certain embodiments, Y1 is of formula:

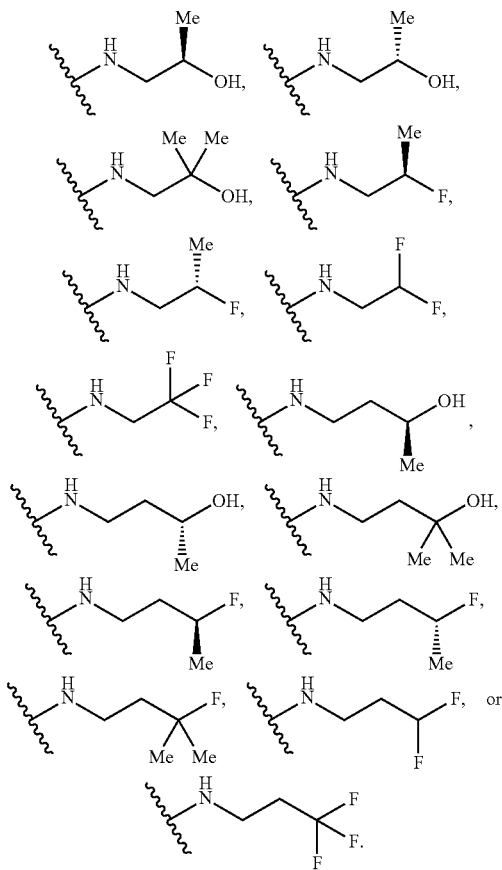

As generally defined herein, $L^{41}$ is unsubstituted branched alkylene or substituted alkylene. In certain embodiments, $L^{41}$ is unsubstituted branched alkylene. In some embodiments, $L^{41}$ is unsubstituted branched $C_{1-12}$ alkylene. In some embodiments, $L^{41}$ is unsubstituted branched $C_{1-8}$ alkylene. In some embodiments, $L^{41}$ is unsubstituted branched $C_{1-6}$ alkylene. In some embodiments, $L^{41}$ is unsubstituted branched $C_{2-6}$ alkylene. In some embodiments, $L^{41}$ is unsubstituted branched $C_{3-6}$ alkylene. In some embodiments, $L^{41}$ is unsubstituted branched $C_{4-6}$ In some embodiments, $L^{41}$ is unsubstituted branched $C_{5-6}$ alkylene. In some embodiments, $L^{41}$ is unsubstituted branched $C_{1-5}$ alkylene. In some embodiments, $L^{41}$ is unsubstituted branched $C_{2-5}$ alkylene. In some embodiments, $L^{41}$ is unsubstituted branched $C_{3-5}$ alkylene. In some embodiments, $L^{41}$ is unsubstituted branched $C_{4-5}$ alkylene. In some embodiments, $L^{41}$ is unsubstituted branched $C_{1-4}$ alkylene. In some embodiments, $L^{41}$ is unsubstituted branched $C_{2-4}$ alkylene. In some embodiments, $L^{41}$ is unsubstituted branched $C_{3-4}$ alkylene. In some embodiments, $L^{41}$ is unsubstituted branched $C_{1-3}$ alkylene. In some embodiments, $L^{41}$ is unsubstituted branched $C_{2-3}$ alkylene. In some embodiments, $L^{41}$ is unsubstituted branched $C_{1-2}$ alkylene. In some embodiments, $L^{41}$ is unsubstituted branched $C_1$ alkylene. In some embodiments, $L^{41}$ is unsubstituted branched $C_2$ alkylene. In some embodiments, $L^{41}$ is unsubstituted branched $C_3$ alkylene. In some embodiments, $L^{41}$ is unsubstituted branched $C_4$ alkylene. In some embodiments, $L^{41}$ is unsubstituted branched $C_5$ alkylene. In some embodiments, $L^{41}$ is unsubstituted branched $C_6$ alkylene.

In certain embodiments, $L^{41}$ is substituted alkylene. Substituted alkylene includes both branched and unbranched substituted alkylenes. In some embodiments, $L^4$ is substituted $C_{1-12}$ alkylene. In some embodiments, $L^{41}$ is substituted $C_{1-8}$ alkylene. In some embodiments, $L^{41}$ is substituted $C_{1-6}$ alkylene. In some embodiments, $L^{41}$ is substituted $C_{2-6}$ alkylene. In some embodiments, $L^{41}$ is substituted $C_{3-6}$ alkylene. In some embodiments, $L^{41}$ is substituted alkylene, wherein the substituents are selected from the group consisting of alkyl, halogen, —OH, —OR$^f$, —NH$_2$, —NHR$^f$, and —N(R$^f$)$_2$. In some embodiments, $L^{41}$ is substituted alkylene, wherein the substituents are selected from the group consisting of halogen, —OH, or —OR$^f$. In some embodiments, $L^{41}$ is substituted alkylene, wherein the substituent or substituents are halogen (e.g., —F, —Cl, —Br).

As generally defined herein $X^4$ is halogen, —OR$^f$, —SR$^f$, or —N(R$^f$)$_2$. In certain embodiments, $X^4$ is halogen or —OH. In some embodiments, $X^4$ is —F or —OH. In certain embodiments, $X^4$ is halogen. In some embodiments, $X^4$ is —F. In some embodiments, $X^4$ is —Cl, —Br, or —I.

In certain embodiments, $X^4$ is —OR$^f$, e.g., —OH. In certain embodiments, $X^4$ is —OR$^f$, and R$^f$ is optionally substituted alkyl. In certain embodiments, $X^4$ is —OR$^f$, and R$^f$ is unsubstituted $C_{1-6}$ alkyl. In certain embodiments, $X^4$ is —OR$^f$, and R$^f$ is optionally substituted alkenyl. In certain embodiments, $X^4$ is —OR$^f$, and R$^f$ is optionally substituted carbocyclyl, optionally substituted heterocyclyl, optionally substituted aryl optionally substituted heteroaryl. In certain embodiments, $X^4$ is —OR$^f$, and R$^f$ is unsubstituted carbocyclyl, unsubstituted heterocyclyl, unsubstituted aryl unsubstituted heteroaryl. In certain embodiments, $X^4$ is —OR$^f$, and R$^f$ is optionally substituted acyl, e.g., $X^4$ is —OC(=O)R$^f$, —OC(=O)OR$^f$, or —OC(=O)N(R$^f$)$_2$. In certain embodiments, $X^4$ is —OR$^f$, and R$^f$ is an oxygen protecting group.

In certain embodiments, $X^4$ is —SR$^f$, e.g., —SH. In certain embodiments, $X^4$ is —SR$^f$, and R$^f$ is optionally substituted alkyl. In certain embodiments, $X^4$ is —SR$^f$, and R$^f$ is unsubstituted $C_{1-6}$ alkyl. In certain embodiments, $X^4$ is —SR$^f$, and R$^f$ is optionally substituted carbocyclyl, optionally substituted heterocyclyl, optionally substituted aryl optionally substituted heteroaryl. In certain embodiments, $X^4$ is —SR$^f$, and R$^f$ is unsubstituted carbocyclyl, unsubstituted heterocyclyl, unsubstituted aryl unsubstituted heteroaryl. In certain embodiments, $X^4$ is —SR$^f$, and R$^f$ is a sulfur protecting group.

In certain embodiments, $X^4$ is —N(R$^f$)$_2$, e.g., —NH$_2$, —NHR$^f$. In certain embodiments, $X^4$ is —NH(R$^f$), and R$^f$ is optionally substituted alkyl. In certain embodiments, $X^4$ is —N(R$^f$)$_2$, and at least one R$^f$ is optionally substituted alkyl. In certain embodiments, $X^4$ is —NH(R$^f$), and R$^f$ is unsubstituted alkyl. In certain embodiments, $X^4$ is —N(R$^f$)$_2$, and at least one R$^f$ is unsubstituted alkyl. In certain embodiments, $X^4$ is —NHR$^f$, and R$^f$ is optionally substituted carbocyclyl, optionally substituted heterocyclyl, optionally substituted aryl, or optionally substituted heteroaryl. In certain embodiments, $X^4$ is —NHR$^f$, and R$^f$ is unsubstituted carbocyclyl, unsubstituted heterocyclyl, unsubstituted aryl, or unsubstituted heteroaryl. In certain embodiments, $X^4$ is —NHR$^f$, and R$^f$ is optionally substituted acyl, e.g., $X^4$ is —NHC(=O)R$^f$, —NHC(=O)OR$^f$, or —NHC(=O)NHR$^f$. In certain embodiments, $X^4$ is —N(R$^f$)$_2$, and at least one R$^f$ is a nitrogen protecting group. In certain embodiments, $X^4$ is —N(R$^f$)$_2$, and both R$^f$ are joined to form an optionally substituted heterocyclic or optionally substituted heteroaryl ring. In certain embodiments, $X^4$ is —N(R$^f$)$_2$, and both R$^f$ are joined to form an unsubstituted heterocyclic or unsubstituted heteroaryl ring.

In certain embodiments, Y1 is of formula:
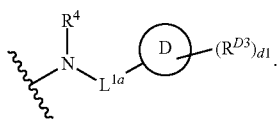
In certain embodiments, Y1 is of formula:
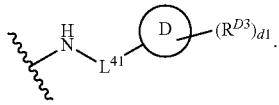
In certain embodiments, Y1 is of formula:
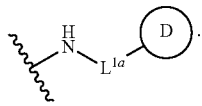
In certain embodiments, Y1 is of formula:
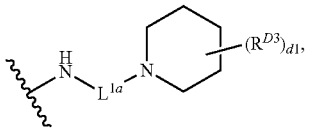
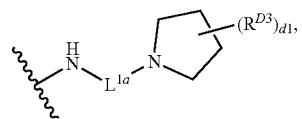
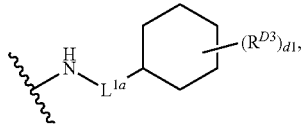
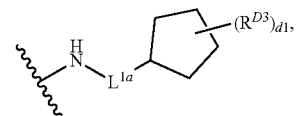
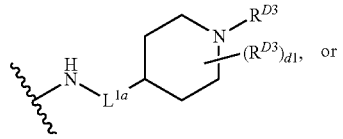
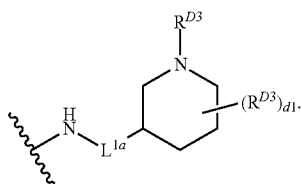
In certain embodiments, Y1 is of formula:
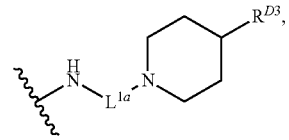
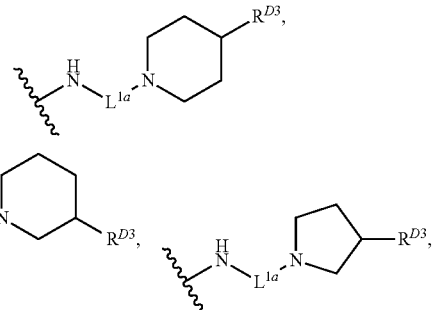
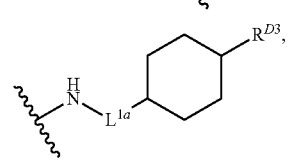
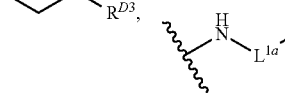
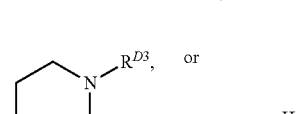
In certain embodiments, Y1 is of formula:
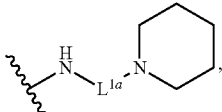 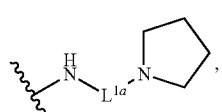
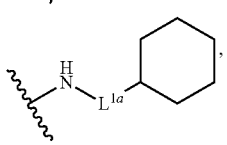 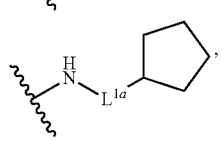
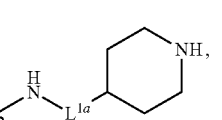 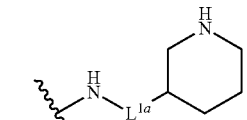
In certain embodiments, Ring D is of formula:
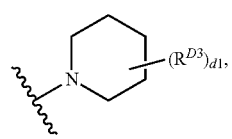 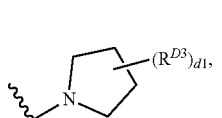

-continued

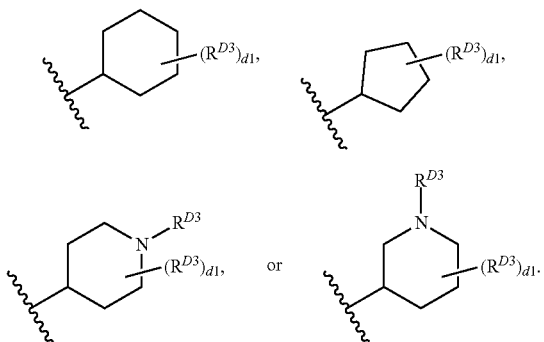

In certain embodiments, Ring D is of formula:

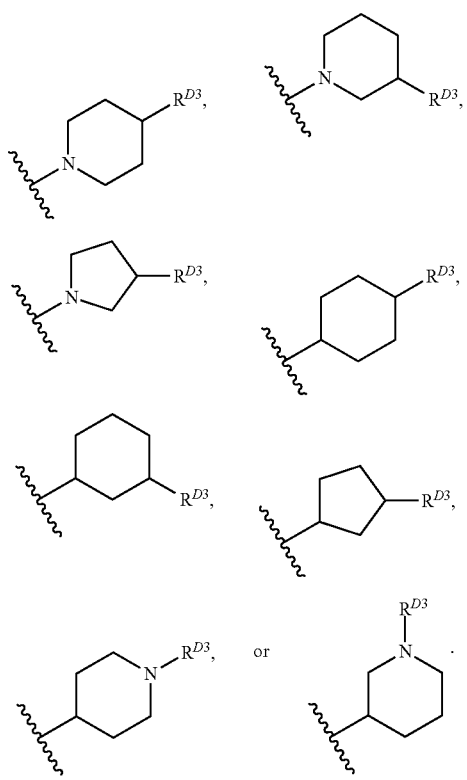

In certain embodiments, Ring D is of formula:

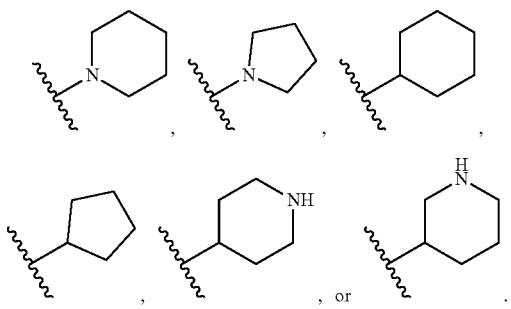

In certain embodiments, Y1 is of formula:

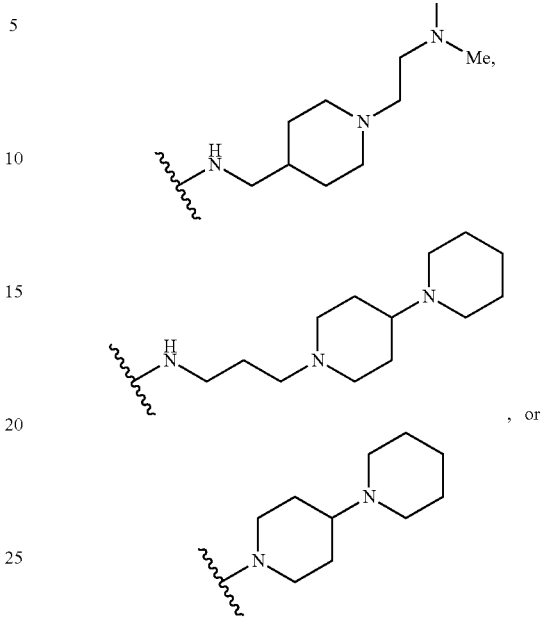

As generally defined herein, $L^{1a}$ is optionally substituted alkylene. In certain embodiments, $L^{1a}$ is optionally substituted $C_{1-12}$ alkylene. In some embodiments, $L^{1a}$ is optionally substituted $C_{1-8}$ alkylene. In some embodiments, $L^{1a}$ is optionally substituted $C_{1-6}$ alkylene. In some embodiments, $L^{1a}$ is optionally substituted $C_{1-6}$ alkylene. In some embodiments, $L^{1a}$ is optionally substituted $C_{2-6}$ alkylene. In some embodiments, $L^{1a}$ is optionally substituted $C_{3-6}$ alkylene. In certain embodiments, $L^{1a}$ is unsubstituted $C_{1-12}$ alkylene. In some embodiments, $L^{1a}$ is unsubstituted $C_{1-12}$ alkylene. In some embodiments, $L^{1a}$ is unsubstituted $C_{1-6}$ alkylene. In some embodiments, La is unsubstituted $C_{2-6}$ alkylene. In some embodiments, $L^{1a}$ is unsubstituted $C_{3-6}$ alkylene. In some embodiments, $L^{1a}$ is unsubstituted $C_{1-6}$ alkylene. In some embodiments, $L^{1a}$ is unsubstituted $C_{2-6}$ alkylene. In some embodiments, $L^{1a}$ is unsubstituted $C_{3-6}$ alkylene. In some embodiments, $L^{1a}$ is substituted alkylene, wherein the substituents are selected from the group consisting of alkyl, halogen, —OH, —OR$^f$, —NH$_2$, —NHR$^f$, and —N(R$^f$)$_2$. In certain embodiments, $L^{1a}$ is —(CH$_2$)$_{q1}$—, wherein q1 is 1, 2, 3, 4, 5, or 6.

As generally defined herein, Ring D is carbocyclic or a heterocyclic ring, wherein the heterocyclic ring contains one heteroatom, and the heteroatom is N. Ring D may be substituted with 0, 1, 2, 3, or 4 R$^D$. In some embodiments, two R$^D$ are attached geminally.

As generally defined herein, d1 is 0, 1, 2, 3, or 4. In certain embodiments, d1 is 0. In certain embodiments, d1 is 1. In certain embodiments, d1 is 2. In certain embodiments, d1 is 3. In certain embodiments, d1 is 4. In certain embodiments, d1 is 0, 1, 2, or 3. In certain embodiments, d1 is 0, 1, or 2. In certain embodiments, d1 is 0 or 1. In certain embodiments, d1 is 1, 2, 3, or 4. In certain embodiments, d1 is 2, 3, or 4. In certain embodiments, d1 is 3 or 4.

In certain embodiments, Ring D is carbocyclyl. e.g., optionally substituted $C_{3-6}$ carbocyclyl, optionally substituted $C_{3-4}$ carbocyclyl, optionally substituted $C_{4-5}$ carbocyclyl, or optionally substituted $C_{5-6}$ carbocyclyl. In certain embodiments, Ring D is unsubstituted carbocyclyl, e.g., unsubstituted $C_{3-6}$ carbocyclyl. In some embodiments, Ring D is cyclopropyl, cyclobutyl, cyclopentyl, or cyclohexyl.

In certain embodiments, Ring D is heterocyclyl with one heteroatom, and the heteroatom is nitrogen. Ring D is optionally substituted heterocyclyl, e.g., optionally substituted 3-6 membered heterocyclyl, optionally substituted 3-4 membered heterocyclyl, optionally substituted 4-5 membered heterocyclyl, or optionally substituted 5-6 membered heterocyclyl. In certain embodiments, Ring D is unsubstituted heterocyclyl, e.g., unsubstituted 3-6 membered heterocyclyl, unsubstituted 3-4 membered heterocyclyl, unsubstituted 4-5 membered heterocyclyl, or unsubstituted 5-6 membered heterocyclyl. In some embodiments, Ring D is piperidinyl, dihydropyridinyl, pyrrolidinyl, azetidinyl, azepanyl, azocanyl, or aziridinyl. In some embodiments, Ring D is piperidinyl or pyrrolidinyl.

In certain embodiments, Y1 is of formula:

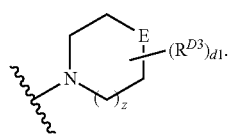

In certain embodiments, Y1 is of formula:

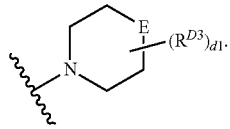

In certain embodiments, Y1 is of formula:

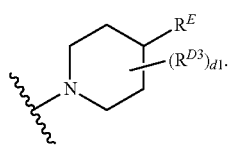

In certain embodiments, Y1 is of formula:

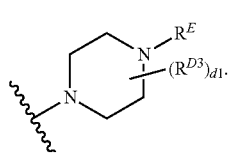

In certain embodiments, Y1 is of formula:

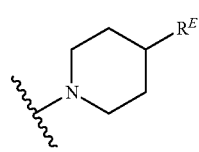

In certain embodiments, Y1 is of formula:

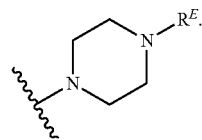

In certain embodiments, Y1 is of formula:

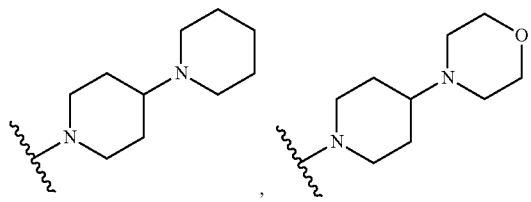

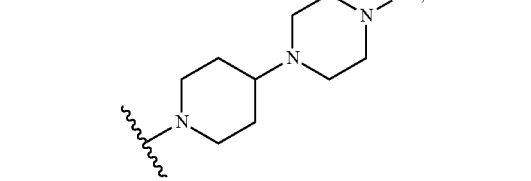

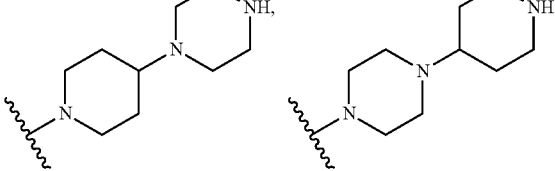

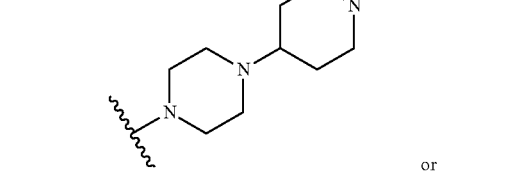

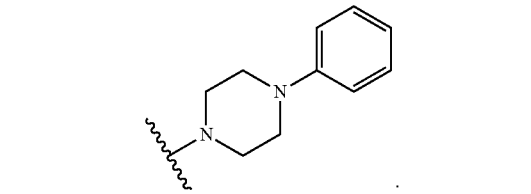

As generally defined herein, z is 0, 1, or 2. When z is 0, the ring comprising E is a 5-membered ring. When z is 1, the ring comprising E is a 6-membered ring. When z is 2, the ring comprising z is a 7-membered ring. The ring comprising E may be substituted with 0, 1, 2, 3, or 4 $R^D$. In some embodiments, two $R^D$ are attached geminally.

As generally defined herein, E is —O—, —S—, —N($R^E$)—, or —CH($R^E$)—. In certain embodiments, E is —N($R^E$)—, or —CH($R^E$)—. In some embodiments, E is —O—. In some embodiments, E is —S—. In some embodiments, E is —N($R^E$)—. In some embodiments, E is —CH($R^E$)—.

As generally defined herein, $R^E$ is optionally substituted carbocyclyl, optionally substituted heterocyclyl, optionally substituted aryl, or optionally substituted heteroaryl.-

In certain embodiments, $R^E$ is optionally substituted carbocyclyl, e.g., optionally substituted $C_{3-6}$ carbocyclyl, optionally substituted $C_{3-4}$ carbocyclyl, optionally substituted $C_{4-5}$ carbocyclyl, or optionally substituted $C_{5-6}$ carbocyclyl. In certain embodiments, $R^E$ is unsubstituted carbocyclyl, e.g., unsubstituted $C_{3-6}$ carbocyclyl. In some embodiments, $R^E$ is optionally substituted cyclopropyl, cyclobutyl, cyclopentyl, or cyclohexyl. In certain embodiments, $R^E$ is optionally substituted heterocyclyl, e.g., optionally substituted 3-6 membered heterocyclyl, optionally substituted 3-4 membered heterocyclyl, optionally substituted 4-5 membered heterocyclyl, or optionally substituted 5-6 membered heterocyclyl. In certain embodiments, $R^E$ is unsubstituted heterocyclyl, e.g., unsubstituted 3-6 membered heterocyclyl, unsubstituted 3-4 membered heterocyclyl, unsubstituted 4-5 membered heterocyclyl, or unsubstituted 5-6 membered heterocyclyl. In some embodiments, $R^E$ is optionally substituted piperidinyl, dihydropyridinyl, pyrrolidinyl, azetidinyl, azepanyl, azocanyl, or aziridinyl. In some embodiments, $R^E$ is optionally substituted piperidinyl, pyrrolidinyl, or morpholinyl.

In certain embodiments, $R^E$ is optionally substituted aryl, e.g., optionally substituted phenyl. In certain embodiments, $R^E$ is unsubstituted aryl, e.g., unsubstituted phenyl. In certain embodiments, $R^E$ is optionally substituted heteroaryl, e.g., optionally substituted 5-6 membered heteroaryl, or optionally substituted 9-10 membered bicyclic heteroaryl. In certain embodiments, $R^E$ is unsubstituted heteroaryl, e.g., unsubstituted 5-6 membered heteroaryl, or unsubstituted 9-10 membered bicyclic heteroaryl. In some embodiments, $R^E$ is imidazolyl, pyrazolyl, oxazolyl, isoxazolyl, thiazolyl, and isothiazolyl. In some embodiments, $R^E$ is triazolyl, oxadiazolyl, thiadiazolyl, or tetrazolyl. In certain embodiments, $R^E$ is 6-membered heteroaryl. In some embodiments, $R^E$ is pyridinyl. In some embodiments, $R^E$ is pyridazinyl, pyrimidinyl, and pyrazinyl.

In certain embodiments, Y1 is of formula:

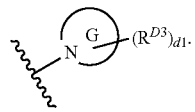

In certain embodiments, Y1 is of formula:

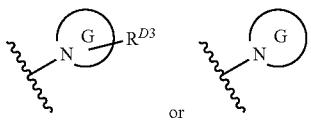

As generally defined Ring G is a bicyclic heterocyclic or bicyclic heteroaryl ring, wherein the rings share exactly two atoms. Ring G is a fused bicyclic (e.g., quinoline, decahydroquinoline) sharing two atoms, as opposed to a bridged bicyclic (e.g., 7-azabicyclo[2.2.1]heptane) sharing more than 2 atoms, or spiro bicyclic (e.g., 3-azaspiro[5.5]undecane) sharing one atom.

In certain embodiments, Ring G is a bicyclic heterocyclic ring, wherein the rings share exactly two atoms. In certain embodiments, Ring G is a bicyclic heteroaryl ring, wherein the rings share exactly two atoms. In some embodiments, Ring G is a 9-10 membered bicyclic heteroaryl. In some embodiments, Ring G comprises two fused 6-membered rings. In some embodiments, Ring G comprises two fused 5-membered rings. In some embodiments, Ring G comprises a 6-membered ring fused to a 5-membered ring. In some embodiments, Ring G is indolinyl, isoindolinyl, tetrahydroindolyl, tetrahydroquinolinyl, tetrahydroisoquinolinyl, decahydroquinolinyl, decahydroisoquinolinyl, decahydronaphthyridinyl, decahydro-1,8-naphthyridinyl, octahydropyrrolo[3,2-b]pyrrole, indolinyl, phthalimidyl, naphthalimidyl, 1H-benzo[e][1,4]diazepinyl, 1,4,5,7-tetrahydropyrano[3,4-b]pyrrolyl, 5,6-dihydro-4H-furo[3,2-b]pyrrolyl, 2,3-dihydro-1H-pyrrolo[2,3-b]pyridinyl, 2,3-dihydrofuro[2,3-b]pyridinyl, 4,5,6,7-tetrahydro-H-pyrrolo[2,3-b]pyridinyl, 4,5,6,7-tetrahydrofuro[3,2-c]pyridinyl, 4,5,6,7-tetrahydrothieno[3,2-b]pyridinyl, or 1,2,3,4-tetrahydro-1,6-naphthyridinyl.

In certain embodiments, Ring G comprises Ring $G^1$ and Ring $G^2$, and Y1 is of formula:

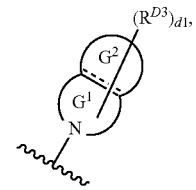

wherein Ring $G^1$ monocyclic heterocyclyl or heteroaryl, Ring $G^2$ is carbocyclyl, heterocyclyl, aryl, or heteroaryl; and === is a single or double bond. In some embodiments, === is a single bond. In some embodiments, === is a double bond. Ring $G^1$ and Ring $G^2$ may together be substituted with 0, 1, 2, 3, or 4 $R^{D3}$.

In certain embodiments, Ring $G^1$ is heterocyclyl, e.g., 3-6 membered heterocyclyl, 3-4 membered heterocyclyl, 4-5 membered heterocyclyl, or 5-6 membered heterocyclyl. In certain embodiments, Ring $G^1$ is unsubstituted heterocyclyl, e.g., unsubstituted 3-6 membered heterocyclyl, unsubstituted 3-4 membered heterocyclyl, unsubstituted 4-5 membered heterocyclyl, or unsubstituted 5-6 membered heterocyclyl. In some embodiments, Ring $G^1$ is piperidinyl, dihydropyridinyl, pyrrolidinyl, azetidinyl, azepanyl, azocanyl, or aziridinyl. In some embodiments, Ring $G^1$ is piperidinyl or pyrrolidinyl. In some embodiments, Ring $G^1$ is piperazinyl, or morpholinyl.

In certain embodiments, Ring $G^1$ is heteroaryl. In certain embodiments, Ring $G^1$ is monocyclic heteroaryl. In certain embodiments, Ring $G^1$ is 5-membered heteroaryl. In some embodiments, Ring $G^1$ is pyrrolyl, furanyl, or thiophenyl. In some embodiments, Ring $G^1$ is imidazolyl, pyrazolyl, oxazolyl, isoxazolyl, thiazolyl, and isothiazolyl. In some embodiments, Ring $G^1$ is triazolyl, oxadiazolyl, thiadiazolyl, or tetrazolyl. In certain embodiments, Ring $G^1$ is 6-membered heteroaryl. In some embodiments, Ring Gi is pyridinyl. In some embodiments, Ring $G^1$ is pyridazinyl, pyrimidinyl, and pyrazinyl.

In certain embodiments, Ring $G^2$ is carbocyclyl, e.g., $C_{3-6}$ carbocyclyl, $C_{3-4}$ carbocyclyl, $C_{4-5}$ carbocyclyl, or $C_{5-6}$ carbocyclyl. In certain embodiments, Ring $G^2$ is unsubstituted carbocyclyl, e.g., unsubstituted $C_{3-6}$ carbocyclyl. In some embodiments, Ring $G^2$ is cyclopropyl, cyclobutyl, cyclopentyl, or cyclohexyl. In certain embodiments, Ring $G^2$ is heterocyclyl, e.g., 3-6 membered heterocyclyl, 3-4 membered heterocyclyl, 4-5 membered heterocyclyl, or 5-6 membered heterocyclyl. In certain embodiments, Ring $G^2$ is unsubstituted heterocyclyl, e.g., unsubstituted 3-6 membered heterocyclyl, unsubstituted 3-4 membered heterocyclyl, unsubstituted 4-5 membered heterocyclyl, or unsubstituted 5-6 membered heterocyclyl.

In certain embodiments, Ring $G^2$ is aryl, e.g., phenyl. In certain embodiments, Ring $G^2$ is unsubstituted aryl, e.g., unsubstituted phenyl. In certain embodiments, Ring $G^2$ is heteroaryl, e.g., 5-6 membered heteroaryl. In certain embodiments, Ring $G^2$ is unsubstituted heteroaryl, e.g., unsubstituted 5-6 membered heteroaryl.

In certain embodiments Y1 is of formula:

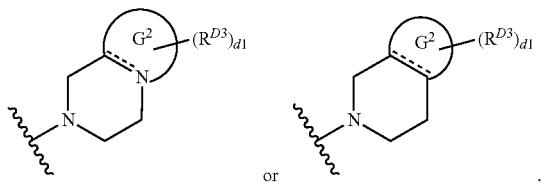

In certain embodiments Y1 is of formula:

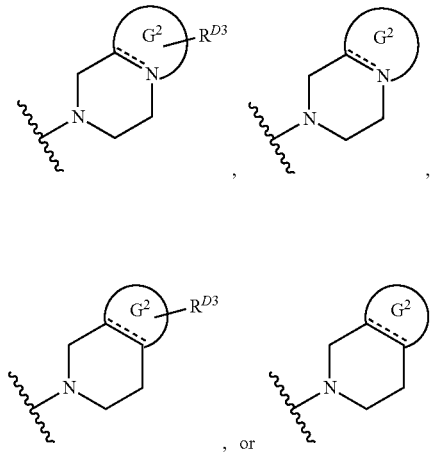

In certain embodiments Y1 is of formula:

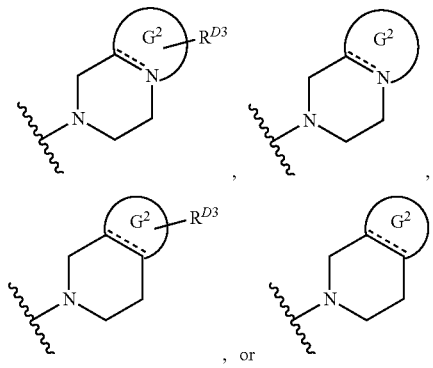

In certain embodiments Y1 is of formula:

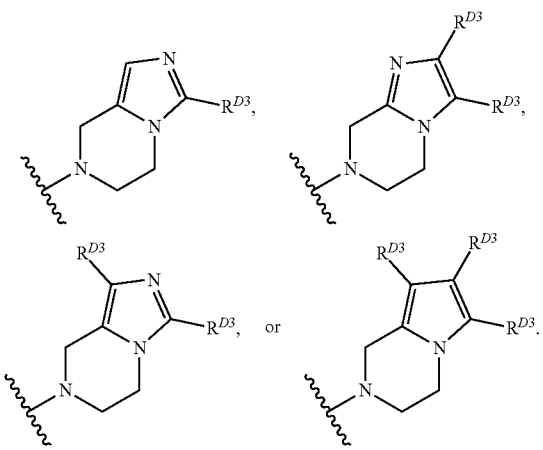

In certain embodiments Y1 is of formula:

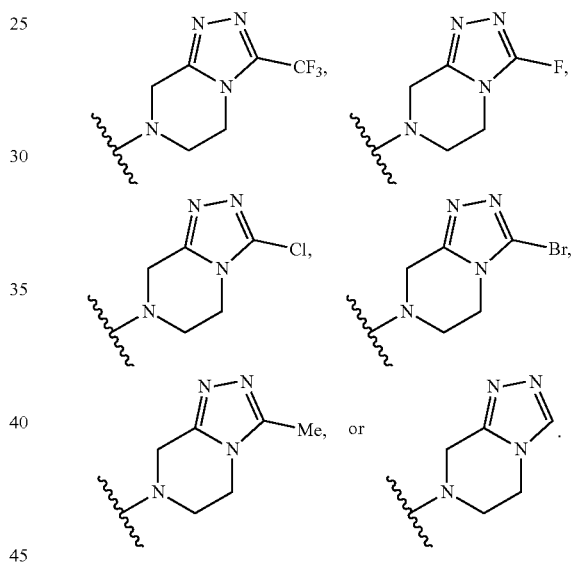

$R^2$

Formulae (II), (III), (IV), and (V) include substituent $R^2$. As generally defined herein, $R^2$ is hydrogen, halogen, or optionally substituted alkyl. In certain embodiments, the carbon to which $R^2$ is attached is in the (S)-configuration. In certain embodiments, the carbon to which $R^2$ is attached is in the (R)-configuration. In certain embodiments, $R^2$ is hydrogen, and the carbon to which $R^2$ is attached is in the (S)-configuration. In certain embodiments, $R^2$ is hydrogen, and the carbon to which $R^2$ is attached is in the (R)-configuration. In certain embodiments, $R^2$ is hydrogen. In certain embodiments, $R^2$ is a non-hydrogen group. In certain embodiments, $R^2$ is deuterium (D). In certain embodiments, $R^2$ is halogen. In certain embodiments, $R^2$ is —F. In certain embodiments, $R^2$ is —Cl, —Br, or —I.

In certain embodiments, $R^2$ is optionally substituted alkyl, e.g., optionally substituted $C_{1-6}$ alkyl, optionally substituted $C_{1-2}$ alkyl, optionally substituted $C_{2-3}$ alkyl, optionally substituted $C_{3-4}$ alkyl, optionally substituted $C_{4-5}$ alkyl, or optionally substituted $C_{5-6}$ alkyl. In certain embodiments, $R^2$ is unsubstituted alkyl, e.g., unsubstituted $C_{1-6}$ alkyl, unsubstituted $C_{1-2}$ alkyl, unsubstituted $C_{2-3}$ alkyl, unsubstituted $C_{3-4}$ alkyl, unsubstituted $C_{4-5}$ alkyl, or unsubstituted $C_{5-6}$ alkyl. In certain embodiments, $R^2$ is methyl. In certain embodiments, $R^2$ is ethyl, propyl, or butyl. In certain embodiments, $R^2$ is haloalkyl, e.g., —CHF$_2$, —CHCl$_2$, —CH$_2$CHF$_2$, —CH$_2$CHCl$_2$. In certain embodiments, $R^2$ is perhaloalkyl, e.g., —CF$_3$, —CF$_2$CF$_3$, —CCl$_3$. In certain embodiments, $R^2$ is hydroxyalkyl, e.g., —CH$_2$OH, —CH$_2$CH$_2$OH, —CH$_2$OR$^f$, —CH$_2$CH$_2$OR$^f$. In certain embodiments, $R^2$ is aminoalkyl, e.g., —CH$_2$NH$_2$, —CH$_2$CH$_2$NH$_2$, —CH$_2$NMe$_2$, —CH$_2$CH$_2$NMe$_2$, —CH$_2$N(R$^f$)$_2$, —CH$_2$CH$_2$N(R$^f$)$_2$.

$R^{A12}$ and $R^{A3}$

Formulas (II), (III), and (IV) include substituents $R^{A12}$ and $R^{A3}$

As generally defined herein, $R^{A12}$ is hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, —OR$^f$, —SR$^f$, —N(R$^f$)$_2$, —NO$_2$, or —CN. In certain embodiments, $R^{A12}$ is —CH$_2$R$^M$, wherein R$^M$ is —CN, —N(R$^f$)$_2$, or —CH$_2$N(R$^f$)$_2$. In certain embodiments, R$^M$ is —CN, —N(R$^f$)$_2$, or —CH$_2$N(R$^f$)$_2$.

In certain embodiments, $R^{A12}$ is hydrogen. In certain embodiments, $R^{A12}$ is a non-hydrogen group. In certain embodiments, $R^{A12}$ is halogen. In certain embodiments, $R^{A12}$ is —F. In certain embodiments, $R^{A12}$ is —Cl, —Br, or —I. In certain embodiments, $R^{A12}$ is —NO$_2$. In certain embodiments, $R^{A12}$ is —CN.

In certain embodiments, $R^{A12}$ is optionally substituted alkyl, e.g., optionally substituted $C_{1-6}$ alkyl, optionally substituted $C_{1-2}$ alkyl, optionally substituted $C_{2-3}$ alkyl, optionally substituted $C_{3-4}$ alkyl, optionally substituted $C_{4-5}$ alkyl, or optionally substituted $C_{5-6}$ alkyl. In certain embodiments, $R^{A12}$ is unsubstituted alkyl, e.g., unsubstituted $C_{1-6}$ alkyl, unsubstituted $C_{1-2}$ alkyl, unsubstituted $C_{2-3}$ alkyl, unsubstituted $C_{3-4}$ alkyl, unsubstituted $C_{4-5}$ alkyl, or unsubstituted $C_{5-6}$ alkyl. In certain embodiments, $R^{A12}$ is methyl. In certain embodiments, $R^{A12}$ is ethyl, propyl, or butyl. In certain embodiments, $R^{A12}$ is haloalkyl, e.g., —CHF$_2$, —CHCl$_2$, —CH$_2$CHF$_2$, —CH$_2$CHCl$_2$. In certain embodiments, $R^{A12}$ is perhaloalkyl, e.g., —CF$_3$, —CF$_2$CF$_3$, —CCl$_3$. In certain embodiments, $R^{A12}$ is hydroxyalkyl, e.g., —CH$_2$OH, —CH$_2$CH$_2$OH, —CH$_2$OR$^f$, —CH$_2$CH$_2$OR$^f$. In certain embodiments, $R^{A12}$ is aminoalkyl, e.g., —CH$_2$NH$_2$, —CH$_2$CH$_2$NH$_2$, —CH$_2$NMe$_2$, —CH$_2$CH$_2$NMe$_2$, —CH$_2$N(R$^f$)$_2$, —CH$_2$CH$_2$N(R$^f$)$_2$.

In certain embodiments, $R^{A12}$ is optionally substituted alkenyl, e.g., optionally substituted $C_{2-6}$ alkenyl. In certain embodiments, $R^{A12}$ is unsubstituted alkenyl, e.g., unsubstituted $C_{2-6}$ alkenyl. In certain embodiments, $R^{A12}$ is vinyl, allyl, or prenyl. In certain embodiments, $R^{A12}$ is optionally substituted alkynyl, e.g., optionally substituted $C_{2-6}$ alkynyl. In certain embodiments, $R^{A12}$ is unsubstituted alkynyl, e.g., unsubstituted $C_{2-6}$ alkynyl.

In certain embodiments, $R^{A12}$ is optionally substituted carbocyclyl, e.g., optionally substituted $C_{3-6}$ carbocyclyl, optionally substituted $C_{3-4}$ carbocyclyl, optionally substituted $C_{4-5}$ carbocyclyl, or optionally substituted $C_{5-6}$ carbocyclyl. In certain embodiments, $R^{A12}$ is unsubstituted carbocyclyl, e.g., unsubstituted $C_{3-6}$ carbocyclyl. In some embodiments, $R^{A12}$ is cyclopropyl, cyclobutyl, cyclopentyl, or cyclohexyl. In certain embodiments, $R^{A12}$ is optionally substituted heterocyclyl, e.g., optionally substituted 3-6 membered heterocyclyl, optionally substituted 3-4 membered heterocyclyl, optionally substituted 4-5 membered heterocyclyl, or optionally substituted 5-6 membered heterocyclyl. In certain embodiments, $R^{A12}$ is unsubstituted heterocyclyl, e.g., unsubstituted 3-6 membered heterocyclyl, unsubstituted 3-4 membered heterocyclyl, unsubstituted 4-5 membered heterocyclyl, or unsubstituted 5-6 membered heterocyclyl.

In certain embodiments, $R^{A12}$ is optionally substituted aryl, e.g., optionally substituted phenyl. In certain embodiments, $R^{A12}$ is unsubstituted aryl, e.g., unsubstituted phenyl. In certain embodiments, $R^{A12}$ is optionally substituted heteroaryl, e.g., optionally substituted 5-6 membered heteroaryl, or optionally substituted 9-10 membered bicyclic heteroaryl. In certain embodiments, $R^{A12}$ is unsubstituted heteroaryl, e.g., unsubstituted 5-6 membered heteroaryl, or unsubstituted 9-10 membered bicyclic heteroaryl. In certain embodiments, $R^{A12}$ is optionally substituted aralkyl, e.g., optionally substituted benzyl. In certain embodiments, $R^{A12}$ is optionally substituted heteroaralkyl, e.g., methyl substituted with an optionally substituted 5-6 membered heteroaryl ring. In certain embodiments, $R^{A12}$ is unsubstituted aralkyl, e.g., unsubstituted benzyl. In certain embodiments, $R^{A12}$ is unsubstituted heteroaralkyl, e.g., methyl substituted with an unsubstituted 5-6 membered heteroaryl ring.

In certain embodiments, $R^{A12}$ is optionally substituted acyl, e.g., —CHO, —CO$_2$H, or —C(=O)NH$_2$. In certain embodiments, $R^{A12}$ is —C(=O)R$^f$, —C(=O)OR$^f$, —C(=O)NH(R$^f$), or —C(=O)N(R$^f$)$_2$. In certain embodiments, $R^{A12}$ is —C(=O)R$^f$, and R$^f$ is optionally substituted alkyl, e.g., —C(=O)Me. In certain embodiments, $R^{A12}$ is —C(=O)R$^f$, and R$^f$ is optionally substituted alkenyl. In certain embodiments, $R^{A12}$ is —C(=O)R$^f$, and R$^f$ is optionally substituted carbocyclyl, heterocyclyl, aryl, or heteroaryl. In certain embodiments, $R^{A12}$ is —C(=O)OR$^f$, and R$^f$ is optionally substituted alkyl. In certain embodiments, $R^{A12}$ is —C(=O)OR$^f$, and R$^f$ is optionally substituted alkenyl. In certain embodiments, $R^{A12}$ is —C(=O)OR$^f$, and R$^f$ is optionally substituted carbocyclyl, heterocyclyl, aryl, or heteroaryl. In certain embodiments, $R^{A12}$ is —C(=O)N(R$^f$)$_2$, and at least one R$^f$ is optionally substituted alkyl. In certain embodiments, $R^{A12}$ is —C(=O)NHR$^f$, and R$^f$ is optionally substituted alkyl. In certain embodiments, $R^{A12}$ is —C(=O)NHR$^f$, and R$^f$ is optionally substituted alkenyl. In certain embodiments, $R^{A12}$ is —C(=O)NHR$^f$, and R$^f$ is optionally substituted carbocyclyl, heterocyclyl, aryl, or heteroaryl.

In certain embodiments, $R^{A12}$ is —OR$^f$, e.g., —OH. In certain embodiments, $R^{A12}$ is —OR$^f$, and R$^f$ is optionally substituted alkyl. In certain embodiments, $R^{A12}$ is —OR$^f$, and R$^f$ is unsubstituted $C_{1-6}$ alkyl. In certain embodiments, $R^{A12}$ is —OR$^f$, and R$^f$ is optionally substituted alkenyl. In certain embodiments, $R^{A12}$ is —OR$^f$, and R$^f$ is optionally substituted carbocyclyl, optionally substituted heterocyclyl, optionally substituted aryl optionally substituted heteroaryl. In certain embodiments, $R^{A12}$ is —OR$^f$, and R$^f$ is unsubstituted carbocyclyl, unsubstituted heterocyclyl, unsubstituted aryl unsubstituted heteroaryl. In certain embodiments, $R^{A12}$ is —OR$^f$, and R$^f$ is optionally substituted acyl, e.g., $R^{A12}$ is —OC(=O)R$^f$, —OC(=O)OR$^f$, or —OC(=O)N(R$^f$)$_2$. In certain embodiments, $R^{A12}$ is —OR$^f$, and R$^f$ is an oxygen protecting group.

In certain embodiments, $R^{A12}$ is —SR$^f$, e.g., —SH. In certain embodiments, $R^{A12}$ is —SR$^f$, and R$^f$ is optionally substituted alkyl. In certain embodiments, $R^{A12}$ is —SR$^f$, and R$^f$ is unsubstituted $C_{1-6}$ alkyl. In certain embodiments, $R^{A12}$ is —SR$^f$, and R$^f$ is optionally substituted carbocyclyl, optionally substituted heterocyclyl, optionally substituted aryl optionally substituted heteroaryl. In certain embodiments, $R^{A12}$ is —SR$^f$, and R$^f$ is unsubstituted carbocyclyl, unsubstituted heterocyclyl, unsubstituted aryl unsubstituted heteroaryl. In certain embodiments, $R^{412}$ is —$SR^f$, and $R^f$ is a sulfur protecting group.

In certain embodiments, $R^{412}$ is —$N(R^f)_2$, e.g., —$NH_2$, —$NHR^f$. In certain embodiments, $R^{412}$ is —$NH(R^f)$, and $R^f$ is optionally substituted alkyl. In certain embodiments, $R^{412}$ is —$N(R^f)_2$, and at least one $R^f$ is optionally substituted alkyl. In certain embodiments, $R^{412}$ is —$NH(R^f)$, and $R^f$ is unsubstituted alkyl. In certain embodiments, $R^{412}$ is —$N(R^f)_2$, and at least one $R^f$ is unsubstituted alkyl. In certain embodiments, $R^{412}$ is —$NHR^f$, and $R^f$ is optionally substituted carbocyclyl, optionally substituted heterocyclyl, optionally substituted aryl, or optionally substituted heteroaryl. In certain embodiments, $R^{412}$ is —$NHR^f$, and $R^f$ is unsubstituted carbocyclyl, unsubstituted heterocyclyl, unsubstituted aryl, or unsubstituted heteroaryl. In certain embodiments, $R^{412}$ is —$NHR^f$, and $R^f$ is optionally substituted acyl, e.g., $R^{412}$ is —$NHC(=O)R^f$, —$NHC(=O)OR^f$, or —$NHC(=O)NHR^f$. In certain embodiments, $R^{412}$ is —$N(R^f)_2$, and at least one $R^f$ is a nitrogen protecting group. In certain embodiments, $R^{412}$ is —$N(R^f)_2$, and both $R^f$ are joined to form an optionally substituted heterocyclic or optionally substituted heteroaryl ring. In certain embodiments, $R^{412}$ is —$N(R^f)_2$, and both $R^f$ are joined to form an unsubstituted heterocyclic or unsubstituted heteroaryl ring.

As generally defined herein, $R^{43}$ is hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, —$OR^f$, —$SR^f$, —$N(R^f)_2$, —$NO_2$, or —CN.

In certain embodiments, $R^{43}$ is hydrogen. In certain embodiments, $R^{43}$ is a non-hydrogen group. In certain embodiments, $R^{43}$ is halogen. In certain embodiments, $R^{43}$ is —F. In certain embodiments, $R^{43}$ is —Cl, —Br, or —I. In certain embodiments, $R^{43}$ is —$NO_2$. In certain embodiments, $R^{43}$ is —CN.

In certain embodiments, $R^{43}$ is optionally substituted alkyl, e.g., optionally substituted $C_{1-6}$ alkyl, optionally substituted $C_{1-2}$ alkyl, optionally substituted $C_{2-3}$ alkyl, optionally substituted $C_{3-4}$ alkyl, optionally substituted $C_{4-5}$ alkyl, or optionally substituted $C_{5-6}$ alkyl. In certain embodiments, $R^{43}$ is unsubstituted alkyl, e.g., unsubstituted $C_{1-6}$ alkyl, unsubstituted $C_{1-2}$ alkyl, unsubstituted $C_{2-3}$ alkyl, unsubstituted $C_{3-4}$ alkyl, unsubstituted $C_{4-5}$ alkyl, or unsubstituted $C_{5-6}$ alkyl. In certain embodiments, $R^{43}$ is methyl. In certain embodiments, $R^{43}$ is ethyl, propyl, or butyl. In certain embodiments, $R^{43}$ is haloalkyl, e.g., —$CHF_2$, —$CHCl_2$, —$CH_2CHF_2$, —$CH_2CHCl_2$. In certain embodiments, $R^{43}$ is perhaloalkyl, e.g., —$CF_3$, —$CF_2CF_3$, —$CCl_3$. In certain embodiments, $R^{43}$ is hydroxyalkyl, e.g., —$CH_2OH$, —$CH_2CH_2OH$, —$CH_2OR^f$, —$CH_2CH_2OR^f$. In certain embodiments, $R^{43}$ is aminoalkyl, e.g., —$CH_2NH_2$, —$CH_2CH_2NH_2$, —$CH_2NMe_2$, —$CH_2CH_2NMe_2$, —$CH_2N(R^f)_2$, —$CH_2CH_2N(R^f)_2$.

In certain embodiments, $R^{43}$ is optionally substituted alkenyl, e.g., optionally substituted $C_{2-6}$ alkenyl. In certain embodiments, $R^{43}$ is unsubstituted alkenyl, e.g., unsubstituted $C_{2-6}$ alkenyl. In certain embodiments, $R^{43}$ is vinyl, allyl, or prenyl. In certain embodiments, $R^{43}$ is optionally substituted alkynyl, e.g., optionally substituted $C_{2-6}$ alkynyl. In certain embodiments, $R^{43}$ is unsubstituted alkynyl, e.g., unsubstituted $C_{2-6}$ alkynyl.

In certain embodiments, $R^{43}$ is optionally substituted carbocyclyl, e.g., optionally substituted $C_{3-6}$ carbocyclyl, optionally substituted $C_{3-4}$ carbocyclyl, optionally substituted $C_{4-5}$ carbocyclyl, or optionally substituted $C_{5-6}$ carbocyclyl. In certain embodiments, $R^{43}$ is unsubstituted carbocyclyl, e.g., unsubstituted $C_{3-6}$ carbocyclyl. In some embodiments, $R^{43}$ is cyclopropyl, cyclobutyl, cyclopentyl, or cyclohexyl. In certain embodiments, $R^{43}$ is optionally substituted heterocyclyl, e.g., optionally substituted 3-6 membered heterocyclyl, optionally substituted 3-4 membered heterocyclyl, optionally substituted 4-5 membered heterocyclyl, or optionally substituted 5-6 membered heterocyclyl. In certain embodiments, $R^{43}$ is unsubstituted heterocyclyl, e.g., unsubstituted 3-6 membered heterocyclyl, unsubstituted 3-4 membered heterocyclyl, unsubstituted 4-5 membered heterocyclyl, or unsubstituted 5-6 membered heterocyclyl.

In certain embodiments, $R^{43}$ is optionally substituted aryl, e.g., optionally substituted phenyl. In certain embodiments, $R^{43}$ is unsubstituted aryl, e.g., unsubstituted phenyl. In certain embodiments, $R^{43}$ is optionally substituted heteroaryl, e.g., optionally substituted 5-6 membered heteroaryl, or optionally substituted 9-10 membered bicyclic heteroaryl. In certain embodiments, $R^{43}$ is unsubstituted heteroaryl, e.g., unsubstituted 5-6 membered heteroaryl, or unsubstituted 9-10 membered bicyclic heteroaryl. In certain embodiments, $R^{43}$ is optionally substituted aralkyl, e.g., optionally substituted benzyl. In certain embodiments, $R^{43}$ is optionally substituted heteroaralkyl, e.g., methyl substituted with an optionally substituted 5-6 membered heteroaryl ring. In certain embodiments, $R^{43}$ is unsubstituted aralkyl, e.g., unsubstituted benzyl. In certain embodiments, $R^{43}$ is unsubstituted heteroaralkyl, e.g., methyl substituted with an unsubstituted 5-6 membered heteroaryl ring.

In certain embodiments, $R^{43}$ is optionally substituted acyl, e.g., —CHO, —$CO_2H$, or —$C(=O)NH_2$. In certain embodiments, $R^{43}$ is —$C(=O)R^f$, —$C(=O)OR^f$, —$C(=O)NH(R^f)$, or —$C(=O)N(R^f)_2$. In certain embodiments, $R^{43}$ is —$C(=O)R^f$, and $R^f$ is optionally substituted alkyl, e.g., —$C(=O)Me$. In certain embodiments, $R^{43}$ is —$C(=O)R^f$, and $R^f$ is optionally substituted alkenyl. In certain embodiments, $R^{43}$ is —$C(=O)R^f$, and $R^f$ is optionally substituted carbocyclyl, heterocyclyl, aryl, or heteroaryl. In certain embodiments, $R^{43}$ is —$C(=O)OR^f$, and $R^f$ is optionally substituted alkyl. In certain embodiments, $R^{43}$ is —$C(=O)OR^f$, and $R^f$ is optionally substituted alkenyl. In certain embodiments, $R^{43}$ is —$C(=O)OR^f$, and $R^f$ is optionally substituted carbocyclyl, heterocyclyl, aryl, or heteroaryl. In certain embodiments, $R^{43}$ is —$C(=O)N(R^f)_2$, and at least one $R^f$ is optionally substituted alkyl. In certain embodiments, $R^{43}$ is —$C(=O)NHR^f$, and $R^f$ is optionally substituted alkyl. In certain embodiments, $R^{43}$ is —$C(=O)NHR^f$, and $R^f$ is optionally substituted alkenyl. In certain embodiments, $R^{43}$ is —$C(=O)NHR^f$, and $R^f$ is optionally substituted carbocyclyl, heterocyclyl, aryl, or heteroaryl.

In certain embodiments, $R^{43}$ is —$OR^f$, e.g., —OH. In certain embodiments, $R^{43}$ is —$OR^f$, and $R^f$ is optionally substituted alkyl. In certain embodiments, $R^{43}$ is —$OR^f$, and $R^f$ is unsubstituted $C_{1-6}$ alkyl. In certain embodiments, $R^{43}$ is —$OR^f$, and $R^f$ is optionally substituted alkenyl. In certain embodiments, $R^{43}$ is —$OR^f$, and $R^f$ is optionally substituted carbocyclyl, optionally substituted heterocyclyl, optionally substituted aryl optionally substituted heteroaryl. In certain embodiments, $R^{43}$ is —$OR^f$, and $R^f$ is unsubstituted carbocyclyl, unsubstituted heterocyclyl, unsubstituted aryl unsubstituted heteroaryl. In certain embodiments, $R^{43}$ is —$OR^f$, and $R^f$ is optionally substituted acyl, e.g., $R^{43}$ is —$OC(=O)R^f$, —$OC(=O)OR^f$, or —$OC(=O)N(R^f)_2$. In certain embodiments, $R^{43}$ is —$OR^f$, and $R^f$ is a sulfur protecting group.

In certain embodiments, $R^{A3}$ is —$SR^f$, e.g., —SH. In certain embodiments, $R^{A3}$ is —$SR^f$, and $R^f$ is optionally substituted alkyl. In certain embodiments, $R^{A3}$ is —$SR^f$, and $R^f$ is unsubstituted $C_{1-6}$ alkyl. In certain embodiments, $R^{A3}$ is —$SR^f$, and $R^f$ is optionally substituted carbocyclyl, optionally substituted heterocyclyl, optionally substituted aryl optionally substituted heteroaryl. In certain embodiments, $R^{A3}$ is —$SR^f$, and $R^f$ is unsubstituted carbocyclyl, unsubstituted heterocyclyl, unsubstituted aryl unsubstituted heteroaryl. In certain embodiments, $R^{A3}$ is —$SR^f$, and $R^f$ is an oxygen protecting group.

In certain embodiments, $R^{A3}$ is —$N(R^f)_2$, e.g., —$NH_2$, —$NHR^f$. In certain embodiments, $R^{A3}$ is —$NH(R^f)$, and $R^f$ is optionally substituted alkyl. In certain embodiments, $R^{A3}$ is —$N(R^f)_2$, and at least one $R^f$ is optionally substituted alkyl. In certain embodiments, $R^{A3}$ is —$NH(R^f)$, and $R^f$ is unsubstituted alkyl. In certain embodiments, $R^{A3}$ is —$N(R^f)_2$, and at least one $R^f$ is unsubstituted alkyl. In certain embodiments, $R^{A3}$ is —$NHR^f$, and $R^f$ is optionally substituted carbocyclyl, optionally substituted heterocyclyl, optionally substituted aryl, or optionally substituted heteroaryl. In certain embodiments, $R^{A3}$ is —$NHR^f$, and $R^f$ is unsubstituted carbocyclyl, unsubstituted heterocyclyl, unsubstituted aryl, or unsubstituted heteroaryl. In certain embodiments, $R^{A3}$ is —$NHR^f$, and $R^f$ is optionally substituted acyl, e.g., $R^{A3}$ is —$NHC(=O)R^f$, —$NHC(=O)OR^f$, or —$NHC(=O)NHR^f$. In certain embodiments, $R^{A3}$ is —$N(R^f)_2$, and at least one $R^f$ is a nitrogen protecting group. In certain embodiments, $R^{A3}$ is —$N(R^f)_2$, and both $R^f$ are joined to form an optionally substituted heterocyclic or optionally substituted heteroaryl ring. In certain embodiments, $R^{A3}$ is —$N(R^f)_2$, and both $R^f$ are joined to form an unsubstituted heterocyclic or unsubstituted heteroaryl ring.

In some embodiments, $R^{A12}$ and $R^{A3}$ are the same. In some embodiments, $R^{A1}$ and $R^{A2}$ are different. In certain embodiments, both $R^{A12}$ and $R^{A3}$ are hydrogen. In certain embodiments, both $R^{A12}$ and $R^{A3}$ are optionally substituted halogen. In certain embodiments, both $R^{A12}$ and $R^{A3}$ are optionally substituted alkyl. In certain embodiments, both $R^{A12}$ and $R^{A3}$ are optionally substituted $C_{1-6}$ alkyl. In certain embodiments, both $R^{A12}$ and $R^{A3}$ are unsubstituted $C_{1-6}$ alkyl. In certain embodiments, both $R^{A12}$ and $R^{A3}$ are methyl.

$R^{B41}$ and $X^1$

Formulas (II), (III), (IV), and (V) include substituents $R^{B41}$ and $X^1$. Formula (V) includes substituent $X^1$. As generally defined herein, $R^{B41}$ is hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, —$OR^f$, —$SR^f$, —$N(R^f)_2$, —$NO_2$, or —CN. In certain embodiments, $R^{B41}$ is —$CH_2R^M$, wherein $R^M$ is —CN, —$N(R^f)_2$, or —$CH_2N(R^f)_2$.

In certain embodiments, $R^{B41}$ is hydrogen. In certain embodiments, $R^{B41}$ is a non-hydrogen group. In certain embodiments, $R^{B41}$ is halogen. In certain embodiments, RB is —F. In certain embodiments, $R^{B41}$ is —Cl, —Br, or —I. In certain embodiments, $R^{B41}$ is —$NO_2$. In certain embodiments, $R^{B41}$ is —CN.

In certain embodiments, $R^{B41}$ is optionally substituted alkyl, e.g., optionally substituted $C_{1-6}$ alkyl, optionally substituted $C_{1-2}$ alkyl, optionally substituted $C_{2-3}$ alkyl, optionally substituted $C_{3-4}$ alkyl, optionally substituted $C_{4-5}$ alkyl, or optionally substituted $C_{5-6}$ alkyl. In certain embodiments, $R^{B41}$ is unsubstituted alkyl, e.g., unsubstituted $C_{1-6}$ alkyl, unsubstituted $C_{1-2}$ alkyl, unsubstituted $C_{2-3}$ alkyl, unsubstituted $C_{3-4}$ alkyl, unsubstituted $C_{4-5}$ alkyl, or unsubstituted $C_{5-6}$ alkyl. In certain embodiments, $R^{B41}$ is methyl. In certain embodiments, $R^{B41}$ is ethyl, propyl, or butyl. In certain embodiments, $R^{B41}$ is haloalkyl, e.g., —$CHF_2$, —$CHCl_2$, —$CH_2CHF_2$, —$CH_2CHCl_2$. In certain embodiments, $R^{B41}$ is perhaloalkyl, e.g., —$CF_3$, —$CF_2CF_3$, —$CCl_3$. In certain embodiments, $R^{B41}$ is hydroxyalkyl, e.g., —$CH_2OH$, —$CH_2CH_2OH$, —$CH_2OR^f$, —$CH_2CH_2OR^f$. In certain embodiments, $R^{B41}$ is aminoalkyl, e.g., —$CH_2NH_2$, —$CH_2CH_2NH_2$, —$CH_2NMe_2$, —$CH_2CH_2NMe_2$, —$CH_2N(R^f)_2$, —$CH_2CH_2N(R^f)_2$.

In certain embodiments, $R^{B41}$ is optionally substituted alkenyl, e.g., optionally substituted $C_{2-6}$ alkenyl. In certain embodiments, $R^{B41}$ is unsubstituted alkenyl, e.g., unsubstituted $C_{2-6}$ alkenyl. In certain embodiments, $R^{B41}$ is vinyl, allyl, or prenyl. In certain embodiments, $R^{B41}$ is optionally substituted alkynyl, e.g., optionally substituted $C_{2-6}$ alkynyl. In certain embodiments, $R^{B41}$ is unsubstituted alkynyl, e.g., unsubstituted $C_{2-6}$ alkynyl.

In certain embodiments, $R^{B41}$ is optionally substituted carbocyclyl, e.g., optionally substituted $C_{3-6}$ carbocyclyl, optionally substituted $C_{3-4}$ carbocyclyl, optionally substituted $C_{4-5}$ carbocyclyl, or optionally substituted $C_{5-6}$ carbocyclyl. In certain embodiments, $R^{B41}$ is unsubstituted carbocyclyl, e.g., unsubstituted $C_{3-6}$ carbocyclyl. In some embodiments, $R^{B41}$ is cyclopropyl, cyclobutyl, cyclopentyl, or cyclohexyl. In certain embodiments, $R^{B41}$ is optionally substituted heterocyclyl, e.g., optionally substituted 3-6 membered heterocyclyl, optionally substituted 3-4 membered heterocyclyl, optionally substituted 4-5 membered heterocyclyl, or optionally substituted 5-6 membered heterocyclyl. In certain embodiments, $R^{B41}$ is unsubstituted heterocyclyl, e.g., unsubstituted 3-6 membered heterocyclyl, unsubstituted 3-4 membered heterocyclyl, unsubstituted 4-5 membered heterocyclyl, or unsubstituted 5-6 membered heterocyclyl.

In certain embodiments, $R^{B41}$ is optionally substituted aryl, e.g., optionally substituted phenyl. In certain embodiments, $R^{B41}$ is unsubstituted aryl, e.g., unsubstituted phenyl. In certain embodiments, $R^{B41}$ is optionally substituted heteroaryl, e.g., optionally substituted 5-6 membered heteroaryl, or optionally substituted 9-10 membered bicyclic heteroaryl. In certain embodiments, $R^{B41}$ is unsubstituted heteroaryl, e.g., unsubstituted 5-6 membered heteroaryl, or unsubstituted 9-10 membered bicyclic heteroaryl. In certain embodiments, $R^{B41}$ is optionally substituted aralkyl, e.g., optionally substituted benzyl. In certain embodiments, $R^{B41}$ is optionally substituted heteroaralkyl, e.g., methyl substituted with an optionally substituted 5-6 membered heteroaryl ring. In certain embodiments, $R^{B41}$ is unsubstituted aralkyl, e.g., unsubstituted benzyl. In certain embodiments, $R^{B41}$ is unsubstituted heteroaralkyl, e.g., methyl substituted with an unsubstituted 5-6 membered heteroaryl ring.

In certain embodiments, $R^{B41}$ is optionally substituted acyl, e.g., —CHO, —$CO_2H$, or —$C(=O)NH_2$. In certain embodiments, $R^{B41}$ is —$C(=O)R^f$, —$C(=O)OR^f$, —$C(=O)NH(R^f)$, or —$C(=O)N(R^f)_2$. In certain embodiments, $R^{B41}$ is —$C(=O)R^f$, and $R^f$ is optionally substituted alkyl, e.g., —$C(=O)Me$. In certain embodiments, $R^{B41}$ is —$C(=O)R^f$, and $R^f$ is optionally substituted alkenyl. In certain embodiments, $R^{B41}$ is —$C(=O)R^f$, and $R^f$ is optionally substituted carbocyclyl, heterocyclyl, aryl, or heteroaryl. In certain embodiments, $R^{B41}$ is —$C(=O)OR^f$, and $R^f$ is optionally substituted alkyl. In certain embodiments, $R^{B41}$ is —$C(=O)OR^f$, and $R^f$ is optionally substituted alkenyl. In certain embodiments, $R^{B41}$ is —$C(=O)OR^f$, and $R^f$ is optionally substituted carbocyclyl, heterocyclyl, aryl, or heteroaryl. In certain embodiments, $R^{B41}$ is —C(=O)N($R^f$)$_2$, and at least one $R^f$ is optionally substituted alkyl. In certain embodiments, $R^{B41}$ is —C(=O)NH$R^f$, and $R^f$ is optionally substituted alkyl. In certain embodiments, $R^{B41}$ is —C(=O)NH$R^f$, and $R^f$ is optionally substituted alkenyl. In certain embodiments, $R^{B41}$ is —C(=O)NH$R^f$, and $R^f$ is optionally substituted carbocyclyl, heterocyclyl, aryl, or heteroaryl.

In certain embodiments, $R^{B41}$ is —O$R^f$, e.g., —OH. In certain embodiments, $R^{B41}$ is —O$R^f$, and $R^f$ is optionally substituted alkyl. In certain embodiments, $R^{B41}$ is —O$R^f$, and $R^f$ is unsubstituted $C_{1-6}$ alkyl. In certain embodiments, $R^{B41}$ is —O$R^f$, and $R^f$ is optionally substituted alkenyl. In certain embodiments, $R^{B41}$ is —O$R^f$, and $R^f$ is optionally substituted carbocyclyl, optionally substituted heterocyclyl, optionally substituted aryl optionally substituted heteroaryl. In certain embodiments, $R^{B41}$ is —O$R^f$, and $R^f$ is unsubstituted carbocyclyl, unsubstituted heterocyclyl, unsubstituted aryl unsubstituted heteroaryl. In certain embodiments, $R^{B41}$ is —O$R^f$, and $R^f$ is optionally substituted acyl, e.g., $R^{B41}$ is —OC(=O)$R^f$, —OC(=O)O$R^f$, or —OC(=O)N($R^f$)$_2$. In certain embodiments, $R^{B41}$ is —O$R^f$, and $R^f$ is an oxygen protecting group.

In certain embodiments, $R^{B41}$ is —S$R^f$, e.g., —SH. In certain embodiments, $R^{B41}$ is —S$R^f$, and $R^f$ is optionally substituted alkyl. In certain embodiments, $R^{B41}$ is —S$R^f$, and $R^f$ is unsubstituted $C_{1-6}$ alkyl. In certain embodiments, $R^{B41}$ is —S$R^f$, and $R^f$ is optionally substituted carbocyclyl, optionally substituted heterocyclyl, optionally substituted aryl optionally substituted heteroaryl. In certain embodiments, $R^{B41}$ is —S$R^f$, and $R^f$ is unsubstituted carbocyclyl, unsubstituted heterocyclyl, unsubstituted aryl unsubstituted heteroaryl. In certain embodiments, R $R^{B41^B}$ is —S$R^f$, and $R^f$ is a sulfur protecting group.

In certain embodiments, $R^{B41}$ is —N($R^f$)$_2$, e.g., —NH$_2$, —NH$R^f$. In certain embodiments, $R^{B41}$ is —NH(R), and $R^f$ is optionally substituted alkyl. In certain embodiments, $R^{B41}$ is —N(R)$_2$, and at least one $R^f$ is optionally substituted alkyl. In certain embodiments, $R^{B41}$ is —NH($R^f$), and $R^f$ is unsubstituted alkyl. In certain embodiments, $R^{B41}$ is —N($R^f$)$_2$, and at least one $R^f$ is unsubstituted alkyl. In certain embodiments, $R^{B41}$ is —NH$R^f$, and $R^f$ is optionally substituted carbocyclyl, optionally substituted heterocyclyl, optionally substituted aryl, or optionally substituted heteroaryl. In certain embodiments, $R^{B41}$ is —NH$R^f$, and $R^f$ is unsubstituted carbocyclyl, unsubstituted heterocyclyl, unsubstituted aryl, or unsubstituted heteroaryl. In certain embodiments, $R^{B41}$ is —NH$R^f$, and $R^f$ is optionally substituted acyl, e.g., $R^{B41}$ is —NHC(=O)$R^f$, —NHC(=O)O$R^f$, or —NHC(=O)NH$R^f$. In certain embodiments, $R^{B41}$ is —N($R^f$)$_2$, and at least one $R^f$ is a nitrogen protecting group. In certain embodiments, $R^{B41}$ is —N($R^f$)$_2$, and both $R^f$ are joined to form an optionally substituted heterocyclic or optionally substituted heteroaryl ring. In certain embodiments, $R^{B41}$ is —N($R^f$)$_2$, and both $R^f$ are joined to form an unsubstituted heterocyclic or unsubstituted heteroaryl ring.

As generally defined herein, $X^1$ is N or $CR^5$, wherein $R^5$ is hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, —O$R^f$, —S$R^f$, —N($R^f$)$_2$, —NO$_2$, or —CN.

In certain embodiments, $X^1$ is N. In certain embodiments, $X^1$ is $CR^5$. In some embodiments, $X^1$ is CMe. In certain embodiments, $X^1$ is CH.

As generally defined herein, $R^5$ is hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, —O$R^f$, —S$R^f$, —N($R^f$)$_2$, —NO$_2$, or —CN. In certain embodiments, $R^5$ is —CH$_2R^M$, wherein $R^M$ is —CN, —N($R^f$)$_2$, or —CH$_2$N($R^f$)$_2$.

In certain embodiments, $R^5$ is hydrogen. In certain embodiments, $R^5$ is a non-hydrogen group. In certain embodiments, $R^5$ is halogen. In certain embodiments, $R^5$ is —F. In certain embodiments, $R^5$ is —Cl, —Br, or —I. In certain embodiments, $R^5$ is —NO$_2$. In certain embodiments, $R^5$ is —CN.

In certain embodiments, $R^5$ is optionally substituted alkyl, e.g., optionally substituted $C_{1-6}$ alkyl, optionally substituted $C_{1-2}$ alkyl, optionally substituted $C_{2-3}$ alkyl, optionally substituted $C_{3-4}$ alkyl, optionally substituted $C_{4-5}$ alkyl, or optionally substituted $C_{5-6}$ alkyl. In certain embodiments, $R^5$ is unsubstituted alkyl, e.g., unsubstituted $C_{1-6}$ alkyl, unsubstituted $C_{1-2}$ alkyl, unsubstituted $C_{2-3}$ alkyl, unsubstituted $C_{3-4}$ alkyl, unsubstituted $C_{4-5}$ alkyl, or unsubstituted $C_{5-6}$ alkyl. In certain embodiments, $R^5$ is methyl. In certain embodiments, $R^5$ is ethyl, propyl, or butyl. In certain embodiments, $R^5$ is haloalkyl, e.g., —CHF$_2$, —CHCl$_2$, —CH$_2$CHF$_2$, —CH$_2$CHCl$_2$. In certain embodiments, $R^5$ is perhaloalkyl, e.g., —CF$_3$, —CF$_2$CF$_3$, —CCl$_3$. In certain embodiments, $R^5$ is hydroxyalkyl, e.g., —CH$_2$OH, —CH$_2$CH$_2$OH, —CH$_2$O$R^f$, —CH$_2$CH$_2$O$R^f$. In certain embodiments, $R^5$ is aminoalkyl, e.g., —CH$_2$NH$_2$, —CH$_2$CH$_2$NH$_2$, —CH$_2$NMe$_2$, —CH$_2$CH$_2$NMe$_2$, —CH$_2$N($R^f$)$_2$, —CH$_2$CH$_2$N($R^f$)$_2$.

In certain embodiments, $R^5$ is optionally substituted alkenyl, e.g., optionally substituted $C_{2-6}$ alkenyl. In certain embodiments, $R^5$ is unsubstituted alkenyl, e.g., unsubstituted $C_{2-6}$ alkenyl. In certain embodiments, $R^5$ is vinyl, allyl, or prenyl. In certain embodiments, $R^5$ is optionally substituted alkynyl, e.g., optionally substituted $C_{2-6}$ alkynyl. In certain embodiments, $R^5$ is unsubstituted alkynyl, e.g., unsubstituted $C_{2-6}$ alkynyl.

In certain embodiments, $R^5$ is optionally substituted carbocyclyl, e.g., optionally substituted $C_{3-6}$ carbocyclyl, optionally substituted $C_{3-4}$ carbocyclyl, optionally substituted $C_{4-5}$ carbocyclyl, or optionally substituted $C_{5-6}$ carbocyclyl. In certain embodiments, $R^5$ is unsubstituted carbocyclyl, e.g., unsubstituted $C_{3-6}$ carbocyclyl. In some embodiments, $R^5$ is cyclopropyl, cyclobutyl, cyclopentyl, or cyclohexyl. In certain embodiments, $R^5$ is optionally substituted heterocyclyl, e.g., optionally substituted 3-6 membered heterocyclyl, optionally substituted 3-4 membered heterocyclyl, optionally substituted 4-5 membered heterocyclyl, or optionally substituted 5-6 membered heterocyclyl. In certain embodiments, $R^5$ is unsubstituted heterocyclyl, e.g., unsubstituted 3-6 membered heterocyclyl, unsubstituted 3-4 membered heterocyclyl, unsubstituted 4-5 membered heterocyclyl, or unsubstituted 5-6 membered heterocyclyl.

In certain embodiments, $R^5$ is optionally substituted aryl, e.g., optionally substituted phenyl. In certain embodiments, $R^5$ is unsubstituted aryl, e.g., unsubstituted phenyl. In certain embodiments, $R^5$ is optionally substituted heteroaryl, e.g., optionally substituted 5-6 membered heteroaryl, or optionally substituted 9-10 membered bicyclic heteroaryl. In certain embodiments, $R^5$ is unsubstituted heteroaryl, e.g., unsubstituted 5-6 membered heteroaryl, or unsubstituted 9-10 membered bicyclic heteroaryl. In certain embodiments, $R^5$ is optionally substituted aralkyl, e.g., optionally substituted benzyl. In certain embodiments, $R^5$ is optionally substituted heteroaralkyl, e.g., methyl substituted with an optionally substituted 5-6 membered heteroaryl ring. In certain embodiments, $R^5$ is unsubstituted aralkyl, e.g., unsubstituted benzyl. In certain embodiments, $R^5$ is unsubstituted heteroaralkyl, e.g., methyl substituted with an unsubstituted 5-6 membered heteroaryl ring.

In certain embodiments, $R^5$ is optionally substituted acyl, e.g., —CHO, —CO$_2$H, or —C(=O)NH$_2$. In certain embodiments, $R^5$ is —C(=O)R$^f$, —C(=O)OR$^f$, —C(=O)NH(R$^f$), or —C(=O)N(R$^f$)$_2$. In certain embodiments, $R^5$ is —C(=O)R$^f$, and R$^f$ is optionally substituted alkyl, e.g., —C(=O)Me. In certain embodiments, $R^5$ is —C(=O)R$^f$, and R$^f$ is optionally substituted alkenyl. In certain embodiments, $R^5$ is —C(=O)R$^f$, and R$^f$ is optionally substituted carbocyclyl, heterocyclyl, aryl, or heteroaryl. In certain embodiments, $R^5$ is —C(=O)OR$^f$, and R$^f$ is optionally substituted alkyl. In certain embodiments, $R^5$ is —C(=O)OR$^f$, and R$^f$ is optionally substituted alkenyl. In certain embodiments, $R^5$ is —C(=O)OR$^f$, and R$^f$ is optionally substituted carbocyclyl, heterocyclyl, aryl, or heteroaryl. In certain embodiments, $R^5$ is —C(=O)N(R$^f$)$_2$, and at least one R$^f$ is optionally substituted alkyl. In certain embodiments, $R^5$ is —C(=O)NHR$^f$, and R$^f$ is optionally substituted alkyl. In certain embodiments, $R^5$ is —C(=O)NHR$^f$, and R$^f$ is optionally substituted alkenyl. In certain embodiments, $R^5$ is —C(=O)NHR$^f$, and R$^f$ is optionally substituted carbocyclyl, heterocyclyl, aryl, or heteroaryl.

In certain embodiments, $R^5$ is —OR$^f$, e.g., —OH. In certain embodiments, $R^5$ is —OR$^f$, and R$^f$ is optionally substituted alkyl. In certain embodiments, $R^5$ is —OR$^f$, and R$^f$ is unsubstituted C$_{1-6}$ alkyl. In certain embodiments, $R^5$ is —OR$^f$, and R$^f$ is optionally substituted alkenyl. In certain embodiments, $R^5$ is —OR$^f$, and R$^f$ is optionally substituted carbocyclyl, optionally substituted heterocyclyl, optionally substituted aryl optionally substituted heteroaryl. In certain embodiments, $R^5$ is —OR$^f$, and R$^f$ is unsubstituted carbocyclyl, unsubstituted heterocyclyl, unsubstituted aryl unsubstituted heteroaryl. In certain embodiments, $R^5$ is —OR$^f$, and R$^f$ is optionally substituted acyl, e.g., $R^5$ is —OC(=O)R$^f$, —OC(=O)OR$^f$, or —OC(=O)N(R$^f$)$_2$. In certain embodiments, $R^5$ is —OR$^f$, and R$^f$ is an oxygen protecting group.

In certain embodiments, $R^5$ is —SR$^f$, e.g., —SH. In certain embodiments, $R^5$ is —SR$^f$, and R$^f$ is optionally substituted alkyl. In certain embodiments, $R^5$ is —SR$^f$, and R$^f$ is unsubstituted C$_{1-6}$ alkyl. In certain embodiments, $R^5$ is —SR$^f$, and R$^f$ is optionally substituted carbocyclyl, optionally substituted heterocyclyl, optionally substituted aryl optionally substituted heteroaryl. In certain embodiments, $R^5$ is —SR$^f$, and R$^f$ is unsubstituted carbocyclyl, unsubstituted heterocyclyl, unsubstituted aryl unsubstituted heteroaryl. In certain embodiments, $R^5$ is —SR$^f$, and R$^f$ is a sulfur protecting group.

In certain embodiments, $R^5$ is —N(R$^f$)$_2$, e.g., —NH$_2$, —NHR$^f$. In certain embodiments, $R^5$ is —NH(R$^f$), and R$^f$ is optionally substituted alkyl. In certain embodiments, $R^5$ is —N(R$^f$)$_2$, and at least one R$^f$ is optionally substituted alkyl. In certain embodiments, $R^5$ is —NH(R$^f$), and R$^f$ is unsubstituted alkyl. In certain embodiments, $R^5$ is —N(R$^f$)$_2$, and at least one R$^f$ is unsubstituted alkyl. In certain embodiments, $R^5$ is —NHR$^f$, and R$^f$ is optionally substituted carbocyclyl, optionally substituted heterocyclyl, optionally substituted aryl, or optionally substituted heteroaryl. In certain embodiments, $R^5$ is —NHR$^f$, and R$^f$ is unsubstituted carbocyclyl, unsubstituted heterocyclyl, unsubstituted aryl, or unsubstituted heteroaryl. In certain embodiments, $R^5$ is —NHR$^f$, and R$^f$ is optionally substituted acyl, e.g., $R^5$ is —NHC(=O)R$^f$, —NHC(=O)OR$^f$, or —NHC(=O)NHR$^f$.

In certain embodiments, $R^5$ is —N(R$^f$)$_2$, and at least one R$^f$ is a nitrogen protecting group. In certain embodiments, $R^5$ is —N(R$^f$)$_2$, and both R$^f$ are joined to form an optionally substituted heterocyclic or optionally substituted heteroaryl ring. In certain embodiments, $R^5$ is —N(R$^f$)$_2$, and both R$^f$ are joined to form an unsubstituted heterocyclic or unsubstituted heteroaryl ring.

In some embodiments, $X^1$ is CR$^5$, and R$^{B41}$ and $R^5$ are the same. In some embodiments, $X^1$ is CR$^5$, and R$^{B41}$ and $R^5$ are different. In certain embodiments, $X^1$ is CR$^5$, and both R$^{B41}$ and $R^5$ are hydrogen. In certain embodiments, $X^1$ is CR$^5$, and both R$^{B41}$ and $R^5$ are optionally substituted halogen. In certain embodiments, $X^1$ is CR$^5$, and both R$^{B41}$ and $R^5$ are optionally substituted alkyl. In certain embodiments, $X^1$ is CR$^5$, and both R$^{B41}$ and $R^5$ are optionally substituted C$_{1-6}$ alkyl. In certain embodiments, $X^1$ is CR$^5$, and both R$^{B41}$ and $R^5$ are unsubstituted C$_{1-6}$ alkyl. In certain embodiments, $X^1$ is CR$^5$, and both R$^{B41}$ and $R^5$ are methyl.

Ring C and $R^{C3}$

Formulas (II), (III), and (IV) include substituents Ring C and $R^{C3}$. As generally defined herein, Ring C is aryl or heteroaryl. Ring C may be substituted by 1, 2, 3, or 4 $R^{C3}$ As generally defined herein, c is 0, 1, 2, 3, or 4. In certain embodiments, c is 0. In certain embodiments, c is 1. In certain embodiments, c is 2. In certain embodiments, c is 3. In certain embodiments, c is 4. In certain embodiments, c is 0, 1, 2, or 3. In certain embodiments, c is 0, 1, or 2. In certain embodiments, c is 0 or 1. In certain embodiments, c is 1, 2, 3, or 4. In certain embodiments, c is 2, 3, or 4. In certain embodiments, c is 3 or 4.

In certain embodiments, Ring C is aryl. In certain embodiments, Ring C is monocyclic aryl. In certain embodiments, Ring C is phenyl. In certain embodiments, Ring C is bicyclic aryl. In certain embodiments, Ring C is naphthyl.

In certain embodiments, Ring C is heteroaryl. In certain embodiments, Ring C is monocyclic heteroaryl. In certain embodiments, Ring C is 5-membered heteroaryl. In some embodiments, Ring C is pyrrolyl, furanyl, or thiophenyl. In some embodiments, Ring C is imidazolyl, pyrazolyl, oxazolyl, isoxazolyl, thiazolyl, and isothiazolyl. In some embodiments, Ring C is triazolyl, oxadiazolyl, thiadiazolyl, or tetrazolyl. In certain embodiments, Ring C is 6-membered heteroaryl. In some embodiments, Ring C is pyridinyl. In some embodiments, Ring C is pyridazinyl, pyrimidinyl, and pyrazinyl. In certain embodiments, Ring C is bicyclic heteroaryl. In certain embodiments, Ring C is 9- to 10-membered bicyclic heteroaryl. In some embodiments, Ring C is indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, or purinyl. In some embodiments, Ring C is naphthyridinyl, pteridinyl, quinolinyl, isoquinolinyl, cinnolinyl, quinoxalinyl, phthalazinyl, or quinazolinyl.

In certain embodiments, Ring C is of formula:

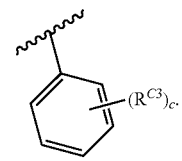

In certain embodiments, Ring C is of formula:
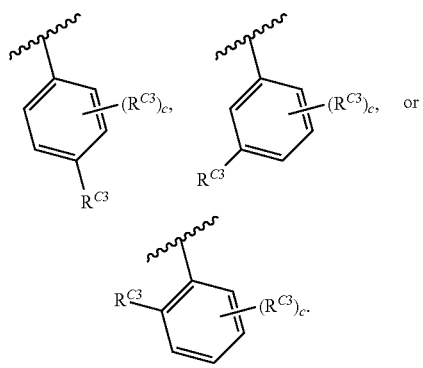
In certain embodiments, Ring C is of formula:
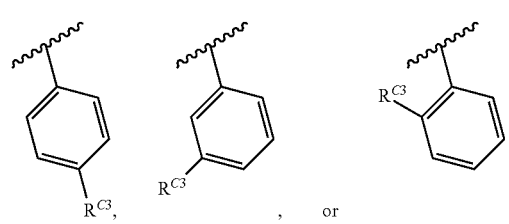
In certain embodiments, Ring C is of formula:
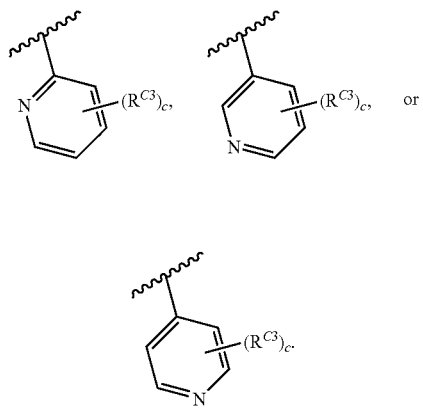
In certain embodiments, Ring C is of formula:
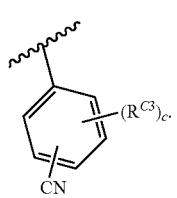
In certain embodiments, Ring C is of formula:
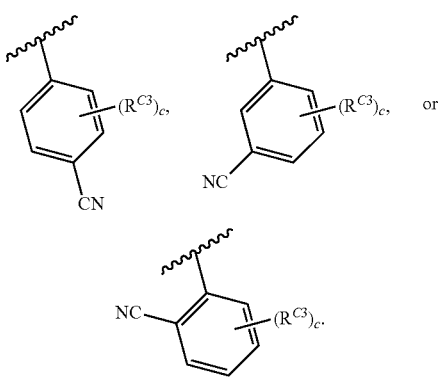
In certain embodiments, Ring C is of formula:
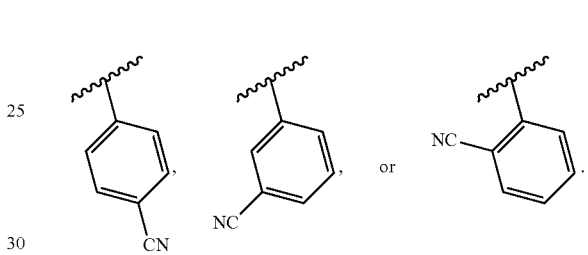
In certain embodiments, Ring C is of formula:
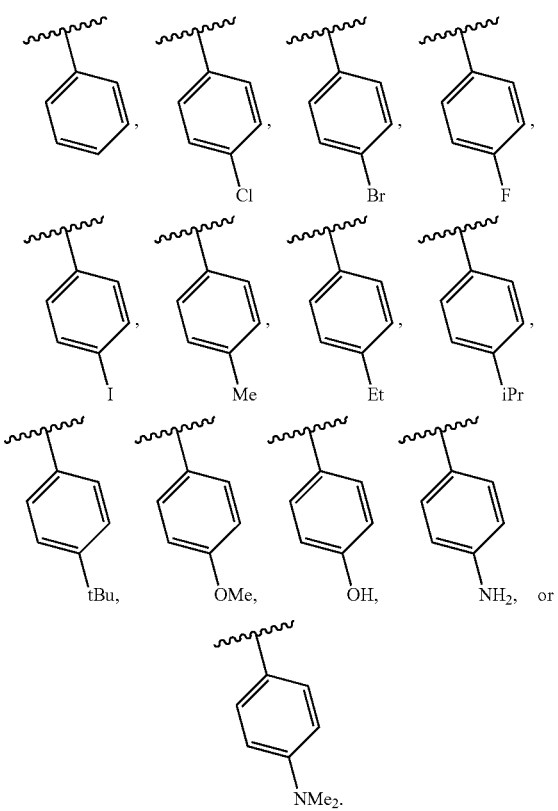

In certain embodiments, Ring C is of formula:

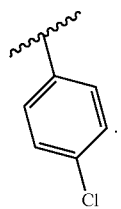

In certain embodiments, Ring C is of formula:

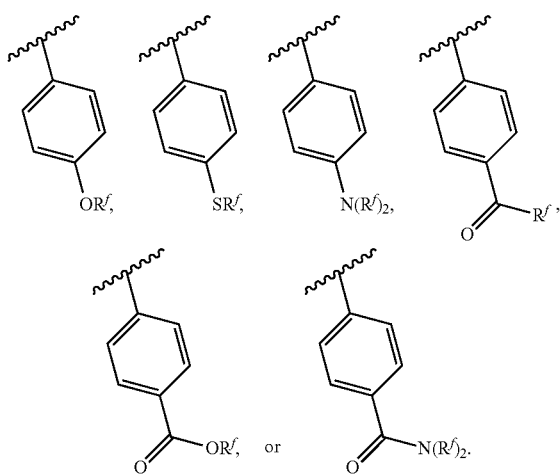

As generally defined herein, $R^{C3}$ is halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, optionally substituted sulfonyl, —$OR^f$, —$SR^f$, —$N(R^f)_2$, —$NO_2$, or —CN.

In certain embodiments, $R^{C3}$ is halogen. In certain embodiments, $R^{C3}$ is —F. In certain embodiments, $R^{C3}$ is —Cl, —Br, or —I. In certain embodiments, $R^{C3}$ is —$NO_2$. In certain embodiments, $R^{C3}$ is —CN.

In certain embodiments, $R^{C3}$ is optionally substituted alkyl, e.g., optionally substituted $C_{1-6}$ alkyl, optionally substituted $C_{1-2}$ alkyl, optionally substituted $C_{2-3}$ alkyl, optionally substituted $C_{3-4}$ alkyl, optionally substituted $C_{4-5}$ alkyl, or optionally substituted $C_{5-6}$ alkyl. In certain embodiments, $R^{C3}$ is unsubstituted alkyl, e.g., unsubstituted $C_{1-6}$ alkyl, unsubstituted $C_{1-2}$ alkyl, unsubstituted $C_{2-3}$ alkyl, unsubstituted $C_{3-4}$ alkyl, unsubstituted $C_{4-5}$ alkyl, or unsubstituted $C_{5-6}$ alkyl. In certain embodiments, $R^{C3}$ is methyl. In certain embodiments, $R^{C3}$ is ethyl, propyl, or butyl. In certain embodiments, $R^{C3}$ is haloalkyl, e.g., —$CHF_2$, —$CHCl_2$, —$CH_2CHF_2$, —$CH_2CHCl_2$. In certain embodiments, $R^{C3}$ is perhaloalkyl, e.g., —$CF_3$, —$CF_2CF_3$, —$CCl_3$. In certain embodiments, $R^{C3}$ is hydroxyalkyl, e.g., —$CH_2OH$, —$CH_2CH_2OH$, —$CH_2OR^f$, —$CH_2CH_2OR^f$. In certain embodiments, $R^{C3}$ is aminoalkyl, e.g., —$CH_2NH_2$, —$CH_2CH_2NH_2$, —$CH_2NMe_2$, —$CH_2CH_2NMe_2$, —$CH_2N(R^f)_2$, —$CH_2CH_2N(R^f)_2$.

In certain embodiments, $R^{C3}$ is optionally substituted alkenyl, e.g., optionally substituted $C_{2-6}$ alkenyl. In certain embodiments, $R^{C3}$ is unsubstituted alkenyl, e.g., unsubstituted $C_{2-6}$ alkenyl. In certain embodiments, $R^{C3}$ is vinyl, allyl, or prenyl. In certain embodiments, $R^{C3}$ is optionally substituted alkynyl, e.g., optionally substituted $C_{2-6}$ alkynyl. In certain embodiments, $R^{C3}$ is unsubstituted alkynyl, e.g., unsubstituted $C_{2-6}$ alkynyl.

In certain embodiments, $R^{C3}$ is optionally substituted carbocyclyl, e.g., optionally substituted $C_{3-6}$ carbocyclyl, optionally substituted $C_{3-4}$ carbocyclyl, optionally substituted $C_{4-5}$ carbocyclyl, or optionally substituted $C_{5-6}$ carbocyclyl. In certain embodiments, $R^{C3}$ is unsubstituted carbocyclyl, e.g., unsubstituted $C_{3-6}$ carbocyclyl. In some embodiments, $R^{C3}$ is cyclopropyl, cyclobutyl, cyclopentyl, or cyclohexyl. In certain embodiments, $R^{C3}$ is optionally substituted heterocyclyl, e.g., optionally substituted 3-6 membered heterocyclyl, optionally substituted 3-4 membered heterocyclyl, optionally substituted 4-5 membered heterocyclyl, or optionally substituted 5-6 membered heterocyclyl. In certain embodiments, $R^{C3}$ is unsubstituted heterocyclyl, e.g., unsubstituted 3-6 membered heterocyclyl, unsubstituted 3-4 membered heterocyclyl, unsubstituted 4-5 membered heterocyclyl, or unsubstituted 5-6 membered heterocyclyl.

In certain embodiments, $R^{C3}$ is optionally substituted aryl, e.g., optionally substituted phenyl. In certain embodiments, $R^{C3}$ is unsubstituted aryl, e.g., unsubstituted phenyl. In certain embodiments, $R^{C3}$ is optionally substituted heteroaryl, e.g., optionally substituted 5-6 membered heteroaryl, or optionally substituted 9-10 membered bicyclic heteroaryl. In certain embodiments, $R^{C3}$ is unsubstituted heteroaryl, e.g., unsubstituted 5-6 membered heteroaryl, or unsubstituted 9-10 membered bicyclic heteroaryl. In certain embodiments, $R^{C3}$ is optionally substituted aralkyl, e.g., optionally substituted benzyl. In certain embodiments, $R^{C3}$ is optionally substituted heteroaralkyl, e.g., methyl substituted with an optionally substituted 5-6 membered heteroaryl ring. In certain embodiments, $R^{C3}$ is unsubstituted aralkyl, e.g., unsubstituted benzyl. In certain embodiments, $R^{C3}$ is unsubstituted heteroaralkyl, e.g., methyl substituted with an unsubstituted 5-6 membered heteroaryl ring.

In certain embodiments, $R^{C3}$ is optionally substituted acyl, e.g., —CHO, —$CO_2H$, or —$C(=O)NH_2$. In certain embodiments, $R^{C3}$ is —$C(=O)R^f$, —$C(=O)OR^f$, —$C(=O)NH(R^f)$, or —$C(=O)N(R^f)_2$. In certain embodiments, $R^{C3}$ is —$C(=O)R^f$, and $R^f$ is optionally substituted alkyl, e.g., —$C(=O)Me$. In certain embodiments, $R^{C3}$ is —$C(=O)R^f$, and $R^f$ is optionally substituted alkenyl. In certain embodiments, $R^{C3}$ is —$C(=O)R^f$, and $R^f$ is optionally substituted carbocyclyl, heterocyclyl, aryl, or heteroaryl. In certain embodiments, $R^{C3}$ is —$C(=O)OR^f$, and $R^f$ is optionally substituted alkyl. In certain embodiments, $R^{C3}$ is —$C(=O)OR^f$, and $R^f$ is optionally substituted alkenyl. In certain embodiments, $R^{C3}$ is —$C(=O)OR^f$, and $R^f$ is optionally substituted carbocyclyl, heterocyclyl, aryl, or heteroaryl. In certain embodiments, $R^{C3}$ is —$C(=O)N(R^f)_2$, and at least one $R^f$ is optionally substituted alkyl. In certain embodiments, $R^3$ is —$C(=O)NHR^f$, and $R^f$ is optionally substituted alkyl. In certain embodiments, $R^{C3}$ is —$C(=O)NHR^f$, and $R^f$ is optionally substituted alkenyl. In certain embodiments, $R^{C3}$ is —$C(=O)NHR^f$, and $R^f$ is optionally substituted carbocyclyl, heterocyclyl, aryl, or heteroaryl.

In certain embodiments, $R^{C3}$ is optionally substituted sulfonyl, e.g., —$S(=O)_2OH$. In certain embodiments, $R^{C3}$ is —$S(=O)_2R^f$, —$S(=O)_2OR^f$, —$S(=O)_2NH(R^f)$, or —$S(=O)_2N(R^f)_2$. In certain embodiments, $R^{C3}$ is —$S(=O)_2R^f$, and $R^f$ is optionally substituted alkyl, e.g., —$S(=O)_2Me$. In certain embodiments, $R^{C3}$ is —$S(=O)_2R^f$, and $R^f$ is optionally substituted carbocyclyl, heterocyclyl, aryl, or heteroaryl. In certain embodiments, $R^3$ is —S(=O)$_2$OR$^f$, and R$^f$ is optionally substituted alkyl. In certain embodiments, $R^{C3}$ is —S(=O)$_2$OR$^f$, and R$^f$ is optionally substituted aryl. In certain embodiments, $R^{C3}$ is —S(=O)$_2$N(R$^f$)$_2$, and at least one R$^f$ is optionally substituted alkyl. In certain embodiments, $R^{C3}$ is —S(=O)$_2$NHR$^f$, and R$^f$ is optionally substituted carbocyclyl, heterocyclyl, aryl, or heteroaryl.

In certain embodiments, $R^{C3}$ is —OR$^f$, e.g., —OH. In certain embodiments, $R^{C3}$ is —OR$^f$, and R$^f$ is optionally substituted alkyl. In certain embodiments, $R^{C3}$ is —OR$^f$, and R$^f$ is unsubstituted C$_{1-6}$ alkyl. In certain embodiments, $R^{C3}$ is —OR$^f$, and R$^f$ is optionally substituted alkenyl. In certain embodiments, $R^{C3}$ is —OR$^f$, and R$^f$ is optionally substituted carbocyclyl, optionally substituted heterocyclyl, optionally substituted aryl optionally substituted heteroaryl. In certain embodiments, $R^{C3}$ is —OR$^f$, and R$^f$ is unsubstituted carbocyclyl, unsubstituted heterocyclyl, unsubstituted aryl unsubstituted heteroaryl. In certain embodiments, $R^{C3}$ is —OR$^f$, and R$^f$ is optionally substituted acyl, e.g., $R^{C3}$ is —OC(=O)R$^f$, —OC(=O)OR$^f$, or —OC(=O)N(R$^f$)$_2$. In certain embodiments, $R^{C3}$ is —OR$^f$, and R$^f$ is an oxygen protecting group.

In certain embodiments, $R^{C3}$ is —SR$^f$, e.g., —SH. In certain embodiments, $R^{C3}$ is —SR$^f$, and R$^f$ is optionally substituted alkyl. In certain embodiments, $R^{C3}$ is —SR$^f$, and R$^f$ is unsubstituted C$_{1-6}$ alkyl. In certain embodiments, $R^{C3}$ is —SR$^f$, and R$^f$ is optionally substituted carbocyclyl, optionally substituted heterocyclyl, optionally substituted aryl, or optionally substituted heteroaryl. In certain embodiments, $R^{C3}$ is —SR$^f$, and R$^f$ is unsubstituted carbocyclyl, unsubstituted heterocyclyl, unsubstituted aryl, or unsubstituted heteroaryl. In certain embodiments, $R^{C3}$ is —SR$^f$, and R$^f$ is a sulfur protecting group.

In certain embodiments, $R^{C3}$ is —N(R$^f$)$_2$, e.g., —NH$_2$, —NHR$^f$. In certain embodiments, $R^{C3}$ is —NH(R$^f$), and R$^f$ is optionally substituted alkyl. In certain embodiments, $R^{C3}$ is —N(R$^f$)$_2$, and at least one R$^f$ is optionally substituted alkyl. In certain embodiments, $R^{C3}$ is —NH(R$^f$), and R$^f$ is unsubstituted alkyl. In certain embodiments, $R^{C3}$ is —N(R$^f$)$_2$, and at least one R$^f$ is unsubstituted alkyl. In certain embodiments, $R^{C3}$ is —NHR$^f$, and R$^f$ is optionally substituted carbocyclyl, optionally substituted heterocyclyl, optionally substituted aryl, or optionally substituted heteroaryl. In certain embodiments, $R^{C3}$ is —NHR$^f$, and R$^f$ is unsubstituted carbocyclyl, unsubstituted heterocyclyl, unsubstituted aryl, or unsubstituted heteroaryl. In certain embodiments, $R^{C3}$ is —NHR$^f$, and R$^f$ is optionally substituted acyl, e.g., $R^{C3}$ is —NHC(=O)R$^f$, —NHC(=O)OR$^f$, or —NHC(=O)NHR$^f$. In certain embodiments, $R^{C3}$ is —N(R$^f$)$_2$, and at least one R$^f$ is a nitrogen protecting group. In certain embodiments, $R^{C3}$ is —N(R$^f$)$_2$, and both R$^f$ are joined to form an optionally substituted heterocyclic or optionally substituted heteroaryl ring. In certain embodiments, $R^{C3}$ is —N(R$^f$)$_2$, and both R$^f$ are joined to form an unsubstituted heterocyclic or unsubstituted heteroaryl ring.

In certain embodiments, an $R^{C3}$ attached para to the diazepine is halogen. In certain embodiments, an $R^{C3}$ attached para to the diazepine is —F. In certain embodiments, an $R^{C3}$ attached para to the diazepine is —Cl, —Br, or —I. In certain embodiments, an $R^{C3}$ attached para to the diazepine is —NO$_2$. In certain embodiments, an $R^{C3}$ attached para to the diazepine is —CN.

In certain embodiments, an $R^{C3}$ attached para to the diazepine is optionally substituted alkyl, e.g., optionally substituted C$_{1-6}$ alkyl, optionally substituted C$_{1-2}$ alkyl, optionally substituted C$_{2-3}$ alkyl, optionally substituted C$_{3-4}$ alkyl, optionally substituted C$_{4-5}$ alkyl, or optionally substituted C$_{5-6}$ alkyl. In certain embodiments, an $R^{C3}$ attached para to the diazepine is unsubstituted alkyl, e.g., unsubstituted C$_{1-6}$ alkyl, unsubstituted C$_{1-2}$ alkyl, unsubstituted C$_{2-3}$ alkyl, unsubstituted C$_{3-4}$ alkyl, unsubstituted C$_{4-5}$ alkyl, or unsubstituted C$_{5-6}$ alkyl. In certain embodiments, an $R^{C3}$ attached para to the diazepine is methyl. In certain embodiments, an $R^{C3}$ attached para to the diazepine is ethyl, propyl, or butyl. In certain embodiments, an $R^{C3}$ attached para to the diazepine is haloalkyl, e.g., —CHF$_2$, —CHCl$_2$, —CH$_2$CHF$_2$, —CH$_2$CHCl$_2$. In certain embodiments, an $R^{C3}$ attached para to the diazepine is perhaloalkyl, e.g., —CF$_3$, —CF$_2$CF$_3$, —CCl$_3$. In certain embodiments, an $R^{C3}$ attached para to the diazepine is hydroxyalkyl, e.g., —CH$_2$H, —CH$_2$CH$_2$OH, —CH$_2$OR$^f$, —CH$_2$CH$_2$OR$^f$. In certain embodiments, an $R^{C3}$ attached para to the diazepine is aminoalkyl, e.g., —CH$_2$NH$_2$, —CH$_2$CH$_2$NH$_2$, —CH$_2$NMe$_2$, —CH$_2$CH$_2$NMe$_2$, —CH$_2$N(R$^f$)$_2$, —CH$_2$CH$_2$N(R$^f$)$_2$.

In certain embodiments, an $R^{C3}$ attached para to the diazepine is optionally substituted alkenyl, e.g., optionally substituted C$_{2-6}$ alkenyl. In certain embodiments, an $R^{C3}$ attached para to the diazepine is unsubstituted alkenyl, e.g., unsubstituted C$_{2-6}$ alkenyl. In certain embodiments, an $R^C$ attached para to the diazepine is vinyl, allyl, or prenyl. In certain embodiments, an $R^{C3}$ attached para to the diazepine is optionally substituted alkynyl, e.g., optionally substituted C$_{2-6}$ alkynyl. In certain embodiments, an $R^{C3}$ attached para to the diazepine is unsubstituted alkynyl, e.g., unsubstituted C$_{2-6}$ alkynyl.

In certain embodiments, an $R^{C3}$ attached para to the diazepine is optionally substituted carbocyclyl, e.g., optionally substituted C$_{3-6}$ carbocyclyl, optionally substituted C$_{3-4}$ carbocyclyl, optionally substituted C$_{4-5}$ carbocyclyl, or optionally substituted C$_{5-6}$ carbocyclyl. In certain embodiments, an $R^{C3}$ attached para to the diazepine is unsubstituted carbocyclyl, e.g., unsubstituted C$_{3-6}$ carbocyclyl. In some embodiments, an $R^{C3}$ attached para to the diazepine is cyclopropyl, cyclobutyl, cyclopentyl, or cyclohexyl. In certain embodiments, an $R^{C3}$ attached para to the diazepine is optionally substituted heterocyclyl, e.g., optionally substituted 3-6 membered heterocyclyl, optionally substituted 3-4 membered heterocyclyl, optionally substituted 4-5 membered heterocyclyl, or optionally substituted 5-6 membered heterocyclyl. In certain embodiments, an $R^{C3}$ attached para to the diazepine is unsubstituted heterocyclyl, e.g., unsubstituted 3-6 membered heterocyclyl, unsubstituted 3-4 membered heterocyclyl, unsubstituted 4-5 membered heterocyclyl, or unsubstituted 5-6 membered heterocyclyl.

In certain embodiments, an $R^{C3}$ attached para to the diazepine is optionally substituted aryl, e.g., optionally substituted phenyl. In certain embodiments, an $R^{C3}$ attached para to the diazepine is unsubstituted aryl, e.g., unsubstituted phenyl. In certain embodiments, an $R^{C3}$ attached para to the diazepine is optionally substituted heteroaryl, e.g., optionally substituted 5-6 membered heteroaryl, or optionally substituted 9-10 membered bicyclic heteroaryl. In certain embodiments, an $R^{C3}$ attached para to the diazepine is unsubstituted heteroaryl, e.g., unsubstituted 5-6 membered heteroaryl, or unsubstituted 9-10 membered bicyclic heteroaryl. In certain embodiments, an $R^{C3}$ attached para to the diazepine is optionally substituted aralkyl, e.g., optionally substituted benzyl. In certain embodiments, an $R^{C3}$ attached para to the diazepine is optionally substituted heteroaralkyl, e.g., methyl substituted with an optionally substituted 5-6 membered heteroaryl ring. In certain embodiments, an $R^{C3}$ attached para to the diazepine is unsubstituted aralkyl, e.g., unsubstituted benzyl. In certain embodiments, an $R^{C3}$ attached para to the diazepine is unsubstituted heteroarlkyl, e.g., methyl substituted with an unsubstituted 5-6 membered heteroaryl ring.

In certain embodiments, an $R^{C3}$ attached para to the diazepine is optionally substituted acyl, e.g., —CHO, —CO$_2$H, or —C(=O)NH$_2$. In certain embodiments, an $R^{C3}$ attached para to the diazepine is —C(=O)R$^f$, —C(=O)OR$^f$, —C(=)NH(R$^f$), or —C(=O)N(R$^f$)$_2$. In certain embodiments, an $R^{C3}$ attached para to the diazepine is —C(=O)R$^f$, and R$^f$ is optionally substituted alkyl, e.g., —C(=O)Me. In certain embodiments, an $R^{C3}$ attached para to the diazepine is —C(=O)R$^f$, and R$^f$ is optionally substituted alkenyl. In certain embodiments, an $R^{C3}$ attached para to the diazepine is —C(=O)R$^f$, and R$^f$ is optionally substituted carbocyclyl, heterocyclyl, aryl, or heteroaryl. In certain embodiments, an R$^3$ attached para to the diazepine is —C(=O)OR$^f$, and R$^f$ is optionally substituted alkyl. In certain embodiments, an $R^{C3}$ attached para to the diazepine is —C(=O)OR$^f$, and R$^f$ is optionally substituted alkenyl. In certain embodiments, an $R^C$ attached para to the diazepine is —C(=O)OR$^f$, and R$^f$ is optionally substituted carbocyclyl, heterocyclyl, aryl, or heteroaryl. In certain embodiments, an $R^{C3}$ attached para to the diazepine is —C(=O)N(R$^f$)$_2$, and at least one R$^f$ is optionally substituted alkyl. In certain embodiments, an $R^{C3}$ attached para to the diazepine is —C(=O)NHR$^f$, and R$^f$ is optionally substituted alkyl. In certain embodiments, an $R^{C3}$ attached para to the diazepine is —C(=O)NHR$^f$, and R$^f$ is optionally substituted alkenyl. In certain embodiments, an $R^{C3}$ attached para to the diazepine is —C(=O)NHR$^f$, and R$^f$ is optionally substituted carbocyclyl, heterocyclyl, aryl, or heteroaryl.

In certain embodiments, an $R^{C3}$ attached para to the diazepine is —OR$^f$, e.g., —OH. In certain embodiments, an $R^C$ attached para to the diazepine is —OR$^f$, and R$^f$ is optionally substituted alkyl. In certain embodiments, an $R^{C3}$ attached para to the diazepine is —OR$^f$, and R$^f$ is unsubstituted $C_{1-6}$ alkyl. In certain embodiments, an $R^{C3}$ attached para to the diazepine is —OR$^f$, and R$^f$ is optionally substituted alkenyl. In certain embodiments, an $R^{C3}$ attached para to the diazepine is —OR$^f$, and R$^f$ is optionally substituted carbocyclyl, optionally substituted heterocyclyl, optionally substituted aryl optionally substituted heteroaryl. In certain embodiments, an $R^{C3}$ attached para to the diazepine is —OR$^f$, and R$^f$ is unsubstituted carbocyclyl, unsubstituted heterocyclyl, unsubstituted aryl unsubstituted heteroaryl. In certain embodiments, an $R^{C3}$ attached para to the diazepine is —OR$^f$, and R$^f$ is optionally substituted acyl, e.g., an $R^{C3}$ attached para to the diazepine is —OC(=O)R$^f$, —OC(=O)OR$^f$, or —OC(=O)N(R$^f$)$_2$. In certain embodiments, an $R^{C3}$ attached para to the diazepine is —OR$^f$, and R$^f$ is an oxygen protecting group.

In certain embodiments, an $R^{C3}$ attached para to the diazepine is optionally substituted sulfonyl, e.g., —S(=O)$_2$OH. In certain embodiments, an $R^{C3}$ attached para to the diazepine is —S(=O)$_2$R$^f$, —S(=O)$_2$OR$^f$, —S(=O)$_2$NH(R$^f$), or —S(=O)$_2$N(R$^f$)$_2$. In certain embodiments, an $R^{C3}$ attached para to the diazepine is —S(=O)$_2$R$^f$, and R$^f$ is optionally substituted alkyl, e.g., —S(=O)$_2$Me. In certain embodiments, an $R^{C3}$ attached para to the diazepine is —S(=O)$_2$R$^f$, and R$^f$ is optionally substituted carbocyclyl, heterocyclyl, aryl, or heteroaryl. In certain embodiments, an $R^{C3}$ attached para to the diazepine is —S(=O)$_2$OR$^f$, and R$^f$ is optionally substituted alkyl. In certain embodiments, an $R^{C3}$ attached para to the diazepine is —S(=O)$_2$OR$^f$, and R$^f$ is optionally substituted aryl. In certain embodiments, an $R^{C3}$ attached para to the diazepine is —S(=O)$_2$N(R$^f$)$_2$, and at least one R$^f$ is optionally substituted alkyl. In certain embodiments, an $R^{C3}$ attached para to the diazepine is —S(=O)$_2$NHR$^f$, and R$^f$ is optionally substituted carbocyclyl, heterocyclyl, aryl, or heteroaryl.

In certain embodiments, an $R^{C3}$ attached para to the diazepine is —SR$^f$, e.g., —SH. In certain embodiments, an $R^{C3}$ attached para to the diazepine is —SR$^f$, and R$^f$ is optionally substituted alkyl. In certain embodiments, an $R^{C3}$ attached para to the diazepine is —SR$^f$, and R$^f$ is unsubstituted $C_{1-6}$ alkyl. In certain embodiments, an $R^{C3}$ attached para to the diazepine is —SR$^f$, and R$^f$ is optionally substituted carbocyclyl, optionally substituted heterocyclyl, optionally substituted aryl optionally substituted heteroaryl. In certain embodiments, an $R^{C3}$ attached para to the diazepine is —SR$^f$, and R$^f$ is unsubstituted carbocyclyl, unsubstituted heterocyclyl, unsubstituted aryl unsubstituted heteroaryl. In certain embodiments, an $R^{C3}$ attached para to the diazepine is —SR$^f$, and R$^f$ is a sulfur protecting group.

In certain embodiments, an $R^{C3}$ attached para to the diazepine is —N(R$^f$)$_2$, e.g., —NH$_2$, —NHR$^f$. In certain embodiments, an $R^{C3}$ attached para to the diazepine is —NH(R$^f$), and R$^f$ is optionally substituted alkyl. In certain embodiments, an $R^{C3}$ attached para to the diazepine is —N(R)$_2$, and at least one R$^f$ is optionally substituted alkyl. In certain embodiments, an $R^{C3}$ attached para to the diazepine is —NH(R$^f$), and R$^f$ is unsubstituted alkyl. In certain embodiments, an $R^{C3}$ attached para to the diazepine is —N(R$^f$)$_2$, and at least one R$^f$ is unsubstituted alkyl. In certain embodiments, an $R^{C3}$ attached para to the diazepine is —NHR$^f$, and R$^f$ is optionally substituted carbocyclyl, optionally substituted heterocyclyl, optionally substituted aryl, or optionally substituted heteroaryl. In certain embodiments, an $R^{C3}$ attached para to the diazepine is —NHR$^f$, and R$^f$ is unsubstituted carbocyclyl, unsubstituted heterocyclyl, unsubstituted aryl, or unsubstituted heteroaryl. In certain embodiments, an $R^{C3}$ attached para to the diazepine is —NHR$^f$, and R$^f$ is optionally substituted acyl, e.g., an $R^{C3}$ attached para to the diazepine is —NHC(=O)R$^f$, —NHC(=O)OR$^f$, or —NHC(=O)NHR$^f$. In certain embodiments, an $R^{C3}$ attached para to the diazepine is —N(R$^f$)$_2$, and at least one R$^f$ is a nitrogen protecting group. In certain embodiments, an $R^{C3}$ attached para to the diazepine is —N(R)$_2$, and both R$^f$ are joined to form an optionally substituted heterocyclic or optionally substituted heteroaryl ring. In certain embodiments, an $R^{C3}$ attached para to the diazepine is —N(R)$_2$, and both R$^f$ are joined to form an unsubstituted heterocyclic or unsubstituted heteroaryl ring. R$^1$ and R$^2$ Formulas (III), (IV), and (V) include substituent R$^1$. Formulas (II), (III), and (IV) include substituent R$^2$. R$^2$ is discussed above. In some embodiments, the carbon to which R$^1$ and R$^2$ is attached is in the (R)-configuration. In some embodiments, the carbon to which R$^1$ and R$^2$ is attached is in the (S)-configuration. In some embodiments, R$^2$ is hydrogen, and the carbon to which R$^1$ is attached is in the (R)-configuration. In some embodiments, R$^2$ is hydrogen, and the carbon to which R$^1$ is attached is in the (S)-configuration. In some embodiments, R$^1$ and R$^2$ are the same. In some embodiments, R$^1$ and R$^2$ are different.

In certain embodiments, R$^1$ is optionally substituted alkyl, e.g., optionally substituted $C_{1-6}$ alkyl, optionally substituted $C_{1-2}$ alkyl, optionally substituted $C_{2-3}$ alkyl, optionally substituted $C_{3-4}$ alkyl, optionally substituted $C_{4-5}$ alkyl, or optionally substituted $C_{5-6}$ alkyl. In certain embodiments, R$^1$ is unsubstituted alkyl, e.g., unsubstituted $C_{1-6}$ alkyl, unsubstituted $C_{1-2}$ alkyl, unsubstituted $C_{2-3}$ alkyl, unsubstituted $C_{3-4}$ alkyl, unsubstituted $C_{4-5}$ alkyl, or unsubstituted $C_{5-6}$ alkyl. In certain embodiments, $R^1$ is methyl. In certain embodiments, $R^1$ is ethyl, propyl, or butyl. In certain embodiments, $R^1$ is haloalkyl, e.g., —$CHF_2$, —$CHCl_2$, —$CH_2CHF_2$, —$CH_2CHCl_2$. In certain embodiments, $R^1$ is perhaloalkyl, e.g., —$CF_3$, —$CF_2CF_3$, —$CCl_3$. In certain embodiments, $R^1$ is hydroxyalkyl, e.g., —$CH_2H$, —$CH_2CH_2OH$, —$CH_2OR^f$, —$CH_2CH_2OR^f$. In certain embodiments, $R^1$ is aminoalkyl, e.g., —$CH_2NH_2$, —$CH_2CH_2NH_2$, —$CH_2NMe_2$, —$CH_2CH_2NMe_2$, —$CH_2N(R^f)_2$, —$CH_2CH_2N(R^f)_2$.

In certain embodiments, $R^1$ is —$(CH_2)_nL_2$, wherein n is 0, 1, 2, 3 or 4, and L is —$C(=O)R^3$, —$C(=O)OR^3$, —$C(=O)NR^3R^4$, —$S(=O)_2R^3$, —$S(=O)_2OR^3$, —$S(=O)_2NR^3R^4$, —$OR^3$, —$NR^3R^4$, —$N(R^4)C(=O)R^3$, optionally substituted carbocyclyl, optionally substituted heterocyclyl, optionally substituted aryl, or optionally substituted heteroaryl. In certain embodiments, n is 0. In certain embodiments, n is 1. In certain embodiments, n is 2. In certain embodiments, n is 3. In certain embodiments, n is 4. In certain embodiments, n is 0, 1, 2, or 3. In certain embodiments, n is 0, 1, or 2. In certain embodiments, n is 0 or 1. In certain embodiments, n is 1, 2, 3, or 4. In certain embodiments, n is 2, 3, or 4. In certain embodiments, n is 3 or 4. When n is 0, $R^1$ is -L, such that $R^1$ is —$C(=O)R^3$, —$C(=O)OR^3$, —$C(=O)NR^3R^4$, —$S(=O)_2R^3$, —$S(=O)_2OR^3$, —$S(=O)_2NR^3R^4$, —$OR^3$, —$NR^3R^4$, —$N(R^4)C(=O)R^3$, optionally substituted carbocyclyl, optionally substituted heterocyclyl, optionally substituted aryl, or optionally substituted heteroaryl.

In certain embodiments, $L_2$ is H. In certain embodiments, $L_2$ is —$C(=O)R^3$. In certain embodiments, $L_2$ is —$C(=O)OR^3$. In certain embodiments, $L_2$ is —$C(=O)NR^3R^4$. In certain embodiments, $L_2$ is —$C(=O)NHR^3$. In certain embodiments, $L_2$ is —$S(=O)_2R^3$. In certain embodiments, $L_2$ is —$S(=O)_2OR^3$. In certain embodiments, $L_2$ is —$S(=O)_2NR^3R^4$. In certain embodiments, $L_2$ is —$S(=O)_2OR^3$. In certain embodiments, $L_2$ is —$S(=O)_2NHR^3$. In certain embodiments, $L_2$ is —$OR^3$. In certain embodiments, $L_2$ is —$NR^3R^4$. In certain embodiments, $L_2$ is —$NHR^3$. In certain embodiments, $L_2$ is —$N(R^4)C(=O)R^3$. In certain embodiments, $L_2$ is —$NHC(=O)R^3$.

$R^3$ and $R^4$; $R^6$

Formulas (III), (IV), and (V) include substituents $R^3$ and $R^4$. Formula (V) includes substituent $R^6$. As generally defined herein, each of $R^3$ and $R^4$ is independently hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl, or optionally substituted acyl, an oxygen protecting group, or a nitrogen protecting group, or $R^3$ and $R^4$ are joined to form an optionally substituted heterocyclic or optionally substituted heteroaryl ring.

In certain embodiments, $R^3$ is hydrogen. In certain embodiments, $R^3$ is a non-hydrogen group. In certain embodiments, $R^3$ is halogen. In certain embodiments, $R^3$ is —F. In certain embodiments, $R^3$ is —Cl, —Br, or —I. In certain embodiments, $R^3$ is —$NO_2$. In certain embodiments, $R^3$ is —CN.

In certain embodiments, $R^3$ is optionally substituted alkyl, e.g., optionally substituted $C_{1-6}$ alkyl, optionally substituted $C_{1-2}$ alkyl, optionally substituted $C_{2-3}$ alkyl, optionally substituted $C_{3-4}$ alkyl, optionally substituted $C_{4-5}$ alkyl, or optionally substituted $C_{5-6}$ alkyl. In certain embodiments, $R^3$ is unsubstituted alkyl, e.g., unsubstituted $C_{1-6}$ alkyl, unsubstituted $C_{1-2}$ alkyl, unsubstituted $C_{2-3}$ alkyl, unsubstituted $C_{3-4}$ alkyl, unsubstituted $C_{4-5}$ alkyl, or unsubstituted $C_{5-6}$ alkyl. In certain embodiments, $R^3$ is methyl. In certain embodiments, $R^3$ is ethyl, propyl, or butyl. In certain embodiments, $R^3$ is haloalkyl, e.g., —$CHF_2$, —$CHCl_2$, —$CH_2CHF_2$, —$CH_2CHCl_2$. In certain embodiments, $R^3$ is perhaloalkyl, e.g., —$CF_3$, —$CF_2CF_3$, —$CCl_3$. In certain embodiments, $R^3$ is hydroxyalkyl, e.g., —$CH_2H$, —$CH_2CH_2OH$, —$CH_2OR^f$, —$CH_2CH_2OR^f$. In certain embodiments, $R^3$ is aminoalkyl, e.g., —$CH_2NH_2$, —$CH_2CH_2NH_2$, —$CH_2NMe_2$, —$CH_2CH_2NMe_2$, —$CH_2N(R^f)_2$, —$CH_2CH_2N(R^f)_2$.

In certain embodiments, $R^3$ is optionally substituted alkenyl, e.g., optionally substituted $C_{2-6}$ alkenyl. In certain embodiments, $R^3$ is unsubstituted alkenyl, e.g., unsubstituted $C_{2-6}$ alkenyl. In certain embodiments, $R^3$ is vinyl, allyl, or prenyl. In certain embodiments, $R^3$ is optionally substituted alkynyl, e.g., optionally substituted $C_{2-6}$ alkynyl. In certain embodiments, $R^3$ is unsubstituted alkynyl, e.g., unsubstituted $C_{2-6}$ alkynyl.

In certain embodiments, $R^3$ is optionally substituted carbocyclyl, e.g., optionally substituted $C_{3-6}$ carbocyclyl, optionally substituted $C_{3-4}$ carbocyclyl, optionally substituted $C_{4-5}$ carbocyclyl, or optionally substituted $C_{5-6}$ carbocyclyl. In certain embodiments, $R^3$ is unsubstituted carbocyclyl, e.g., unsubstituted $C_{3-6}$ carbocyclyl. In some embodiments, $R^3$ is cyclopropyl, cyclobutyl, cyclopentyl, or cyclohexyl. In certain embodiments, $R^3$ is optionally substituted heterocyclyl, e.g., optionally substituted 3-6 membered heterocyclyl, optionally substituted 3-4 membered heterocyclyl, optionally substituted 4-5 membered heterocyclyl, or optionally substituted 5-6 membered heterocyclyl. In certain embodiments, $R^3$ is unsubstituted heterocyclyl, e.g., unsubstituted 3-6 membered heterocyclyl, unsubstituted 3-4 membered heterocyclyl, unsubstituted 4-5 membered heterocyclyl, or unsubstituted 5-6 membered heterocyclyl.

In certain embodiments, $R^3$ is optionally substituted aryl, e.g., optionally substituted phenyl. In certain embodiments, $R^3$ is unsubstituted aryl, e.g., unsubstituted phenyl. In certain embodiments, $R^3$ is optionally substituted heteroaryl, e.g., optionally substituted 5-6 membered heteroaryl, or optionally substituted 9-10 membered bicyclic heteroaryl. In certain embodiments, $R^3$ is unsubstituted heteroaryl, e.g., unsubstituted 5-6 membered heteroaryl, or unsubstituted 9-10 membered bicyclic heteroaryl. In certain embodiments, $R^3$ is optionally substituted aralkyl, e.g., optionally substituted benzyl. In certain embodiments, $R^3$ is optionally substituted heteroaralkyl, e.g., methyl substituted with an optionally substituted 5-6 membered heteroaryl ring. In certain embodiments, $R^3$ is unsubstituted aralkyl, e.g., unsubstituted benzyl. In certain embodiments, $R^3$ is unsubstituted heteroaralkyl, e.g., methyl substituted with an unsubstituted 5-6 membered heteroaryl ring. In certain embodiments, $R^3$ is optionally substituted acyl, e.g., —CHO, —$CO_2H$, or —$C(=O)NH_2$. In certain embodiments, $R^3$ is —$C(=O)R^f$, —$C(=O)OR^f$, —$C(=O)NH(R_f)$, or —$C(=O)N(R^f)_2$. In certain embodiments, $R^3$ is —$C(=O)R^f$, and $R^f$ is optionally substituted alkyl, e.g., —$C(=O)Me$. In certain embodiments, $R^3$ is —$C(=O)R^f$, and $R^f$ is optionally substituted alkenyl. In certain embodiments, $R^3$ is —$C(=O)R^f$, and $R^f$ is optionally substituted carbocyclyl, heterocyclyl, aryl, or heteroaryl. In certain embodiments, $R^3$ is —$C(=O)OR^f$, and $R^f$ is optionally substituted alkyl. In certain embodiments, $R^3$ is —$C(=O)OR^f$, and $R^f$ is optionally substituted alkenyl. In certain embodiments, $R^3$ is —$C(=O)OR^f$, and $R^f$ is optionally substituted carbocyclyl, heterocyclyl, aryl, or heteroaryl. In certain embodiments, $R^3$ is —$C(=O)N(R^f)_2$, and at least one $R^f$ is optionally substituted alkyl. In certain embodiments, $R^3$ is —C(=O)NHR$^f$, and R$^f$ is optionally substituted alkyl. In certain embodiments, $R^3$ is —C(=O)NHR$^f$, and R$^f$ is optionally substituted alkenyl. In certain embodiments, $R^3$ is —C(=O)NHR$^f$, and R$^f$ is optionally substituted carbocyclyl, heterocyclyl, aryl, or heteroaryl. In certain embodiments, $R^3$ is a nitrogen protecting group. In some embodiments, $R^3$ is Bn, Boc, Cbz, Fmoc, trifluoroacetyl, triphenylmethyl, acetyl, or Ts. In certain embodiments, $R^3$ and $R^4$ are taken together with the nitrogen atom to which they are attached to form a 4-10-membered ring (e.g., a 4-10-membered heterocyclic ring).

In certain embodiments, each $R^3$ is independently selected from the group consisting of:

(i) H, aryl, substituted aryl, heteroaryl, or substituted heteroaryl;

(ii) heterocycloalkyl or substituted heterocycloalkyl;

(iii) —$C_1$-$C_8$ alkyl, —$C_2$-$C_8$ alkenyl or —$C_2$-$C_8$ alkynyl, each containing 0, 1, 2, or 3 heteroatoms selected from O, S, or N; —$C_3$-$C_{12}$ cycloalkyl, substituted —$C_3$-$C_{12}$ cycloalkyl, —$C_3$-$C_{12}$ cycloalkenyl, or substituted —$C_3$-$C_{12}$ cycloalkenyl, each of which may be optionally substituted; and (iv) N=CR$^4$R$^6$.

In certain embodiments, each $R^4$ is independently hydrogen, alkyl, cycloalkyl, heterocycloalkyl, aryl, or heteroaryl, each of which is optionally substituted. In certain embodiments, $R^4$ is hydrogen. In certain embodiments, $R^4$ is a non-hydrogen group. In certain embodiments, $R^4$ is halogen. In certain embodiments, $R^4$ is —F. In certain embodiments, $R^4$ is —Cl, —Br, or —I. In certain embodiments, $R^4$ is —NO$_2$. In certain embodiments, $R^4$ is —CN.

In certain embodiments, $R^4$ is optionally substituted alkyl, e.g., optionally substituted $C_{1-6}$ alkyl, optionally substituted $C_{1-2}$ alkyl, optionally substituted $C_{2-3}$ alkyl, optionally substituted $C_{3-4}$ alkyl, optionally substituted $C_{4-5}$ alkyl, or optionally substituted $C_{5-6}$ alkyl. In certain embodiments, $R^4$ is unsubstituted alkyl, e.g., unsubstituted $C_{1-6}$ alkyl, unsubstituted $C_{1-2}$ alkyl, unsubstituted $C_{2-3}$ alkyl, unsubstituted $C_{3-4}$ alkyl, unsubstituted $C_{4-5}$ alkyl, or unsubstituted $C_{5-6}$ alkyl. In certain embodiments, $R^4$ is methyl. In certain embodiments, $R^4$ is ethyl, propyl, or butyl. In certain embodiments, $R^4$ is haloalkyl, e.g., —CHF$_2$, —CHCl$_2$, —CH$_2$CHF$_2$, —CH$_2$CHCl$_2$. In certain embodiments, $R^4$ is perhaloalkyl, e.g., —CF$_3$, —CF$_2$CF$_3$, —CCl$_3$. In certain embodiments, $R^4$ is hydroxyalkyl, e.g., —CH$_2$H, —CH$_2$CH$_2$OH, —CH$_2$OR$^f$, —CH$_2$CH$_2$OR$^f$. In certain embodiments, $R^4$ is aminoalkyl, e.g., —CH$_2$NH$_2$, —CH$_2$CH$_2$NH$_2$, —CH$_2$NMe$_2$, —CH$_2$CH$_2$NMe$_2$, —CH$_2$N(R$^f$)$_2$, —CH$_2$CH$_2$N(R$^f$)$_2$.

In certain embodiments, $R^4$ is optionally substituted alkenyl, e.g., optionally substituted $C_{2-6}$ alkenyl. In certain embodiments, $R^4$ is unsubstituted alkenyl, e.g., unsubstituted $C_{2-6}$ alkenyl. In certain embodiments, $R^4$ is vinyl, allyl, or prenyl. In certain embodiments, $R^4$ is optionally substituted alkynyl, e.g., optionally substituted $C_{2-6}$ alkynyl. In certain embodiments, $R^4$ is unsubstituted alkynyl, e.g., unsubstituted $C_{2-6}$ alkynyl.

In certain embodiments, $R^4$ is optionally substituted carbocyclyl, e.g., optionally substituted $C_{3-6}$ carbocyclyl, optionally substituted $C_{3-4}$ carbocyclyl, optionally substituted $C_{4-5}$ carbocyclyl, or optionally substituted $C_{5-6}$ carbocyclyl. In certain embodiments, $R^4$ is unsubstituted carbocyclyl, e.g., unsubstituted $C_{3-6}$ carbocyclyl. In some embodiments, $R^4$ is cyclopropyl, cyclobutyl, cyclopentyl, or cyclohexyl. In certain embodiments, $R^4$ is optionally substituted heterocyclyl, e.g., optionally substituted 3-6 membered heterocyclyl, optionally substituted 3-4 membered heterocyclyl, optionally substituted 4-5 membered heterocyclyl, or optionally substituted 5-6 membered heterocyclyl. In certain embodiments, $R^4$ is unsubstituted heterocyclyl, e.g., unsubstituted 3-6 membered heterocyclyl, unsubstituted 3-4 membered heterocyclyl, unsubstituted 4-5 membered heterocyclyl, or unsubstituted 5-6 membered heterocyclyl.

In certain embodiments, $R^4$ is optionally substituted aryl, e.g., optionally substituted phenyl. In certain embodiments, $R^4$ is unsubstituted aryl, e.g., unsubstituted phenyl. In certain embodiments, $R^4$ is optionally substituted heteroaryl, e.g., optionally substituted 5-6 membered heteroaryl, or optionally substituted 9-10 membered bicyclic heteroaryl. In certain embodiments, $R^4$ is unsubstituted heteroaryl, e.g., unsubstituted 5-6 membered heteroaryl, or unsubstituted 9-10 membered bicyclic heteroaryl. In certain embodiments, $R^4$ is optionally substituted aralkyl, e.g., optionally substituted benzyl. In certain embodiments, $R^4$ is optionally substituted heteroaralkyl, e.g., methyl substituted with an optionally substituted 5-6 membered heteroaryl ring. In certain embodiments, $R^4$ is unsubstituted aralkyl, e.g., unsubstituted benzyl. In certain embodiments, $R^4$ is unsubstituted heteroaralkyl, e.g., methyl substituted with an unsubstituted 5-6 membered heteroaryl ring.

In certain embodiments, $R^4$ is optionally substituted acyl, e.g., —CHO, —CO$_2$H, or —C(=O)NH$_2$. In certain embodiments, $R^4$ is —C(=O)R$^f$, —C(=O)OR$^f$, —C(=O)NH(R$^f$), or —C(=O)N(R$^f$)$_2$. In certain embodiments, $R^4$ is —C(=O)R$^f$, and R$^f$ is optionally substituted alkyl, e.g., —C(=O)Me. In certain embodiments, $R^4$ is —C(=O)R$^f$, and R$^f$ is optionally substituted alkenyl. In certain embodiments, $R^4$ is —C(=O)R$^f$, and R$^f$ is optionally substituted carbocyclyl, heterocyclyl, aryl, or heteroaryl. In certain embodiments, $R^4$ is —C(=O)OR$^f$, and R$^f$ is optionally substituted alkyl. In certain embodiments, $R^4$ is —C(=O)OR$^f$, and R$^f$ is optionally substituted alkenyl. In certain embodiments, $R^4$ is —C(=O)OR$^f$, and R$^f$ is optionally substituted carbocyclyl, heterocyclyl, aryl, or heteroaryl. In certain embodiments, $R^4$ is —C(=O)N(R$^f$)$_2$, and at least one R$^f$ is optionally substituted alkyl. In certain embodiments, $R^4$ is —C(=O)NHR$^f$, and R$^f$ is optionally substituted alkyl. In certain embodiments, $R^4$ is —C(=O)NHR$^f$, and R$^f$ is optionally substituted alkenyl. In certain embodiments, $R^4$ is —C(=O)NHR$^f$, and R$^f$ is optionally substituted carbocyclyl, heterocyclyl, aryl, or heteroaryl. In certain embodiments, $R^4$ is a nitrogen protecting group. In some embodiments, $R^4$ is Bn, Boc, Cbz, Fmoc, trifluoroacetyl, triphenylmethyl, acetyl, or Ts.

In certain embodiments, $R^3$ and $R^4$ are the same. In certain embodiments, $R^3$ and $R^4$ are different. In certain embodiments, $R^3$ and $R^4$ are both hydrogen. In certain embodiments, $R^3$ and $R^4$ are both optionally substituted alkyl. In certain embodiments, $R^3$ and $R^4$ are both optionally substituted $C_{1-6}$ alkyl. In certain embodiments, $R^3$ and $R^4$ are both unsubstituted $C_{1-6}$ alkyl. In certain embodiments, $R^3$ and $R^4$ are both methyl. In certain embodiments, $R^3$ and $R^4$ are both ethyl, propyl, or butyl.

In certain embodiments, $R^3$ and $R^4$ are joined to form an optionally substituted heterocyclic ring. In certain embodiments, $R^3$ and $R^4$ are joined to form an unsubstituted heterocyclic ring. In some embodiments, $R^3$ and $R^4$ are joined to form a substituted or unsubstituted piperidinyl, dihydropyridinyl, piperazinyl, or morpholinyl ring. In certain embodiments, $R^3$ and $R^4$ are joined to form a substituted or unsubstituted piperidinyl ring. In certain embodiments, $R^3$ and $R^4$ are joined to form a substituted or unsubstituted dihydropyridinyl ring. In certain embodiments, $R^3$ and $R^4$ are joined to form a substituted or unsubstituted piperazinyl ring. In certain embodiments, $R^3$ and $R^4$ are joined to form a substituted or unsubstituted morpholinyl ring. In certain embodiments, $R^3$ and $R^4$ are joined to form an optionally substituted heteroaryl ring. In certain embodiments, $R^3$ and $R^4$ are joined to form an unsubstituted heteroaryl ring. In some embodiments, $R^3$ and $R^4$ are joined to form a substituted or unsubstituted pyrrolyl, imidazolyl, pyrazolyl, triazolyl, or tetrazolyl ring. In certain embodiments, $R^3$ and $R^4$ are joined to form a substituted or unsubstituted pyrrolyl ring. In certain embodiments, $R^3$ and $R^4$ are joined to form a substituted or unsubstituted imidazolyl ring. In certain embodiments, $R^3$ and $R^4$ are joined to form a substituted or unsubstituted pyrazolyl ring. In certain embodiments, $R^3$ and $R^4$ are joined to form a substituted or unsubstituted triazolyl ring. In certain embodiments, $R^3$ and $R^4$ are joined to form a substituted or unsubstituted tetrazolyl ring.

In certain embodiments, $R^L$ is optionally substituted carbocyclyl, e.g., optionally substituted $C_{3-6}$ carbocyclyl, optionally substituted $C_{3-4}$ carbocyclyl, optionally substituted $C_{4-5}$ carbocyclyl, or optionally substituted $C_{5-6}$ carbocyclyl. In certain embodiments, $R^L$ is unsubstituted carbocyclyl, e.g., unsubstituted $C_{3-6}$ carbocyclyl. In some embodiments, $R^L$ is cyclopropyl, cyclobutyl, cyclopentyl, or cyclohexyl. In certain embodiments, $R^L$ is optionally substituted heterocyclyl, e.g., optionally substituted 3-6 membered heterocyclyl, optionally substituted 3-4 membered heterocyclyl, optionally substituted 4-5 membered heterocyclyl, or optionally substituted 5-6 membered heterocyclyl. In certain embodiments, $R^L$ is unsubstituted heterocyclyl, e.g., unsubstituted 3-6 membered heterocyclyl, unsubstituted 3-4 membered heterocyclyl, unsubstituted 4-5 membered heterocyclyl, or unsubstituted 5-6 membered heterocyclyl.

In certain embodiments, $R^6$ is alkyl, alkenyl, cycloalkyl, cycloalkenyl, heterocycloalkyl, aryl, or heteroaryl, each of which is optionally substituted. In certain embodiments, $R^4$ and $R^6$ are taken together with the carbon atom to which they are attached to form a 4-10-membered ring (e.g., a 4-10-membered heterocyclic ring).

In certain embodiments, $R^L$ is optionally substituted aryl, e.g., optionally substituted phenyl. In certain embodiments, $R^L$ is unsubstituted aryl, e.g., unsubstituted phenyl. In certain embodiments, $R^L$ is optionally substituted heteroaryl, e.g., optionally substituted 5-6 membered heteroaryl, or optionally substituted 9-10 membered bicyclic heteroaryl. In certain embodiments, $R^L$ is unsubstituted heteroaryl, e.g., unsubstituted 5-6 membered heteroaryl, or unsubstituted 9-10 membered bicyclic heteroaryl. In certain embodiments, $R^L$ is optionally substituted aralkyl, e.g., optionally substituted benzyl. In certain embodiments, $R^L$ is optionally substituted heteroaralkyl, e.g., methyl substituted with an optionally substituted 5-6 membered heteroaryl ring. In certain embodiments, $R^L$ is unsubstituted aralkyl, e.g., unsubstituted benzyl. In certain embodiments, $R^L$ is unsubstituted heteroaralkyl, e.g., methyl substituted with an unsubstituted 5-6 membered heteroaryl ring.

In certain embodiments, $L_2$ is —$OR^3$, e.g., —OH. In certain embodiments, $L_2$ is —$OR^3$, and $R^3$ is optionally substituted alkyl. In certain embodiments, $L_2$ is —$OR^3$, and $R^3$ is unsubstituted $C_{1-6}$ alkyl. In certain embodiments, $L_2$ is —$OR^3$, and $R^3$ is optionally substituted alkenyl. In certain embodiments, $L_2$ is —$OR^3$, and $R^3$ is optionally substituted carbocyclyl, optionally substituted heterocyclyl, optionally substituted aryl optionally substituted heteroaryl. In certain embodiments, $L_2$ is —$OR^3$, and $R^3$ is unsubstituted carbocyclyl, unsubstituted heterocyclyl, unsubstituted aryl unsubstituted heteroaryl. In certain embodiments, $L_2$ is —$OR^3$, and $R^3$ is optionally substituted acyl, e.g., $L_2$ is —OC(=O)$R^f$, —OC(=O)$OR^f$, or —OC(=O)N($R^f$)$_2$. In certain embodiments, $L_2$ is —$OR^3$, and $R^3$ is an oxygen protecting group.

In certain embodiments, $L_2$ is —$NR^3R^4$, e.g., —$NH_2$, —$NHR^3$. In certain embodiments, $L_2$ is —$NHR^3$, and $R^3$ is optionally substituted alkyl. In certain embodiments, $L_2$ is —$NR^3R^4$, and at least one of $R^3$ and $R^4$ is optionally substituted alkyl. In certain embodiments, $L_2$ is —$NHR^3$, and $R^3$ is unsubstituted alkyl. In certain embodiments, $L_2$ is —$NR^3R^4$, and at least one of $R^3$ and $R^4$ is unsubstituted alkyl. In certain embodiments, $R^1$ is —(CH$_2$)NH (optionally substituted $C_{1-6}$ alkyl). In certain embodiments, $L_2$ is —$NHR^3$, and $R^3$ is optionally substituted carbocyclyl, optionally substituted heterocyclyl, optionally substituted aryl, or optionally substituted heteroaryl. In certain embodiments, $L_2$ is —$NHR^3$, and $R^3$ is optionally substituted phenyl. In certain embodiments, $R^1$ is of the formula:

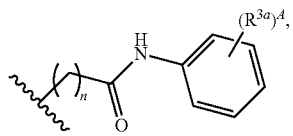

wherein $R^{3a}$ is halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, —$OR^f$, —$SR^f$, —$N(R^g)_2$, or —$NO_2$; $R^g$ is optionally substituted alkyl, optionally substituted alkenyl, optionally substituted alkynyl, optionally substituted carbocyclyl, optionally substituted heterocyclyl, optionally substituted aryl, optionally substituted heteroaryl, or nitrogen protecting group; n is 0, 1, 2, 3 or 4; and A is 0, 1, 2, 3, 4, or 5. In certain embodiments, $R^{3a}$ is halogen (e.g., F, Cl, Br, or I). In certain embodiments, at least one $R^{A1}$ is substituted or unsubstituted alkyl (e.g., substituted or unsubstituted $C_{1-6}$ alkyl). In certain embodiments, $R^{3a}$ is substituted or unsubstituted methyl. In certain embodiments, $R^{3a}$ is substituted or unsubstituted ethyl. In certain embodiments, $R^{3a}$ is substituted or unsubstituted propyl. In certain embodiments, $R^{3a}$ is substituted or unsubstituted alkenyl (e.g., substituted or unsubstituted $C_{2-6}$ alkenyl). In certain embodiments, $R^{3a}$ is substituted or unsubstituted alkynyl (e.g., substituted or unsubstituted $C_{2-6}$ alkynyl). In certain embodiments, $R^{3a}$ is substituted or unsubstituted carbocyclyl (e.g., substituted or unsubstituted, 3- to 7-membered, monocyclic carbocyclyl comprising zero, one, or two double bonds in the carbocyclic ring system). In certain embodiments, $R^{3a}$ is substituted or unsubstituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, $R^{3a}$ is substituted or unsubstituted aryl (e.g., substituted or unsubstituted, 6- to 10-membered aryl). In certain embodiments, $R^{3a}$ is benzyl. In certain embodiments, $R^{3a}$ is substituted or unsubstituted phenyl. In certain embodiments, $R^{3a}$ is substituted or unsubstituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur). In certain embodiments, $R^{3a}$ is —OR (e.g., —OH or —OMe). In certain embodiments, $R^{3a}$ is optionally substituted acyl (e.g., —C(=O)$R^f$) (e.g., —C(=O)Me). In certain embodiments, $R^{3a}$ is —$SR^f$, —N($R^g$)$_2$, or —NO$_2$. In certain embodiments, $R^9$ is optionally substituted alkyl, optionally substituted alkenyl, optionally substituted alkynyl, optionally substituted carbocyclyl, optionally substituted heterocyclyl, optionally substituted aryl, optionally substituted heteroaryl, or nitrogen protecting group. In certain embodiments, n is 0. In certain embodiments, n is 1. In certain embodiments, n is 2. In certain embodiments, n is 3. In certain embodiments, n is 4. In certain embodiments, A is 0. In certain embodiments, A is 1. In certain embodiments, A is 2. In certain embodiments, A is 3. In certain embodiments, A is 4. In certain embodiments, A is 5. In certain embodiments, $R^f$ is hydrogen. In certain embodiments, $R^f$ is optionally substituted alkyl (e.g., substituted or unsubstituted $C_{1-6}$ alkyl). In certain embodiments, $R^f$ is substituted or unsubstituted methyl. In certain embodiments, $R^f$ is substituted or unsubstituted ethyl. In certain embodiments, $R^f$ is substituted or unsubstituted propyl. In certain embodiments, $R^f$ is substituted or unsubstituted alkenyl (e.g., substituted or unsubstituted $C_{2-6}$ alkenyl). In certain embodiments, $R^f$ is substituted or unsubstituted alkynyl (e.g., substituted or unsubstituted $C_{2-6}$ alkynyl). In certain embodiments, $R^f$ is substituted or unsubstituted carbocyclyl (e.g., substituted or unsubstituted, 3- to 7-membered, monocyclic carbocyclyl comprising zero, one, or two double bonds in the carbocyclic ring system). In certain embodiments, $R^f$ is substituted or unsubstituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, $R^f$ is substituted or unsubstituted aryl (e.g., substituted or unsubstituted, 6- to 10-membered aryl). In certain embodiments, $R^f$ is substituted or unsubstituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur). In certain embodiments, two $R^f$ are joined to form an optionally substituted heterocyclic ring (e.g., substituted or unsubstituted, 5- to 10-membered monocyclic or bicyclic heterocyclic ring, wherein one or two atoms in the heterocyclic ring are independently nitrogen, oxygen, or sulfur), or optionally substituted heteroaryl ring (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur). In certain embodiments, $R^f$ is a nitrogen protecting group (e.g., benzyl (Bn), t-butyl carbonate (BOC or Boc), benzyl carbamate (Cbz), 9-fluorenylmethyl carbonate (Fmoc), trifluoroacetyl, triphenylmethyl, acetyl, or p-toluenesulfonamide (Ts)). In certain embodiments, $R^f$ is optionally substituted acyl or optionally substituted sulfonyl. In certain embodiments, $L_2$ is —$NHR^3$, and $R^3$ is unsubstituted carbocyclyl, unsubstituted heterocyclyl, unsubstituted aryl, or unsubstituted heteroaryl. In certain embodiments, $L_2$ is —$NHR^3$, and $R^3$ is optionally substituted acyl, e.g., $L_2$ is —NHC(=O)$R^f$, —NHC(=O)O$R^f$, or —NHC(=O)NH$R^f$. In certain embodiments, $L_2$ is —$NR^3R^4$, and at least one of $R^3$ and $R^4$ is a nitrogen protecting group. In certain embodiments, $L_2$ is —$NR^3R^4$, and $R^3$ and $R^4$ are joined to form an optionally substituted heterocyclic or optionally substituted heteroaryl ring. In certain embodiments, $L_2$ is —$NR^3R^4$, and $R^3$ and $R^4$ are joined to form an unsubstituted heterocyclic or unsubstituted heteroaryl ring.

In certain embodiments, $L_2$ is optionally substituted carbocyclyl (e.g., substituted or unsubstituted, 3- to 7-membered, monocyclic carbocyclyl comprising zero, one, or two double bonds in the carbocyclic ring system). In certain embodiments, $L_2$ is optionally substituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, $L_2$ is optionally substituted aryl (e.g., substituted or unsubstituted, 6- to 10-membered aryl). In certain embodiments, $L_2$ is optionally substituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur).

In certain embodiments, $R^1$ is of formula:

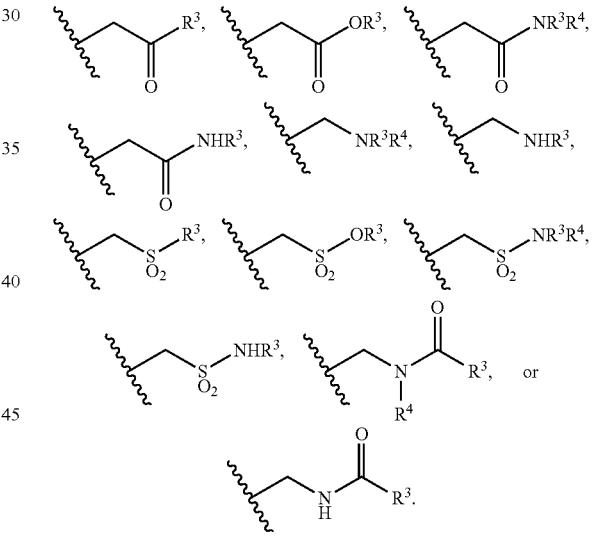

In certain embodiments, $R^1$ is of formula:

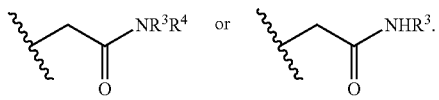

In certain embodiments, $R^1$ is of formula:

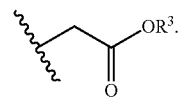

In certain embodiments, $R^1$ is of formula:
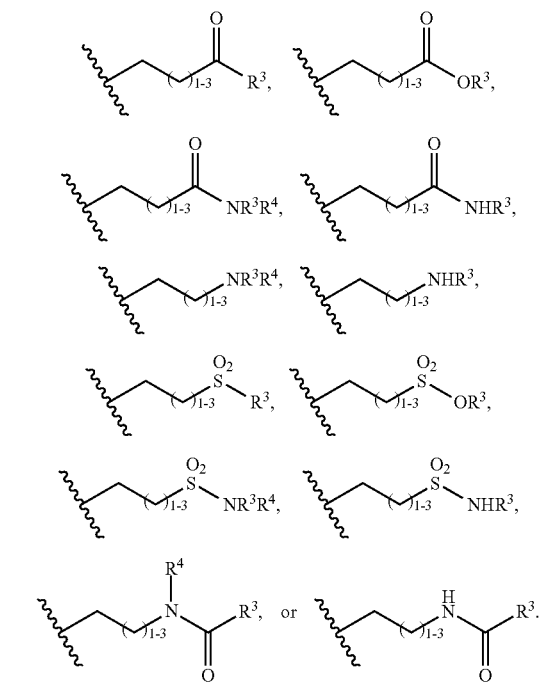
In certain embodiments, $R^1$ is of formula:
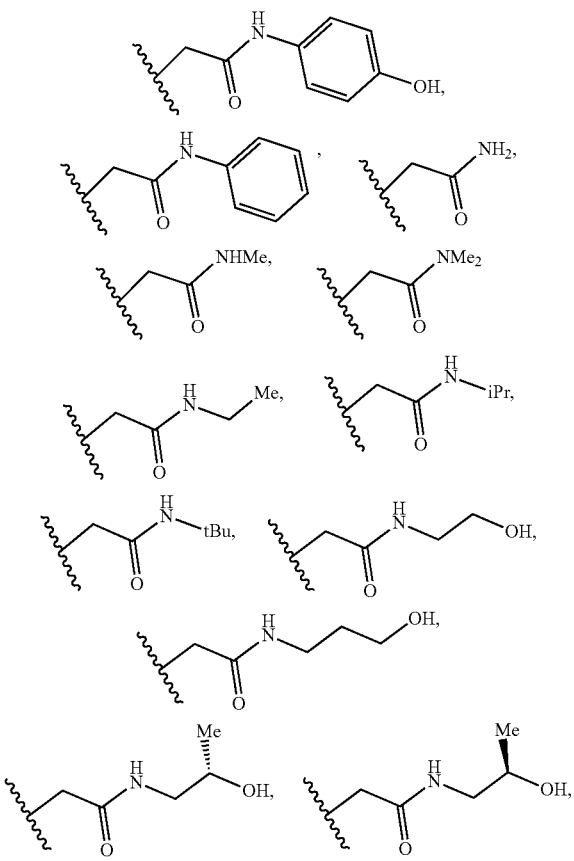
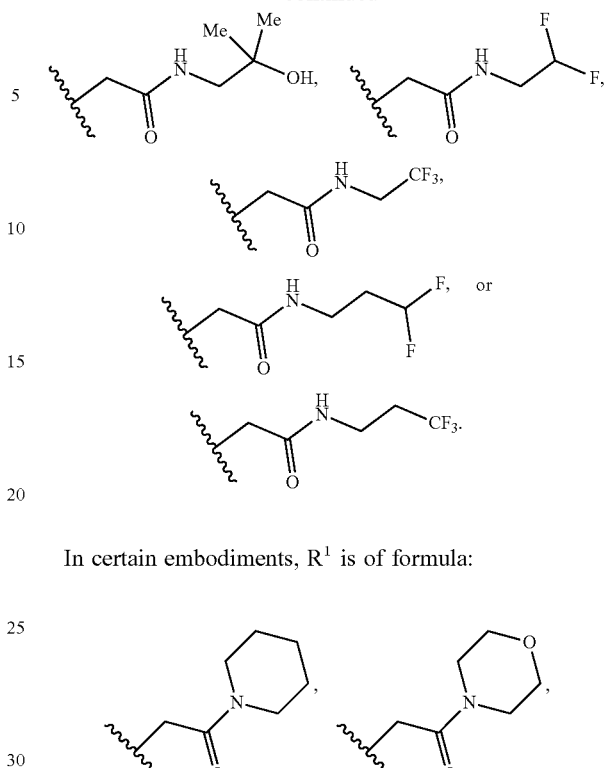
In certain embodiments, $R^1$ is of formula:
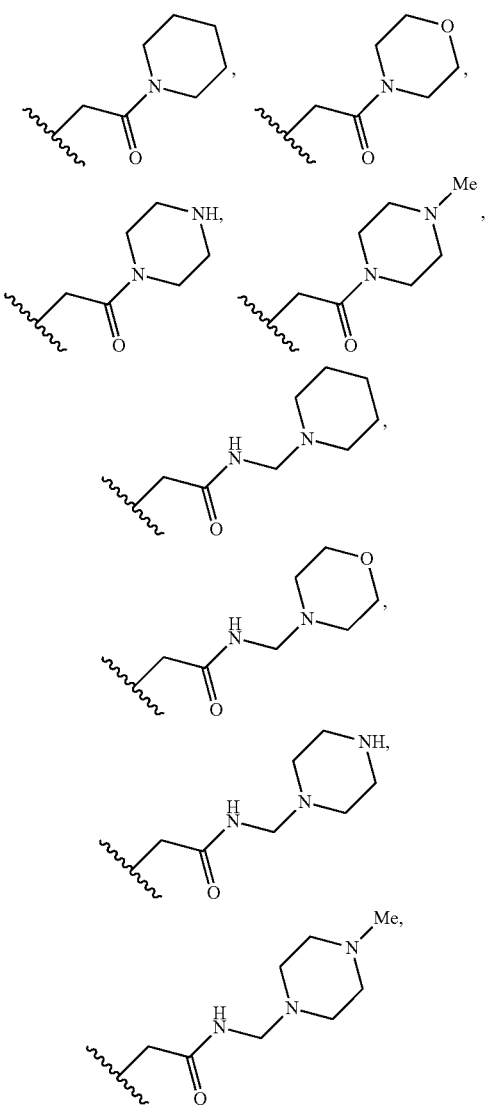

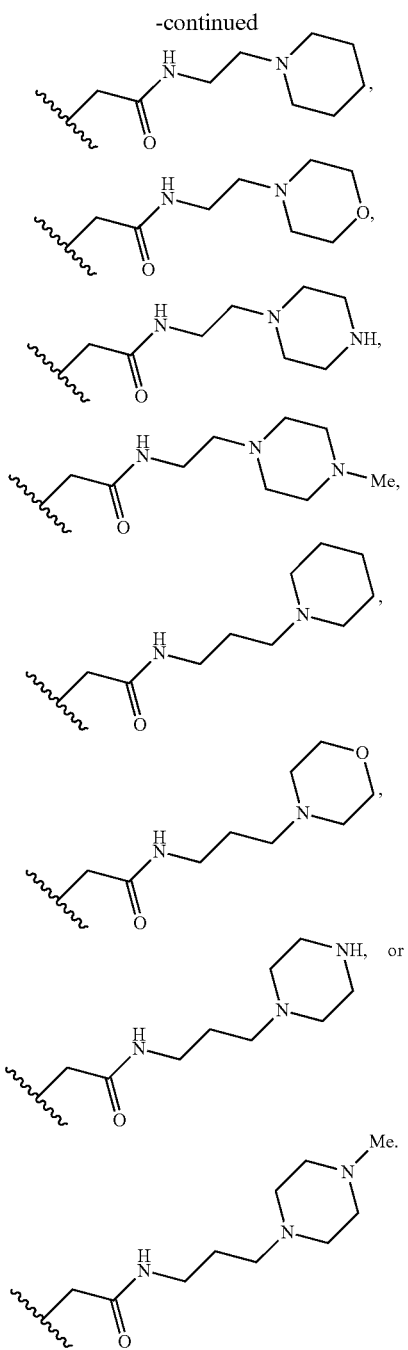

embodiments, R is substituted or unsubstituted methyl. In certain embodiments, R is substituted or unsubstituted ethyl. In certain embodiments, R is substituted or unsubstituted propyl. In certain embodiments, R is substituted or unsubstituted alkenyl (e.g., substituted or unsubstituted $C_{2-6}$ alkenyl). In certain embodiments, R is substituted or unsubstituted alkynyl (e.g., substituted or unsubstituted $C_{2-6}$ alkynyl). In certain embodiments, R is substituted or unsubstituted cycloalkyl (e.g., substituted or unsubstituted, 3- to 7-membered, monocyclic cycloalkyl comprising zero, one, or two double bonds in the carbocyclic ring system). In certain embodiments, R is substituted or unsubstituted heterocycloalkyl (e.g., substituted or unsubstituted, 5- to 10-membered monocyclic or bicyclic heterocycloalkyl ring, wherein one or two atoms in the heterocycloalkyl ring are independently nitrogen, oxygen, or sulfur). In certain embodiments, R is substituted or unsubstituted heterocyclyl (e.g., substituted or unsubstituted, 5- to 10-membered monocyclic or bicyclic heterocyclyl ring, wherein one or two atoms in the heterocyclic ring are independently nitrogen, oxygen, or sulfur). In certain embodiments, R is substituted or unsubstituted aryl (e.g., substituted or unsubstituted, 6- to 10-membered aryl). In certain embodiments, R is benzyl. In certain embodiments, R is substituted or unsubstituted phenyl. In certain embodiments, R is substituted or unsubstituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur).

In certain embodiments, J is a moiety of Formula (II) of formula:

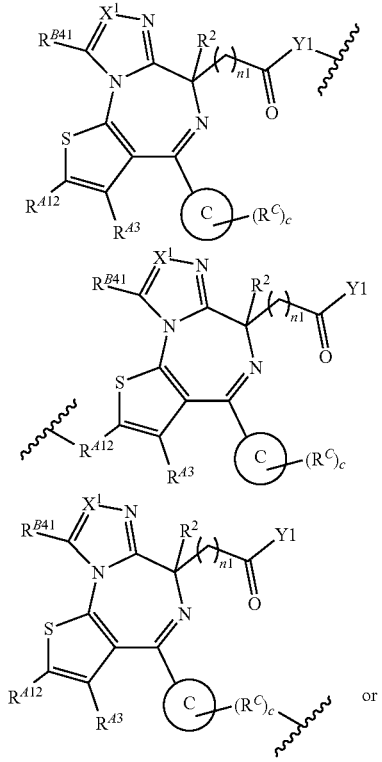

$R^{A41}$

Formula (V) includes substituent $R^{A41}$. In certain embodiments, $R^{A41}$ is independently alkyl, cycloalkyl, heterocycloalkyl, aryl, or heteroaryl, each of which is optionally substituted. In certain embodiments, any two $R^{A41}$ together with the atoms to which each is attached, can form a fused aryl or heteroaryl group. In certain embodiments, m is 0. In certain embodiments, m is 1. In certain embodiments, m is 2. In certain embodiments, m is 3.

Group R

Formula (V) includes group R. R is alkyl, cycloalkyl, heterocycloalkyl, aryl, or heteroaryl; each of which is optionally substituted.

In certain embodiments, R is substituted or unsubstituted alkyl (e.g., substituted or unsubstituted $C_{1-6}$ alkyl). In certain -continued
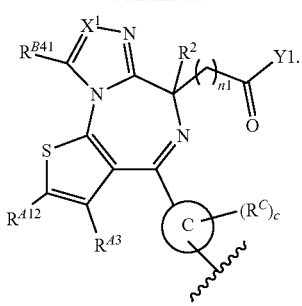
In certain embodiments, J is a moiety of Formula (II) of formula:
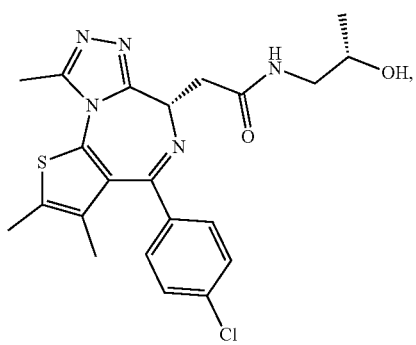
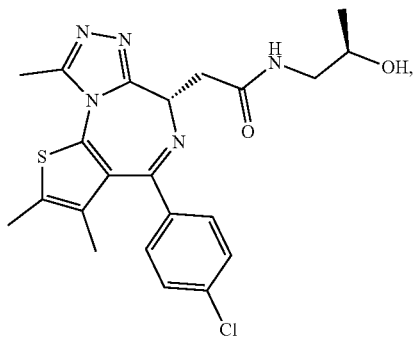
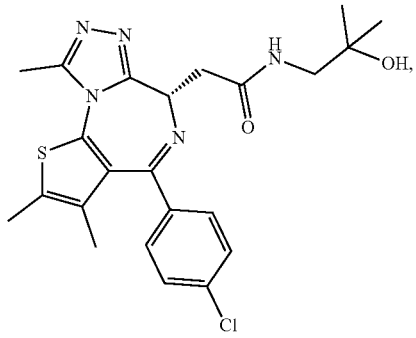
-continued
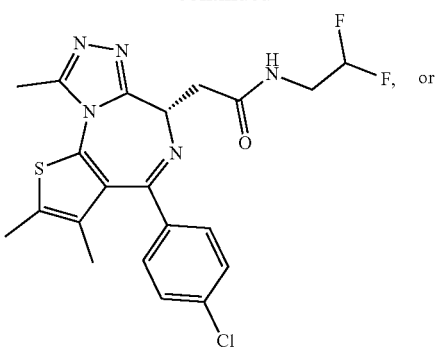
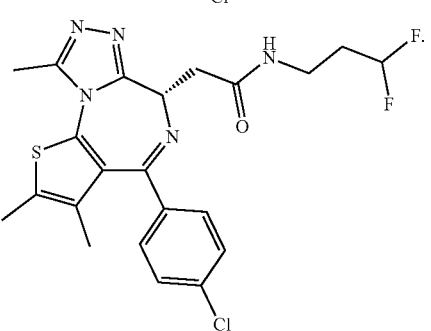
In certain embodiments, J is a moiety of Formula (II) of formula:
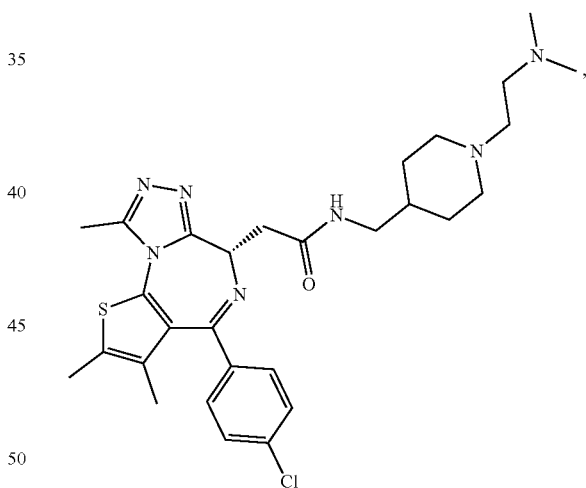
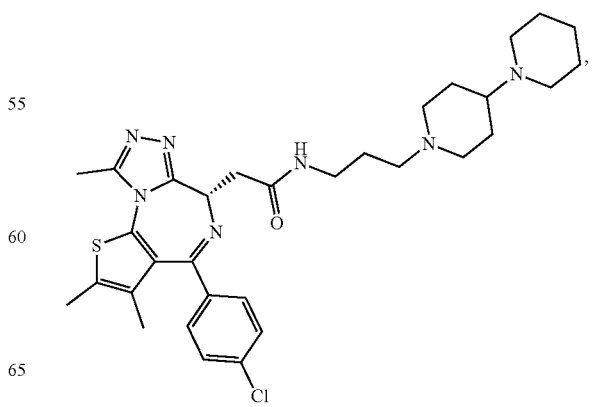

145
-continued
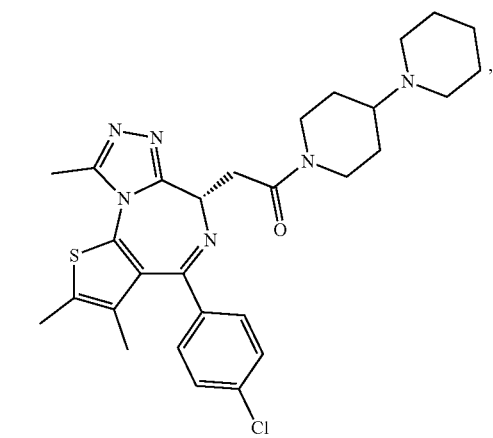
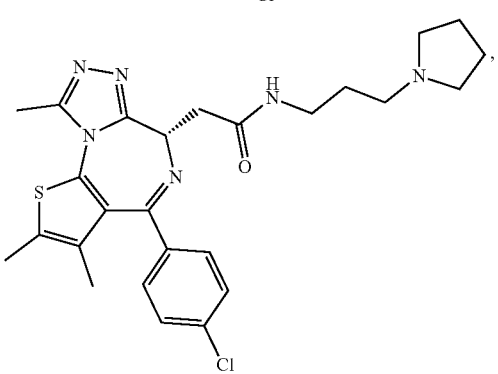
, or
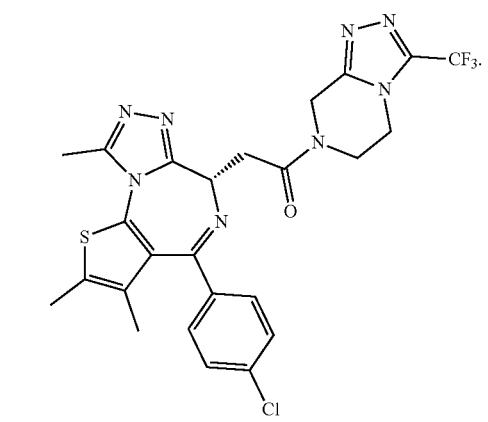
In certain embodiments, J is a moiety of Formula (III) of formula:
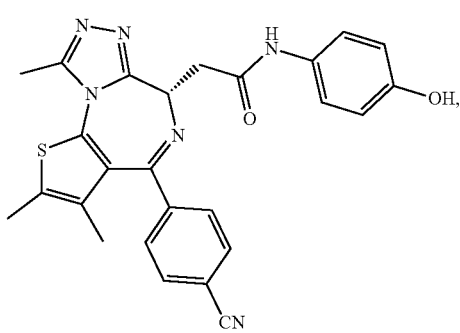
146
-continued
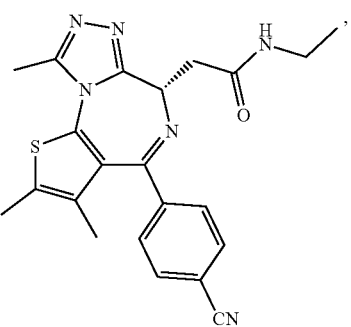
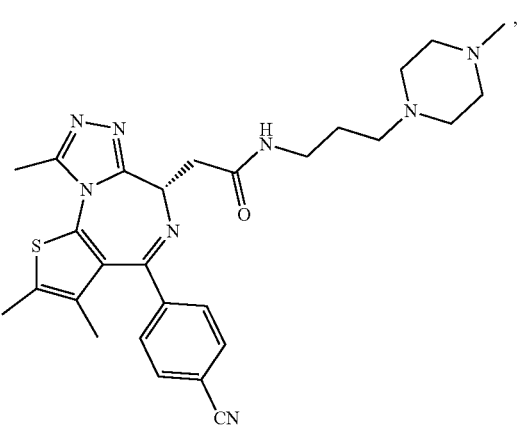
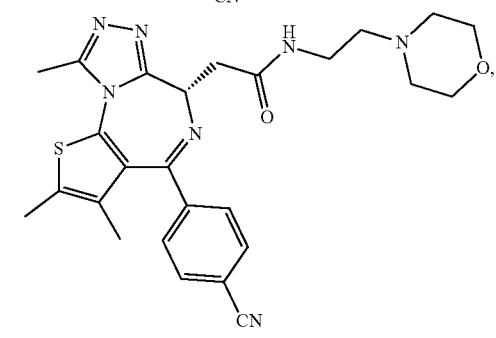
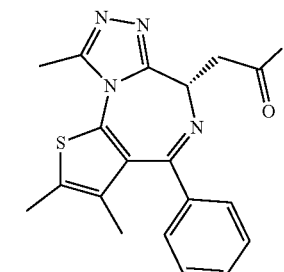
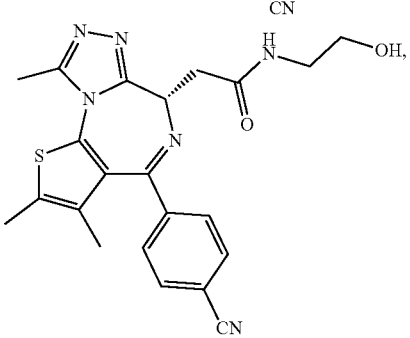

147
-continued
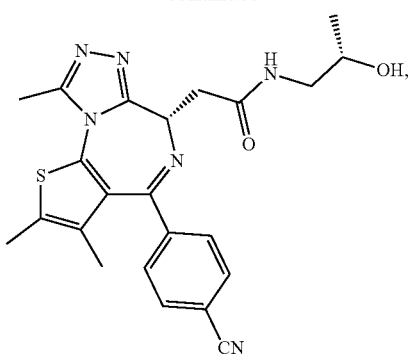
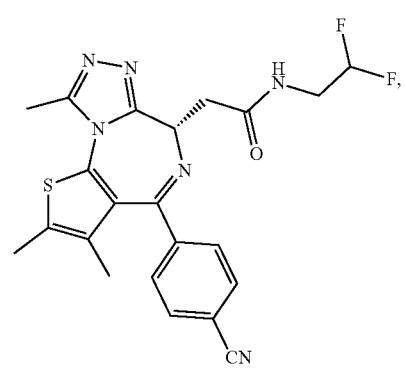
148
-continued
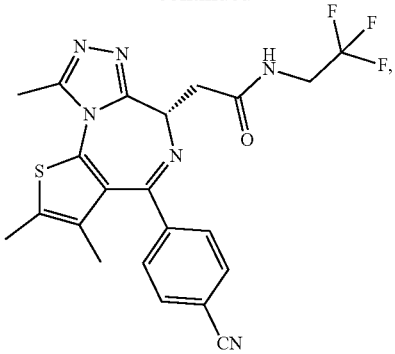
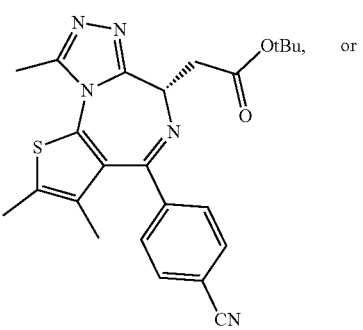
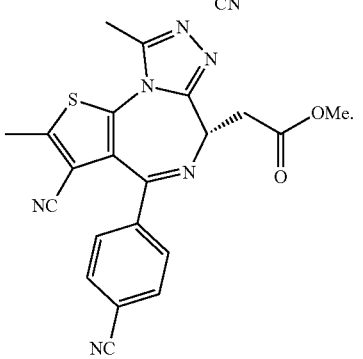
In certain embodiments, J is a moiety of Formula (IV) of formula:
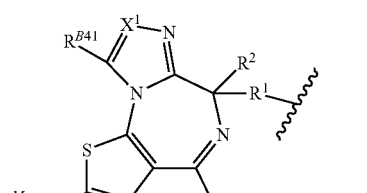
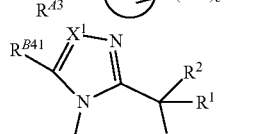
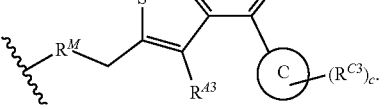

In certain embodiments, J is a moiety of Formula (IV) of formula:
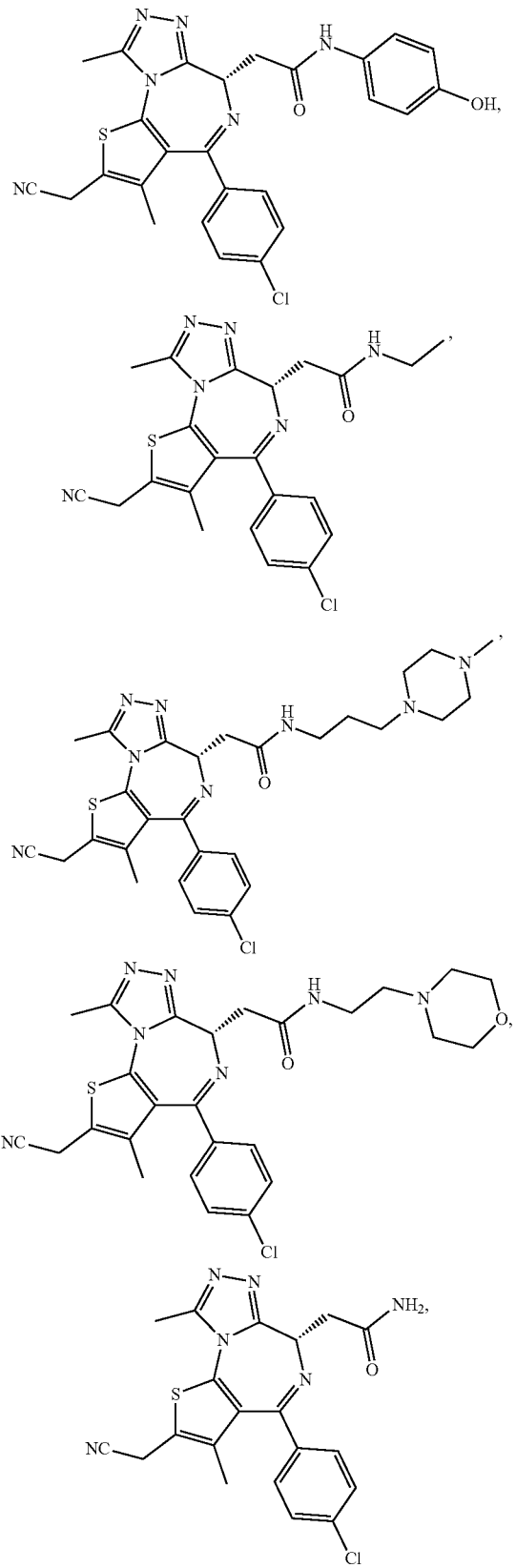
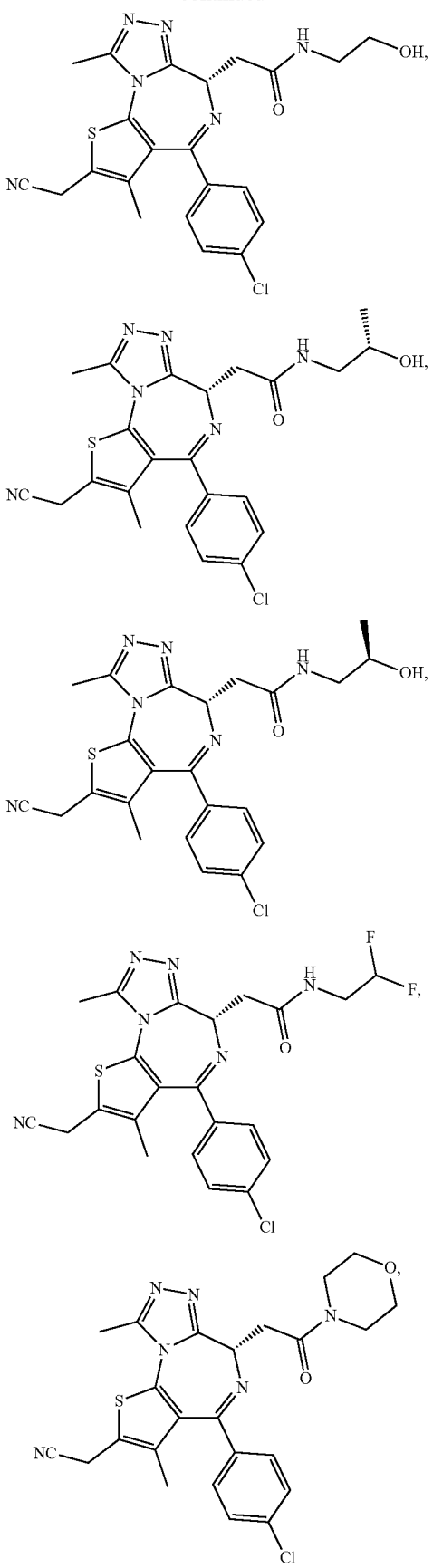

-continued
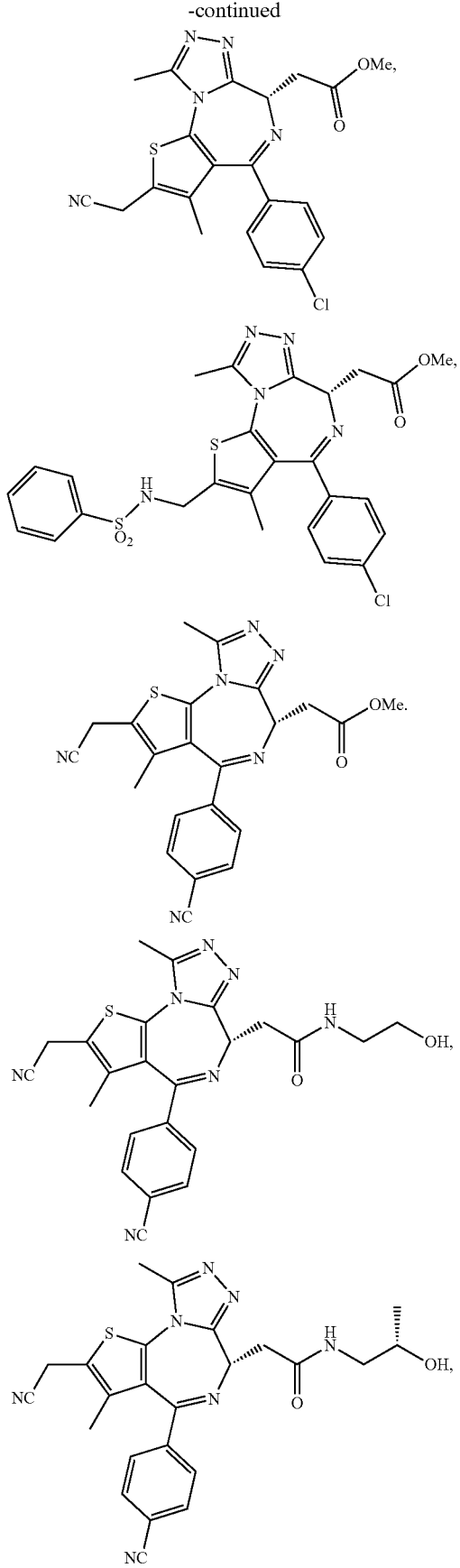
-continued
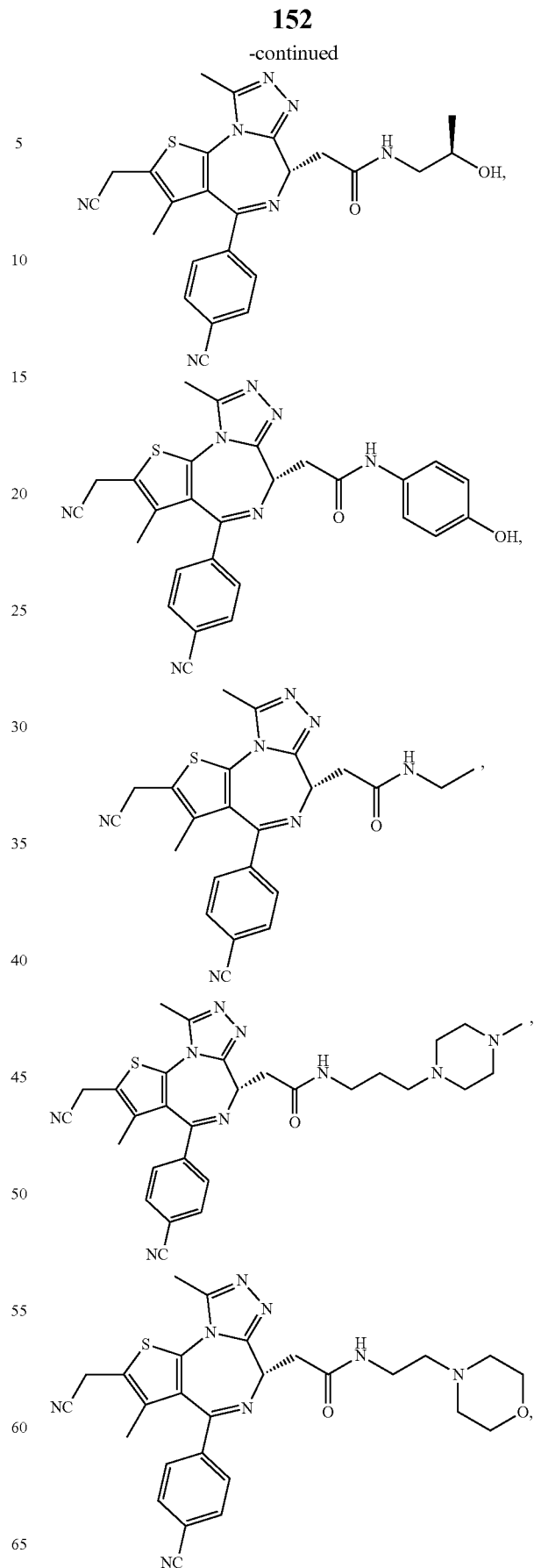

-continued
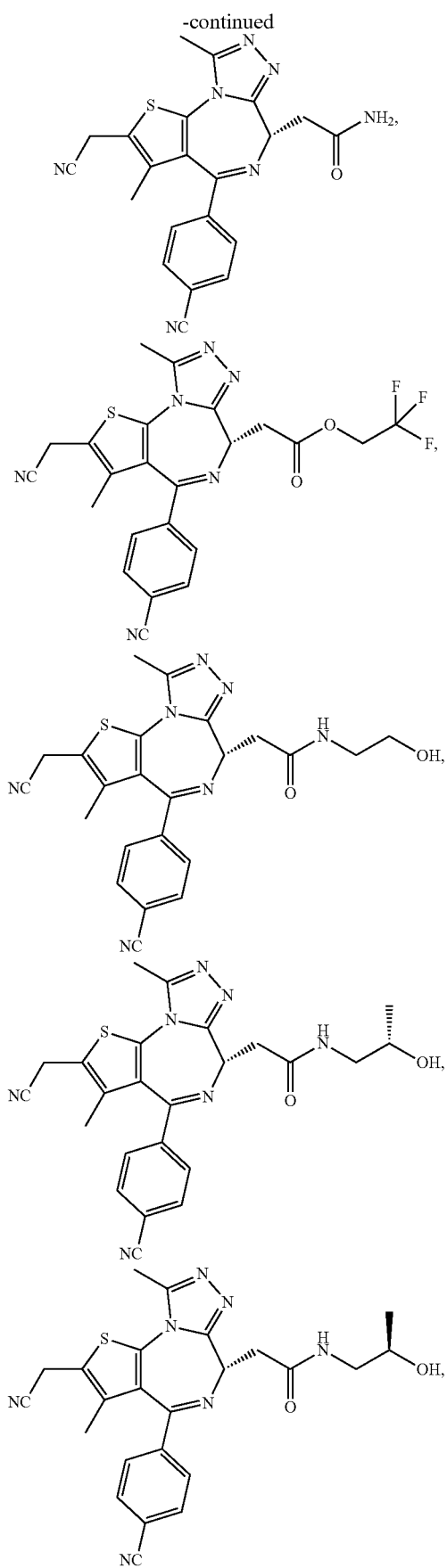
-continued
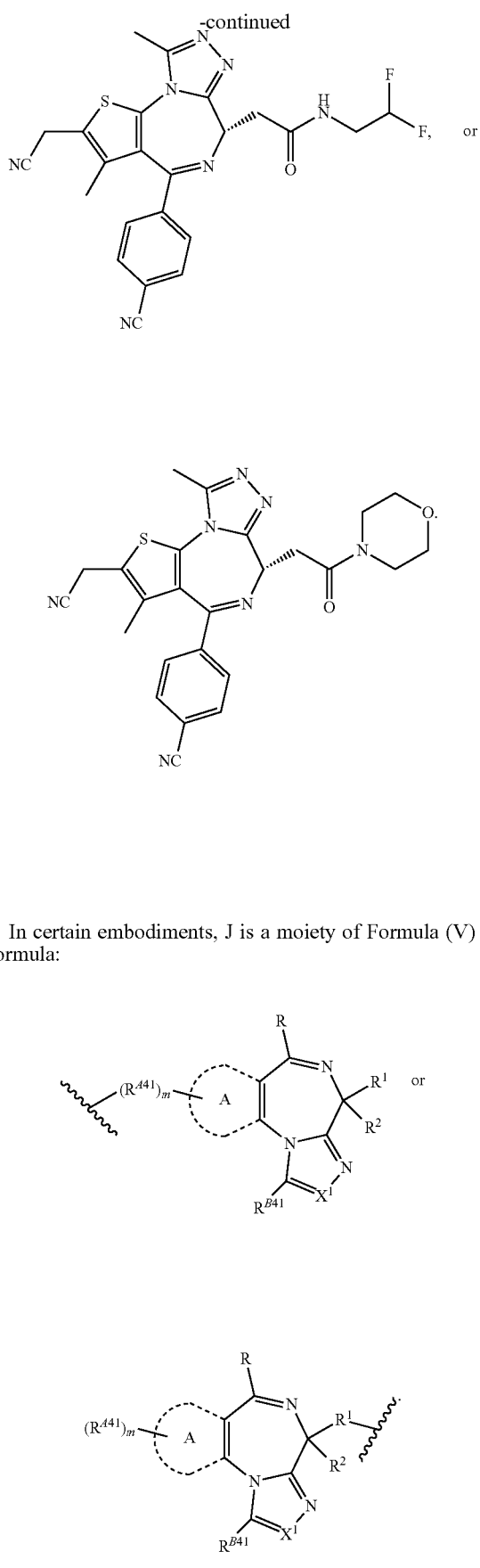
In certain embodiments, J is a moiety of Formula (V) of formula:

In certain embodiments, J is a moiety of Formula (V) of formula:
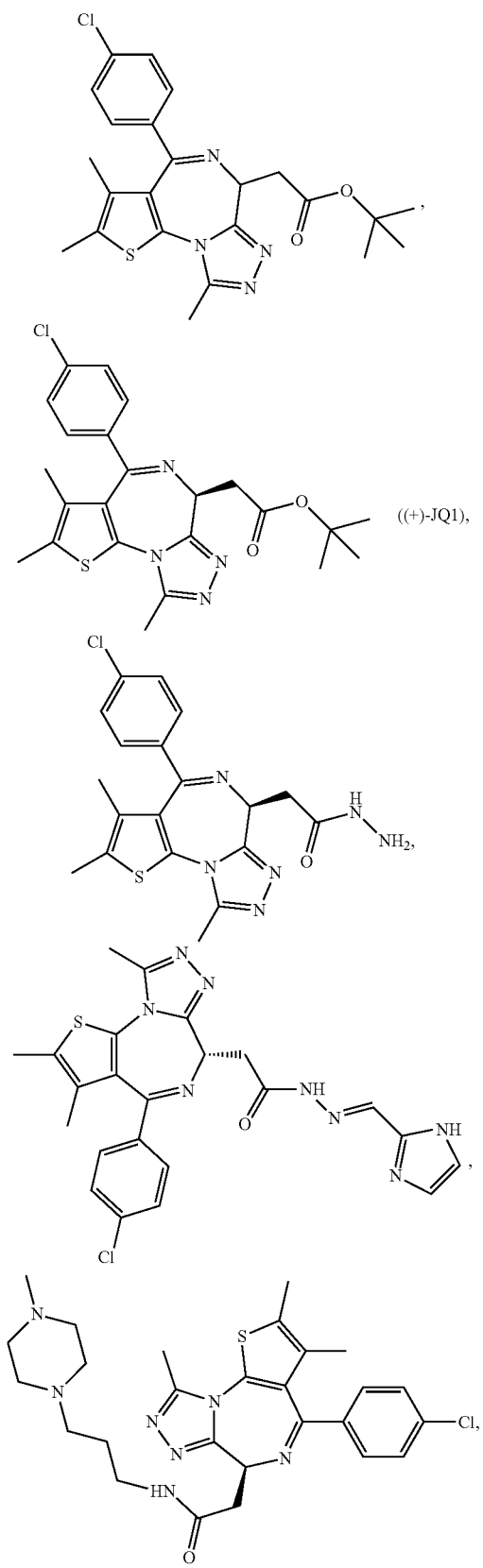
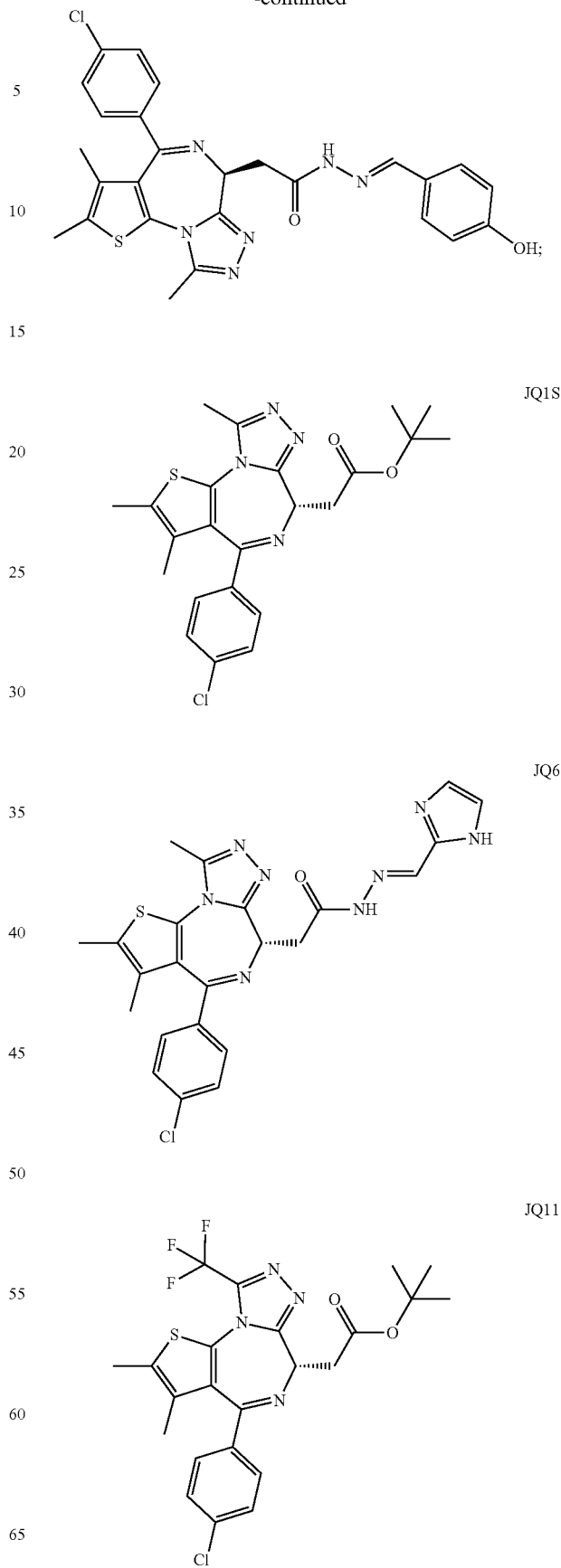

-continued
JQ1R
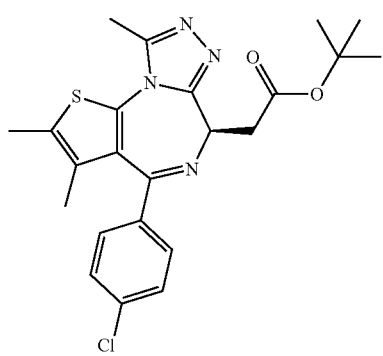
JQ19
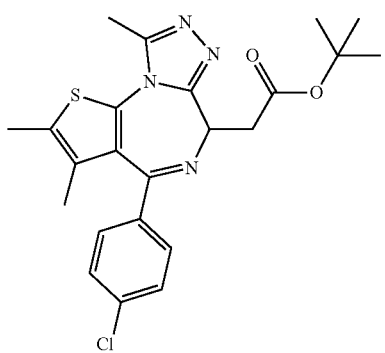
JQ13
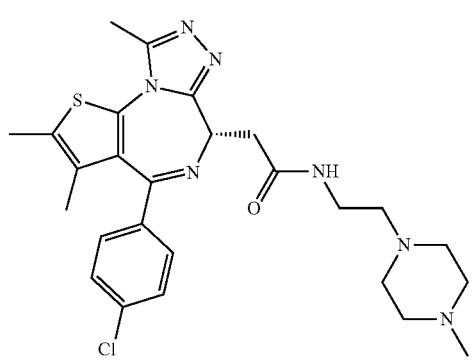
JQ24B
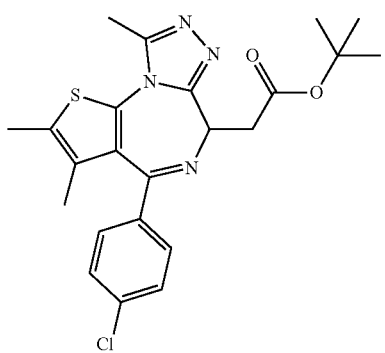
JQ21
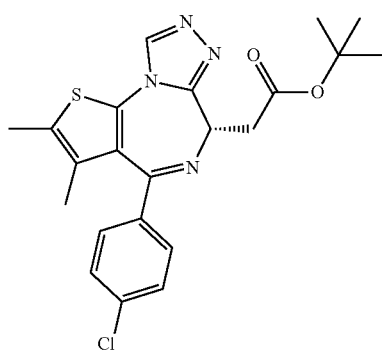
JQ8
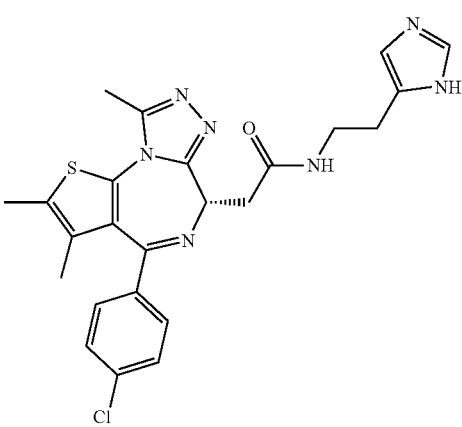
JQ20
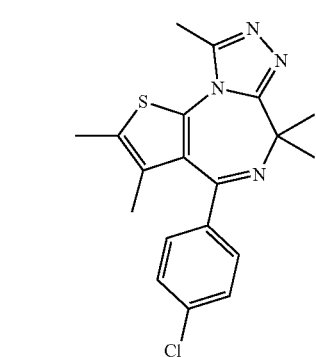
JQ18

159
-continued
160
-continued
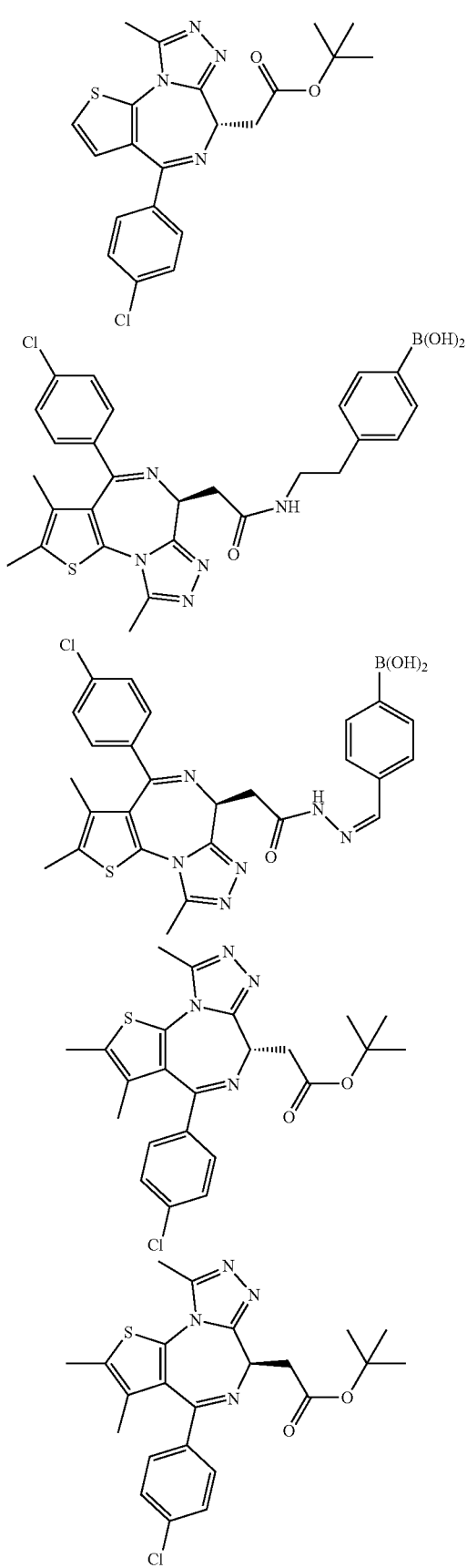
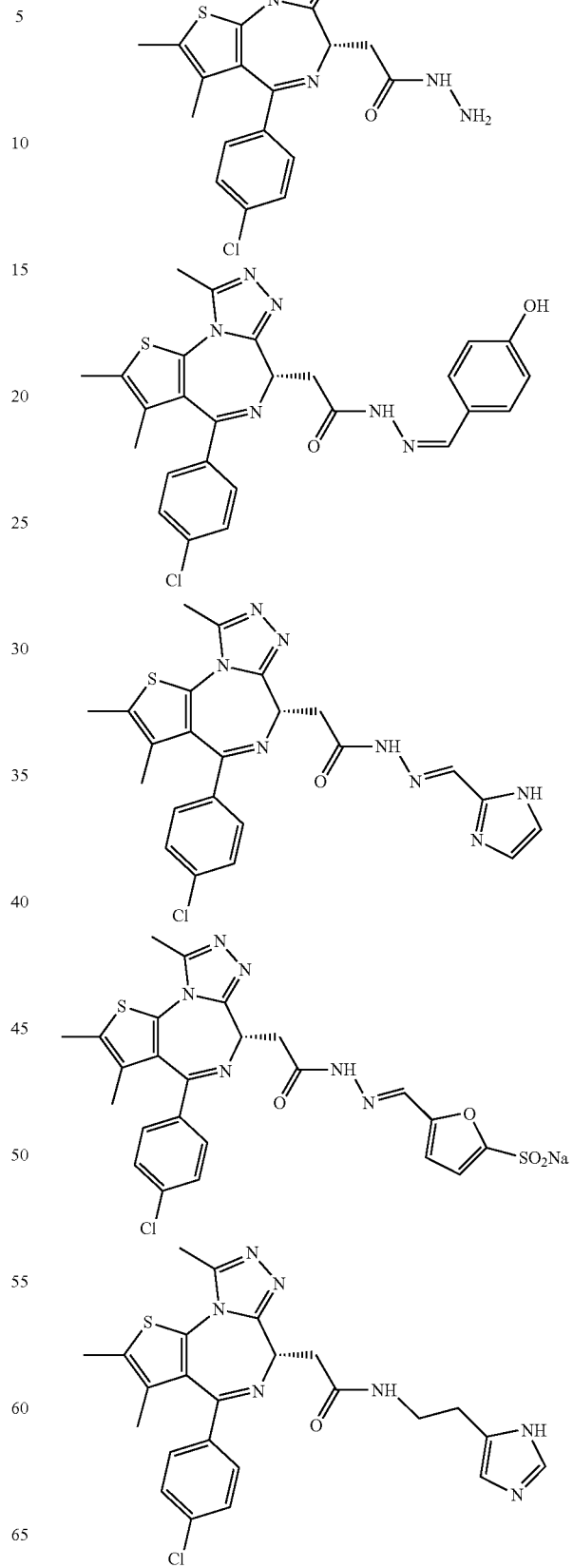

161
-continued
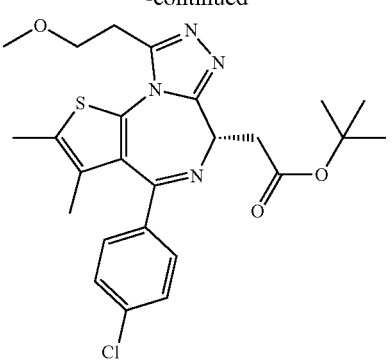
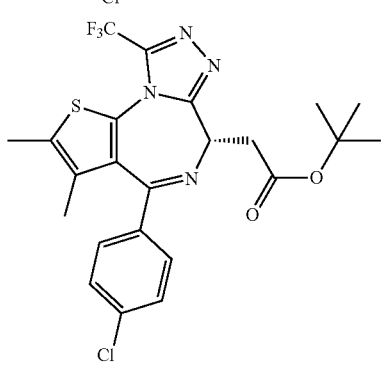
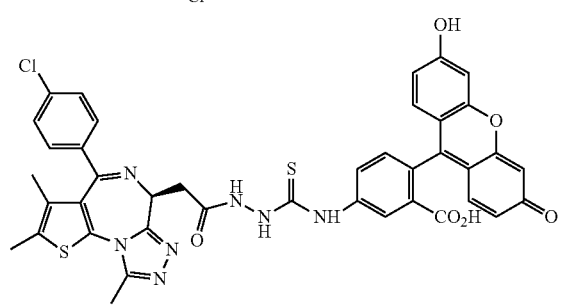
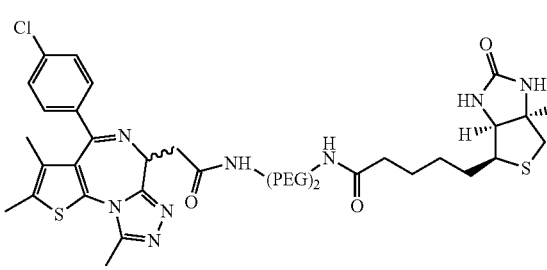
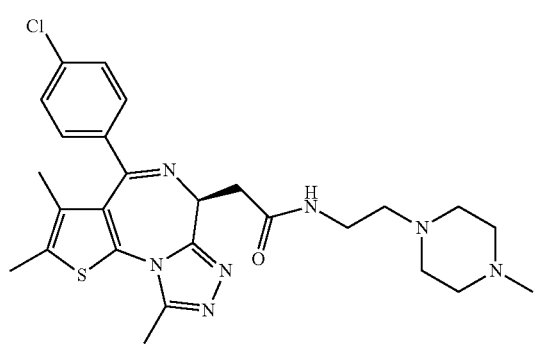
162
-continued
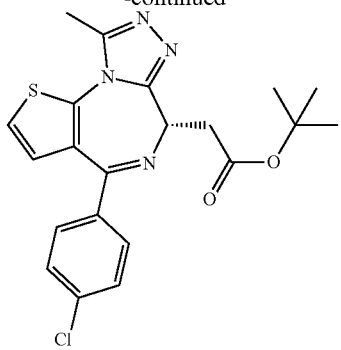
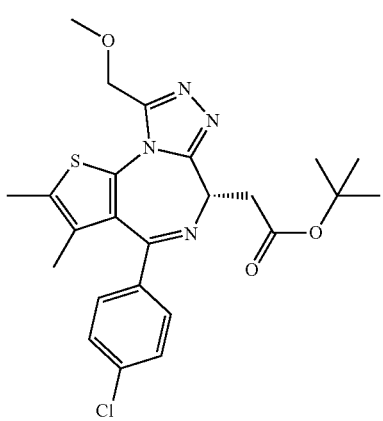
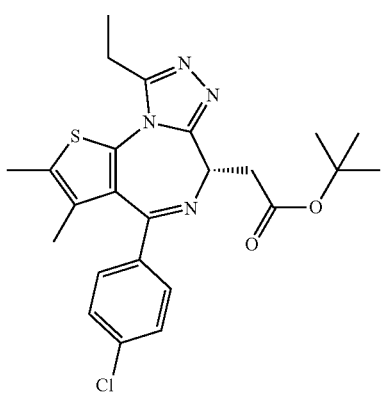
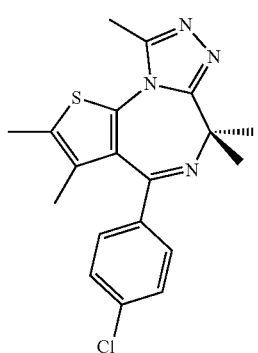

163
-continued
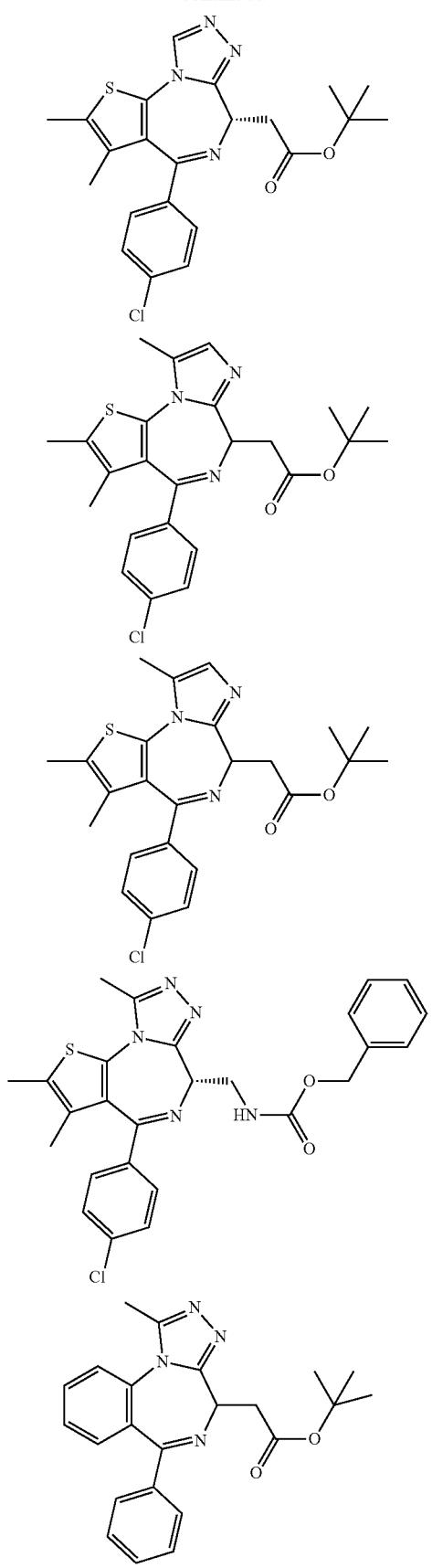
164
-continued
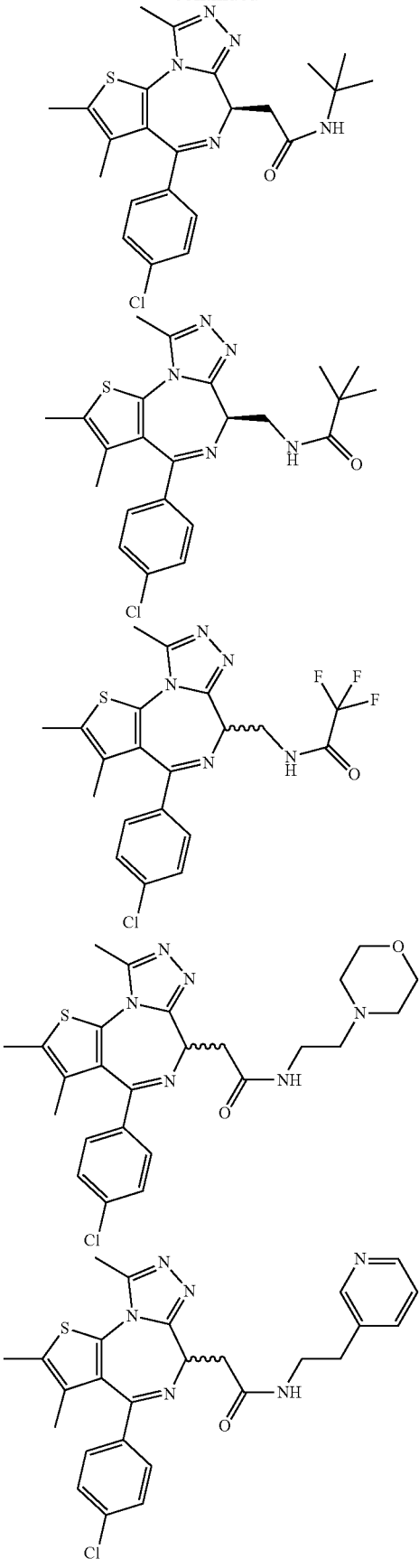

165
-continued
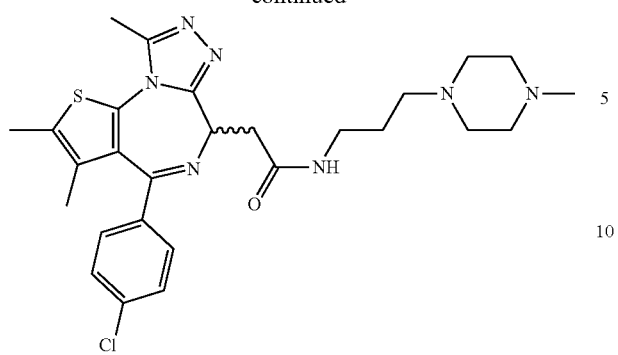
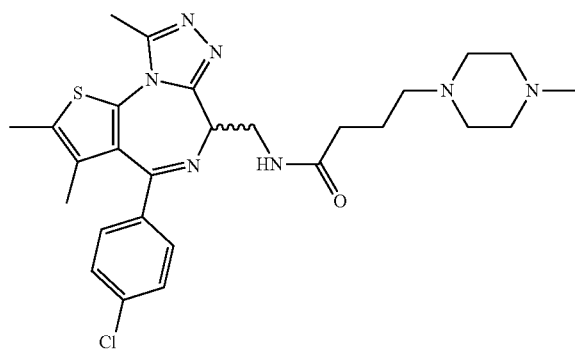
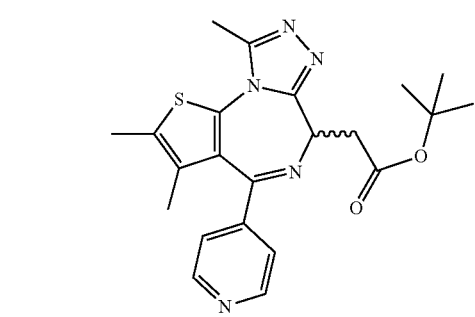
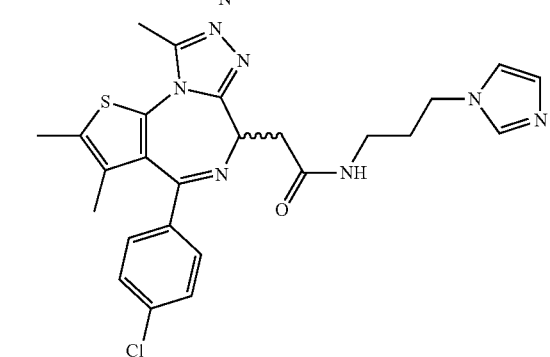
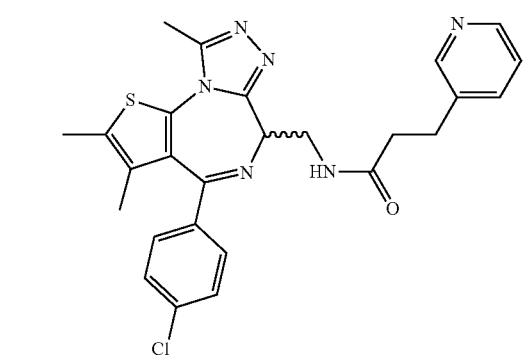
166
-continued
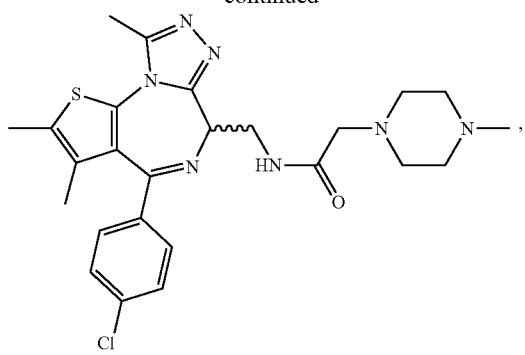
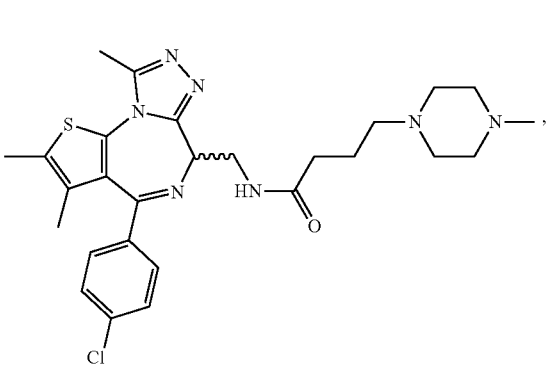
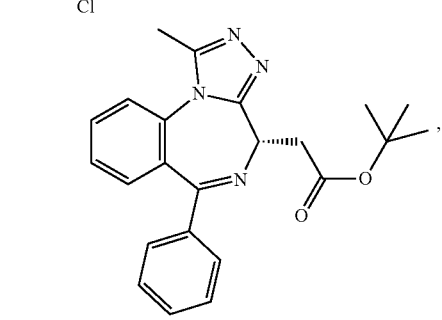
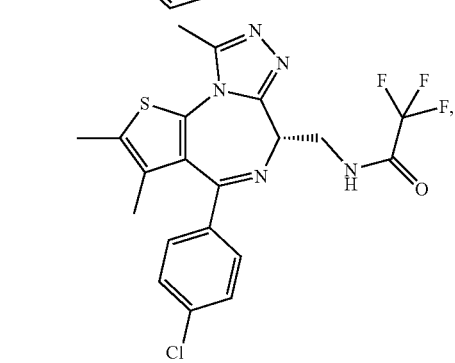
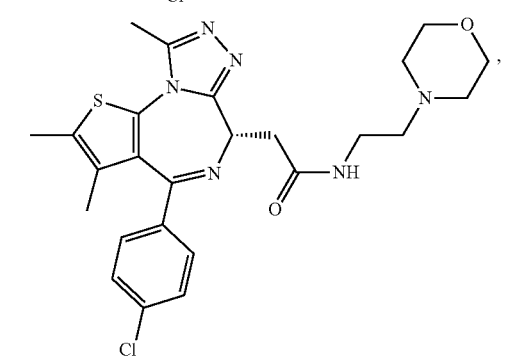

167
-continued
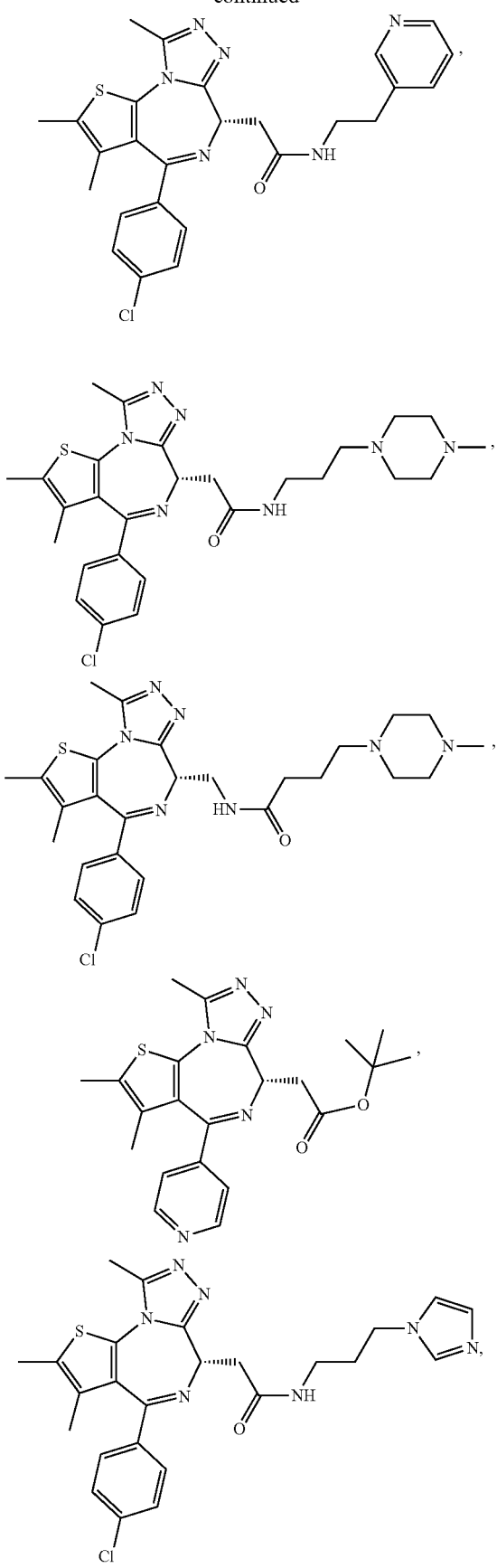
168
-continued
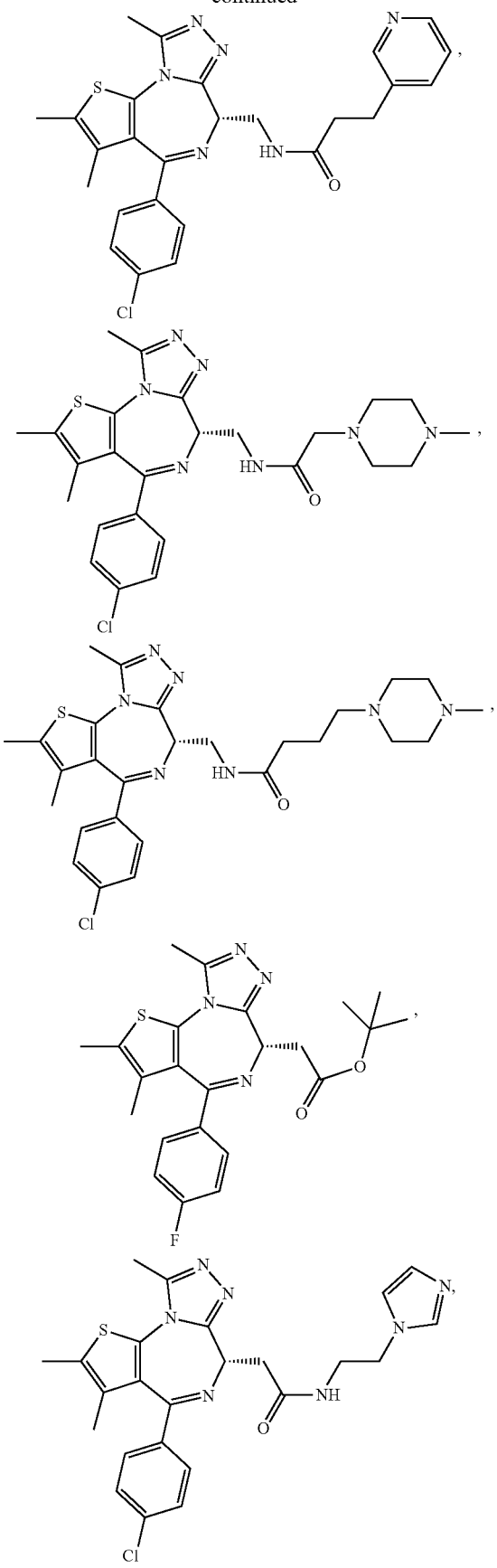

169
-continued
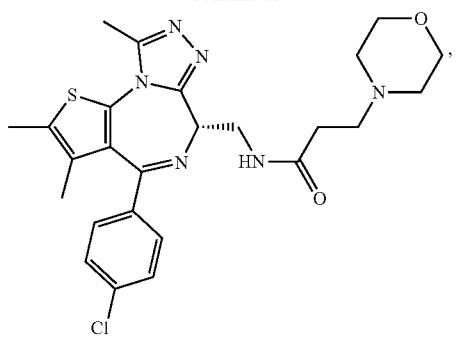
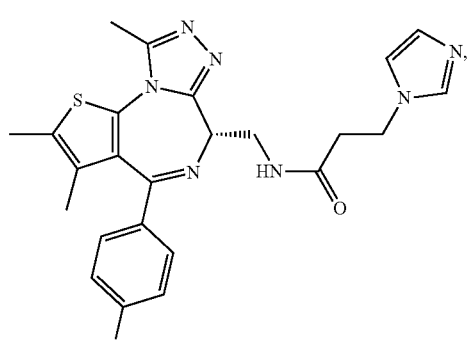
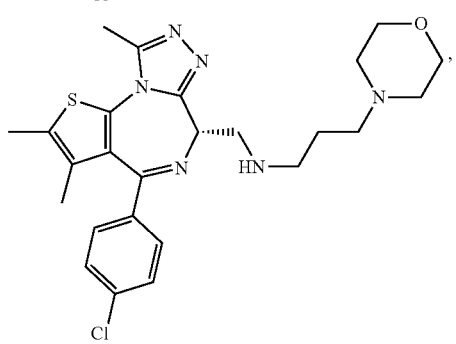
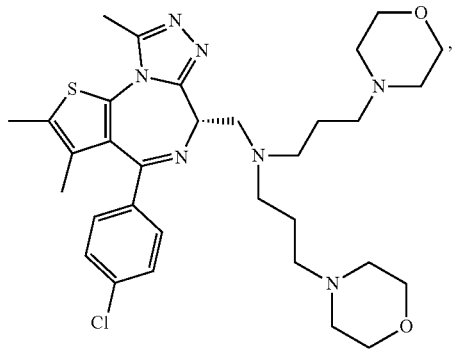
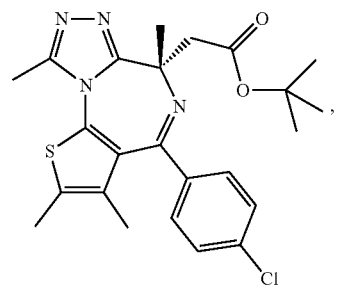
170
-continued
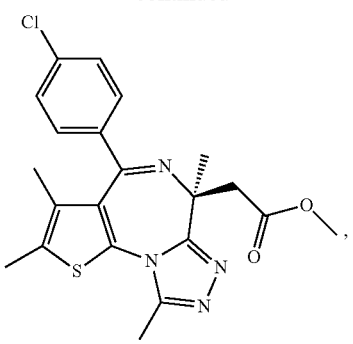
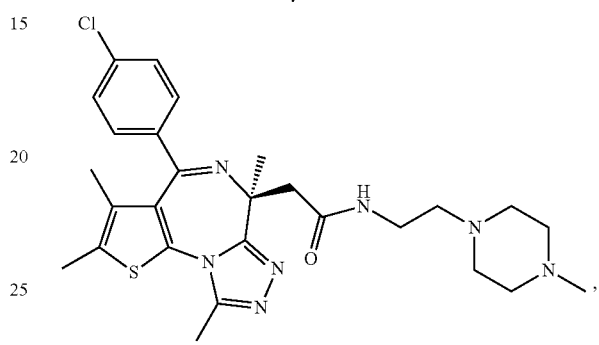
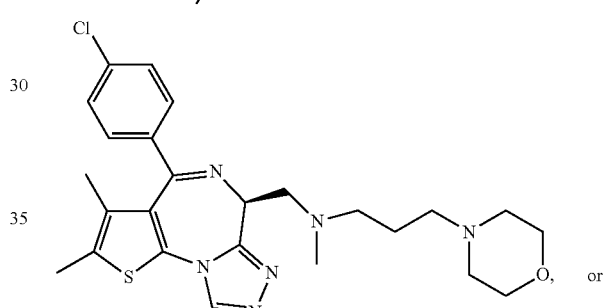
or
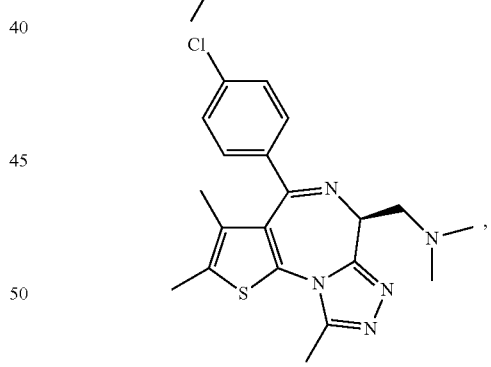
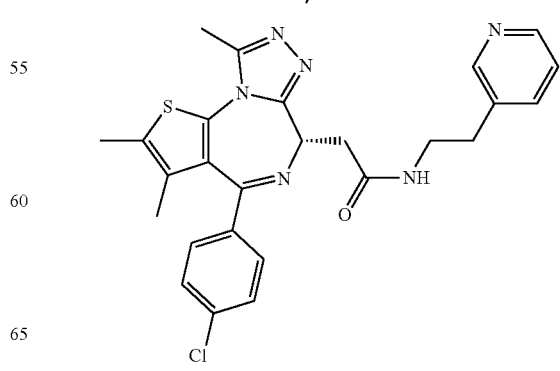

171
-continued
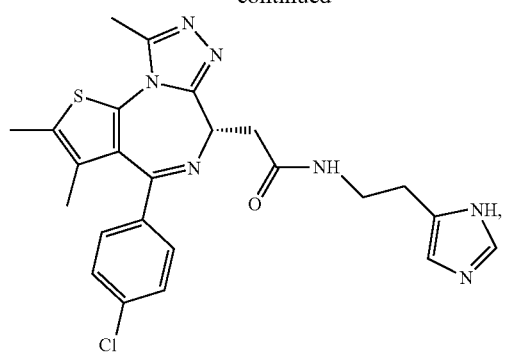
or
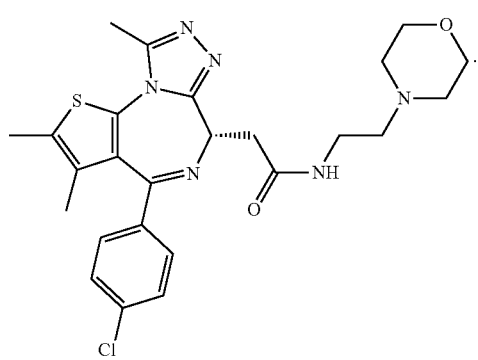
In certain embodiments, J is a moiety of formula:
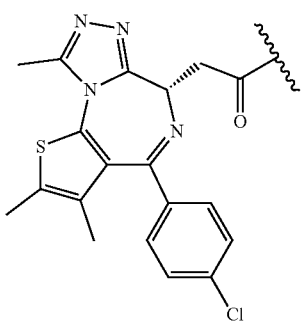
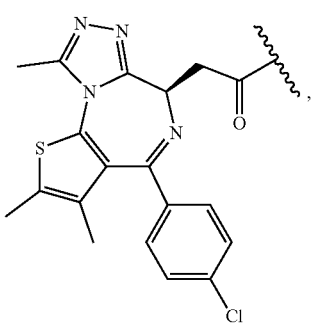
172
-continued
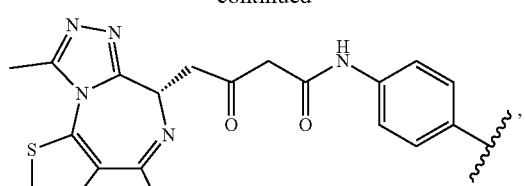
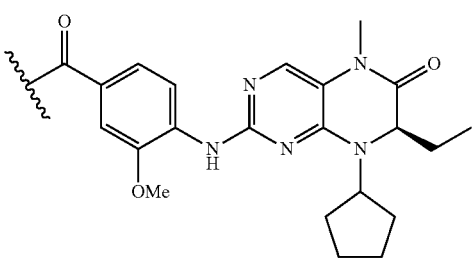
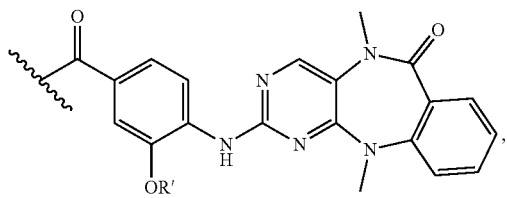, or
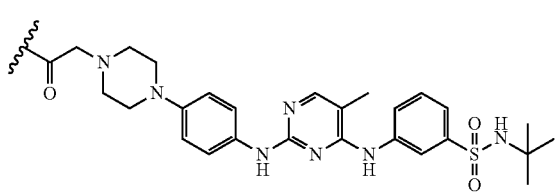
wherein:
each R' is independently methyl or ethyl.
In some embodiments, the linker L is attached to any position on the compound of Formulae (TL-I) through (TL-VII), as indicated by the attachment
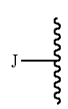
on the moiety of J.

In certain embodiments J is of Formula (TL-I):

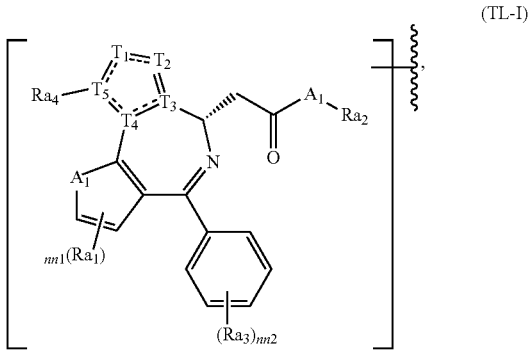

(TL-I)

or a pharmaceutically acceptable salt thereof, wherein:

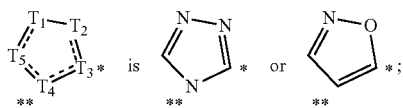

$A_1$ is S or C=C;
$A_2$ is $NR_{a5}$ or O;
nn1 is 0, 1, or 2;
each $Ra_1$ is independently $C_1$-$C_3$ alkyl, $(CH_2)_{0-3}$—CN, $(CH_2)_{0-3}$—halogen, $(CH_2)_{0-3}$—OH, $(CH_2)_{0-3}$—$C_1$-$C_3$ alkoxy, —C(O)$NRa_5$, —O—, $NRa_5$—;
$Ra_2$ is H, $C_1$-$C_6$ alkyl, $(CH_2)_{0-3}$-heterocyclyl, $(CH_2)_{0-3}$-phenyl, wherein the heterocyclyl comprises one saturated 5- or 6-membered ring and 1-2 heteroatoms selected from N, O, and S and is optionally substituted with $C_1$-$C_3$ alkyl, or C(O), and wherein the phenyl is optionally substituted with $C_1$-$C_3$ alkyl, CN, halogen, OH, $C_1$-$C_3$ alkoxy;
nn2 is 0, 1, 2, or 3;
each $Ra_3$ is independently $C_1$-$C_3$ alkyl, $(CH_2)_{0-3}$—CN, $(CH_2)_{0-3}$-halogen, or C(O)$NR_{a5}$—;
$Ra_4$ is $C_1$-$C_3$ alkyl; and
$Ra_5$ is H or $C_1$-$C_3$ alkyl.
In certain embodiments,

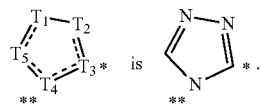

In certain embodiments,

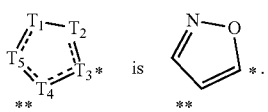

In certain embodiments, $A_1$ is S. In certain embodiments, $A_1$ is C=C.
In certain embodiments, $A_2$ is $NRa_5$. In further embodiments, $Ra_5$ is H. In other embodiments, $Ra_5$ is $C_1$-$C_3$ alkyl (e.g., methyl, ethyl, propyl, or i-propyl). In further embodiments, $Ra_5$ is methyl.

In certain embodiments, $A_2$ is O. In certain embodiments, nn1 is 0. In certain embodiments, nn1 is 0. In certain embodiments, nn1 is 2.

In certain embodiments, at least one $Ra_1$ is $C_1$-$C_3$ alkyl (e.g., methyl, ethyl, propyl, or i-propyl). In further embodiments, at least one $Ra_1$ is methyl. In further embodiments, two $Ra_1$ are methyl.

In certain embodiments, at least one $Ra_1$ is CN, $(CH_2)$—CN, $(CH_2)_2$—CN, or $(CH_2)_3$—CN. In further embodiments, at least one $Ra_1$ is $(CH_2)$—CN.

In certain embodiments, at least one $Ra_1$ is halogen (e.g., F, Cl, or Br), —$(CH_2)$-halogen, —$(CH_2)_2$-halogen, or —$(CH_2)_3$-halogen. In further embodiments, at least one $Ra_1$ is Cl, —$(CH_2)$—Cl, —$(CH_2)_2$—Cl, or —$(CH_2)_3$—Cl.

In certain embodiments, at least one $Ra_1$ is OH, —$(CH_2)$—OH, —$(CH_2)_2$—OH, or —$(CH_2)_3$—OH.

In certain embodiments, at least one $Ra_1$ is $C_1$-$C_3$ alkoxy (e.g., methoxy, ethoxy, or propoxy), —$(CH_2)$—$C_1$-$C_3$ alkoxy, —$(CH_2)_2$—$C_1$-$C_3$ alkoxy, or —$(CH_2)_3$—$C_1$-$C_3$ alkoxy. In certain embodiments, at least one $Ra_1$ is methoxy.

In certain embodiments, one $Ra_1$ is —C(O)$NRa_5$—. In certain embodiments, one $Ra_1$ is —C(O)$NRa_5$— and attached to L. In further embodiments, $Ra_5$ is H. In other embodiments, $Ra_5$ is $C_1$-$C_3$ alkyl (e.g., methyl, ethyl, propyl, or i-propyl).

In certain embodiments, one $Ra_1$ is —O—. In certain embodiments, one $Ra_1$ is —O— and attached to L. In certain embodiments, one $Ra_1$ is attached to L.

In certain embodiments, one $Ra_1$ is —$NRa_5$—. In certain embodiments, one $Ra_1$ is —$NRa_5$— and attached to L. In further embodiments, $Ra_5$ is H. In other embodiments, $Ra_5$ is $C_1$-$C_3$ alkyl (e.g., methyl, ethyl, propyl, or i-propyl). In other embodiments, $Ra_5$ is methyl.

In certain embodiments, $Ra_2$ is H. In certain embodiments, $Ra_2$ is straight-chain $C_1$-$C_6$ or branched $C_3$-$C_6$ alkyl (e.g., methyl, ethyl, propyl, i-propyl, butyl, i-butyl, t-butyl, pentyl, or hexyl). In further embodiments, $Ra_2$ is methyl, ethyl, or t-butyl. In certain embodiments, $Ra_2$ is heterocyclyl, —$(CH_2)$-heterocyclyl, —$(CH_2)_2$-heterocyclyl, or —$(CH_2)_3$-heterocyclyl. In further embodiments, $Ra_2$ is —$(CH_2)_3$-heterocyclyl. In further embodiments, the heterocyclyl is selected from pyrrolidinyl, pyrazolidinyl, imidazolidinyl, oxazolidinyl, isoxazolidinyl, thiazolidinyl, isothiazolidinyl, piperidinyl, piperazinyl, hexahydropyrimidinyl, morpholinyl, and thiomorpholinyl. In further embodiments, the heterocyclyl is piperazinyl. In certain embodiments, the heterocyclyl is substituted with $C_1$-$C_3$ alkyl (e.g., methyl, ethyl, propyl, or i-propyl). In certain embodiments, the heterocyclyl is substituted with C(O)—. In certain embodiments, the heterocyclyl is substituted with C(O)— and attached to L. In certain embodiments, the heterocyclyl is attached to L.

In certain embodiments, $Ra_2$ is phenyl, —$(CH_2)$-phenyl, —$(CH_2)_2$-phenyl, or —$(CH_2)_3$-phenyl. In further embodiments, $Ra_2$ is phenyl. In certain embodiments, the phenyl is substituted with $C_1$-$C_3$ alkyl (e.g., methyl, ethyl, propyl, or i-propyl). In certain embodiments, the phenyl is substituted with CN. In certain embodiments, the phenyl is substituted with halogen (e.g., F, Cl, or Br). In certain embodiments, the phenyl is substituted with OH. In certain embodiments, the phenyl is substituted with $C_1$-$C_3$ alkoxy (e.g., methoxy, ethoxy, or propoxy). In certain embodiments, the phenyl is attached to dL. In certain embodiments, $Ra_2$ is attached to L. In certain embodiments, nn2 is 0. In certain embodiments, nn2 is 1. In certain embodiments, nn2 is 2. In certain embodiments, nn2 is 3.

In certain embodiments, at least one $Ra_3$ is $C_1$-$C_3$ alkyl (e.g., methyl, ethyl, propyl, or i-propyl). In further embodiments, at least one $Ra_3$ is methyl. In certain embodiments, at least one $Ra_3$ is CN, —(CH$_2$)—CN, —(CH$_2$)$_2$—CN, or —(CH$_2$)$_3$—CN. In further embodiments, at least one $Ra_3$ is CN. In certain embodiments, at least one $Ra_3$ is halogen (e.g., F, Cl, or Br), —(CH$_2$)-halogen, —(CH$_2$)$_2$-halogen, or —(CH$_2$)$_3$-halogen. In further embodiments, at least one $Ra_3$ is Cl, —(CH$_2$)—Cl, —(CH$_2$)$_2$—Cl, or —(CH$_2$)$_3$—Cl. In further embodiments, at least one $Ra_3$ is Cl.

In certain embodiments, one $Ra_3$ is attached to L. In certain embodiments, one $Ra_3$ is —C(O)NRa$_5$—. In certain embodiments, one $Ra_3$ is —C(O)NRa$_5$— and attached to L. In further embodiments, $Ra_5$ is H. In other embodiments, $Ra_5$ is $C_1$-$C_3$ alkyl (e.g., methyl, ethyl, propyl, or i-propyl). In certain embodiments, $Ra_4$ is $C_1$-$C_3$ alkyl (e.g., methyl, ethyl, propyl, or i-propyl). In further embodiments, $Ra_4$ is methyl.

In certain embodiments, $Ra_5$ is H. In certain embodiments, $Ra_5$ is $C_1$-$C_3$ alkyl (e.g., methyl, ethyl, propyl, or i-propyl). In further embodiments, $Ra_5$ is methyl.

Each of the moieties defined for one of $T_1$, $T_2$, $T_3$, $T_4$, $T_5$, $A_1$, $A_2$, $Ra_1$, $Ra_2$, $Ra_3$, $Ra_4$, $Ra_5$, nn1, and nn2, can be combined with any of the moieties defined for the others of $T_1$, $T_2$, $T_3$, $T_4$, $T_5$, $A_1$, $A_2$, $Ra_1$, $Ra_2$, $Ra_3$, $Ra_4$, $Ra_5$, nn1, and nn2.

In certain embodiments,

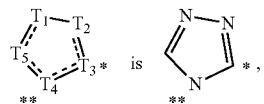

and $A_1$ is S. In certain embodiments,

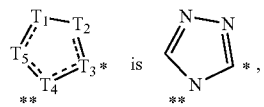

and $A_1$ is C=C. In certain embodiments,

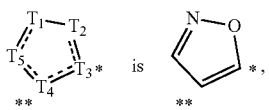

and $A_1$ is C=C.

In certain embodiments, $A_2$ is NH, and $Ra_2$ is —(CH$_2$)$_{0-3}$-heterocyclyl. In further embodiments, $Ra_2$ is —(CH$_2$)$_3$-heterocyclyl. In further embodiments, the heterocyclyl is piperazinyl. In further embodiments, the heterocyclyl is substituted with $C_1$-$C_3$ alkyl, attached to L, or C(O) and attached to L.

In certain embodiments, $A_2$ is NH, and $Ra_2$ is —(CH$_2$)$_{0-3}$-phenyl. In further embodiments, $Ra_2$ is phenyl. In further embodiments, the phenyl is substituted with OH or attached to L.

In certain embodiments, $A_2$ is NH, and $Ra_2$ is attached to L. In certain embodiments, $A_2$ is NH, and $Ra_2$ is H or $C_1$-$C_6$ alkyl. In further embodiments, $Ra_2$ is $C_1$-$C_4$ alkyl. In certain embodiments, $A_2$ is O, and $Ra_2$ is H or $C_1$-$C_6$ alkyl. In further embodiments, $Ra_2$ is $C_1$-$C_4$ alkyl.

In certain embodiments, J is of Formula (TL-I1):

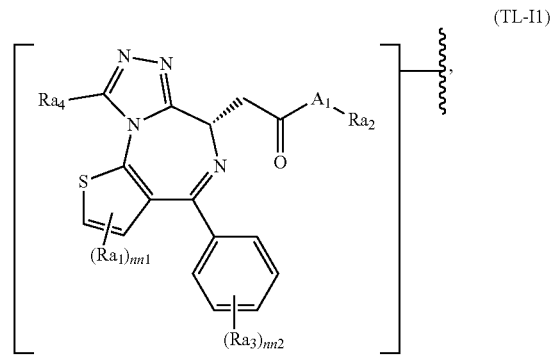

(TL-I1)

or a pharmaceutically acceptable salt thereof, wherein A2, Ra1, Ra2, Ra3, Ra4, Ra5, nn1, and nn2 are each as defined above in Formula (TL-I).

Each of $A_2$, $Ra_1$, $Ra_2$, $Ra_3$, $Ra_4$, $Ra_5$, nn1, and nn2 may be selected from the moieties described above for Formula (TL-I). Each of the moieties defined for one of $A_2$, $Ra_1$, $Ra_2$, $Ra_3$, $Ra_4$, $Ra_5$, nn1, and nn2, can be combined with any of the moieties defined for the others of $A_2$, $Ra_1$, $Ra_2$, $Ra_3$, $Ra_4$, $Ra_5$, nn1, and nn2, as described above in Formula (TL-I).

In certain embodiments, J is a compound of Formulae (TL-I1a)-(TL-I1d):

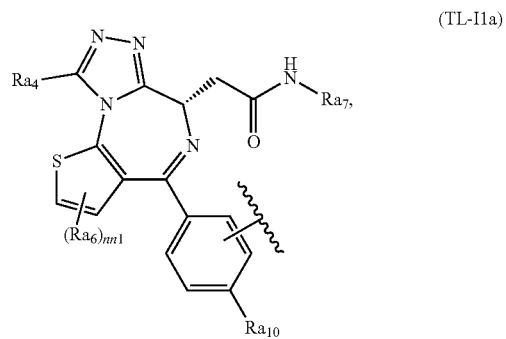

(TL-I1a)

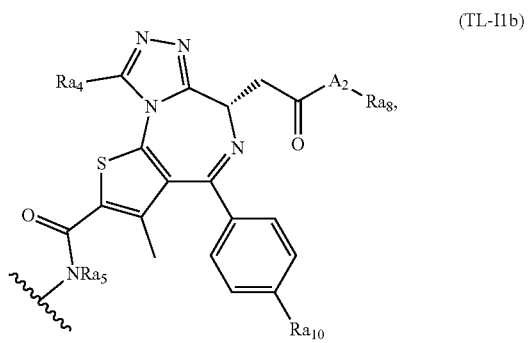

(TL-I1b)

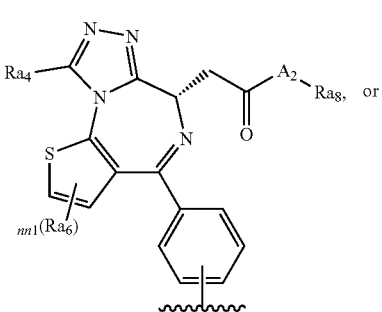

(TL-IId)

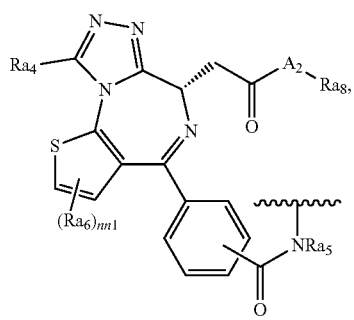

or a pharmaceutically acceptable salt thereof, wherein:
  each $Ra_6$ is independently $C_1$-$C_3$ alkyl, —$(CH_2)_{0-3}$—CN, —$(CH_2)_{0-3}$-halogen, —$(CH_2)_{0-3}$—OH, or —$(CH_2)_{0-3}$—$C_1$-$C_3$ alkoxy;
  $Ra_7$ is —$(CH_2)_{0-3}$-heterocyclyl, —$(CH_2)_{0-3}$-phenyl, or attached to L, wherein the heterocyclyl comprises one saturated 5- or 6-membered ring and 1-2 heteroatoms selected from N, O, and S and is attached to L or —C(O)—, and wherein the phenyl is attached to L;
  $Ra_8$ is H, $C_1$-$C_6$ alkyl, —$(CH_2)_{0-3}$-heterocyclyl, or —$(CH_2)_{0-3}$-phenyl, wherein the heterocyclyl comprises one saturated 5- or 6-membered ring and 1-2 heteroatoms selected from N, O, and S and is optionally substituted with $C_1$-$C_3$ alkyl, and wherein the phenyl is optionally substituted with $C_1$-$C_3$ alkyl, CN, halogen, OH, or $C_1$-$C_3$ alkoxy;
  $Ra_{10}$ is $C_1$-$C_3$ alkyl, —$(CH_2)_{0-3}$—CN, or —$(CH_2)_{0-3}$-halogen; and
  $A_2$, $Ra_4$, $Ra_5$, and nn1 are each as defined above in Formula (TL-I).

In certain embodiments, nn1 is 0. In certain embodiments, nn1 is 1. In certain embodiments, nn1 is 2.

In certain embodiments, at least one $Ra_6$ is $C_1$-$C_3$ alkyl (e.g., methyl, ethyl, propyl, or i-propyl). In further embodiments, at least one $Ra_6$ is methyl. In further embodiments, two $Ra_6$ are methyl. In certain embodiments, at least one $Ra_6$ is CN, —$(CH_2)$—CN, —$(CH_2)_2$—CN, or —$(CH_2)_3$—CN. In further embodiments, at least one $Ra_6$ is —$(CH_2)$—CN. In certain embodiments, at least one $Ra_6$ is halogen (e.g., F, Cl, or Br), —$(CH_2)$-halogen, $(CH_2)_2$-halogen, or $(CH_2)_3$-halogen. In further embodiments, at least one $Ra_6$ is Cl, —$(CH_2)$—Cl, —$(CH_2)_2$—Cl, or —$(CH_2)_3$—Cl. In certain embodiments, at least one $Ra_6$ is OH, —$(CH_2)$—OH, —$(CH_2)_2$—OH, or —$(CH_2)_3$—OH. In certain embodiments, at least one $Ra_6$ is $C_1$-$C_3$ alkoxy (e.g., methoxy, ethoxy, or propoxy), —$(CH_2)$—$C_1$-$C_3$ alkoxy, —$(CH_2)_2$—$C_1$-$C_3$ alkoxy, or —$(CH_2)_3$—$C_1$-$C_3$ alkoxy. In certain embodiments, at least one $Ra_6$ is methoxy.

In certain embodiments, $Ra_7$ is heterocyclyl, —$(CH_2)$-heterocyclyl, —$(CH_2)_2$-heterocyclyl, or —$(CH_2)_3$-heterocyclyl. In further embodiments, $Ra_7$ is —$(CH_2)_3$-heterocyclyl.

In further embodiments, the heterocyclyl is selected from pyrrolidinyl, pyrazolidinyl, imidazolidinyl, oxazolidinyl, isoxazolidinyl, thiazolidinyl, isothiazolidinyl, piperidinyl, piperazinyl, hexahydropyrimidinyl, morpholinyl, and thiomorpholinyl. In further embodiments, the heterocyclyl is piperazinyl. In certain embodiments, the heterocyclyl is substituted with C(O) and attached to L. In certain embodiments, the heterocyclyl is attached to L.

In certain embodiments, $Ra_7$ is phenyl, —$(CH_2)$-phenyl, —$(CH_2)_2$-phenyl, or —$(CH_2)_3$-phenyl. In further embodiments, $Ra_7$ is phenyl. In certain embodiments, $Ra_7$ is attached to L.

In certain embodiments, $Ra_8$ is H. In certain embodiments, $Ra_8$ is straight-chain $C_1$-$C_6$ or branched $C_3$-$C_6$ alkyl (e.g., methyl, ethyl, propyl, i-propyl, butyl, i-butyl, t-butyl, pentyl, or hexyl). In further embodiments, $Ra_8$ is methyl, ethyl, or t-butyl. In certain embodiments, $Ra_8$ is heterocyclyl, —$(CH_2)$-heterocyclyl, —$(CH_2)_2$-heterocyclyl, or —$(CH_2)_3$-heterocyclyl. In further embodiments, $Ra_8$ is —$(CH_2)_3$-heterocyclyl. In further embodiments, the heterocyclyl is selected from pyrrolidinyl, pyrazolidinyl, imidazolidinyl, oxazolidinyl, isoxazolidinyl, thiazolidinyl, isothiazolidinyl, piperidinyl, piperazinyl, hexahydropyrimidinyl, morpholinyl, and thiomorpholinyl. In further embodiments, the heterocyclyl is piperazinyl. In certain embodiments, the heterocyclyl is substituted with $C_1$-$C_3$ alkyl (e.g., methyl, ethyl, propyl, or i-propyl).

In certain embodiments, $Ra_8$ is phenyl, —$(CH_2)$-phenyl, —$(CH_2)_2$-phenyl, or —$(CH_2)_3$-phenyl. In further embodiments, $Ra_8$ is phenyl. In certain embodiments, the phenyl is substituted with $C_1$-$C_3$ alkyl (e.g., methyl, ethyl, propyl, or i-propyl). In certain embodiments, the phenyl is substituted with CN. In certain embodiments, the phenyl is substituted with halogen (e.g., F, Cl, or Br). In certain embodiments, the phenyl is substituted with OH. In certain embodiments, the phenyl is substituted with $C_1$-$C_3$ alkoxy (e.g., methoxy, ethoxy, or propoxy).

In certain embodiments, $Ra_{10}$ is $C_1$-$C_3$ alkyl (e.g., methyl, ethyl, propyl, or i-propyl).

In certain embodiments, $Ra_{10}$ is CN, —$(CH_2)$—CN, —$(CH_2)_2$—CN, or —$(CH_2)_3$—CN. In certain embodiments, $Ra_{10}$ is halogen (e.g., F, Cl, or Br), —$(CH_2)$-halogen, —$(CH_2)_2$-halogen, or $(CH_2)_3$-halogen. In further embodiments, $Ra_{10}$ is Cl, —$(CH_2)$—Cl, —$(CH_2)_2$—Cl, or —$(CH_2)_3$—Cl. In further embodiments, $Ra_{10}$ is Cl.

Each of $A_2$, $Ra_4$, $Ra_5$, and nn1 may be selected from the moieties described above in Formula (TL-I). Each of the moieties defined for one of $A_2$, $Ra_4$, $Ra_5$, $Ra_6$, $Ra_7$, $Ra_8$, $Ra_{10}$ and nn1, can be combined with any of the moieties defined for the others of $A_2$, $Ra_4$, $Ra_5$, $Ra_6$, $Ra_7$, $Ra_8$, $Ra_{10}$, and nn1, as described above and in Formula (TL-I).

In certain embodiments, J is a compound of Formula (TL-I2):

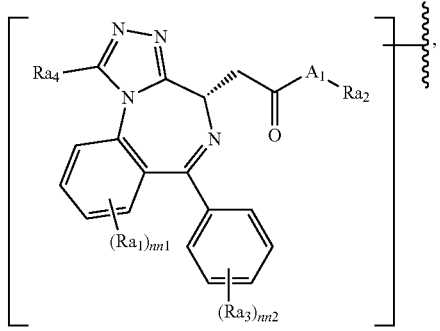

(TL-I2)

or a pharmaceutically acceptable salt thereof, wherein $A_2$, $Ra_1$, $Ra_2$, $Ra_3$, $Ra_4$, $Ra_5$, nn1, and nn2 are each as defined above in Formula (TL-I).

Each of $A_2$, $Ra_1$, $Ra_2$, $Ra_3$, $Ra_4$, $Ra_5$, nn1, and nn2 may be selected from the moieties described above in Formula (TL-I). Each of the moieties defined for one of $A_2$, $Ra_1$, $Ra_2$, $Ra_3$, $Ra_4$, $Ra_5$, nn1, and nn2, can be combined with any of the moieties defined for the others of $A_2$, $Ra_1$, $Ra_2$, $Ra_3$, $Ra_4$, $Ra_5$, nn1, and nn2, as described above in Formula (TL-I).

In certain embodiments, J is a compound of Formula (TL-12a)-(TL-12c):

(TL-I2a)

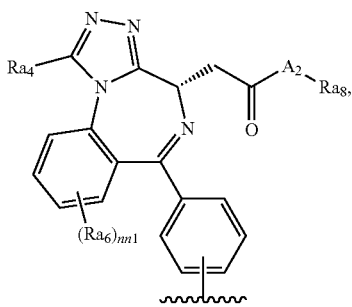

(TL-I2b)

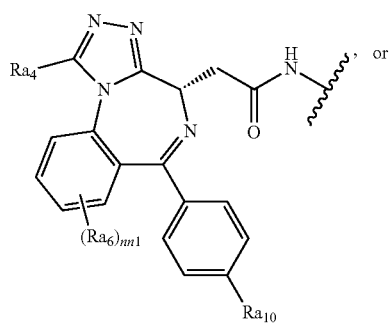

-continued (TL-I2c)

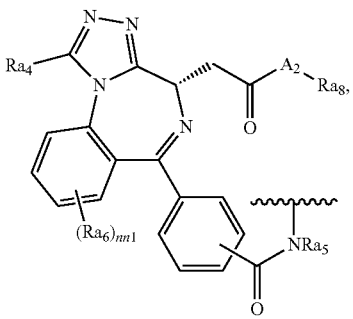

or a pharmaceutically acceptable salt thereof, wherein $A_2$, $Ra_4$, $Ra_5$, and nn1 are each as defined above in Formula (TL-I), and $Ra_6$, $Ra_7$, $Ra_8$, and $Ra_{10}$ are each as defined above in Formula (TL-I1a)-(TL-I1d).

Each of $A_2$, $Ra_4$, $Ra_5$, and nn1 may be selected from the moieties described above in Formula (TL-I), and each of $Ra_6$, $Ra_7$, $Ra_8$, and $Ra_{10}$ may be selected from the moieties described above in Formula (TL-I1a)-(TL-I1d). Each of the moieties defined for one of $A_2$, $Ra_4$, $Ra_5$, $Ra_6$, $Ra_7$, $Ra_8$, $Ra_{10}$, and nn1, can be combined with any of the moieties defined for the others of $A_2$, $Ra_4$, $Ra_5$, $Ra_6$, $Ra_7$, $Ra_8$, $Ra_{10}$, and nn1, as described above in Formulae (TL-I) and (TL-I1a)-(TL-I1 d).

In certain embodiments, J is a compound of Formula (TL-I3):

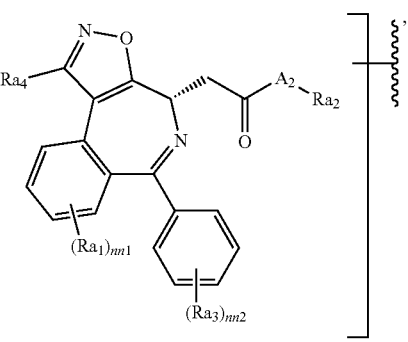

(TL-I3)

or a pharmaceutically acceptable salt thereof.

$A_2$, $Ra_1$, $Ra_2$, $Ra_3$, $Ra_4$, $Ra_5$, nn1, and nn2 are each as defined above in Formula TL-I. Each of $A_2$, $Ra_1$, $Ra_2$, $Ra_3$, $Ra_4$, $Ra_5$, nn1, and nn2 may be selected from the moieties described above in Formula (TL-I). Each of the moieties defined for one of $A_2$, $Ra_1$, $Ra_2$, $Ra_3$, $Ra_4$, $Ra_5$, nn1, and nn2, can be combined with any of the moieties defined for the others of $A_2$, $Ra_1$, $Ra_2$, $Ra_3$, $Ra_4$, $Ra_5$, nn1, and nn2, as described above in Formula (TL-I).

In certain embodiments, J is a compound of Formula (TL-I3a)-(TL-I3c):

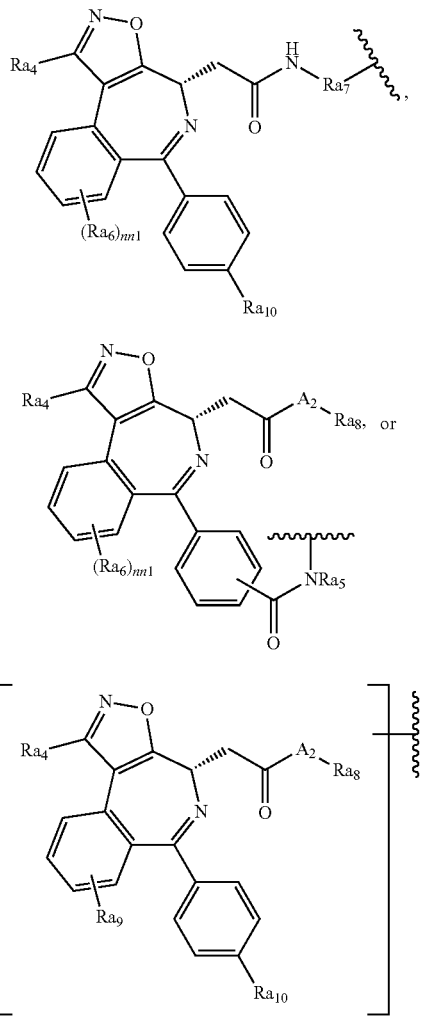

or a pharmaceutically acceptable salt thereof, wherein:
Ra$_9$ is C(O)NRa$_5$L, O—, or —NRa$_5$—;
A$_2$, Ra$_4$, Ra$_5$, and nn1 are each as defined above in Formula (TL-I); and
Ra$_6$, Ra$_7$, Ra$_8$, and Ra$_{10}$ are each as defined above in Formula (TL-I1a)-(TL-I1d).

In certain embodiments, Ra$_9$ is —C(O)NRa$_5$—. In further embodiments, Ra$_5$ is H. In other embodiments, Ra$_5$ is C$_1$-C$_3$ alkyl (e.g., methyl, ethyl, propyl, or i-propyl).

In certain embodiments, Ra$_9$ is —O— and attached to L.
In certain embodiments, Ra$_9$ is NRa$_5$— and attached to L. In further embodiments, Ra$_5$ is H. In other embodiments, Ra$_9$ is C$_1$-C$_3$ alkyl (e.g., methyl, ethyl, propyl, or i-propyl). In other embodiments, Ra$_5$ is methyl.

In certain embodiments, Ra$_9$ is attached to L.

Each of A$_2$, Ra$_4$, Ra$_5$, and nn1 may be selected from the moieties described above in Formula (TL-I), and each of Ra$_6$, Ra$_7$, Ra$_8$, and Ra$_{10}$ may be selected from the moieties described above in Formula (TL-I1a)-(TL-I1d). Each of the moieties defined for one of A$_2$, Ra$_4$, Ra$_5$, Ra$_6$, Ra$_7$, Ra$_8$, Ra$_9$, Ra$_{10}$, and nn1, can be combined with any of the moieties defined for the others of A$_2$, Ra$_4$, Ra$_5$, Ra$_6$, Ra$_7$, Ra$_8$, Ra$_9$, Ra$_{10}$, and nn1, as described above and in Formulae (TL-I) and (TL-I1a)-(TL-I1d).

Binders of FKBP
In certain embodiments, J is a binder of FKBP. In certain embodiments, J is a binder of FKBP12. In certain embodiments, J is a binder of FKBP, which is a compound of Formula (IX). In some embodiments, the linker L is attached to any position on the compound of Formula (IX).

In certain embodiments, J is a moiety of Formula (IX):

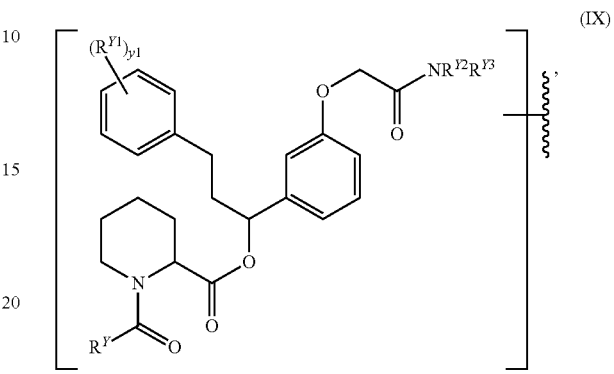

or a pharmaceutically acceptable salt, solvate, hydrate, tautomer, or stereoisomer thereof, wherein:
each instance of R$^{Y1}$ is independently halogen, optionally substituted C$_{1-6}$ alkyl, —OR$^f$, —SR$^f$, —N(R$^g$)$_2$, —NO$_2$, or —CN;
y1 is 0, 1, 2, 3, 4, or 5;
R$^Y$ is —OR$^f$, optionally substituted alkyl, optionally substituted acyl, optionally substituted alkenyl, optionally substituted alkynyl, optionally substituted carbocyclyl, optionally substituted heterocyclyl, optionally substituted aryl, or optionally substituted heteroaryl;
each instance of R$^{Y1}$ is independently halogen, optionally substituted C$_{1-6}$ alkyl, —OR$^f$, —SR$^f$, —N(R$^g$)$_2$, —NO$_2$, or —CN;
R$^{Y2}$ is hydrogen, optionally substituted acyl, or optionally substituted C$_{1-6}$ alkyl;
R$^{Y3}$ is hydrogen, optionally substituted acyl, or optionally substituted C$_{1-6}$ alkyl;
R$^f$ is hydrogen, optionally substituted alkyl, optionally substituted acyl, optionally substituted alkenyl, optionally substituted alkynyl, optionally substituted carbocyclyl, optionally substituted heterocyclyl, optionally substituted aryl, optionally substituted heteroaryl, an oxygen protecting group when attached to an oxygen atom, or a sulfur protecting group when attached to a sulfur atom; and
R$^g$ is optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group.

In some embodiments, at least one instance of R$^Y$ is optionally substituted acyl. In some embodiments, at least one instance of R$^Y$ is —C(=O)(optionally substituted alkyl). In some embodiments, at least one instance of R$^Y$ is —C(=O)(optionally substituted C$_{1-6}$ branched alkyl). In some embodiments, at least one instance of R$^Y$ is

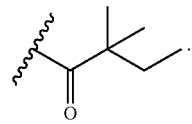 [SMILES: *C(=O)C(C)(C)CC]

In some embodiments, at least one instance of $R^Y$ is —$OR^f$, optionally substituted alkyl, optionally substituted alkenyl, optionally substituted alkynyl, optionally substituted carbocyclyl, optionally substituted heterocyclyl, optionally substituted aryl, or optionally substituted heteroaryl.

In certain embodiments, at least one instance of $R^{Y1}$ is halogen, optionally substituted $C_{1-6}$ alkyl, —$OR^f$, —$SR^f$, —$N(R^g)_2$, —$NO_2$, or —CN. In some embodiments, at least one instance of $R^{Y1}$ is —O(optionally substituted $C_{1-6}$ alkyl). In certain embodiments, at least one instance of $R^{Y1}$ is —O(unsubstituted $C_{1-6}$ alkyl). In certain embodiments, at least one instance of $R^{Y1}$ is —OMe. In certain embodiments, y1 is 0. In certain embodiments, y1 is 2. In certain embodiments, y1 is 3. In certain embodiments, y1 is 4. In certain embodiments, y1 is 5.

In certain embodiments, $R^{Y2}$ is hydrogen, optionally substituted acyl, or optionally substituted $C_{1-6}$ alkyl. In certain embodiments, $R^{Y2}$ is hydrogen. In certain embodiments, $R^{Y2}$ is optionally substituted $C_{1-6}$ alkyl (e.g., optionally substituted methyl or optionally substituted ethyl). In certain embodiments, $R^{Y2}$ is optionally substituted acyl. In certain embodiments, $R^{Y2}$ is —C(=O)($R^f$). In certain embodiments, $R^{Y2}$ is —C(=O)(optionally substituted alkyl). In certain embodiments, $R^{Y2}$ is —C(=O)(optionally substituted $C_{1-6}$ alkyl).

In certain embodiments, $R^{Y3}$ is hydrogen, optionally substituted acyl, or optionally substituted $C_{1-6}$ alkyl. In certain embodiments, $R^{Y3}$ is hydrogen. In certain embodiments, $R^{Y3}$ is optionally substituted $C_{1-6}$ alkyl (e.g., optionally substituted methyl or optionally substituted ethyl). In certain embodiments, $R^{Y3}$ is optionally substituted acyl. In certain embodiments, $R^{Y3}$ is —C(=O)($R^f$). In certain embodiments, $R^{Y3}$ is —C(=O)(optionally substituted alkyl). In certain embodiments, $R^{Y3}$ is —C(=O)(optionally substituted $C_{1-6}$ alkyl).

In certain embodiments, a compound of Formula (IX) is of Formula (IX-i):

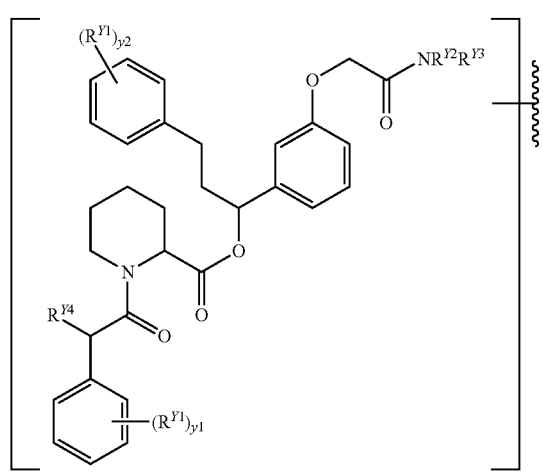

(IX-i)

or a pharmaceutically acceptable salt, solvate, hydrate, tautomer, or stereoisomer thereof, wherein:

each instance of $R^{Y1}$ is independently halogen, optionally substituted $C_{1-6}$ alkyl, —$OR^f$, —$SR^f$, —$N(R^g)_2$, —$NO_2$, or —CN;

y1 is 0, 1, 2, 3, 4, or 5; and $R^{Y4}$ is halogen, optionally substituted $C_{1-6}$ alkyl, —$OR^f$, —$SR^f$, —$N(R^g)_2$, —$NO_2$, or —CN.

In certain embodiments, at least one instance of $R^{Y1}$ is halogen, optionally substituted $C_{1-6}$ alkyl, —$OR^f$, —$SR^f$, —$N(R^g)_2$, —$NO_2$, or —CN. In some embodiments, at least one instance of $R^{Y1}$ is —O(optionally substituted $C_{1-6}$ alkyl). In certain embodiments, at least one instance of $R^{Y1}$ is —O(unsubstituted $C_{1-6}$ alkyl). In certain embodiments, at least one instance of $R^{Y1}$ is —OMe. In certain embodiments, y2 is 0. In certain embodiments, y2 is 2. In certain embodiments, y2 is 3. In certain embodiments, y2 is 4. In certain embodiments, y2 is 5.

In certain embodiments, $R^{Y4}$ is halogen, optionally substituted $C_{1-6}$ alkyl, —$OR^f$, —$SR^f$, —$N(R^g)_2$, —$NO_2$, or —CN. In certain embodiments, $R^{Y4}$ is optionally substituted $C_{1-6}$ alkyl. In certain embodiments, $R^{Y4}$ is unsubstituted methyl. In certain embodiments, $R^{Y4}$ is unsubstituted ethyl.

In certain embodiments, a compound of Formula (X-i) is of the formula:

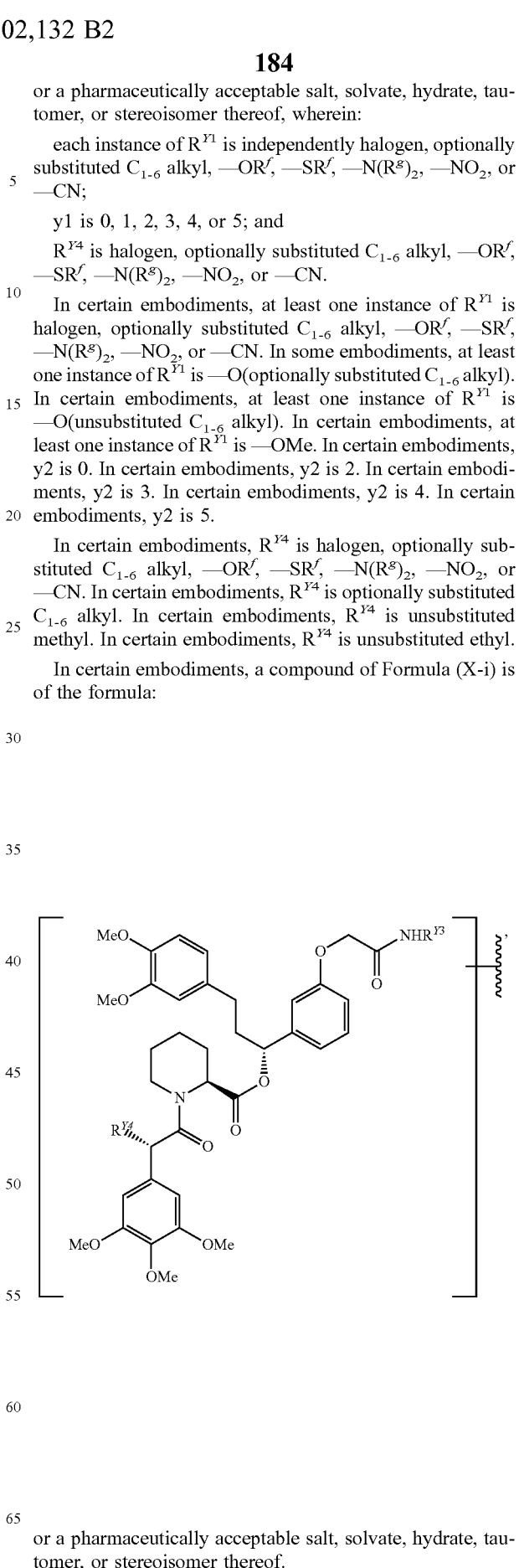

or a pharmaceutically acceptable salt, solvate, hydrate, tautomer, or stereoisomer thereof.

In certain embodiments, a compound of Formula (X) is of Formula (X-ii):

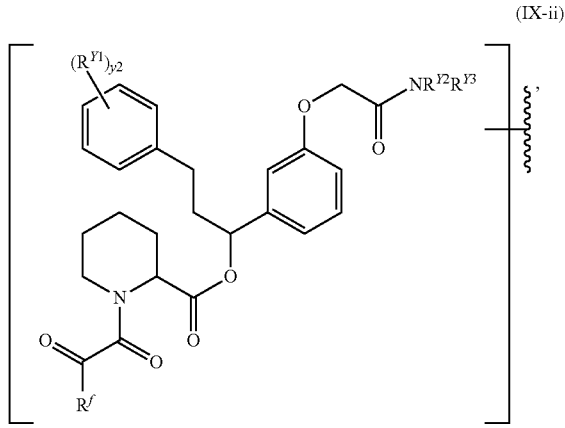

(IX-ii)

or a pharmaceutically acceptable salt, solvate, hydrate, tautomer, or stereoisomer thereof, wherein:

$R^f$ is hydrogen, optionally substituted alkyl, optionally substituted acyl, optionally substituted alkenyl, optionally substituted alkynyl, optionally substituted carbocyclyl, optionally substituted heterocyclyl, optionally substituted aryl, optionally substituted heteroaryl, or an oxygen protecting group.

In certain embodiments, $R^f$ is hydrogen. In certain embodiments, $R^f$ is optionally substituted alkyl, optionally substituted acyl, optionally substituted alkenyl, optionally substituted alkynyl, optionally substituted carbocyclyl, optionally substituted heterocyclyl, optionally substituted aryl, optionally substituted heteroaryl, or an oxygen protecting group.

In certain embodiments, $R^f$ is optionally substituted $C_{1-6}$ alkyl. In certain embodiments, $R^f$ is optionally substituted, branched $C_{1-6}$ alkyl. In certain embodiments, $R^f$ is unsubstituted isopentane.

In certain embodiments, a compound of Formula (IX) is of the formula:

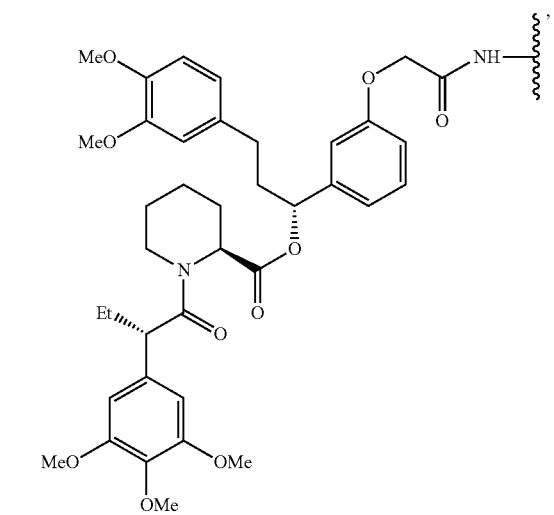

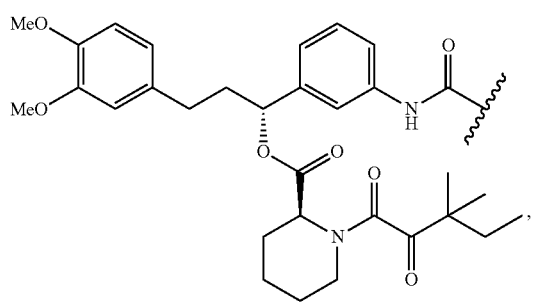

or a pharmaceutically acceptable salt, solvate, hydrate, tautomer, or stereoisomer thereof.

In certain embodiments, a compound of Formulae (I) or (IA) is of the formula:

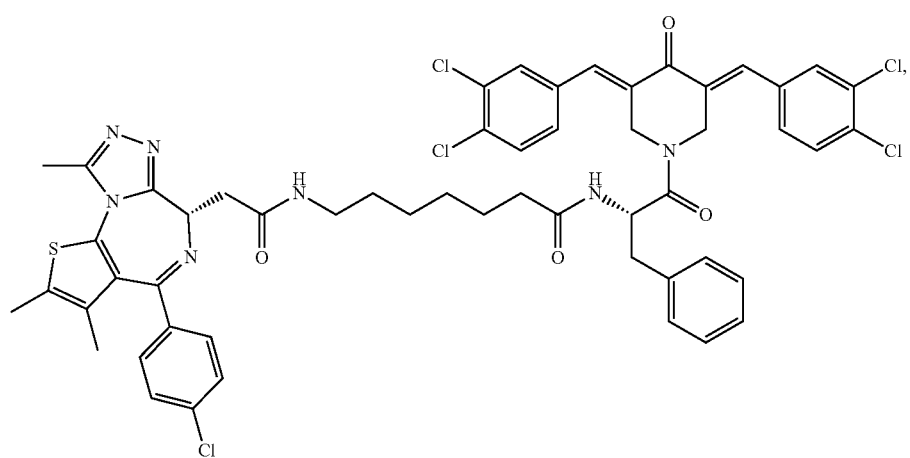

-continued
(RA-JQ2; LW-RPN13-5)
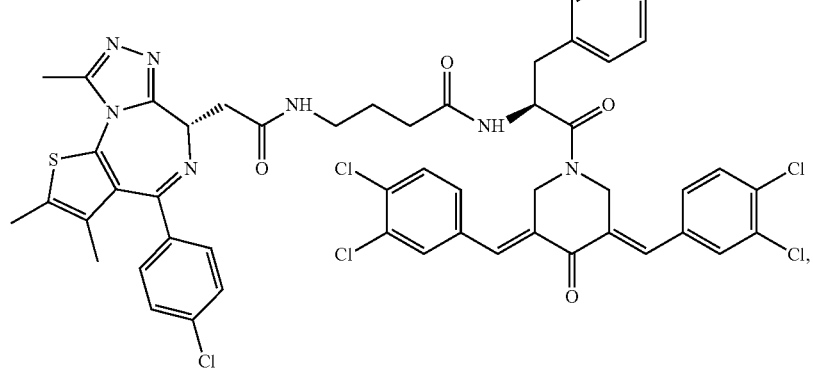
(RA-JQ3; LW-RPN13-6)
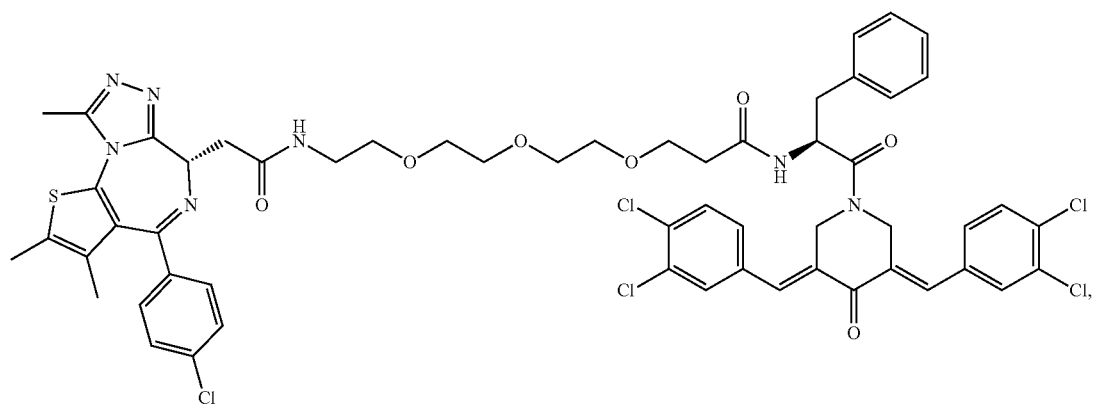
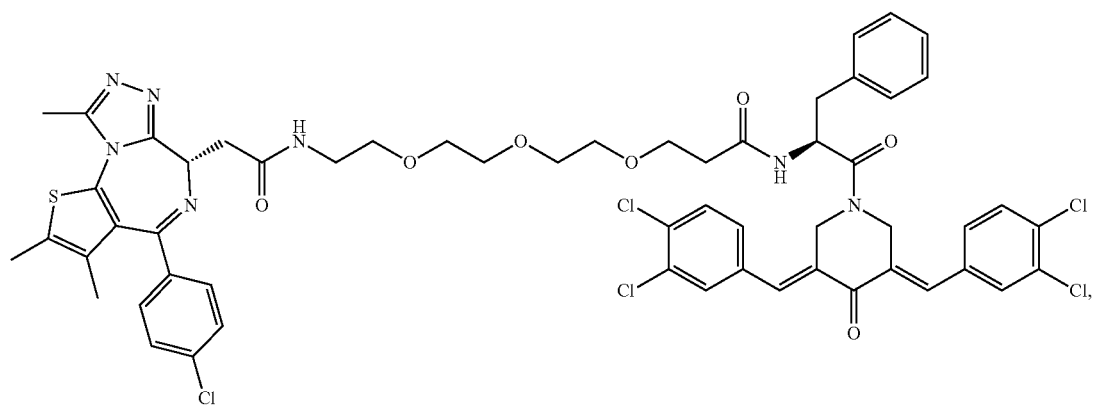

-continued
D-RAJQ1
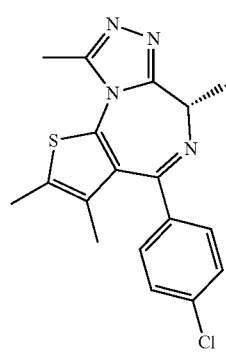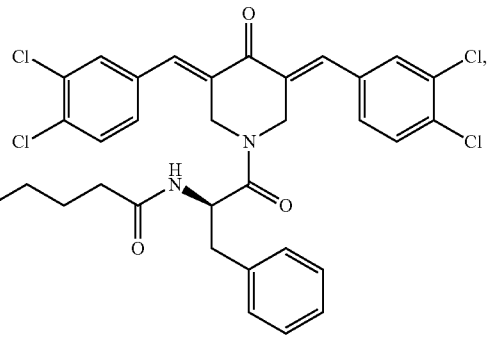
RAJQ8
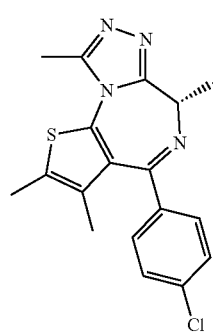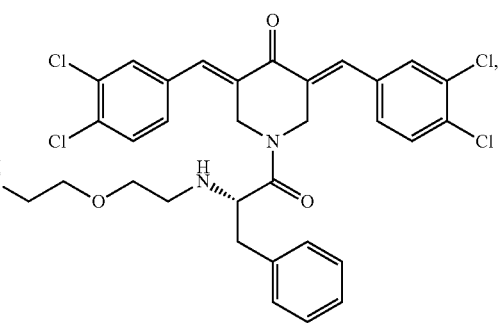
RA-JQ-9
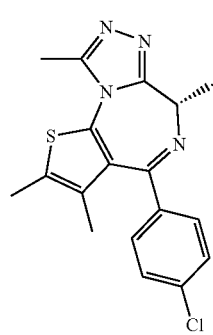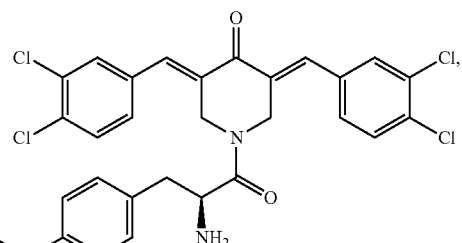
RAFKBP-1
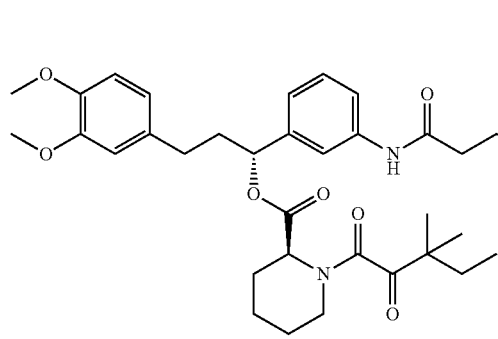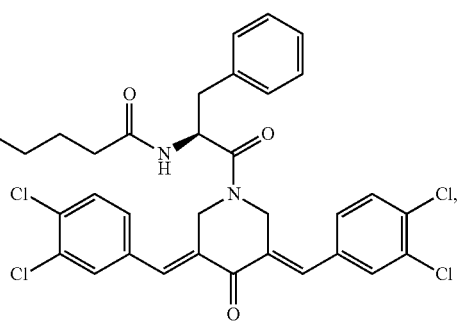

191
192
-continued
RAFKBP-2
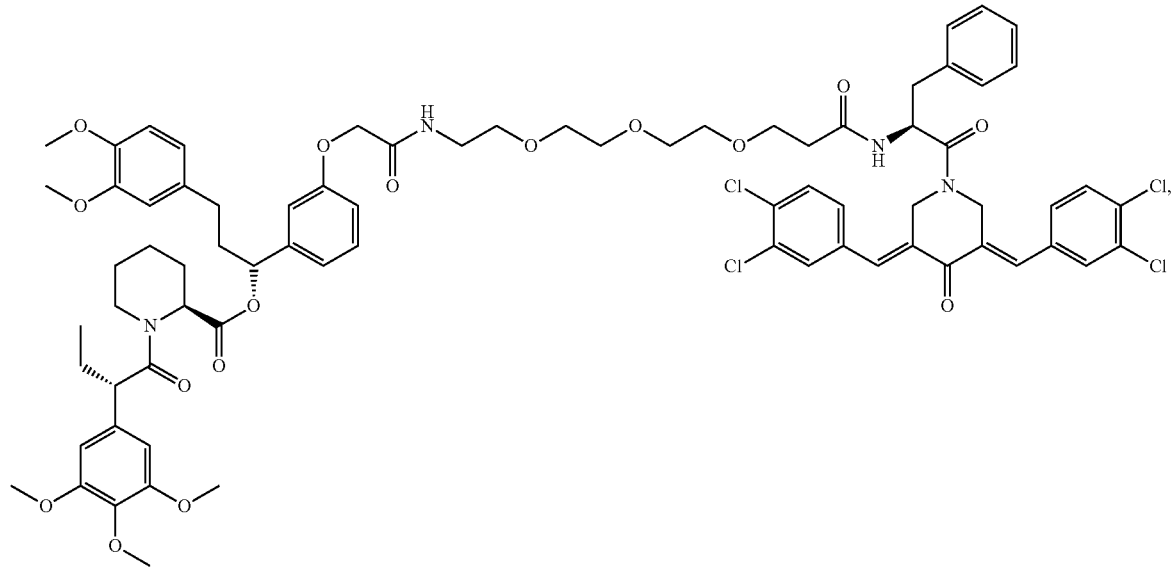
RAFKBP-3
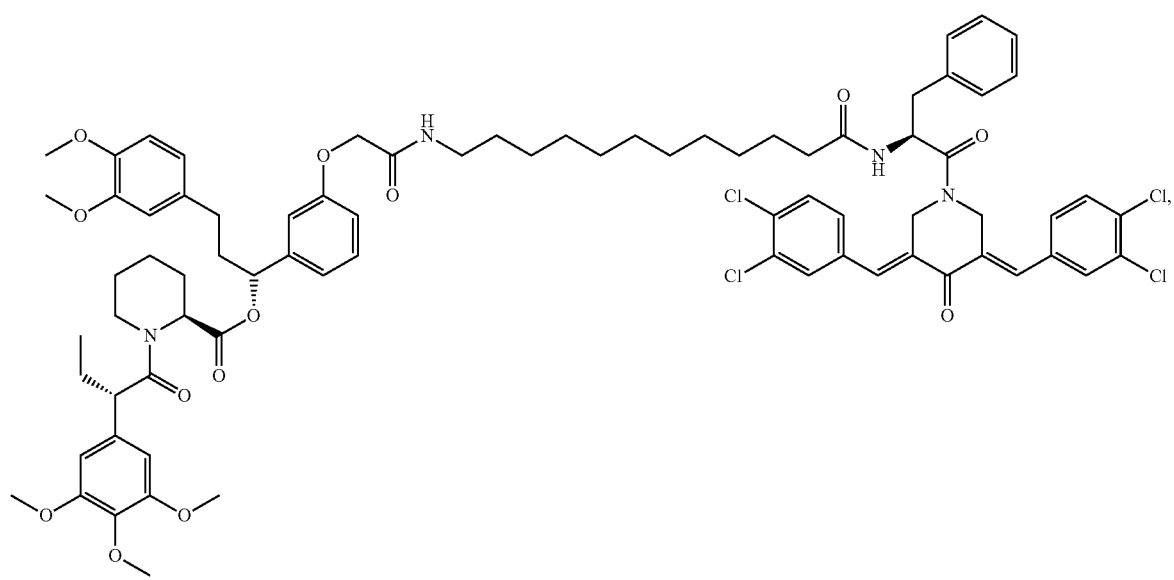

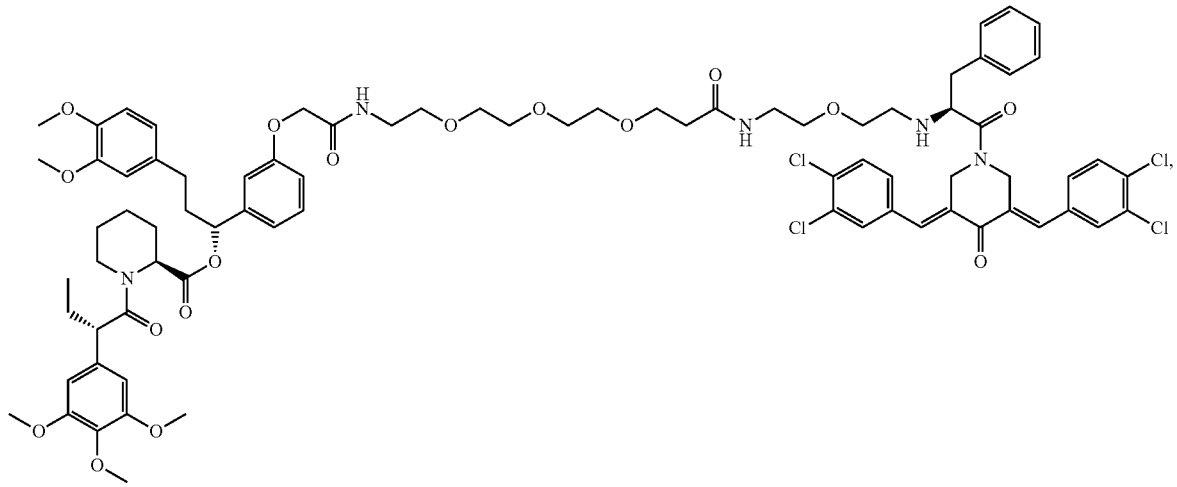
RAFKBP-4
or a pharmaceutically acceptable salt, solvate, hydrate, tautomer, or stereoisomer thereof.
In certain embodiments, a compound of Formulae (I), (IA), or (IB) is of the formula:
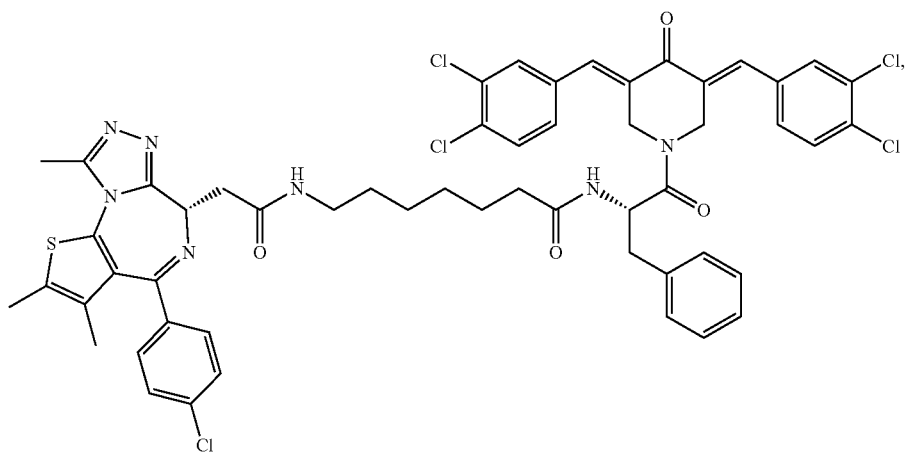
(RA-JQ1; LW-RPN13-3)
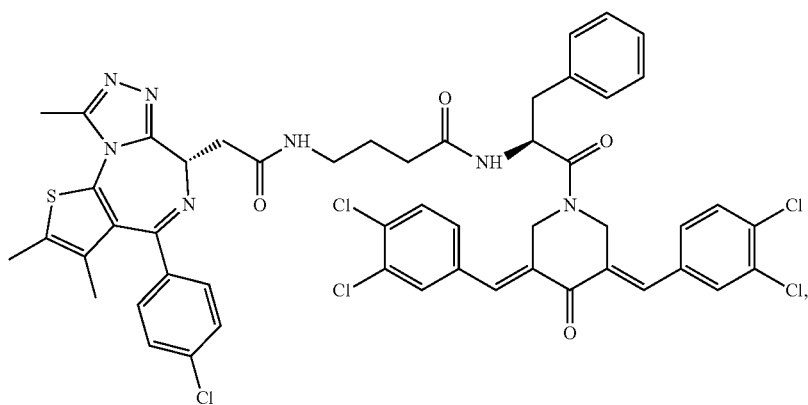
(RA-JQ2; LW-RPN13-5)

(RA-JQ3; LW-RPN13-6)
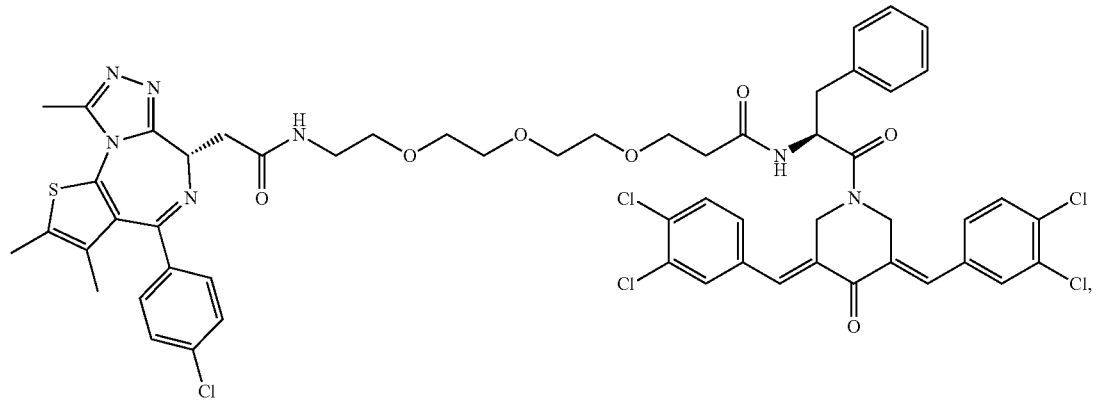
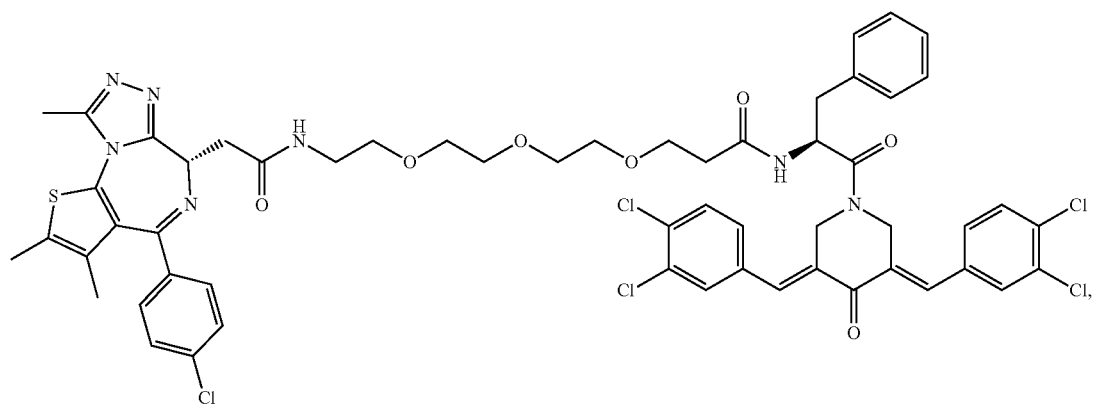
(LW-RPN13-7)
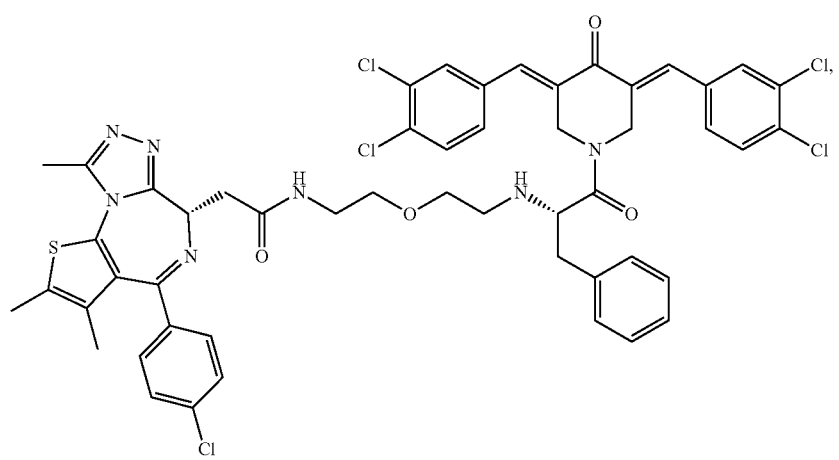

-continued
D-RAJQ1
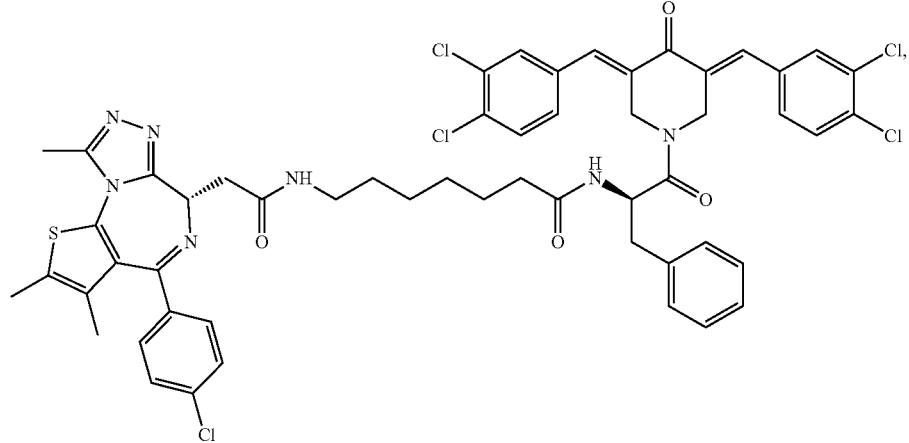
RAJQ8
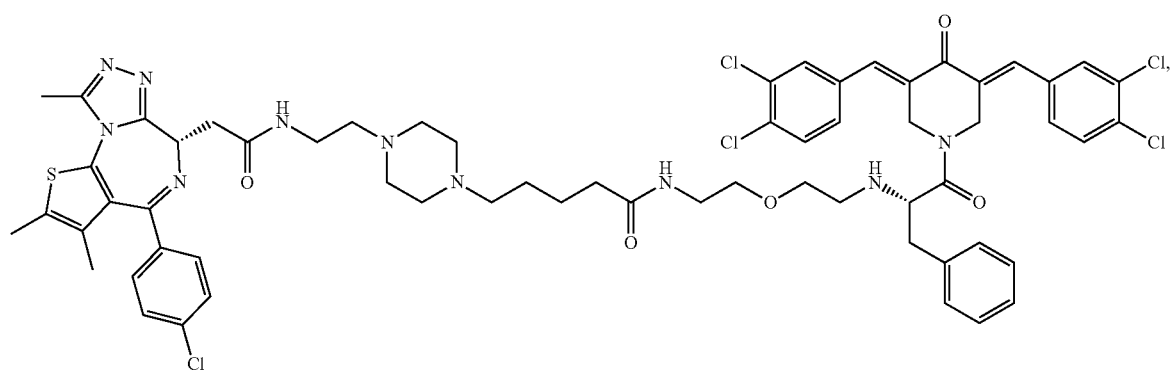
RA-JQ-9
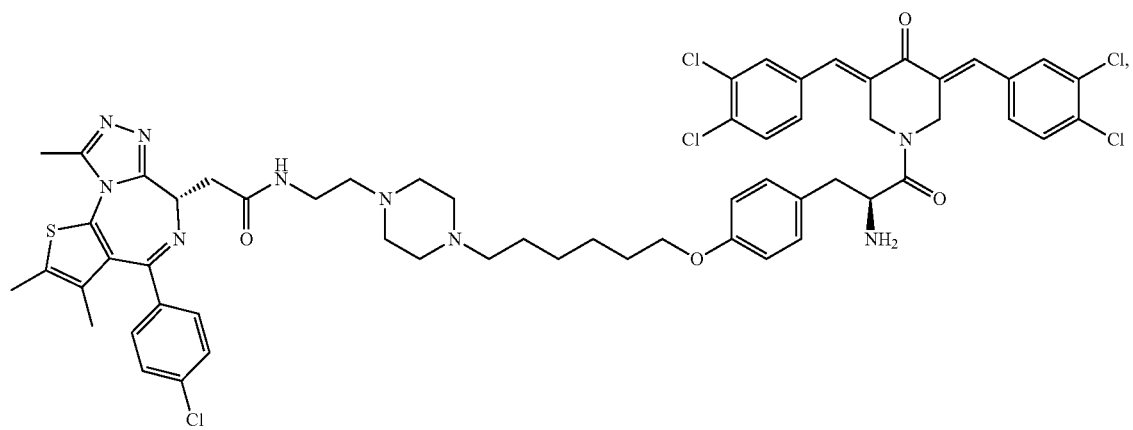
(RA-JQ10; RAJQ10)
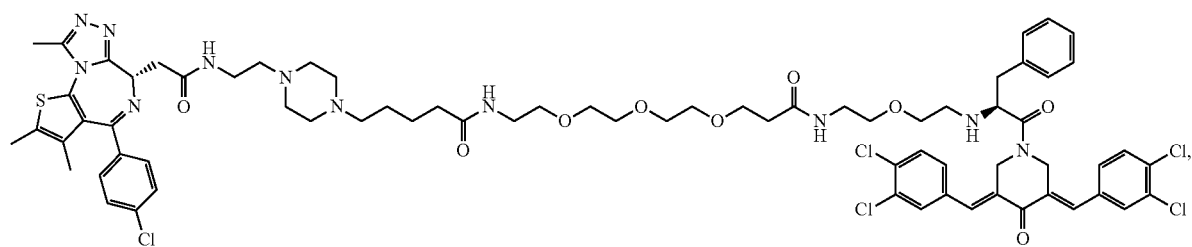

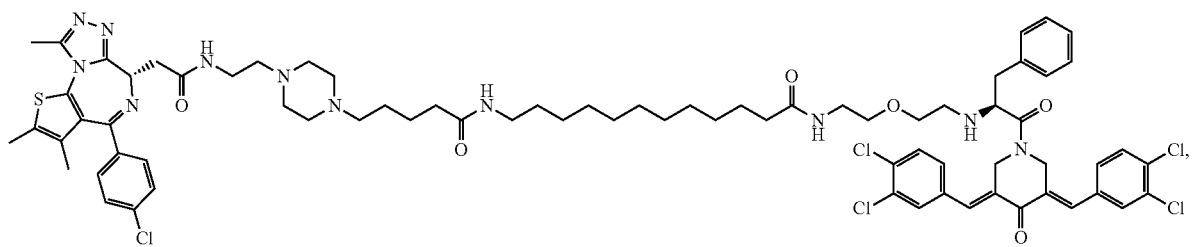
(RA-JQ11; RAJQ11)
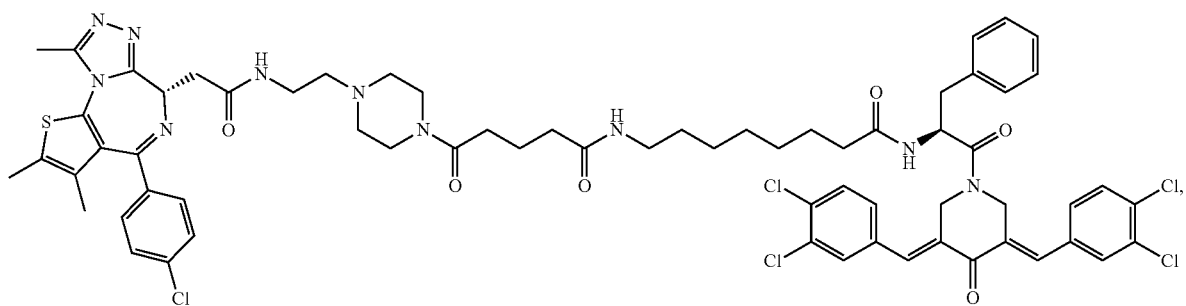
(LW-9296-205)
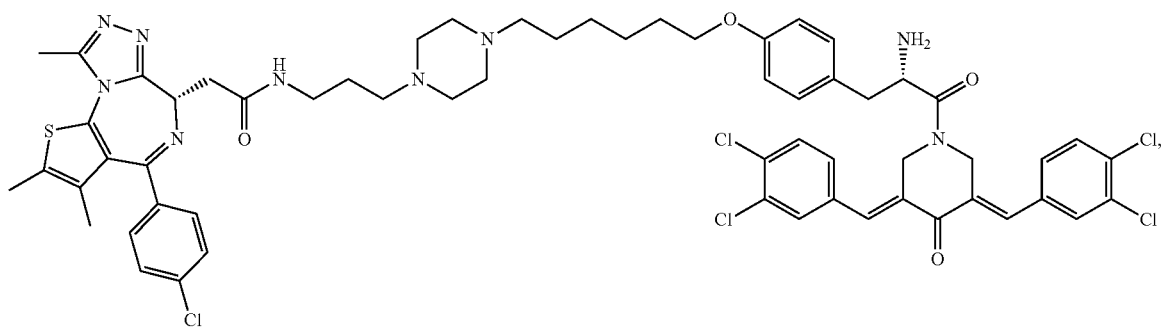
(RA-JQ14)
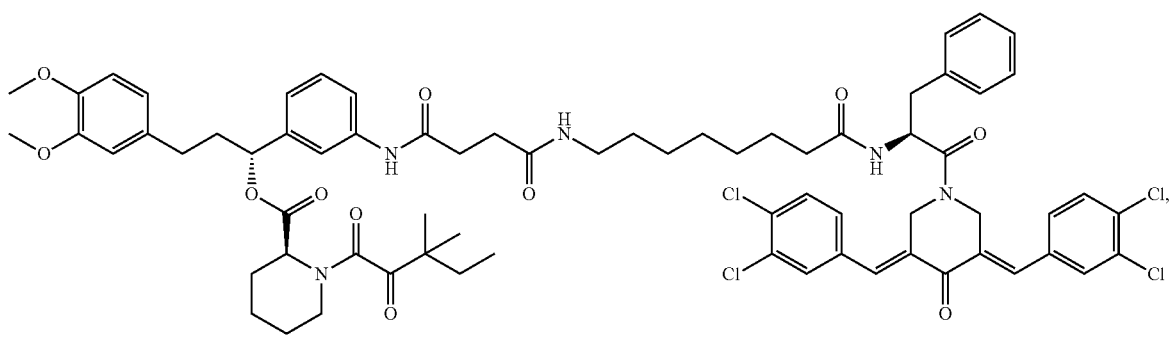
RAFKBP-1

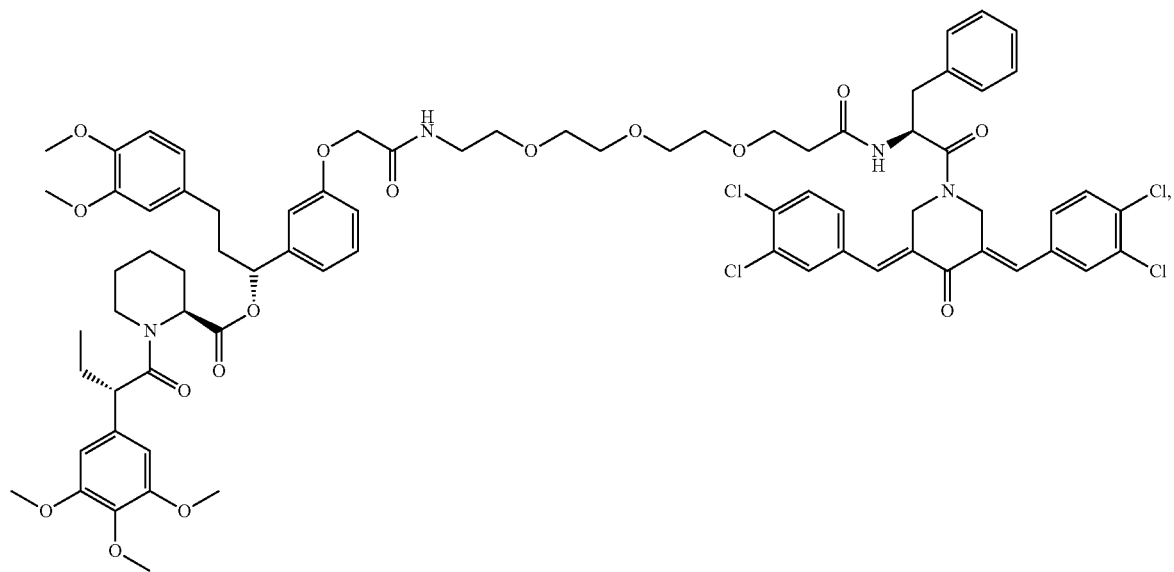
RAFKBP-2
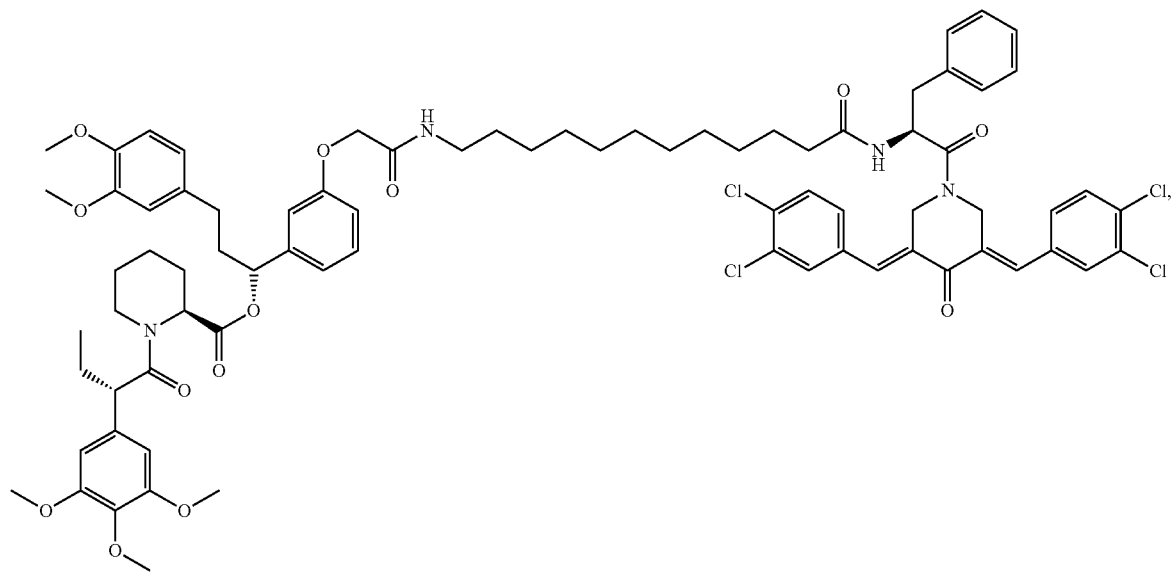
RAFKBP-3

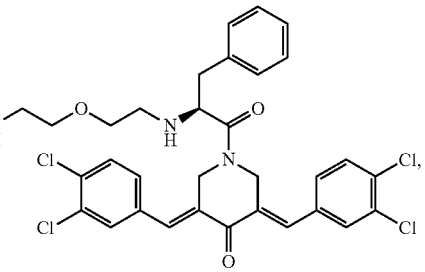

RAFKBP-4 or a pharmaceutically acceptable salt, solvate, hydrate, tautomer, or stereoisomer thereof.

In certain embodiments, a compound of Formulae (I), (IA), or (IB) is not of the formula:

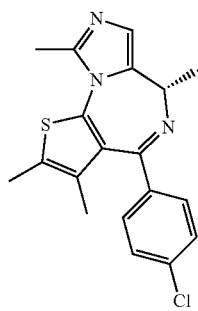

(LW-9296-205)

or a pharmaceutically acceptable salt, solvate, hydrate, tautomer, or stereoisomer, thereof.

In certain embodiments, a compound of Formulate (I), (IA), or (IB) is a final product (IA), or (IB) is a product compound depicted in Example 2. In certain embodiments, a compound of Formulae (I), (IA), or (IB) is a product compound depicted in Example 1 or Example 2. In certain embodiments, a compound of Formulae (I), (IA), or (IB) is a product compound depicted in one of the Figures.

In certain embodiments, the compound of Formulae (I), (IA), or (IB) selectively binds a target protein over another protein. In certain embodiments, the compound of Formulae (I), (IA), or (IB) selectively binds a bromodomain or a bromodomain-containing protein over another protein. In certain embodiments, the compound of Formulae (I), (IA), or (IB) selectively binds BRD4 over another protein. In certain embodiments, the compound of Formulae (I), (IA), or (IB) selectively binds BRD4 over another bromodomain or a bromodomain-containing protein. In certain embodiments, the compound of Formulae (I), (IA), or (IB) selectively binds BRD4 over BRD2 or BRD3.

In certain embodiments, the compound of Formulae (I), (IA), or (IB) selectively degrades a target protein over another protein. In certain embodiments, the compound of Formulae (I), (IA), or (IB) selectively degrades a bromodomain or a bromodomain-containing protein over another protein. In certain embodiments, the compound of Formulae (I), (IA), or (IB) selectively degrades BRD4 over another protein. In certain embodiments, the compound of Formulae (I), (IA), or (IB) selectively degrades BRD4 over another bromodomain or a bromodomain-containing protein. In certain embodiments, the compound of Formulae (I), (IA), or (IB) selectively degrades BRD4 over BRD2 or BRD3.

In certain embodiments, the compound of Formulae (I), (IA), or (IB) selectively binds a FKBP over another protein. In certain embodiments, the compound of Formulae (I), (IA), or (IB) selectively binds FKBP12 over another protein. In certain embodiments, the compound of Formulae (I), (IA), or (IB) selectively degrades an FKBP over another protein. In certain embodiments, the compound of Formulae (I), (IA), or (IB) selectively degrades FKBP12 over another protein. In certain embodiments, the selectivity is between about 2-fold and about 5-fold. In certain embodiments, the selectivity is between about 5-fold and about 10-fold. In certain embodiments, the selectivity is between about 10-fold and about 20-fold. In certain embodiments, the selectivity is between about 20-fold and about 50-fold. In certain embodiments, the selectivity is between about 50-fold and about 100-fold. In certain embodiments, the selectivity is between about 100-fold and about 200-fold. In certain embodiments, the selectivity is between about 200-fold and about 500-fold. In certain embodiments, the selectivity is between about 500-fold and about 1000-fold. In certain embodiments, the selectivity is at least about 1000-fold.

In some embodiments, the compound of Formulae (I), (IA), or (IB) selectively binds ubiquitin receptor RPN13 over another protein. In some embodiments, the compound of Formulae (I), (IA), or (IB) selectively binds ubiquitin receptor RPN13 over another ubiquitin receptor. In certain embodiments, the selectivity is between about 2-fold and about 5-fold. In certain embodiments, the selectivity is between about 5-fold and about 10-fold. In certain embodiments, the selectivity is between about 10-fold and about 20-fold. In certain embodiments, the selectivity is between about 20-fold and about 50-fold. In certain embodiments, the selectivity is between about 50-fold and about 100-fold. In certain embodiments, the selectivity is between about 100-fold and about 200-fold. In certain embodiments, the selectivity is between about 200-fold and about 500-fold. In certain embodiments, the selectivity is between about 500-fold and about 1000-fold. In certain embodiments, the selectivity is at least about 1000-fold.

In certain embodiments, the compound of Formulae (I), (IA), or (IB) induces the degradation of up to 10%, up to 15%, up to 20%, up to 25%, up to 30%, up to 35%, up to 40%, up to 45%, up to 50%, up to 55%, up to 60%, up to 65%, up to 70%, up to 75%, up to 80%, up to 85%, up to 90%, up to 95%, up to 99%, or up to 100% of a target protein at a concentration of 100,000 nM or less, 50,000 nM or less, 20,000 nM or less, 10,000 nM or less, 5,000 nM or less, 3,500 nM or less, 2,500 nM or less, 1,000 nM or less, 900 nM or less, 800 nM or less, 700 nM or less, 600 nM or less, 500 nM or less, 400 nM or less, 300 nM or less, 200 nM or less, 100 nM or less, 90 nM or less, 80 nM or less, 70 nM or less, 60 nM or less, 50 nM or less, 40 nM or less, 30 nM or less, 20 nM or less, 10 nM or less, 5 nM or less, 4 nM or less, 3 nM or less, 2 nM or less, or 1 nM or less. In certain embodiments, the target protein is a bromodomain, a bromodomain-containing protein, or FKBP12.

In certain embodiments, the compound of Formulae (I), (IA), or (IB) increases the rate of degradation of a target protein up to 10%, up to 15%, up to 20%, up to 25%, up to 30%, up to 35%, up to 40%, up to 45%, up to 50%, up to 55%, up to 60%, up to 65%, up to 70%, up to 75%, up to 80%, up to 85%, up to 90%, up to 95%, up to 99%, or up to 100% at a concentration of 100,000 nM or less, 50,000 nM or less, 20,000 nM or less, 10,000 nM or less, 5,000 nM or less, 3,500 nM or less, 2,500 nM or less, 1,000 nM or less, 900 nM or less, 800 nM or less, 700 nM or less, 600 nM or less, 500 nM or less, 400 nM or less, 300 nM or less, 200 nM or less, 100 nM or less, 90 nM or less, 80 nM or less, 70 nM or less, 60 nM or less, 50 nM or less, 40 nM or less, 30 nM or less, 20 nM or less, 10 nM or less, 5 nM or less, 4 nM or less, 3 nM or less, 2 nM or less, or 1 nM or less.

Pharmaceutical Compositions, Kits, and Administration

The present disclosure provides pharmaceutical compositions comprising a compound of Formulae (I), (IA), or (IB), or a pharmaceutically acceptable salt, co-crystal, tautomer, stereoisomer, solvate, hydrate, polymorph, isotopically enriched derivative, or prodrug thereof, and optionally a pharmaceutically acceptable excipient. In certain embodiments, the pharmaceutical composition described herein comprises a compound of Formulae (I), (IA), or (IB), or a pharmaceutically acceptable salt thereof, and a pharmaceutically acceptable excipient.

In certain embodiments, the compound of Formulae (I), (IA), or (IB) is provided in an effective amount in the pharmaceutical composition. In certain embodiments, the effective amount is a therapeutically effective amount. In certain embodiments, the effective amount is a prophylactically effective amount. In certain embodiments, the effective amount is an amount effective for treating a proliferative disease in a subject in need thereof. In certain embodiments, the effective amount is an amount effective for preventing a proliferative disease in a subject in need thereof. In certain embodiments, the effective amount is an amount effective for treating cancer in a subject in need thereof. In certain embodiments, the effective amount is an amount effective for preventing cancer in a subject in need thereof. In certain embodiments, the effective amount is an amount effective for reducing the risk of developing a disease (e.g., proliferative disease or cancer) in a subject in need thereof.

In certain embodiments, the subject is an animal. The animal may be of either sex and may be at any stage of development. In certain embodiments, the subject described herein is a human. In certain embodiments, the subject is a non-human animal. In certain embodiments, the subject is a mammal. In certain embodiments, the subject is a non-human mammal. In certain embodiments, the subject is a domesticated animal, such as a dog, cat, cow, pig, horse, sheep, or goat. In certain embodiments, the subject is a companion animal, such as a dog or cat. In certain embodiments, the subject is a livestock animal, such as a cow, pig, horse, sheep, or goat. In certain embodiments, the subject is a zoo animal. In another embodiment, the subject is a research animal, such as a rodent (e.g., mouse, rat), dog, pig, or non-human primate. In certain embodiments, the animal is a genetically engineered animal. In certain embodiments, the animal is a transgenic animal (e.g., transgenic mice and transgenic pigs). In certain embodiments, the subject is a fish or reptile.

In certain embodiments, the effective amount is an amount effective for inducing the degradation of at least about 10%, at least about 20%, at least about 30%, at least about 40%, at least about 50%, at least about 60%, at least about 70%, at least about 80%, at least about 90%, at least about 95%, at least about 98%, or at least about 99% of a target protein. In certain embodiments, the target protein is a bromodomain, a bromodomain-containing protein, or FKBP12. In certain embodiments, the target protein is a methyltransferase. In certain embodiments, the target protein is a cytosolic signaling protein. In certain embodiments, the target protein is FKBP. In certain embodiments, the target protein is FKBP12. In certain embodiments, the effective amount is an amount effective for inducing the degradation of a target protein (e.g., a bromodomain, a bromodomain-containing protein, or FKBP12) by a range between a percentage described in this paragraph and another percentage described in this paragraph, inclusive.

The present disclosure provides pharmaceutical compositions comprising a compound that interacts with a target protein (e.g., a bromodomain, a bromodomain-containing protein, or FKBP12) and the ubiquitin receptor RPN13 for use in treating a proliferative disease in a subject in need thereof. In certain embodiments, the composition is for use in treating a neurodegenerative disease. In certain embodiments, the composition is for use in treating cancer. In certain embodiments, the composition is for use in treating multiple myeloma, leukemia, lymphoma, or a cancer resistant to proteasome inhibitors. In certain embodiments, the composition is for use in treating cancer resistant to bortezomib. In certain embodiments, the composition is for use in treating cancer resistant to carfilzomib. In certain embodiments, the composition is for use in treating multiple myeloma.

Pharmaceutical compositions can be prepared, packaged, and/or sold in bulk, as a single unit dose, and/or as a plurality of single unit doses. A "unit dose" is a discrete amount of the pharmaceutical composition comprising a predetermined amount of the active ingredient. The amount of the active ingredient is generally equal to the dosage of the active ingredient which would be administered to a subject and/or a convenient fraction of such a dosage, such as one-half or one-third of such a dosage.

Relative amounts of the active ingredient, the pharmaceutically acceptable excipient, and/or any additional ingredients in a pharmaceutical composition described herein will vary, depending upon the identity, size, and/or condition of the subject treated and further depending upon the route by which the composition is to be administered. The composition may comprise between 0.1% and 100% (w/w) active ingredient.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and mixtures thereof.

Exemplary granulating and/or dispersing agents include potato starch, corn starch, tapioca starch, sodium starch glycolate, clays, alginic acid, guar gum, citrus pulp, agar, bentonite, cellulose, and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, and mixtures thereof.

Exemplary surface active agents and/or emulsifiers include natural emulsifiers (e.g., acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g., bentonite (aluminum silicate) and Veegum (magnesium aluminum silicate)), long chain amino acid derivatives, high molecular weight alcohols (e.g., stearyl alcohol, cetyl alcohol, oleyl alcohol, triacetin monostearate, ethylene glycol distearate, glyceryl monostearate, and propylene glycol monostearate, polyvinyl alcohol), carbomers (e.g., carboxy polymethylene, polyacrylic acid, acrylic acid polymer, and carboxyvinyl polymer), carrageenan, cellulosic derivatives (e.g., carboxymethylcellulose sodium, powdered cellulose, hydroxymethyl cellulose, hydroxypropyl cellulose, hydroxypropyl methylcellulose, methylcellulose), sorbitan fatty acid esters (e.g., polyoxyethylene sorbitan monolaurate (Tween® 20), polyoxyethylene sorbitan (Tween® 60), polyoxyethylene sorbitan monooleate (Tween® 80), sorbitan monopalmitate (Span® 40), sorbitan monostearate (Span® 60), sorbitan tristearate (Span® 65), glyceryl monooleate, sorbitan monooleate (Span® 80), polyoxyethylene esters (e.g., polyoxyethylene monostearate (Myrj® 45), polyoxyethylene hydrogenated castor oil, polyethoxylated castor oil, polyoxymethylene stearate, and Solutol®), sucrose fatty acid esters, polyethylene glycol fatty acid esters (e.g., Cremophor®), polyoxyethylene ethers, (e.g., polyoxyethylene lauryl ether (Brij® 30)), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic® F-68, poloxamer P-188, cetrimonium bromide, cetylpyridinium chloride, benzalkonium chloride, docusate sodium, and/or mixtures thereof.

Exemplary binding agents include starch (e.g., cornstarch and starch paste), gelatin, sugars (e.g., sucrose, glucose, dextrose, dextrin, molasses, lactose, lactitol, mannitol, etc.), natural and synthetic gums (e.g., acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum®), and larch arabogalactan), alginates, polyethylene oxide, polyethylene glycol, inorganic calcium salts, silicic acid, polymethacrylates, waxes, water, alcohol, and/or mixtures thereof.

Exemplary preservatives include antioxidants, chelating agents, antimicrobial preservatives, antifungal preservatives, antiprotozoan preservatives, alcohol preservatives, acidic preservatives, and other preservatives. In certain embodiments, the preservative is an antioxidant. In other embodiments, the preservative is a chelating agent.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant® Plus, Phenonip®, methylparaben, Germall® 115, Germaben® II, Neolone®, Kathon®, and Euxyl®.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and mixtures thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and mixtures thereof.

Exemplary natural oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macadamia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and mixtures thereof.

Liquid dosage forms for oral and parenteral administration include pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates described herein are mixed with solubilizing agents such as Cremophor®, alcohols, oils, modified oils, glycols, polysorbates, cyclodextrins, polymers, and mixtures thereof.

Injectable preparations, for example, sterile injectable aqueous or oleaginous suspensions can be formulated according to the known art using suitable dispersing or wetting agents and suspending agents. The sterile injectable preparation can be a sterile injectable solution, suspension, or emulsion in a nontoxic parenterally acceptable diluent or solvent, for example, as a solution in 1,3-butanediol. Among the acceptable vehicles and solvents that can be employed are water, Ringer's solution, U.S.P., and isotonic sodium chloride solution. In addition, sterile, fixed oils are conventionally employed as a solvent or suspending medium. For this purpose any bland fixed oil can be employed including synthetic mono- or di-glycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form may be accomplished by dissolving or suspending the drug in an oil vehicle.

Compositions for rectal or vaginal administration are typically suppositories which can be prepared by mixing the conjugates described herein with suitable non-irritating excipients or carriers such as cocoa butter, polyethylene glycol, or a suppository wax which are solid at ambient temperature but liquid at body temperature and therefore melt in the rectum or vaginal cavity and release the active ingredient.

Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidinone, sucrose, and acacia, (c) humectants such as glycerol, (d) disintegrating agents such as agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets, and pills, the dosage form may include a buffering agent.

Solid compositions of a similar type can be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the art of pharmacology.

They may optionally comprise opacifying agents and can be of a composition that they release the active ingredient(s) only, or preferentially, in a certain part of the intestinal tract, optionally, in a delayed manner. Examples of encapsulating compositions which can be used include polymeric substances and waxes. Solid compositions of a similar type can be employed as fillers in soft and hard-filled gelatin capsules using such excipients as lactose or milk sugar as well as high molecular weight polethylene glycols and the like.

The active ingredient can be in a micro-encapsulated form with one or more excipients as noted above. The solid dosage forms of tablets, dragees, capsules, pills, and granules can be prepared with coatings and shells such as enteric coatings, release controlling coatings, and other coatings well known in the pharmaceutical formulating art. In such solid dosage forms the active ingredient can be admixed with at least one inert diluent such as sucrose, lactose, or starch. Such dosage forms may comprise, as is normal practice, additional substances other than inert diluents, e.g., tableting lubricants and other tableting aids such a magnesium stearate and microcrystalline cellulose. In the case of capsules, tablets and pills, the dosage forms may comprise buffering agents. They may optionally comprise opacifying agents and can be of a composition that they release the active ingredient(s) only, or preferentially, in a certain part of the intestinal tract, optionally, in a delayed manner. Examples of encapsulating agents which can be used include polymeric substances and waxes.

Dosage forms for topical and/or transdermal administration of a compound described herein may include ointments, pastes, creams, lotions, gels, powders, solutions, sprays, inhalants, and/or patches. Generally, the active ingredient is admixed under sterile conditions with a pharmaceutically acceptable carrier or excipient and/or any needed preservatives and/or buffers as can be required. Additionally, the present disclosure contemplates the use of transdermal patches, which often have the added advantage of providing controlled delivery of an active ingredient to the body. Such dosage forms can be prepared, for example, by dissolving and/or dispensing the active ingredient in the proper medium. Alternatively or additionally, the rate can be controlled by either providing a rate controlling membrane and/or by dispersing the active ingredient in a polymer matrix and/or gel.

Suitable devices for use in delivering intradermal pharmaceutical compositions described herein include short needle devices. Intradermal compositions can be administered by devices which limit the effective penetration length of a needle into the skin. Alternatively or additionally, conventional syringes can be used in the classical mantoux method of intradermal administration. Jet injection devices which deliver liquid formulations to the dermis via a liquid jet injector and/or via a needle which pierces the stratum corneum and produces a jet which reaches the dermis are suitable. Ballistic powder/particle delivery devices which use compressed gas to accelerate the compound in powder form through the outer layers of the skin to the dermis are suitable.

Formulations suitable for topical administration include, but are not limited to, liquid and/or semi-liquid preparations such as liniments, lotions, oil-in-water and/or water-in-oil emulsions such as creams, ointments, and/or pastes, and/or solutions and/or suspensions. Topically administrable formulations may, for example, comprise from about 1% to about 10% (w/w) active ingredient, although the concentration of the active ingredient can be as high as the solubility limit of the active ingredient in the solvent. Formulations for topical administration may further comprise one or more of the additional ingredients described herein.

A pharmaceutical composition described herein can be prepared, packaged, and/or sold in a formulation suitable for pulmonary administration via the buccal cavity. Such a formulation may comprise dry particles which comprise the active ingredient and which have a diameter in the range from about 0.5 to about 7 nanometers, or from about 1 to about 6 nanometers. Such compositions are conveniently in the form of dry powders for administration using a device comprising a dry powder reservoir to which a stream of propellant can be directed to disperse the powder and/or using a self-propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 nanometers and at least 95% of the particles by number have a diameter less than 7 nanometers. Alternatively, at least 95% of the particles by weight have a diameter greater than 1 nanometer and at least 90% of the particles by number have a diameter less than 6 nanometers. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic and/or solid anionic surfactant and/or a solid diluent (which may have a particle size of the same order as particles comprising the active ingredient).

Pharmaceutical compositions described herein formulated for pulmonary delivery may provide the active ingredient in the form of droplets of a solution and/or suspension. Such formulations can be prepared, packaged, and/or sold as aqueous and/or dilute alcoholic solutions and/or suspensions, optionally sterile, comprising the active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. The droplets provided by this route of administration may have an average diameter in the range from about 0.1 to about 200 nanometers.

Formulations described herein as being useful for pulmonary delivery are useful for intranasal delivery of a pharmaceutical composition described herein. Another formulation suitable for intranasal administration is a coarse powder comprising the active ingredient and having an average particle from about 0.2 to 500 micrometers. Such a formulation is administered by rapid inhalation through the nasal passage from a container of the powder held close to the nares.

Formulations for nasal administration may, for example, comprise from about as little as 0.1% (w/w) to as much as 100% (w/w) of the active ingredient, and may comprise one or more of the additional ingredients described herein. A pharmaceutical composition described herein can be prepared, packaged, and/or sold in a formulation for buccal administration. Such formulations may, for example, be in the form of tablets and/or lozenges made using conventional methods, and may contain, for example, 0.1 to 20% (w/w) active ingredient, the balance comprising an orally dissolvable and/or degradable composition and, optionally, one or more of the additional ingredients described herein. Alternately, formulations for buccal administration may comprise a powder and/or an aerosolized and/or atomized solution and/or suspension comprising the active ingredient. Such powdered, aerosolized, and/or aerosolized formulations, when dispersed, may have an average particle and/or droplet size in the range from about 0.1 to about 200 nanometers, and may further comprise one or more of the additional ingredients described herein.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation.

Compounds provided herein are typically formulated in dosage unit form for ease of administration and uniformity of dosage. It will be understood, however, that the total daily usage of the compositions described herein will be decided by a physician within the scope of sound medical judgment. The specific therapeutically effective dose level for any particular subject or organism will depend upon a variety of factors including the disease being treated and the severity of the disorder; the activity of the specific active ingredient employed; the specific composition employed; the age, body weight, general health, sex, and diet of the subject; the time of administration, route of administration, and rate of excretion of the specific active ingredient employed; the duration of the treatment; drugs used in combination or coincidental with the specific active ingredient employed; and like factors well known in the medical arts.

The compounds and compositions provided herein can be administered by any route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, sublingual; by intratracheal instillation, bronchial instillation, and/or inhalation; and/or as an oral spray, nasal spray, and/or aerosol. Specifically contemplated routes are oral administration, intravenous administration (e.g., systemic intravenous injection), regional administration via blood and/or lymph supply, and/or direct administration to an affected site. In general, the most appropriate route of administration will depend upon a variety of factors including the nature of the agent (e.g., its stability in the environment of the gastrointestinal tract), and/or the condition of the subject (e.g., whether the subject is able to tolerate oral administration). In certain embodiments, the compound or pharmaceutical composition described herein is suitable for topical administration to the eye of a subject.

The exact amount of a compound required to achieve an effective amount will vary from subject to subject, depending, for example, on species, age, and general condition of a subject, severity of the side effects or disorder, identity of the particular compound, mode of administration, and the like. An effective amount may be included in a single dose (e.g., single oral dose) or multiple doses (e.g., multiple oral doses). In certain embodiments, when multiple doses are administered to a subject or applied to a biological sample, tissue, or cell, any two doses of the multiple doses include different or substantially the same amounts of a compound described herein. In certain embodiments, when multiple doses are administered to a subject or applied to a biological sample, tissue, or cell, the frequency of administering the multiple doses to the subject or applying the multiple doses to the biological sample, tissue, or cell is three doses a day, two doses a day, one dose a day, one dose every other day, one dose every third day, one dose every week, one dose every two weeks, one dose every three weeks, or one dose every four weeks. In certain embodiments, the frequency of administering the multiple doses to the subject or applying the multiple doses to the biological sample, tissue, or cell is one dose per day. In certain embodiments, the frequency of administering the multiple doses to the subject or applying the multiple doses to the biological sample, tissue, or cell is two doses per day. In certain embodiments, the frequency of administering the multiple doses to the subject or applying the multiple doses to the biological sample, tissue, or cell is three doses per day. In certain embodiments, when multiple doses are administered to a subject or applied to a biological sample, tissue, or cell, the duration between the first dose and last dose of the multiple doses is one day, two days, four days, one week, two weeks, three weeks, one month, two months, three months, four months, six months, nine months, one year, two years, three years, four years, five years, seven years, ten years, fifteen years, twenty years, or the lifetime of the subject, tissue, or cell. In certain embodiments, the duration between the first dose and last dose of the multiple doses is three months, six months, or one year. In certain embodiments, the duration between the first dose and last dose of the multiple doses is the lifetime of the subject, tissue, or cell. In certain embodiments, a dose (e.g., a single dose, or any dose of multiple doses) described herein includes independently between 0.1 pg and 1 g, between 0.001 mg and 0.01 mg, between 0.01 mg and 0.1 mg, between 0.1 mg and 1 mg, between 1 mg and 3 mg, between 3 mg and 10 mg, between 10 mg and 30 mg, between 30 mg and 100 mg, between 100 mg and 300 mg, between 300 mg and 1,000 mg, or between 1 g and 10 g, inclusive, of a compound described herein. In certain embodiments, a dose described herein includes independently between 1 mg and 3 mg, inclusive, of a compound described herein. In certain embodiments, a dose described herein includes independently between 3 mg and 10 mg, inclusive, of a compound described herein. In certain embodiments, a dose described herein includes independently between 10 mg and 30 mg, inclusive, of a compound described herein. In certain embodiments, a dose described herein includes independently between 30 mg and 100 mg, inclusive, of a compound described herein.

Dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

A compound or composition, as described herein, can be administered in combination with one or more additional pharmaceutical agents (e.g., therapeutically and/or prophylactically active agents). The compounds or compositions can be administered in combination with additional pharmaceutical agents that improve their activity (e.g., activity (e.g., potency and/or efficacy) in treating a disease in a subject in need thereof, in preventing a disease in a subject in need thereof, in inducing degradation of a target protein, and/or in reducing the risk to develop a disease in a subject in need thereof), improve bioavailability, improve their ability to cross the blood-brain barrier, improve safety, reduce drug resistance, reduce and/or modify metabolism, inhibit excretion, and/or modify distribution in a subject or cell. It will also be appreciated that the therapy employed may achieve a desired effect for the same disorder, and/or it may achieve different effects. In certain embodiments, a pharmaceutical composition described herein including a compound described herein and an additional pharmaceutical agent exhibit a synergistic effect that is absent in a pharmaceutical composition including one of the compound and the additional pharmaceutical agent, but not both.

The compound or composition can be administered concurrently with, prior to, or subsequent to one or more additional pharmaceutical agents, which may be useful as, e.g., combination therapies. Pharmaceutical agents include therapeutically active agents. Pharmaceutical agents also include prophylactically active agents. Pharmaceutical agents include small organic molecules such as drug compounds (e.g., compounds approved for human or veterinary use by the U.S. Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins, and cells. In certain embodiments, the additional pharmaceutical agent is a pharmaceutical agent useful for treating and/or preventing a disease (e.g., proliferative disease, inflammatory disease, autoimmune disease, genetic disease, hematological disease, neurological disease, painful condition, psychiatric disorder, or metabolic disorder). Each additional pharmaceutical agent may be administered at a dose and/or on a time schedule determined for that pharmaceutical agent. The additional pharmaceutical agents may also be administered together with each other and/or with the compound or composition described herein in a single dose or administered separately in different doses. The particular combination to employ in a regimen will take into account compatibility of the compound described herein with the additional pharmaceutical agent(s) and/or the desired therapeutic and/or prophylactic effect to be achieved. In general, it is expected that the additional pharmaceutical agent(s) in combination be utilized at levels that do not exceed the levels at which they are utilized individually. In some embodiments, the levels utilized in combination will be lower than those utilized individually.

The additional pharmaceutical agents include, but are not limited to, anti-proliferative agents, anti-cancer agents, anti-angiogenesis agents, anti-inflammatory agents, immunosuppressants, anti-bacterial agents, anti-viral agents, cardiovascular agents, cholesterol-lowering agents, anti-diabetic agents, anti-allergic agents, contraceptive agents, pain-relieving agents, and a combination thereof. In certain embodiments, the additional pharmaceutical agent is an anti-proliferative agent (e.g., anti-cancer agent). In certain embodiments, the additional pharmaceutical agent is an anti-leukemia agent. In certain embodiments, the additional pharmaceutical agent is ABITREXATE (methotrexate), ADE, Adriamycin RDF (doxorubicin hydrochloride), Ambochlorin (chlorambucil), ARRANON (nelarabine), ARZERRA (ofatumumab), BOSULIF (bosutinib), BUSULFEX (busulfan), CAMPATH (alemtuzumab), CERUBIDINE (daunorubicin hydrochloride), CLAFEN (cyclophosphamide), CLOFAREX (clofarabine), CLOLAR (clofarabine), CVP, CYTOSAR-U (cytarabine), CYTOXAN (cyclophosphamide), ERWINAZE (Asparaginase Erwinia Chrysanthemi), FLUDARA (fludarabine phosphate), FOLEX (methotrexate), FOLEX PFS (methotrexate), GAZYVA (obinutuzumab), GLEEVEC (imatinib mesylate), Hyper-CVAD, ICLUSIG (ponatinib hydrochloride), IMBRUVICA (ibrutinib), LEUKERAN (chlorambucil), LINFOLIZIN (chlorambucil), MARQIBO (vincristine sulfate liposome), METHOTREXATE LPF (methorexate), MEXATE (methotrexate), MEXATE-AQ (methotrexate), mitoxantrone hydrochloride, MUSTARGEN (mechlorethamine hydrochloride), MYLERAN (busulfan), NEOSAR (cyclophosphamide), ONCASPAR (Pegaspargase), PURINETHOL (mercaptopurine), PURIXAN (mercaptopurine), Rubidomycin (daunorubicin hydrochloride), SPRYCEL (dasatinib), SYNRIBO (omacetaxine mepesuccinate), TARABINE PFS (cytarabine), TASIGNA (nilotinib), TREANDA (bendamustine hydrochloride), TRISENOX (arsenic trioxide), VINCASAR PFS (vincristine sulfate), ZYDELIG (idelalisib), or a combination thereof. In certain embodiments, the additional pharmaceutical agent is an anti-lymphoma agent. In certain embodiments, the additional pharmaceutical agent is ABITREXATE (methotrexate), ABVD, ABVE, ABVE-PC, ADCETRIS (brentuximab vedotin), ADRIAMYCIN PFS (doxorubicin hydrochloride), ADRIAMYCIN RDF (doxorubicin hydrochloride), AMBOCHLORIN (chlorambucil), AMBOCLORIN (chlorambucil), ARRANON (nelarabine), BEACOPP, BECENUM (carmustine), BELEODAQ (belinostat), BEXXAR (tositumomab and iodine I 131 tositumomab), BICNU (carmustine), BLENOXANE (bleomycin), CARMUBRIS (carmustine), CHOP, CLAFEN (cyclophosphamide), COPP, COPP-ABV, CVP, CYTOXAN (cyclophosphamide), DEPOCYT (liposomal cytarabine), DTIC-DOME (dacarbazine), EPOCH, FOLEX (methotrexate), FOLEX PFS (methotrexate), FOLOTYN (pralatrexate), HYPER-CVAD, ICE, IMBRUVICA (ibrutinib), INTRON A (recombinant interferon alfa-2b), ISTODAX (romidepsin), LEUKERAN (chlorambucil), LINFOLIZIN (chlorambucil), Lomustine, MATULANE (procarbazine hydrochloride), METHOTREXATE LPF (methotrexate), MEXATE (methotrexate), MEXATE-AQ (methotrexate), MOPP, MOZOBIL (plerixafor), MUSTARGEN (mechlorethamine hydrochloride), NEOSAR (cyclophosphamide), OEPA, ONTAK (denileukin diftitox), OPPA, R-CHOP, REVLIMID (lenalidomide), RITUXAN (rituximab), STANFORD V, TREANDA (bendamustine hydrochloride), VAMP, VELBAN (vinblastine sulfate), VELCADE (bortezomib), VELSAR (vinblastine sulfate), VINCASAR PFS (vincristine sulfate), ZEVALIN (ibritumomab tiuxetan), ZOLINZA (vorinostat), ZYDELIG (idelalisib), or a combination thereof. In certain embodiments, the additional pharmaceutical agent is REVLIMID (lenalidomide), DACOGEN (decitabine), VIDAZA (azacitidine), CYTOSAR-U (cytarabine), IDAMYCIN (idarubicin), CERUBIDINE (daunorubicin), LEUKERAN (chlorambucil), NEOSAR (cyclophosphamide), FLUDARA (fludarabine), LEUSTATIN (cladribine), or a combination thereof. In certain embodiments, the additional pharmaceutical agent is ABITREXATE (methotrexate), ABRAXANE (paclitaxel albumin-stabilized nanoparticle formulation), AC, AC-T, ADE, ADRIAMYCIN PFS (doxorubicin hydrochloride), ADRUCIL (fluorouracil), AFINITOR (everolimus), AFINITOR DISPERZ (everolimus), ALDARA (imiquimod), ALIMTA (pemetrexed disodium), AREDIA (pamidronate disodium), ARIMIDEX (anastrozole), AROMASIN (exemestane), AVASTIN (bevacizumab), BECENUM (carmustine), BEP, BICNU (carmustine), BLENOXANE (bleomycin), CAF, CAMPTOSAR (irinotecan hydrochloride), CAPOX, CAPRELSA (vandetanib), CARBOPLATIN-TAXOL, CARMUBRIS (carmustine), CASODEX (bicalutamide), CEENU (lomustine), CERUBIDINE (daunorubicin hydrochloride), CERVARIX (recombinant HPV bivalent vaccine), CLAFEN (cyclophosphamide), CMF, COMETRIQ (cabozantinib-s-malate), COSMEGEN (dactinomycin), CYFOS (ifosfamide), CYRAMZA (ramucirumab), CYTOSAR-U (cytarabine), CYTOXAN (cyclophosphamide), DACOGEN (decitabine), DEGARELIX, DOXIL (doxorubicin hydrochloride liposome), DOXORUBICIN HYDROCHLORIDE, DOX-SL (doxorubicin hydrochloride liposome), DTIC-DOME (dacarbazine), EFUDEX (fluorouracil), ELLENCE (epirubicin hydrochloride), ELOXATIN (oxaliplatin), ERBITUX (cetuximab), ERIVEDGE (vismodegib), ETOPOPHOS (etoposide phosphate), EVACET (doxorubicin hydrochloride liposome), FARESTON (toremifene), FASLODEX (fulvestrant), FEC, FEMARA (letrozole), FLUOROPLEX (fluorouracil), FOLEX (methotrexate), FOLEX PFS (methotrexate), FOLFIRI, FOLFIRI-BEVACIZUMAB, FOLFIRI-CETUXIMAB, FOLFIRINOX, FOLFOX, FU-LV, GARDASIL (recombinant human papillomavirus (HPV) quadrivalent vaccine), GEMCITABINE-CISPLATIN, GEMCITABINE-OXALIPLATIN, GEMZAR (gemcitabine hydrochloride), GILOTRIF (afatinib dimaleate), GLEEVEC (imatinib mesylate), GLIADEL (carmustine implant), GLIADEL WAFER (carmustine implant), HERCEPTIN (trastuzumab), HYCAMTIN (topotecan hydrochloride), IFEX (ifosfamide), IFOSFAMIDUM (ifosfamide), INLYTA (axitinib), INTRON A (recombinant interferon alfa-2b), IRESSA (gefitinib), IXEMPRA (ixabepilone), JAKAFI (ruxolitinib phosphate), JEVTANA (cabazitaxel), KADCYLA (ado-trastuzumab emtansine), KEYTRUDA (pembrolizumab), KYPROLIS (carfilzomib), LIPODOX (doxorubicin hydrochloride liposome), LUPRON (leuprolide acetate), LUPRON DEPOT (leuprolide acetate), LUPRON DEPOT-3 MONTH (leuprolide acetate), LUPRON DEPOT-4 MONTH (leuprolide acetate), LUPRON DEPOT-PED (leuprolide acetate), MEGACE (megestrol acetate), MEKINIST (trametinib), METHAZOLASTONE (temozolomide), METHOTREXATE LPF (methotrexate), MEXATE (methotrexate), MEXATE-AQ (methotrexate), MITOXANTRONE HYDROCHLORIDE, MITOZYTREX (mitomycin c), MOZOBIL (plerixafor), MUSTARGEN (mechlorethamine hydrochloride), MUTAMYCIN (mitomycin c), MYLOSAR (azacitidine), NAVELBINE (vinorelbine tartrate), NEOSAR (cyclophosphamide), NEXAVAR (sorafenib tosylate), NOLVADEX (tamoxifen citrate), NOVALDEX (tamoxifen citrate), OFF, PAD, PARAPLAT (carboplatin), PARAPLATIN (carboplatin), PEG-INTRON (peginterferon alfa-2b), PEMETREXED DISODIUM, PERJETA (pertuzumab), PLATINOL (cisplatin), PLATINOL-AQ (cisplatin), POMALYST (pomalidomide), prednisone, PROLEUKIN (aldesleukin), PROLIA (denosumab), PROVENGE (sipuleucel-t), REVLIMID (lenalidomide), RUBIDOMYCIN (daunorubicin hydrochloride), SPRYCEL (dasatinib), STIVARGA (regorafenib), SUTENT (sunitinib malate), SYLATRON (peginterferon alfa-2b), SYLVANT (siltuximab), SYNOVIR (thalidomide), TAC, TAFINLAR (dabrafenib), TARABINE PFS (cytarabine), TARCEVA (erlotinib hydrochloride), TASIGNA (nilotinib), TAXOL (paclitaxel), TAXOTERE (docetaxel), TEMODAR (temozolomide), THALOMID (thalidomide), TOPOSAR (etoposide), TORISEL (temsirolimus), TPF, TRISENOX (arsenic trioxide), TYKERB (lapatinib ditosylate), VECTIBIX (panitumumab), VEIP, VELBAN (vinblastine sulfate), VELCADE (bortezomib), VELSAR (vinblastine sulfate), VEPESID (etoposide), VIADUR (leuprolide acetate), VIDAZA (azacitidine), VINCASAR PFS (vincristine sulfate), VOTRIENT (pazopanib hydrochloride), WELLCOVORIN (leucovorin calcium), XALKORI (crizotinib), XELODA (capecitabine), XELOX, XGEVA (denosumab), XOFIGO (radium 223 dichloride), XTANDI (enzalutamide), YERVOY (ipilimumab), ZALTRAP (ziv-aflibercept), ZELBORAF (vemurafenib), ZOLADEX (goserelin acetate), ZOMETA (zoledronic acid), ZYKADIA (ceritinib), ZYTIGA (abiraterone acetate), ENMD-2076, PCI-32765, AC220, dovitinib lactate (TK1258, CHIR-258), BIBW 2992 (TOVOKTM), SGX523, PF-04217903, PF-02341066, PF-299804, BMS-777607, ABT-869, MP470, BIBF 1120 (VARGATEF®), AP24534, JNJ-26483327, MGCD265, DCC-2036, BMS-690154, CEP-11981, tivozanib (AV-951), OSI-930, MM-121, XL-184, XL-647, and/or XL228), proteasome inhibitors (e.g., bortezomib (Velcade)), mTOR inhibitors (e.g., rapamycin, temsirolimus (CCI-779), everolimus (RAD-001), ridaforolimus, AP23573 (Ariad), AZD8055 (AstraZeneca), BEZ235 (Novartis), BGT226 (Norvartis), XL765 (Sanofi Aventis), PF-4691502 (Pfizer), GDC0980 (Genetech), SF1126 (Semafoe) and OSI-027 (OSI)), oblimersen, gemcitabine, carminomycin, leucovorin, pemetrexed, cyclophosphamide, dacarbazine, procarbizine, prednisolone, dexamethasone, campathecin, plicamycin, asparaginase, aminopterin, methopterin, porfiromycin, melphalan, leurosidine, leurosine, chlorambucil, trabectedin, procarbazine, discodermolide, carminomycin, aminopterin, and hexamethyl melamine, or a combination thereof. In certain embodiments, the additional pharmaceutical agent is a binder or inhibitor of an a bromodomain or bromodomain-containing protein. In certain embodiments, the additional pharmaceutical agent is a binder or inhibitor of an HMT (e.g., EZH1). In certain embodiments, the additional pharmaceutical agent is a protein kinase inhibitor (e.g., tyrosine protein kinase inhibitor). In certain embodiments, the additional pharmaceutical agent is selected from the group consisting of epigenetic or transcriptional modulators (e.g., DNA methyltransferase inhibitors, histone deacetylase inhibitors (HDAC inhibitors), lysine methyltransferase inhibitors), antimitotic drugs (e.g., taxanes and vinca alkaloids), hormone receptor modulators (e.g., estrogen receptor modulators and androgen receptor modulators), cell signaling pathway inhibitors (e.g., tyrosine protein kinase inhibitors), modulators of protein stability (e.g., proteasome inhibitors), Hsp90 inhibitors, glucocorticoids, all-trans retinoic acids, and other agents that promote differentiation. In certain embodiments, the compounds described herein or pharmaceutical compositions can be administered in combination with an anti-cancer therapy including, but not limited to, surgery, radiation therapy, transplantation (e.g., stem cell transplantation, bone marrow transplantation), immunotherapy, and chemotherapy.

Also encompassed by the disclosure are kits (e.g., pharmaceutical packs). The kits provided may comprise a pharmaceutical composition or compound described herein and a container (e.g., a vial, ampule, bottle, syringe, and/or dispenser package, or other suitable container). In some embodiments, provided kits may optionally further include a second container comprising a pharmaceutical excipient for dilution or suspension of a pharmaceutical composition or compound described herein. In some embodiments, the pharmaceutical composition or compound described herein provided in the first container and the second container are combined to form one unit dosage form.

Thus, in one aspect, provided are kits including a first container comprising a compound or pharmaceutical composition described herein. In certain embodiments, the kits are useful for treating a disease (e.g., proliferative disease, inflammatory disease, autoimmune disease, genetic disease, hematological disease, neurological disease, painful condition, psychiatric disorder, or metabolic disorder) in a subject in need thereof. In certain embodiments, the kits are useful for preventing a disease (e.g., proliferative disease, inflammatory disease, autoimmune disease, genetic disease, hematological disease, neurological disease, painful condition, psychiatric disorder, or metabolic disorder) in a subject in need thereof. In certain embodiments, the kits are useful for inhibiting the activity (e.g., aberrant activity, such as increased activity) of an HMT in a subject, biological sample, tissue, or cell. In certain embodiments, the kits are useful for inducing apoptosis in a cell.

In certain embodiments, a kit described herein further includes instructions for using the compound or pharmaceutical composition included in the kit. A kit described herein may also include information as required by a regulatory agency such as the U.S. Food and Drug Administration (FDA). In certain embodiments, the information included in the kits is prescribing information. In certain embodiments, the kits and instructions provide for treating a disease (e.g., proliferative disease, inflammatory disease, autoimmune disease, genetic disease, hematological disease, neurological disease, painful condition, psychiatric disorder, or metabolic disorder) in a subject in need thereof. In certain embodiments, the kits and instructions provide for preventing a disease (e.g., proliferative disease, inflammatory disease, autoimmune disease, genetic disease, hematological disease, neurological disease, painful condition, psychiatric disorder, or metabolic disorder) in a subject in need thereof. In certain embodiments, the kits and instructions provide for inducing degradation of a target protein (e.g., a bromodomain, a bromodomain-containing protein, or FKBP12) in a subject, biological sample, tissue, or cell. In certain embodiments, the kits and instructions provide for inducing apoptosis in a cell. A kit described herein may include one or more additional pharmaceutical agents described herein as a separate composition.

Methods of Treatment and Uses

The compounds described herein are capable of binding (e.g., reversibly binding or irreversibly binding) target proteins and inducing degradation of a target protein (e.g., a bromodomain, a bromodomain-containing protein, or FKBP12). The present disclosure thus also provides methods of inducing degradation of a bromodomain in a subject, biological sample, tissue, or cell. The present disclosure thus also provides methods of inducing degradation of a bromodomain-containing protein in a subject, biological sample, tissue, or cell. The present disclosure provides methods of inducing degradation of FKBP12 in a subject, biological sample, tissue, or cell. The present disclosure further provides methods for the treatment of a wide range of diseases, such as proliferative diseases, inflammatory diseases, autoimmune diseases, genetic diseases, hematological diseases, neurological diseases, painful conditions, psychiatric disorders, and metabolic disorders in a subject in need thereof.

In another aspect, the present disclosure provides methods of inducing degradation of a bromodomain-containing protein in a subject in need thereof, the methods comprise administering to the subject an effective amount of a compound or pharmaceutical composition described herein. In another aspect, the present disclosure provides methods of inducing degradation of a bromodomain-containing protein in a biological sample, tissue, or cell, the methods comprise contacting the biological sample, tissue, or cell with an effective amount of a compound or pharmaceutical composition described herein. In another aspect, the present disclosure provides methods of inducing degradation of FKBP12 in a biological sample, tissue, or cell, the methods comprise contacting the biological sample, tissue, or cell with an effective amount of a compound or pharmaceutical composition described herein.

In certain embodiments, the application provides a method of binding an ubiquitin receptor RPN13 and promoting the degradation of a target protein (e.g., a bromodomain, a bromodomain-containing protein, or FKBP12). In certain embodiments, the ubiquitin receptor is RPN13. In certain embodiments, the binder of the ubiquitin receptor RPN13 is RA190 (shown below).

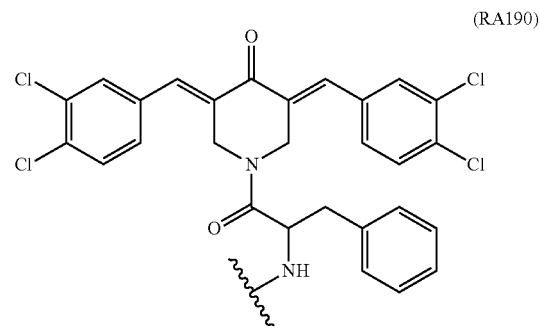 [SMILES: *NC(Cc1ccccc1)C(=O)N1C/C(=C\c2ccc(Cl)c(Cl)c2)C(=O)/C(=C/c2ccc(Cl)c(Cl)c2)C1]

(RA190)

Use of a bifunctional compound that binds a target protein (e.g., a bromodomain, a bromodomain-containing protein, or FKBP12) and a ubiquitin receptor RPN13 provides a strategy for treating diseases associated with the target protein (e.g. proliferative diseases).

The present disclosure also provides a compound of Formulae (I), (IA), or (IB), or a pharmaceutically acceptable salt, co-crystal, tautomer, stereoisomer, solvate, hydrate, polymorph, isotopically enriched derivative, or prodrug, or composition thereof, for use in the treatment of diseases, such as proliferative diseases, inflammatory diseases, autoimmune diseases, genetic diseases, hematological diseases, neurological diseases, painful conditions, psychiatric disorders, and metabolic disorders in a subject in need thereof.

The present disclosure also provides uses of a compound of Formulae (I), (IA), or (IB), or a pharmaceutically acceptable salt, co-crystal, tautomer, stereoisomer, solvate, hydrate, polymorph, isotopically enriched derivative, or prodrug, or composition thereof, in the manufacture of a medicament for the treatment of diseases, such as proliferative diseases, inflammatory diseases, autoimmune diseases, genetic diseases, hematological diseases, neurological diseases, painful conditions, psychiatric disorders, and metabolic disorders in a subject in need thereof.

In certain embodiments, the methods of the disclosure comprise administering to the subject an effective amount of a compound of Formulae (I), (IA), or (IB), or a pharmaceutically acceptable salt, co-crystal, tautomer, stereoisomer, solvate, hydrate, polymorph, isotopically enriched derivative, or prodrug, or composition thereof. In some embodiments, the effective amount is a therapeutically effective amount. In some embodiments, the effective amount is a prophylactically effective amount.

In certain embodiments, the subject being treated is an animal. The animal may be of either sex and may be at any stage of development. In certain embodiments, the subject is a mammal. In certain embodiments, the subject being treated is a human. In certain embodiments, the subject is a domesticated animal, such as a dog, cat, cow, pig, horse, sheep, or goat. In certain embodiments, the subject is a companion animal, such as a dog or cat. In certain embodiments, the subject is a livestock animal, such as a cow, pig, horse, sheep, or goat. In certain embodiments, the subject is a zoo animal. In another embodiment, the subject is a research animal such as a rodent (e.g., mouse, rat), dog, pig, or non-human primate. In certain embodiments, the animal is a genetically engineered animal. In certain embodiments, the animal is a transgenic animal.

Certain methods described herein may comprise administering one or more additional pharmaceutical agent(s) in combination with the compounds described herein. The additional pharmaceutical agent(s) may be administered at the same time as the compound of Formulae (I), (IA), or (IB), or at different times than the compound of Formula (I). For example, the compound of Formulae (I), (IA), or (IB) and any additional pharmaceutical agent(s) may be on the same dosing schedule or different dosing schedules. All or some doses of the compound of Formulae (I), (IA), or (IB) may be administered before all or some doses of an additional pharmaceutical agent, after all or some does an additional pharmaceutical agent, within a dosing schedule of an additional pharmaceutical agent, or a combination thereof. The timing of administration of the compound of Formulae (I), (IA), or (IB) and additional pharmaceutical agents may be different for different additional pharmaceutical agents.

In certain embodiments, the additional pharmaceutical agent comprises an agent useful in the treatment of diseases, such as proliferative diseases, inflammatory diseases, autoimmune diseases, genetic diseases, hematological diseases, neurological diseases, painful conditions, psychiatric disorders, and metabolic disorders in a subject in need thereof. In certain embodiments, the additional pharmaceutical agent is useful in the treatment of a proliferative disease. In certain embodiments, the additional pharmaceutical agent is useful in the treatment of an inflammatory disease. In certain embodiments, the additional pharmaceutical agent is useful in the treatment of proliferative diseases, inflammatory diseases, autoimmune diseases, genetic diseases, hematological diseases, neurological diseases, painful conditions, psychiatric disorders, or metabolic disorders. In certain embodiments, the additional pharmaceutical agent is useful in the treatment of multiple myeloma. In certain embodiments, the additional pharmaceutical agent is useful in the treatment of leukemia. In certain embodiments, the additional pharmaceutical agent is useful in the treatment of lymphoma. In certain embodiments, the additional pharmaceutical agent is useful in the treatment of a non-Hodgkin's lymphoma. In certain embodiments, the additional pharmaceutical agent is useful in the treatment of cancer resistant to proteasome inhibitors (e.g., resistant to bortezomib).

In another aspect, the present disclosure provides methods for inducing degradation of a bromodomain, the method comprising administering to the subject a compound of Formulae (I), (IA), (IB), or a pharmaceutically acceptable salt, co-crystal, tautomer, stereoisomer, solvate, hydrate, polymorph, isotopically enriched derivative, or prodrug, or composition thereof. In another aspect, the present disclosure provides methods for inducing degradation of a bromodomain-containing protein, the method comprising administering to the subject a compound of Formulae (I), (IA), (IB), or a pharmaceutically acceptable salt, co-crystal, tautomer, stereoisomer, solvate, hydrate, polymorph, isotopically enriched derivative, or prodrug, or composition thereof. In another aspect, the present disclosure provides methods for inducing the degradation of FKBP, the method comprising administering to the subject a compound of Formulae (I) (IA), (IB), or a pharmaceutically acceptable salt, co-crystal, tautomer, stereoisomer, solvate, hydrate, polymorph, isotopically enriched derivative, or prodrug, or composition thereof. In another aspect, the present disclosure provides methods for inducing the degradation of FKBP12, the method comprising administering to the subject a compound of Formulae (I), (IA), (IB), or a pharmaceutically acceptable salt, co-crystal, tautomer, stereoisomer, solvate, hydrate, polymorph, isotopically enriched derivative, or prodrug, or composition thereof.

In another aspect, the present disclosure provides methods for binding a ubiquitin receptor RPN13 and promoting the degradation of a target protein (e.g., a bromodomain, a bromodomain-containing protein, or FKBP12), the method comprising administering to the subject a compound of Formulae (I), (IA), (IB), or a pharmaceutically acceptable salt, co-crystal, tautomer, stereoisomer, solvate, hydrate, polymorph, isotopically enriched derivative, or prodrug, or composition thereof.

EXAMPLES

In order that the invention described herein may be more fully understood, the following examples are set forth. The examples described in this application are offered to illustrate the compounds, pharmaceutical compositions, and methods provided herein and are not to be construed in any way as limiting their scope.

Compounds of Formulae (I), (IA), and (IB) may be prepared using the synthetic schemes and procedures described in detail below.

Example 1. Synthesis of RPN13 Related Degraders

Experimental Procedures for Synthesis of RPN13 Related Degraders

In an exemplary synthesis, LW-RPN13-3 was synthesized using the steps shown in Scheme 1.

Scheme 1. Exemplary synthesis of LW-RPN13-3 as described herein

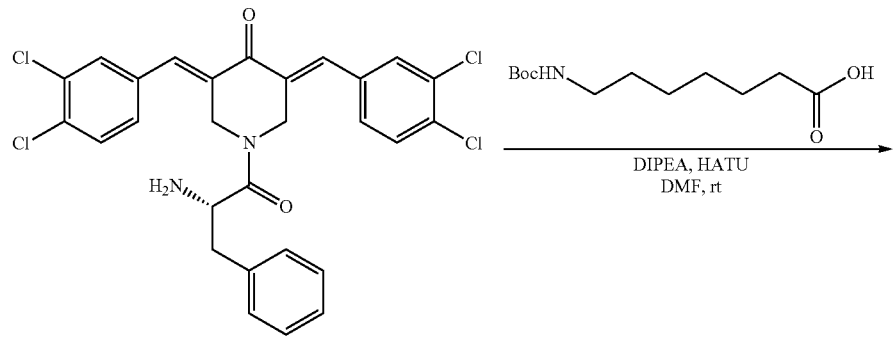

RA190

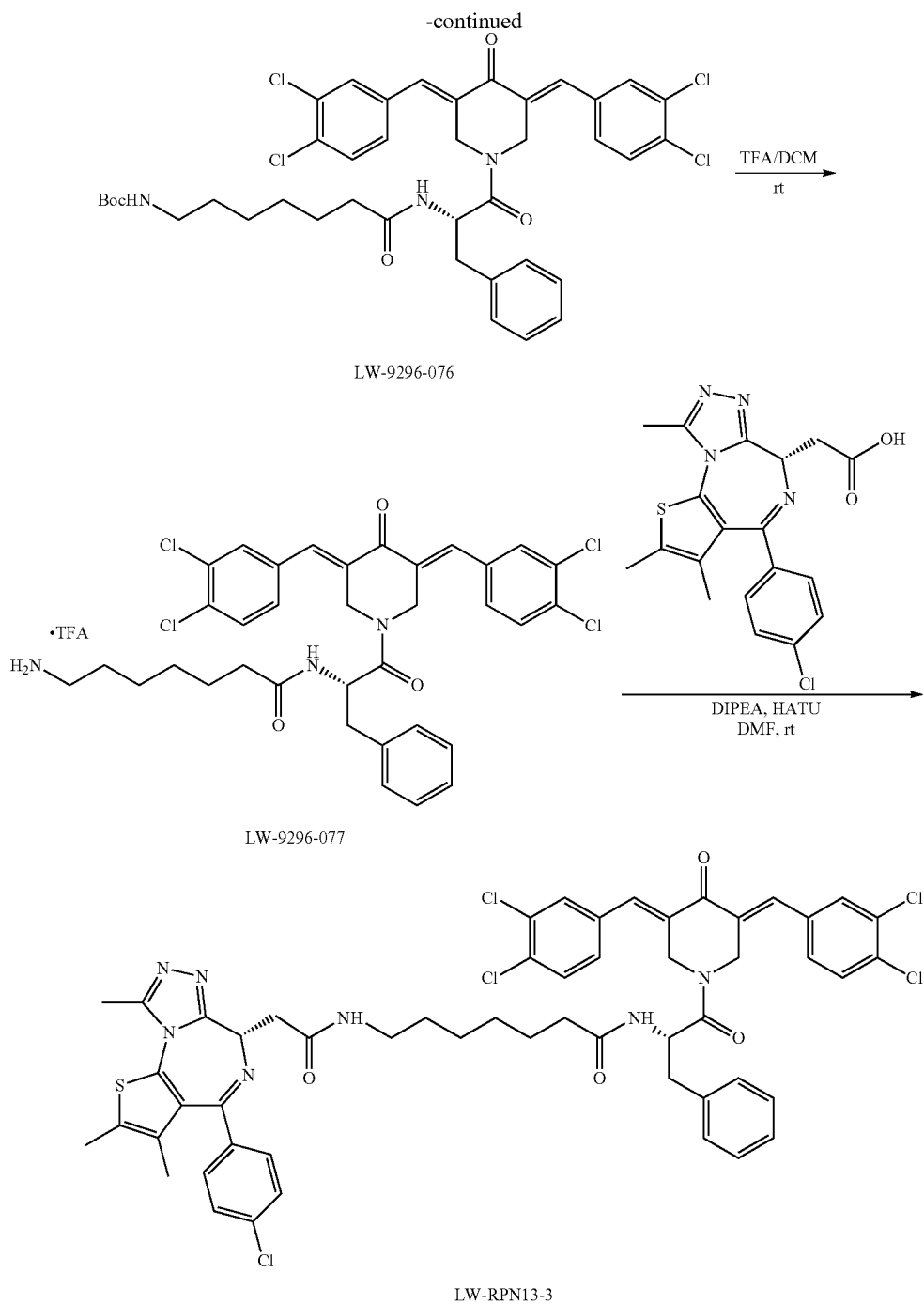

LW-9296-076

LW-9296-077

LW-RPN13-3 tert-butyl (7-(((S)-1-(3,5-bis((E)-3,4-dichlorobenzylidene)-4-oxopiperidin-1-yl)-1-oxo-3-phenylpropan-2-yl)amino)-7-oxoheptyl)carbamate: To a solution of 7-((tert-butoxycarbonyl)amino)heptanoic acid (2.37 mg, 0.0097 mmol), RA190 (5.44 mg, 0.0097 mmol) and HATU (4.06 mg, 0.0107 mmol) in DMF (0.2 mL) was added DIPEA (12 mg, 0.097 mmol) at room temperature. The reaction mixture was stirred at room temperature for an hour, and purified via HPLC (0.1% TFA/MeCN) to afford LW-9296-076 (6 mg). MS: m/z (M+1)+: 788.27.

7-amino-N—((S)-1-(3,5-bis((E)-3,4-dichlorobenzylidene)-4-oxopiperidin-1-yl)-1-oxo-3-phenylpropan-2-yl)heptanamide: To a solution of LW-9296-076 (3.15 mg, 0.004 mmol) in DCM (0.2 mL) was added TFA (50 µL) at room temperature. The reaction mixture was stirred at room temperature for an hour, concentrated and dried in vacuo to afford LW-9296-077. MS: m/z (M+1)+: 688.25.

$N^1$—((S)-1-(3,5-bis((E)-3,4-dichlorobenzylidene)-4-oxopiperidin-1-yl)-1-oxo-3-phenylpropan-2-yl)-$N^5$-(15-oxo-19-((4S)-2-oxohexahydro-1H-thieno[3,4-d]imidazol-4-yl)-4,7,10-trioxa-14-azanonadecyl)glutaramide: To a solution of LW-9296-077 (0.004 mmol) in DMF (0.4 mL) was added DIPEA (7 drops). To a solution of (S)-2-(4-(4-chlorophenyl)-2,3,9-trimethyl-6H-thieno[3,2-f][1,2,4]triazolo[4,3-a][1,4]diazepin-6-yl)acetic acid (1.44 mg, 0.0036 mmol) and HATU (3 mg, 0.0079 mmol) in DMF (0.2 mL) was added DIPEA (3 drops) at room temperature. The former solution was added to the latter, and the combined reaction mixture was stirred at room temperature for an hour, and purified via HPLC (0.1% TFA/MeCN) to afford LW-RPN13-3 (2.68 mg). MS: m/z (M+1)$^+$: 1070.35. The synthesis is shown in Scheme 1.

In an exemplary synthesis, LW-RPN13-5 was synthesized using the steps shown in Scheme 2.

Scheme 2. Exemplary synthesis of LW-RPN13-5 as described herein

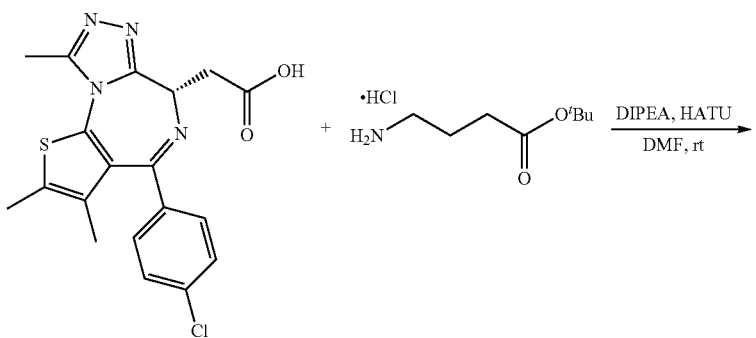

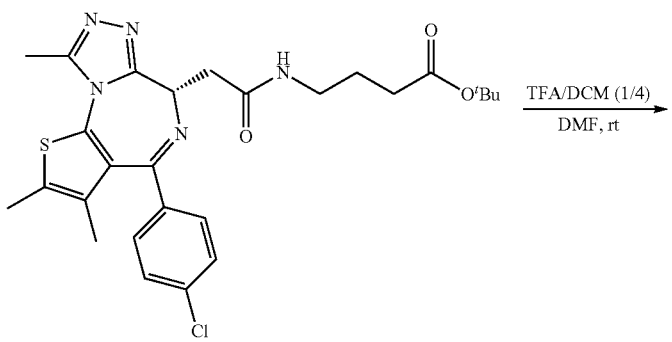

LW-9296-091

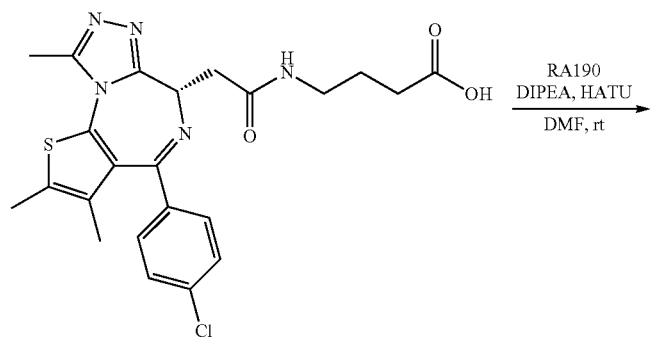

LW-9296-096

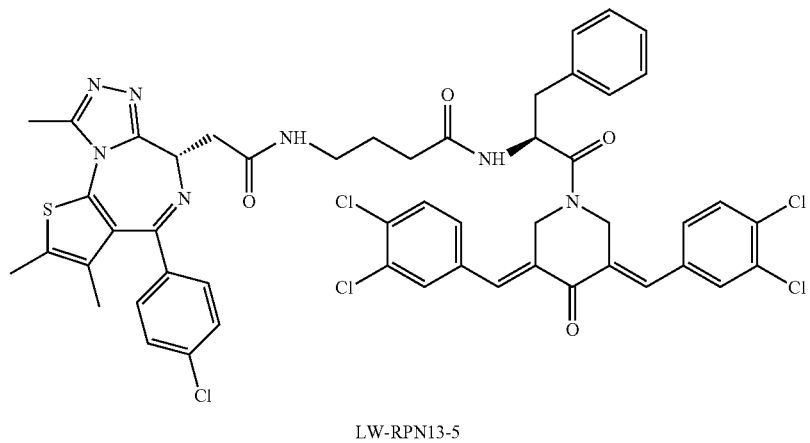

LW-RPN13-5 tert-butyl (S)-4-(2-(4-(4-chlorophenyl)-2,3,9-trimethyl-6H-thieno[3,2-f][1,2,4]triazolo[4,3-a][1,4]diazepin-6-yl)acetamido)butanoate: To a solution of (S)-2-(4-(4-chlorophenyl)-2,3,9-trimethyl-6H-thieno[3,2-f][1,2,4][1,4]diazepin-6-yl)acetic acid (5 mg, 0.0125 mmol), tert-butyl 4-aminobutanoate hydrogen chloride (7 mg, 0.0358 mmol), and HATU (5 mg, 0.0132 mmol) in DMF (0.2 mL) was added DIPEA (16 mg, 0.125 mmol) at room temperature. The reaction mixture was stirred at room temperature for an hour, and purified via HPLC (0.1% TFA/MeCN) to afford LW-9296-091 (9.60 mg). MS: m/z (M+1)$^+$: 542.29.

(S)-4-(2-(4-(4-chlorophenyl)-2,3,9-trimethyl-6H-thieno[3,2-f][1,2,4]triazolo[4,3-a][1,4]diazepin-6-yl)acetamido)butanoic acid:

To a solution of LW-9296-091 (1.34 mg, 0.0025 mmol) in DCM (0.2 mL) was added TFA (50 μL). The reaction mixture was stirred at room temperature for an hour, concentrated and dried in vacuo to afford LW-9296-096. MS: m/z (M+1)$^+$: 486.24.

N—((S)-1-(3,5-bis((E)-3,4-dichlorobenzylidene)-4-oxopiperidin-1-yl)-1-oxo-3-phenylpropan-2-yl)-4-(2-((S)-4-(4-chlorophenyl)-2,3,9-trimethyl-6H-thieno[3,2-f][1,2,4]triazolo[4,3-a][1,4]diazepin-6-yl)acetamido)butanamide:

To a solution of LW-9296-096 (0.0025 mmol), and HATU (1.05 mg, 0.0028 mmol) in DMF (0.2 mL) was added DIPEA (5 drops), followed by the addition of RA190 (2.13 mg, 0.0038 mmol) at room temperature. The reaction mixture was stirred at room temperature for 30 minutes, and purified via HPLC (0.1% TFA/MeCN) to afford LW-RPN13-5 (2.14 mg). MS: m/z (M+1)$^+$: 1028.25. The synthesis is shown in Scheme 2.

In an exemplary synthesis, LW-RPN13-6 was synthesized using the steps shown in Scheme 3.

Scheme 3. Exemplary synthesis of LW-RPN13-6 as described herein.

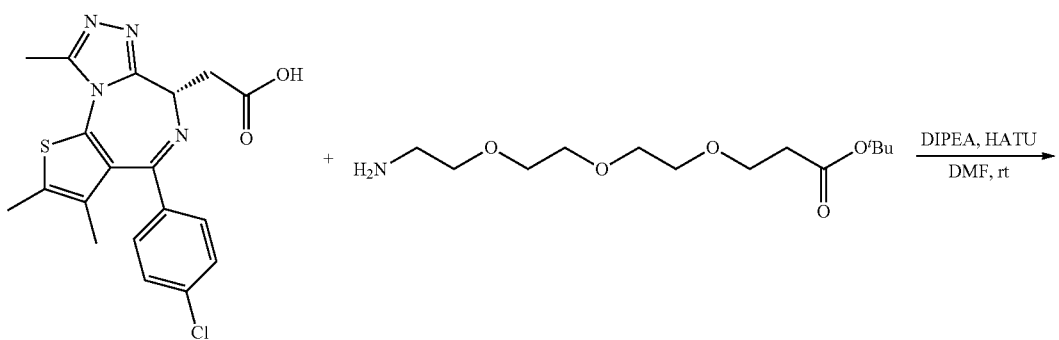

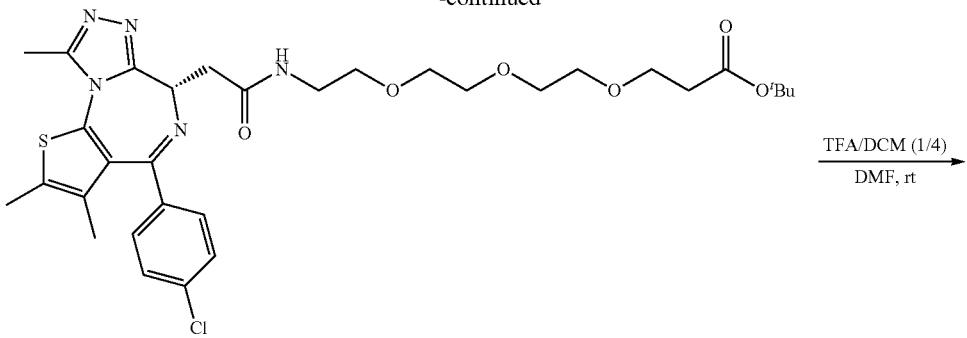

LW-9296-092

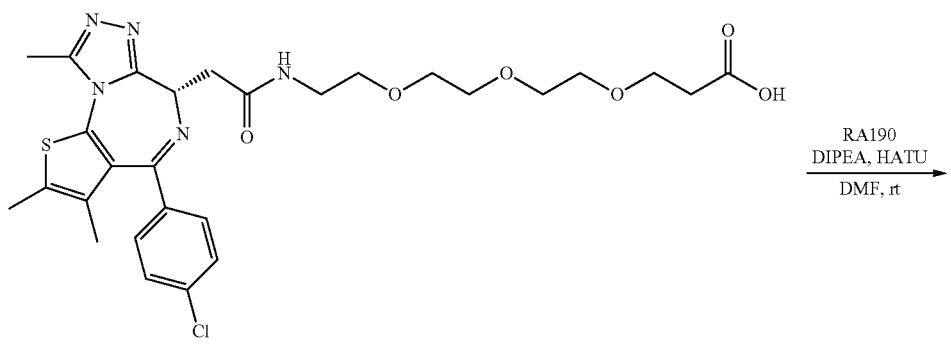

LW-9296-095

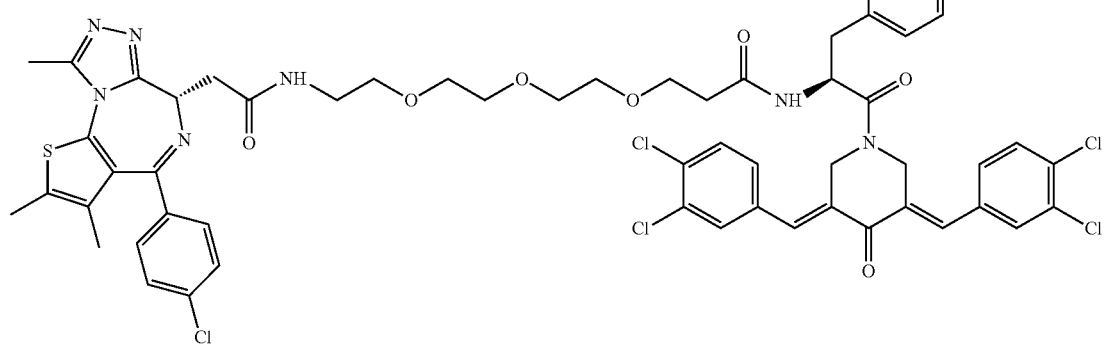

LW-RPN13-6 tert-butyl (S)-4-(2-(4-(4-chlorophenyl)-2,3,9-trimethyl-6H-thieno[3,2-f][1,2,4]triazolo[4,3-a][1,4]diazepin-6-yl)acetamido)butanoate: To a solution of (S)-2-(4-(4-chlorophenyl)-2,3,9-trimethyl-6H-thieno[3,2-f][1,2,4]triazolo[4,3-a][1,4]diazepin-6-yl)acetic acid (5 mg, 0.0125 mmol), tert-butyl 3-(2-(2-(2-aminoethoxy)ethoxy)ethoxy)propanoate (20 mg, 0.0721 mmol), and HATU (7 mg, 0.0084 mmol) in DMF (0.2 mL) was added DIPEA (16 mg, 0.125 mmol) at room temperature. The reaction mixture was stirred at room temperature for an hour, and purified via HPLC (0.1% TFA/MeCN) to afford LW-9296-092 (8.86 mg). MS: m/z (M+1)$^+$: 660.37.

(S)-1-(4-(4-chlorophenyl)-2,3,9-trimethyl-6H-thieno[3,2-f][1,2,4]triazolo[4,3-a][1,4]diazepin-6-yl)-2-oxo-6,9,12-trioxa-3-azapentadecan-15-oic acid: To a solution of LW-9296-092 (2.86 mg, 0.0043 mmol) in DCM (0.2 mL) was added TFA (50 □L). The reaction mixture was stirred at room temperature for an hour, concentrated and dried in vacuo to afford LW-9296-095. MS: m/z (M+1)$^+$: 604.33.

N—((S)-1-(3,5-bis((E)-3,4-dichlorobenzylidene)-4-oxopiperidin-1-yl)-1-oxo-3-phenylpropan-2-yl)-3-(2-(2-(2-(2-((S)-4-(4-chlorophenyl)-2,3,9-trimethyl-6H-thieno[3,2-f][1,2,4]triazolo[4,3-a][1,4]diazepin-6-yl)acetamido)ethoxy)ethoxy)ethoxy)propanamide: To a solution of LW-9296-095 (0.0043 mmol), and HATU (1.80 mg, 0.0047 mmol) in DMF (0.2 mL) was added DIPEA (5 drops), followed by the addition of RA190 (2.42 mg, 0.0043 mmol) at room temperature. The reaction mixture was stirred at room temperature for 30 minutes, and purified via HPLC (0.1% TFA/MeCN) to afford LW-RPN13-6 (0.54 mg). MS: m/z (M+1)$^+$: 1146.28. The synthesis is shown in Scheme 3.

In an exemplary synthesis, LW-RPN13-7 was synthesized using the steps shown in Scheme 4.

Scheme 4. Exemplary synthesis of LW-RPN13-7 as described herein.
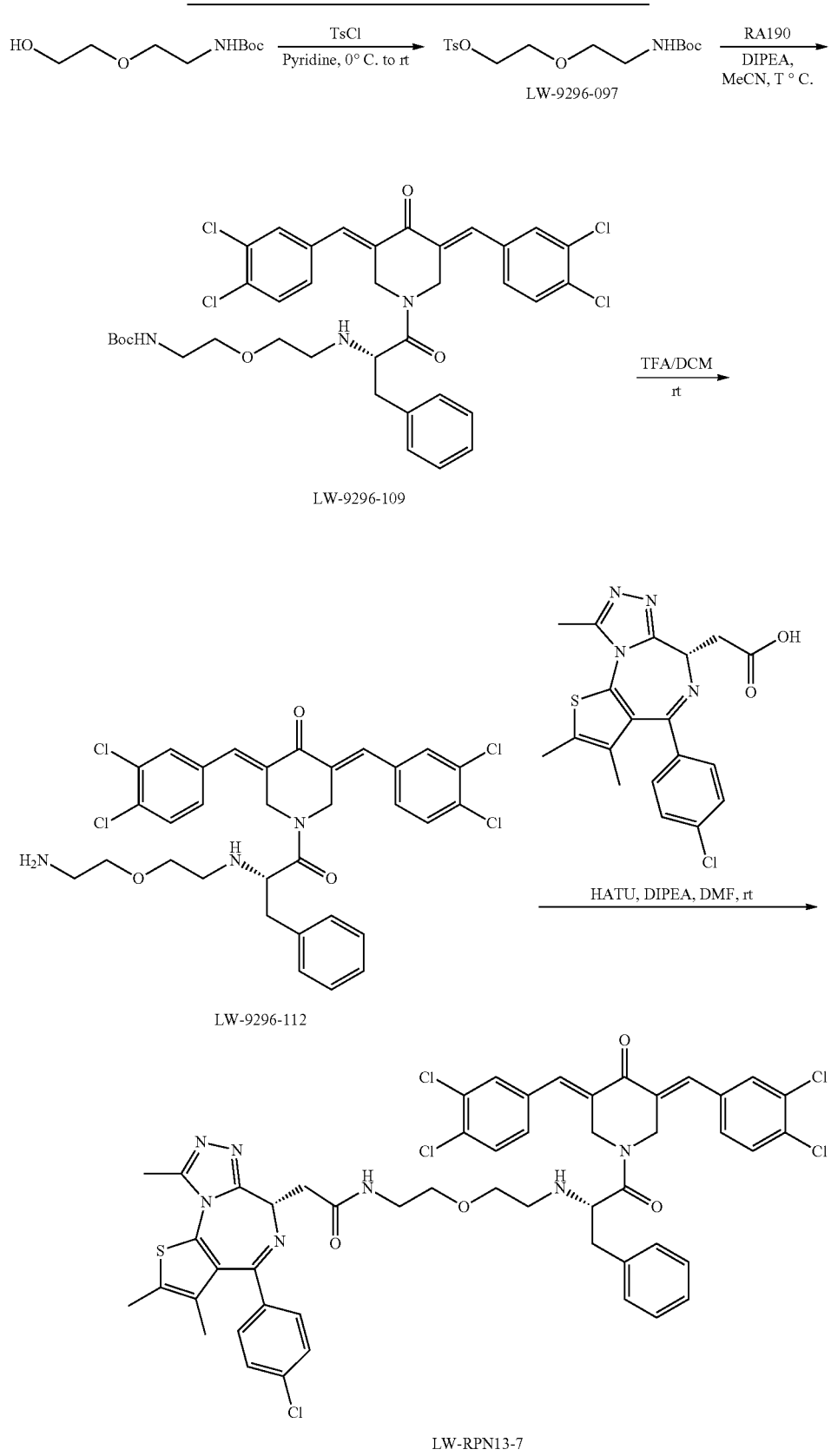

2-(2-((tert-butoxycarbonyl)amino)ethoxy)ethyl 4-methylbenzenesulfonate: To a solution of tert-butyl (2-(2-hydroxyethoxy)ethyl)carbamate (205 mg, 1.0 mmol) in pyridine (2 mL) was added 4-methylbenzenesulfonyl chloride (286 mg, 1.5 mmol) in portions at 0° C. After addition, the reaction mixture was allowed to stir at room temperature overnight, diluted with DCM (50 mL), and washed with 4N HCl (20 mL×3). The organic phase was dried over anhydrous $Na_2SO_4$, and filtered. The filtrate was concentrated in vacuo, and the residue was purified via silica gel column chromatography (EtOAc/Hexane: 1/4, $R_f$=0.2) to afford LW-9296-097 (330 mg). MS: m/z $(M+1)^+$: 360.24.

tert-butyl (2-(2-(((S)-1-(3,5-bis((E)-3,4-dichlorobenzylidene)-4-oxopiperidin-1-yl)-1-oxo-3-phenylpropan-2-yl)amino)ethoxy)ethyl)carbamate: The mixture of LW-9296-097 (7.2 mg, 0.02 mmol), RA190 (11.2 mg, 0.02 mmol) and DIPEA (20 mL, 0.1 mmol) in acetonitrile (0.4 mL) was stirred at room temperature for 6 hours and then at 80° C. overnight. The reaction mixture was purified via HPLC (0.1% TFA/MeCN) to afford LW-9296-109 (3.8 mg). MS: m/z $(M+1)^+$: 748.22.

1-((2-(2-aminoethoxy)ethyl)-L-phenylalanyl)-3,5-bis((E)-3,4-dichlorobenzylidene)piperidin-4-one: To a solution of LW-9296-109 (3.8 mg, 0.0051 mmol) in DCM (0.2 mL) was added TFA (50 μL) at room temperature. The reaction mixture was stirred for 2 hours, concentrated and dried in vacuo to afford LW-9296-112 (0.0051 mmol). MS: m/z $(M+1)^+$: 648.19.

N-(2-(2-(((S)-1-(3,5-bis((E)-3,4-dichlorobenzylidene)-4-oxopiperidin-1-yl)-1-oxo-3-phenylpropan-2-yl)amino)ethoxy)ethyl)-2-((S)-4-(4-chlorophenyl)-2,3,9-trimethyl-6H-thieno[3,2-f][1,2,4]triazolo[4,3-a][1,4]diazepin-6-yl)acetamide: To a solution of (S)-2-(4-(4-chlorophenyl)-2,3,9-trimethyl-6H-thieno[3,2-f][1,2,4]triazolo[4,3-a][1,4]diazepin-6-yl)acetic acid (2.0 mg, 0.0050 mmol) and HATU (2.08 mg, 0.0055 mmol) in DMF (0.2 mL) was added DIPEA (3 drops) at room temperature. To a solution of LW-9296-112 (0.0051 mmol) in DMF (0.4 mL) was added DIPEA (5 drops). The latter solution was added to the former, and the combined reaction mixture was stirred at room temperature for an hour, and purified via HPLC (0.1% TFA/MeCN) to afford LW-RPN13-7 (5.58 mg). MS: m/z (M+1)+: 1030.37. The synthesis is shown in Scheme 4.

Example 2

RPN Induced Degradation

Figure 40A:
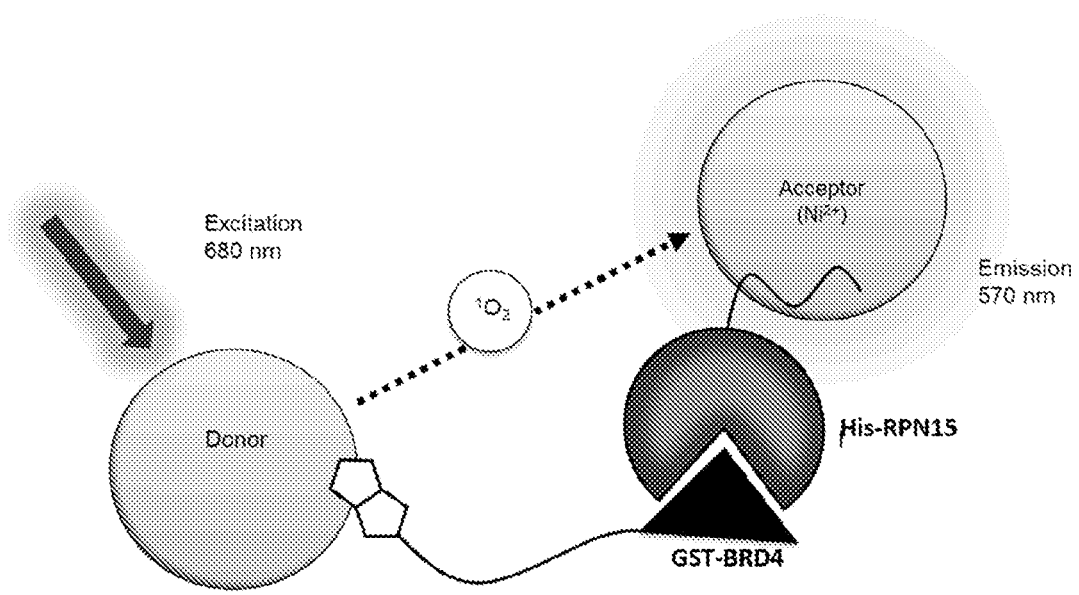
FIG. 40A shows a dimerization assay to detect the RPN13 and BRD4 dimerization by exemplary compound RAJQ9.
Figure 40B:
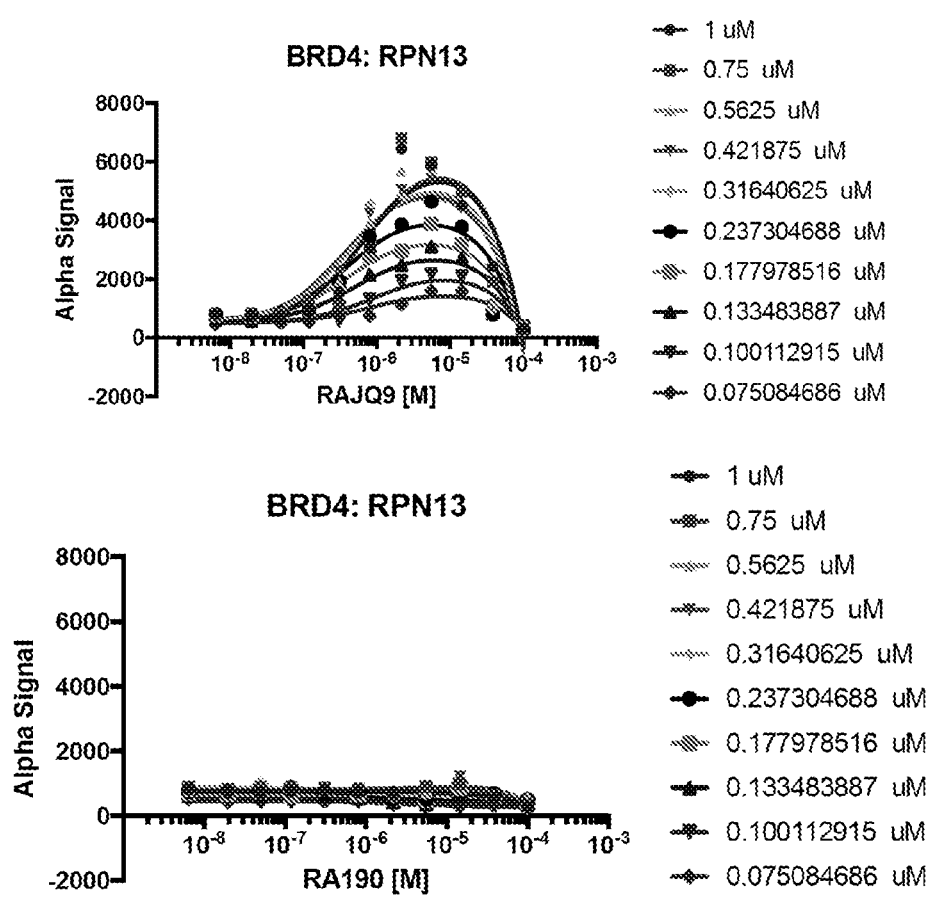
In FIG. 40B, the data suggests that treatment with the exemplary compound RAJQ9 (at the indicated concentrations) can bring these two proteins (RPN13 and BRD4) together.
Figure 41:
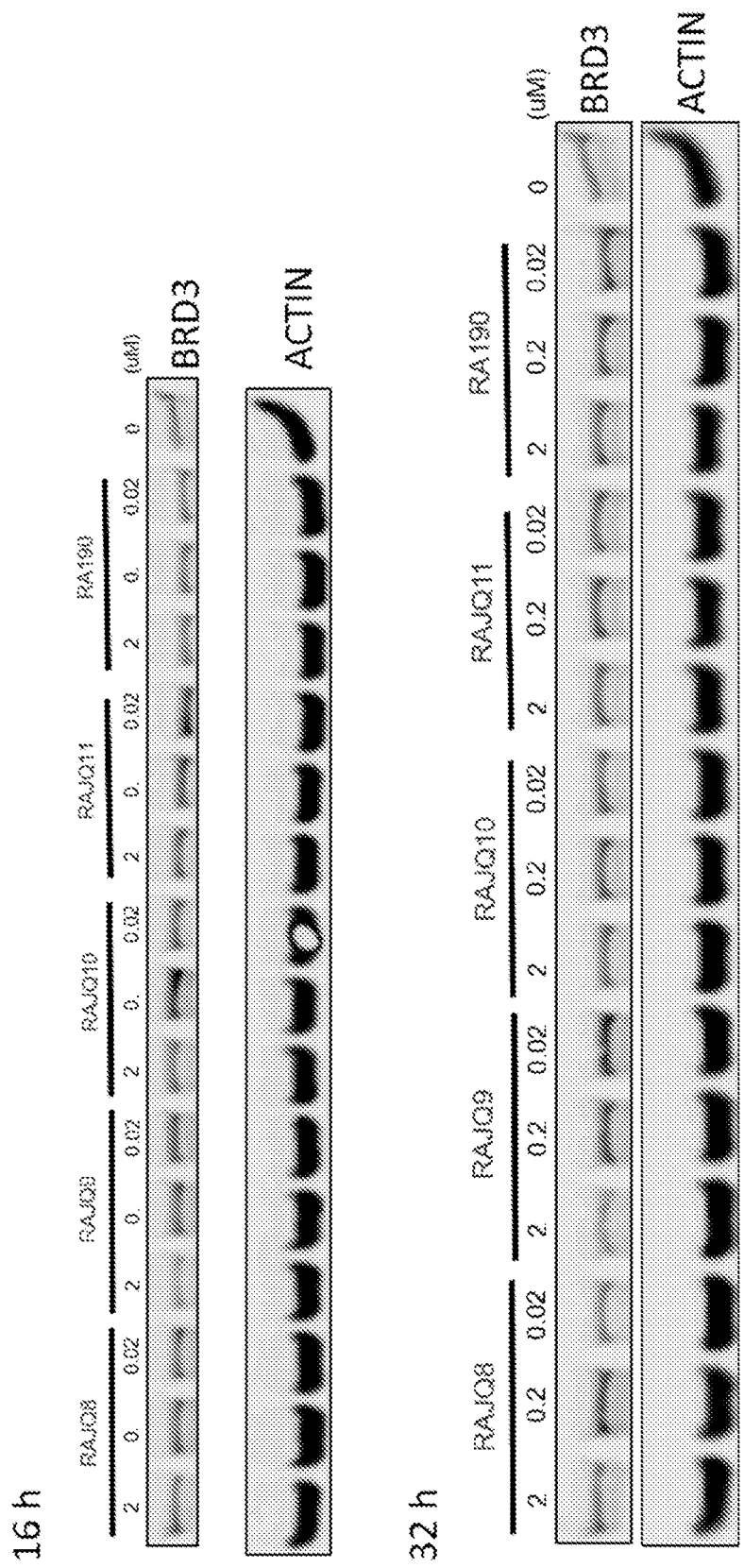
FIG. 41 shows an assay of bromodomain (BRD3) degradation in 293T cells upon treatment of exemplary bromodomain degraders RAJQ8, RAJQ9, RAJQ10

A dimerization assay was used to detect the RPN13 and BRD4 dimerization by RAJQ9 (FIG. 40A). The data suggests that the molecule RAJQ9 can dimerize these two proteins together (FIG. 40B). Bromodomain degradation was observed in 293T cells and the dimerization of RPN13 with a bromodomain (BRD3 or BRD4) was reconfirmed (FIGS. 41-42). New compounds were synthesized in the series using the same conditions as RAJQ9 synthesis (See FIG. 26). For example, the synthesis of exemplary BRD4 inhibitor RAJQ14 is shown in FIG. 43. It was confirmed in the BRD4 assay that the exemplary BRD4 degrader compounds (RAJQ14, RAJQ14-ester) bind to BRD4 (FIG. 44). It was observed that Myc was lost with BRD4 degraders in the MCF7 breast cancer cell line (FIG. 45). For the results shown in FIG. 45, the cells used were MCF7 WT, the exemplary BRD4 degrader compound was RAJQ14 (at 3 μM concentration), and the time points shown in the assay were 2 hours, 6 hours, 16 hours, and 24 hours. FKBP12 degradation in the MCF7 breast cancer line was reconfirmed (FIG. 46). For the results shown in FIG. 46, the cells used were MCF7 WT, the drug was the exemplary FKBP12 degrader RAFKBP4 (at 3 μM concentration), and the time points shown in the assay were 2 hours, 6 hours, 16 hours, and 24 hours.

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:

1. A compound of Formula (I), Formula (IA), or Formula (IB):

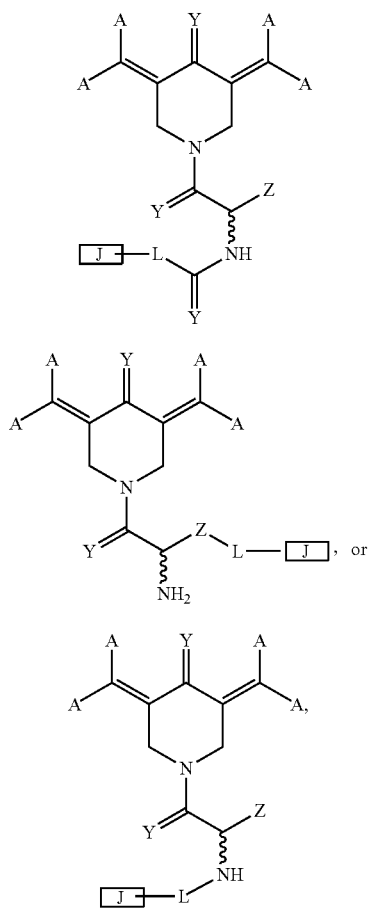

or a pharmaceutically acceptable salt, solvate, hydrate, tautomer, or stereoisomer thereof, wherein:
in each pair of A's, one A is hydrogen, and the other A is one of:
(i) phenyl, optionally substituted with 1-5 substituents selected from the group consisting of $R^1$, $OR^1$, $NR^1R^2$, $S(O)_qR^1$, $SO_2R^1R^2$, $NR^1SO_2R^2$, $C(O)R^1$, $C(O)OR^1$, $C(O)NR^1R^2$, $NR^1C(O)R^2$, $NR^1C(O)OR^2$, $CF_3$, and $OCF_3$;
(ii) naphthyl, optionally substituted with 1-5 substituents selected from the group consisting of $R^1$, $OR^1$, $NR^1R^2$, $S(O)_qR^1$, $SO_2R^1R^2$, $NR^1SO_2R^2$, $C(O)R^1$, $C(O)OR^1$, $C(O)NR^1R^2$, $NR^1C(O)R^2$, $NR^1C(O)OR^2$, $CF_3$, and $OCF_3$;
(iii) a 5 or 6 membered monocyclic heteroaryl group, having 1-3 heteroatoms selected from the group consisting of O, N, and S, optionally substituted with 1-3 substituents selected from the group consisting of $R^1$, $OR^1$, $NR^1R^2$, $S(O)_qR^1$, $SO_2R^1R^2$, $NR^1SO_2R^2$, $C(O)R^1$, $C(O)OR^1$, $C(O)NR^1R^2$, $NR^1C(O)R^2$, $NR^1C(O)OR^2$, $CF_3$, and $OCF_3$; and
(iv) an 8 to 10 membered bicyclic heteroaryl group containing 1-3 heteroatoms selected from the group consisting of O, N, and S; and the second ring is fused to the first ring using 2 carbon atoms, and the bicyclic heteroaryl group is optionally substituted with 1-3 substituents selected from the group consisting of $R^1$, $OR^1$, $NR^1R^2$, $S(O)_qR^1$, $SO_2R^1R^2$, $NR^1SO_2R^2$, $C(O)R^1$, $C(O)OR^1$, $C(O)NR^1R^2$, $NR^1C(O)R^2$, $NR^1C(O)OR^2$, $CF_3$, and $OCF_3$;
wherein Y is selected from the group consisting of O, S, $NR^1$ and $CR^1R^2$, and wherein $R^1$ and $R^2$ are selected from the group consisting of hydrogen, nitro, hydroxyl, carboxy, amino, halogen, cyano and $C_1$-$C_{14}$ linear or branched alkyl groups, that are optionally substituted with 1-3 substituents selected from the group consisting of $C_1$-$C_{14}$ linear or branched alkyl, up to perhalo substituted $C_1$-$C_{14}$ linear or branched alkyl, $C_1$-$C_{14}$ alkoxy, hydrogen, nitro, hydroxyl, carboxy, amino, $C_1$-$C_{14}$ alkylamino, $C_1$-$C_{14}$ dialkylamino, halogen, and cyano; and
wherein Z is selected from the group consisting of hydrogen; $C_1$ to $C_{14}$ linear, branched, or cyclic alkyl; phenyl; benzyl, 1-5 substituted benzyl, $C_1$ to $C_3$ alkyl-phenyl, wherein the alkyl moiety is optionally substituted with halogen up to perhalo; $C_1$ to $C_{14}$ linear or branched alkyl, wherein the alkyl moiety is optionally substituted with halogen up to perhalo; —$(CH_2)_q$—K, where K is a 5 or 6 membered monocyclic heterocyclic ring, containing 1 to 4 atoms selected from oxygen, nitrogen and sulfur, which is saturated, partially saturated, or aromatic, or an 8 to 10 membered bicyclic heteroaryl having 1-4 heteroatoms selected from the group consisting of O, N, and S, and wherein the variable q is an integer ranging from 0 to 4, provided that when the compound is of Formula (IA), Z is not hydrogen, and provided that when A is substituted with $S(O)_qR^1$, q is an integer ranging from 0 to 2;
L is a linker; and
J is a binder of a target selected from the group consisting of a bromodomain, a bromodomain-containing protein, and FKBP12, wherein J is of Formula (II):

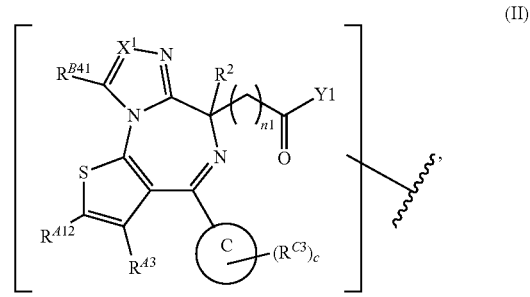

wherein:
Y1 is of formula:

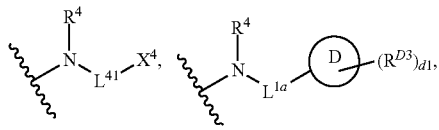

-continued

[chemical structures showing piperidine-type ring with E and $(R^{D3})_{d1}$, and a bicyclic ring G with $(R^{D3})_{d1}$]

wherein:
$R^4$ is hydrogen, optionally substituted alkyl, optionally substituted acyl, or a nitrogen protecting group;
$L^{1a}$ is optionally substituted alkylene;
$L^{41}$ is unsubstituted branched alkylene or substituted alkylene;
$X^4$ is halogen, $-OR^f$, $-SR^f$, or $-N(R^f)_2$;
Ring D is a carbocyclic or a heterocyclic ring, wherein the heterocyclic ring contains one heteroatom, and the heteroatom is N;
Ring G is a bicyclic heterocyclic or bicyclic heteroaryl ring, wherein the rings share exactly two atoms;
E is O, S, $NR^{E11}$, or $CHR^{E11}$, wherein $R^{E11}$ is optionally substituted carbocyclyl, optionally substituted heterocyclyl, optionally substituted aryl, or optionally substituted heteroaryl;
each occurrence of $R^{D3}$ is independently hydrogen, halogen, optionally substituted alkyl, optionally substituted heteroalkyl, optionally substituted alkenyl, optionally substituted alkynyl, optionally substituted carbocyclyl, optionally substituted heterocyclyl, optionally substituted aryl, optionally substituted heteroaryl, optionally substituted acyl, $-OR^f$, $-SR^f$, $-N(R^f)_2$, $-NO_2$, or $-CN$, or two $R^{D3}$ attached to adjacent atoms are joined to form an optionally substituted carbocyclyl, optionally substituted heterocyclyl, optionally substituted aryl, or optionally substituted heteroaryl ring;
z is 0, 1, or 2; and
d1 is 0, 1, 2, 3, or 4;
$R^{412}$ is hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, $-OR^f$, $-SR^f$, $-N(R^f)_2$, $-NO_2$, or $-CN$;
$R^{43}$ is hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, $-OR^f$, $-SR^f$, $-N(R^f)_2$, $-NO_2$, or $-CN$;
$X^1$ is N or $CR^5$, wherein $R^5$ is hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, $-OR^f$, $-SR^f$, $-N(R^f)_2$, $-NO_2$, or $-CN$;
$R^{B41}$ is hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, $-OR^f$, $-SR^f$, $-N(R^f)_2$, $-NO_2$, or $-CN$;
Ring C is aryl or heteroaryl;
each occurrence of $R^{C3}$ is independently halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, substituted sulfonyl, $-OR^f$, $-SR^f$, $-N(R^f)_2$, $-NO_2$, or $-CN$;
c is 0, 1, 2, 3, or 4;
n1 is 0, 1, 2, 3, or 4;
$R^2$ is hydrogen, halogen, or optionally substituted alkyl;
each occurrence of $R^f$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, substituted sulfonyl, an oxygen protecting group, or a nitrogen protecting group, or two $R^f$ are joined to form an optionally substituted heterocyclic or optionally substituted heteroaryl ring; and
the Linker L is attached to Y1, $R^{412}$, $R^{C3}$, or Ring C; or
wherein J is of Formula (III):

(III)

[chemical structure of Formula (III) showing a thieno-diazepine system with $R^{B41}$, $X^1$, N, $R^2$, $R^1$, S, $R^{412}$, $R^{43}$, Ring C with $(R^{C3})_c$, and CN substituents]

wherein:
$R^{412}$ is hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, $-OR^f$, $-SR^f$, $-N(R^f)_2$, $-NO_2$, or $-CN$;
$R^{43}$ is hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, $-OR^f$, $-SR^f$, $-N(R^f)_2$, $-NO_2$, or $-CN$;
$X^1$ is N or $CR^5$, wherein $R^5$ is hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, $-OR^f$, $-SR^f$, $-N(R^f)_2$, $-NO_2$, or $-CN$;
$R^{B41}$ is hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, $-OR^f$, $-SR^f$, $-N(R^f)_2$, $-NO_2$, or $-CN$;
Ring C is aryl or heteroaryl;
each occurrence of $R^{C3}$ is independently halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, substituted sulfonyl, $-OR^f$, $-SR^f$, $-N(R^f)_2$, $-NO_2$, or $-CN$;

c is 0, 1, 2, 3, or 4;

$R^1$ is hydrogen, halogen, optionally substituted alkyl, or —$(CH_2)_nL_2$, wherein n is 0, 1, 2, 3 or 4, and $L_2$ is —C(=O)$R^3$, —C(=O)O$R^3$, —C(=O)N$R^3R^4$, —S(=O)$_2R^3$, —S(=O)$_2$O$R^3$, —S(=O)$_2$N$R^3R^4$, —O$R^3$, —N$R^3R^4$, —N($R^4$)C(=O)$R^3$, optionally substituted carbocyclyl, optionally substituted heterocyclyl, optionally substituted aryl, or optionally substituted heteroaryl;

$R^2$ is hydrogen, halogen, or optionally substituted alkyl;

each of $R^3$ and $R^4$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or optionally substituted acyl, an oxygen protecting group, or a nitrogen protecting group, or $R^3$ and $R^4$ are joined to form an optionally substituted heterocyclic or optionally substituted heteroaryl ring; and each occurrence of $R^f$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, substituted sulfonyl, an oxygen protecting group, or a nitrogen protecting group, or two $R^f$ are joined to form an optionally substituted heterocyclic or optionally substituted heteroaryl ring; or wherein J is of Formula (IV):

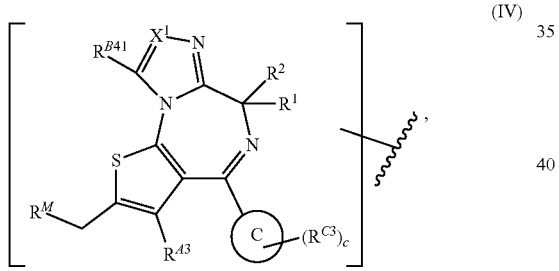

(IV)

wherein:

$R^M$ is —CN, —N($R^f$)$_2$, or —CH$_2$N($R^f$)$_2$;

$R^{A3}$ is hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, —O$R^f$, —S$R^f$, —N($R^f$)$_2$, —NO$_2$, or —CN;

$X^1$ is N or C$R^5$, wherein $R^5$ is hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, —O$R^f$, —S$R^f$, —N($R^f$)$_2$, —NO$_2$, or —CN;

$R^{B41}$ is hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, —O$R^f$, —S$R^f$, —N($R^f$)$_2$, —NO$_2$, or —CN;

Ring C is aryl or heteroaryl;

each occurrence of $R^{C3}$ is independently halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, substituted sulfonyl, —O$R^f$, —S$R^f$, —N($R^f$)$_2$, —NO$_2$, or —CN;

c is 0, 1, 2, 3, or 4;

$R^1$ is hydrogen, halogen, optionally substituted alkyl, or —$(CH_2)_nL_2$, wherein n is 0, 1, 2, 3, or 4, and $L_2$ is —C(=O)$R^3$, —C(=O)O$R^3$, —C(=O)N$R^3R^4$, —S(=O)$_2R^3$, —S(=O)$_2$O$R^3$, —S(=O)$_2$N$R^3R^4$, —O$R^3$, —N$R^3R^4$, —N($R^4$)C(=O)$R^3$, optionally substituted carbocyclyl, optionally substituted heterocyclyl, optionally substituted aryl, or optionally substituted heteroaryl;

$R^2$ is hydrogen, halogen, or optionally substituted alkyl;

each $R^3$ and $R^4$ is independently hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl, or optionally substituted acyl, an oxygen protecting group, or a nitrogen protecting group, or $R^3$ and $R^4$ are joined to form an optionally substituted heterocyclic or optionally substituted heteroaryl ring;

each occurrence of $R^f$ is independently, hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, substituted sulfonyl, an oxygen protecting group, or a nitrogen protecting group, or two $R^f$ are joined to form an optionally substituted heterocyclic or optionally substituted heteroaryl ring; and the Linker L is attached to $R^1$ or $R^M$; or wherein J is of Formula (V):

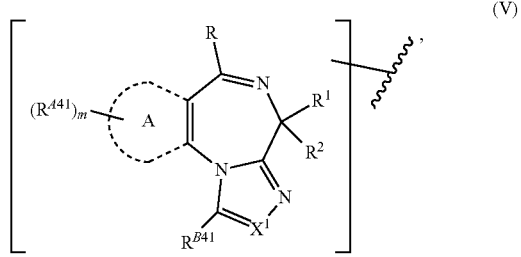

(V)

wherein:

$X^1$ is N or C$R^5$;

$R^5$ is hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, —O$R^f$, —S$R^f$, —N($R^f$)$_2$, —NO$_2$, or —CN;

$R^{B41}$ is H, hydroxy or alkyl, hydroxylalkyl, aminoalkyl, alkoxyalkyl, haloalkyl, alkoxy, or —COO—$R^3$, each of which is optionally substituted;

ring A is aryl or heteroaryl;

each $R^{A41}$ is independently alkyl, cycloalkyl, heterocycloalkyl, aryl, or heteroaryl, each of which is optionally substituted; or any two $R^{A41}$ together with the atoms to which each is attached, can form a fused aryl or heteroaryl group;

R is alkyl, cycloalkyl, heterocycloalkyl, aryl, or heteroaryl; each of which is optionally substituted;

$R^1$ is —$(CH_2)_n$-$L_2$, in which n is 0, 1, 2, or 3 and $L_2$ is H, —C(=O)$R^3$, —C(=O)O$R^3$, —C(=O)N$R^3R^4$, —S(=O)$_2R^3$, —S(=O)$_2$N$R^3R^4$—N$R^3R^4$, —N($R^4$)C (=O)$R^3$, optionally substituted aryl, or optionally substituted heteroaryl; $R^2$ is H, D (deuterium), halogen, or optionally substituted alkyl;

each $R^3$ is independently selected from the group consisting of:

(i) H, aryl, substituted aryl, heteroaryl, or substituted heteroaryl;

(ii) heterocycloalkyl or substituted heterocycloalkyl;

(iii) —$C_1$-$C_8$ alkyl, —$C_2$-$C_8$ alkenyl or —$C_2$-$C_8$ alkynyl, each containing 0, 1, 2, or 3 heteroatoms selected from O, S, or N; —$C_3$-$C_{12}$ cycloalkyl, substituted —$C_3$-$C_{12}$ cycloalkyl, —$C_3$-$C_{12}$ cycloalkenyl, or substituted —$C_3$-$C_{12}$ cycloalkenyl, each of which may be optionally substituted; and (iv) N=C$R^4R^6$;

each $R^4$ is independently hydrogen or alkyl, cycloalkyl, heterocycloalkyl, aryl, or heteroaryl, each of which is optionally substituted;

or $R^3$ and $R^4$ are taken together with the nitrogen atom to which they are attached to form a 4-10-membered ring;

$R^6$ is alkyl, alkenyl, cycloalkyl, cycloalkenyl, heterocycloalkyl, aryl, or heteroaryl, each of which is optionally substituted; or $R^4$ and $R^6$ are taken together with the carbon atom to which they are attached to form a 4-10-membered ring;

m is 0, 1, 2, or 3; and the Linker L is attached to $R^{A41}$ or $R^1$; or wherein J is of the formula:

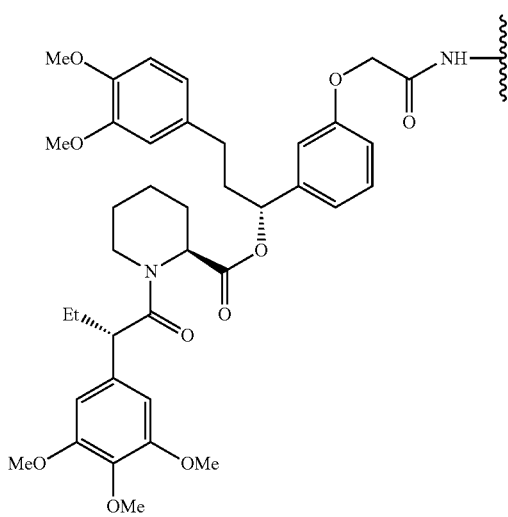

or

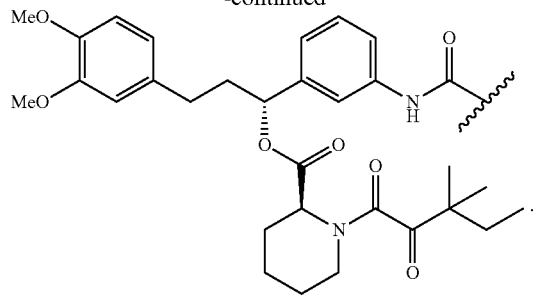

2. The compound of claim 1, or a pharmaceutically acceptable salt, solvate, hydrate, tautomer, or stereoisomer thereof, wherein J is a binder of a bromodomain and/or a bromodomain-containing protein, wherein J is of Formula (II), Formula (III), Formula (IV) or Formula (V).

3. The compound of claim 1, or a pharmaceutically acceptable salt solvate, hydrate, tautomer, or stereoisomer thereof, wherein J is a binder of FKBP12, wherein J is of the formula

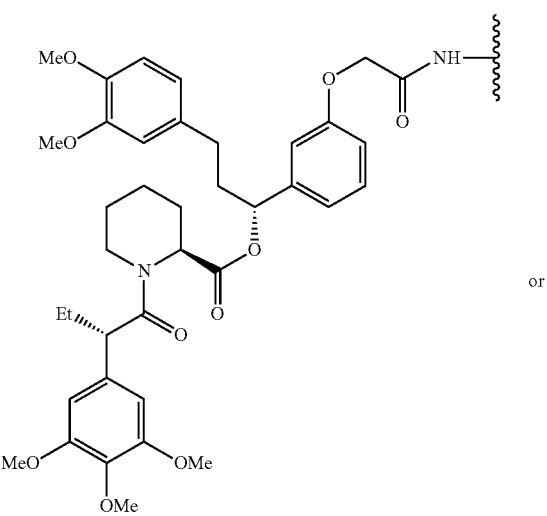

or

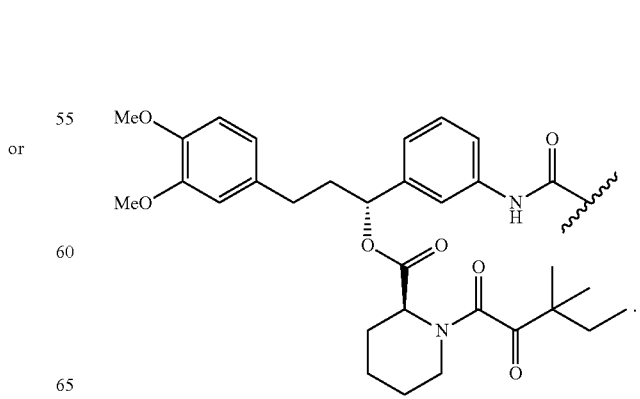

4. The compound of claim 1, or a pharmaceutically acceptable salt, solvate, hydrate, tautomer, or stereoisomer thereof, wherein the compound is of formula:

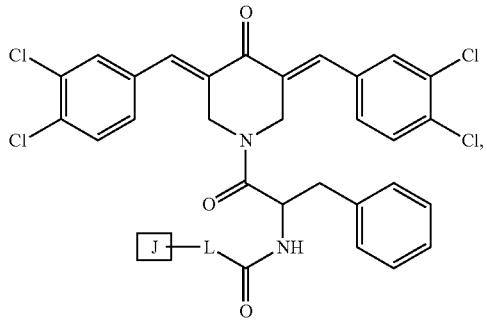

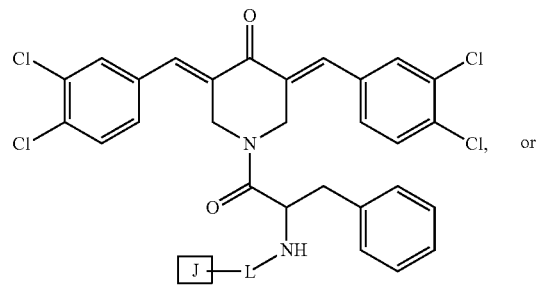
or

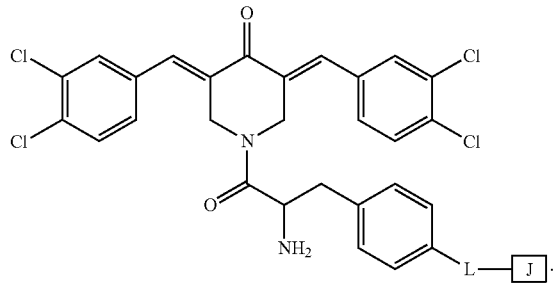

5. The compound of claim 1, wherein in each pair of A's, one A is hydrogen and the other A is phenyl substituted with halogen.

6. The compound of claim 1, wherein at least two instances of Y are O.

7. The compound of claim 1, wherein Z is benzyl.

8. The compound of claim 1, or a pharmaceutically acceptable salt, solvate, hydrate, tautomer, or stereoisomer thereof, wherein L is a bond, a substituted or unsubstituted $C_{1-12}$ hydrocarbon chain, optionally wherein one or more chain atoms of the hydrocarbon chain are independently replaced with —C(=O)—, —O—, —S—, —$NR^b$—, —N=, or =N—, substituted or unsubstituted carbocyclylene, substituted or unsubstituted heterocyclylene, substituted or unsubstituted arylene, substituted or unsubstituted heteroarylene, or substituted or unsubstituted heteroalkylene, wherein
  each instance of $R^b$ is independently hydrogen, substituted or unsubstituted $C_{1-6}$ alkyl, or a nitrogen protecting group, or optionally two instances of $R^b$ are taken together with their intervening atoms to form a substituted or unsubstituted heterocyclic or substituted or unsubstituted heteroaryl ring.

9. The compound of claim 1, wherein L is of the formula:

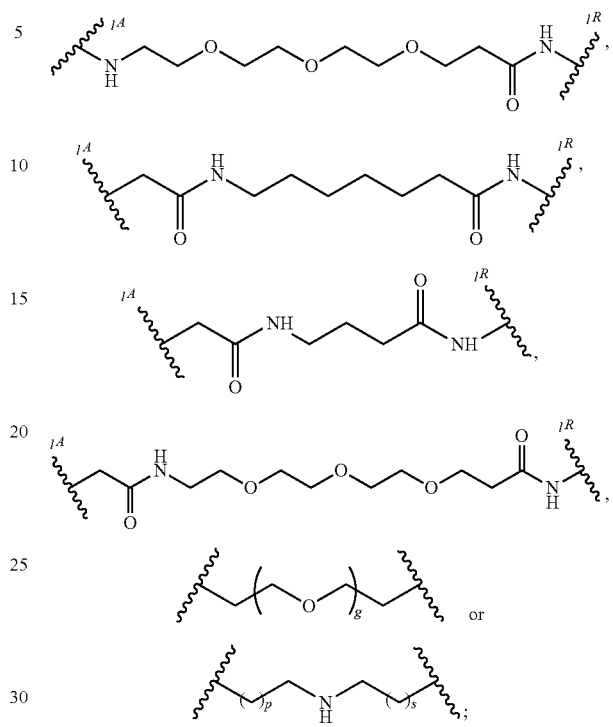

wherein:
g is 1-5;
p is 2-5; and
s is 1-5;

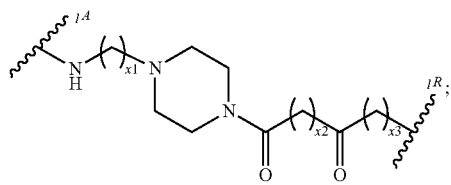

wherein:
x1 is 1-6;
x2 is 1-6; and
x3 is 1-8;

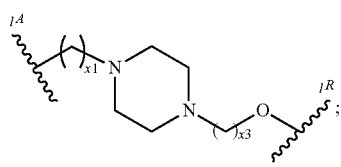

wherein:
x1 is 1-6; and
x3 is 1-8;

wherein:
x1 is 1-6;
x2 is 1-6;
x3 is 1-8; and
x4 is 1-3;

wherein:
x1 is 1-6;
x2 is 1-6;
x3 is 1-8; and
x4 is 1-3;

wherein:
x1 is 1-6;
x2 is 1-6; and
each instance of x3 is independently 1-8;

wherein:
x1 is 1-6; and
x3 is 1-8;

wherein:
x1 is 2 or 3; and
x3 is 6, 7, or 8;

wherein $1^A$ indicates the point of attachment to J, and $1^R$ indicates the point of attachment to for
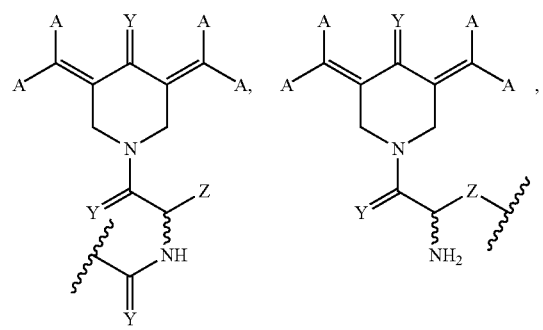
-continued
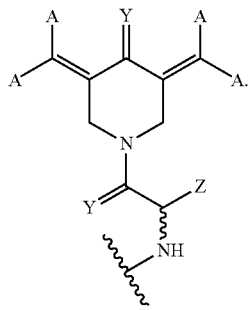
10. The compound of claim 1, wherein L is of the formula:
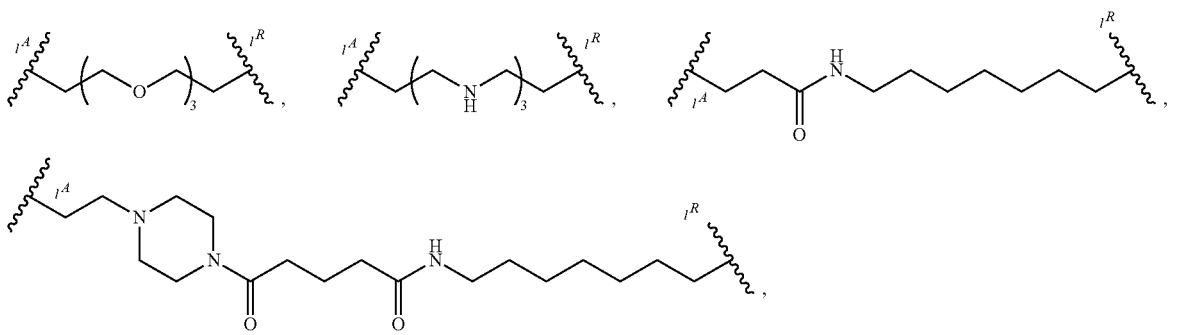
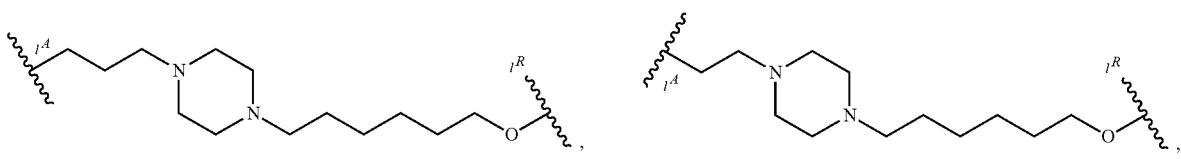
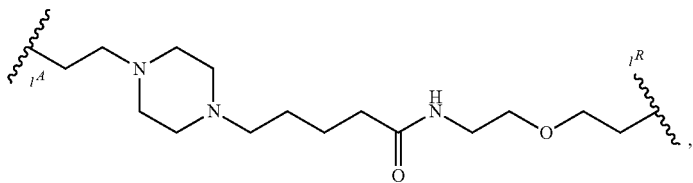
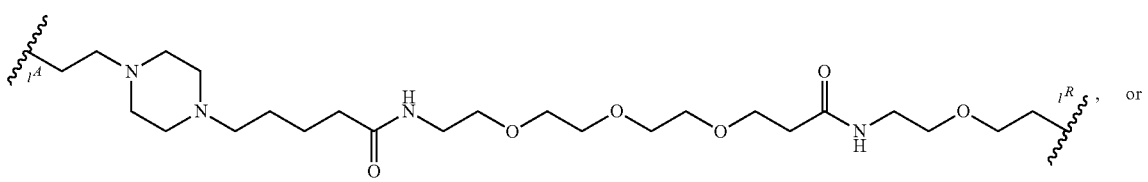
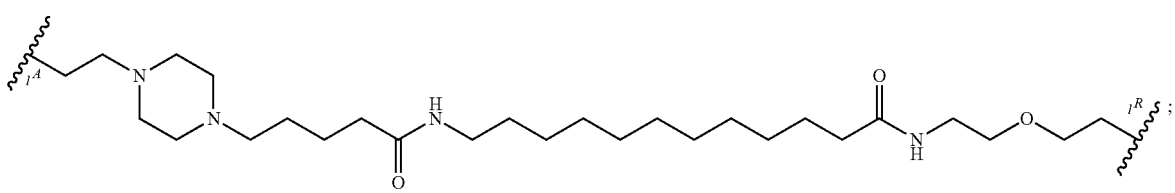

wherein $l^A$ indicates the point of attachment to J, and $l^R$ indicates the point of attachment to formula
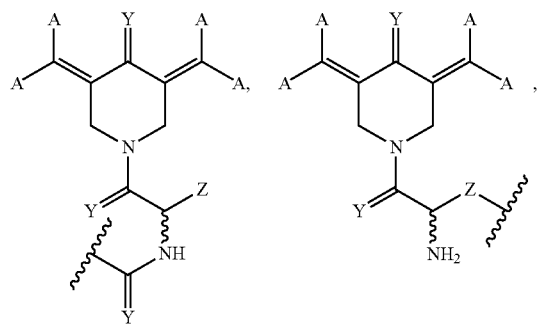
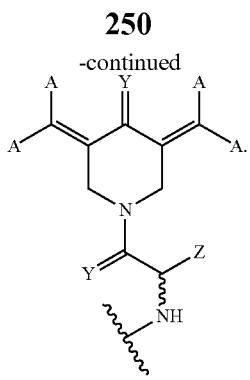
11. The compound of claim 1, or a pharmaceutically acceptable salt, solvate, hydrate, tautomer, or stereoisomer thereof, wherein the compound is of the formula:
(RA-JQ1; LW-RPN13-3)
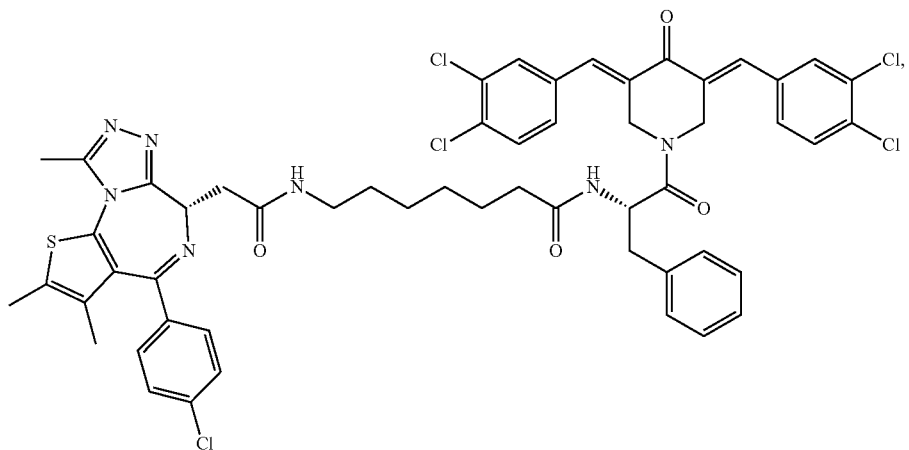
(RA-JQ2; LW-RPN13-5)
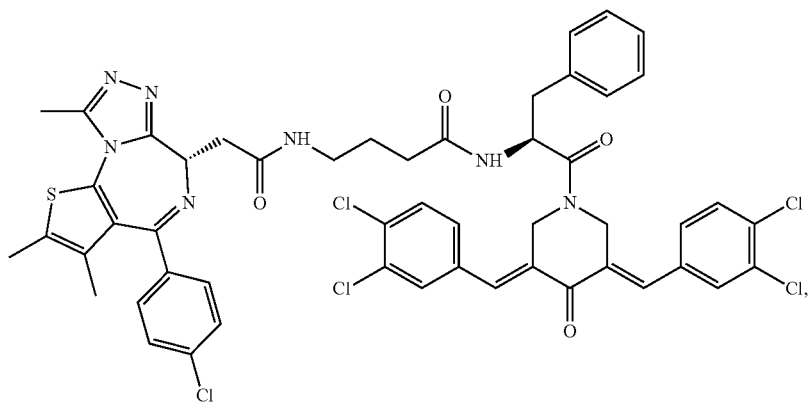

(RA-JQ3; LW-RPN13-6)
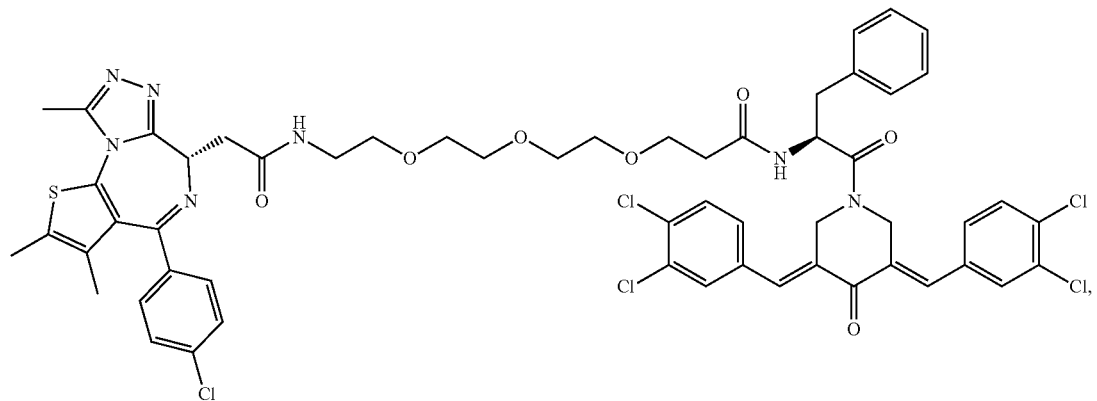
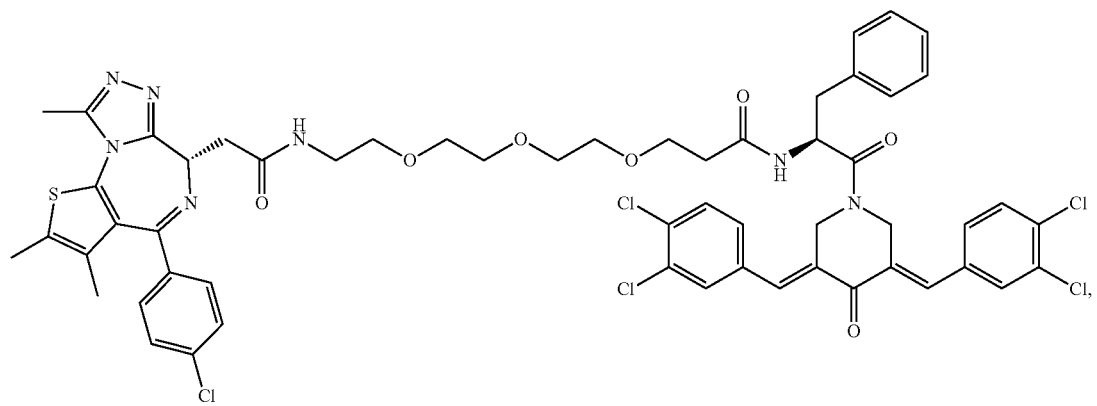
(LW-RPN13-7)
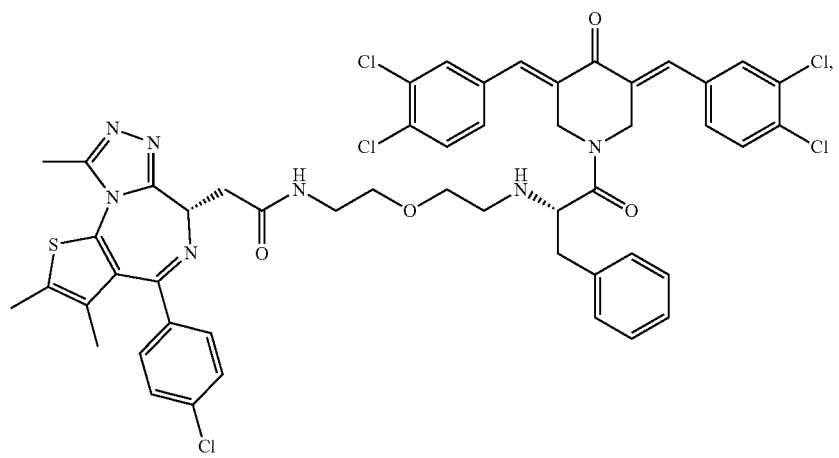

253 254
-continued
D-RAJQ1
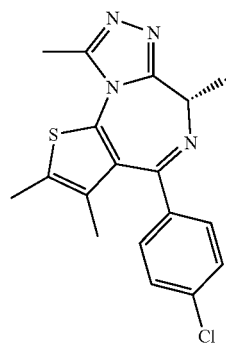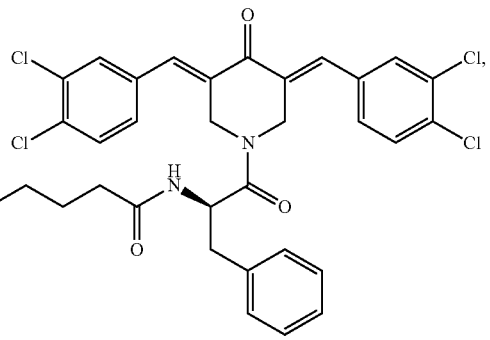
RAJQ8
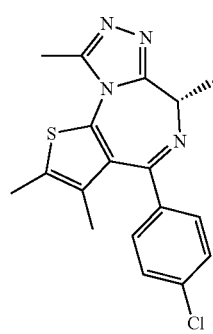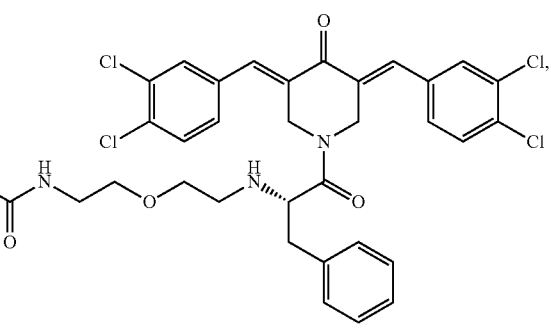
RA-JQ-9
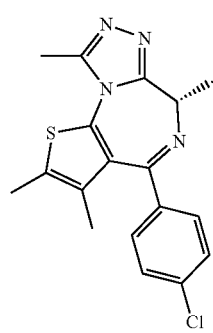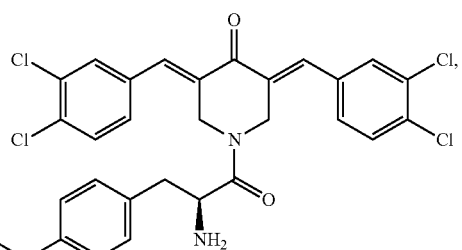
(RA-JQ10; RAJQ10)
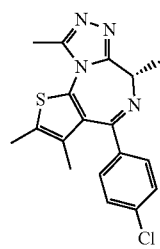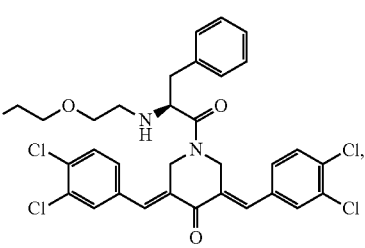

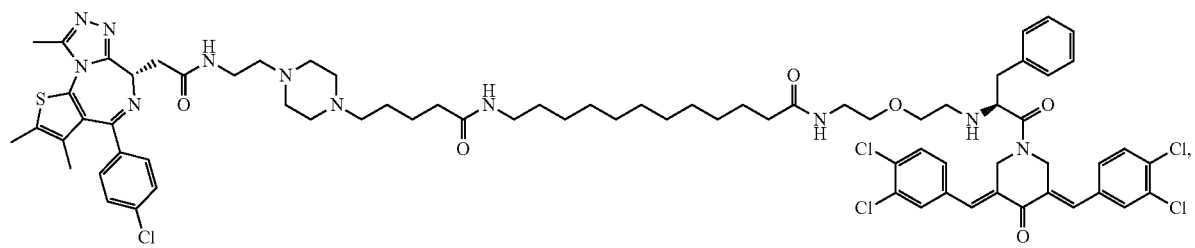
(RA-JQ11; RAJQ11)
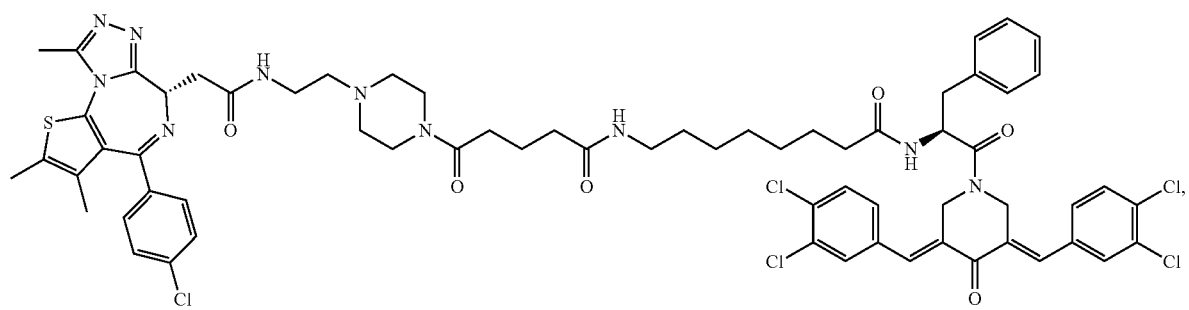
(LW-9296-205)
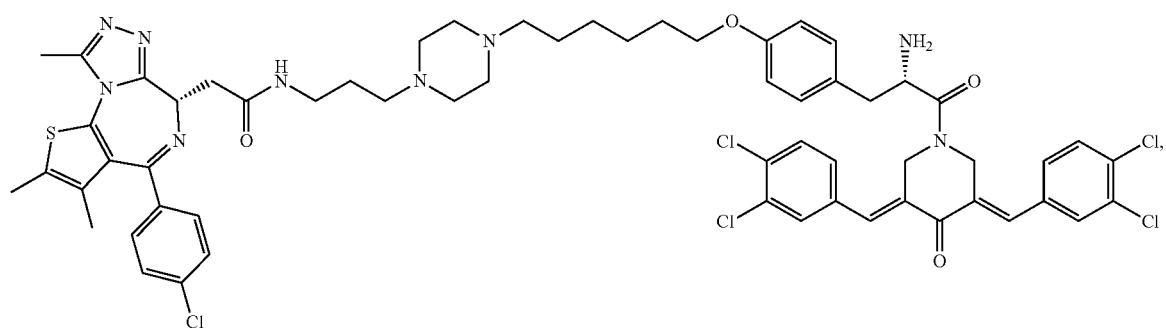
(RA-JQ14)
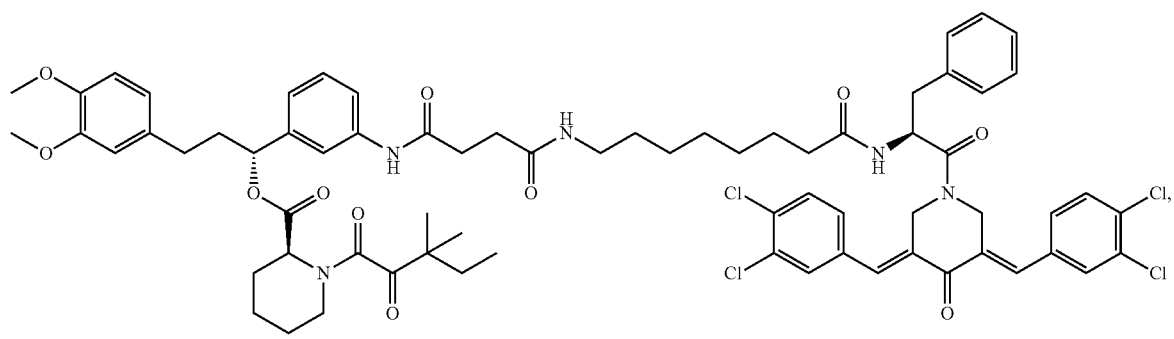
RAFKBP-1

RAFKBP-2
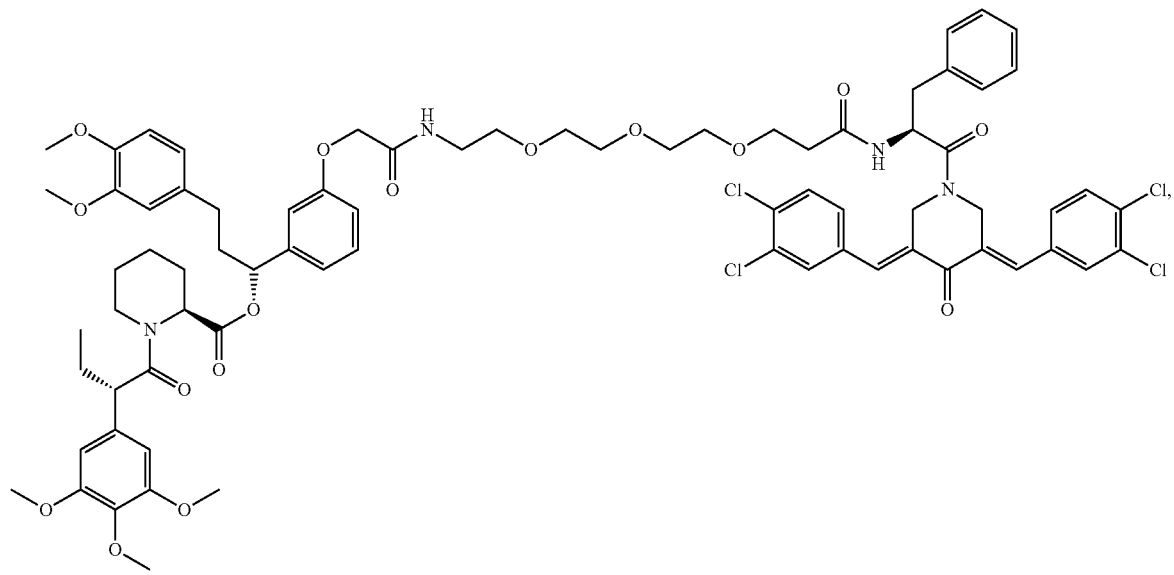
RAFKBP-3
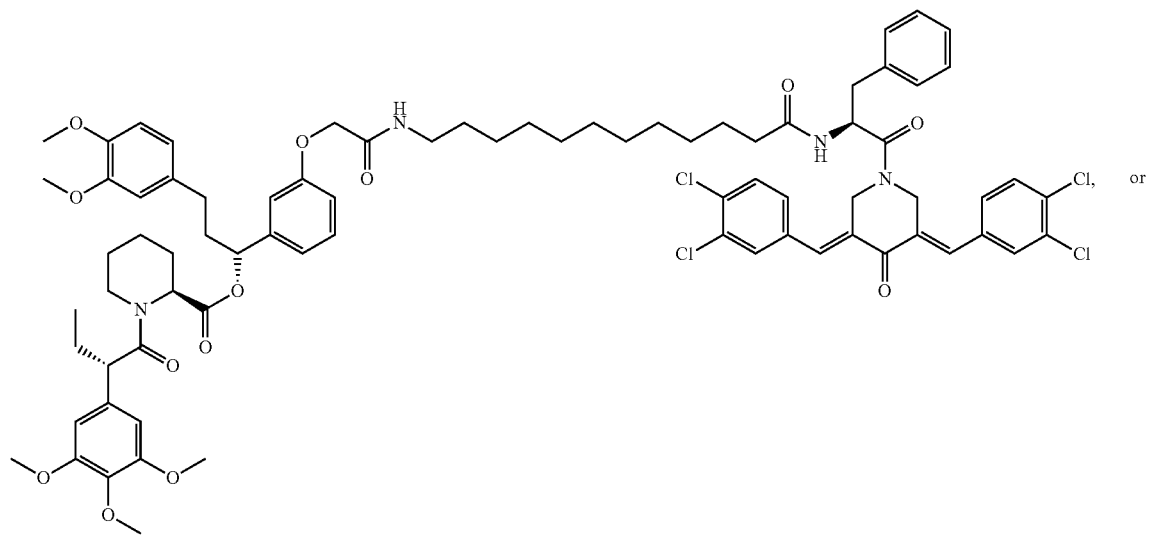
or

-continued

RAFKBP-4

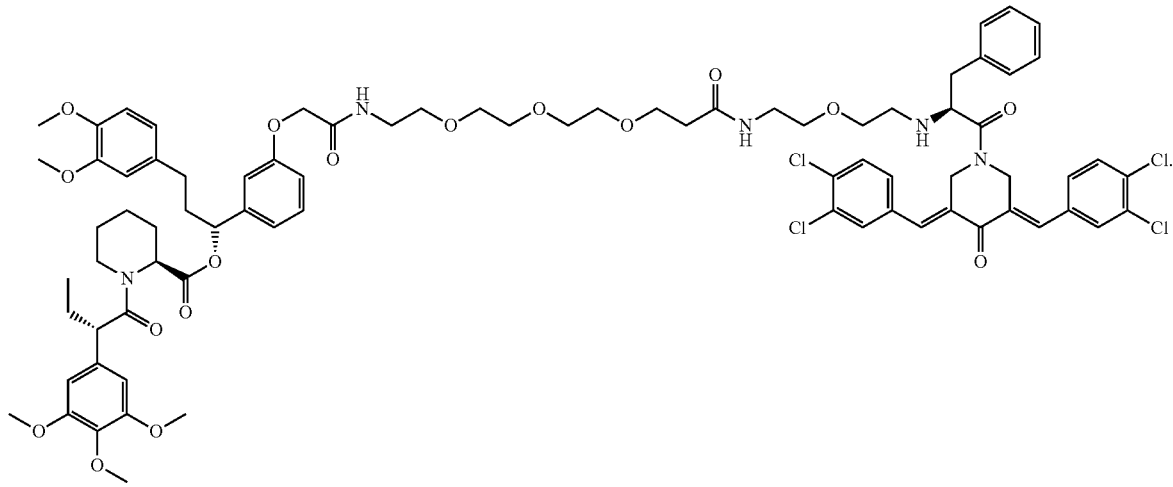

12. A pharmaceutical composition comprising a therapeutically effective amount of the compound of claim 1, or a pharmaceutically acceptable salt, solvate, hydrate, tautomer, or stereoisomer thereof, and optionally a pharmaceutically acceptable excipient.

13. A method of treating cancer which is mediated by a bromodomain, a bromodomain-containing protein, or FKBP12 in a subject in need thereof, the method comprising administering to the subject a therapeutically effective amount of the compound of claim 1, or a pharmaceutically acceptable salt, solvate, hydrate, tautomer, or stereoisomer thereof.

14. The method of claim 13, wherein the cancer is multiple myeloma, leukemia, or lymphoma.

* * * * *